US009943603B2

(12) United States Patent
Barany et al.

(10) Patent No.: US 9,943,603 B2
(45) Date of Patent: *Apr. 17, 2018

(54) COFERONS AND METHODS OF MAKING AND USING THEM

(71) Applicants: CORNELL UNIVERSITY, Ithaca, NY (US); PURDUE RESEARCH FOUNDATION, West Lafayette, IN (US)

(72) Inventors: Francis Barany, New York, NY (US); Maneesh Pingle, New York, NY (US); Donald Bergstrom, Portland, OR (US); Sarah Filippa Giardina, New York, NY (US)

(73) Assignees: Cornell University, Ithaca, NY (US); Purdue Research Foundation, West Lafayette, IN (US)

( * ) Notice: Subject to any disclaimer, the term of this patent is extended or adjusted under 35 U.S.C. 154(b) by 631 days.

This patent is subject to a terminal disclaimer.

(21) Appl. No.: 14/445,887

(22) Filed: Jul. 29, 2014

(65) Prior Publication Data

US 2015/0105553 A1    Apr. 16, 2015

Related U.S. Application Data

(63) Continuation of application No. 12/937,053, filed as application No. PCT/US2009/002223 on Apr. 9, 2009, now Pat. No. 8,853,185.

(60) Provisional application No. 61/043,537, filed on Apr. 9, 2008.

(51) Int. Cl.
| | |
|---|---|
| A61K 47/48 | (2006.01) |
| A61K 31/69 | (2006.01) |
| C07F 5/02 | (2006.01) |
| C07D 233/64 | (2006.01) |
| C07D 307/92 | (2006.01) |
| C07D 309/30 | (2006.01) |
| C07D 319/24 | (2006.01) |
| C07D 493/22 | (2006.01) |
| C07H 7/02 | (2006.01) |
| C07H 9/02 | (2006.01) |
| C40B 30/04 | (2006.01) |
| A61K 47/54 | (2017.01) |

(52) U.S. Cl.
CPC ...... *A61K 47/48061* (2013.01); *A61K 47/545* (2017.08); *C07D 233/64* (2013.01); *C07D 307/92* (2013.01); *C07D 309/30* (2013.01); *C07D 319/24* (2013.01); *C07D 493/22* (2013.01); *C07F 5/02* (2013.01); *C07H 7/02* (2013.01); *C07H 9/02* (2013.01); *C40B 30/04* (2013.01); *A61K 31/69* (2013.01)

(58) Field of Classification Search
None
See application file for complete search history.

(56) References Cited

U.S. PATENT DOCUMENTS

| | | | |
|---|---|---|---|
| 5,643,893 | A | 7/1997 | Benson et al. |
| 6,589,766 | B1 | 7/2003 | Barbas et al. |
| 2005/0153407 | A1 | 7/2005 | Greenberg et al. |
| 2006/0233814 | A1 | 10/2006 | Goldmakher et al. |
| 2007/0010544 | A1 | 1/2007 | Abelman et al. |
| 2008/0234349 | A1 | 9/2008 | Lin et al. |
| 2009/0016974 | A1 | 1/2009 | Pruche et al. |
| 2011/0263688 | A1 | 10/2011 | Barany et al. |
| 2012/0295874 | A1 | 11/2012 | Barany et al. |

FOREIGN PATENT DOCUMENTS

| | | |
|---|---|---|
| JP | 2002508188 A | 3/2002 |
| JP | 2004-532203 A | 10/2004 |
| WO | 1999031263 A1 | 6/1999 |
| WO | 02/076173 A2 | 10/2002 |
| WO | 2005013892 A2 | 2/2005 |
| WO | 2006/050959 A2 | 5/2006 |
| WO | 2006/094813 A2 | 9/2006 |
| WO | 2008124821 A1 | 10/2008 |
| WO | 2009126290 A2 | 10/2009 |
| WO | 2011043817 A1 | 4/2011 |

OTHER PUBLICATIONS

Yu et al., "Formation of the intermediate nitronyl nitroxide-anthracene dyad sensing saccharides," Bioorg. Med. Chem. Lett. 2007, 17:94-96, published online Sep. 30, 2006.*
Takeuchi et al., "Dopamine selective molecularly imprinted polymers via post-imprinting modification," Org. Biomol. Chem. 2006, 4:565-568.*
Schlienger et al., "The Boronic Mannich Reaction in a Solid-Phase Approach," Tertrahedon 56: 10023-10030 (2000).
Carboni et al., "Boronic ester as a linker system for solid phase synthesis," Tetrahedron Letters 40: 7979-7983 (1999).
Abed et al., "Preparative Manipulation of Gold Nanoparticles by Reversible Binding to a Polymeric Solid Support," Chem. Eur. J. 11: 2836-2841 (2005).

(Continued)

*Primary Examiner* — Kaijiang Zhang

(57) ABSTRACT

The present invention is directed to a monomer useful in preparing therapeutic compounds. The monomer includes a diversity element which potentially binds to a target molecule with a dissociation constant of less than 300 μM and a linker element connected to the diversity element. The linker element has a molecular weight less than 500 daltons, is connected, directly or indirectly through a connector, to said diversity element, and is capable of forming a reversible covalent bond or non-covalent interaction with a binding partner of the linker element. The monomers can be covalently or non-covalently linked together to form a therapeutic multimer or a precursor thereof. Also disclosed is a method of screening for therapeutic multimer precursors which bind to a target molecule associated with a condition and a method of screening for linker elements capable of binding to one another. The present invention additionally relates to a therapeutic multimer, which includes a plurality of covalently or non-covalently linked monomers, therapeutic monomers, and uses of such dimers and monomers.

5 Claims, 180 Drawing Sheets

(56) References Cited

OTHER PUBLICATIONS

Priestley et al., "P1 Phenethyl Peptide Bornoic Acid Inhibitors of HCV NS3 Protease," Bioorganic & Medicinal Chemistry Letters 12: 3199-3202 (2002).
Settepani et al., "Insect Chemosterilants. VIII. Boron Compounds," J. Med. Chem. 13: 128-131 (1970).
Machida et al., "Module Assembly for Protein-Surface Recognition: Geranylgeranyltransferase I Bivalent Inhibitors for Simultaneous Targeting of Interior and Exterior Protein Surfaces," Chem. Eur. J. 14:1392-1401 (2008).
Maly et al., "Combinatorial Target-Guided Ligand Assembly: Identification of Potent Subytpe-Selective c-Src Inhibitors," PNAS 97(6):2419-2424 (2000).
Marks et al., "In Vivo Targeting of Organic Calcium Sensors via Genetically Selected Peptides," Chemistry & Biology 11:347-356 (2004).
McNaughton et al., "Resin-Bound Dynamic Combinatorial Chemistry," Organic Letters 8(9):1803-1806 (2006).
Melkko et al., "Encoded Self-Assembling Chemical Libraries," Nature Biotechnology 22(5):568-574 (2004).
Melkko et al., "Isolation of High-Affinity Trypsin Inhibitors from a DNA-Encoded Chemical Library," Angew. Chem. Int. Ed. 46:4671-4674 (2007).
Melkko et al., "On the Magnitude of the Chelate Effect for the Recognition of Proteins by Pharmacophores Scaffolded by Self-Assembling Oligonucleotides," Chemistry & Biology 13:225-231 (2006).
Monnet et al., "Synthetic Peptides Derived from the Variable Regions of an Anti-CD4 Monoclonal Antibody Bind to CD4 and Inhibit HIV-1 Promoter Activation in Virus-Infected Cells," J. Biol. Chem. 274(6):3789-3796 (1999).
Naresh et al., "Synthesis and Mycobacterial Growth Inhibition Activities of Bivalent and Monovalent Arabinofuranoside Containing Alkyl Glycosides," Org. Biomol. Chem. 6:2388-2393 (2008).
Neri et al., "Encoding Chemistry," Nature Chemical Biology 5(7):452-453 (2009).
Nicolaou et al., "Target-Accelerated Combinatorial Synthesis and Discovery of Highly Potent Antibiotics Effective Against Vancomycin-Resistant Bacteria," Angew. Chem. Int. Ed. 39(21):3823-3828 (2000).
Parang et al., "Designing Bisubstrate Analog Inhibitors for Protein Kinases," Pharmacology & Therapaeutics 93:145-157 (2002).
Passarella et al., "Synthesis and Biological Evaluation of Epothilone A Dimeric Compounds," Bioorganic & Medicinal Chemistry 17:7435-7440 (2009).
Popkov et al., "Multidrug-Resistance Drug-Binding Peptides Generated by Using a Phage Display Library," Eur. J. Biochem. 251:155-163 (1998).
Potashman et al., "Covalent Modifiers: An Orthogonal Approach to Drug Design," J. Med. Chem. 52(5):1231-1246 (2009).
Ramström et al., "Drug Discovery by Dynamic Combinatorial Libraries," Nature Reviews 1:26-36 (2002).
Raynes, K., "Bisquinoline Antimalarials: Their Role in Malaria Chemotherapy," International Journal for Parasitology 29:367-379 (1999).
Rice et al., "Dibasic Inhibitors of Human Mast Cell Tryptase. Part 1: Synthesis and Optimization of a Novel Class of Inhibitors," Bioorg. Med. Chem. Lett. 10:2357-2360 (2000).
Rock et al., "An Antifungal Agent Inhibits an Aminoacyl-tRNA Synthetase by Trapping tRNA in the Editing Site," Science 316:1759-1761 (2007).
Rozenman et al., "Solving Chemical Problems Through the Application of Evolutionary Principles," Curr. Opin. Chem. Biol. 11:259-268 (2007).
Rozinov et al., "Evolution of Peptides that Modulate the Spectral Qualities of Bound, Small-Molecule Fluorophores," Chemistry & Biology 5(12):713-728 (1998).
Saggio et al., "Biotin Binders Selected from a Random Peptide Library Expressed on Phage," Biochem. J. 293:613-616 (1993).
Sakurai et al., "DNA-Templated Functional Group Transformations Enable Sequence-Programmed Synthesis Using Small-Molecule Reagents," J. Am. Chem. Soc. 127:1660-1661 (2005).
Schaller et al., "Structure of Molecular Tweezer Complexes in the Solid State: NMR Experiments, X-ray Investigations, and Quantum Chemical Calculations," J. Am. Chem. Soc. 129:1293-1303 (2007).
Schaschke et al., "Bivalent Inhibition of β-Tryptase: Distance Scan of Neighboring Subunits by Dibasic Inhibitors," Bioorganic & Medicinal Chemistry Letters 12:985-988 (2002).
Scheuermann et al., "DNA-Encoded Chemical Libraries for the Discovery of MMP-3 Inhibitors," Bioconjugate Chem. 19(3):778-785 (2008).
Schmidt et al., "Sensitized Detection of Inhibitory Fragments and Iterative Development of Non-Peptidic Protease Inhibitors by Dynamic Ligation Screening," Angew. Chem. Int. Ed. 47:3275-3278 (2008).
Schmuck et al., "One-Armed Artificial Receptors for the Binding of Polar Tetrapeptides in Water: Probing the Substrate Selectivity of a Combinatorial Receptor Library," Chem. Eur. J. 12:1339-1348 (2006).
Seiradake et al., "Crystal Structures of the Human and Fungal Cytosolic Leucyl-tRNA Synthetase Editing Domains: A Structural Basis for the Rational Design of Antifungal Benzoxaboroles," J. Mol. Biol. 390:196-207 (2009).
Selwood et al., "The Interaction of Human Tryptase-β with Small Molecule Inhibitors Provides New Insights into the Unusual Functional Instability and Quaternary Structure of the Protease," Biochemistry 44(9):3580-3590 (2005).
Sennhauser et al., "Drug Export Pathway of Multidrug Exporter AcrB Revealed by DARPin Inhibitors," PLOS Biology 5(1e7):106-113 (2007).
Shao et al., "Sequence-Selective Receptors of Peptides. A Simple Molecular Design for Construction of Large Combinatorial Libraries of Receptors," J. Org. Chem. 61:6086-6087 (1996).
Shepherd et al., "Synthesis of Unsymmetrical Tweezer Receptor Libraries and Identification of Receptors for Lys-D-Ala-D-Ala in Aqueous Solution," Chem. Eur. J. 12:713-720 (2006).
Sprinz et al., "Self-Assembly of Bivalent Protein-Binding Agents Based on Oligonucleotide-Linked Organic Fragments," Bioorganic & Medicinal Chemistry Letters 15:3908-3911 (2005).
Sridhar et al., "New Bivalent PKC Ligands Linked by a Carbon Spacer: Enhancement in Binding Affinity," J. Med. Chem. 46(19):4196-4204 (2003).
Sriram et al., "Multivalency-Assisted Control of Intracellular Signaling Pathways: Application for Ubiquitin-Dependent N-End Rule Pathway," Chemistry & Biology 16:121-131 (2009).
Steinfeld et al., "A Novel Multivalent Ligand That Bridges the Allosteric and Orthosteric Binding Sites of the M2 Muscarinic Receptor," Molecular Pharmacology 72(2):291-302 (2007).
Still, C., "Discovery of Sequence-Selective Peptide Binding by Synthetic Receptors Using Encoded Combinatorial Libraries," Acc. Chem. Res. 29:155-163 (1996).
Sun et al., "Design of Small-Molecule Peptidic and Nonpeptidic Smac Mimetics," Accounts of Chemical Research 41(10):1264-1277 (2008).
Takakusagi et al., "Camptothecin Binds to a Synthetic Peptide Identified by a T7 Phage Display Screen," Bioorganic & Medicinal Chemistry Letters 15:4850-4853 (2005).
Thanos et al., "Potent Small-Molecule Binding to a Dynamic Hot Spot on IL-2," J. Am. Chem. Soc. 125:15280-15281 (2003).
Tian et al., "Bivalent Ligands with Long Nanometer-Scale Flexible Linkers," Biochemistry 48(2):264-275 (2009).
Tian et al., "Potentially Macrocyclic Peptidyl Boronic Acids as Chymotrypsin Inhibitors," J. Org. Chem. 62(3):514-522 (1997).
Vaz et al., "Design of Bivalent Ligands Using Hydrogen Bond Linkers: Synthesis and Evaluation of Inhibitors for Human β-tryptase," Bioorganic & Medicinal Chemistry Letters 14:6053-6056 (2004).
Vogel et al., Designed Ankyrin Repeat Proteins as Anti-Idiotypic-Binding Molecules, Ann. N.Y. Acad. Sci. 1109:9-18 (2007).
Von Mehren et al., "Monoclonal Antibody Therapy for Cancer," Annu. Rev. Med. 54:343-369 (2003).

(56) References Cited

OTHER PUBLICATIONS

Wennemers et al., "Diketopiperazine Receptors: A Novel Class of Highly Selective Receptors for Binding Small Peptides," Chem. Eur. J. 7(15):3342-3347 (2001).
Wennemers et al., "Flexible but with a Defined Turn—Influence of the Template on the Binding Properties of Two-Armed Receptors," Chem. Eur. J. 9(2):442-448 (2003).
Wong et al., "Acetylcholinesterase Complexed with Bivalent Ligands Related to Huperzine A: Experimental Evidence for Species-Dependent Protein-Ligand Complementarity," J. Am. Chem. Soc. 125(2):363-373 (2003).
Xing et al., "Multivalent Antibiotics Via Metal Complexes: Potent Divalent Vancomycins Against Vancomycin-Resistant Enterococci," J. Med. Chem. 46(23):4904-4909 (2003).
Database Caplus (Online); Chemical Abstracts Service, XP002692232 (as entered on Jun. 28, 2004).
Gareiss et al., "Dynamic Combinatorial Selection of Molecules Capable of Inhibiting the (CUG) Repeat RNA-MBNL1 Interaction in Vitro: Discovery of Lead Compounds Targeting Myotonic Dystrophy (DM1)," J. Am. Chem. Soc. 130:16254-16261 (2008).
Lewis et al., "Click Chemistry in Situ: Acetylcholinesterase as a Reaction Vessel for the Selective Assembly of a Femtomolar Inhibitor From an Array of Building Blocks," Angew. Chem. Int. Ed. 41(6):1053-1057 (2002).
Whiting et al., "Inhibitors of HIV-1 Protease by Using in Situ Click Chemistry," Angew. Chem. Int. Ed. 45:1435-1439 (2006).
Charo et al., "The Many Roles of Chemokines and Chemokine Receptors in Inflammation," N. Engl. J. Med. 354(6):610-621 (2006).
Dolle et al., "Comprehensive Survey of Combinatorial Library Synthesis: 2005," J. Comb. Chem. 8(5):597-635 (2006).
Eliasson et al., "Differential IgG-Binding Characteristics of Staphylococcal Protein A, Streptococcal Protein G, and a Chimeric Protein AG," J. Immunol. 142(2):575-581 (1989).
Ellman, J.A., "Combinatorial Methods to Engineer Small Molecules for Functional Genomics," Ernst Schering Res. Found. Workshop 32:183-204 (2000).
Freeman et al., "Use of Nanobarcodes Particles in Bioassays," Methods Mol. Biol. 303:73-83 (2005).
Gunneriusson et al., "Surface Display of a Functional Single-Chain Fv Antibody on Staphylococci," J. Bacteriol. 178(5):1341-1346 (1996).
Hanahan et al., "The Hallmarks of Cancer," Cell 100:57-70 (2000).
Melkko et al., "Lead Discovery by DNA-Encoded Chemical Libraries," Drug Discov. Today 12(11/12):465-471 (2007).
Nelson et al., "Convergence of Wnt, Beta-Catenin, and Cadherin Pathways," Science 303(5663):1483-1487 (2004).
Nicewarner-Pena et al., "Submicrometer Metallic Barcodes," Science 294:137-141 (2001).
Nord et al., "Binding Proteins Selected From Combinatorial Libraries of an Alpha-Helical Bacterial Receptor Domain," Nat. Biotechnol. 15:772-777 (1997).
Pawson et al., "Protein-Protein Interactions Define Specificity in Signal Transduction," Genes & Development 14:1027-1047 (2000).
Penn et al., "Nanoparticles for Bioanalysis," Curr. Opin. Chem. Biol. 7:609-615 (2003).
Polakis, P., "Wnt Signaling and Cancer," Genes Dev. 14:1837-1851 (2000).
Souers et al., "Optimization of a Somatostatin Mimetic Via Constrained Amino Acid and Backbone Incorporation," Bioorg. Med. Chem. Lett. 10:2731-2733 (2000).
Tolmachev et al., "Affibody Molecules: Potential for in Vivo Imaging of Molecular Targets for Cancer Therapy," Expert Opin. Biol. Ther. 7(4):555-568 (2007).
Walton et al., "Particles for Multiplexed Analysis in Solution: Detection and Identification of Striped Metallic Particles Using Optical Microscopy," Anal. Chem. 74:2240-2247 (2002).
Ladame, S., "Dynamic Combinatorial Chemistry: On the Road to Fulfilling the Promise," Org. Biomol. Chem. 6:219-226 (2008).
Muratovska et al., "Targeting Peptide Nucleic Acid (PNA) Oligomers to Mitochondria Within Cells by Conjugation to Lipophilic Cations: Implications for Mitochondrial DNA Replication, Expression and Disease," Nucleic Acids Research 29(9):1852-1863 (2001).
Tokunaga et al., "Formation of Hetero-Boroxines: Dynamic Combinatorial Libraries Generated Through Trimerization of Pairs of Arylboronic Acids," Heterocycles 74:219-223 (2007).
Xing et al., "Self-Assembled Multivalent Vancomycin on Cell Surfaces Against Vancomycin-Resistant Enterococci (VRE)," Chem. Commun. 17:2224-2225 (2003).
Xu, B., "Internal Construction," Nature Chemistry 2:13-14 (2010).
Zhang et al., "Solution and Crystallographic Studies of Branched Multivalent Ligands that Inhibit the Receptor-Binding of Cholera Toxin," J. Am. Chem. Soc. 124(44):12991-12998 (2002).
Zhou et al., "Design at the Atomic Level: Generation of Novel Hybrid Biaryloxazolidinones as Promising New Antibiotics," Bioorg. Med. Chem. Lett. 18:6179-6183 (2008).
Zimmerman et al., "A Rigid Molecular Tweezer with an Active Site Carboxylic Acid: An Exceptionally Efficient Receptor for Adenine in an Organic Solvent," J. Am. Chem. Soc. 111:8054-8055 (1989).
Zimmerman et al., "Chemically Bonded Stationary Phases that Use Synthetic Hosts Containing Aromatic Binding Clefts: HPLC Analysis of Nitro-Substituted Polycyclic Aromatic Hydrocarbons," Proc. Natl. Acad. Sci. 90(4):1190-1193 (1993).
Zimmerman et al., "Complexation of Nucleotide Bases by Molecular Tweezers with Active Site Carboxylic Acids: Effects of Microenvironment," J. Am. Chem. Soc. 113:196-201 (1991).
Zimmerman et al., "Highly Efficient Complexation of a Pi-Acceptor by a Molecular Tweezer Containing Two Pi-Donors: The Role of Preorganization," J. Am. Chem. Soc. 111:8528-8530 (1989).
Zimmerman et al., "Improved Binding of Adenine by a Synthetic Receptor," J. Org. Chem. 55:4789-4791 (1990).
Zimmerman et al., "Rigid Molecular Tweezers: Preorganized Hosts for Electron Donor—Acceptor Complexation in Organic Solvents," J. Am. Chem. Soc. 111:1373-1381 (1989).
Zimmerman et al., "Synthesis and Structure of Molecular Tweezers Containing Active Site Functionality," J. Am. Chem. Soc. 113:183-96 (1991).
International Search Report and Written Opinion for PCT Patent Application No. PCT/US2009/002223 (dated Nov. 4, 2009).
Extended European Search Report for European Patent Application No. 09729677.6 (dated Feb. 25, 2013).
English Translation of Notice of Reasons for Rejection for Japanese Patent Application No. 2011-503998 (dated Aug. 28, 2013).
International Search Report and Written Opinion for Corresponding PCT Patent Application No. PCT/US10/02708 (dated Dec. 10, 2010).
Supplementary European Search Report for Corresponding European Patent Application No. 10822356.1 (dated Mar. 5, 2013).
Duarte et al., "Privileged Structures: A Useful Concept for the Rational Design of New Lead Drug Candidates," Mini. Rev. Med. Chem. 7:1108-1119 (2007).
Amyes et al., "Rational Design of Transition-State Analogues as Potent Enzyme Inhibitors With Therapeutic Applications," ACS Chem. Biol. 2(11):711-714 (2007).
Sohn et al., "Kinetic and Structural Studies of Specific Protein-Protein Interactions in Substrate Catalysis by Cdc25B Phosphatase," Biochemistry 46:807-818 (2007).
Yadaiah et al., "High Affinity Binding of Bcl-xL to Cytochrome C: Possible Relevance for Interception of Translocated Cytochrome C in Apoptosis," Biochim. Biophys. Acta. 1774:1370-1379 (2007).
Kumar et al., "PINT: Protein-Protein Interactions Thermodynamic Database," Nucleic Acids Research 34:D195-D198 (2006).
Gelinas et al., "Mutational Analysis of the Energetics of the GrpE DnaK Binding Interface: Equilibrium Association Constants by Sedimentation Velocity Analytical Ultracentrifugation," J. Mol. Biol. 339:447-458 (2004).
Desrosiers et al., "A Binding Free Energy Hot Spot in the Ankyrin Repeat Protein GABPbeta Mediated Protein-Protein Interaction," J. Mol. Biol. 354:375-384 (2005).
Porter et al., "Grb7-SH2 Domain Dimerisation is Affected by a Single Point Mutation," Eur. Biophys. J. 34:454-460 (2005).

(56) References Cited

OTHER PUBLICATIONS

Seo et al., "Identification of Erythrocyte p55/MPP1 as a Binding Partner of NF2 Tumor Suppressor Protein/Merlin," Exp. Biol. Med. 234:255-262 (2009).
Connon et al., "Steric Effects in the Cupric Ion Oxidation of alpha-Ketols," Journal of Organic Chemistry 38(11):2020-23 (1973).
Agnew et al., "Iterative in Situ Click Chemistry Creates Antibody-Like Protein-Capture Agents," Angew. Chem. Int. Ed. 48:1-5 (2009).
Ayad et al., "Synthesis, Antimalarial Activity and Inhibition of Haem Detoxification of Novel Bisquinolines," Bioorganic & Medicinal Chemistry Letters 11:2075-2077 (2001).
Berg, T., "Modulation of Protein—Protein Interactions with Small Organic Molecules," Angew. Chem. Int. Ed. 42:2462-2481 (2003).
Bonger et al., "Synthesis and Pharmacological Evaluation of Dimeric Follicle-Stimulating Hormone Receptor Antagonists," ChemMedChem 4:2098-2102 (2009).
Bourne et al., "Freeze-Frame Inhibitor Captures Acetylcholinesterase in a Unique Conformation," PNAS 101(6):1449-1454 (2004).
Brik et al., "Rapid Diversity-Oriented Synthesis in Microtiter Plates for in Situ Screening of HIV Protease Inhibitors," ChemBioChem 4:1246-1248 (2003).
Buck et al., "Disulfide Trapping to Localize Small-Molecule Agonists and Antagonists for a G Protein-Coupled Receptor," PNAS 102(8):2719-2724 (2005).
Bunyapaiboonsri et al., "Generation of Bis-Cationic Heterocyclic Inhibitors of Bacillus subtilis HPr Kinase/Phosphatase from a Ditopic Dynamic Combinatorial Library," J. Med. Chem. 46:5803-5811 (2003).
Calderone et al., "Small-Molecule Diversification from Iterated Branching Reaction Pathways Enabled by DNA-Templated Synthesis," Angew. Chem. Int. Ed. 44:7383-7386 (2005).
Chang et al., "Copper-Free Click Chemistry in Living Animals," PNAS 107(5):1821-1826 (2010) (Epub Dec. 2009).
Chen et al., "Fluorescent, Sequence-Selective Peptide Detection by Synthetic Small Molecules," Science 279:851-853 (1998).
Chène, P., "Drugs Targeting Protein-Protein Interactions," ChemMedChem 1:400-411 (2006).
Cheng et al., "Sequence-Selective Peptide Binding with a Peptido-A,B-trans-steroidal Receptor Selected from an Encoded Combinatorial Receptor Library," J. Am. Chem. Soc. 118:1813-1814 (1996).
Coleska et al., "Interaction of a Cyclic, Bivalent Smac Mimetic with the X-Linked Inhibitor of Apoptosis Protein," Biochemistry 47:9811-9824 (2008).
Conza et al., "Selective Binding of Two-Armed Diketopiperazine Receptors to Side-Chain-Protected Peptides," J. Org. Chem. 67:2696-2698 (2002).
Corson et al., "Design and Applications of Bifunctional Small Molecules: Why Two Heads are Better Than One," ACS Chemical Biology 3(11):677-692 (2008).
De Vega et al., "Modulation of Protein-Protein Interactions by Stabilizing/Mimicking Protein Secondary Structure Elements," Current Topics in Medicinal Chemistry 7:33-62 (2007).
Dumelin et al., "Selection of Streptavidin Binders from a DNA-Encoded Chemical Library," Bioconjugate Chem. 17:366-370 (2006).
Edwards et al., "A Crystal Structure of the Bifunctional Antibiotic Simocyclinone D8, Bound to DNA Gyrase," Science 326:1415-1418 (2009).
Erlanson et al., "In Situ Assembly of Enzyme Inhibitors Using Extended Tethering," Nature Biotechnology 21:308-314 (2003).
Erlanson et al., "Site-Directed Ligand Discovery," PNAS 97(17):9367-9372 (2000).
Franceschi et al., "Structure-Based Drug Design Meets the Ribosome," Biochemical Pharmacology 71:1016-1025 (2006).

Gao et al., "A Dimeric Smac/Diablo Peptide Directly Relieves Caspase-3 Inhibition by XIAP," Journal of Biological Chemistry 282(42):30718-30727 (2007).
Gestwicki et al., "Chemical Control Over Protein-Protein Interactions: Beyond Inhibitors," Combinatorial Chemistry & High Throughput Screening 10(8):667-675 (2007).
Ghosh et al., "From Orbital Hybridization to Chemotherapeutics Neutralization," Blood 113(24):6262 (2009).
Goldberg et al., "Erythropoietin Mimetics Derived from Solution Phase Combinatorial Libraries," J. Am. Chem. Soc. 124(4):544-555 (2002) (Epub Dec. 29, 2001).
Golden et al, "Green Tea Polyphenols Block the Anticancer Effects of Bortezomib and Other Boronic Acid-Based Proteasome Inhibitors," Blood 113(23):5927-5937 (2009).
Goral et al., "Double-Level "Orthogonal" Dynamic Combinatorial Libraries on Transition Metal Template," PNAS 98(4):1347-1352 (2001).
Halpin et al., "DNA Display I. Sequence-Encoded Routing of DNA Populations," PLOS Biology 2(7):1015-1021 (2004).
Halpin et al., "DNA Display II. Genetic Manipulation of Combinatorial Chemistry Libraries for Small-Molecule Evolution," PLOS Biology 2(7):1022-1030 (2004).
Halpin et al., "DNA Display III. Solid-Phase Organic Synthesis on Unprotected DNA," PLOS Biology 2(7):1031-1038 (2004).
Heinis et al., "Phage-Encoded Combinatorial Chemical Libraries Based on Bicyclic Peptides," Nature Chemical Biology 5(7):502-507 (2009).
Hunter, T., "Signaling—2000 and Beyond," Cell 100:113-127 (2000).
Iorio et al., "Sequence-Selective Peptide Detection by Small Synthetic Chemosensors Selected from an Encoded Combinatorial Chemosensor Library," Bioorganic & Medicinal Chemistry Letters 11:1635-1638 (2001).
Ishi-I et al., "Self-Assembled Receptors that Stereoselectively Recognize a Saccharide," Angew. Chem. Int. Ed. 42:2300-2305 (2003).
Jensen et al., Synthesis of Guanidinium-Derived Receptor Libraries and Screening for Selective Peptide Receptors in Water, Chem. Eur. J. 8(6):1300-1309 (2002).
Kawe et al., "Isolation of Intracellular Proteinase Inhibitors Derived from Designed Ankyrin Repeat Proteins by Genetic Screening," Journal of Biological Chemistry 281(52):40252-40263 (2006).
Kehoe et al., "Tyrosylprotein Sulfotransferase Inhibitors Generated by Combinatorial Target-Guided Ligand Assembly," Bioorganic & Medicinal Chemistry Letters 12:329-332 (2002).
Kerckhoffs et al., "Dynamic Combinatorial Libraries Based on Hydrogen-Bonded Molecular Boxes," Chem. Eur. J. 13:2377-2385 (2007).
Kodadek, T., "Antibody Surrogates Click Into Place," Nature Chemistry 1:183-185 (2009).
Kolb et al., "The Growing Impact of Click Chemistry on Drug Discovery," Drug Discovery Today 8(24):1128-1137 (2003).
Laune et al., Systematic Exploration of the Antigen Binding Activity of Synthetic Peptides Isolated from the Variable Regions of Immunoglobulins, J. Biol. Chem. 272(49):30937-30944 (1997).
Lehn et al., "Dynamic Combinatorial Chemistry," Science 291(5512):2331-2332 (2001).
Li et al., "Multivalent Vancomycins and Related Antibiotics Against Infectious Diseases," Current Pharmaceutical Design 11:3111-3124 (2005).
Liang et al., "A Biocompatible Condensation Reaction for Controlled Assembly of Nanostructures in Living Cells," Nature Chemistry 2:54-60 (2010) (Epub Dec. 17, 2009).
Liang et al., "Structure-Activity Relationships of Bivalent Aminoglycosides and Evaluation of Their Microbiological Activities," Bioorganic & Medicinal Chemistry Letters 15:2123-2128 (2005).
Liu et al., "Multivalent Drug Design and Inhibition of Cholera Toxin by Specific and Transient Protein-Ligand Interactions," Chem. Biol. Drug Des. 71:408-419 (2008).
Loll et al., "Vancomycin Forms Ligand-Mediated Supramolecular Complexes," J. Mol. Biol. 385:200-211 (2009).
Long et al., "A Multivalent Approach to Drug Discovery for Novel Antibiotics," J. Antibiot. 61(10):595-602 (2008).

(56) References Cited

OTHER PUBLICATIONS

Lu et al., "SM-164: A Novel, Bivalent Smac Mimetic That Induces Apoptosis and Tumor Regression by Concurrent Removal of the Blockade of cIAP-1/2 and XIAP," Cancer Res. 68(22):9384-9393 (2008).
Office Action dated Oct. 31, 2016, in European National Application No. 09729677.6 corresponding to PCT/US2009/002223.
Office Action dated Nov. 16, 2016, in Canadian National Application No. 2,774,476 corresponding to PCT/US2010/02708.
Patent Examination Report in Australian Application No. 2010303946, 3 pages (dated Sep. 26, 2014).
Office action in European Application No. 10822356.1, 6 pages (dated Apr. 7, 2016).
Office action in European Application No. 10822356.1, 4 pages (dated Jul. 17, 2015).
Office action in European Application No. 10822356.1, 8 pages (dated Nov. 20, 2013).
Office action in European Application No. 09729677.6, 9 pages (dated Nov. 20, 2013).
Office action in European Application No. 09729677.6, 6 pages (dated Jul. 28, 2015).
Office action in U.S. Appl. No. 12/937,053, 21 pages (dated Apr. 3, 2013).
Office action in U.S. Appl. No. 12/937,053, 27 pages (dated Jan. 14, 2014).
Restriction Requirement in U.S. Appl. No. 12/937,053, 9 pages (dated Dec. 10, 2012).
Office action in Canadian Application No. 2,720,587, 7 pages (dated Mar. 3, 2015).
Notice of Reasons for Rejection in Japanese Application No. 2014-226002, 9 pages (dated Sep. 30, 2015).
Notice of Reasons for Rejection in Japanese Application No. 2011-503998, 8 pages (dated Aug. 28, 2013).
Notice of Reasons for Rejection in Japanese Application No. 2011-503998, 6 pages (dated Jul. 7, 2014).
Patent Examination Report in Australian Application No. 2009234373, 6 pages (dated Jun. 12, 2014).
Decision of Rejection in Japanese Application No. 2014-226002, 6 pages (dated May 30, 2016).
Office Action in Canadian National Application No. 2,720,587, dated Mar. 15, 2016, corresponding to PCT/US2009/002223.
Office action in U.S. Appl. No. 14/445,887, 11 pages (dated May 4, 2017).
Summons to Attend Oral Proceedings in European Application No. 10822356.1, dated Mar. 29, 2017.
Examination Report for EP 09729677.6 dated Oct. 2, 2017.

* cited by examiner

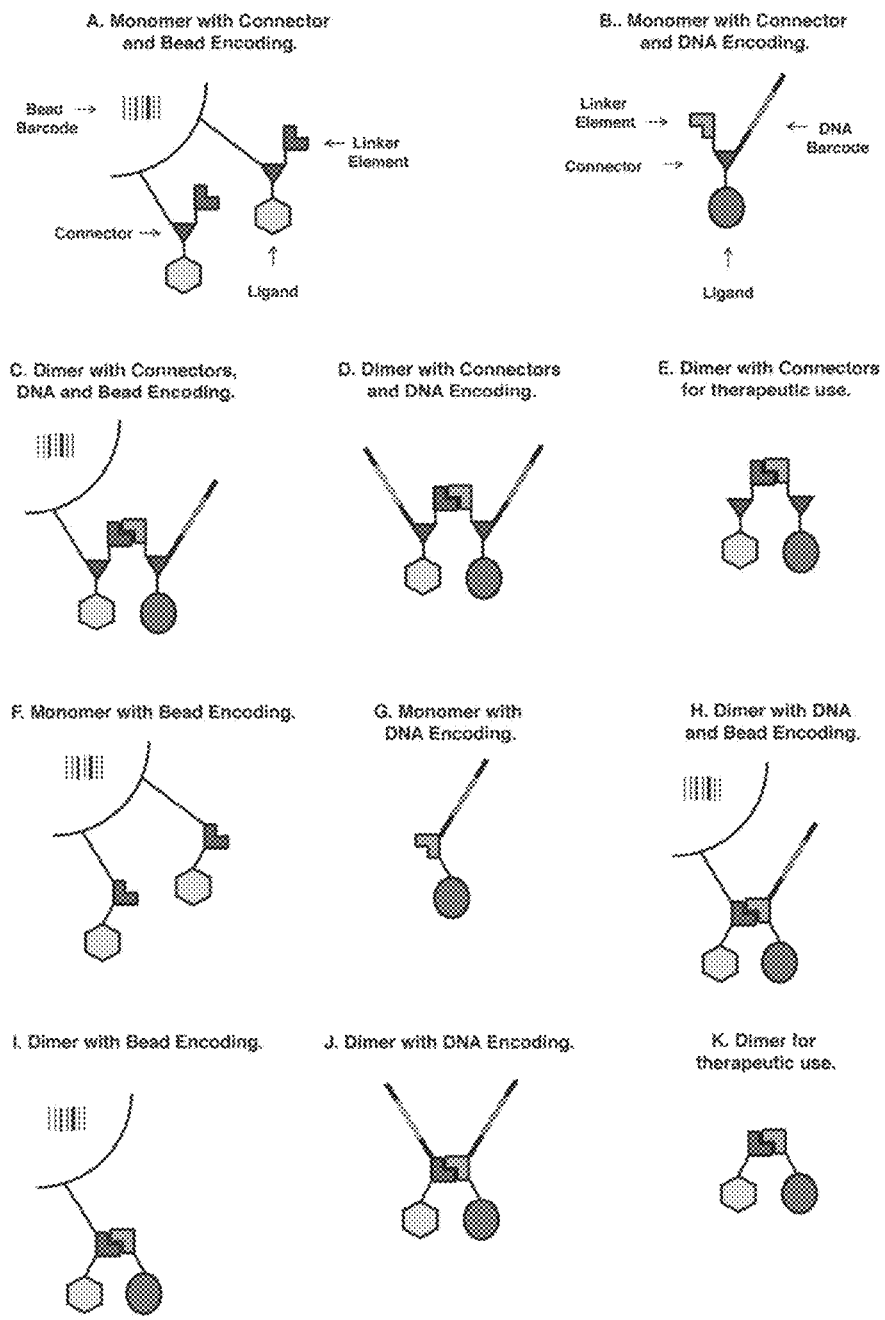
Figure 2.1

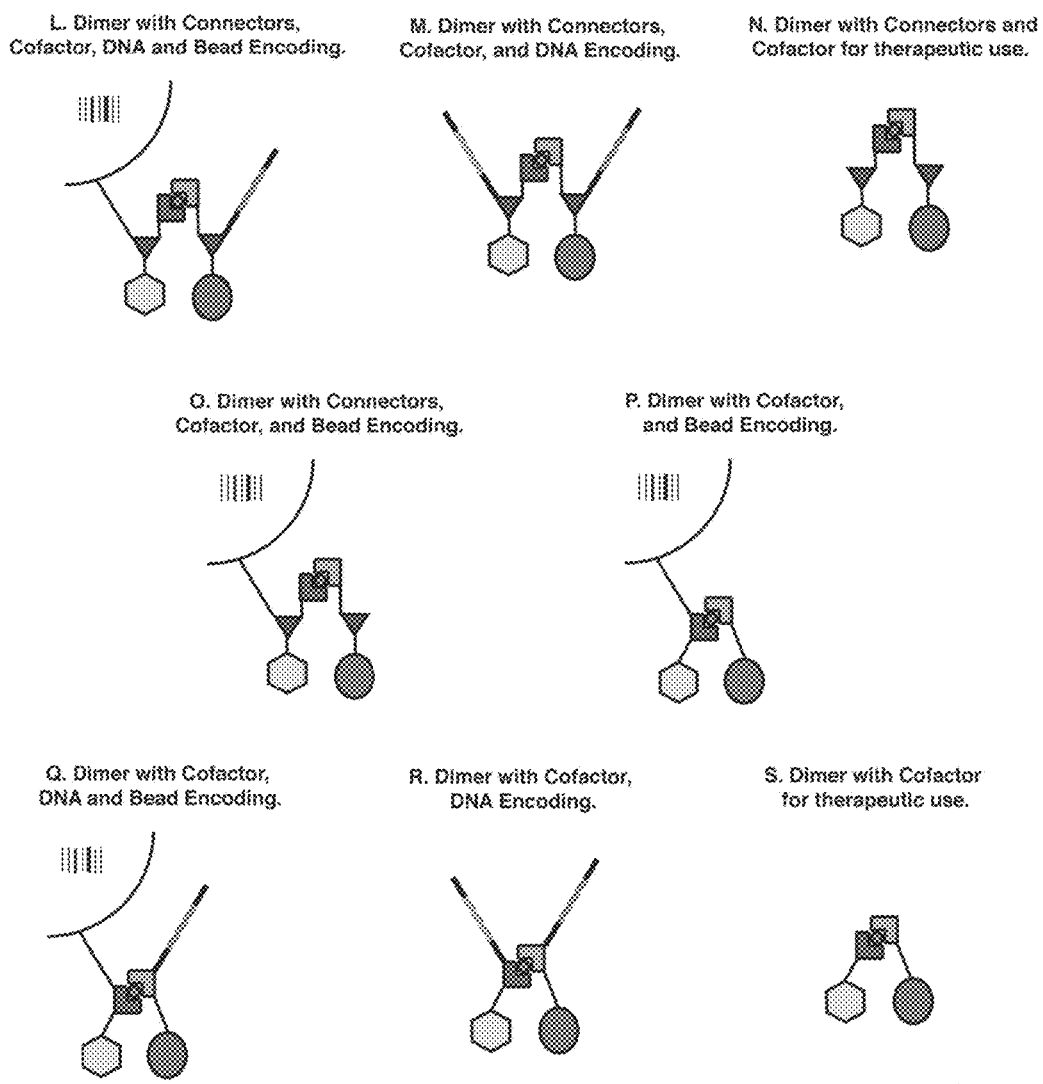
Figure 2.2

Coferon Drug design Components and Variations, Part 3:

A2. Two Monomers with Connectors and Bead Encoding.

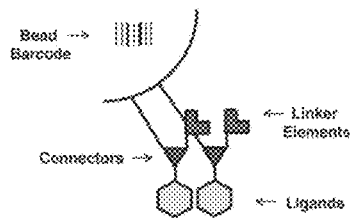

B2. Tethered Dimer with Connectors and DNA Encoding.

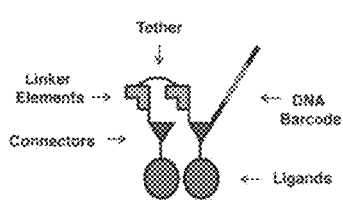

C3. Tethered Dimer with Connectors and Bead Encoding.

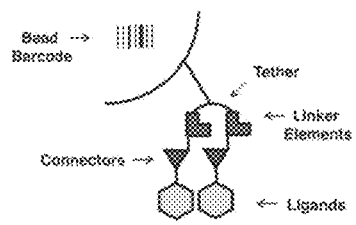

D2. Tethered Dimer with Connectors.

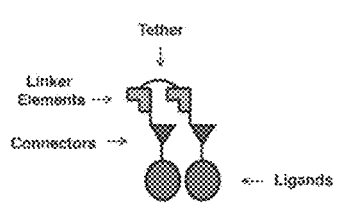

E2. Trimer with Connectors, DNA and Bead Encoding.

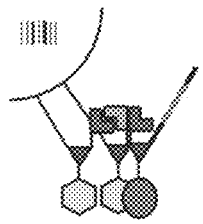

F2. Trimer with Connectors and DNA Encoding.

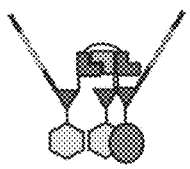

G2. Trimer with Connectors for therapeutic use.

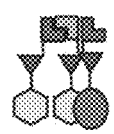

H2. Trimer with Connectors, Bead Encoding.

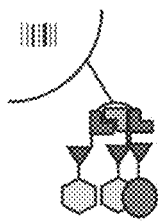

I2. Mixed Trimer with Connectors, DNA and Bead Encoding.

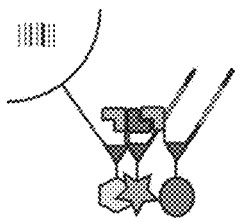

J2. Mixed Trimer with Connectors for therapeutic use.

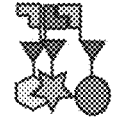

Figure 2.3

Coferon Drug design Components and Variations, Part 4:

K2. Two Monomers with Bead Encoding.
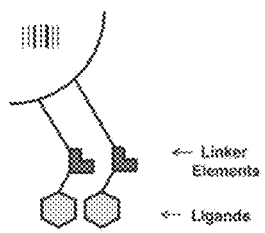

L2. Tethered Dimer with DNA Encoding.
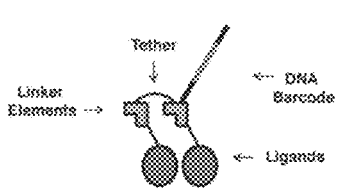

M2. Tethered Dimer with Bead Encoding.
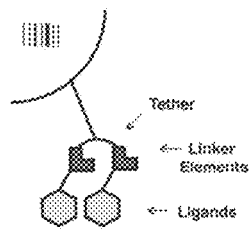

N2. Tethered Dimer.
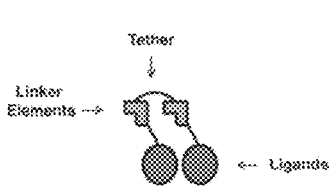

O2. Trimer with DNA and Bead Encoding.
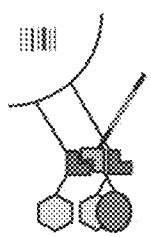

P2. Trimer with DNA Encoding.
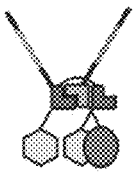

Q2. Trimer for therapeutic use.

R2. Trimer with Bead Encoding.
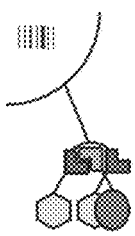

S2. Mixed Trimer with DNA and Bead Encoding.
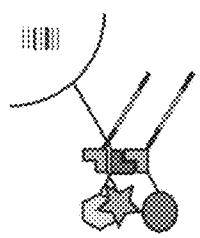

T2. Mixed Trimer for therapeutic use.

Figure 2.4

Coferon Drug design Components and Variations, Part 5:

A3. Tetramer with Connectors, DNA and Bead Encoding.
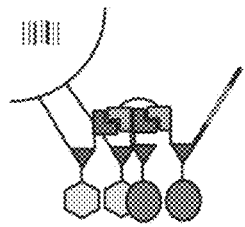

B3. Tetramer with Connectors and DNA Encoding.
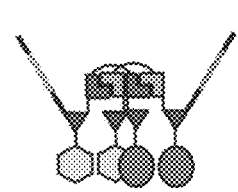

C3. Tetramer with Connectors for therapeutic use.
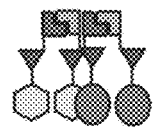

D3. Tetramer with Connectors, DNA and Bead Encoding.
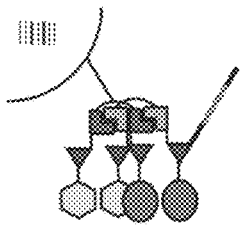

E3. Tetramer with Connectors and Bead Encoding.
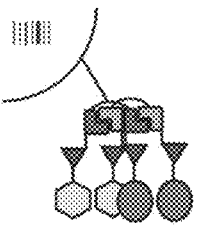

F3. Tetramer with Connectors and Bead Encoding.
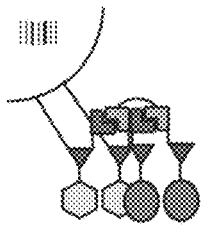

G3. Mixed Tetramer with Connectors, DNA and Bead Encoding.
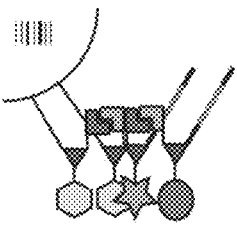

H3. Mixed Tetramer with Connectors and DNA Encoding.
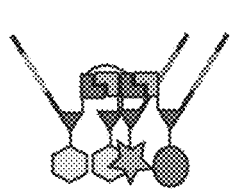

I3. Mixed Tetramer with Connectors for therapeutic use.
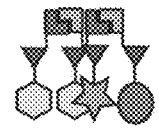

J3. Mixed Tetramer with Connectors, DNA and Bead Encoding.
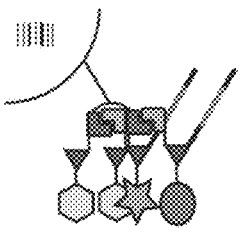

K3. Mixed Tetramer with Connectors and Bead Encoding.
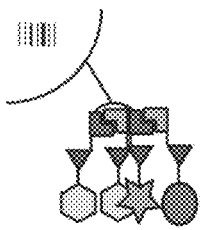

L3. Mixed Tetramer with Connectors, and Bead Encoding.
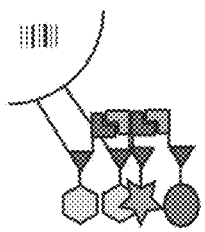

Figure 2.5

Coferon Drug design Components and Variations, Part 6:

M3. Tetramer with DNA and Bead Encoding.
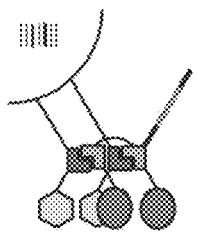

N3. Tetramer with DNA Encoding.
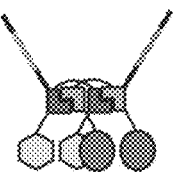

O3. Tetramer for therapeutic use.
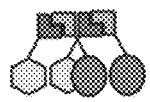

P3. Tetramer with DNA and Bead Encoding.
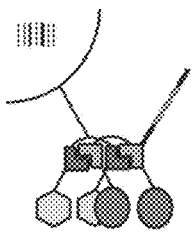

Q3. Tetramer with Bead Encoding.
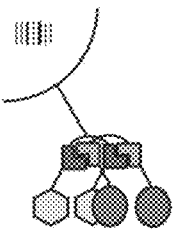

R3. Tetramer with Bead Encoding.
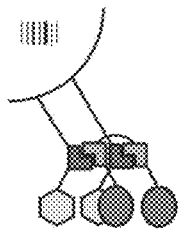

S3. Mixed Tetramer with DNA and Bead Encoding.
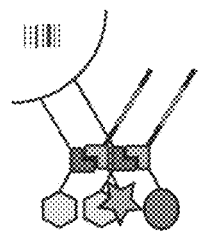

T3. Mixed Tetramer with DNA Encoding.
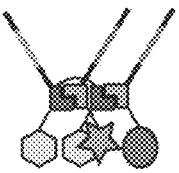

U3. Mixed Tetramer for therapeutic use.

V3. Mixed Tetramer with DNA and Bead Encoding.
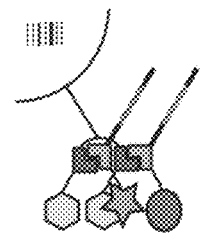

W3. Mixed Tetramer with Bead Encoding.
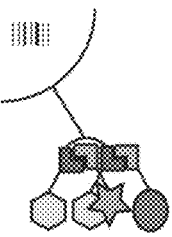

X3. Mixed Tetramer with Bead Encoding.
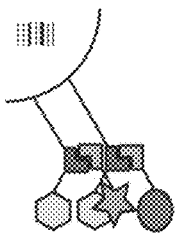

Figure 2.6

Coferon Drug design Components and Variations, Part 7:

A4. Tethered tetramer with Connectors and Bead Encoding.

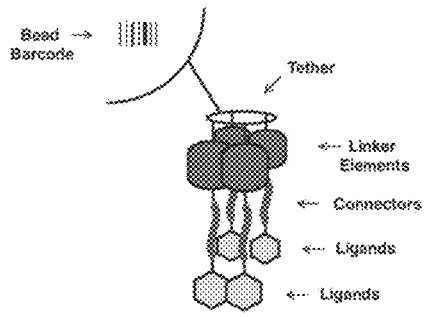

B4. Tethered Tetramer with Connectors and DNA Encoding.

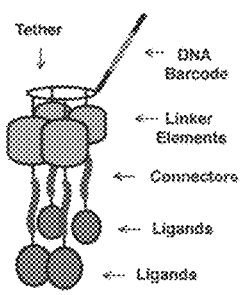

C4. Tethered tetramer with mixed Linkers, Connectors, and Bead Encoding.

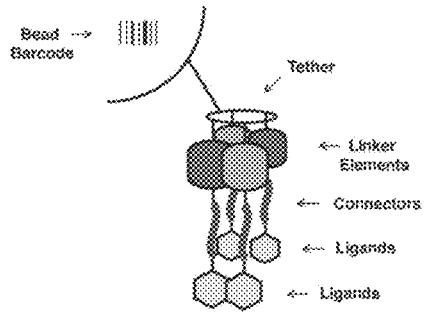

D4. Tethered Tetramer with mixed Linkers, Connectors, and DNA Encoding.

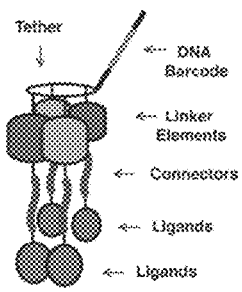

E4. Tethered tetramer with mixed Ligands, Connectors, and Bead Encoding.

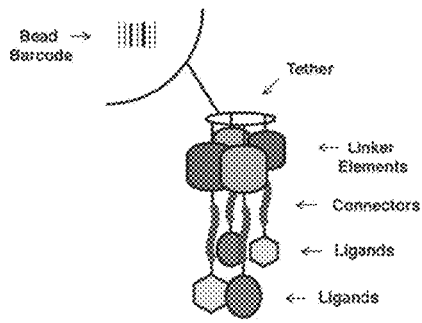

F4. Tethered Tetramer with mixed Linkers, Connectors, and DNA Encoding.

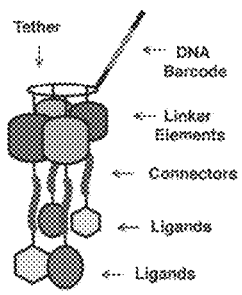

Figure 2.7

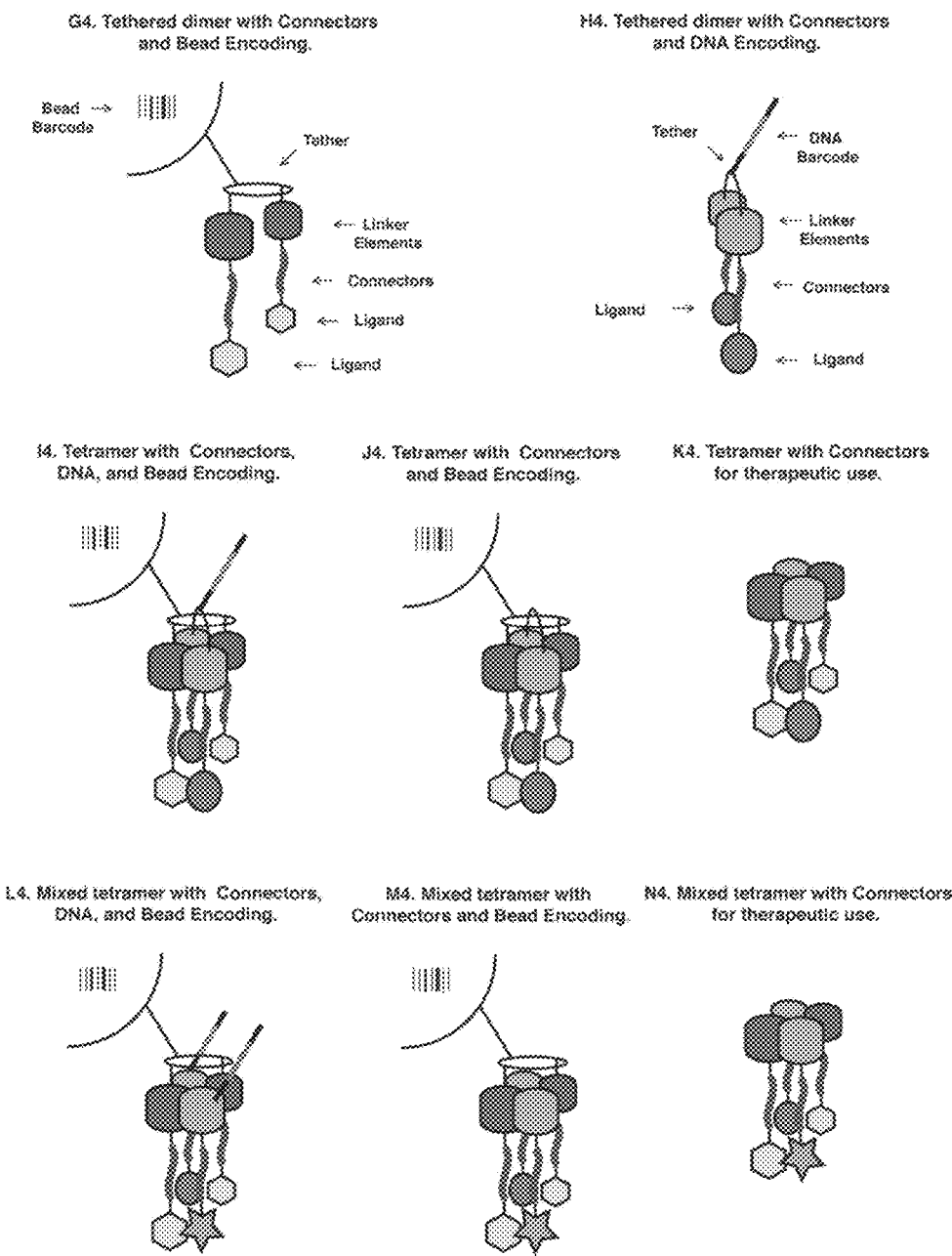
Figure 2.8

Coferon Drug design Components and Variations, Part 9:
O4. Tetramer with Connectors for therapeutic use.
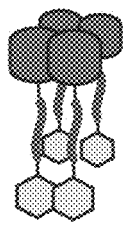
P4. Tetramer with Connectors for therapeutic use.
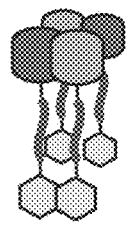
Q4. Tetramer with Connectors for therapeutic use.
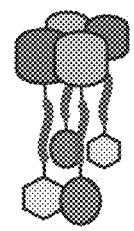
R4. Dimer with Connectors for therapeutic use.
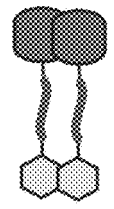
S4. Dimer with Connectors for therapeutic use.
T4. Dimer with Connectors for therapeutic use.
Figure 2.9

Coferon Drug design Components and Variations, Part 10:

A5. Tethered tetramer with Bead Encoding.

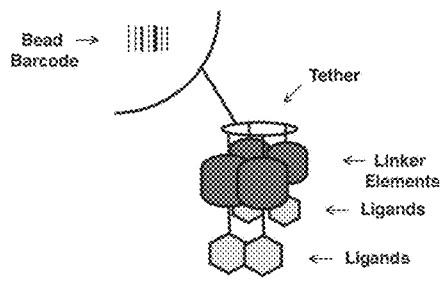

B5. Tethered Tetramer with DNA Encoding.

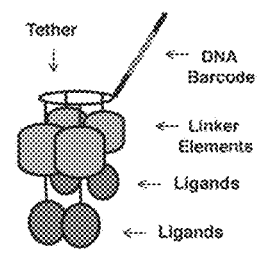

C5. Tethered tetramer with mixed Linkers and Bead Encoding.

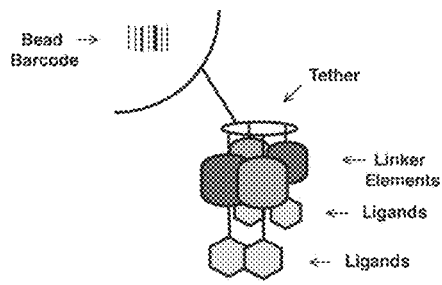

D5. Tethered Tetramer with mixed Linkers and DNA Encoding.

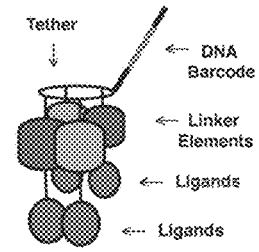

E5. Tethered tetramer with mixed Ligands and Bead Encoding.

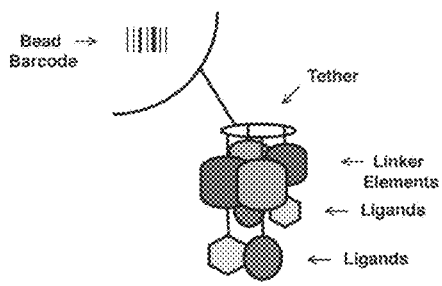

F5. Tethered Tetramer with mixed Linkers and DNA Encoding.

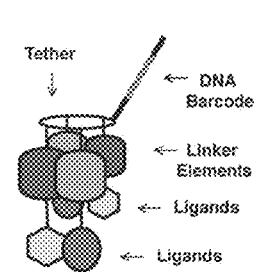

Figure 2.10

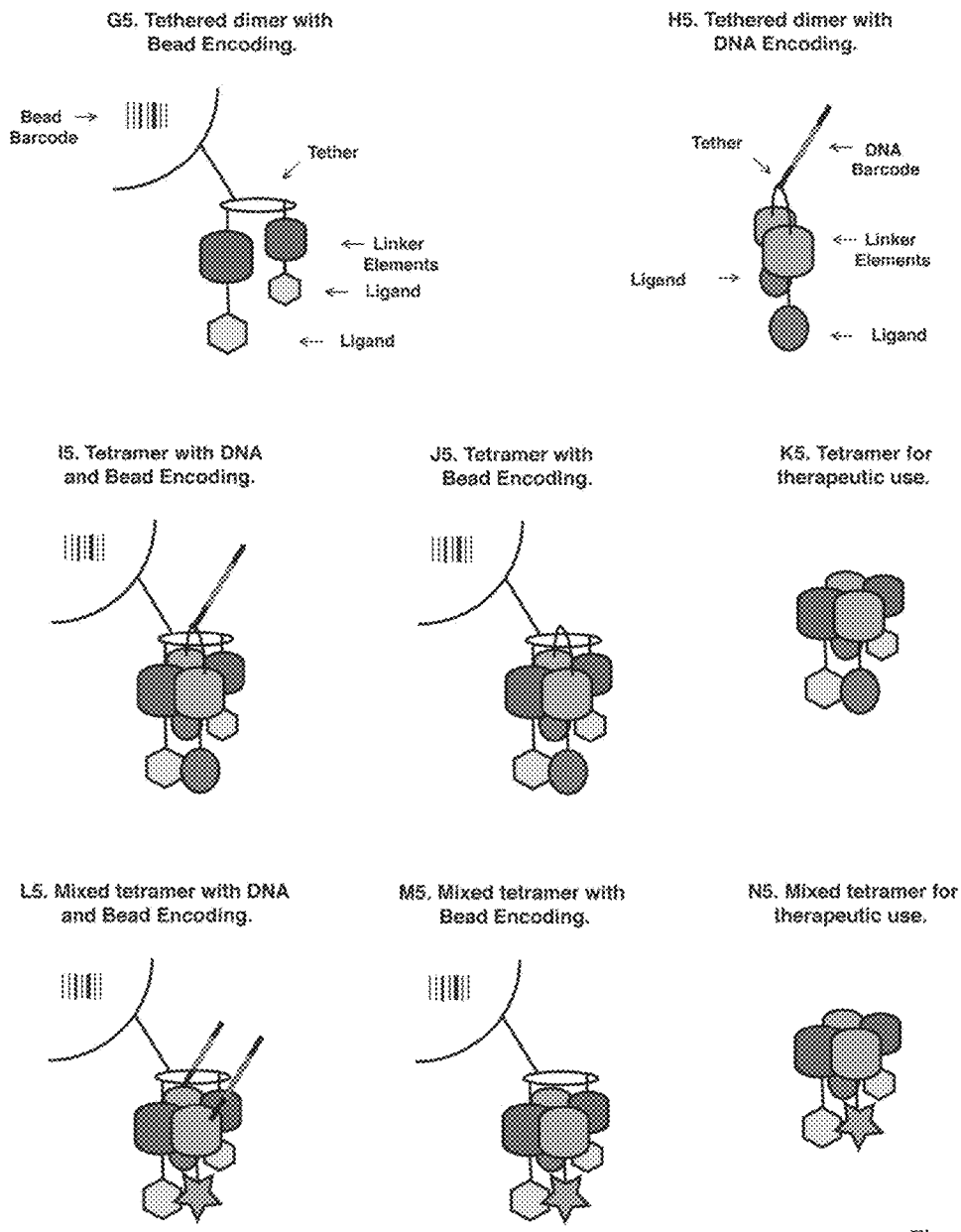
Figure 2.11

Coferon Drug design Components and Variations, Part 12:
O5. Tetramer for therapeutic use.
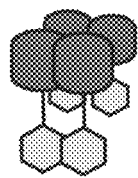
P5. Tetramer for therapeutic use.
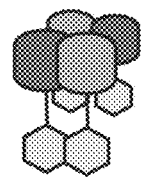
Q5. Tetramer for therapeutic use.
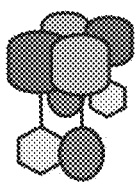
R5. Dimer for therapeutic use.
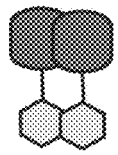
S5. Dimer for therapeutic use.
T5. Dimer for therapeutic use.
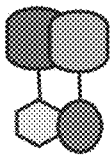
Figure 2.12

Coferon Drug design Components and Variations, Part 13:

A6. Tethered hexamer with Connectors and Bead Encoding.

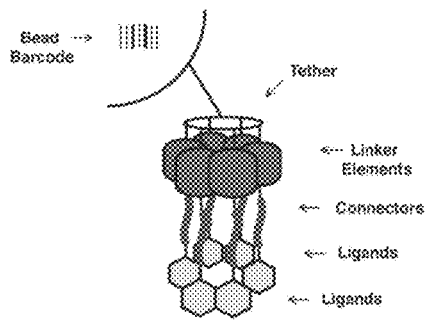

B6. Tethered hexamer with Connectors and DNA Encoding.

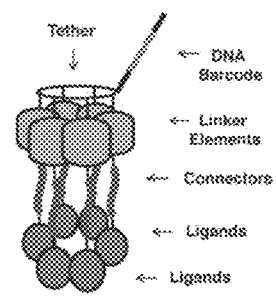

C6. Tethered hexamer with mixed Linkers, Connectors, and Bead Encoding.

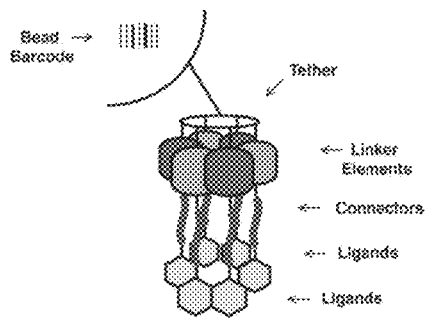

D6. Tethered hexamer with mixed Linkers, Connectors, and DNA Encoding.

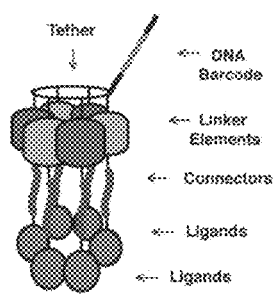

E6. Tethered hexamer with mixed Ligands, Connectors, and Bead Encoding.

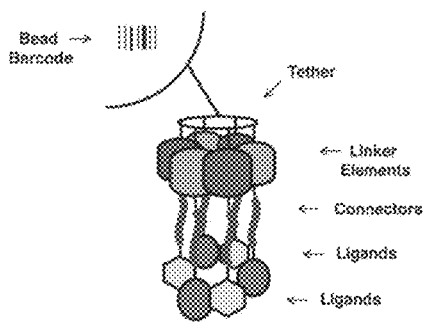

F6. Tethered hexamer with mixed Linkers, Connectors, and DNA Encoding.

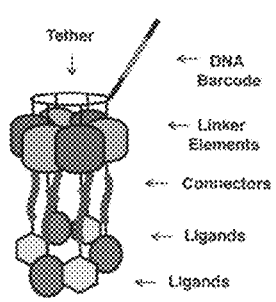

Figure 2.13

Coferon Drug design Components and Variations, Part 14:

G6. Tethered trimer with Connectors and Bead Encoding.

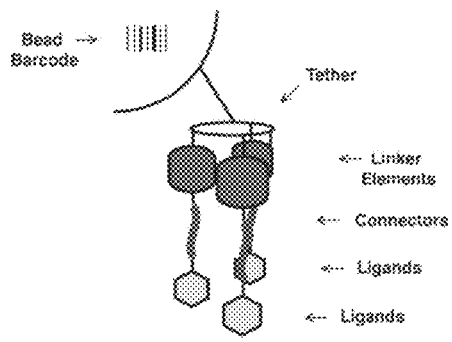

H6. Tethered trimer with Connectors and DNA Encoding.

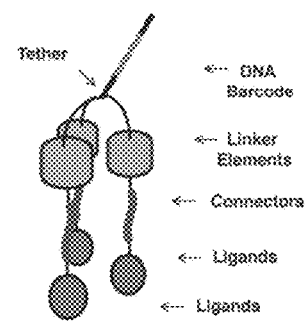

I6. Hexamer with Connectors, DNA, and Bead Encoding.

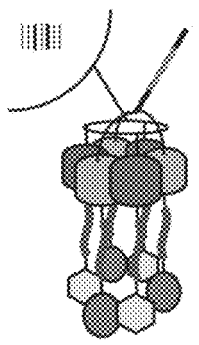

J6. Hexamer with Connectors and Bead Encoding.

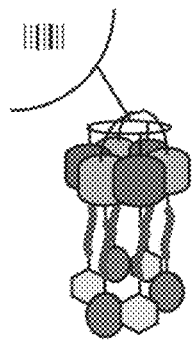

K6. Hexamer with Connectors for therapeutic use.

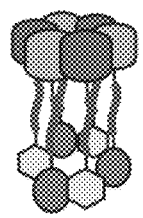

L6. Hexamer with Connectors for therapeutic use.

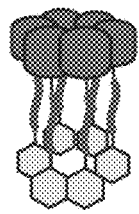

M6. Hexamer with Connectors for therapeutic use.

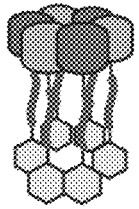

N6. Trimer with Connectors for therapeutic use.

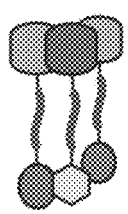

Figure 2.14

Coferon Drug design Components and Variations, Part 15:
A7. Tethered hexamer with Bead Encoding.
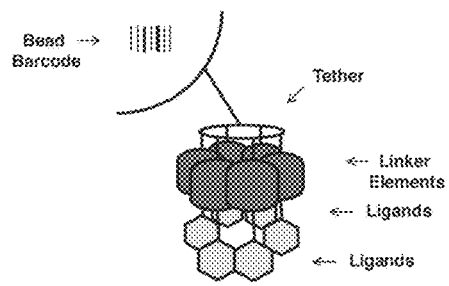
B7. Tethered hexamer with DNA Encoding.
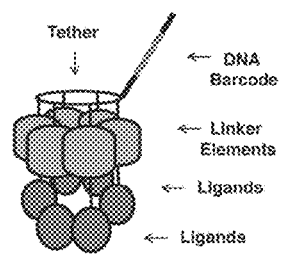
C7. Tethered hexamer with mixed Linkers and Bead Encoding.
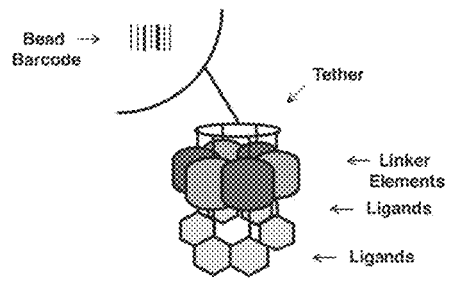
D7. Tethered hexamer with mixed Linkers and DNA Encoding.
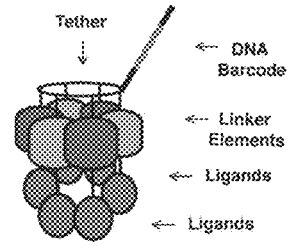
E7. Tethered hexamer with mixed Ligands and Bead Encoding.
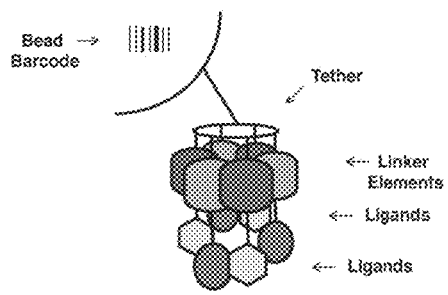
F7. Tethered hexamer with mixed Linkers and DNA Encoding.
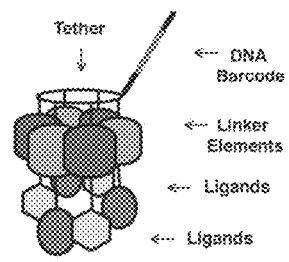
Figure 2.15

Coferon Drug design Components and Variations, Part 16:
G7. Tethered trimer with Bead Encoding.
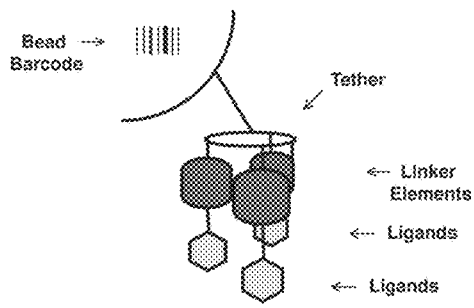
H7. Tethered trimer with DNA Encoding.
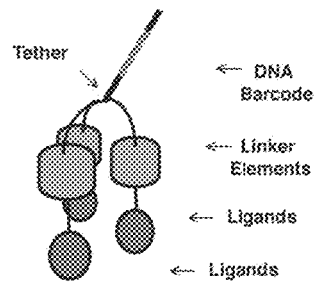
I7. Hexamer with DNA and Bead Encoding.
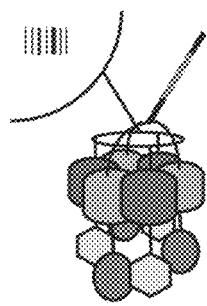
J7. Hexamer with Bead Encoding.
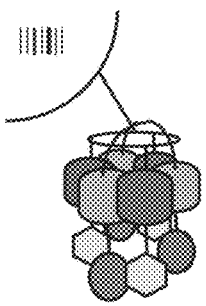
K7. Hexamer for therapeutic use.
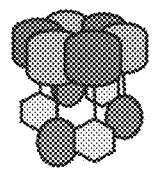
L7. Hexamer for therapeutic use.
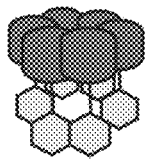
M7. Hexamer for therapeutic use.
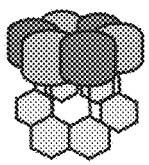
N7. Trimer for therapeutic use.
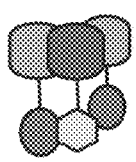
Figure 2.16

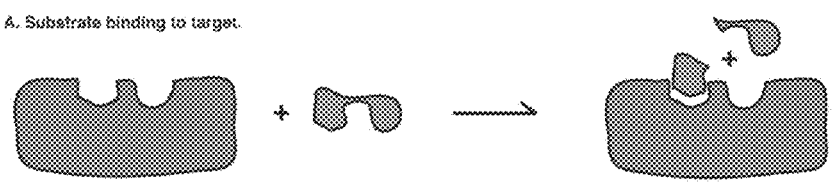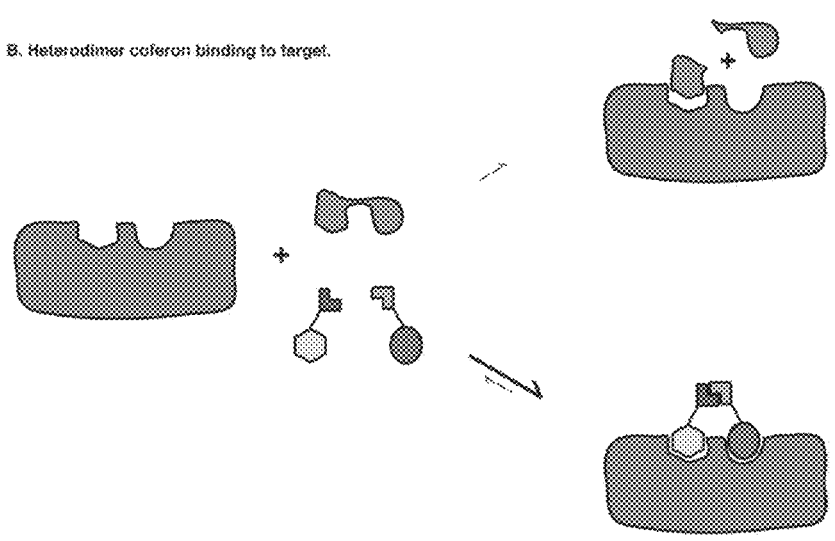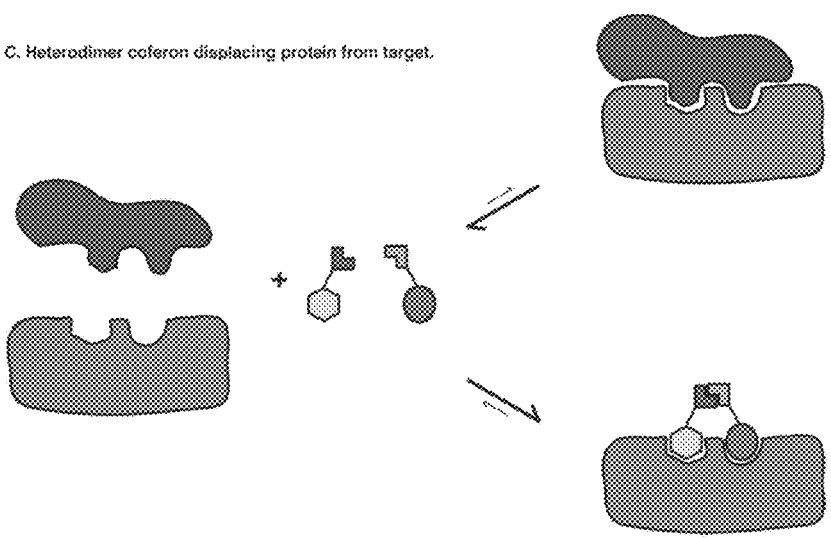
Figure 2.17

Coferon drug interactions with target, Part 2:
D. Protein activating target.
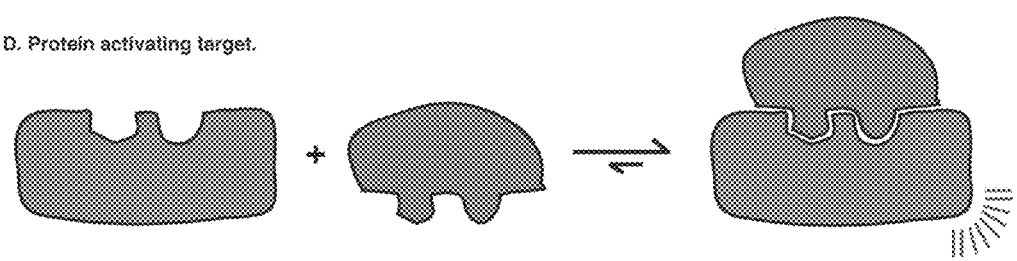
E. Heterodimer coferon activating target.
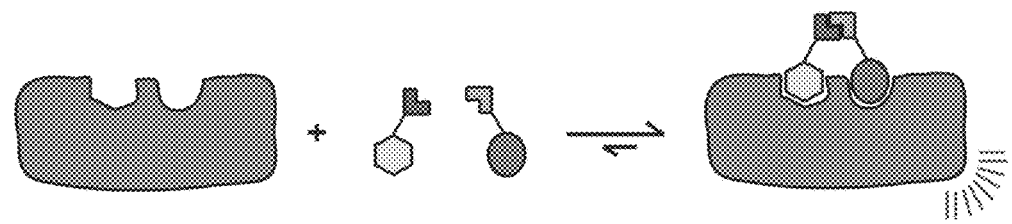
F. Protein inactivating target.
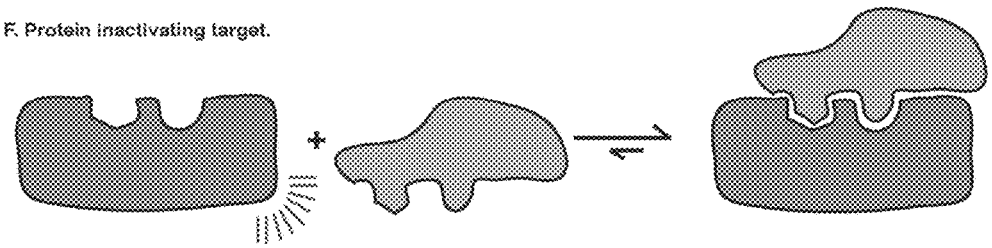
G. Heterodimer coferon inactivating target.
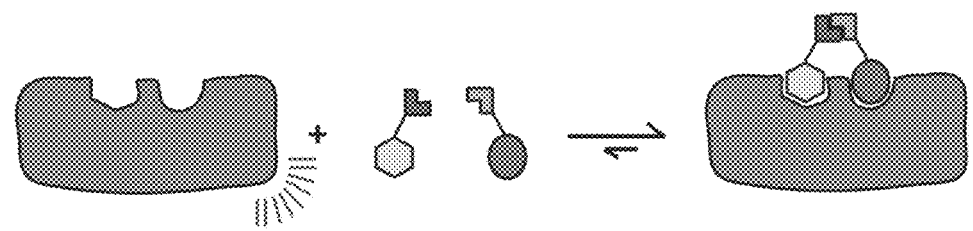
Figure 2.18

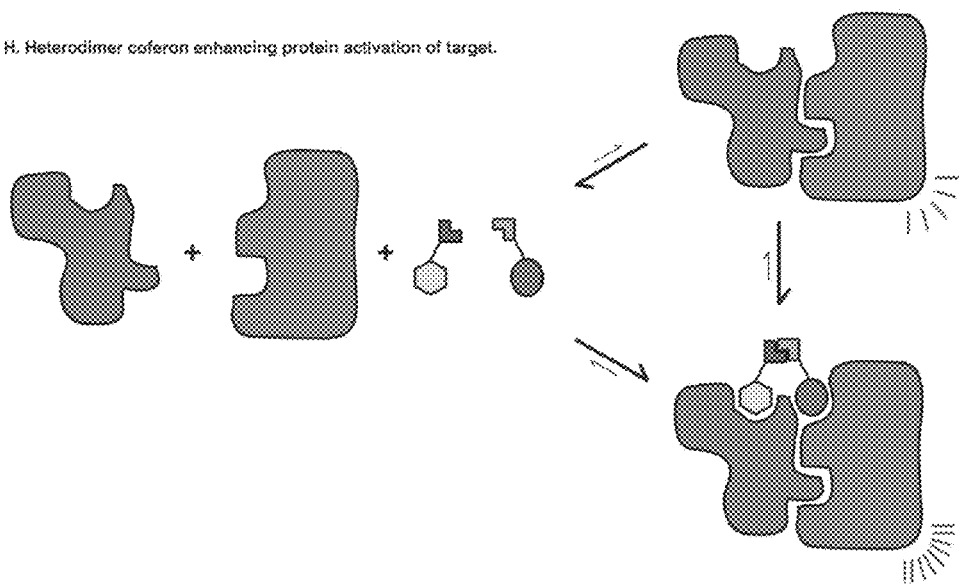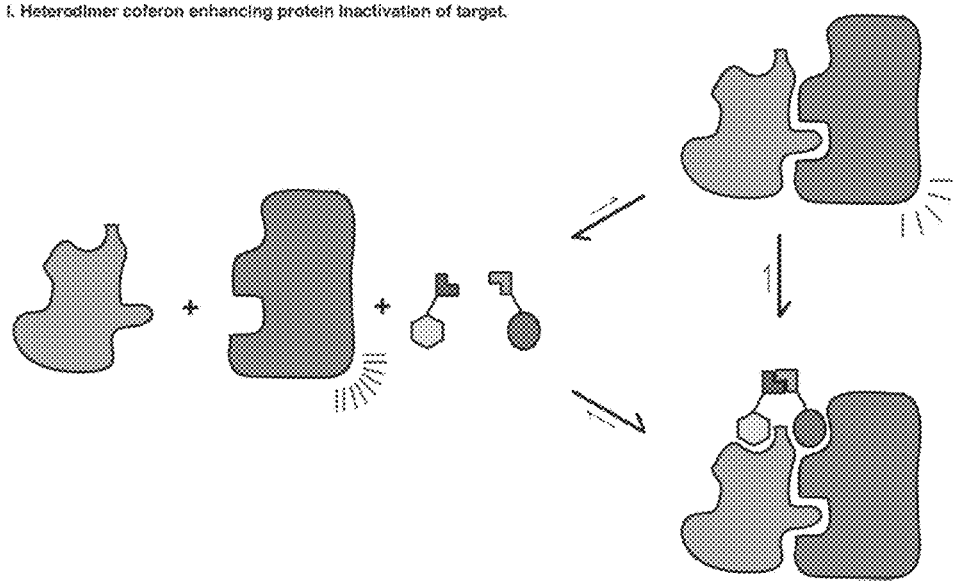
Figure 2.19

Coferon drug interactions with target, Part 4:
J. Protein activating target.
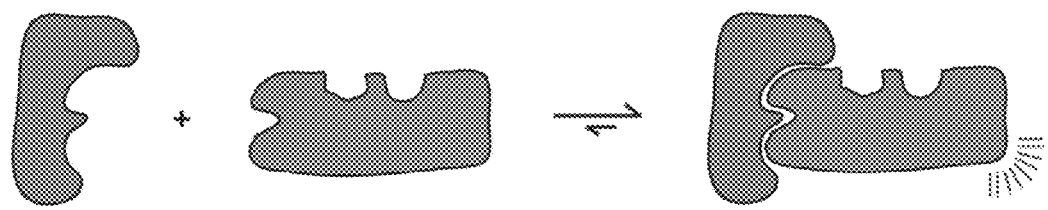
K. Heterodimer coferon enhancing protein activation of mutant target.
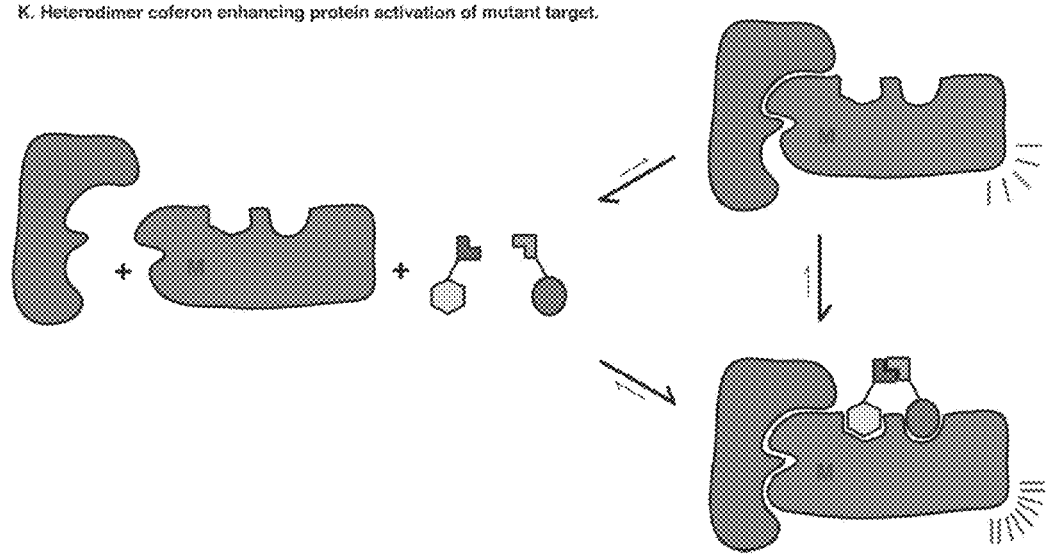
Figure 2.20

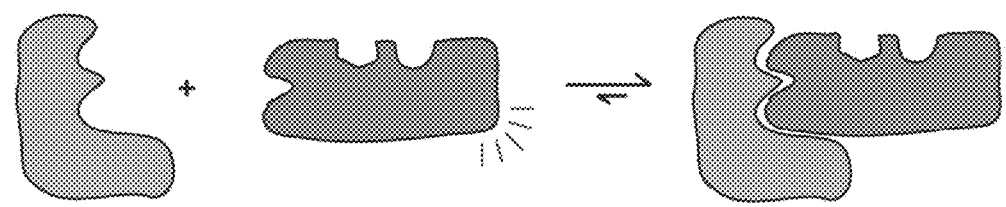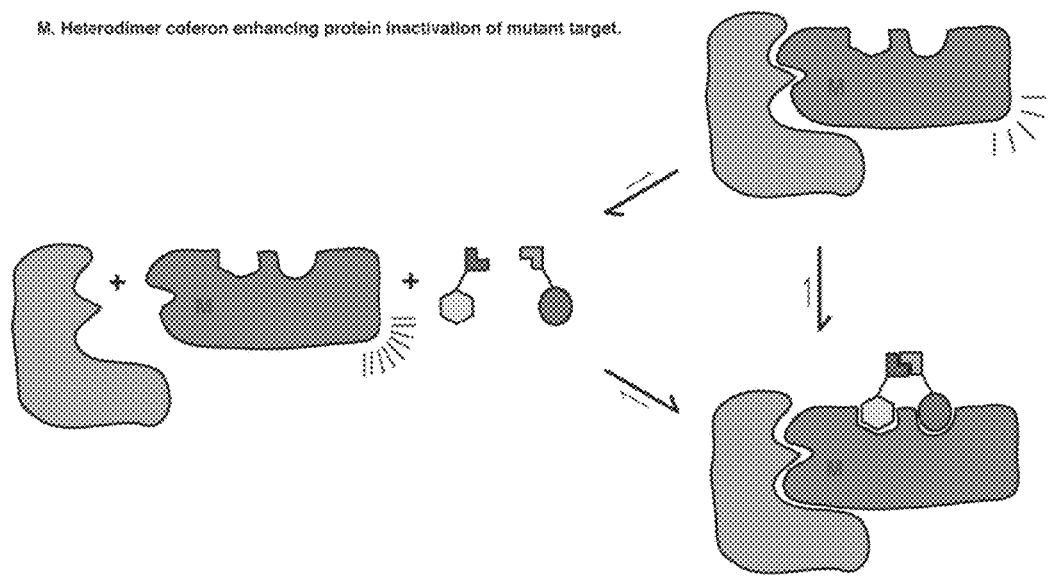
Figure 2.21

Coferon drug interactions with target, Part 6:
N. Protein binding weakly to target.
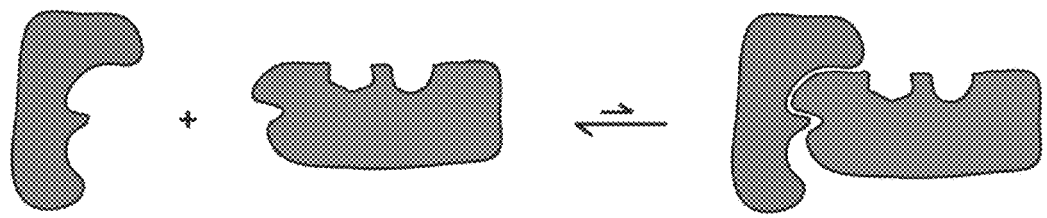
O. Heterodimer coferon and additional protein(s) enhancing protein binding to target.
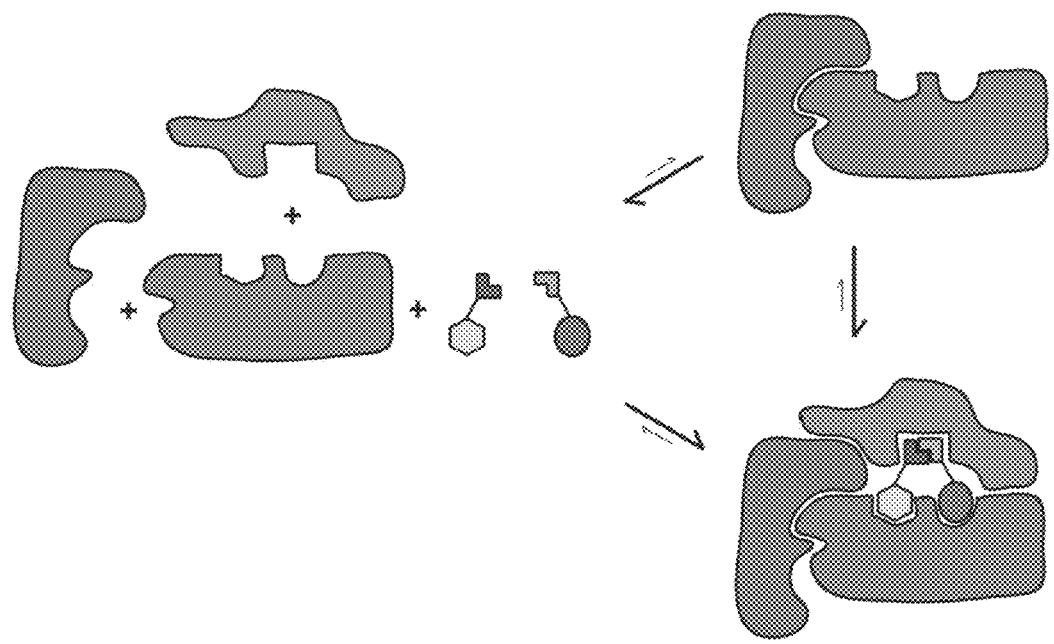
Figure 2.22

Coferon drug interactions with target, Part 7:
P. Protein binding strongly to target.
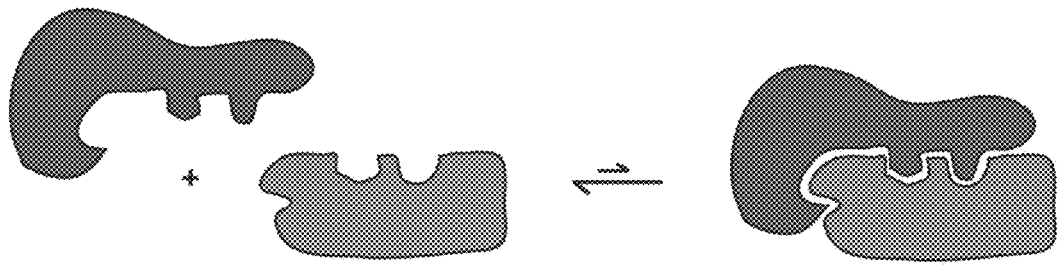
Q. Heterodimer coferon and additional protein(s) inhibiting protein binding to target.
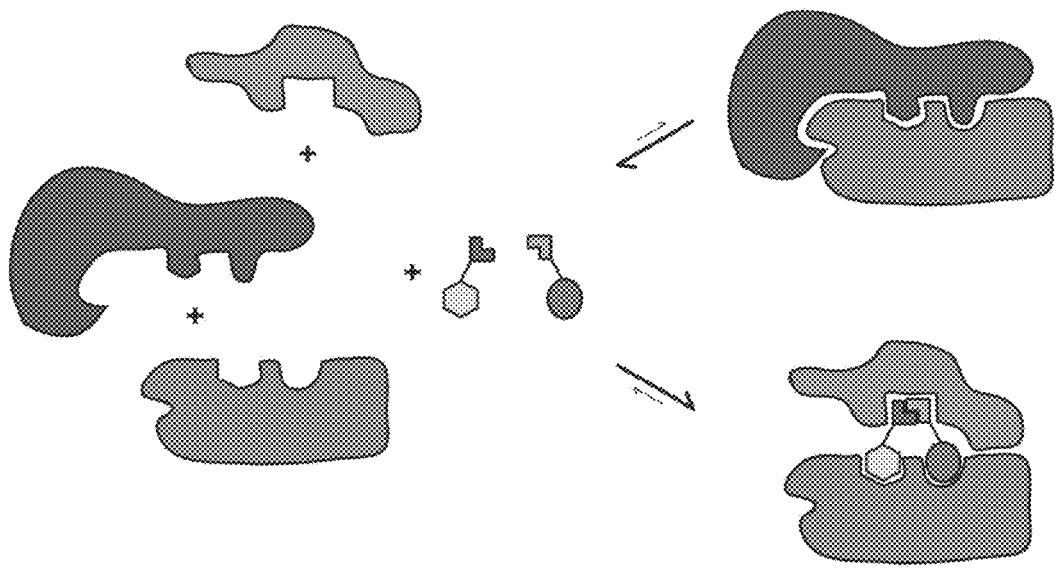
Figure 2.23

Coferon drug interactions with target, Part 8:
R. Heterodimer coferon and additional protein(s) recruiting protein to target.
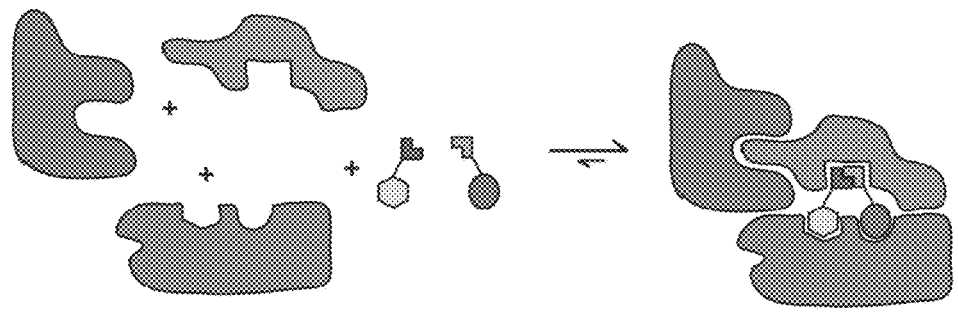
S. Heterodimer coferon and additional protein(s) recruiting protein to target.
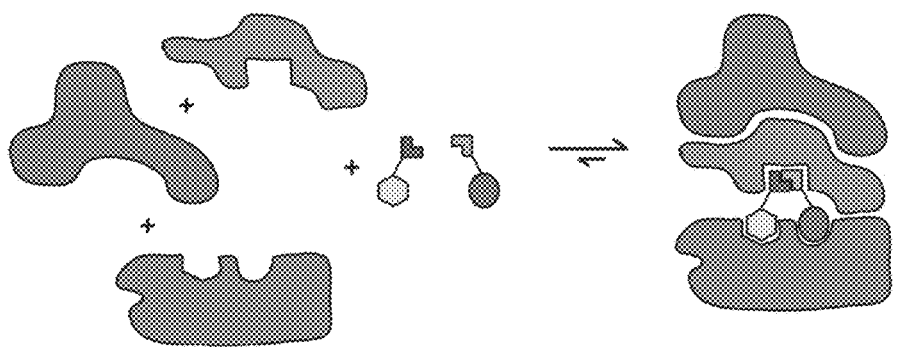
T. Heterodimer coferon and additional protein(s) recruiting protein to target.
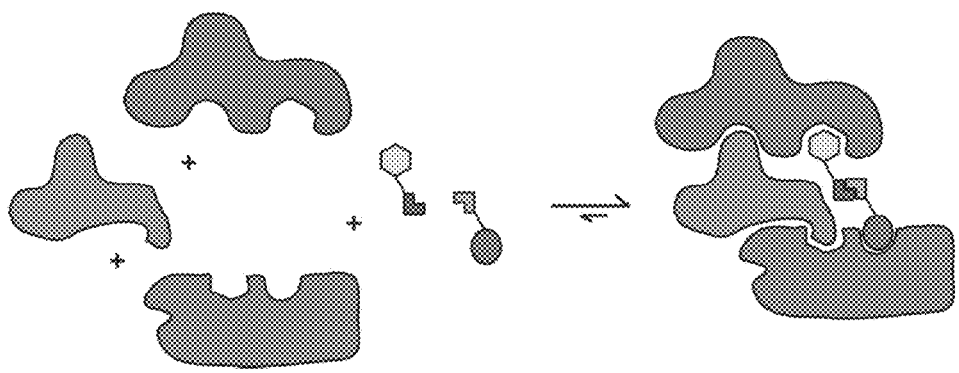
Figure 2.24

Coferon drug interactions with target, Part 9:
A2. Ligand binding to, and activating target receptor.
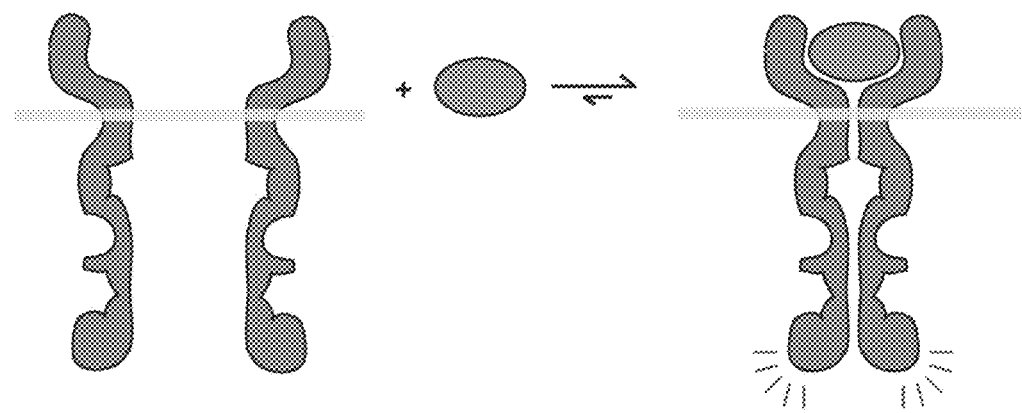
B2. Homodimer coferon activating target receptor.
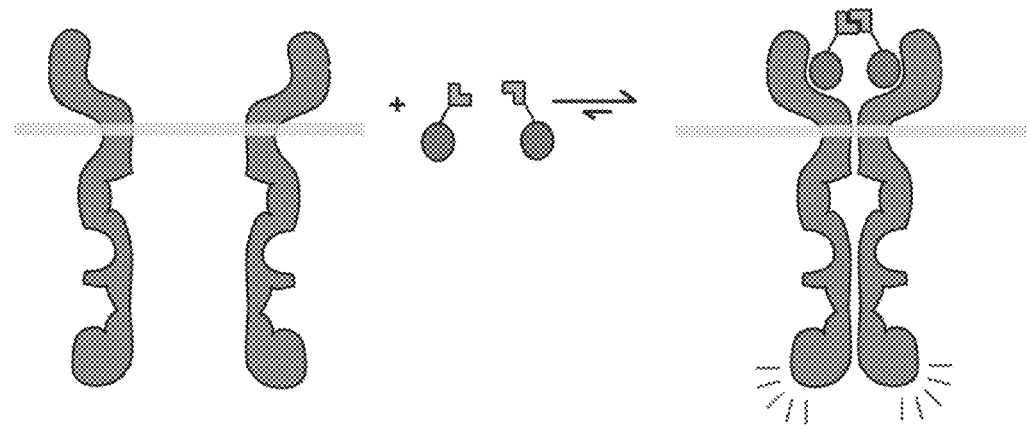
Figure 2.25

Coferon drug interactions with target, Part 10:
C2. Homodimer coferon interfering with activation of target receptor.
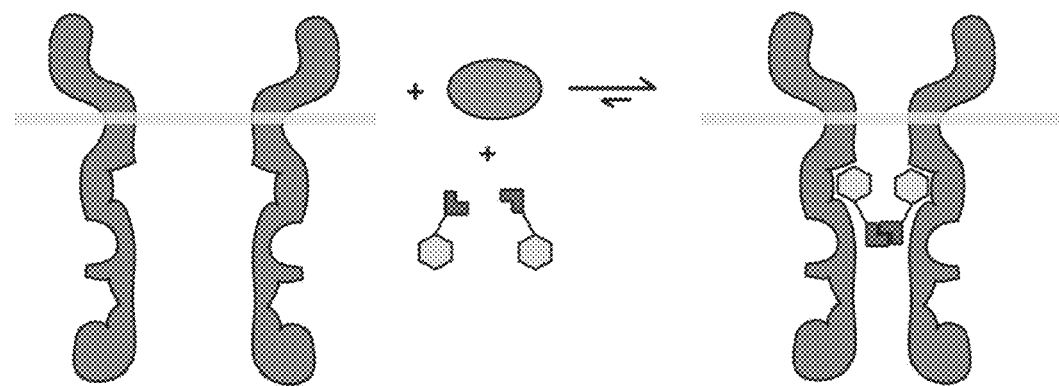
D2. Heterodimer coferon inactivating target receptor.
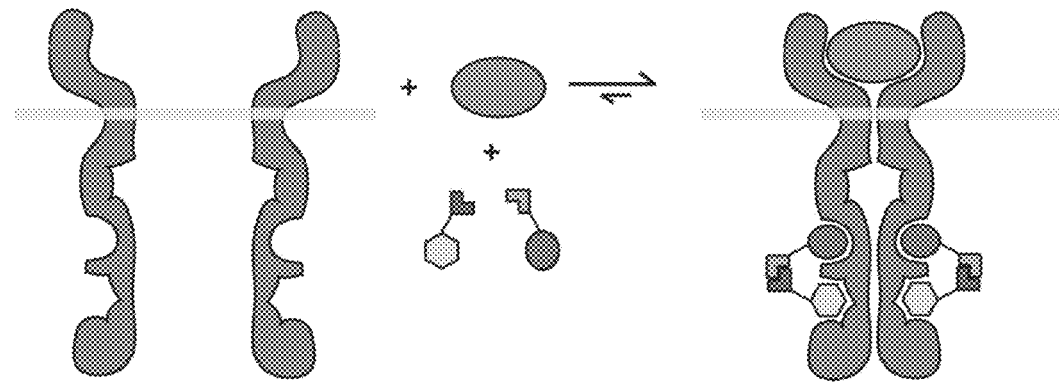
Figure 2.26

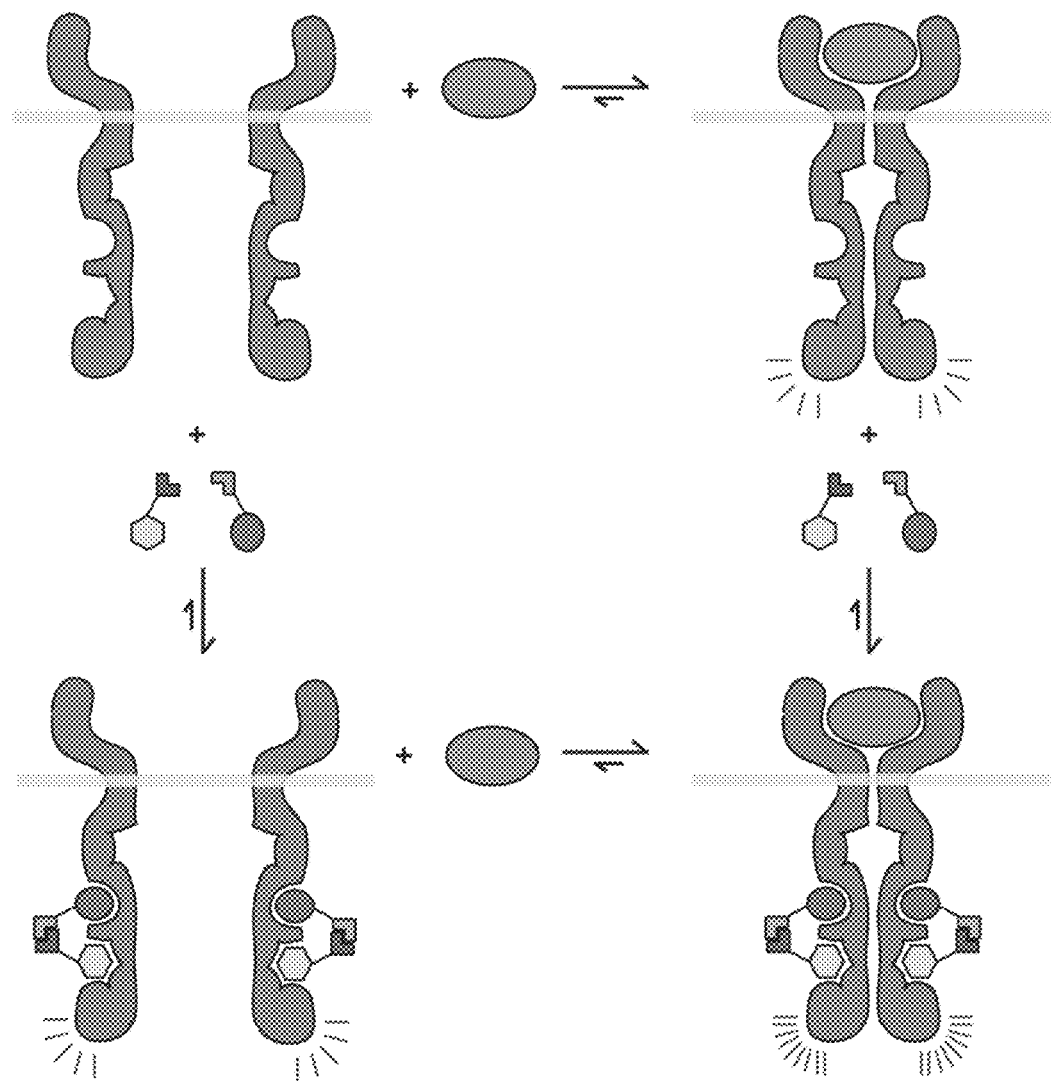
Figure 2.27

Coferon drug interactions with target, Part 12:
F2. Ligand binding to target receptor, recruiting and activating second protein.
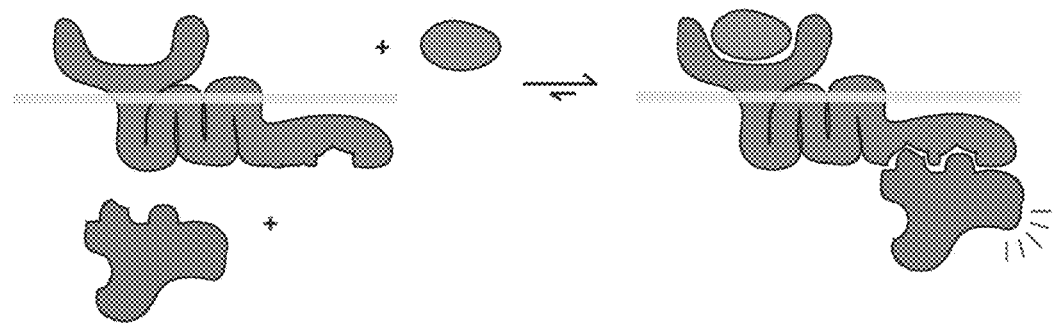
G2. Homodimer coferon binding to target receptor, recruiting and activating second protein.
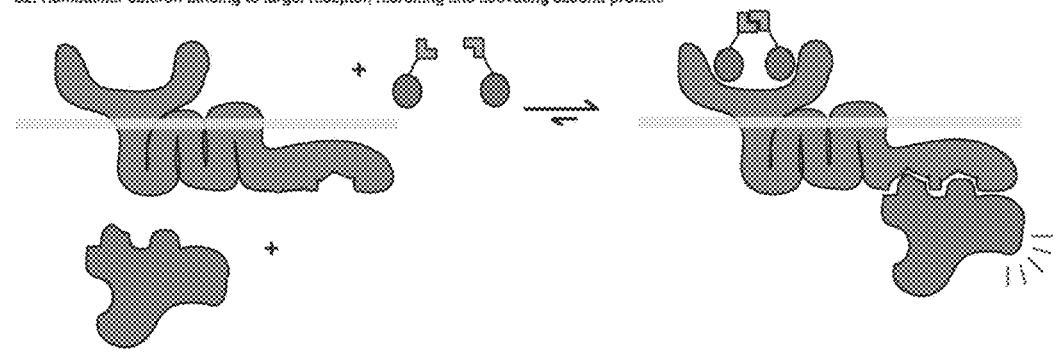
H2. Homodimer coferon binding to target receptor, inhibiting recruitment of second protein.
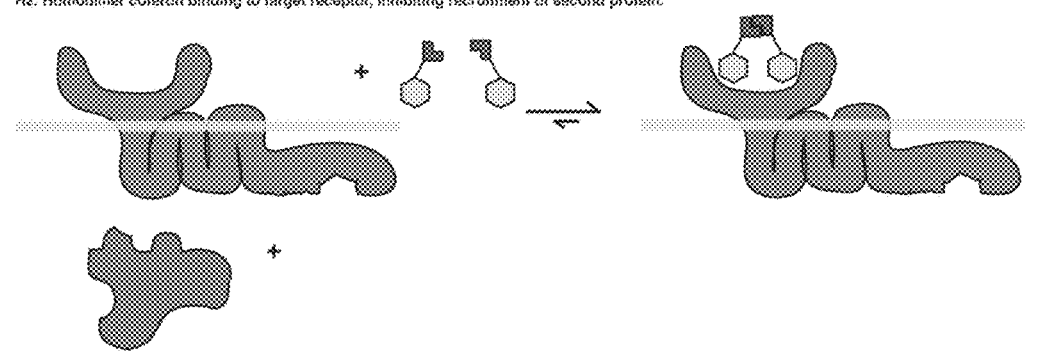
Figure 2.28

Coferon drug interactions with target, Part 13:

I2. Homodimer coferon binding to target receptor, inhibiting recruitment of second protein.

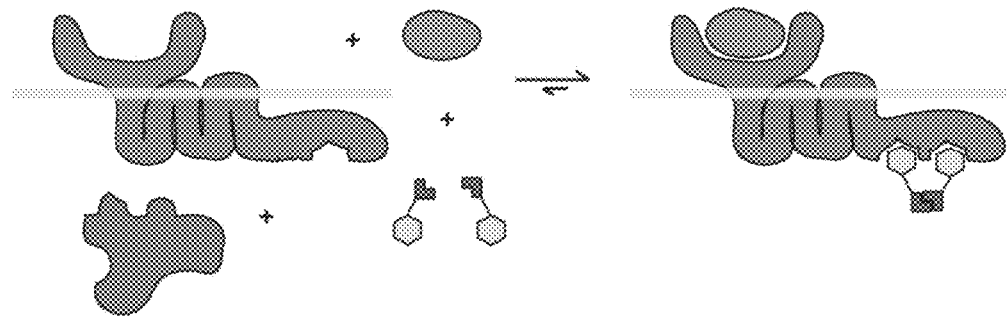

J2. Heterodimer coferon binding to target receptor, enhancing recruitment and activation of second protein.

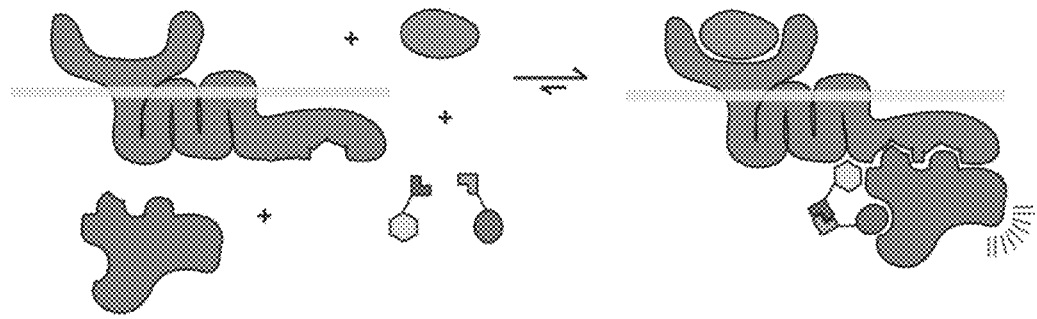

K2. Heterodimer coferon binding to ligand and target receptor, enhancing recruitment and activation of second protein.

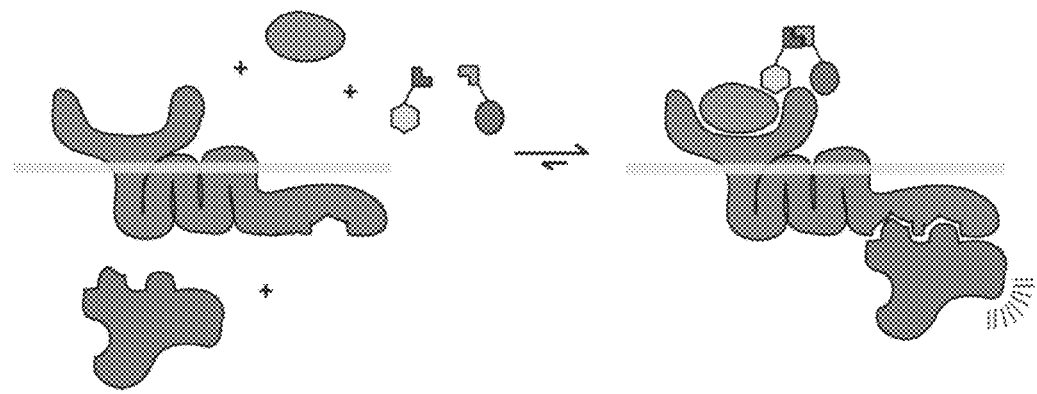

Figure 2.29

Coferon drug interactions with target, Part 14:
A3. Homodimer coferon binding to dimer target.
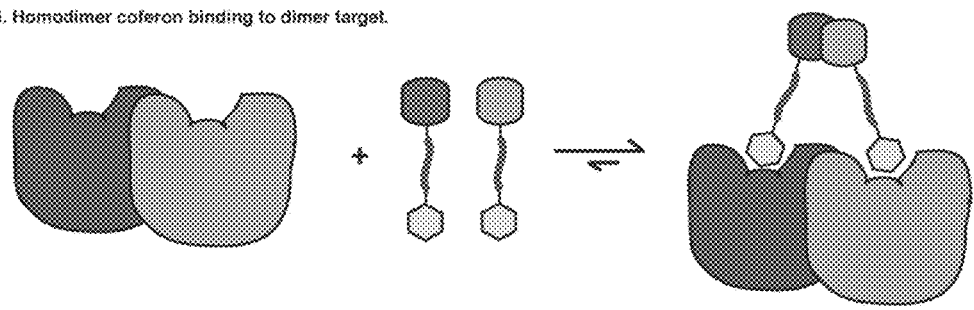
B3. Homotetramer coferon binding to dimer target.
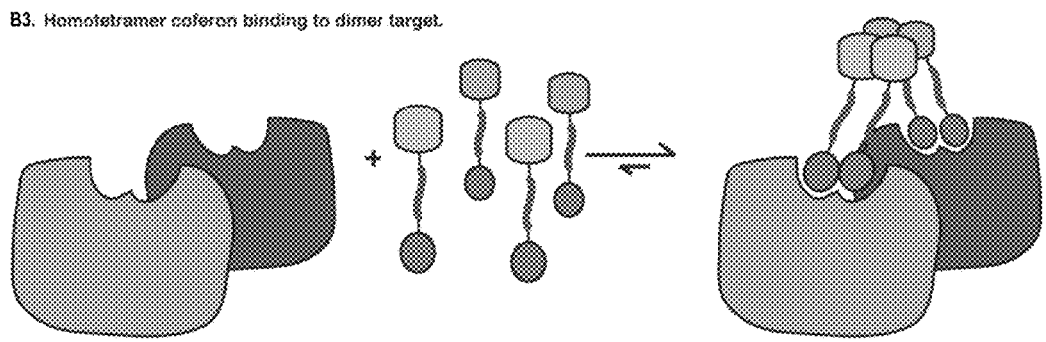
C3. Tetramer coferon binding to dimer target.
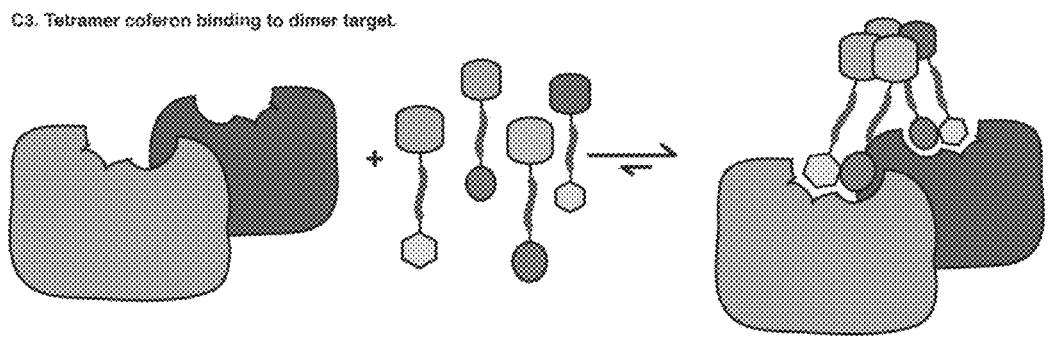
Figure 2.30

Coferon drug interactions with target, Part 15:
D3. Tetramer coferon binding to multimer target.
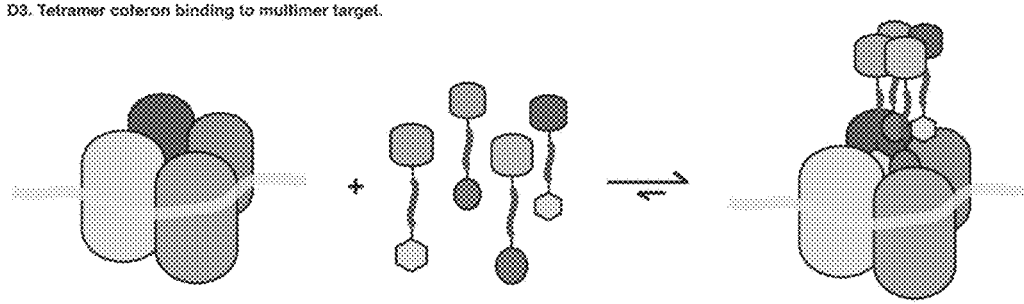
E3. Mixed tetramer coferon binding to multimer target.
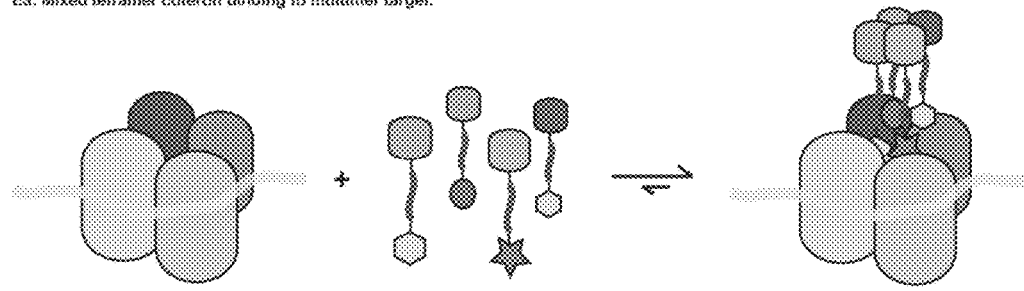
F3. Hexamer coferon binding to multimer target.
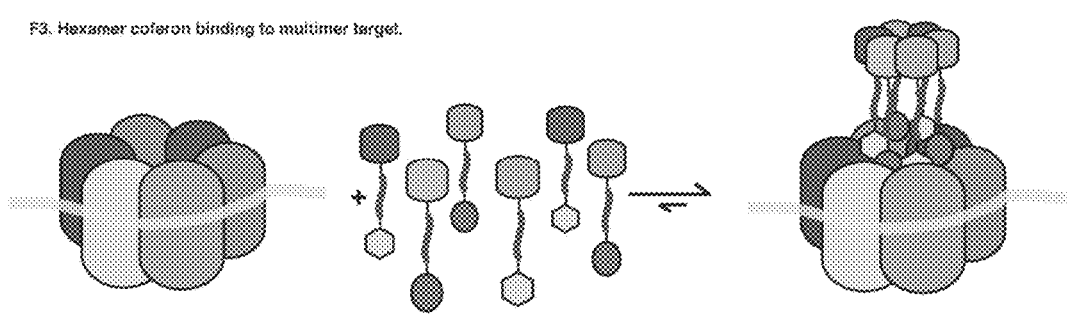
Figure 2.31

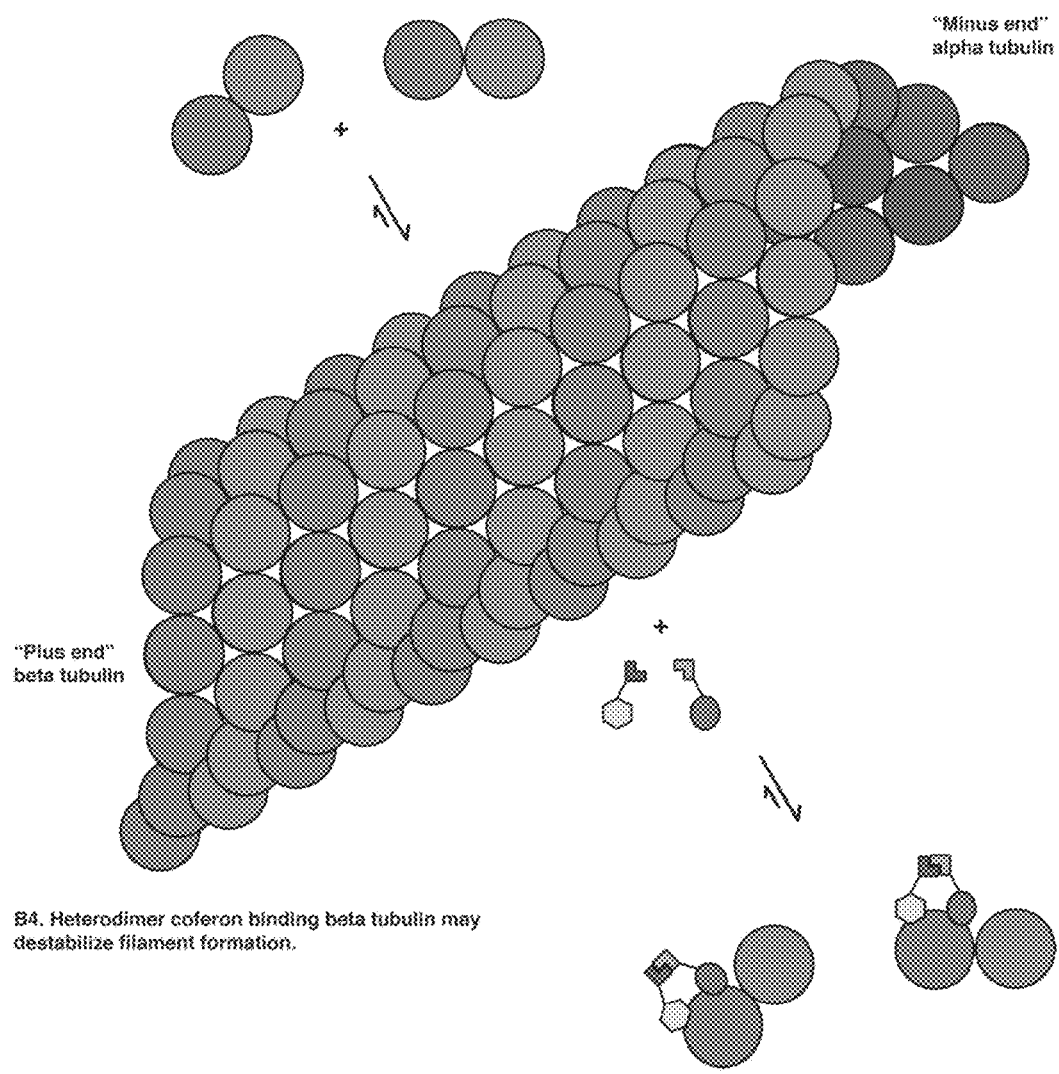
Figure 2.32

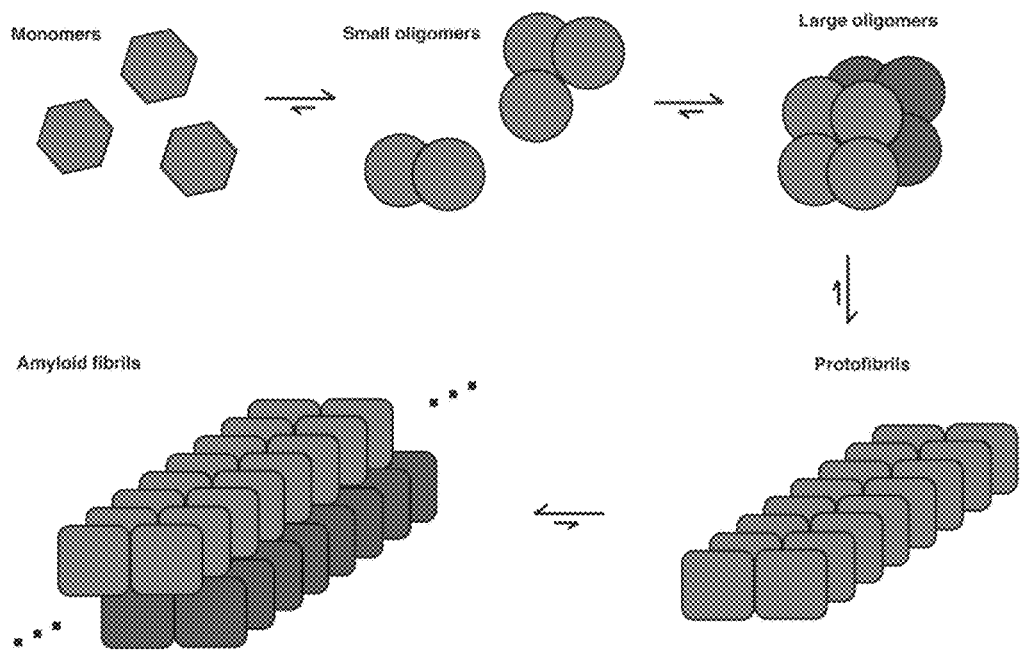
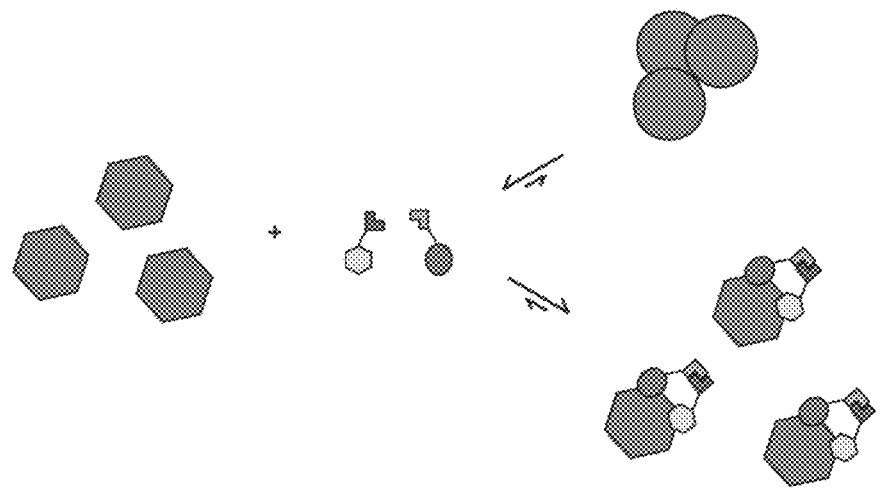
Figure 2.33

Coferon drug interactions with RNA target, Part 1:
A. Antisense oligonucleotide binding to RNA target.
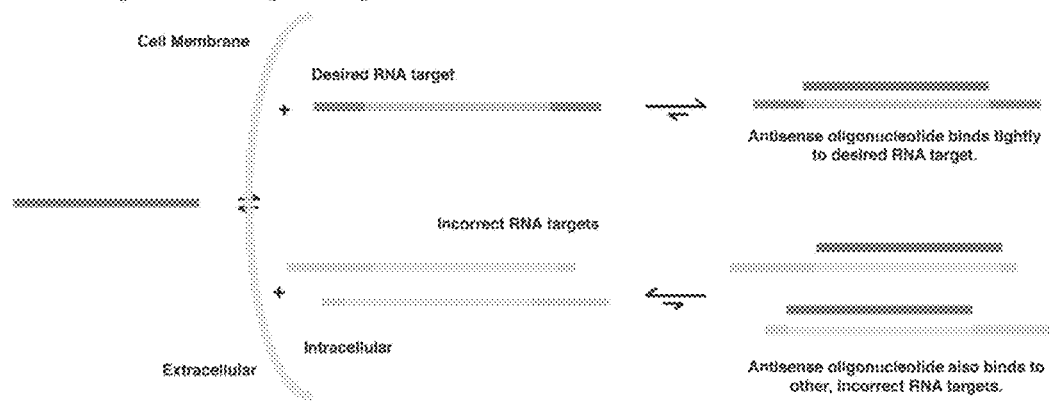
B. RNA coferon dimer binding to RNA target.
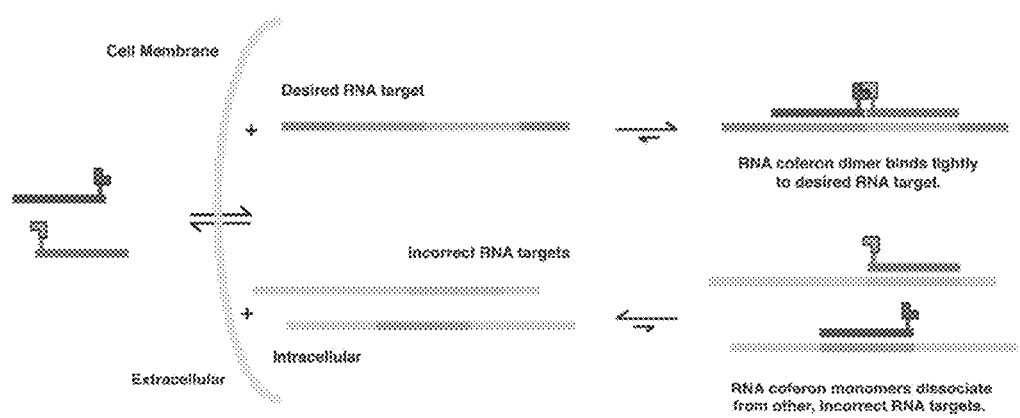
Figure 2.34

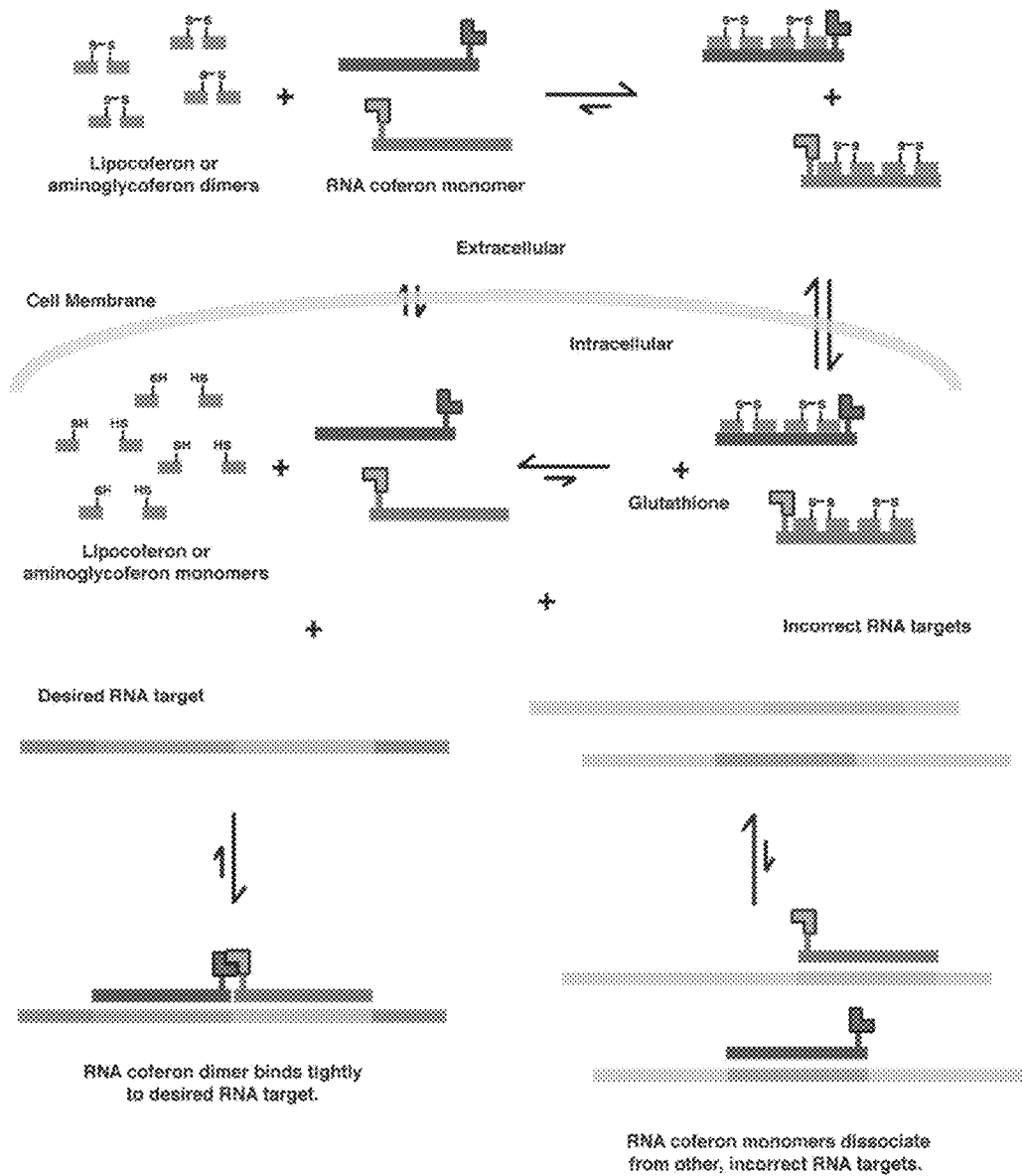
Figure 2.35

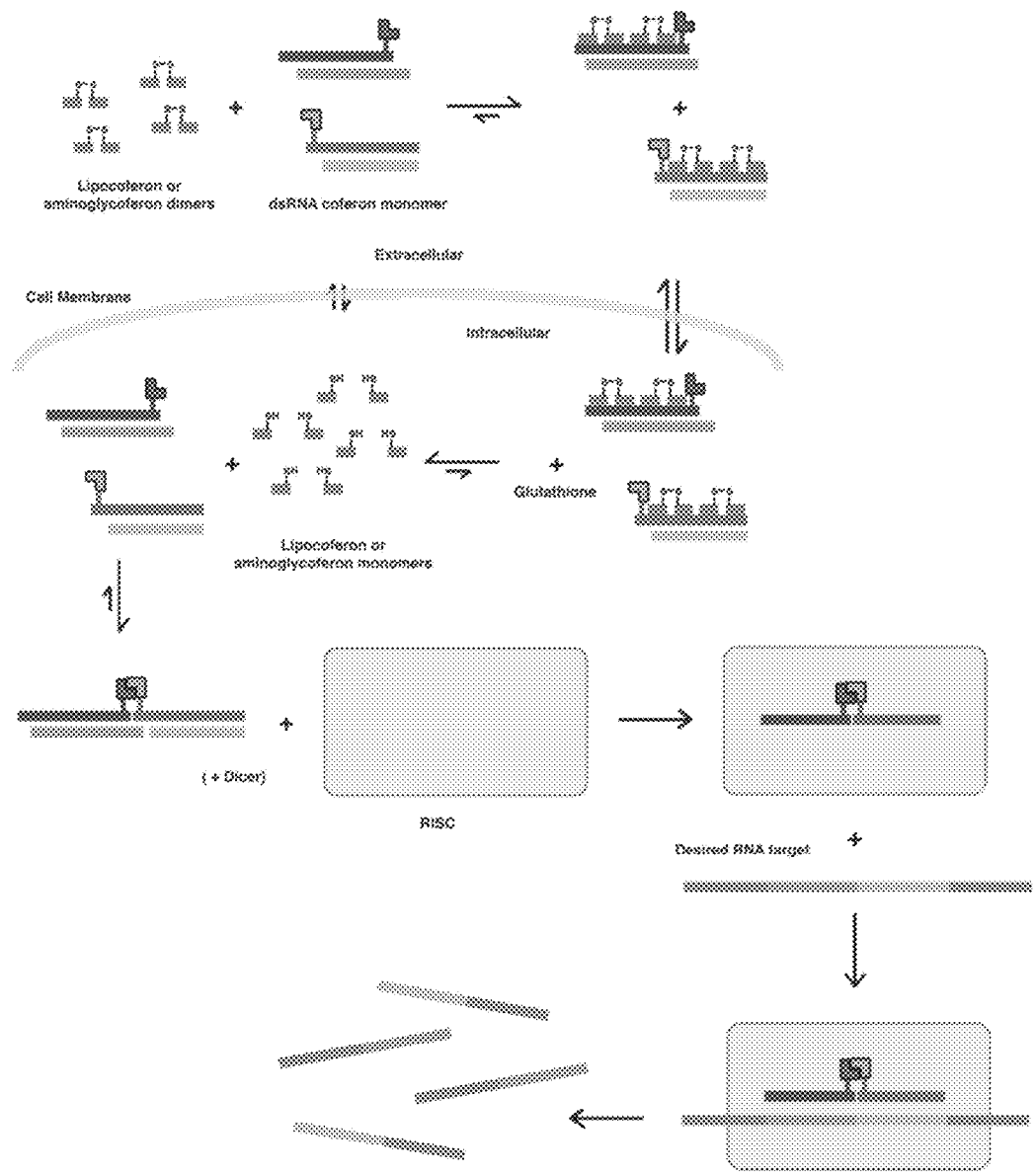
Figure 2.36

2-hydroxycyclohexanone Monomers 2-hydroxycyclohexanone dimer

Hydroxycyclopentane aldehyde linker element dimer

Space filling Linker Element Monomers

Triazole linked linker elements dimerized through intercalation. Translucent surface represents solvent accessible area.

Linker element Dimer with Molecular Surface: Side View

Linker Dimer with Molecular Surface: Top View

Linker Element Screening, Versions 1 & 2

A  Version 1

1. A library of low MW (approx. under 300) linker elements is synthesized on beads which may be individually identified through barcodes. A second library of linker elements is synthesized containing a fluorescent label. Under incubation conditions, different combinations of linker elements can undergo "dynamic combinatorial chemistry", i.e. they are associating and disassociating with each other. Some combinations will bind tighter than others, directing the evolution of combinations to the tightest pairs. For symmetrical libraries, a pair of beads will light up for each monomer. Monomers are resynthesized and tested individually to find the matched pairs.

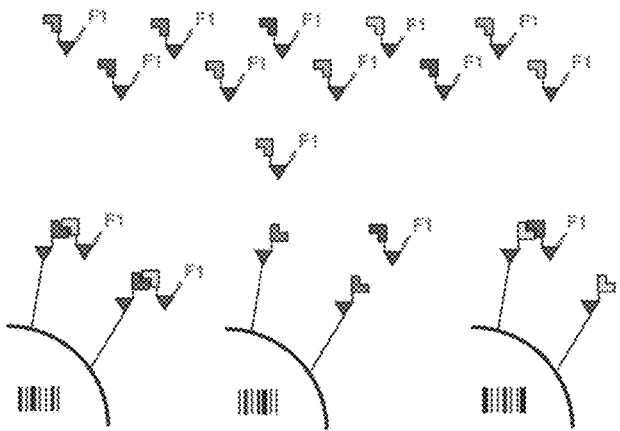

B  Version 2

1. A library of low MW (approx. under 300) linker elements is synthesized on beads which may be individually identified through barcodes. A second library of linker elements is synthesized, each monomer covalently linked to a DNA barcode (allowing for stepwise synthesis and identification of the binding ligand). Under incubation conditions, different combinations of linker elements can undergo "dynamic combinatorial chemistry", i.e. they are associating and disassociating with each other. Some combinations will bind tighter than others, directing the evolution of combinations to the tightest pairs.

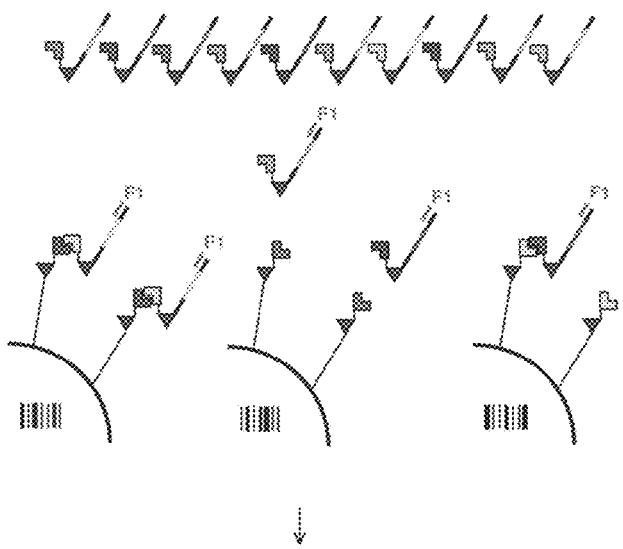

2. DNA barcodes (colored lines) may be amplified using universal primers (black lines) to identify individual linker elements.

Figure 14

Linker Element Screening, Versions 3 & 4

A  Version 3

1. A library of low MW (approx. under 300) linker elements is synthesized on beads which may be individually identified through barcodes. A second library of linker elements is synthesized containing a fluorescent label. The bead library linkers contain tethered disulfide groups, while the solution library linkers contain tethered sulfhydryl groups. Under incubation conditions, solution linker elements can undergo disulfide exchange with bead linker elements. Some combinations will bind tighter than others, directing the evolution of combinations to the tightest pairs. For symmetrical libraries, a pair of beads will light up for each monomer. Monomers are resynthesized and tested individually to find the matched pairs.

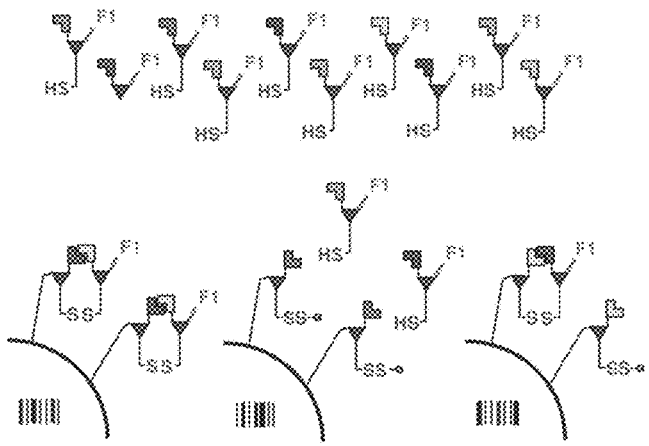

B  Version 4

1. A library of low MW (approx. under 300) linker elements is synthesized on beads which may be individually identified through barcodes. A second library of linker elements is synthesized, each monomer covalently linked to a DNA barcode (allowing for stepwise synthesis and identification of the binding ligand). Under incubation conditions, solution linker elements can undergo disulfide exchange with bead linker elements. Some combinations will bind tighter than others, directing the evolution of combinations to the tightest pairs.

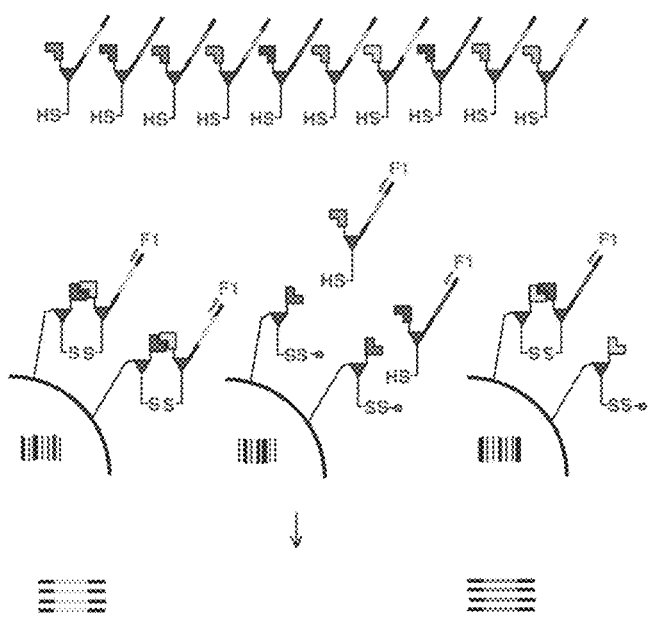

2. DNA barcodes (colored lines) may be amplified using universal primers (black lines) to identify individual linker elements.

Figure 15

Coferon Ligand (Diversity Element) Library Synthesis:
Bead-encoded libraries.
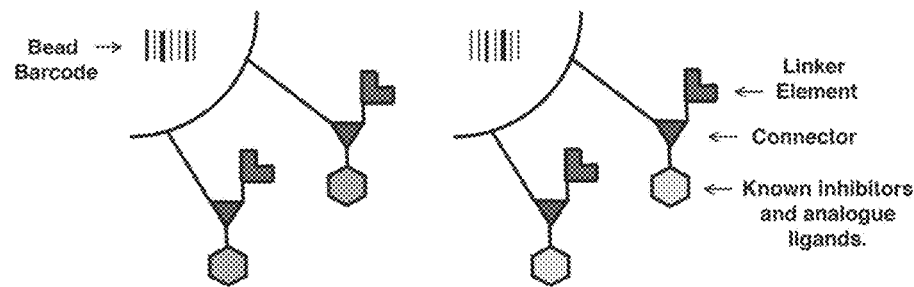
A. Small molecule inhibitors and analogues
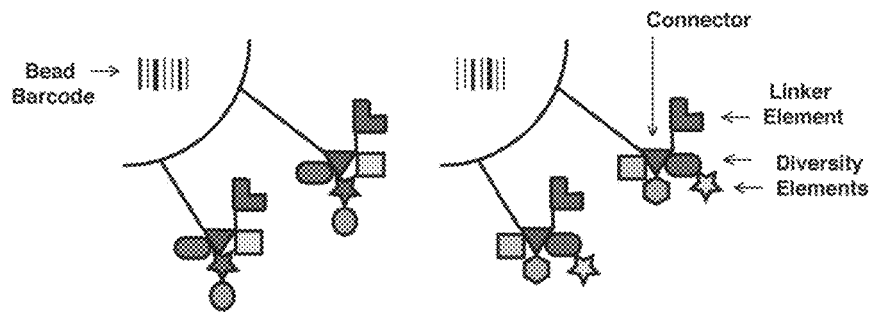
B. Combinatorial chemistry on common platform, version 1.
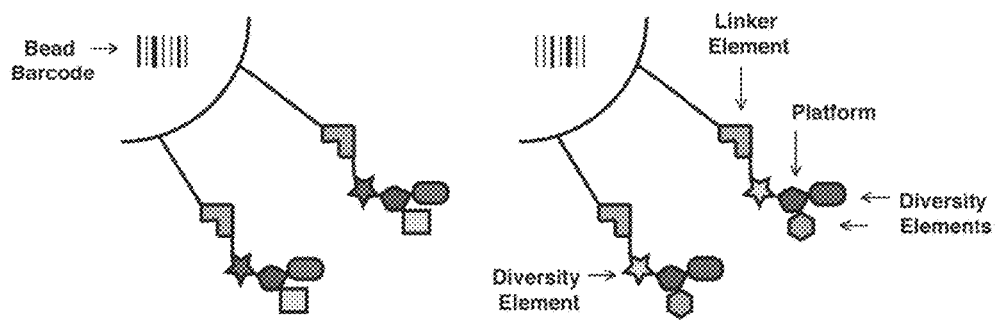
C. Combinatorial chemistry on common platform, version 2.
Figure 17

Directed evolution of Coferons: DNA encoding of diversity elements.

1. Each coferon monomer consists of a binding ligand (diversity element) covalently linked to a DNA barcode as well as a low MW linker element (dynamic combinatorial chemistry element), which allow different combinations of ligands to reversably associate with each other. When coferons are brought in contact with the protein target on a solid support, some combinations will bind tighter than others, and consequently are enriched. Unbound coferons may be washed away. The most tightly bound pair(s) may be both identified and amplified through the DNA barcodes. Repeating this process of synthesis-selection-amplification mimics Darwinian evolution.

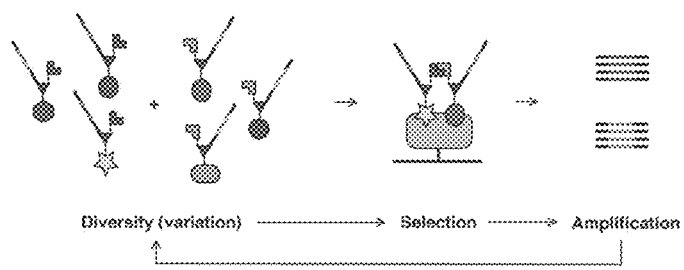

Diversity (variation) ⟶ Selection ⟶ Amplification

2. In a variation of the above approach, one coferon monomer consists of a binding ligand (diversity element) covalently linked to a DNA barcode as well as a low MW linker element (dynamic combinatorial chemistry element), while the other is linked to a coded bead. The linker elements allow different combinations of ligands to reversably associate with each other. When the combination of solid-phase and solution coferons are brought in contact with a labeled protein target, some combinations will bind tighter than others, and consequently are enriched. The winning pair will cause that bead to be highly labeled, and this may be isolated by flow cytometry or other methods, and the code identified. The partner solution phase coferon may be both identified and amplified through the DNA barcodes. Repeating this process of synthesis-selection-amplification mimics Darwinian evolution.

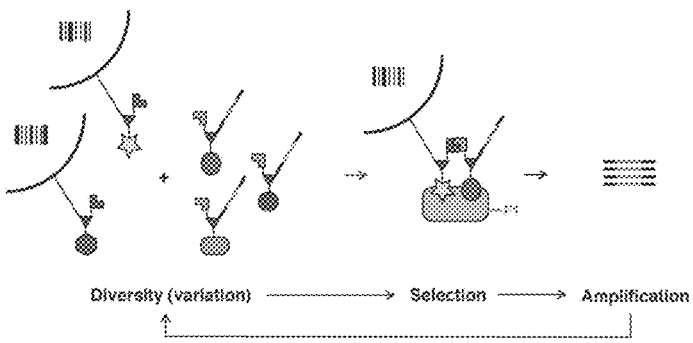

Diversity (variation) ⟶ Selection ⟶ Amplification

3. The best coferon monomers are resynthesized without DNA barcodes for use as orally active drugs. Once ingested coferons are in a dynamic equilibrium between the monomer form (which can traverse the cell membrane), and the dimer form (which binds to and inhibits the protein target).

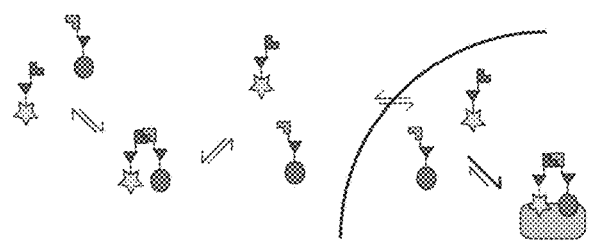

Figure 18A

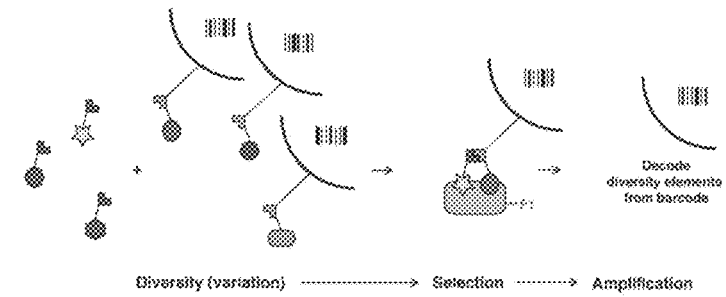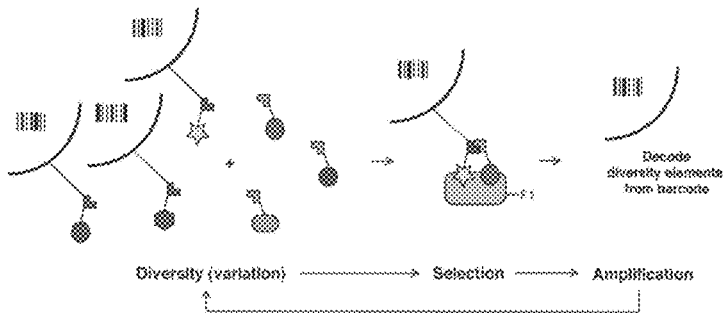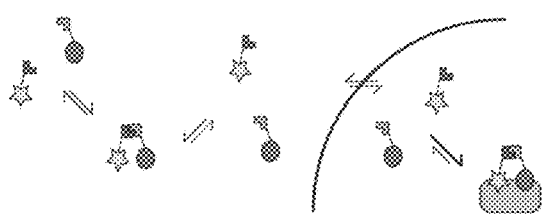
Figure 18B

Coferon Target Screening, Version 1

1. A library of ligands is synthesized on beads which may be individually identified through barcodes. Each monomer element consists of a low MW (approx. 600-800) binding ligand (diversity element) covalently linked to a low MW (approx. under 300) linker element (dynamic combinatorial chemistry element). The beads are incubated with fluorescently labeled target protein to identify ligands that bind most tightly to the target.

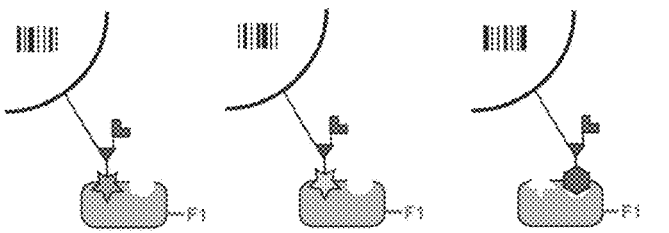

2. The top set of these ligands are resynthesized with the option of adding additional diversity in the connector between the linker element and the ligand diversity element. A second library of ligands is synthesized, where each monomer element consists of a low MW binding ligand (diversity element) covalently linked to a DNA barcode (allowing for stepwise synthesis and identification of the binding ligand) as well as a low MW linker element, suitable for reversible binding to the linker element element in the first library. Under physiological conditions, different combinations of ligands are forming and reassociating with each other. The surface bound and solution diversity element libraries are panned with fluorescently labeled target protein. The protein targets will bind some combinations tighter than others, thus directing the evolution of combinations to the preferred pairs.

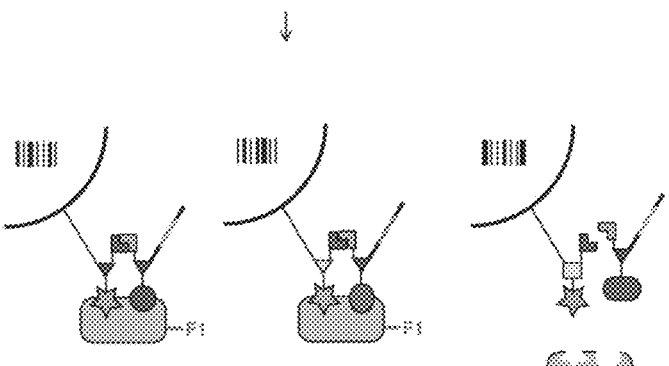

3. DNA barcodes (colored lines) may be amplified using universal primers (black lines) to identify individual ligands, which serve as lead molecules.

Figure 20

Coferon Target Screening, Version 2

1. Two library of ligands are synthesized, one on beads which may be individually identified through barcodes, the second covalently linked to a DNA barcode (allowing for stepwise synthesis and identification of the binding ligand). Each monomer element consists of a low MW (approx. 600-800) binding ligand (diversity element) covalently linked to a low MW (approx. under 300) linker element (dynamic combinatorial chemistry element). Under physiological conditions, different combinations of ligands are forming and reassociating with each other through the linker elements. The two libraries are panned with fluorescently labeled target protein. The protein targets will bind some combinations tighter than others, thus directing the evolution of combinations to the preferred pairs.

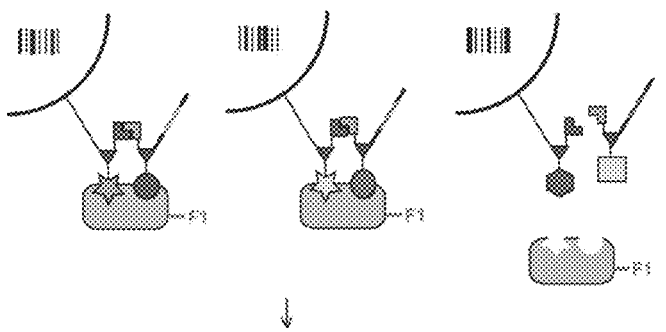

2. DNA barcodes (colored lines) may be amplified using universal primers (black lines) to identify individual ligands.

3. The top set of these ligands are resynthesized in both bead and solution format, with the option of adding additional diversity in the connector between the linker element and the ligand diversity element. The surface bound and solution diversity element libraries are panned with fluorescently labeled target protein. The protein targets will bind some combinations tighter than others, thus directing the evolution of combinations to the preferred pairs.

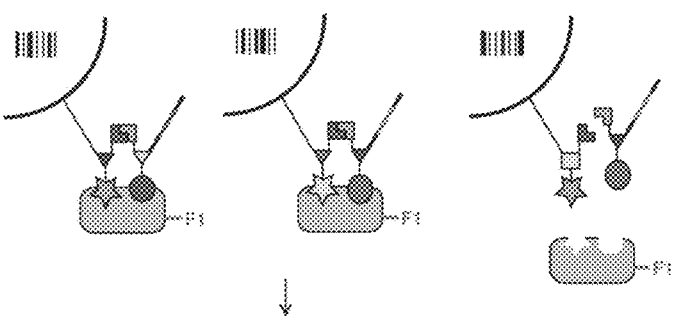

4. DNA barcodes (colored lines) may be amplified using universal primers (black lines) to identify individual ligands, which serve as lead molecules.

Figure 21

Coferon Target Screening, Version 3

1. A library of ligands is synthesized, where each monomer element consists of a low MW (approx. 600-800) binding ligand (diversity element) covalently linked to DNA barcode (allowing for stepwise synthesis and identification of the binding ligand) as well as a low MW (approx. under 300) linker element (dynamic combinatorial chemistry element). The ligands are allowed to bind to target protein covalently linked to a solid support.

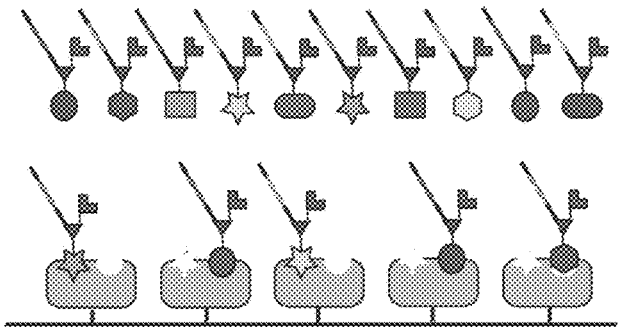

2. DNA barcodes (colored lines) may be amplified using universal primers (black lines) to identify individual ligands.

3. The top set of these ligands are resynthesized with the option of adding additional diversity in the connector between the "summa linker" and the ligand diversity element. A second library of ligands is synthesized, where each monomer element consists of a low MW binding ligand (diversity element) covalently linked to a DNA barcode as well as a low MW linker element, suitable for reversible binding to the linker element element in the first library. Under physiological conditions, different combinations of ligands are forming and reassociating with each other. The two diversity element libraries are panned with target protein on beads. The protein targets will bind some combinations tighter than others, thus directing the evolution of combinations to the preferred pairs. (This enrichment-amplification-resynthesis selection process may be repeated to identify higher affinity ligand pairs.)

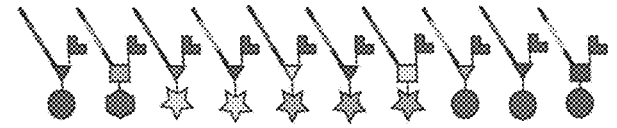

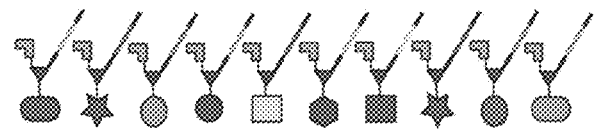

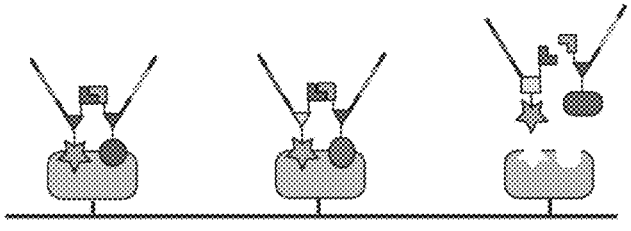

4. DNA barcodes (colored lines) may be amplified using universal primers (black lines) to identify individual ligands, which serve as lead molecules.

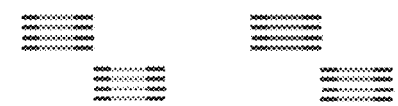

Figure 22

Coferon Target Screening, Version 4

1. A library of known ligands to a protein target such as a tyrosine kinase is synthesized. These ligands are covalently linked through a diverse number of connectors to DNA barcode (allowing for identification of the binding ligand) as well as a low MW (approx. under 300) linker element (dynamic combinatorial chemistry element). The ligands are all capable of binding to target protein covalently linked to a solid support.

2. A second library of ligands is synthesized, where each monomer element consists of a low MW binding ligand (diversity element) covalently linked to a DNA barcode as well as a low MW linker element, suitable for reversible binding to the linker element element in the first library. Under physiological conditions, different combinations of ligands are forming and reassociating with each other. The two diversity element libraries are panned with target protein on beads. The protein targets will bind some combinations tighter than others, thus directing the evolution of combinations to the preferred pairs. (This enrichment-amplification-resynthesis selection process may be repeated to identify higher affinity ligand pairs.)

3. DNA barcodes (colored lines) may be amplified using universal primers (black lines) to identify individual ligands, which serve as lead molecules.

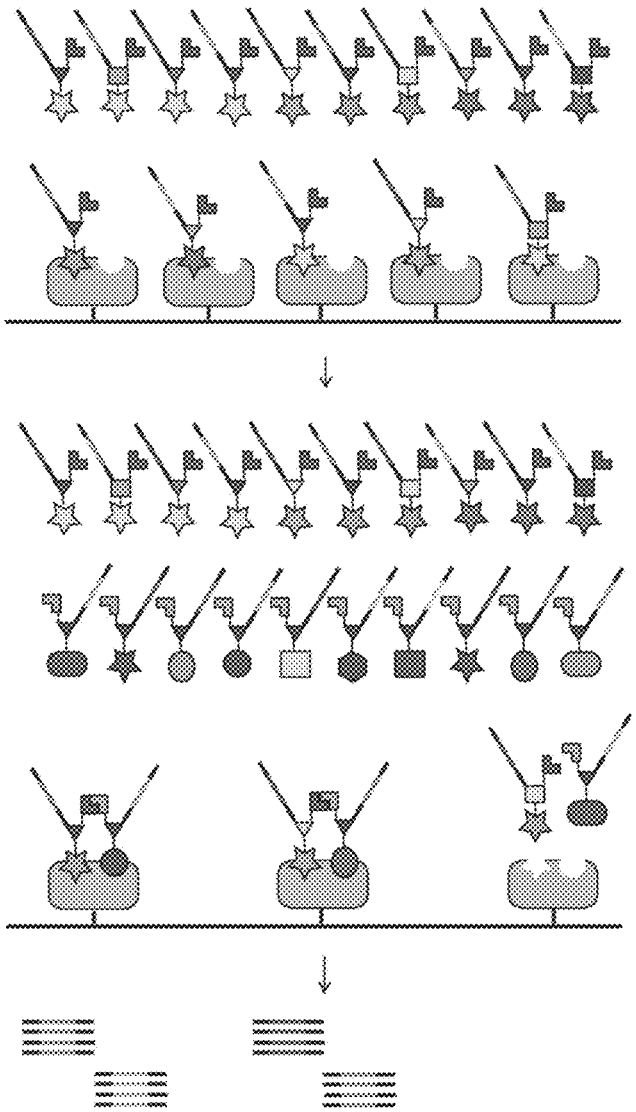

Figure 23

Coferon Target Screening, Version 5

1. Two libraries of ligands are synthesized, where each monomer element consists of a low MW (approx. 600-800) binding ligand (diversity element) covalently linked to DNA barcode (allowing for stepwise synthesis and identification of the binding ligand) as well as a low MW (approx. under 300) linker element (dynamic combinatorial chemistry element). The linker element element from the first library binds reversibly with the linker element from the second library, such that different combinations of ligands are forming and reassociating with each other. The two diversity element libraries are panned with target protein on beads. The protein targets will bind some combinations tighter than others, thus directing the evolution of combinations to the preferred pairs.

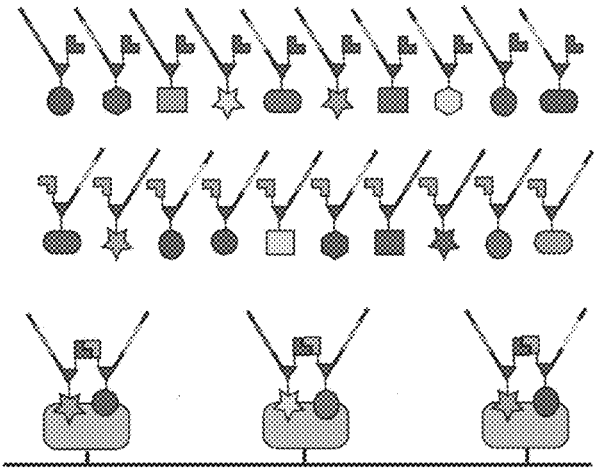

2. DNA barcodes (colored lines) may be amplified using universal primers (black lines) to identify individual ligands.

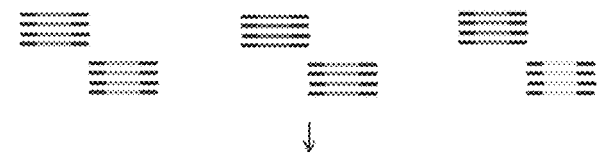

3. The top set of these ligands are resynthesized with the option of adding additional diversity in the connector between the linker element and the ligand diversity element. The extra diversity may be encoded in the DNA barcode in a region not used for generating ligand diversity in the first round of synthesis. The two refined diversity element libraries are again panned with target protein on beads. The protein targets will bind some combinations tighter than others, thus directing the evolution of combinations to the preferred pairs. This enrichment-amplification-resynthesis-selection process is analogous to Darwinian selection on diploid organisms, and may be repeated to identify higher affinity ligand pairs.

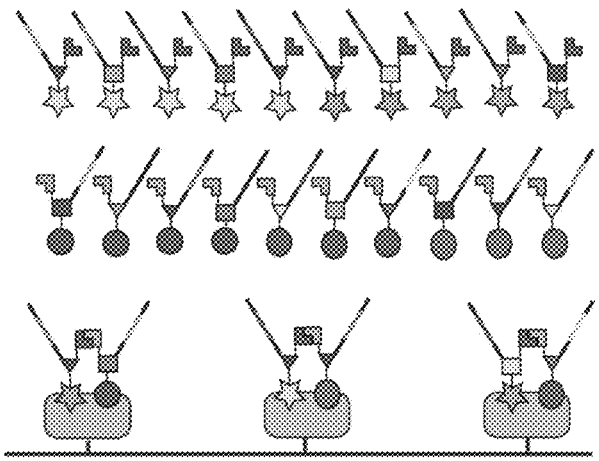

4. DNA barcodes (colored lines) may be amplified using universal primers (black lines) to identify individual ligands, which serve as lead molecules.

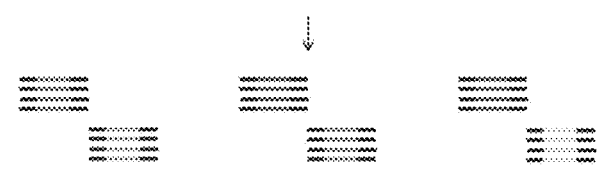

Figure 24

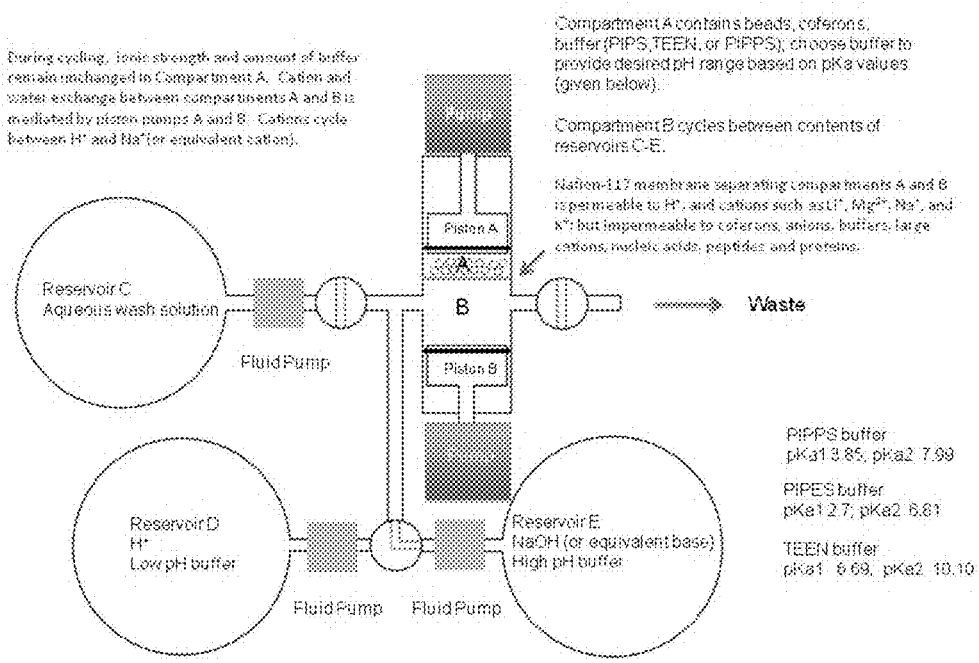
Figure 25: Schematic for a system to achieve selection by pH cycling combinatorial chemistry

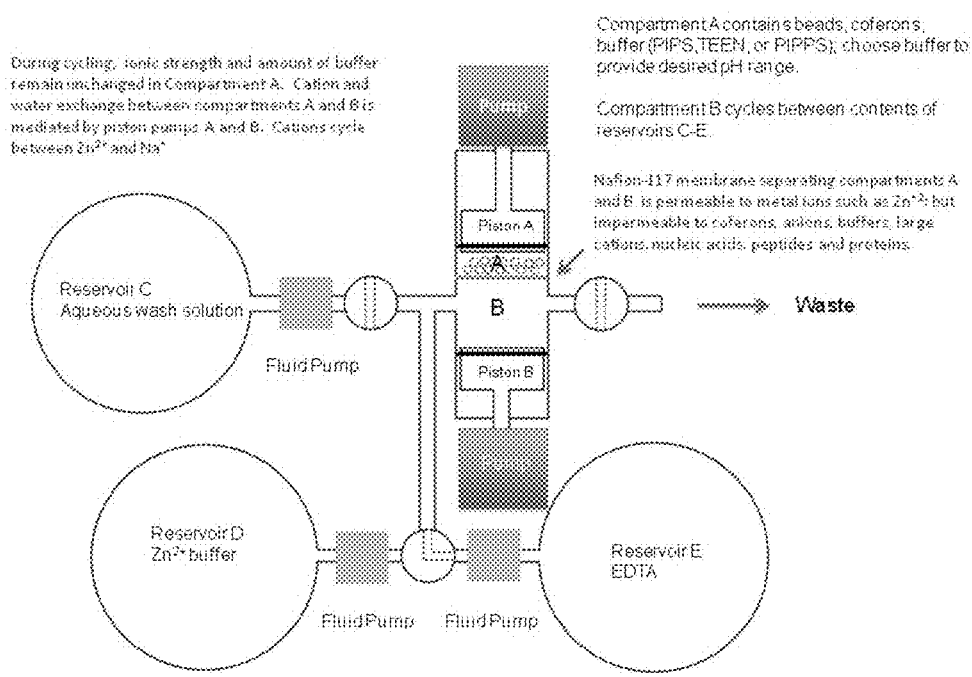
Figure 26: Schematic for a system to achieve selection by metal ion cycling combinatorial Chemistry (illustrated for $Zn^{2+}$ ion)

Figure 27

COFERONS AND METHODS OF MAKING AND USING THEM

This application is a continuation of U.S. application Ser. No. 12/937,053, filed May 25, 2011, which is the National Stage of International Application No. PCT/US2009/002223, filed Apr. 9, 2009, which claims the benefit of U.S. Provisional Patent Application Ser. No. 61/043,537, filed Apr. 9, 2008; all of which are hereby incorporated by reference in their entirety.

This invention was made with government support under Public Health Service grant AI062579-03 from the National Institute of Allergy and Infectious Diseases and Grant No. CA65930-08 from the National Cancer Institute. The government has certain rights in this invention.

FIELD OF THE INVENTION

The present invention is directed to coferons and methods of making and using them.

BACKGROUND OF THE INVENTION

Cancers arise due to mutations or dysregulation of genes involved in DNA replication and repair, cell cycle control, anchorage independent growth, angiogenesis, apoptosis, tissue invasion, and metastasis (Hanahan, D. et al., *Cell* 100(1): 57-70 (2000)). These processes are controlled by networks of genes in the p53, cell cycle, apoptosis, Wnt signaling, RPTK signaling, and TGF-beta signaling pathways. Such genes and their protein products are the targets of many current and developing therapies.

Signaling pathways are used by cells to generate biological responses to external or internal stimuli. A few thousand gene products control both ontogeny/development of higher organisms and sophisticated behavior by their many different cell types. These gene products work in different combinations to achieve their goals, and do so through protein-protein interactions. The evolutionary architecture of such proteins is through modular protein domains that recognize and/or modify certain motifs. For example, different tyrosine kinases (such as Abl) will add phosphate groups to specific tyrosines inbedded in particular peptide sequences, while other enzymes (such as PTEN) act as phosphatases to remove certain signals. Proteins and other macromolecules may also be modified through methylation, acetylation, sumolation, ubiquitination, and these signals in turn are recognized by specific domains that activate the next step in the pathway. Such pathways usually are initiated through signals to receptors on the surface, which move to intracellular protein interactions and often lead to signaling through transcription factor interactions that regulate gene transcription. For example, in the Wnt pathway, Wnt interacts with the Frizzled receptor, signaling through Disheveled, which inhibits the Axin-APC-GSK3 complex, which binds to beta-catenin to inhibit the combination of beta-catenin with TCF4, translocation of this complex into the nucleus, and activation of Myc, Cyclin D, and other oncogenic protein transcription (Polakis, P. et al., *Genes Dev* 14(15):1837-1851 (2000); Nelson, W. J. et al., *Science* 303(5663):1483-1487 (2004)). Signaling may also proceed from the nucleus to secreted factors such as chemokines and cytokines (Charo, I. F. et al., *N Engl J Med* 354(6):610-621 (2006)). Protein-protein and protein-nucleic acid recognition often work through protein interactions domains, such as the SH2, SH3, and PDZ domains. Currently, there are over 75 such motifs reported in the literature (Hunter, et. al., *Cell* 100:113-127 (2000); Pawson et. al., *Genes & Development* 14:1027-1047 (2000)). These protein-interaction domains comprise a rich opportunity for developing targeted therapies.

Cancer therapies may be divided into two classical groups: (i) small molecule drugs such as Gleevec that bind into a compact pocket, and (ii) antibody therapeutics such as herceptin which binds and inhibits the HER-2/neu member of the epidermal growth factor receptor (EGFR) family. Antibody and protein therapeutics work by binding over an extended area of the target protein. Antibodies fight cancers by inducing apoptosis, interfering with ligand-receptor interactions, or preventing expression of proteins required for tumor growth (Mehren et al., *Ann Rev. Med.* 54:343-69 (2003)). Additional successful cancer antibody therapeutics include Rituximab, an anti CD20 antibody, Erbitux (cetuximab) targeted to EGFR, and Avastin (bevacizumab) which interferes with vascular endothelial growth factor (VEGF) binding to its receptor (Mehren et al., *Ann Rev. Med.* 54:343-69 (2003)). Except for the skin rash associated with EGFR receptor antibodies (which ironically correlates with efficacy), antibody therapies are generally well tolerated and do not have the side-effects associated with traditional chemotherapy.

Antibodies achieve their extraordinary specificity through the diversity generated in their complementarity-determining regions ("CDR's"). An IgG antibody binding surface consists of three CDRs from the variable heavy chain paired with three CDRs from the variable light chain domain. Each CDR consists of a loop of around a dozen amino acid residues, whose structure binds to the target surface with nanomolar affinity (Laune, et. al., *J. Biol. Chem* 272:30937-30944 (1997); Monnet, et al., *J. Biol. Chem* 274:3789-3796 (1999)). Thus, antibodies achieve their specificity by combining multiple weak interactions across a generally flat surface of approximately 1200-3000 Å$^2$. Monoclonal antibodies may be readily generated to most proteins, and artificial antibodies screened for using in vitro phage or bacterial systems (Mehren et al., *Ann Rev. Med.* 54:343-69 (2003)). Mouse monoclonal antibodies may be "humanized" to reduce development of undesired human antimouse antibodies. Limitations of using monoclonal antibodies include production of anti-idiotypic antibodies, disordered tumor vasculature, increased hydrostatic pressure within tumor, and heterogeneity of surface antigen within tumors. Due to these barriers, it takes 2 days for an IgG antibody to travel 1 mm and 7-8 months to travel 1 cm into a tumor (Mehren et al., *Ann Rev. Med.* 54:343-69 (2003)). Smaller variations of the IgG motif's have been engineered, including scFv and Affibodies (Eliasson, M. et al., *J Immunol* 142(2):575-581 (1989); Gunneriusson, E. et al., *J Bacteriol* 178(5):1341-1346 (1996); Nord, K. et al., *Nat Biotechnol* 15(8):772-777 (1997)), and these have improved tumor penetration by cutting down penetration time in about half.

Antibodies can achieve tighter binding and higher specificity than any artificially synthesized therapy. Nevertheless, antibody therapies are limited to interfering with protein-protein interactions or protein receptor activity that are on the surface of tumors or circulating targets, cannot be ingested orally, and are not able to use their extraordinary specificity to inhibit intracellular protein signaling.

On the other end of the spectrum are small molecule drugs. These have the advantages of being orally active, being sufficiently small enough (usually with a molecular weight<750) to diffuse across cell membranes, and binding tightly into compact binding pockets used by all enzymes to bind their substrates (or interfering with macromolecular machinery used in cellular processes) (Landry, Y., et al.,

*Fundam Clin Pharmacol* 22(1):1-18(2008); Duarte, C. D., et al., *Mini Rev Med Chem* 7(11):1108-1119(2007); Amyes, T. L., et al., *ACS Chem Biol* 2(11):711-714(2007)). Recently, the field of combinatorial chemistry has greatly improved the ability of chemists to identify lead molecules that bind and inhibit specific protein targets (Dolle, et al., *J. Combinatorial Chem.* 6(5):597-635 (2005)).

Thus, current drug design and drug therapy approaches do not address the urgent need to find drugs which interfere with intracellular protein-protein interactions, or protein signaling. Antibodies have the required specificity to distinguish among closely related protein surfaces, yet are too large to be taken orally or enter cells. Orally active pharmaceuticals are too small (i.e. have a molecular weight less than 750) to disrupt protein-protein surface interactions (generally flat, and over 1200-3000 Å$^2$).

Attempts to identify small molecule drugs that bind over an extended area have mostly been limited to traditional targets containing at least one compact binding site. One approach is based on: (i) preparing a set of potential binding elements where each molecule has a common chemical linkage group; (ii) identifying all binding elements that inhibit even weakly the target enzyme; (iii) preparing a combinatorial library of all the winning binding elements connected by a common chemical linkage group and a series of flexible linkers; and (iv) screening the combinatorial library to identify the tightest binding compound drugs. This approach was used to identify a small molecule inhibitor of the c-Src tyrosine kinase (Maly, et. al., *Proc. Nat'l Acad. Sci. USA* 97: 2419-2424 (2000)) as well as the tyrosylprotein sulfotransferase (Kehoe, et al., *Bio Org & Medicinal Chem Lett.* 12:329-332 (2002)). One flaw in this approach is that the initial screen finds mostly molecules that bind within the initial pocket, but the final product needs to have both binding elements bind with high affinity. Thus, the success of the above approach was the result of a fortuitous alternative binding of one of the elements identified in the initial screen. A second disadvantage is the need to screen each of the potential combinatorial library elements individually.

To overcome the limitation of testing various combinations of ligands and connectors individually, Lehn and coworkers developed dynamic combinatorial chemistry ("DCC") as a new means for drug discovery (Lehn, et. al., *Science* 291:2331-2332 (2001); Ramstrom, et. al., *Nat. Rev. Drug Discovery* 1:26-36 (2002)). In this approach, potential ligand molecules form reversible adducts to different bifunctional connector molecules, and these interconnections are in continuous exchange with each other. When the enzyme target is added, the best bound library constituent is selected from all the possible combinations, allowing for identification of the active species. Using 16 hydrazides, 2 monoaldehydes, and 3 dialdehydes, 440 different combinations were formed and selected against the bifunctional *B. subtilis* HPr. kinase/phosphatase (Bunyapaiboonsri, et. al., *J. Med. Chem.* 46:5803-5811 (2003)). Improvement in synthesis and spatial identification of specific library members is achieved by using resin-bound DCC approaches (McNaughton, et. al., *Organic Letters* 8:1803-1806 (2006)).

The use of DNA to encode self-assembling chemical (ESAC) libraries has extended the potential for dynamic combinatorial chemistry drug discovery (Melkko et al., *Nature Biotech,* 22:568-574 (2004)). The DNA strands are partially complementary to allow for reversible binding to each other under standard incubation conditions and also contain bar codes to identify the ligand element. After using DCC to select for the tightest binding combinations, and identification of ligands based on their DNA code, the ligands are resynthesized with a variety of spacers to identify the tightest binding tethered combinations. This approach was used to find binding molecules with nanomolar affinities to serum albumin, carbonic anhydrase, streptavidin, and trypsin respectively (Melkko et al., *Nature Biotech,* 22:568-574 (2004); Dumelin et al., *Bioconjugate Chem.* 17:366-370 (2006); Melkko et al., *Angew. Chem.* 46:4671-4674 (2007)). One disadvantage of this approach is the wide footprint of about 15.4 Angstroms introduced by using double-stranded DNA as the dynamic combinatorial chemistry element, separating the ligands by a considerable distance, and requiring a higher MW tether to reestablish tight binding affinities.

In an inversion of the standard small-molecule drug binding within a compact binding pocket in the target enzyme, the macrocycle vancomycin binds to its L-Lys-D-Ala-D-Ala tripeptide target by forming a dimer that surrounds the tripeptide. By using the actual target to accelerate combinatorial synthesis of vancomycin and vancomycin analogue dimers, tethered dimers were isolated with tighter affinities and in vitro activity against some vancomycin resistant bacterial strains (Nicolaou et al., *Angew. Chem.* 39:3823-3828 (2000)). It is unlikely that these derivatives would be orally active due to their high molecular weight and potential for disulfide dimers to be reduced to monomers within the bloodstream.

Many receptors (for example, the erythropoietin receptor) are activated by ligand-induced homodimerization, which leads to internal cellular signals. By using bi- or multifunctional connectors to link ligand molecules to form dimers, trimers, and tetramer libraries, a number of small molecule agonists could be isolated that assisted in erythropoietin receptor homodimerization (Goldberg et. al., *J. Am. Chem. Sec.* 124:544-555 (2002)). These molecules demonstrate the ability of multi-ligand drugs to influence protein-protein interactions, in a manner that mimics the natural activity of cytokines and chemokines.

Sharpless and coworkers have identified reactions that occur readily when the constituent chemical linkage groups are brought in close proximity with each other, termed "click chemistry" (Kolb, et. al., *Drug Discovery Today* 8:1128-1137 (2003)). By adding various ligands connected to these reactive groups (such as an azide on one set of ligands and acetylene on the other ligands) and combining these library compounds in solution in the presence of enzyme targets, highly potent inhibitors form, for example for the acetylcholine esterase or the HIV protease (Kolb et. al., *Drug Discovery Today,* 8:1128-1137 (2003); Brik et. al., *Chem. Bio Chem* 4:1246-1248 (2003); Whiting, et. al., *Angew. Chem. Int. Ed.* 45:1435-1439 (2006); Lewis et. al., *Angew Chem* 41:1053-1057 (1002); Bourne et. al., *Proc. Nat'l Acad. Sci. USA* 101:1449-1454 (2004)). In short, the target enzyme acts as a catalyst for the proximal ligation of its own inhibitor. The advantage of this approach is the enrichment of the best binding compound in a single step.

An elegant approach to finding low molecular weight ligands that bind weakly to targeted sites on proteins was developed by Wells and coworkers (Erlanson et. al., *Proc. Nat'l Acad. Sci. USA* 97:9367-9372 (2000); Thanos, et. al., *J. Am. Chem. Sco.* 125:15280-15281 (2003); Erlanson et. al., *Nature Biotechnology* 21:308-314 (2003); Buck et. al., *Proc. Nat'l Acad. Sci. USA* 102:2719-2724 (2005)). A native or engineered cysteine in a protein is allowed to react reversibly with a small library of disulfide-containing molecules. The process of dynamic combinatorial chemistry takes place as the most stable molecules are enriched on the surface of the protein target. These are then readily identified by mass spectroscopy, and serve as lead compounds for further modification.

Dynamic combinatorial or "click" chemistry increases yields of appropriate binding ligand combinations, but still requires enzymatic assays. The disadvantages of these approaches are that they are limited to enzymes with one or more deep binding pockets, where knowledge of at least one potential ligand is often needed. Further, the starting blocks are not readily available and require independent synthesis for each diversity element or ligand to be tested. The chemical linkage groups used for click chemistry are not suitable for use in vivo as they would react readily and irreversibly with cellular components. The reactions need to take place with sufficient efficiency and at a large enough scale such that the enzyme selected inhibitor is synthesized in sufficient amounts to allow for purification and identification of the correct product. This last constraint limits the number of ligands that may be screened in a single assay, and limits the throughput of these approaches.

Several groups have recognized that macrocycles provide an opportunity for recognition of extended binding motifs within targets. Several of these are orally active, despite having molecular weight beyond the traditional 750 cutoff. These include cyclosporin (molecular weight 1202.64), rapamycin (molecular weight 914.2), tacrolimus (molecular weight 822.03), erythromycin (molecular weight 733.94), azithromycin (molecular weight 748.88), and clarithromycin (molecular weight 747.9). Note that although vancomycin (molecular weight 1485.74) is used orally for treatment of gastrointestinal infections, it is not absorbed into the body. Cyclosporin is the largest of the groups listed above and illustrates a few features common to these drugs. Their cyclic nature reduces entropic loss upon binding and the extended structure allows for enhanced binding. Cyclosporin has torroidal flexibility, allowing it to bring its polar side-chains into the interior so the outside is nonpolar and this allows for transfer across membranes. Likewise, the drug is in structural equilibrium with its polar conformer, allowing for binding to its target.

As promising as macrocycle and synthetic peptide mimetics are for lead drug candidates, it is not trivial to use synthetic chemistry to generate sufficient diversity required for high affinity binding to extended binding sites in target proteins. Two groups have sought to address this issue using DNA encoded approaches with evolutionary selection. In the first approach, a functional group is attached to a long DNA barcode sequence containing multiple zip-codes (Halpin, D. R. et al., *PLoS Biol* 2(7):E173 (2004); Halpin, D. R. et al., *PLoS Biol* 2(7):E174 (2004); Halpin, D. R. et al., *PLoS Biol* 2(7):E175 (2004)). The molecules are equilibrated with a set of columns (e.g., 10 columns), containing beads with complementary zip-code sequences. DNA hybridization captures library members containing the complementary zip-code sequence on their DNA tag. The library members are eluted into separate new chambers and reacted with a bifunctional moiety (for example, a protected amino acid residue) that corresponds to the given zip-code. The library members are then re-pooled, and then rerouted to the next series of columns. This process was repeated through several rounds to generate $10^6$ pentapeptides. After only two rounds of translation, selection with an antibody to the pentapeptide enkephalin, and amplification, the library converged on enkephalin and slight variants. Potential disadvantages of this approach are the need for DNA encryption strands of 200 or more bases. In the second approach, a bifunctional group is attached to a DNA template sequence containing adjacent zipcode sequences (Calderone, C. T. et al., *Angew Chem Int Ed Engl* 44(45):7383-7386 (2005); Sakurai, K. et al., *J Am Chem Soc* 127(6):1660-1661 (2005)). The DNA sequence serves as a template for adding bifunctional moieties to one end of the bifunctional group on the DNA tag. Each bifunctional moiety (for example, a protected amino acid residue) is attached to a complementary zip-code DNA molecule, which hybridizes on the DNA template containing the original bifunctional group. This hybridization increases the local concentration of the reactant to such an extent that it can drive synthesis to very high yields. This method does not require split-pooling techniques. If 4 sets of 10 each bifunctional moieties are added, this will result in 10,000 diversity elements in the library. At the end of the synthesis, the last amino acid residue may be reacted with the other end of the original bifunctional group to create a circular diversity element. In this version, the identity of the diversity element is defined by the zipcode sequences in the DNA template. It may be identified by PCR amplification and sequencing. Further, the PCR amplicons may serve as starting templates for a new round of translation, selection, and amplification, allowing for application of evolutionary principles to synthesize high affinity binding elements. However, the extent of diversity elements synthesized by the above two approaches are still several orders of magnitude lower than the diversity and affinity achieved by just a single CDR loop from an antibody molecule.

Several groups have investigated the ability of small molecules to interact with each other or encircle other small molecule targets; these are known as "guest-host" interactions or artificial receptors. However, these compounds are not suitable, because they are not of low enough molecular weight or interact under non-physiological conditions or would be too reactive with other intracellular molecules.

A common approach to designing artificial receptors is to construct a "molecular tweezer", consisting of a two armed structure joined by a conformationally restricted linker, such that the two arms point in the same direction (analogous to a tweezer). These "host" structures are often designed with a dye or on a bead, and then screened for binding of the "guest", most often a tri-peptide, again with either a dye or on a bead. (Shao et. al., *J Org. Chem* 61:6086-6087 (1996); Still et. al., *Acc. Chem. Res.* 29:155-163 (1996); Cheng, et. al., *J. Am. Chem. Soc.* 118:1813-1814 (1996); Jensen et. al., *Chem. Eur. J.* 8:1300-1309 (2002)). In a variation of this theme, binding of the peptide displaces a quenched fluorescent group from the host pocket, thus creating a fluorescent signal upon binding (Chen, et. al., *Science* 279:851-853 (1998); Iorio et. al., *Bioorganic & Medicinal Chem Lett.* 11:1635:1638 (2001)). Rigid diketopiperazine backbone receptors with tri-peptide arms have demonstrated both tight binding, as well as how small structural changes in the backbone significantly reduce that binding (Wennemers et al., *Chem. Eur. J.* 7:3342-3347 (2001); Conza et. al., *J. Org. Chem.* 67:2696-2698 (2002); Wennemers et al., *Chem. Eur. J.* 9:442-448 (2003)). Unsymmetrical tweezer and one-armed receptor hosts have been designed to mimic vancomycin binding of an L-Lys-D-Ala-D-Ala tripeptide guest (Shepard et al., *Chem. Eur. J.* 12:713-720 (2006); Schmuck et al., *Chem. Eur. J.* 12:1339-1348 (2006)). Other host-guest systems include napthalene-spaced tweezers and cyanobenzene derivatives (Schaller et al., *J. Am. Chem. Soc.* 129:1293-1303 (2007)). In some of the examples above, the selection was performed in organic solvents, and, in all cases, at least one of the entities had a molecular weight in excess of 400 and often in excess of 800. Thus, these examples would not be suitable for lead molecules.

Another approach to designing low molecular weight affinity binders is to use phage display. This approach was used to find peptides from 9-13 mers that bind fluorescent dyes; however, only one of these retained sufficient affinity to bind a dye when resynthesized outside the context of the phage protein (Rozinov et. al., *Chemistry & Biology* 5:713-728 (1998), Marks, et. al., *Chemistry & Biology* 11:347-356 (2004)). Other groups have used phage display to design synthetic peptides 8-12 mers that bind biotin (Saggio et. al., *Biochem. J.* 293:613-616 (1993)), camptothecin (Takakusagi et al., *Bioorganic & Medicinal Chem Lett.* 15:4850-4853 (2005)), as well as doxorubicin and other hydrophobic cancer drugs (Popkov et al, *Eur. J. Biochem.* 251:155-163 (1998)). In all these cases, the fluorescent dye or similarly hydrophobic guest moiety is held in place by a pocket comprised from hydrophobic amino acids, and then additional residues may provide further stability. Since the peptides have molecular weights ranging from about 900 to about 1500, they are too large and not suitable for lead molecules.

Thus, there is a need to design new small molecules that associate with good affinities for one another under physiological conditions. The present invention is directed to overcoming this deficiency in the art.

SUMMARY OF THE INVENTION

One aspect of the present invention is directed to a monomer useful in preparing therapeutic compounds. The monomer includes a diversity element which potentially binds to a target molecule with a dissociation constant of less than 300 µM and a linker element connected, directly or indirectly through a connector, to said diversity element. The linker element has a molecular weight less than 500 daltons and is capable of forming a reversible covalent bond or non-covalent interaction with a binding partner of said linker element with a dissociation constant of less than 300 µM with or without a co-factor under physiological conditions.

Another aspect of the present invention relates to a therapeutic multimer precursor. The therapeutic multimer precursor includes a plurality of covalently or non-covalently linked monomers. Each monomer comprises a diversity element which potentially binds to a target molecule with a dissociation constant less than 300 µM, a linker element, and an encoding element. The linker element has a molecular weight less than 500 daltons and is capable of forming a reversible covalent bond or non-covalent tight interaction with a binding partner of said linker element with a dissociation constant less than 300 µM, with or without a co-factor, under physiological conditions. The diversity element and the linker element for each monomer are connected together, directly or indirectly through a connector, and the plurality of monomers are covalently bonded together or non-covalently linked together through their linker elements. The diversity elements for the plurality of monomers bind to proximate locations of the target molecule.

Yet a further embodiment of the present invention is directed to a method of screening for therapeutic compound precursors which bind to a target molecule associated with a condition. This method includes providing a plurality of monomers. Each monomer comprises a diversity element which potentially binds to a target molecule with a dissociation constant less than 300 µM and a linker element capable of forming a reversible covalent bond or non-covalent interaction with a binding partner of the linker element with or without a co-factor under physiological conditions. The linker has a molecular weight of less than 500 daltons. The diversity element and said linker element of each monomer are joined together directly or indirectly through a connector. The plurality of monomers are contacted with the target molecule under conditions effective to permit diversity elements able to bind to the target molecule to undergo such binding. The monomers are then subjected to reaction conditions effective for the linker elements of different monomers to undergo covalent bonding or non-covalent interactions to form therapeutic multimer precursors, either before, after, or during the contacting step. The monomers forming each therapeutic multimer precursor are then identified.

Another embodiment of the present invention involves a method of screening for linker elements capable of binding to one another. This method includes providing a first and a second set of monomers. Each of the monomers in the first set comprise a linker element, having a molecular weight of less than 500 daltons and being capable of forming a reversible covalent bond or non-covalent interaction with a binding partner of said linker element, with or without a co-factor under physiological conditions and a sulfhydryl group. The linker element, with or without a co-factor, and the sulfhydryl group for each monomer of the first set of monomers are coupled together. Each of the monomers in the second set comprise a linker element capable of forming a reversible covalent bond or reversible non-covalent bonds with a binding partner of the linker element under physiological conditions, an encoded bead, and a sulfhydryl group. The linker element, the encoded bead, and the sulfhydryl group for each monomer of the second set of monomers are coupled together. The first and second sets of monomers are contacted with one another under physiological conditions so that monomers from the first set of monomers and monomers from the second set of monomers bind together to form multimers linked together by disulfide bonds formed from their sulfhydryl groups and, potentially, covalent bonds or non-covalent interactions between their linker elements. The dimers where the linker elements from the monomers of the first and second sets of monomers are covalently bound or non-covalently linked together are then identified as being candidate multimers. The linker elements from the first and second monomers that are covalently bound or non-covalently joined together are then identified in the candidate multimers.

An additional embodiment of the present invention relates to a therapeutic multimer which includes a plurality of covalently or non-covalently linked monomers. Each monomer comprises a diversity element which binds to a target molecule with a dissociation constant of less than 300 µM and a linker element having a molecular weight less than 500 daltons, and capable of forming a reversible covalent bond or non-covalent tight interaction with a binding partner of the linker element with a dissociation constant less than 300 µM, with or without a co-factor, under physiological conditions. The diversity element and the linker element are joined together for each monomer, directly or indirectly through a connector. The plurality of monomers are covalently bonded together or non-covalently linked together through their linker elements, and the diversity elements for the plurality of monomers bind to proximate locations of the target molecule.

Another embodiment of the present invention relates to a plurality of therapeutic monomers capable of combining to form a therapeutic multimer. Each monomer includes a diversity element which binds to a target molecule and a linker element having a molecular weight less than 500 daltons and capable of forming a covalent bond or non-covalent tight interaction with a binding partner of the linker element with a dissociation constant less than 300 µM, with or without a co-factor, under physiological conditions. The diversity element, which has a dissociation constant less than 300 µM, and the linker element are connected together directly or indirectly through a connector for each monomer. A plurality of monomers are capable of covalently bonding together or being non-covalently linked together through their linker elements, and the diversity elements for the plurality of monomers bind to proximate locations of the target molecule.

The linker elements of the present invention are small molecules that exclusively associate with each other in vivo and do not react with cellular components. Each linker element has attachment points for introducing diverse ligands and individual DNA encryption elements. They are compatible with "click chemistry" and DNA-templated synthesis. The association between the linker elements is reversible, allowing for dynamic combinatorial chemistry selection of the best ligands. The linker elements allow in vivo assembly of multiple small ligands to produce structures having a molecular weight up to about 4800 and potentially disrupt protein-protein interactions.

The linker elements of the present invention have the potential to modulate or inhibit protein-protein signaling. The combined size of the linker element-ligand dimers and multimers provides sufficient surface area to interact with protein surfaces with increased selectivity and reduced toxicity. Directed evolution selects for tightest binding lead compounds, with the potential to drive affinities to sub-nmol range.

The present invention is directed to a novel class of drug molecules (referred to here as coferons) that assemble in vivo. A coferon monomer is composed of a diversity element or ligand that binds to the target and a dynamic combinatorial chemistry element herein termed a linker element. The linker element of one coferon monomer may reversibly combine with the linker element of another coferon monomer in vivo to form a coferon dimer. In some cases, the linker element binding to each other may be essentially irreversible. In additional cases, the linker elements bind to each other with the aid of a co-factor. In other cases, the linker elements are in a precursor form, and are activated upon entering the body or cells. The linker elements bind to each other through hydrophobic, polar, ionic, hydrogen bonding, and/or reversible covalent interactions. In the presence of the target, the combinations of multiple (weak) interactions between the diversity element of one coferon monomer and a target protein, the diversity element of a second coferon monomer and the target protein, as well as the two coferons with each other combine to produce a tight binding coferon dimer with highly specific binding to its target. The concept may be extended to include multimer coferons and multimer targets.

Since coferon monomers associate in a reversible manner, the principals of dynamic combinatorial chemistry selection may be used to identify the best ligands for each target in vitro. Combining two coferon libraries, for example with $10^4$ diversity elements provides the opportunity to screen $10^8$ combinations simultaneously. Use of repeated synthesis, selection, and amplification strategies will allow for evolutionary selection of coferon dimers with nanomolar and even subnanomolar binding affinities. The combined size of linker element dimers provides sufficient surface area to interact with extended binding protein surfaces. Nevertheless, since coferon assembly on the target is dependent on multiple additive interactions, false binding to incorrect proteins will be rare (and can be selected against), and, thus, such drugs should have minimal to no off-target toxicity. Use of circular peptide and peptide analogue containing diversity elements will also allow for switching between polar and non-polar conformers for easier transport across membranes. Coferon monomers may be designed to have a molecular weight of less than 1000, allowing them to be orally active, penetrate deeply into tumors, and cross membrane barriers to enter inside cells—significant advantages over antibodies—while providing equal specificity.

The key to the linker elements is identifying small molecules (with molecular weights preferably within the range of 45 to 450 daltons) that associate with good affinities for one another in vivo, and preferably associate exclusively with each other in vivo. They should not react with cellular components. The more sophisticated linker elements described below help catalyze formation of reversible covalent bonds when binding to each other under physiological conditions. The variety of coferon designs may be expanded by uncoupling the screening process for diversity element ligands from the final coferon structure used in the drug. This allows the use of linker elements in the final drug whose binding is essentially irreversible. Essentially irreversible linker elements are generally, but not limited to, linker elements that may associate slowly or even very slowly, either in the absence or presence of the target. However, once formed, such linker elements essentially do not dissociate.

Even though each individual bond between two linker elements may be reversible, once both bonds are established, reversal of one bond still keeps the two reactants in such close proximity that they will de facto reform the bond again.

Certain linker elements may be reversible under some conditions (used during screening), yet essentially irreversible under other conditions, for example when formulated in the final drug. For those linker elements that have the potential to combine irreversibly during formulation, or alternatively in the body prior to entering the target cells, the reactive groups may be protected and rendered unreactive. Upon entering the target cells, the protecting group may be removed by cellular processes, such as disulfide reduction to the thiol by intracellular glutathione, enzymatic cleavage (i.e. esterase), or pH change (if entry is via endosomes or linker elements enter lysosomal compartments) or simply by reversible dissociation upon dilution into the blood stream (i.e. reversible alcohol protection of a reactive boronate group). Linker elements that are essentially irreversible under dynamic combinatorial chemistry (DCC) screening conditions may be rendered reversible using a new approach described herein, which we term "cyclic combinatorial chemistry" (C3) screening.

Subcategories of coferons will be divided into those that bind their target as dimers and those that work as multimers. Some of the coferons may be easily modified to bring two dimers together in a head-to-head fashion to create tetramers or even higher-order coferon multimers.

BRIEF DESCRIPTION OF THE DRAWINGS

FIG. 2.1 show the variations of the components of coferon drug design. A is a schematic drawing of coferon monomers in accordance with the present invention attached to encoded beads via connectors. B is a schematic drawing of a coferon monomer in accordance with the present invention with a DNA barcode attached through a connector. C is a schematic drawing of a coferon dimer attached to an encoded bead via a connector to one monomer, with a DNA barcode attached to the other monomer. D is a schematic drawing of a coferon dimer, with DNA barcodes attached to each monomer via the connectors. E is a schematic drawing of a coferon dimer with connectors pursuant to the present invention. F is a schematic drawing of coferon monomers in accordance with the present invention attached to an encoded bead via the linker element. G is a schematic drawing of a coferon monomer in accordance with the present invention with a DNA barcode attached to the linker element. H is a schematic drawing of a coferon dimer attached to an encoded bead via the linker element to one monomer, with a DNA barcode attached to the other monomer. I is a schematic drawing of a coferon dimer, with an encoded bead attached one monomer via its linker element. J is a schematic drawing of a coferon dimer, with DNA barcodes attached to each monomer via the linker elements. K is a schematic drawing of a coferon dimer pursuant to the present invention.

FIG. 2.2 show additional variations of the components of coferon drug design. L is a schematic drawing of a coferon dimer attached to an encoded bead via a connector to one monomer, with a DNA barcode attached to the other monomer. The linker elements bind to each other via a cofactor, such as a metal ion (blue dot). M is a schematic drawing of a coferon dimer, with DNA barcodes attached to each monomer via the connectors. The linker elements bind to each other via a cofactor, such as a metal ion. N is a schematic drawing of a coferon dimer, which bind to each other via a cofactor, pursuant to the present invention. O is a schematic drawing of a coferon dimer attached to an encoded bead via a connector to one monomer. The linker elements bind to each other via a cofactor, such as a metal ion. P is a schematic drawing of a coferon dimer attached to an encoded bead via the linker element of one monomer. The linker elements bind to each other via a cofactor, such as a metal ion. Q is a schematic drawing of a coferon dimer attached to an encoded bead via the linker element to one monomer, with a DNA barcode attached to the other monomer. The linker elements bind to each other via a cofactor, such as a metal ion. R is a schematic drawing of a coferon dimer, with DNA barcodes attached to each monomer via the linker elements, which bind to each other via a cofactor, such as a metal ion. S is a schematic drawing of a coferon dimer, which bind to each other via a cofactor, pursuant to the present invention.

FIG. 2.3 show variations of the components of coferon drug design. A2 is a schematic drawing of two coferon monomers in accordance with the present invention attached to an encoded bead via separate connectors. B2 is a schematic drawing of a tethered coferon dimer in accordance with the present invention with a DNA barcode attached through a connector. C2 is a schematic drawing of a tethered coferon dimer attached to an encoded bead via a connector to the linker elements. D2 is a schematic drawing of a tethered coferon dimer, in accordance with the present invention. E2 is a schematic drawing of a coferon trimer consisting of two coferon monomers attached to an encoded bead via connectors and a coferon monomer with a DNA barcode attached through a connector. The linker elements of the latter monomer and one of the former monomers are joined. F2 is a schematic drawing of a coferon trimer including two tethered coferon monomers with a DNA barcode attached via connectors and a coferon monomer with a DNA barcode attached through a connector. The linker elements of the latter monomer and one of the former monomers are joined. G2 is a schematic drawing of a coferon trimer including two coferons with the same ligand, and one coferon with a different ligand, pursuant to the present invention. The linker elements of the latter monomer and one of the former monomers are joined. H2 is a schematic drawing of a coferon trimer including two coferon monomers in accordance with the present invention attached to an encoded bead via the linker element, and another coferon monomer. The linker elements of the latter monomer and one of the former monomers are joined. I2 is a schematic drawing of a coferon trimer comprising a coferon monomer attached to an encoded bead through a connector, and two other coferon monomers, each with a DNA barcode attached through a connector. The linker elements of the former monomer and one of the latter monomers are joined. J2 is a schematic drawing of a coferon trimer comprising three monomer coferons with different ligands, pursuant to the present invention.

FIG. 2.4 show variations of the components of coferon drug design. K2 is a schematic drawing of two coferon monomers in accordance with the present invention attached to an encoded bead via linker elements. L2 is a schematic drawing of a tethered coferon dimer in accordance with the present invention with a DNA barcode attached through a linker element. M2 is a schematic drawing of a tethered coferon dimer attached to an encoded bead via a tether to the linker elements. N2 is a schematic drawing of a tethered coferon dimer, in accordance with the present invention. O2 is a schematic drawing of a coferon trimer including two coferon monomers attached to an encoded bead via their linker element and a coferon monomer with a DNA barcode attached through a linker element. P2 is a schematic drawing of a coferon trimer comprising two tethered coferon monomers with a DNA barcode attached via a linker element and a coferon monomer with a DNA barcode attached through a linker element. Q2 is a schematic drawing of a coferon trimer including two coferons with the same ligand, and one coferon with a different ligand, pursuant to the present invention. R2 is a schematic drawing of a coferon trimer including two tethered coferon monomers in accordance with the present invention attached to an encoded bead via their tethered linker elements, and another coferon monomer which is joined through to one of the tethered monomers by their linker elements. S2 is a schematic drawing of a coferon trimer comprising a coferon monomer attached to an encoded bead through a linker element, and two other coferon monomers, each with a DNA barcode attached through a connector. T2 is a schematic drawing of a coferon trimer including three monomer coferons with different ligands, pursuant to the present invention.

FIG. 2.5 show the variations of the components of coferon drug design. A3 is a schematic drawing of a coferon tetramer comprised of two coferon monomers in accordance with the present invention attached to an encoded bead via connectors and to themselves via their linker element, and a tethered coferon dimer in accordance with the present invention with a DNA barcode attached through a connector. B3 is a schematic drawing of a coferon tetramer comprised of a tethered coferon dimer in accordance with the present invention with a DNA barcode attached through a connector, and another tethered coferon dimer in accordance with the present invention with a DNA barcode attached through a connector. C3 is a schematic drawing of a coferon tetramer including two monomer coferons with one ligand and two monomer coferons with another ligand pursuant to the present invention. D3 is a schematic drawing of a coferon tetramer comprised of a tethered coferon dimer in accordance with the present invention attached to an encoded bead via tethers, and a tethered coferon dimer in accordance with the present invention with a DNA barcode attached through a connector. E3 is a schematic drawing of a coferon tetramer comprised of a tethered coferon dimer in accordance with the present invention attached to an encoded bead via tethers, and a tethered coferon dimer in accordance with the present invention. F3 is a schematic drawing of a coferon tetramer comprised of two coferon monomers in accordance with the present invention attached to an encoded bead via connectors, and a tethered coferon dimer in accordance with the present invention. G3 is a schematic drawing of a coferon tetramer comprised of two coferon monomers in accordance with the present invention attached to an encoded bead via connectors, and two coferon monomers with different ligands in accordance with the present invention with DNA barcodes attached through connectors. H3 is a schematic drawing of a coferon tetramer comprised of a tethered coferon dimer in accordance with the present invention with a DNA barcode attached through a connector, and two tethered coferon monomers with different ligands in accordance with the present invention with DNA barcodes attached through connectors. I3 is a schematic drawing of a coferon tetramer consisting of two monomer coferons with one ligand and two monomer coferons with two different ligands pursuant to the present invention. J3 is a schematic drawing of a coferon tetramer comprised of a coferon dimer in accordance with the present invention attached to an encoded bead via the tether, and two coferon monomers with different ligands in accordance with the present invention with DNA barcodes attached through connectors. K3 is a schematic drawing of a coferon tetramer comprised of a tethered coferon dimer in accordance with the present invention attached to encoded beads via the tether, and two coferon monomers with different ligands in accordance with the present invention. L3 is a schematic drawing of a coferon tetramer comprised of two coferon monomers in accordance with the present invention attached to an encoded bead via connector, and two coferon monomers with different ligands in accordance with the present invention.

FIG. 2.6 show variations of the components of coferon drug design. M3 is a schematic drawing of a coferon tetramer comprised of two coferon monomers in accordance with the present invention attached to an encoded bead via linker elements, and a tethered coferon dimer in accordance with the present invention with a DNA barcode attached through a linker element. N3 is a schematic drawing of a coferon tetramer comprised of a tethered coferon dimer in accordance with the present invention with a DNA barcode attached through a linker element, and another tethered coferon dimer in accordance with the present invention with a DNA barcode attached through a linker element. O3 is a schematic drawing of a coferon tetramer comprising two monomer coferons with one ligand and two monomer coferons with another ligand pursuant to the present invention. P3 is a schematic drawing of a coferon tetramer comprised of a tethered coferon dimer in accordance with the present invention attached to an encoded bead via tethers, and a tethered coferon dimer in accordance with the present invention with a DNA barcode attached through a linker element. Q3 is a schematic drawing of a coferon tetramer comprised of a tethered coferon dimer in accordance with the present invention attached to an encoded bead via tethers, and a tethered coferon dimer in accordance with the present invention. R3 is a schematic drawing of a coferon tetramer comprised of two tethered coferon dimers in accordance with the present invention attached to an encoded bead via linker elements in accordance with the present invention. S3 is a schematic drawing of a coferon tetramer comprised of two coferon monomers in accordance with the present invention attached to an encoded bead via linker elements, and two coferon monomers with different ligands in accordance with the present invention with DNA barcodes attached through linker elements. T3 is a schematic drawing of a coferon tetramer comprised of a tethered coferon dimer in accordance with the present invention with DNA barcodes attached through the linker elements, and two coferon monomers with different ligands in accordance with the present invention with DNA barcodes attached through linker elements. U3 is a schematic drawing of a coferon tetramer consisting of two coferon monomers with one ligand and two coferon monomers with two different ligands pursuant to the present invention. V3 is a schematic drawing of a coferon tetramer comprised of a tethered coferon dimer in accordance with the present invention attached to an encoded bead via the tether, and two coferon monomers with different ligands in accordance with the present invention with DNA barcodes attached through linker elements. W3 is a schematic drawing of a coferon tetramer comprised of a tethered coferon dimer in accordance with the present invention attached to an encoded bead via the tether, and two coferon monomers with different ligands in accordance with the present invention. X3 is a schematic drawing of a coferon tetramer comprised of two coferon monomers in accordance with the present invention attached to an encoded bead via linker elements, and two coferon monomers with different ligands in accordance with the present invention.

FIG. 2.7 show variations of the components of coferon drug design. A4 is a schematic drawing of a coferon tetramer comprised of four tethered coferon monomers with the same linker elements, connectors, and the same ligands in accordance with the present invention attached to an encoded bead via tethers. B4 is a schematic drawing of a coferon tetramer comprised of four tethered coferon monomers with the same linker elements, connectors, and the same ligands in accordance with the present invention with a DNA barcode attached through the tether. C4 is a schematic drawing of a coferon tetramer comprised of four tethered coferon monomers with two different linker elements, connectors, and the same ligands in accordance with the present invention attached to encoded beads via tethers. D4 is a schematic drawing of a coferon tetramer comprised of four tethered coferon monomers with two different linker elements, connectors, and the same ligands in accordance with the present invention with a DNA barcode attached through the tether. E4 is a schematic drawing of a coferon tetramer comprised of four tethered coferon monomers with two different linker elements, connectors, and two different ligands in accordance with the present invention attached to an encoded bead via tethers. F4 is a schematic drawing of a coferon tetramer comprised of four tethered coferon monomers with two different linker elements, connectors, and two different ligands in accordance with the present invention with a DNA barcode attached through the tether.

FIG. 2.8 show variations of the components of coferon drug design. G4 is a schematic drawing of a coferon dimer comprised of two tethered coferon monomers with the same linker elements, connectors, and the same ligands in accordance with the present invention attached to an encoded bead via tethers. H4 is a schematic drawing of a coferon dimer comprised of two tethered coferon monomers with the same linker elements, connectors, and the same ligands in accordance with the present invention with a DNA barcode attached through the tether. I4 is a schematic drawing of a coferon tetramer comprised of two tethered coferon monomers with the same ligands in accordance with the present invention attached to an encoded bead via tethers and the coferon monomers comprised of two tethered coferon monomers with the same ligands in accordance with the present invention with a DNA barcode attached through the tether. J4 is a schematic drawing of a coferon tetramer comprised of two tethered coferon monomers with the same ligands in accordance with the present invention attached to an encoded bead via tethers and a coferon dimer comprised of two tethered coferon monomers with the same ligands in accordance with the present invention. K4 is a schematic drawing of a coferon tetramer consisting of two coferon monomers with one ligand and two coferon monomers with another ligand pursuant to the present invention. L4 is a schematic drawing of a coferon tetramer comprised of two tethered coferon monomers with the same ligands in accordance with the present invention attached to an encoded bead via tethers and two coferon monomers with two different ligands in accordance with the present invention with DNA barcodes attached through the linker elements. M4 is a schematic drawing of a coferon tetramer comprised of two tethered coferon monomers with the same ligands in accordance with the present invention attached to an encoded bead via tethers and two coferon monomers with two different ligands in accordance with the present invention. N4 is a schematic drawing of a coferon tetramer consisting of two coferon monomers with one ligand and two coferon monomers with two different ligands pursuant to the present invention.

FIG. 2.9 show variations of the components of coferon drug design. O4 is a schematic drawing of a coferon tetramer comprising four monomer coferons with the same ligand pursuant to the present invention. P4 is a schematic drawing of a coferon tetramer including four monomer coferons with two different linker elements but the same ligand pursuant to the present invention. Q4 is a schematic drawing of a coferon tetramer comprising two coferon monomers with one ligand and two coferon monomers with another ligand pursuant to the present invention. R4 is a schematic drawing of a coferon dimer including of two monomer coferons with the same ligand pursuant to the present invention. S4 is a schematic drawing of a coferon dimer consisting of two coferon monomers with two different linker elements but the same ligand pursuant to the present invention. T4 is a schematic drawing of a coferon dimer consisting of one coferon monomer with one ligand and one coferon monomer with another ligand pursuant to the present invention.

FIG. 2.10 show variations of the components of coferon drug design. A5 is a schematic drawing of a coferon tetramer comprised of four tethered coferon monomers with the same linker elements and the same ligands in accordance with the present invention attached to an encoded bead via tethers. B5 is a schematic drawing of a coferon tetramer comprised of four tethered coferon monomers with the same linker elements and the same ligands in accordance with the present invention with a DNA barcode attached through the tether. C5 is a schematic drawing of a coferon tetramer comprised of four tethered coferon monomers with two different linker elements and the same ligands in accordance with the present invention attached to an encoded bead via tethers. D5 is a schematic drawing of a coferon tetramer comprised of four tethered coferon monomers with two different linker elements and the same ligands in accordance with the present invention with a DNA barcode attached through the tether. E5 is a schematic drawing of a coferon tetramer comprised of four tethered coferon monomers with two different linker elements and two different ligands in accordance with the present invention attached to encoded beads via tethers. F5 is a schematic drawing of a coferon tetramer comprised of four tethered coferon monomers with two different linker elements and two different ligands in accordance with the present invention with a DNA barcode attached through the tether.

FIG. 2.11 show the variations of the components of coferon drug design. G5 is a schematic drawing of a coferon dimer comprised of two tethered coferon monomers with the same linker elements and the same ligands in accordance with the present invention attached to an encoded bead via tethers. H5 is a schematic drawing of a coferon dimer comprised of two tethered coferon monomers with the same linker elements and the same ligands in accordance with the present invention with a DNA barcode attached through the tether. I5 is a schematic drawing of a coferon tetramer comprised of two tethered coferon monomers with the same ligands in accordance with the present invention attached to an encoded bead via tethers and a coferon dimer comprised of two tethered coferon monomers with the same ligands in accordance with the present invention with a DNA barcode attached through the tether. J5 is a schematic drawing of a coferon tetramer comprised of two tethered coferon monomers with the same ligands in accordance with the present invention attached to an encoded bead via tethers and a coferon dimer comprised of two tethered coferon monomers with the same ligands in accordance with the present invention. K5 is a schematic drawing of a coferon tetramer consisting of two coferon monomers with one ligand and two coferon monomers with another ligand pursuant to the present invention. L5 is a schematic drawing of a coferon tetramer comprised of two tethered coferon monomers with the same ligands in accordance with the present invention attached to an encoded bead via tethers and two coferon monomers with two different ligands in accordance with the present invention with DNA barcodes attached through the linker elements. M5 is a schematic drawing of a coferon tetramer comprised of two tethered coferon monomers with the same ligands in accordance with the present invention attached to encoded beads via tethers and two coferon monomers with two different ligands in accordance with the present invention. N5 is a schematic drawing of a coferon tetramer consisting of two monomer coferons with one ligand and two monomer coferons with two different ligands pursuant to the present invention.

FIG. 2.12 show variations of the components of coferon drug design. O5 is a schematic drawing of a coferon tetramer including four monomer coferons with the same ligand pursuant to the present invention. P5 is a schematic drawing of a coferon tetramer comprising four monomer coferons with two different linker elements but the same ligand pursuant to the present invention. Q5 is a schematic drawing of a coferon tetramer including two monomer coferons with one ligand and two monomer coferons with another ligand pursuant to the present invention. R5 is a schematic drawing of a coferon dimer comprising two coferon monomers with the same ligand pursuant to the present invention. S5 is a schematic drawing of a coferon dimer including two coferon monomers with two different linker elements but the same ligand pursuant to the present invention. T5 is a schematic drawing of a coferon dimer comprising one coferon monomer with one ligand and one coferon monomer with another ligand pursuant to the present invention.

FIG. 2.13 show variations of the components of coferon drug design. A6 is a schematic drawing of a coferon hexamer comprised of six tethered coferon monomers with the same linker elements, connectors, and the same ligands in accordance with the present invention attached to an encoded bead via tethers. B6 is a schematic drawing of a coferon hexamer comprised of six tethered coferon monomers with the same linker elements, connectors, and the same ligands in accordance with the present invention with a DNA barcode attached through the tether. C6 is a schematic drawing of a coferon hexamer comprised of six tethered coferon monomers with two different linker elements, connectors, and the same ligands in accordance with the present invention attached to an encoded bead via tethers. D6 is a schematic drawing of a coferon hexamer comprised of six tethered coferon monomers with two different linker elements, connectors, and the same ligands in accordance with the present invention with a DNA barcode attached through the tether. E6 is a schematic drawing of a coferon hexamer comprised of six tethered coferon monomers with two different linker elements, connectors, and two different ligands in accordance with the present invention attached to encoded beads via tethers. F6 is a schematic drawing of a coferon hexamer comprised of six tethered coferon monomers with two different linker elements, connectors, and two different ligands in accordance with the present invention with a DNA barcode attached through the tether.

FIG. 2.14 show variations of the components of coferon drug design. G6 is a schematic drawing of a coferon trimer comprised of three tethered coferon monomers with the same linker elements, connectors, and the same ligands in accordance with the present invention attached to an encoded bead via tethers. H6 is a schematic drawing of a coferon trimer comprised of three tethered coferon monomers with the same linker elements, connectors, and the same ligands in accordance with the present invention with a DNA barcode attached through the tether. I6 is a schematic drawing of a coferon hexamer comprised of three tethered coferon monomers with the same ligands in accordance with the present invention attached to encoded beads via tethers and a coferon trimer comprised of three tethered coferon monomers with the same ligands in accordance with the present invention with a DNA barcode attached through the tether. J6 is a schematic drawing of a coferon hexamer comprised of three tethered coferon monomers with the same ligands in accordance with the present invention attached to an encoded bead via tethers and a coferon trimer comprised of three tethered coferon monomers with the same ligands in accordance with the present invention. K6 is a schematic drawing of a coferon hexamer including three coferon monomers with one ligand and three coferon monomers with another ligand pursuant to the present invention. L6 is a schematic drawing of a coferon hexamer comprising six coferon monomers with the same ligand pursuant to the present invention. M6 is a schematic drawing of a coferon hexamer including six coferon monomers with two different linker elements but the same ligand pursuant to the present invention. N6 is a schematic drawing of a coferon trimer comprising two coferon monomers with one linker element and the same ligand, and one coferon monomer with another linker element and another ligand pursuant to the present invention.

FIG. 2.15 show variations of the components of coferon drug design. A7 is a schematic drawing of a coferon hexamer comprised of six tethered coferon monomers with the same linker elements and the same ligands in accordance with the present invention attached to an encoded bead via tethers. B7 is a schematic drawing of a coferon hexamer comprised of six tethered coferon monomers with the same linker elements, and the same ligands in accordance with the present invention with a DNA barcode attached through the tether. C7 is a schematic drawing of a coferon hexamer comprised of six tethered coferon monomers with two different linker elements and the same ligands in accordance with the present invention attached to encoded beads via tethers. D7 is a schematic drawing of a coferon hexamer comprised of six tethered coferon monomers with two different linker elements and the same ligands in accordance with the present invention with a DNA barcode attached through the tether. E7 is a schematic drawing of a coferon hexamer comprised of six tethered coferon monomers with two different linker elements and two different ligands in accordance with the present invention attached to an encoded bead tethers. F7 is a schematic drawing of a coferon hexamer comprised of six tethered coferon monomers with two different linker elements and two different ligands in accordance with the present invention with a DNA barcode attached through the tether.

FIG. 2.16 show variations of the components of coferon drug design. G7 is a schematic drawing of a coferon trimer comprised of three tethered coferon monomers with the same linker elements and the same ligands in accordance with the present invention attached to an encoded bead via tethers. H7 is a schematic drawing of a coferon trimer comprised of three tethered coferon monomers with the same linker elements and the same ligands in accordance with the present invention with a DNA barcode attached through the tether. I7 is a schematic drawing of a coferon hexamer comprised of three tethered coferon monomers with the same ligands in accordance with the present invention attached to encoded beads via tethers and a coferon trimer comprised of three tethered coferon monomers with the same ligands in accordance with the present invention with a DNA barcode attached through the tether. J7 is a schematic drawing of a coferon hexamer comprised of three tethered coferon monomers with the same ligands in accordance with the present invention attached to an encoded bead via tethers and a coferon trimer comprised of three tethered coferon monomers with the same ligands in accordance with the present invention. K7 is a schematic drawing of a coferon hexamer including three coferon monomers with one ligand and three coferon monomers with another ligand pursuant to the present invention. L7 is a schematic drawing of a coferon hexamer comprising six coferon monomers with the same ligand pursuant to the present invention. M7 is a schematic drawing of a coferon hexamer including six coferon monomers with two different linker elements but the same ligand pursuant to the present invention. N7 is a schematic drawing of a coferon trimer comprising two coferon monomers with one linker element and the same ligand, and one coferon monomer with another linker element and another ligand pursuant to the present invention.

FIG. 2.17 show variations of coferon drug interactions with a target. Coferon 1 is illustrated as a purple "L" linker element tethered to a yellow hexagon ligand, coferon 2 as an orange "upsidedown L" linker element tethered to a green oval ligand, and the target protein as a light blue shape. A substrate is illustrated as a deep orange dumbbell shaped object, and the cleavage products as the two halves. A binding partner of the target is illustrated as a dark blue shape. A is a schematic drawing of a substrate binding to and being cleaved by the target. B is a schematic drawing of two coferon monomers binding to and forming a coferon dimer on the target whose dissociation constant is less than or equal to the dissociation constant of the substrate, thus inhibiting the substrate from binding to and being cleaved by the target. C is a schematic drawing of two coferon monomers binding to and forming a coferon dimer on the target whose dissociation constant is less than or equal to the dissociation constant of a binding protein, thus displacing the binding protein from binding to the target.

FIG. 2.18 show variations of coferon drug interactions with a target. Coferon 1, coferon 2 and the target protein are described above. Activation of the target protein, for example, by turning on a kinase activity, is illustrated by an arc of red lines. An activating binding partner of the target is illustrated as a purple shape. An inhibiting binding partner of the target is illustrated as a green shape. D is a schematic drawing of an activating binding partner binding to and activating the target. E is a schematic drawing of two coferon monomers binding to and forming a coferon dimer on the target, mimicking the activating binding partner by activating the target. F is a schematic drawing of an inactivating binding partner binding to and inactivating the target. G is a schematic drawing of two coferon monomers binding to and forming a coferon dimer on the target, mimicking the inactivating binding partner by inactivating the target.

FIG. 2.19 show the variations of coferon drug interactions with a target. Coferon 1, coferon 2 and the target protein are described above. Activation of the target protein, for example, by turning on a kinase activity, is illustrated by an arc of red lines, with intensity of activation suggested by the number of red lines in the arc. An activating binding partner of the target is illustrated as a green shape. An inhibiting binding partner of the target is illustrated as a purple shape. H is a schematic drawing of an activating binding partner binding to and mildly activating the target (upper pathway). Addition of two coferon monomers allows binding to and forming a coferon dimer on the activating binding partner-target complex, thus enhancing activation of the target (lower pathway). I is a schematic drawing of an inactivating binding partner binding to and mildly inactivating the target (upper pathway). Addition of two coferon monomers allows binding to and forming a coferon dimer on the activating binding partner-target complex, thus enhancing inactivation of the target (lower pathway).

FIG. 2.20 show variations of coferon drug interactions with a target. Coferon 1, coferon 2 and the target protein are described above. A mutant target protein is illustrated as a light blue shape with a red "M". Activation of the target protein, for example, by turning on a kinase activity, is illustrated by an arc of red lines, with intensity of activation suggested by the number of red lines in the arc. An activating binding partner of the target is illustrated as a green shape. J is a schematic drawing of an activating binding partner binding to and activating the wild-type target. K is a schematic drawing of an activating binding partner binding to and mildly activating the mutant target (upper pathway). Addition of two coferon monomers allows binding to and forming a coferon dimer on the mutant target, thus enhancing activation of the mutant target (lower pathway).

FIG. 2.21 show variations of coferon drug interactions with a target. Coferon 1, coferon 2 and the target protein are described above. A mutant target protein is illustrated as a light blue shape with a red "M". Inactivation of the target protein, is illustrated by (loss of) an arc of red lines, with intensity of activation suggested by the number of red lines in the arc. An inactivating binding partner of the target is illustrated as a purple shape. L is a schematic drawing of an inactivating binding partner binding to and inactivating the wild-type target. M is a schematic drawing of an inactivating binding partner binding to and mildly inactivating the (over-activated) mutant target (upper pathway). Addition of two coferon monomers allows binding to and forming a coferon dimer on the mutant target, thus enhancing inactivation of the mutant target (lower pathway).

FIG. 2.22 show variations of coferon drug interactions with a target. Coferon 1, coferon 2 and the target protein are described above. A first binding partner, with weak affinity to the target is illustrated as a green shape. A second binding partner with affinity to the target, coferons, and first binding partner is illustrated as a deep orange shape. N is a schematic drawing of the first binding partner binding weakly to the target. O is a schematic drawing of the first binding partner binding weakly to the target (upper pathway). Addition of two coferon monomers allows binding to and forming a coferon dimer on the target, recruiting the second binding partner to bind to the target, coferons, and first binding partner, forming a coferon dimer-target-second binding protein complex, and thus enhancing binding of the first binding partner to the target (lower pathway).

FIG. 2.23 show variations of coferon drug interactions with a target. Coferon 1, coferon 2 and the target protein are described above. A first binding partner, with strong affinity to the target is illustrated as a dark blue shape. A second binding partner with affinity to the target and coferons is illustrated as a deep orange shape. P is a schematic drawing of the first binding partner binding strongly to the target. Q is a schematic drawing of the first binding partner binding strongly to the target (upper pathway). Addition of two coferon monomers allows binding to and forming a coferon dimer on the target, recruiting the second binding partner to bind to the target and coferons forming a coferon dimer-target-second binding protein complex, whose dissociation constant is less than or equal to the dissociation constant of the first binding protein, thus displacing the first binding protein from binding to the target (lower pathway).

FIG. 2.24 show the variations of coferon drug interactions with a target. Coferon 1, coferon 2 and the target protein are described above. A first binding partner, with weak or no affinity to the target is illustrated as a green shape. A second binding partner with affinity to the target, coferons, and/or first binding partner is illustrated as a deep orange shape. R is a schematic drawing of two coferon monomers binding to and forming a coferon dimer on the target, recruiting the second binding partner to bind to the target, coferons, and first binding partner, forming a coferon dimer-target-second binding protein complex, and thus recruiting the first binding partner to the target. S is a schematic drawing of two coferon monomers binding to and forming a coferon dimer on the target, recruiting the second binding partner to bind to the target, coferons, and first binding partner, forming a coferon dimer-target-second binding protein complex, and thus recruiting the first binding partner to the target. T is a schematic drawing of two coferon monomers binding to and forming a coferon dimer on the target and the first binding protein, recruiting the second binding partner to bind to the target and first binding partner, forming a coferon dimer-target-first binding protein-second binding protein complex, and thus recruiting the first binding partner to the target.

FIG. 2.25 show variations of coferon drug interactions with a target. Coferon 1, coferon 2 and the target protein are described above. The natural ligand for the receptor dimer is a deep orange oval, and the membrane as a semi-transparent yellow line. Activation of the target protein, for example, by turning on a kinase activity, is illustrated by an arc of red lines, with intensity of activation suggested by the number of red lines in the arc. A2 is a schematic drawing of an activating ligand binding to the receptor target, facilitating receptor dimerization, and activating the receptor target. B2 is a schematic drawing of two coferon monomers binding to and forming a coferon dimer on the target, mimicking the activating ligand, facilitating receptor dimerization, and activating the receptor target.

FIG. 2.26 show variations of coferon drug interactions with a target. Coferon 1, coferon 2 and the target protein are described above. The natural ligand for the receptor dimer is a deep orange oval, and the membrane is a semi-transparent yellow line. C2 is a schematic drawing of two coferon monomers binding to and forming a coferon dimer on the target, interfering with proper receptor dimerization, and inhibiting activation of the receptor target. D2 is a schematic drawing of two coferon monomers binding to and forming a coferon dimer on each target, inhibiting activation at an allosteric site, even in the presence of activating ligand that facilitates receptor dimerization.

FIG. 2.27 shows variations of coferon drug interactions with a target. Coferon 1, coferon 2 and the target protein are described above. The natural ligand for the receptor dimer is a deep orange oval, and the membrane is a semi-transparent yellow line. Activation of the target protein, for example, by turning on a kinase activity, is illustrated by an arc of red lines, with intensity of activation suggested by the number of red lines in the arc. FIG. 2.27 is a schematic drawing of two coferon monomers binding to and forming a coferon dimer on each target, enhancing activation at an allosteric site, which is enhanced in the presence of activating ligand that facilitates receptor dimerization.

FIG. 2.28 show variations of coferon drug interactions with a target. Coferon 1, coferon 2 and the target protein are described above, The natural ligand for the receptor dimer is a deep orange imperfect oval, and the membrane is a semi-transparent yellow line. A binding partner, with affinity to the target upon binding its ligand, is illustrated as a green shape. Upon binding the target protein, the binding partner may be activated, for example, by turning on a kinase activity, and is illustrated by an arc of red lines, with intensity of activation suggested by the number of red lines in the arc. F2 is a schematic drawing of the natural ligand binding to the receptor target, which recruits and activates the binding partner. G2 is a schematic drawing of two coferon monomers binding to and forming a coferon dimer on the receptor target at the ligand binding site to act as an agonist, mimicking the natural ligand, which recruits and activates the binding partner. H2 is a schematic drawing of two coferon monomers binding to and forming a coferon dimer on the receptor target at the ligand binding site to act as an antagonist, and thus inhibits recruitment and activation of the binding partner.

FIG. 2.29 show variations of coferon drug interactions with a target. Coferon 1, coferon 2, and the target protein are described above. The natural ligand for the receptor dimer is a deep orange imperfect oval, and the membrane as a semi-transparent yellow line. A binding partner, with affinity to the target upon binding its ligand, is illustrated as a green shape. Upon binding the target protein, the binding partner may be activated, for example, by turning on a kinase activity, and is illustrated by an arc of red lines, with intensity of activation suggested by the number of red lines in the arc. I2 is a schematic drawing of two coferon monomers binding to and forming a coferon dimer on the receptor target at the binding partner binding site to act as an antagonist, and thus inhibit recruitment and activation of the binding partner. J2 is a schematic drawing of the natural ligand binding to the receptor target, which recruits and activates the binding partner, with two coferon monomers binding to and forming a coferon dimer on the receptor target and the binding partner, to enhance activation of the binding partner. K2 is a schematic drawing of the natural ligand binding to the receptor target, which recruits and activates the binding partner, with two coferon monomers binding to and forming a coferon dimer on the receptor target and the natural ligand, to enhance activation of the binding partner.

FIG. 2.30 show the variations of coferon drug interactions with a target. Coferon 1 is illustrated as a purple cylindrical linker element tethered to a yellow hexameric ligand, Coferon 2 is illustrated as an orange cylindrical linker element tethered to a green oval ligand, the dimer target protein as a light blue shape dimerized to the dark blue shape. A3 is a schematic drawing of two coferon monomers binding to form a coferon homodimer on the dimer target. B3 is a schematic drawing of a coferon tetramer comprised of four coferon monomers binding to form a coferon homotetramer on the dimer target. C3 is a schematic drawing of a coferon tetramer comprised of two coferon monomers with one ligand and two coferon monomers with a second ligand binding to form a coferon heterotetramer on the dimer target.

FIG. 2.31 show variations of coferon drug interactions with a target. Coferon 1 is illustrated as a purple cylindrical linker element tethered to a yellow hexameric ligand, Coferon 2 is illustrated as an orange cylindrical linker element tethered to a green oval ligand, Coferon 3 is illustrated as an light pink cylindrical linker element tethered to a pink star ligand, the multimeric target proteins are comprised of the larger cylinders with different shades of blue and orange. A cell membrane is illustrated as a semi-transparent yellow line. D3 is a schematic drawing of a coferon tetramer comprised of two coferon monomers with one ligand and two coferon monomers with a second ligand, binding to form a coferon heterotetramer on a multimeric target. E3 is a schematic drawing of a coferon tetramer comprised of two coferon monomers with one ligand and two different coferon monomers with a second and third ligand, binding to form a coferon heterotetramer on a multimeric target. F3 is a schematic drawing of a coferon hexamer comprised of three coferon monomers with one ligand and three coferon monomers with a second ligand, binding to form a coferon heterohexamer on a multimeric target.

FIG. 2.32 show the variations of coferon drug interactions with a target. Coferon 1 is illustrated as a purple "L" linker element tethered to a yellow hexameric ligand, Coferon 2 is illustrated as an orange "L" linker element tethered to a green oval ligand, and the target tubulin heterodimer as the blue and purple circles. A4 is a schematic drawing of alpha and beta tubulin heterodimers combining to form polymerized tubulin filaments. B4 is a schematic drawing of two coferon monomers binding to form a coferon dimer on the tubulin dimer target, thus destabilizing filament formation.

FIG. 2.33 show variations of coferon drug interactions with a target. Coferon 1 is illustrated as a purple "L" linker element tethered to a yellow hexameric ligand, Coferon 2 is illustrated as an orange "L" linker element tethered to a green oval ligand, the target amyloid beta peptide as the blue hexamers, circles, and rounded squares. D4 is a schematic drawing of amyloid beta peptide monomers aggregating to form small oligomers, large oligomers, protofibriles and amyloid fibrils that cause Alzheimer's Disease. E4 is a schematic drawing of two coferon monomers binding to form a coferon dimer on the amyloid beta peptide monomers, thus inhibiting aggregation and disease.

FIG. 2.34 show variations of coferon drug interactions with an RNA target. Coferon 1 is illustrated as a purple "L" linker element tethered to a thick blue line illustrating RNA or oligomer nucleotide analogue that is complementary to the desired target, Coferon 2 is illustrated as an orange "L" linker element tethered to a thick green line illustrating RNA or oligomer nucleotide analogue that is complementary to the desired target, the desired RNA target illustrated as a deep orange line with complementary sequences illustrated as light blue and light green lines, with the incorrect RNA targets illustrated as light orange line with complementary or nearly complementary sequences illustrated as light blue and light green lines, and with the membrane illustrated as a thick curved line. A is a schematic drawing of the antisense oligonucleotide, which is transported across the membrane, to bind the desired RNA target, obtaining the desired biological effect, as well as some undesired off-target effects. B is a schematic drawing of the coferon oligonucleotides, which are transported across the membrane, they can bind adjacent to each other on the desired RNA target bringing the linker elements into proximity and allowing for formation of either reversible or irreversible bonds—greatly lowering the dissociation constant. If the coferon oligonucleotide monomers bind on off target sites, they will dissociate. Thus the coferon design allows for antisense oligonucleotide therapeutics to obtain the desired biological effect of inhibiting a specific RNA target, while minimizing undesired off-target effects.

FIG. 2.35 shows variations of coferon drug interactions with an RNA target. Coferon 1 is illustrated as a purple "L" linker element tethered to a thick blue line illustrating RNA or oligomer nucleotide analogue that is complementary to the desired target, Coferon 2 is illustrated as an orange "L" linker element tethered to a thick green line illustrating RNA or oligomer nucleotide analogue that is complementary to the desired target, lipocoferons or aminoglycoferons illustrated as short light purple bars tethered by reversible linkers such as disulfide bonds, the desired RNA target illustrated as a deep orange line with complementary sequences illustrated as light blue and light green lines, with the incorrect RNA targets illustrated as light orange line with complementary or nearly complementary sequences illustrated as light blue and light green lines, and with the membrane illustrated as a thick curved line. FIG. 2.35 is a schematic drawing of the coferon oligonucleotides bound to lipocoferons or aminoglycoferons to form lipophilic complexes, which are transported across the membrane. Once inside, intracellular glutathione reduces the disulfide bonds in the lipocoferons or aminoglycoferons, and they dissociate from the coferon oligonucleotides. The coferon oligonucleotides can then bind adjacent to each other on the desired RNA target bringing the linker elements into proximity and allowing for formation of either reversible or irreversible bonds—greatly lowering the dissociation constant. If the coferon oligonucleotide monomers bind on off target sites, they will dissociate. Thus, the coferon design allows for antisense oligonucleotide therapeutics to obtain the desired biological effect of inhibiting a specific RNA target, while minimizing undesired off-target effects.

FIG. 2.36 shows variations of coferon drug interactions with an RNA target. Coferon 1 is illustrated as a purple "L" linker element tethered to a thick blue line above an offset thick light blue line illustrating double-stranded RNA or oligomer nucleotide analogue that is complementary to the desired target, Coferon 2 is illustrated as an orange "L" linker element tethered to a thick green line above an offset thick light green line illustrating double-stranded RNA or oligomer nucleotide analogue that is complementary to the desired target, lipocoferons or aminoglycoferons illustrated as short light purple bars tethered by reversible linkers such as disulfide bonds. The RISC complex is illustrated as a light gray rounded rectangle, the desired RNA target illustrated as a deep orange line with complementary sequences illustrated as light blue and light green lines, with the incorrect RNA targets illustrated as light orange line with complementary or nearly complementary sequences illustrated as light blue and light green lines, and with the membrane illustrated as a thick curved line. FIG. 2.36 is a schematic drawing of the coferon oligonucleotides bound to lipocoferons or aminoglycoferons to form lipophilic complexes, which are transported across the membrane. Once inside, intracellular glutathione reduces the disulfide bonds in the lipocoferons or aminoglycoferons, and they dissociate from the coferon oligonucleotides. The coferon oligonucleotides can then bind adjacent to each other within the RISC complex, bringing the linker elements into proximity and allowing for formation of either reversible or irreversible bonds—and allowing for the complementary strands to be destroyed. The coferon dimer within the RISC complex can now enzymatically degrade multiple copies of the desired RNA target.

FIG. 14 shows schematic drawings for linker element screening in accordance with the present invention. A shows Version 1. B shows Version 2.

FIG. 15 shows schematic drawings for linker element screening in accordance with the present invention. A shows Version 3. B shows Version 4.

FIG. 17 shows schematic drawings of components used in diversity element library synthesis for bead encoded libraries. A shows small molecule inhibitors and analogues. B and C show combinatorial chemistry on a common platform.

FIG. 20 is a first embodiment for target screening in accordance with the present invention. In step 1, a library of ligands is synthesized on beads which may be individually identified through barcodes. Each monomer element consists of a low MW (approx. 600-800) binding ligands (diversity element) covalently linked to a low MW (approx. under 300) linker element (dynamic combinatorial chemistry element). The beads are incubated with fluorescently labeled target protein to identify ligands that bind most tightly to the target. In step 2, the top set of these ligands are resynthesized with the option of adding additional diversity in the connector between the linker element and the ligand diversity element. A second library of ligands is synthesized, where each monomer element consists of a low MW binding ligand (diversity element) covalently linked to a DNA barcode (allowing for stepwise synthesis and identification of the binding ligand) as well as a low MW linker element, suitable for reversible binding to the linker element element in the first library. Under physiological conditions, different combinations of ligands are forming and reassociating with each other. The surface bound and solution diversity element libraries are panned with fluorescently labeled target protein. The protein targets will bind some combinations tighter than others, thus directing the evolution of combinations to the preferred pairs. DNA barcodes (colored lines), as shown in step 3, may be amplified using universal primers (black lines) to identify individual ligands, which serve as lead molecules.

FIG. 21 is a second embodiment for target screening in accordance with the present invention. As shown in step 1, two libraries of ligands are synthesized, one on beads, which may be individually identified through barcodes, and the second covalently linked to a DNA barcode (allowing for stepwise synthesis and identification of the binding ligand). Each monomer element consists of a low MW (approx. 600-800) binding ligand (diversity element) covalently linked to a low MW (approx. under 300) linker element (dynamic combinatorial chemistry element). Under physiological conditions, different combinations of ligands are forming and reassociating with each other through the linker elements. The two libraries are panned with fluorescently labeled target protein. The protein targets will bind some combinations tighter than others, thus directing the evolution of combinations to the preferred pairs. In step 2, DNA barcodes (colored lines) may be amplified using universal primers (black lines) to identify individual ligands. The top set of these ligands are resynthesized, as shown in step 3, in both bead and solution format, with the option of adding additional diversity in the connector between the linker element and the ligand diversity element. The surface bound and solution diversity element libraries are panned with fluorescently labeled target protein. The protein targets will bind some combinations tighter than others, thus directing the evolution of combinations to the preferred pairs. For step 4, DNA barcodes (colored lines) may be amplified using universal primers (black lines) to identify individual ligands, which serve as lead molecules.

FIG. 22 is a third embodiment for target screening in accordance with the present invention. In step 1, a library of ligands is synthesized, where each monomer element comprises a low MW (approx. 600-800) binding ligand (diversity element) covalently linked to DNA barcode (allowing for stepwise synthesis and identification of the binding ligand) as well as a low MW (approx. under 300) linker element (dynamic combinatorial chemistry element). The ligands are allowed to bind to target protein covalently linked to a solid support. For step 2, DNA barcodes (colored lines) may be amplified using universal primers (black lines) to identify individual ligands. The top set of these ligands are resynthesized with the option of adding additional diversity in the connector between the linker element and the ligand diversity element, as shown in step 3. A second library of ligands is synthesized, where each monomer element consists of a low MW binding ligand (diversity element) covalently linked to a DNA barcode as well as a low MW linker element, suitable for reversible binding to the linker element element in the first library. Under physiological conditions, different combinations of ligands are forming and reassociating with each other. The two diversity element libraries are panned with target protein on beads. The protein targets will bind some combinations tighter than others, thus directing the evolution of combinations to the preferred pairs. This enrichment-amplification-resynthesis selection process may be repeated to identify higher affinity ligand pairs. For step 4, DNA barcodes (colored lines) may be amplified using universal primers (black lines) to identify individual ligands, which serve as lead molecules.

FIG. 23 is a fourth embodiment for target screening in accordance with the present invention. A library of known ligands to a protein target such as a tyrosine kinase is synthesized, as shown in step 1. These ligands are covalently linked through a diverse number of connectors to DNA barcode (allowing for identification of the binding ligand) as well as a low MW (approx, under 300) linker element (dynamic combinatorial chemistry element). The ligands are all capable of binding to target protein covalently linked to a solid support. In step 2, a second library of ligands is synthesized, where each monomer element consists of a low MW binding ligand (diversity element) covalently linked to a DNA barcode as well as a low MW linker element, suitable for reversible binding to the linker element in the first library. Under physiological conditions, different combinations of ligands are forming and reassociating with each other. The two diversity element libraries are panned with target protein on beads. The protein targets will bind some combinations tighter than others, thus directing the evolution of combinations to the preferred pairs. (This enrichment-amplification-resynthesis selection process may be repeated to identify higher affinity ligand pairs.) In step 3, DNA barcodes (colored lines) may be amplified using universal primers (black lines) to identify individual ligands, which serve as lead molecules.

FIG. 24 is a fifth embodiment for target screening in accordance with the present invention. Two libraries of ligands are synthesized in step 1, where each monomer element consists of a low MW (approx. 600-800) binding ligand (diversity element) covalently linked to DNA barcode (allowing for stepwise synthesis and identification of the binding ligand) as well as a low MW (approx. under 300) linker element (dynamic combinatorial chemistry element). The linker element from the first library binds reversibly with the linker element from the second library, such that different combinations of ligands are forming and reassociating with each other. The two diversity element libraries are panned with target protein on beads. The protein targets will bind some combinations tighter than others, thus directing the evolution of combinations to the preferred pairs. In step 2, DNA barcodes (colored lines) may be amplified using universal primers (black lines) to identify individual ligands. The top set of these ligands are resynthesized in step 3 with the option of adding additional diversity in the connector between the linker element and the ligand diversity element. The extra diversity may be encoded in the DNA barcode in a region not used for generating ligand diversity in the first round of synthesis. The two refined diversity element libraries are again panned with target protein on beads. The protein targets will bind some combinations tighter than others, thus directing the evolution of combinations to the preferred pairs. This enrichment-amplification-resynthesis-selection process is analogous to Darwinian selection on diploid organisms and may be repeated to identify higher affinity ligand pairs. DNA barcodes (colored lines) may be amplified using universal primers (black lines) to identify individual ligands, which serve as lead molecules.

FIG. 25 is a schematic representation of a system for cycling pH for selection of coferons using cyclic combinatorial chemistry. A Nafion-117 membrane separates an upper compartment A from a lower compartment B. Compartment A contains beads, coferons, buffer (such as PIPS, TEEN, or PIPPS), and target protein. The buffer is chosen to provide the desired pH range based on pKa values for the buffer. Cation and water exchange between compartments A and B is mediated by piston pumps A and B. Cations cycle between $H^+$ and $Na^+$ or other equivalent cation. Compartment B is used to wash in and out different buffers in reservoirs C-E. Reservoir C contains an aqueous wash solution. Reservoir D contains $H^+$ or a low pH buffer. Reservoir E contains NaOH (or equivalent base), or a high pH buffer. During cycling, ionic strength and amount of buffer remain unchanged in Compartment A.

FIG. 26 is a schematic representation of a system for cycling metal ions for selection of metal co-factor coferons using cyclic combinatorial chemistry. A Nafion-117 membrane separates an upper compartment A from a lower compartment B. Compartment A contains beads, coferons, buffer (such as PIPS, TEEN, or PIPPS), and target protein. The buffer is chosen to provide the desired pH range based on pKa values for the buffer. Cation and water exchange between compartments A and B is mediated by piston pumps A and B. Cations cycle between $Zn^{2+}$ and $Na^+$. Compartment B is used to wash in and out different buffers in reservoirs C-E. Reservoir C contains an aqueous wash solution. Reservoir D contains $H^+$ or a low pH buffer. Reservoir E contains NaOH (or equivalent base), or a high pH buffer. During cycling, ionic strength and amount of buffer remain unchanged in Compartment A.

FIG. 27 is a schematic representation of a multimeric protein being inhibited by a coferon monomer that is capable of assembling in to a multimer. Protective antigen (PA) binds to the cellular anthrax receptor (ANTXR). The protective antigen is cleaved by a protease, while a 20 kDa fragment ($PA_{20}$) leaves, a 63 kDa fragment ($PA_{63}$) remains bound to the receptor. $PA_{63}$ self-associates forming a heptamer, $[PA_{63}]_7$, to which the edema factor (EF) and lethal factor (LF) bind. A coferon monomer that can self-assemble (self-recognizing coferon) in to a multimeric structure can bind and inhibit translocation of the EF/LF in to the cell.

Figure 103:
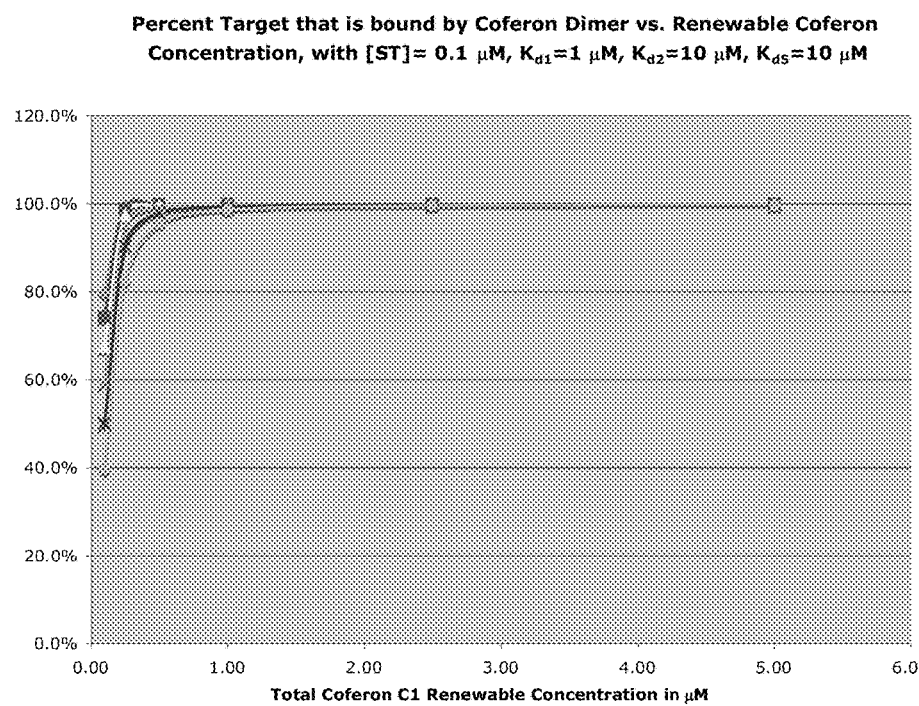

FIG. 103 is a graph showing the percent target T that is bound by coferon dimer C1C2 vs. "renewable" coferon C1 concentration. The total target [ST] is set at 0.1 μM, $K_{d1}$ is set at 1 μM, $K_{d2}$ is set at 10 μM, $K_{d5}$ is set at 10 μM, and steady-state or renewable coferon C1 concentration [C1]=steady-state or renewable coferon C2 concentration [C2], varying from 0.1 μM up to 5 μM concentration.

Figure 104:
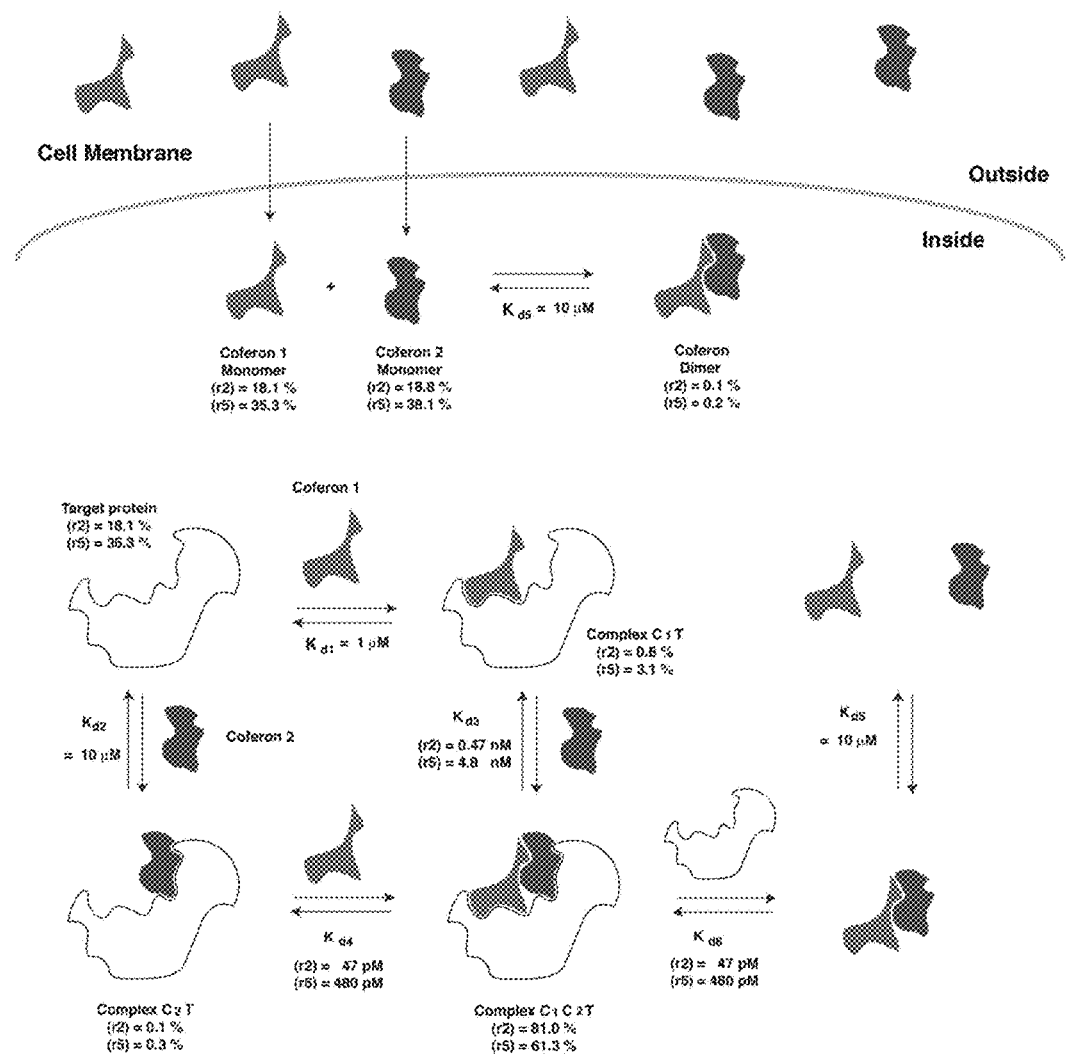

FIG. 104 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.1 μM, reflecting the ability to provide a steady dose of drug over time. The total protein concentration inside the cell is 0.25 μM, about 250,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d5}$ is given at 10 μM.

Figure 105:
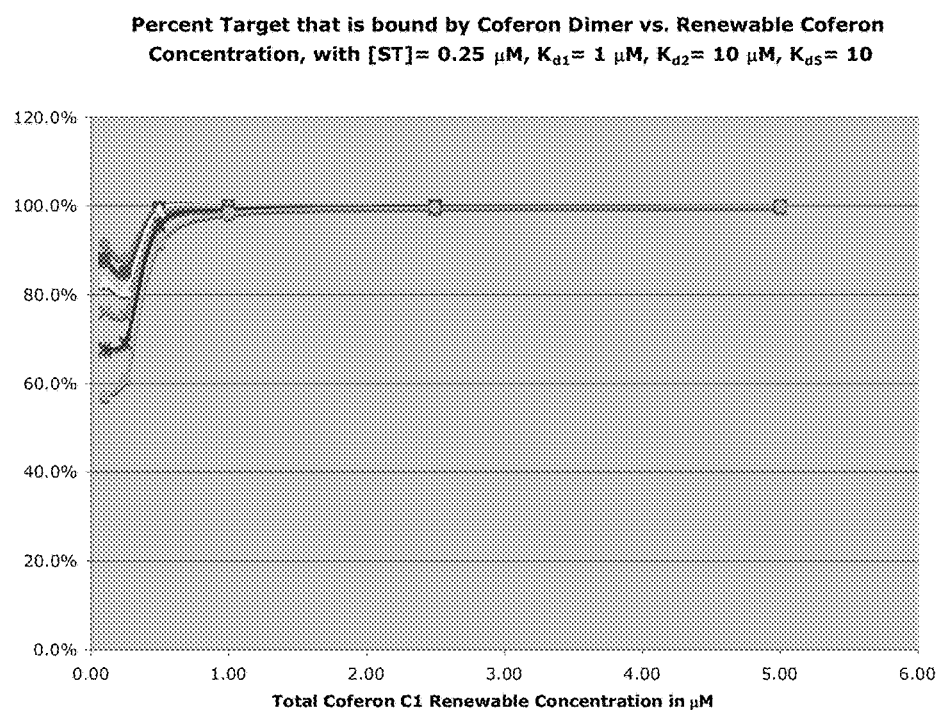

FIG. 105 is a graph showing the percent target T that is bound by coferon dimer C1C2 vs. "renewable" coferon C1 concentration. The total target [ST] is set at 0.25 μM, $K_{d1}$ is set at 1 uM, $K_{d2}$ is set at 10 μM, $K_{d5}$ is set at 10 μM, and steady-state or renewable coferon C1 concentration [C1]=steady-state or renewable coferon C2 concentration [C2], varying from 0.1 μM up to 5 μM concentration.

Figure 106:
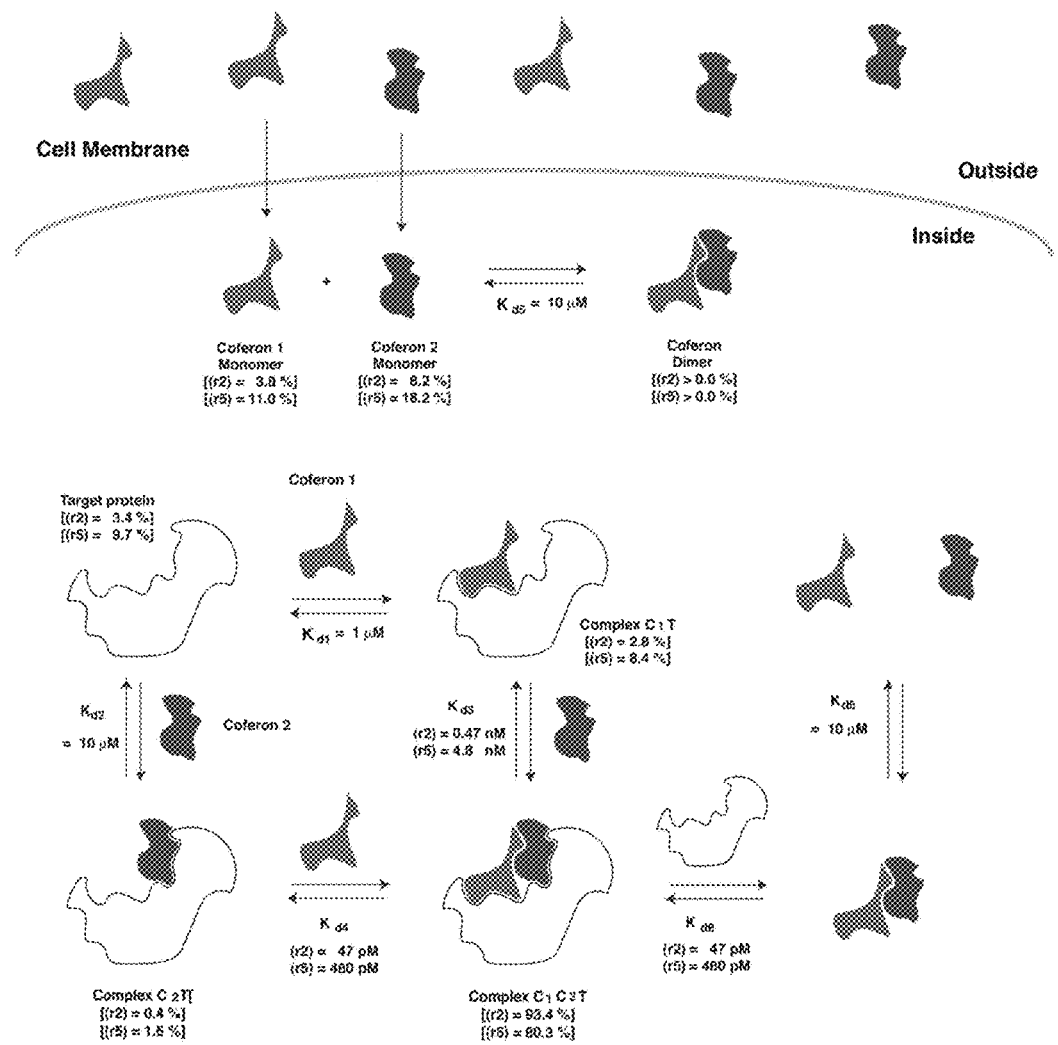

FIG. 106 is a schematic representation of two coferons (C1, and C2) that can enter cells as monomers, and bind to orthogonal sites on an internal protein target (T) to inhibit its activity. Coferon 1 is illustrated as a green shape, coferon 2 as a blue shape, and the target protein as a white shape. To more accurately simulate conditions in vivo, the steady-state or "renewable" concentrations of C1 and C2 are 0.25 μM, reflecting the ability to provide a steady dose of drug over time. The total protein concentration inside the cell is 1 μM, about 1,000,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d5}$ is given at 10 μM.

Figure 107:
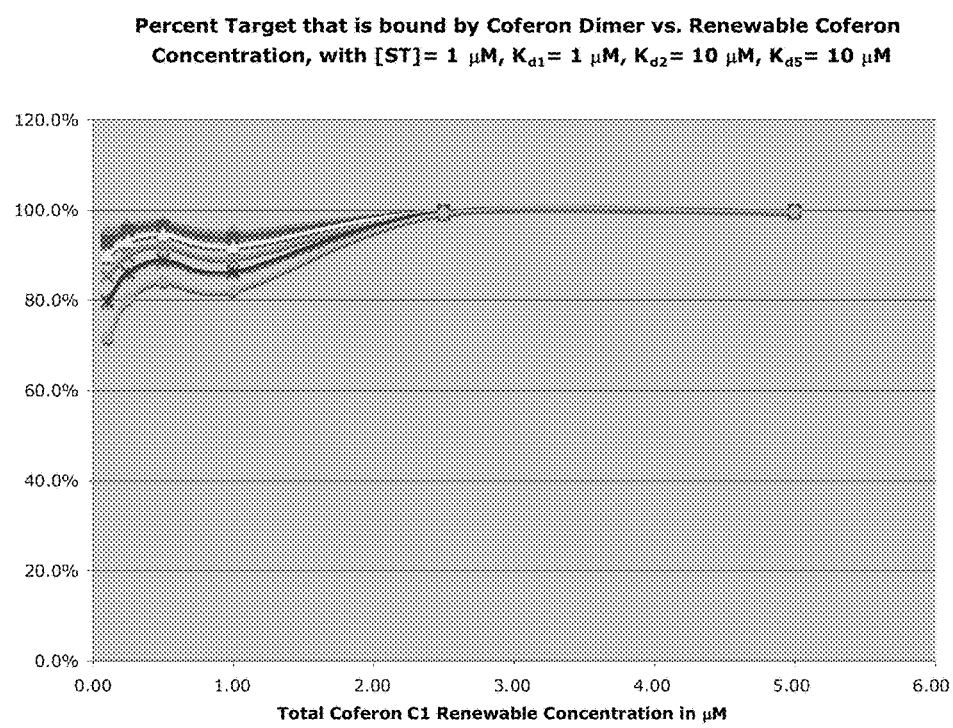

FIG. 107 is a graph showing the percent target T that is bound by coferon dimer C1C2 vs. "renewable" coferon C1 concentration. The total target [ST] is set at 1 μM, $K_{d1}$ is set at 1 μM, $K_{d2}$ is set at 10 μM, $K_{d5}$ is set at 10 μM, and steady-state or renewable coferon C1 concentration [C1]=steady-state or renewable coferon C2 concentration [C2], varying from 0.1 μM up to 5 μM concentration.

Figure 108:
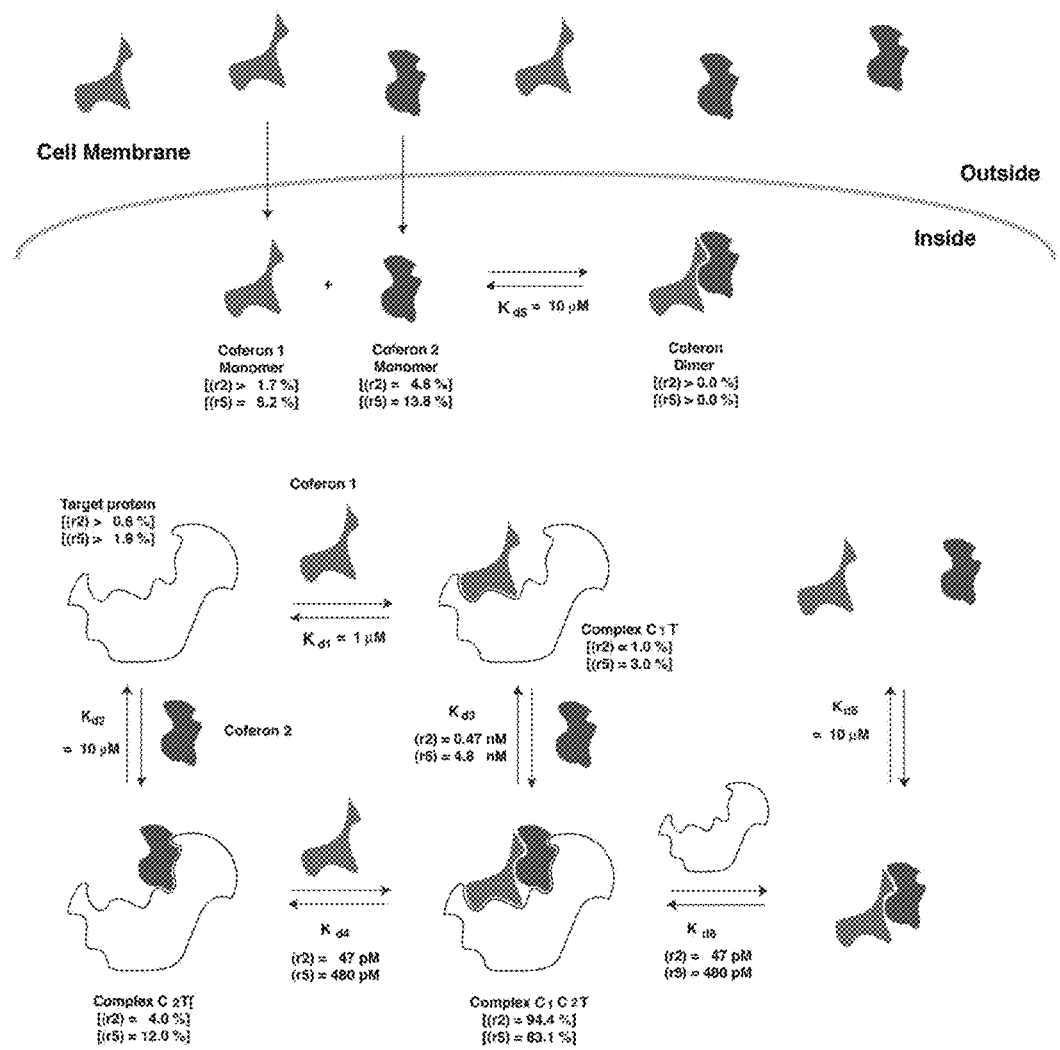

FIG. 108 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 μM, reflecting the ability to provide a steady dose of drug over time. The total protein concentration inside the cell is 2.5 μM, about 2,500,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d5}$ is given at 10 μM.

Figure 109:
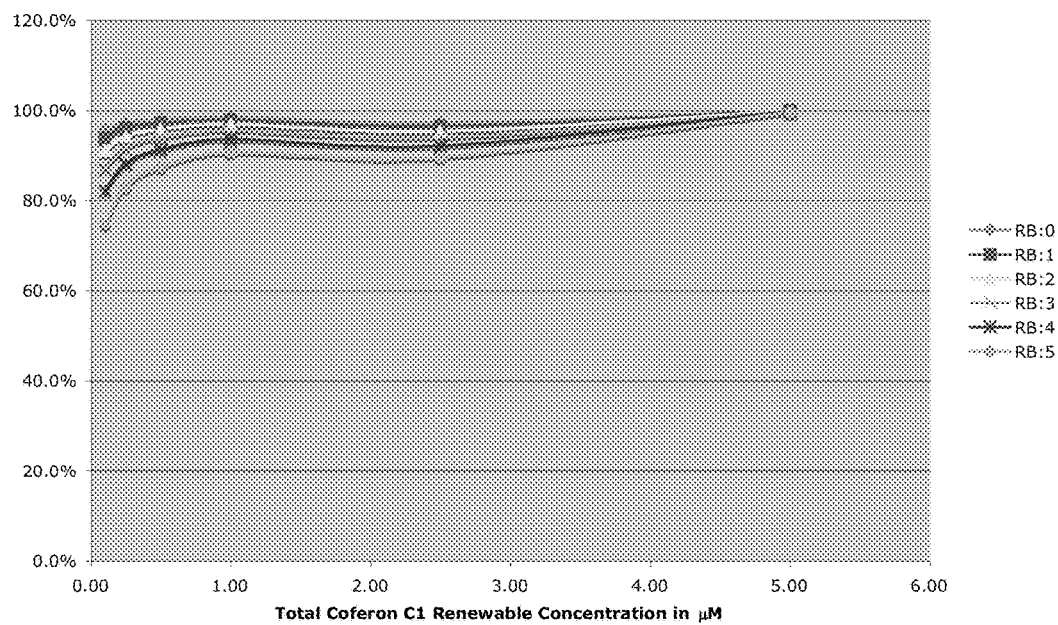

FIG. 109 is a graph showing the percent target T that is bound by coferon dimer C1C2 vs. "renewable" coferon C1 concentration. The total target [ST] is set at 2.5 μM, $K_{d1}$ is set at 1 μM, $K_{d5}$ is set at 10 μM, $K_{d5}$ is set at 10 μM, and steady-state or renewable coferon C1 concentration [C1]=steady-state or renewable coferon C2 concentration [C2], varying from 0.1 μM up to 5 μM concentration.

Figure 110:
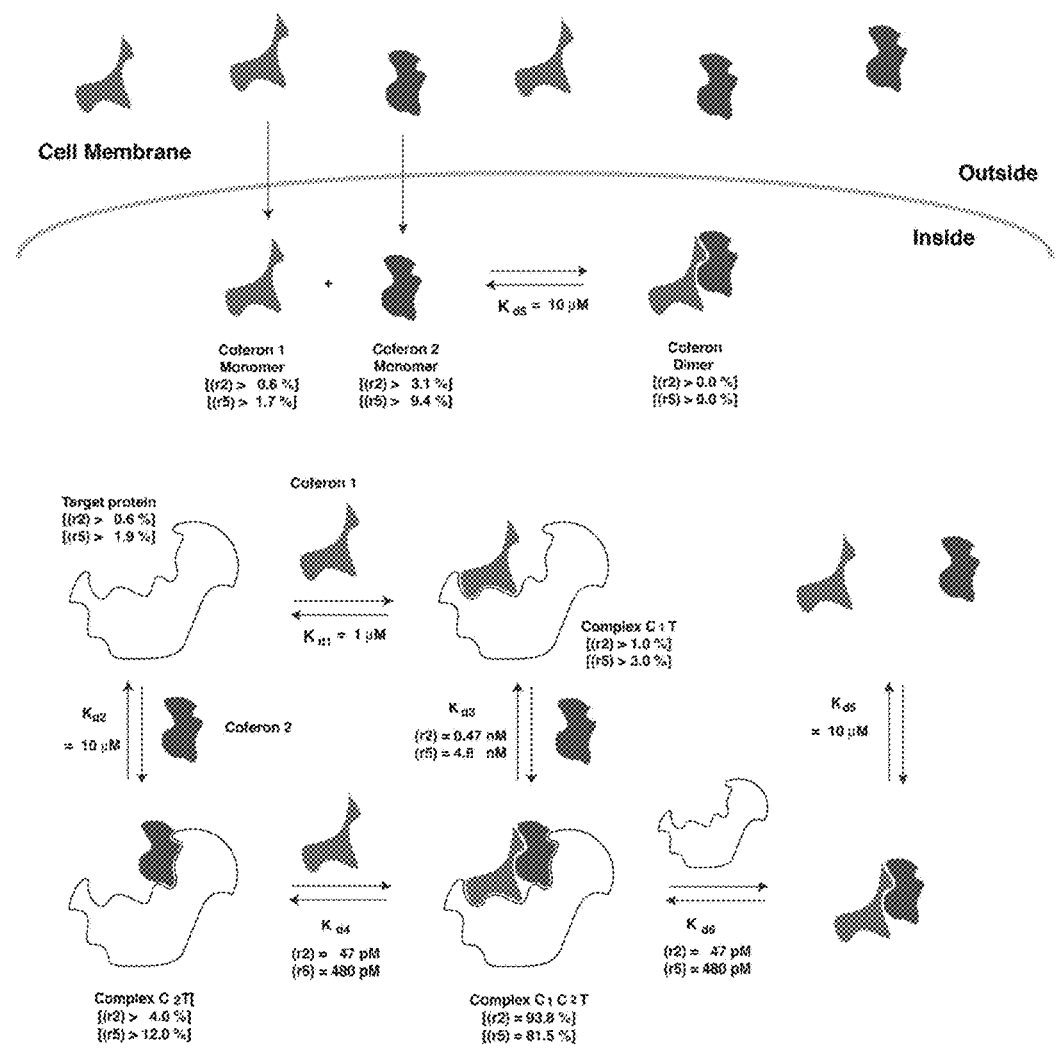

FIG. 110 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 μM, reflecting the ability to provide a steady dose of drug over time. The total protein concentration inside the cell is 10 μM, about 10,000,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d2}$ is given at 10 μM.

Figure 111:
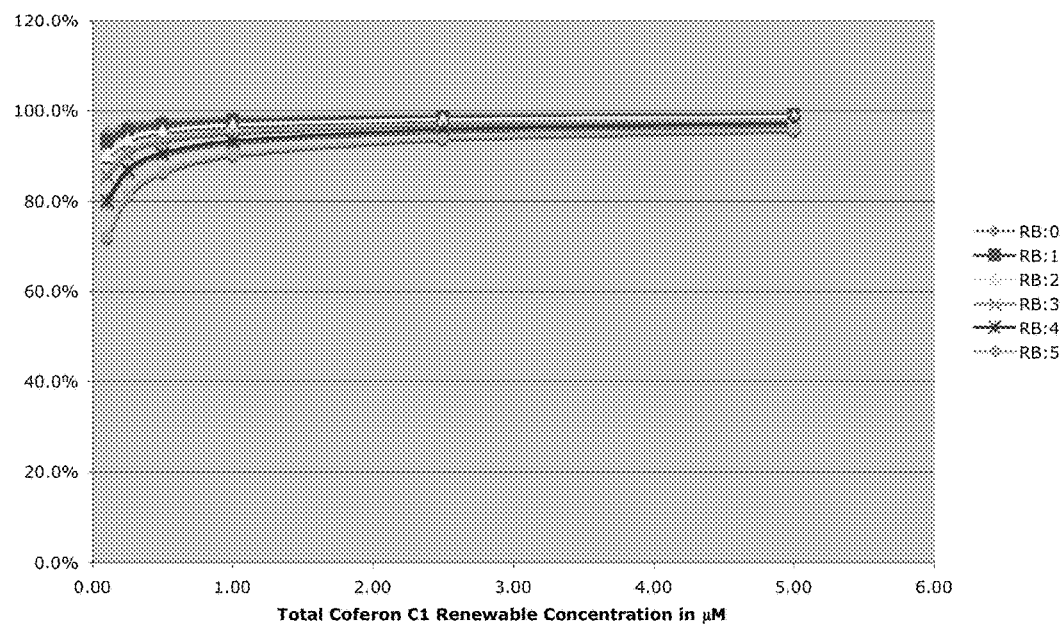

FIG. 111 is a graph showing the percent target T that is bound by coferon dimer C1C2 vs. "renewable" coferon C1 concentration. The total target [ST] is set at 10 μM, $K_{d1}$ is set at 1 μM, $K_{d2}$ is set at 10 μM, $K_{d5}$ is set at 10 μM, and steady-state or renewable coferon C1 concentration [C1]=steady-state or renewable coferon C2 concentration [C2], varying from 0.1 μM up to 5 μM concentration.

Figure 112:
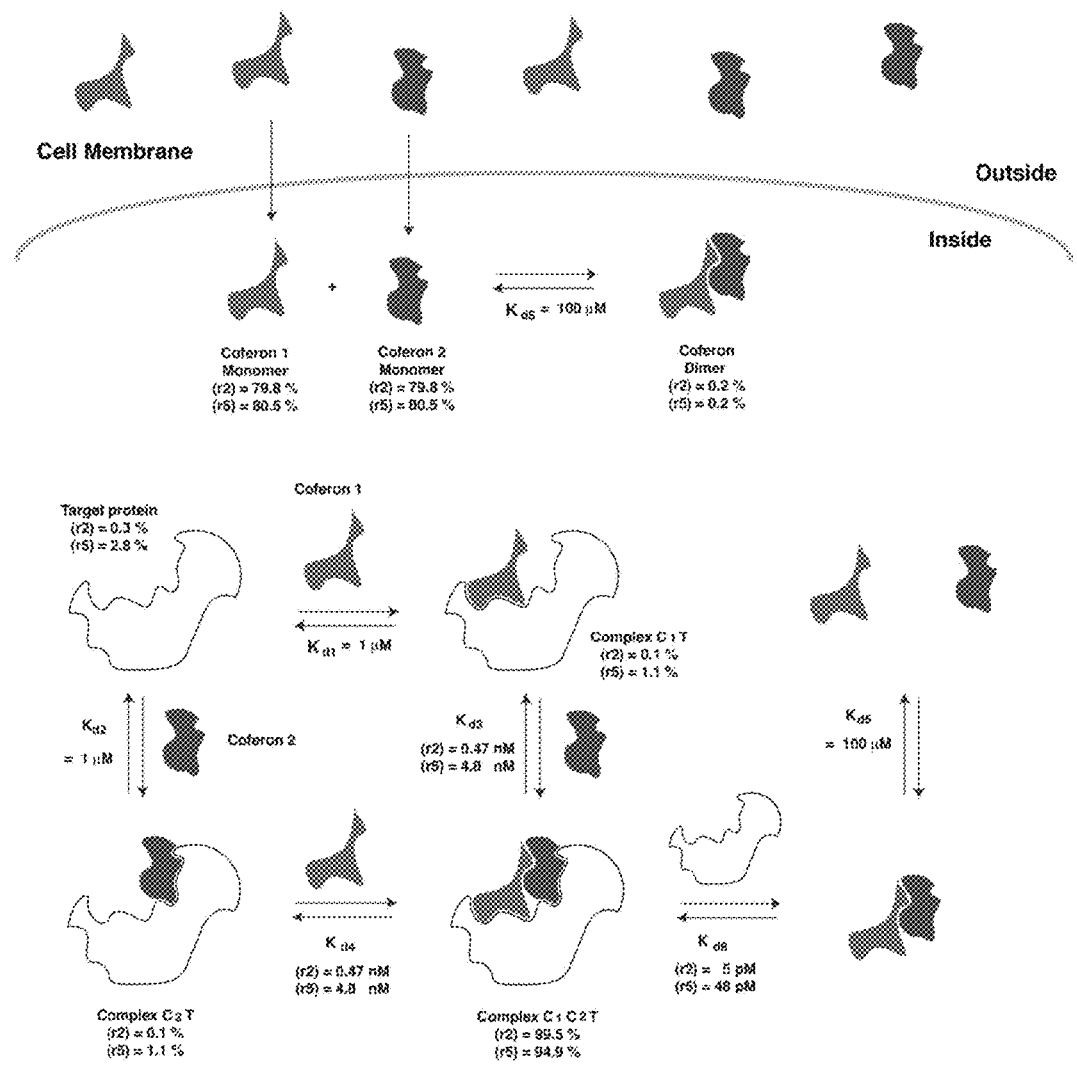

FIG. 112 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.5 μM, reflecting the ability to provide a steady dose of drug over time. The total protein concentration inside the cell is 0.1 μM, about 100,000 targets per cell. The dissociation constants $K_{d1}$ and $K_{d2}$ between coferon C1 and target T, as well as between coferon C2 and target T are given at 1 μM. The dissociation constant between the two coferons, $K_{d5}$ is given at 100 μM.

Figure 113:
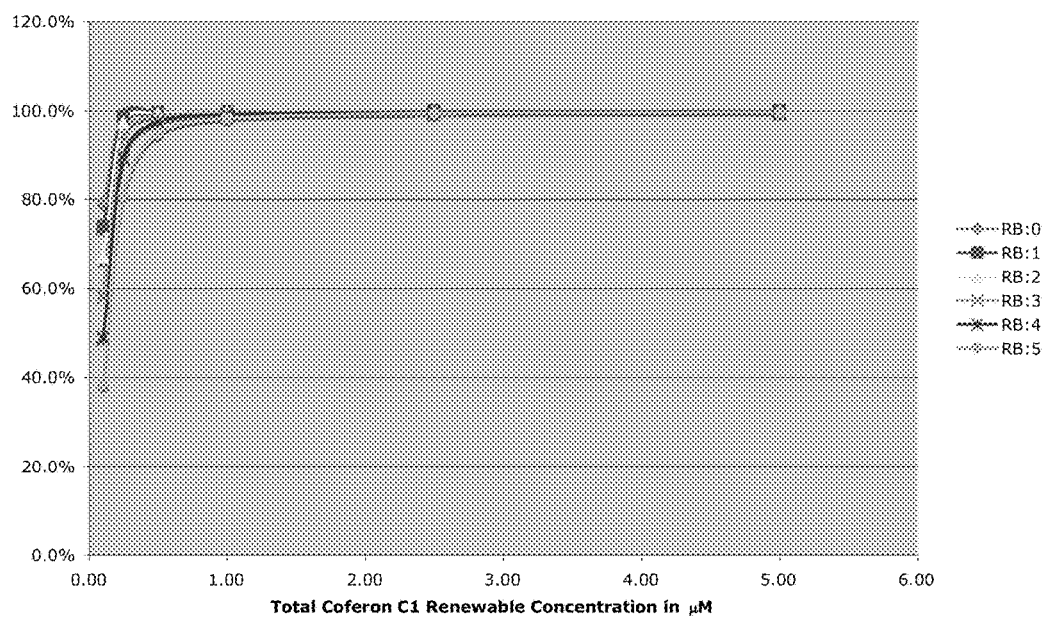

FIG. 113 is a graph showing the percent target T that is bound by coferon dimer C1C2 vs. "renewable" coferon C1 concentration. The total target [ST] is set at 0.1 μM, $K_{d1}=K_{d2}$ is set at 1 μM, $K_{d5}$ is set at 100 μM, and steady-state or renewable coferon C1 concentration [C1]=steady-state or renewable coferon C2 concentration [C2], varying from 0.1 μM up to 5 μM concentration.

Figure 114:
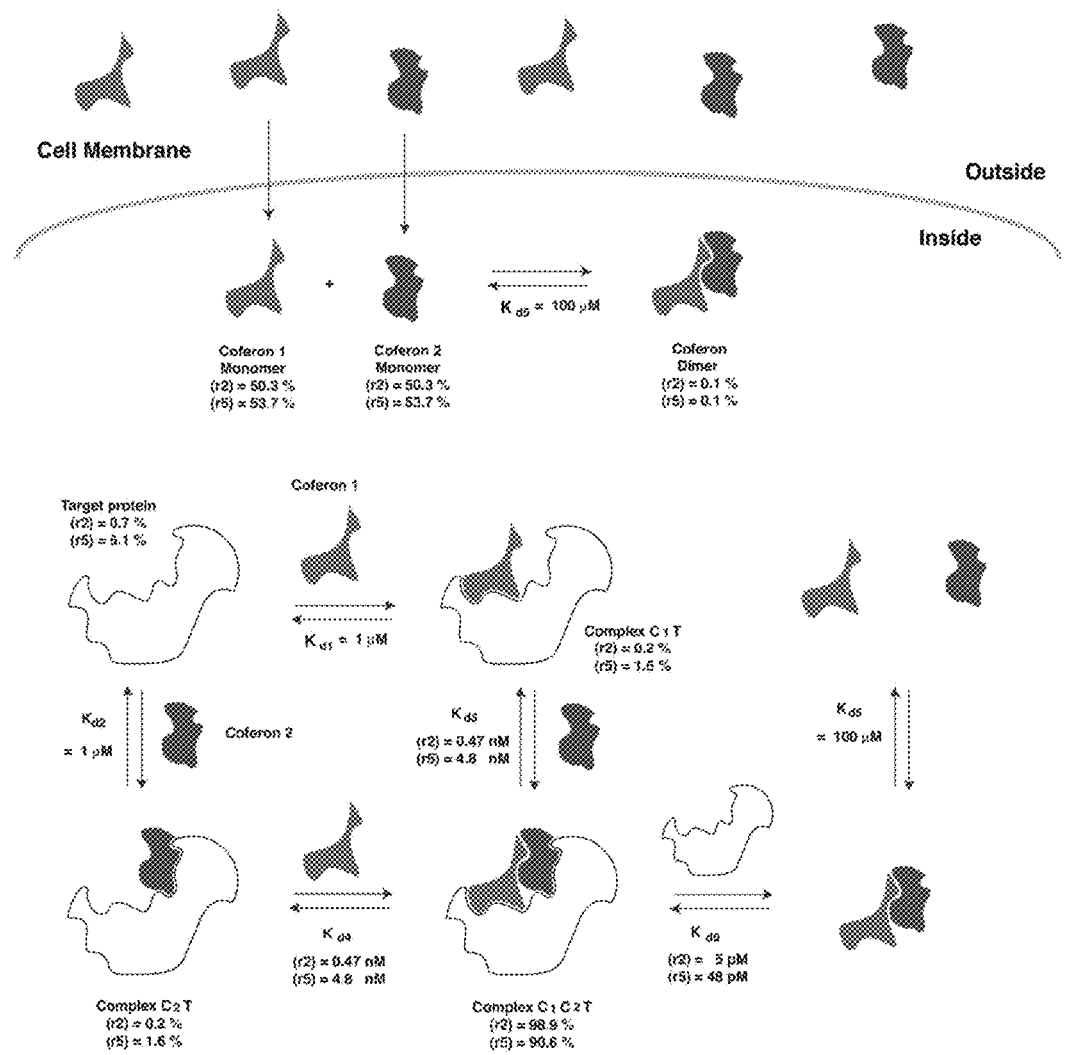

FIG. 114 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.1 µM, reflecting the ability to provide a steady dose of drug over time. The total protein concentration inside the cell is 0.25 µM, about 250,000 targets per cell. The dissociation constants $K_{d1}$ and $K_{d2}$ between coferon C1 and target T, as well as between coferon C2 and target T are given at 1 µM The dissociation constant between the two coferons, $K_{d5}$ is given at 100 µM.

Figure 115:
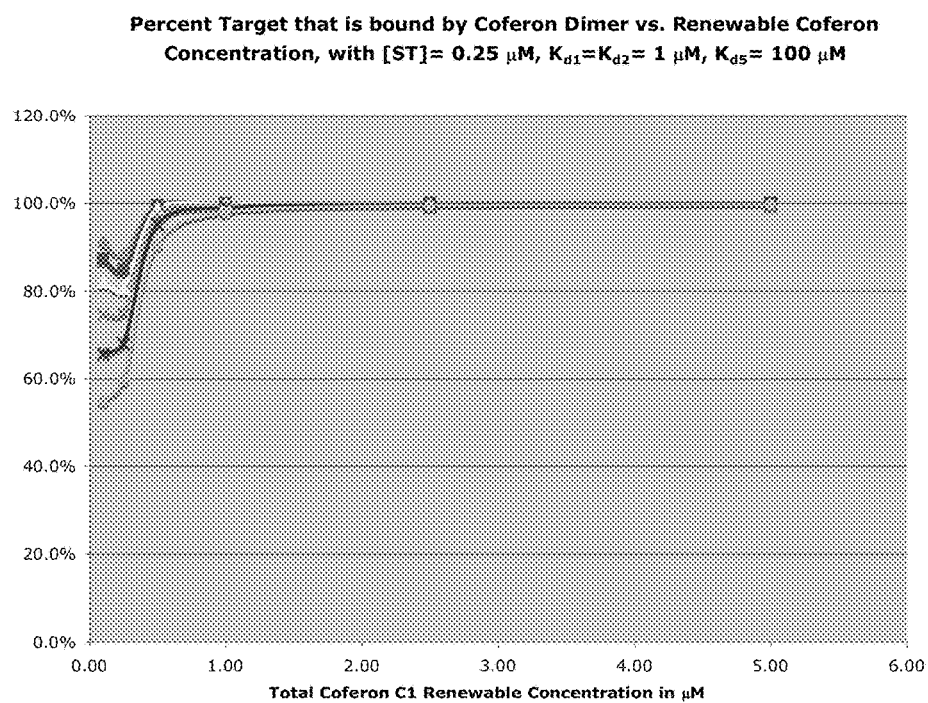

FIG. 115 is a graph showing the percent target T that is bound by coferon dimer C1C2 vs. "renewable" coferon C1 concentration. The total target [ST] is set at 0.25 µM, $K_{d1}=K_{d2}$ is set at 1 µM, $K_{d5}$ is set at 100 µM, and steady-state or renewable coferon C1 concentration [C1]=steady-state or renewable coferon C2 concentration [C2], varying from 0.1 µM up to 5 µM concentration.

Figure 116:
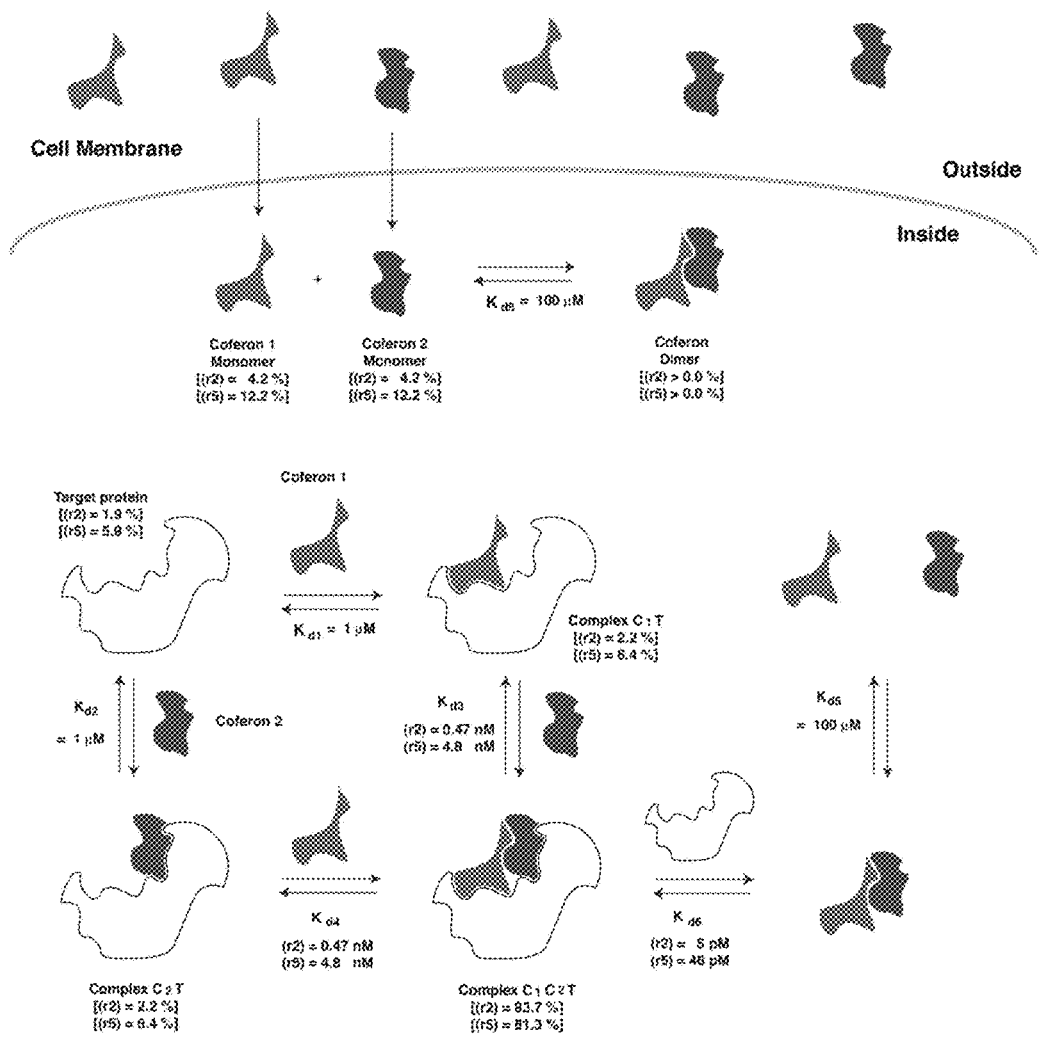

FIG. 116 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 1 µM, about 1,000,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 100 µM.

Figure 117:
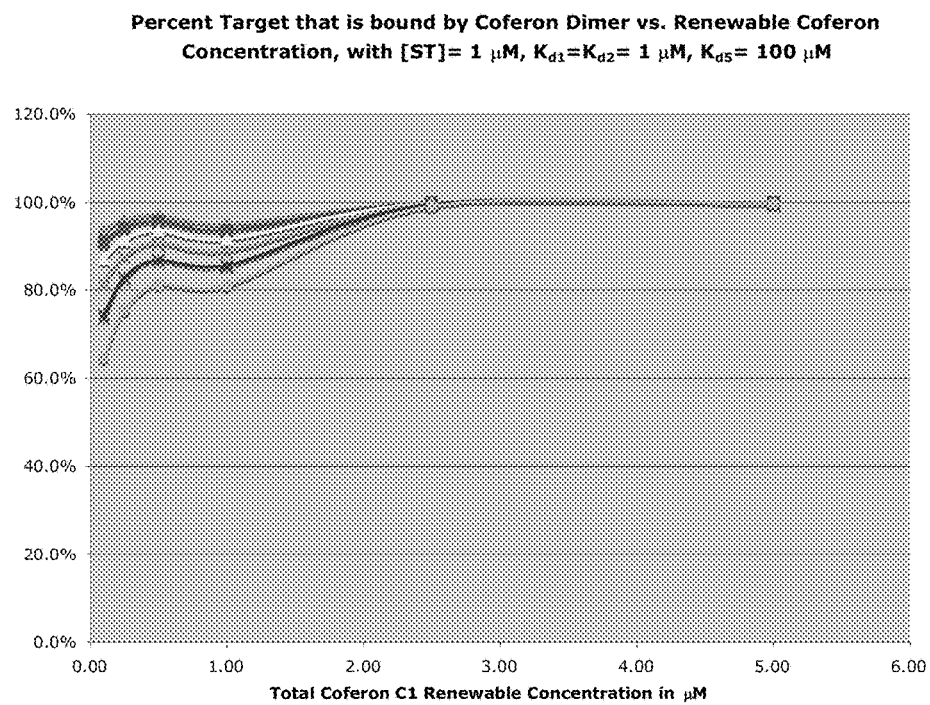

FIG. 117 is a graph showing the percent target T that is bound by coferon dimer C1C2 vs. "renewable" coferon C1 concentration. The total target [ST] is set at 1 µM, $K_{d1}=K_{d2}$ is set at 1 µM, $K_{d5}$ is set at 100 µM, and steady-state or renewable coferon C1 concentration [C1]=steady-state or renewable coferon C2 concentration [C2], varying from 0.1 µM up to 5 µM concentration.

Figure 118:
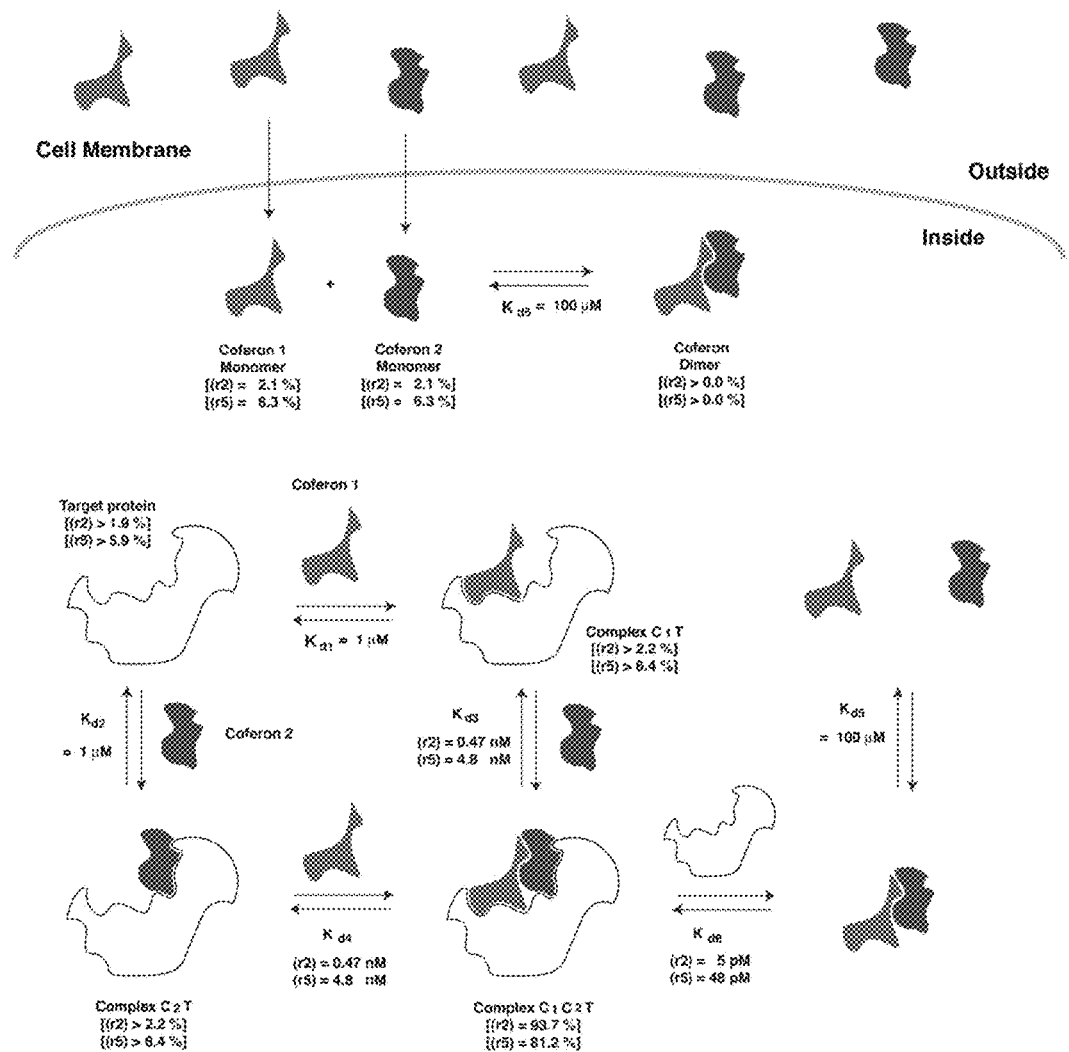

FIG. 118 is a schematic representation of two coferons (C1, and C2) that can enter cells as monomers, and bind to orthogonal sites on an internal protein target (T) to inhibit its activity. Coferon 1 is illustrated as a green shape, coferon 2 as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 2.5 µM, about 2,500,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 100 µM.

Figure 119:
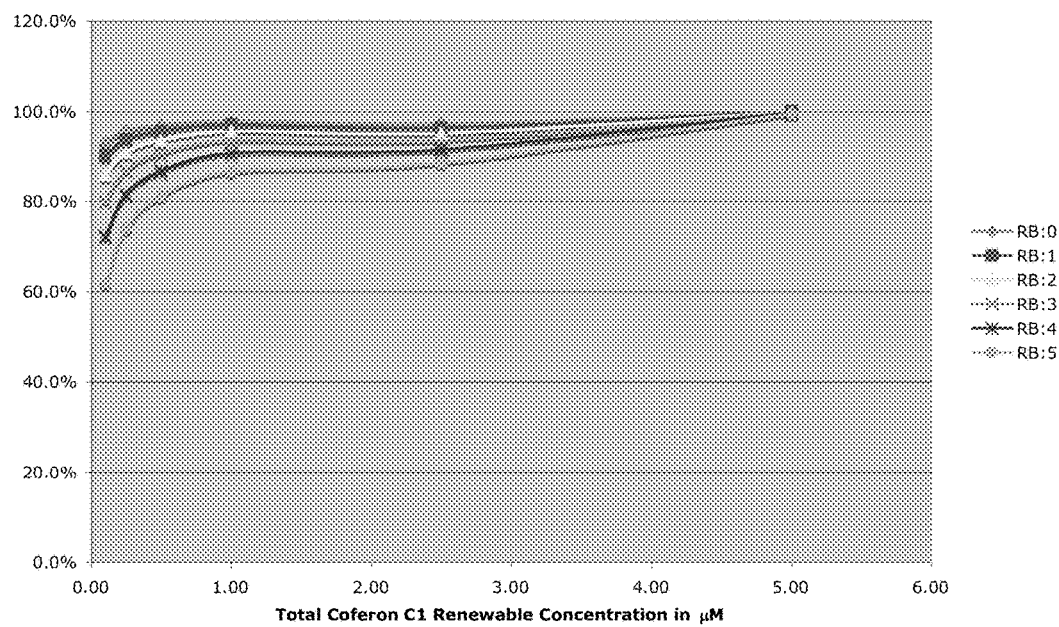

FIG. 119 is a graph showing the percent target T that is bound by coferon dimer C1C2 vs. "renewable" coferon C1 concentration. The total target [ST] is set at 2.5 µM, $K_{d1}=K_{d2}$ is set at 1 µM, $K_{d5}$ is set at 100 µM, and steady-state or renewable coferon C1 concentration [C1]=steady-state or renewable coferon C2 concentration [C2], varying from 0.1 µM up to 5 µM concentration.

Figure 120:
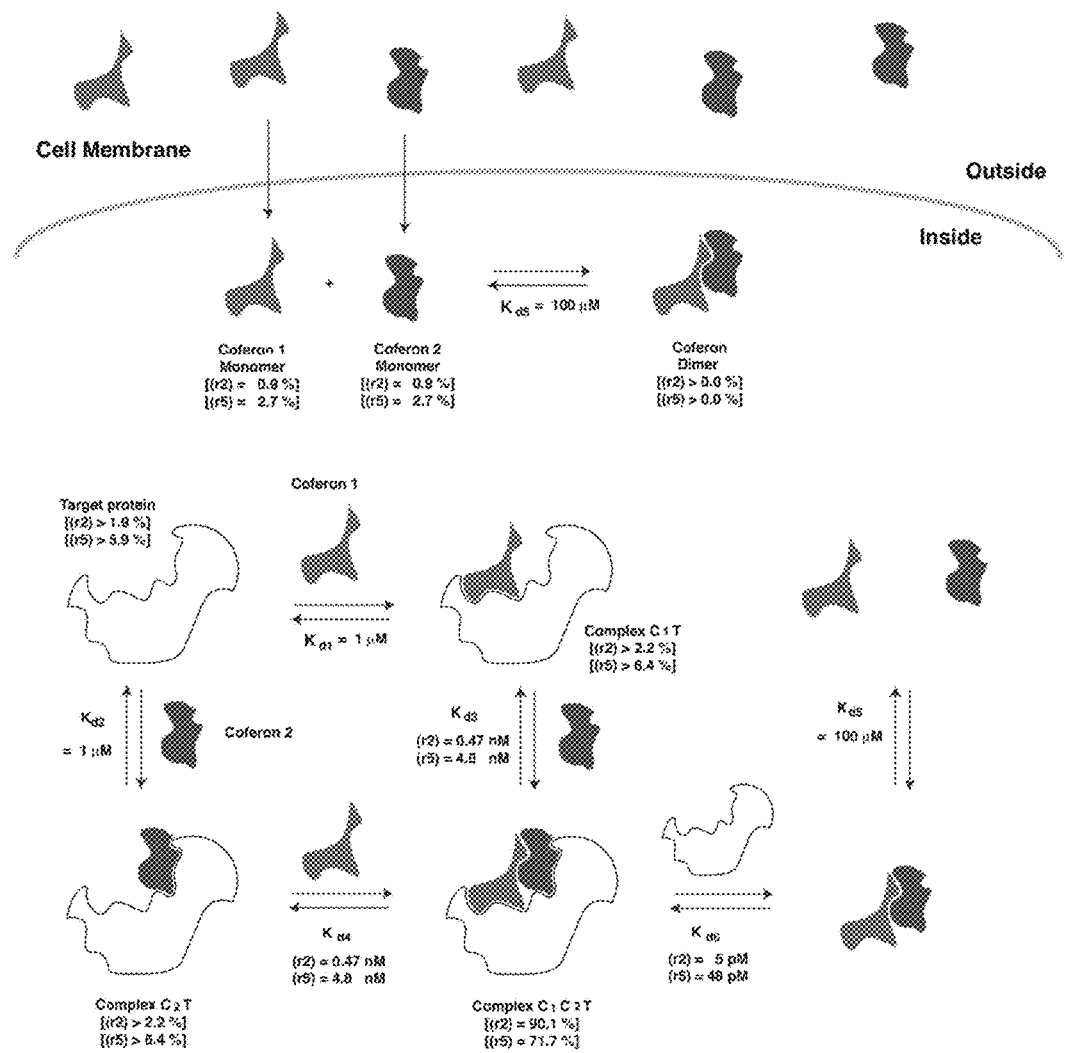

FIG. 120 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 10 µM, about 10,000,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 100 µM.

Figure 121:
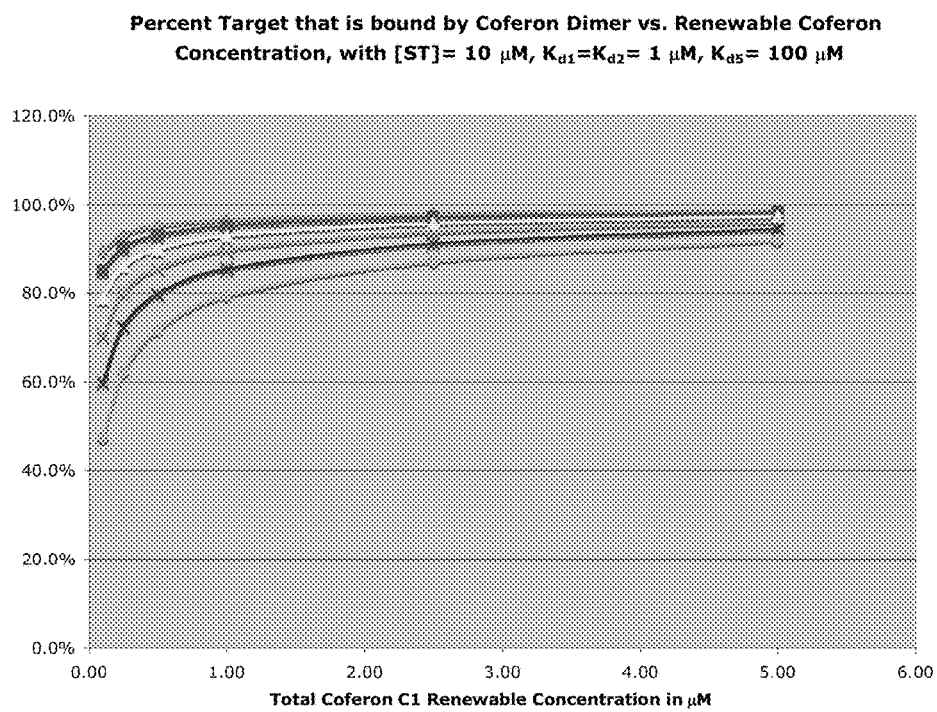

FIG. 121 is a graph showing the percent target T that is bound by coferon dimer C1C2 vs. "renewable" coferon C1 concentration. The total target [ST] is set at 10 µM, $K_{d1}=K_{d2}$ is set at 1 µM, $K_{d5}$ is set at 100 µM, and steady-state or renewable coferon C1 concentration [C1]=steady-state or renewable coferon C2 concentration [C2], varying from 0.1 µM up to 5 µM concentration.

Figure 122:
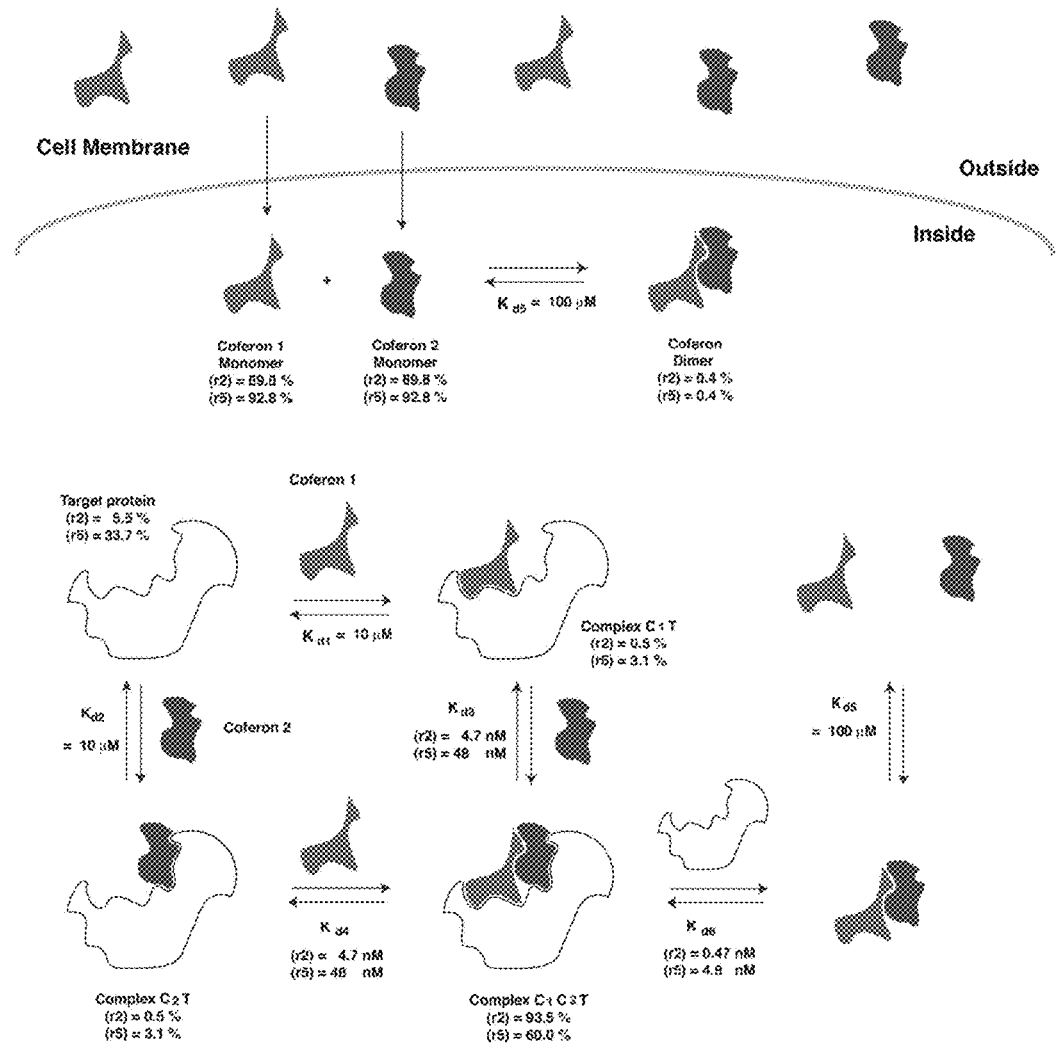

FIG. 122 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 1 µM, reflecting the ability to provide a steady dose of drug over time. The total protein concentration inside the cell is 0.1 µM, about 100,000 targets per cell. The dissociation constants $K_{d1}$ and $K_{d1}$ between coferon C1 and target T, as well as between coferon C2 and target T are given at 10 µM. The dissociation constant between the two coferons, $K_{d5}$ is given at 100 µM.

Figure 123:
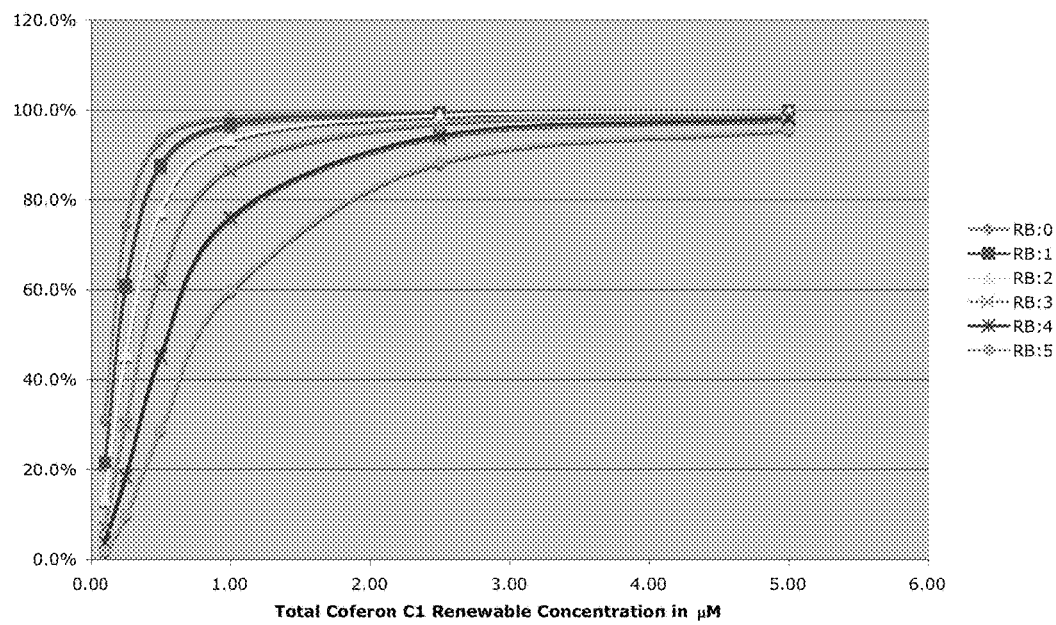

FIG. 123 is a graph showing the percent target T that is bound by coferon dimer C1C2 vs. "renewable" coferon C1 concentration. The total target [ST] is set at 0.1 µM, $K_{d1}=K_{d2}$ is set at 10 µM, $K_{d5}$ is set at 100 µM, and steady-state or renewable coferon C1 concentration [C1]= steady-state or renewable coferon C2 concentration [C2], varying from 0.1 µM up to 5 µM concentration.

Figure 124:
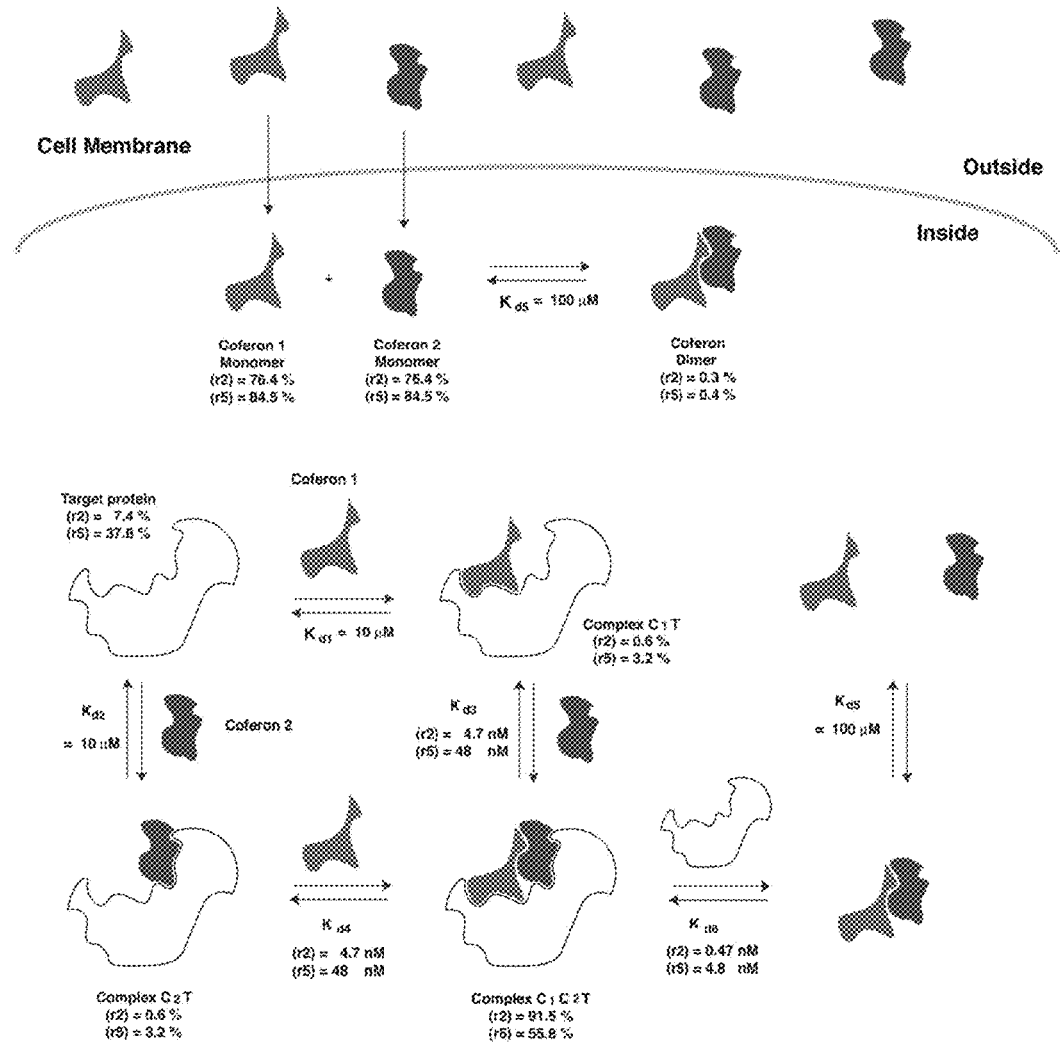

FIG. 124 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 1 µM, reflecting the ability to provide a steady dose of drug over time. The total protein concentration inside the cell is 0.25 µM, about 250,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 100 µM.

Figure 125:
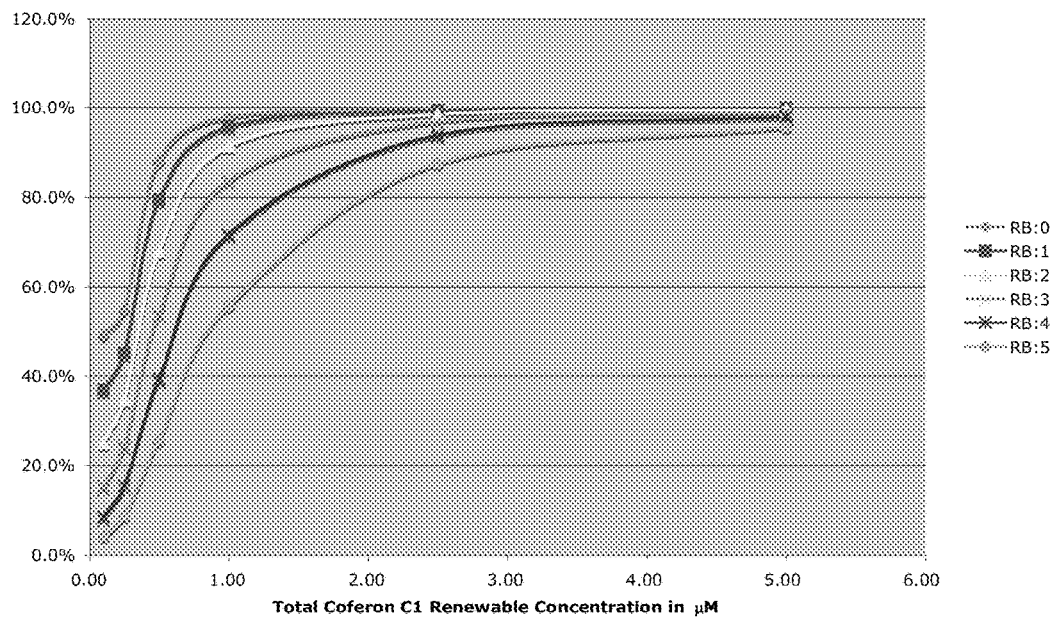

FIG. 125 is a graph showing the percent target T that is bound by coferon dimer C1C2 vs. "renewable" coferon C1 concentration. The total target [ST] is set at 0.25 µM, $K_{d1}=K_{d2}$ is set at 10 µM, $K_{d5}$ is set at 100 µM, and steady-state or renewable coferon C1 concentration [C1]= steady-state or renewable coferon C2 concentration [C2], varying from 0.1 µM up to 5 µM concentration.

Figure 126:
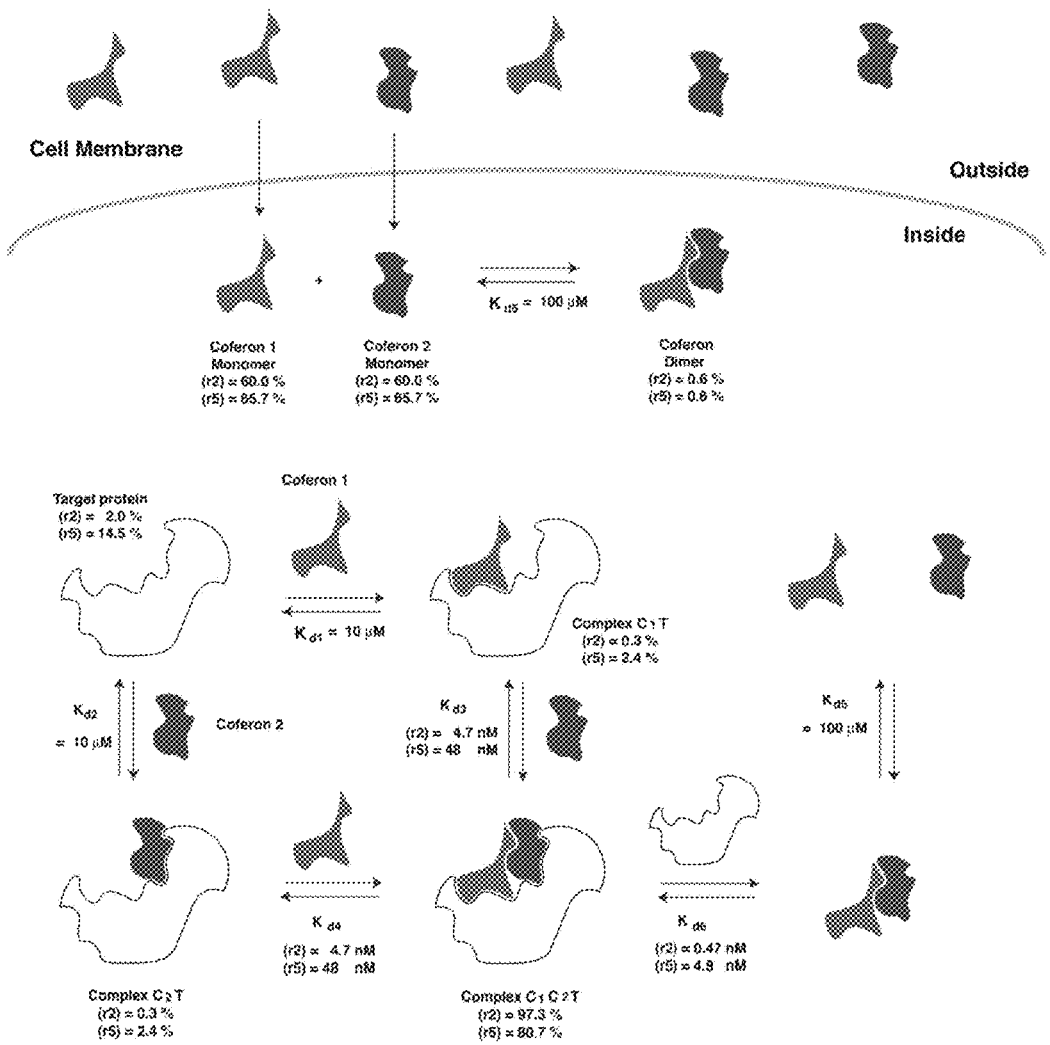

FIG. 126 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 2.5 µM, reflecting the ability to provide a steady dose of drug over time. The total protein concentration inside the cell is 1 μM, about 1,000,000 targets per cell. The dissociation constants $K_{d1}$ and $K_{d2}$ between coferon C1 and target T, as well as between coferon C2 and target T are given at 10 μM. The dissociation constant between the two coferons, $K_{d5}$ is given at 100 μM.

Figure 127:
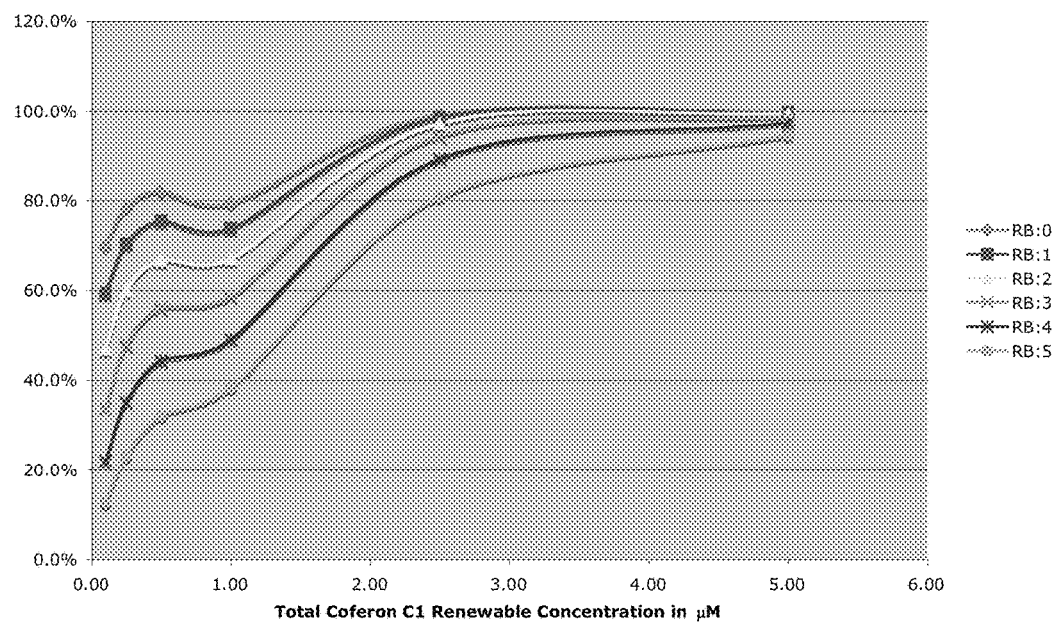

FIG. 127 is a graph showing the percent target T that is bound by coferon dimer C1C2 vs. "renewable" coferon C1 concentration. The total target [ST] is set at 1 μM, $K_{d1}$=$K_{d2}$ is set at 10 μM, $K_{d5}$ is set at 100 μM, and steady-state or renewable coferon C1 concentration [C1]=steady-state or renewable coferon C2 concentration [C2], varying from 0.1 μM up to 5 μM concentration.

Figure 128:
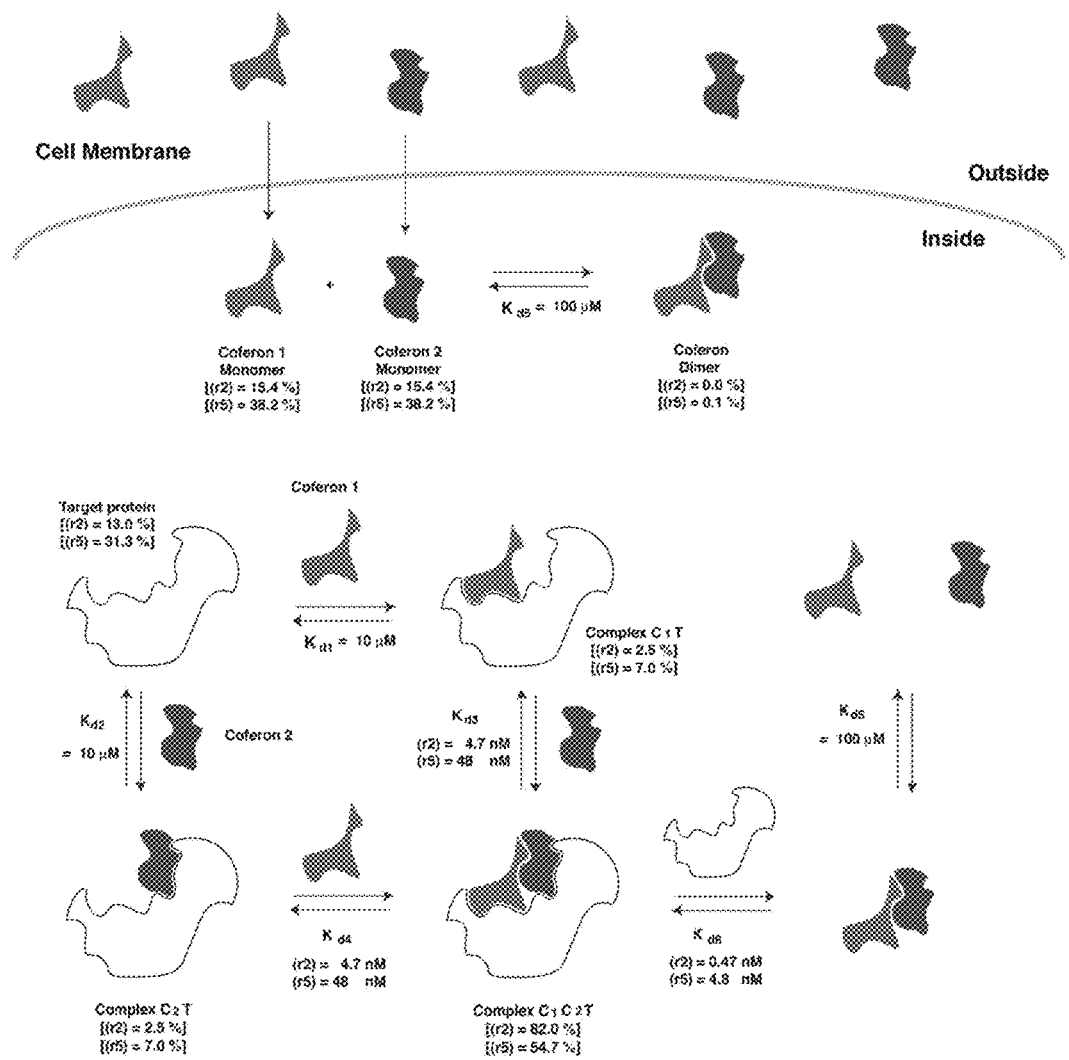

FIG. 128 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 1 μM, reflecting the ability to provide a steady dose of drug over time. The total protein concentration inside the cell is 2.5 μM, about 2,500,000 targets per cell. The dissociation constants $K_{d1}$ and $K_{d2}$ between coferon C1 and target T, as well as between coferon C2 and target T are given at 10 μM. The dissociation constant between the two coferons, $K_{d5}$ is given at 100 μM.

Figure 129:
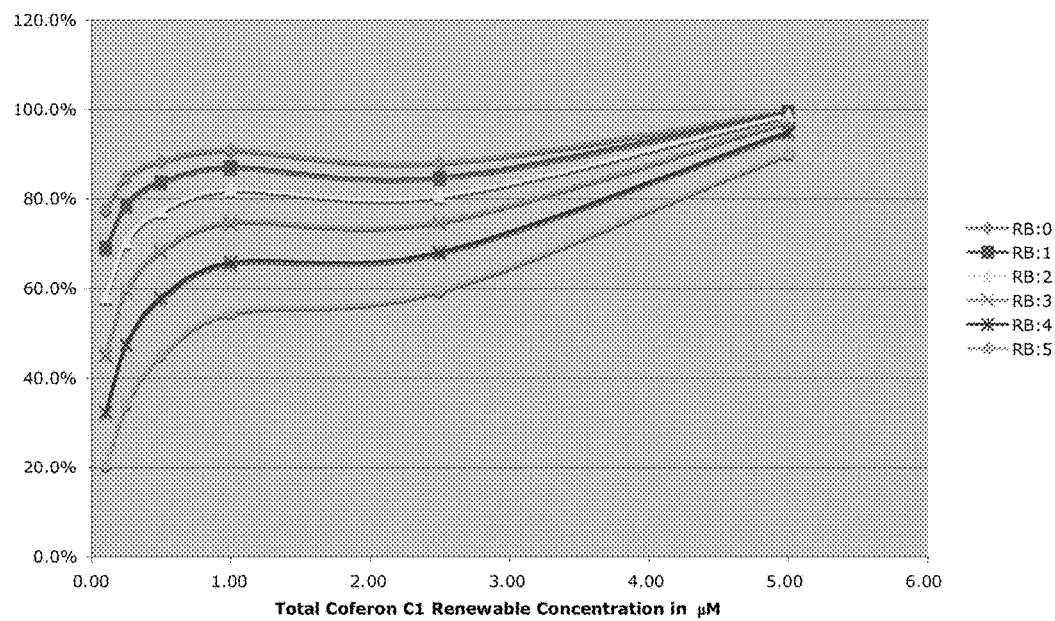

FIG. 129 is a graph showing the percent target T that is bound by coferon dimer C1C2 vs. "renewable" coferon C1 concentration. The total target [ST] is set at 2.5 μM, $K_{d1}$=$K_{d2}$ is set at 10 μM, $K_{d5}$ is set at 100 μM, and steady-state or renewable coferon C1 concentration [C1]=steady-state or renewable coferon C2 concentration [C2], varying from 0.1 μM up to 5 μM concentration.

Figure 130:
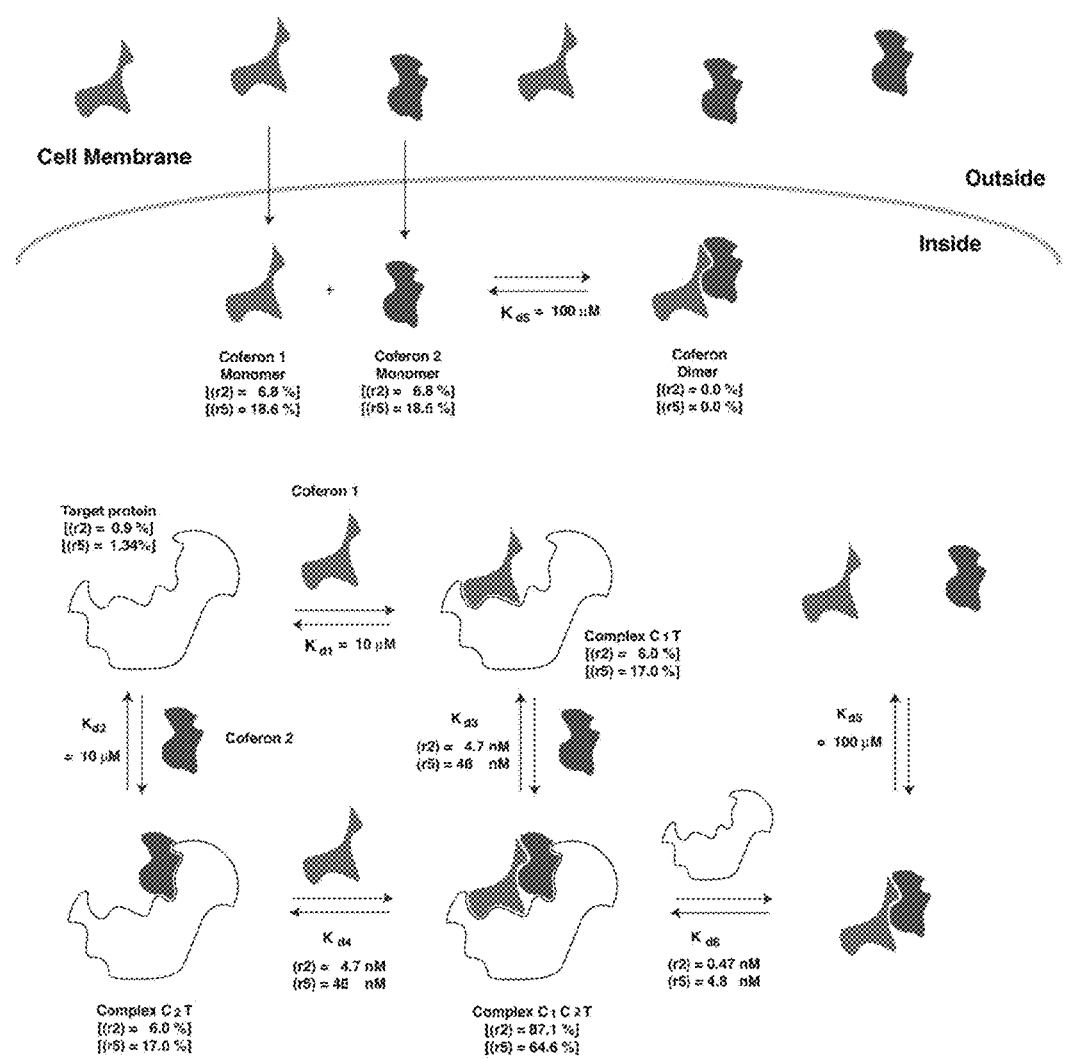

FIG. 130 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 1 μM, reflecting the ability to provide a steady dose of drug over time. The total protein concentration inside the cell is 10 μM, about 10,000,000 targets per cell. The dissociation constants $K_{d1}$ and $K_{d2}$ between coferon C1 and target T, as well as between coferon C2 and target T are given at 10 μM. The dissociation constant between the two coferons, $K_{d5}$ is given at 100 μM.

Figure 131:
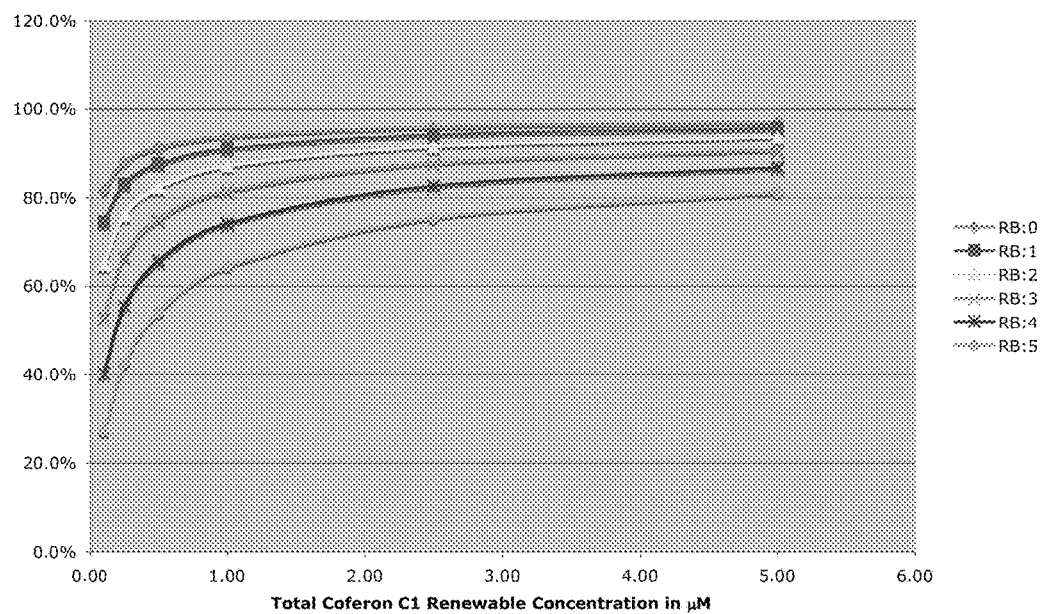

FIG. 131 is a graph showing the percent target T that is bound by coferon dimer C1C2 vs. "renewable" coferon C1 concentration. The total target [ST] is set at 10 μM, $K_{d1}$=$K_{d2}$ is set at 10 μM, $K_{d5}$ is set at 100 μM, and steady-state or renewable coferon C1 concentration [C1]=steady-state or renewable coferon C2 concentration [C2], varying from 0.1 μM up to 5 μM concentration.

Figure 132:
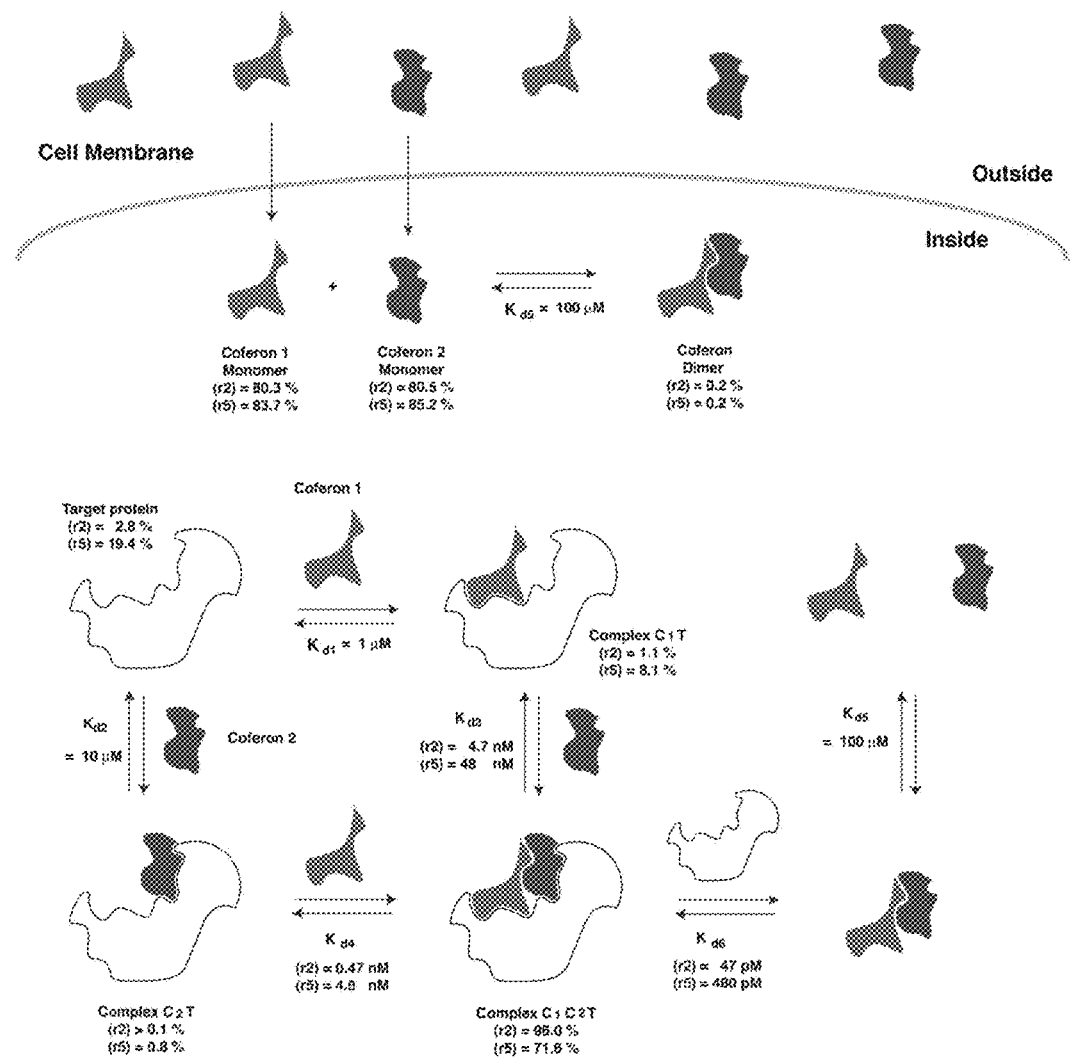

FIG. 132 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.5 μM, reflecting the ability to provide a steady dose of drug over time. The total protein concentration inside the cell is 0.1 μM, about 100,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d5}$ is given at 100 μM.

Figure 133:
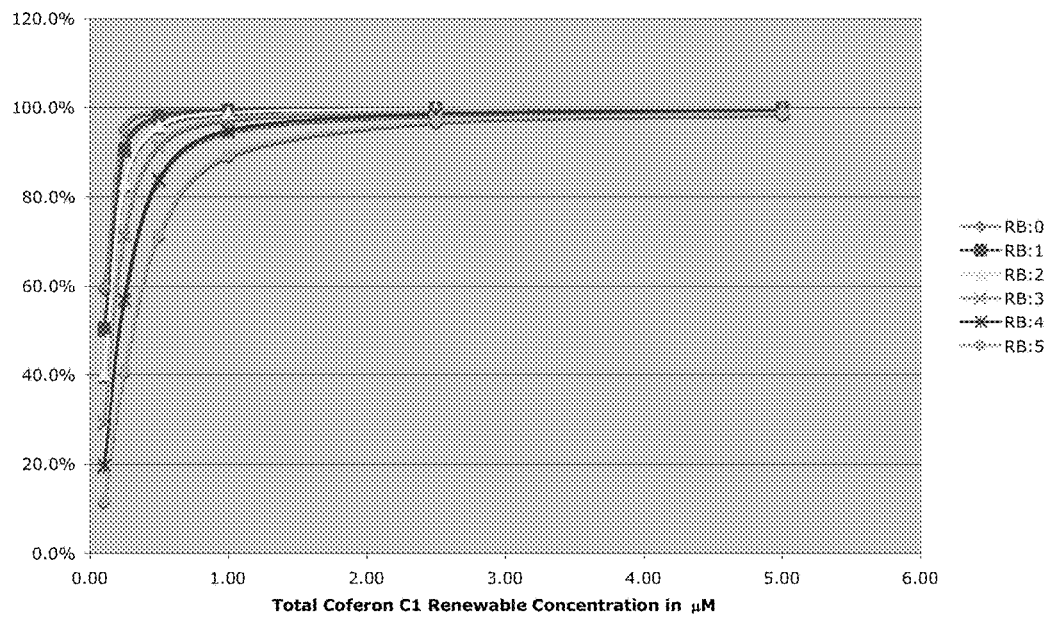

FIG. 133 is a graph showing the percent target T that is bound by coferon dimer C1C2 vs. "renewable" coferon C1 concentration. The total target [ST] is set at 0.1 μM, $K_{d1}$ is set at 1 μM, $K_{d2}$ is set at 10 μM, $K_{d5}$ is set at 100 μM, and steady-state or renewable coferon C1 concentration [C1]= steady-state or renewable coferon C2 concentration [C2], varying from 0.5 μM up to 5 μM concentration.

Figure 134:
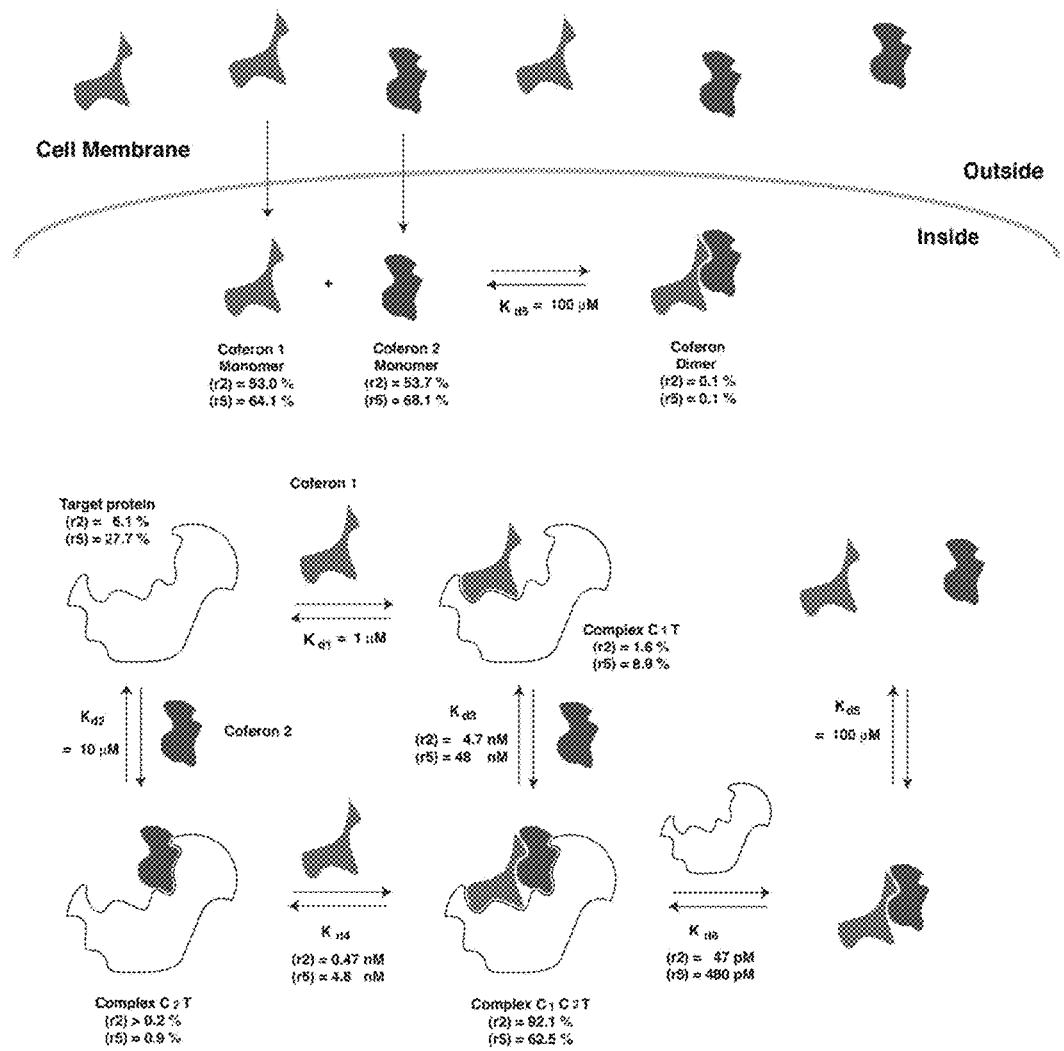

FIG. 134 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.1 μM, reflecting the ability to provide a steady dose of drug over time. The total protein concentration inside the cell is 0.25 μM, about 250,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d5}$ is given at 100 μM.

Figure 135:
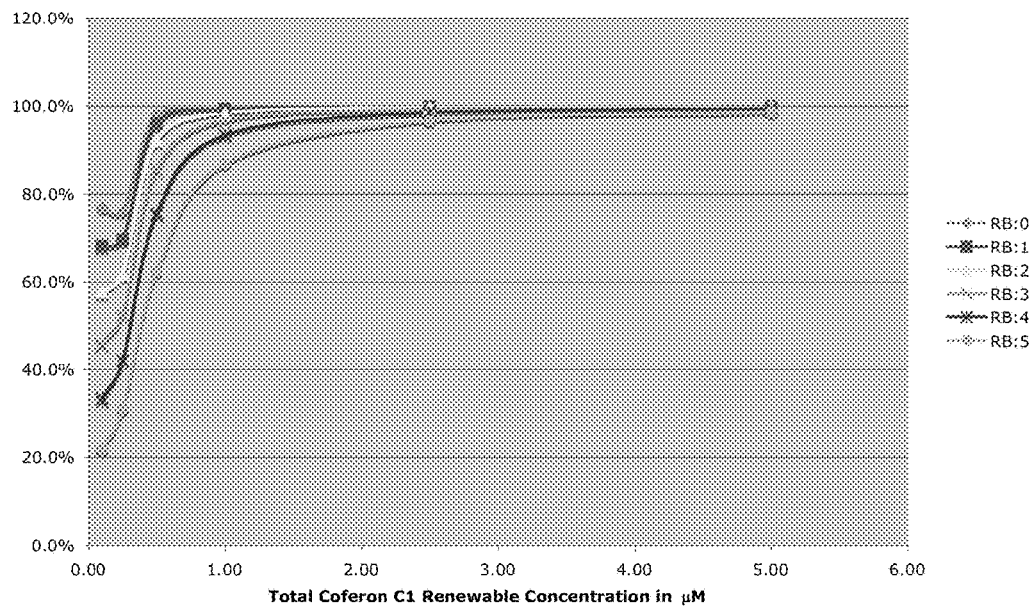

FIG. 135 is a graph showing the percent target T that is bound by coferon dimer C1C2 vs. "renewable" coferon C1 concentration. The total target [ST] is set at 0.25 μM, $K_{d1}$ is set at 1 μM, $K_{d2}$ is set at 10 μM, $K_{d5}$ is set at 100 μM, and steady-state or renewable coferon C1 concentration [C1]= steady-state or renewable coferon C2 concentration [C2], varying from 0.1 μM up to 5 μM concentration.

Figure 136:
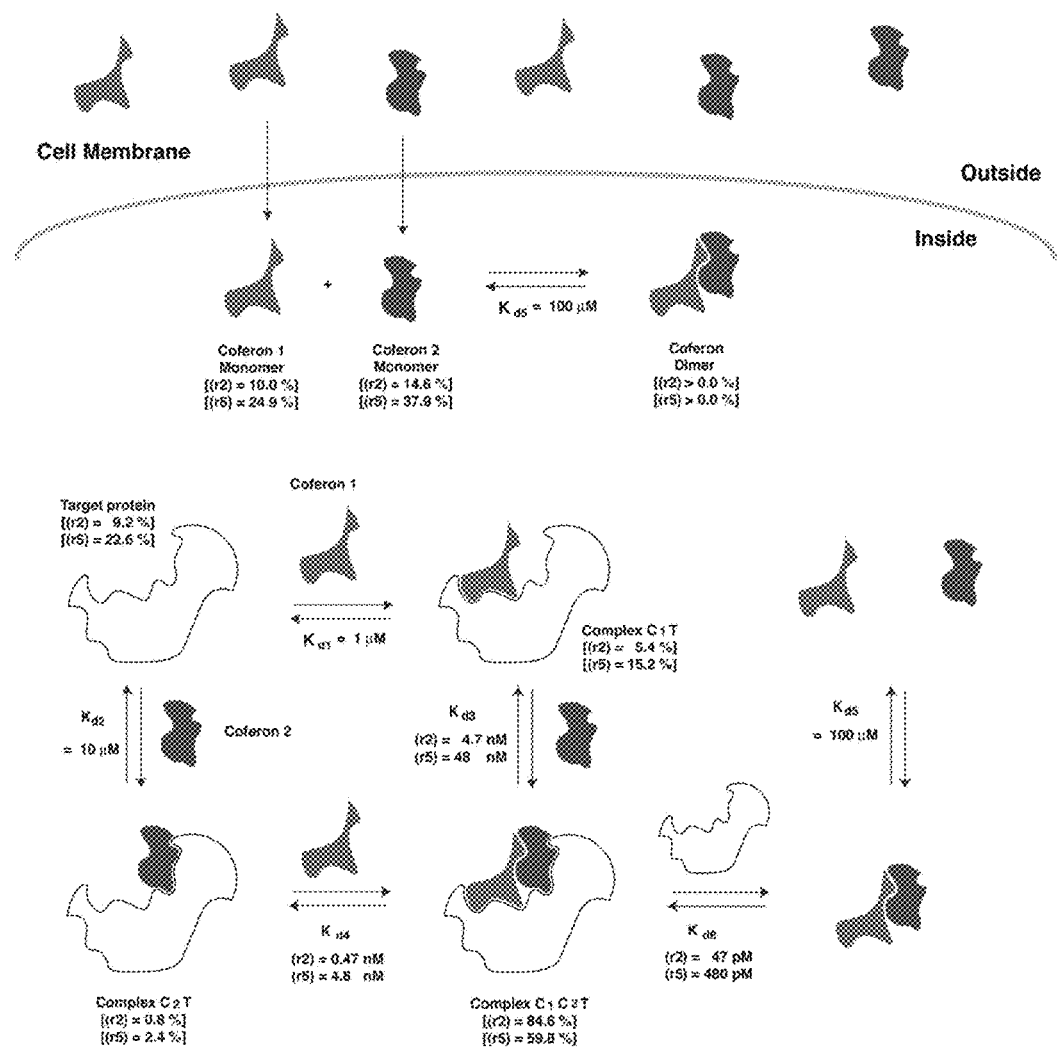

FIG. 136 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 μM, reflecting the ability to provide a steady dose of drug over time. The total protein concentration inside the cell is 1 μM, about 1,000,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d5}$ is given at 100 μM.

Figure 137:
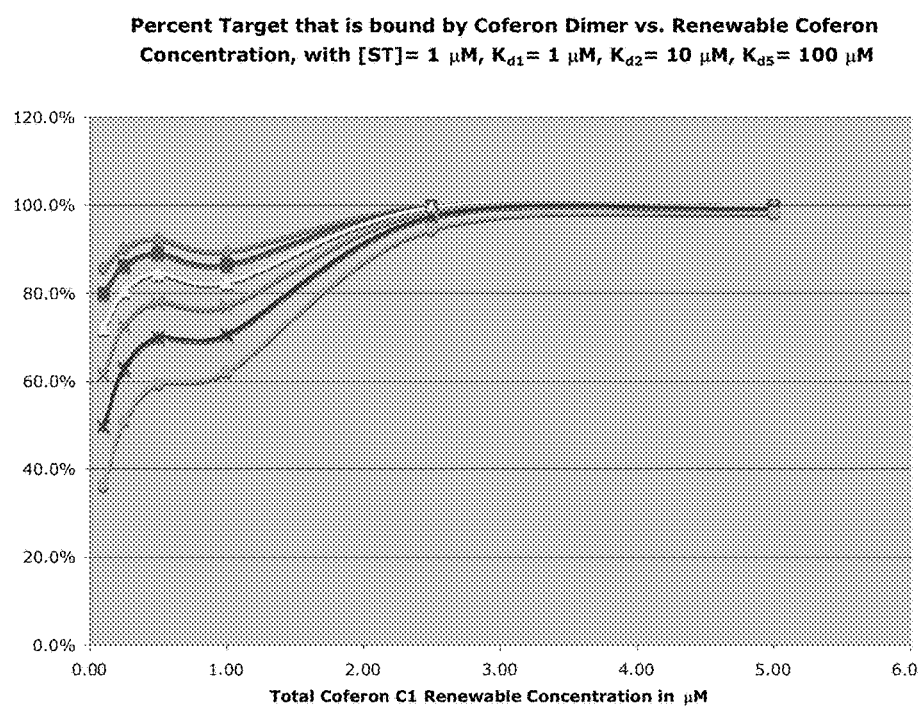

FIG. 137 is a graph showing the percent target T that is bound by coferon dimer C1C2 vs. "renewable" coferon C1 concentration. The total target [ST] is set at 1 μM, $K_{d1}$ is set at 1 μM, $K_{d2}$ is set at 10 μM, $K_{d5}$ is set at 100 μM, and steady-state or renewable coferon C1 concentration [C1]= steady-state or renewable coferon C2 concentration [C2], varying from 0.1 μM up to 5 μM concentration.

Figure 138:
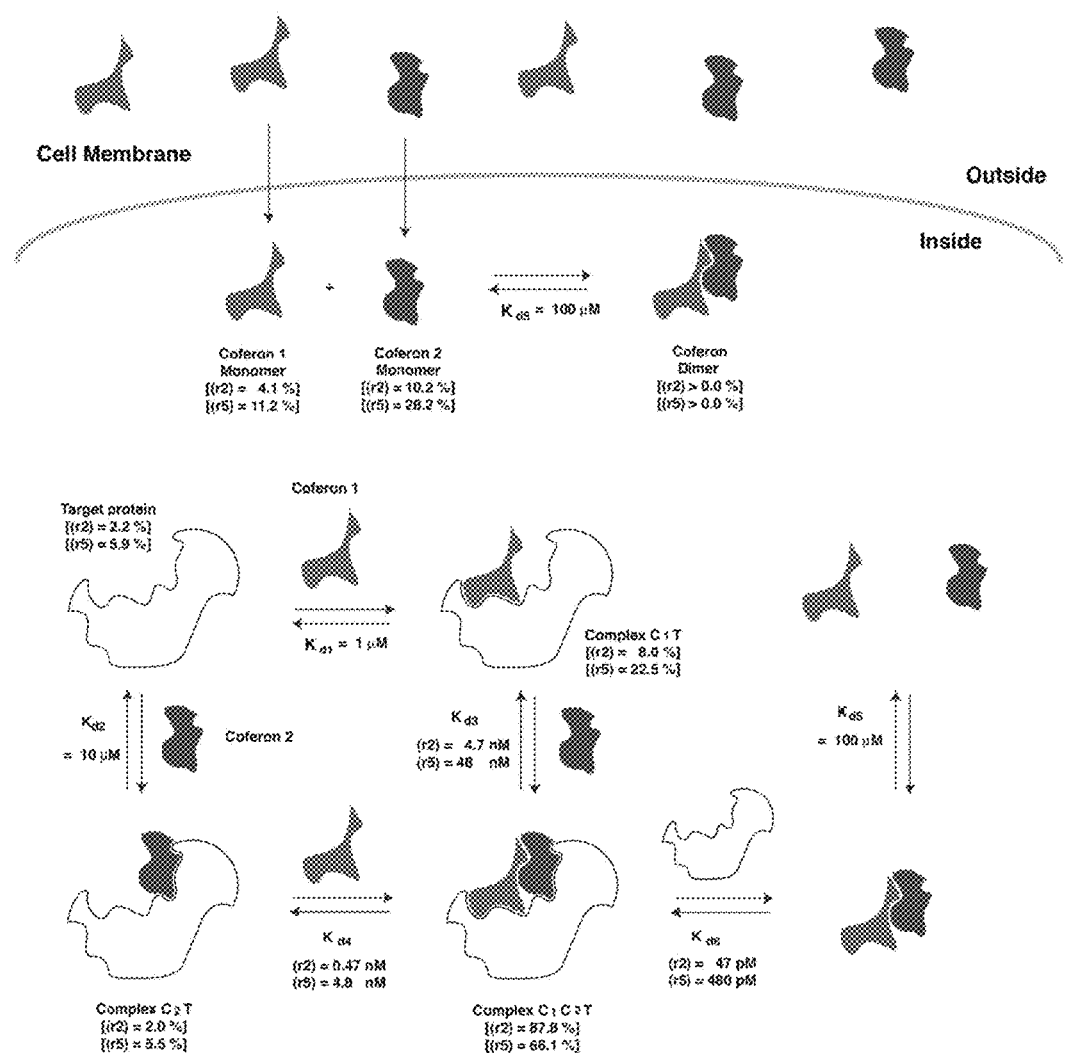

FIG. 138 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 μM, reflecting the ability to provide a steady dose of drug over time. The total protein concentration inside the cell is 2.5 μM, about 2,500,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d5}$ is given at 100 μM.

Figure 139:
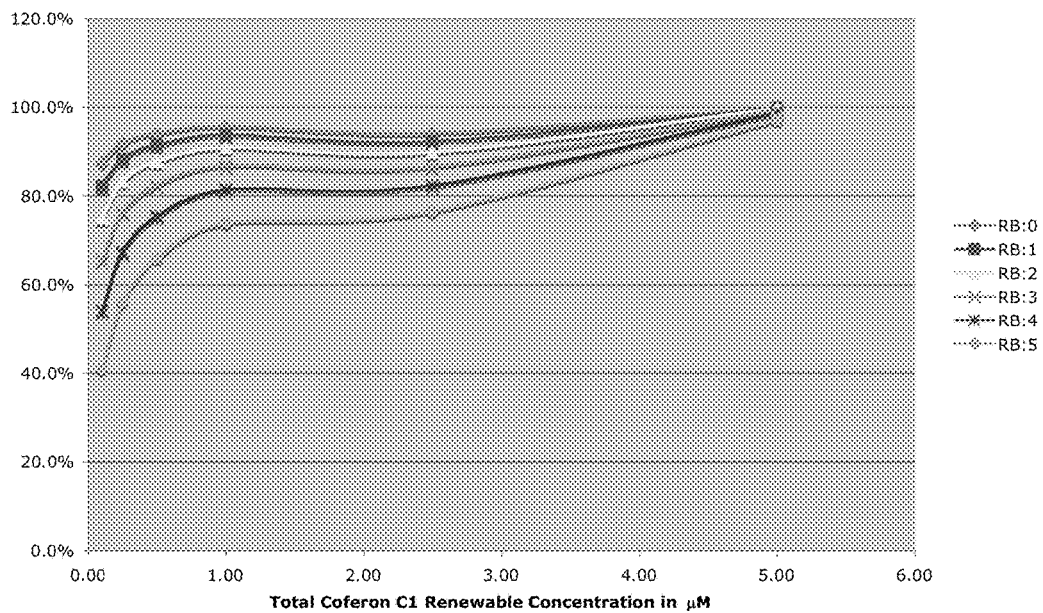

FIG. 139 is a graph showing the percent target T that is bound by coferon dimer C1C2 vs. "renewable" coferon C1 concentration. The total target [ST] is set at 2.5 µM, $K_1$ is set at 1 µM, $K_{d5}$ is set at 10 µM, $K_{d5}$ is set at 100 µM, and steady-state or renewable coferon C1 concentration [C1]= steady-state or renewable coferon C2 concentration [C2], varying from 0.1 µM up to 5 µM concentration.

Figure 140:
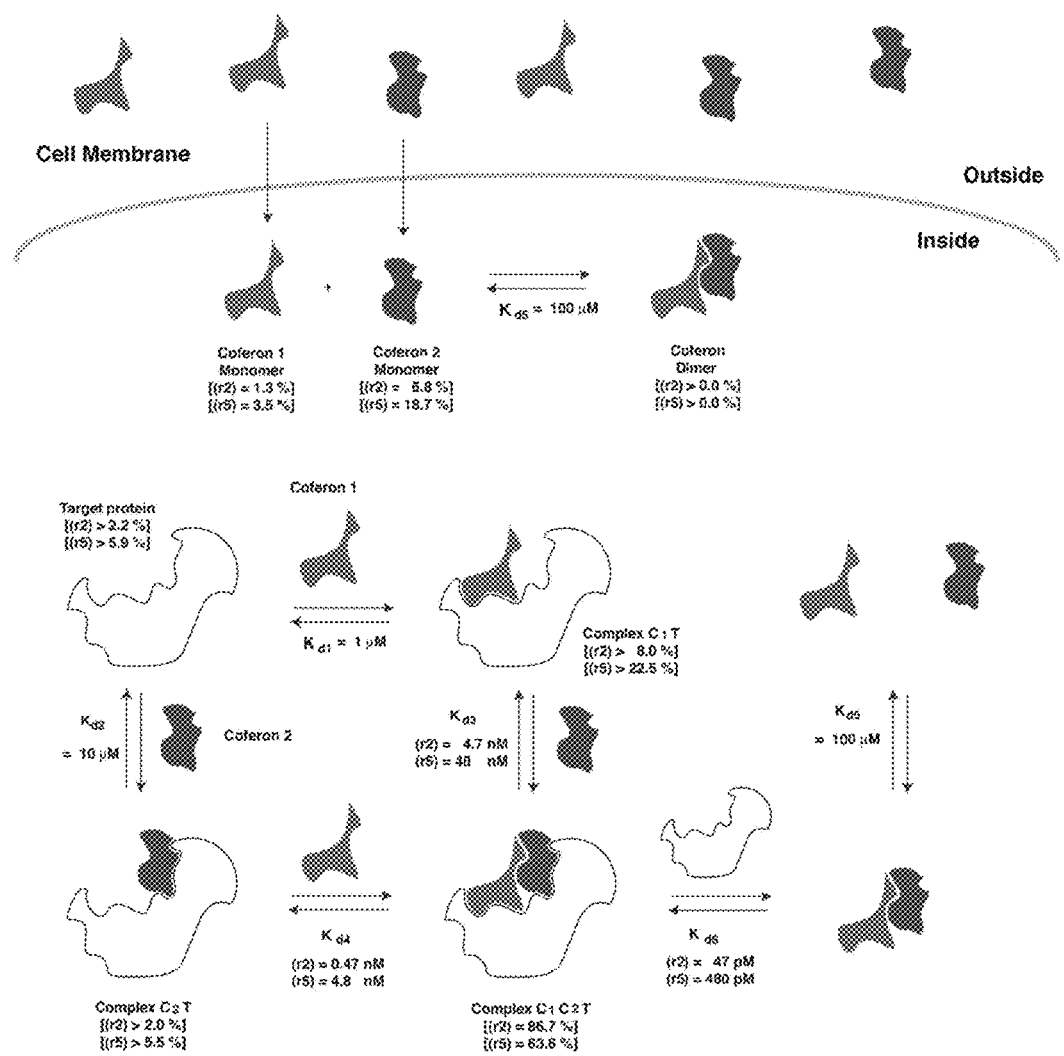

FIG. 140 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 10 µM, about 10,000,000 targets per cell. The dissociation constant $K_{d1}$ between coferon C1 and target T, is given at 1 µM, and the dissociation constant $K_{d2}$ between coferon C2 and target T, is given at 10 µM. The dissociation constant between the two coferons, $K_{d5}$ is given at 100 µM.

Figure 141:
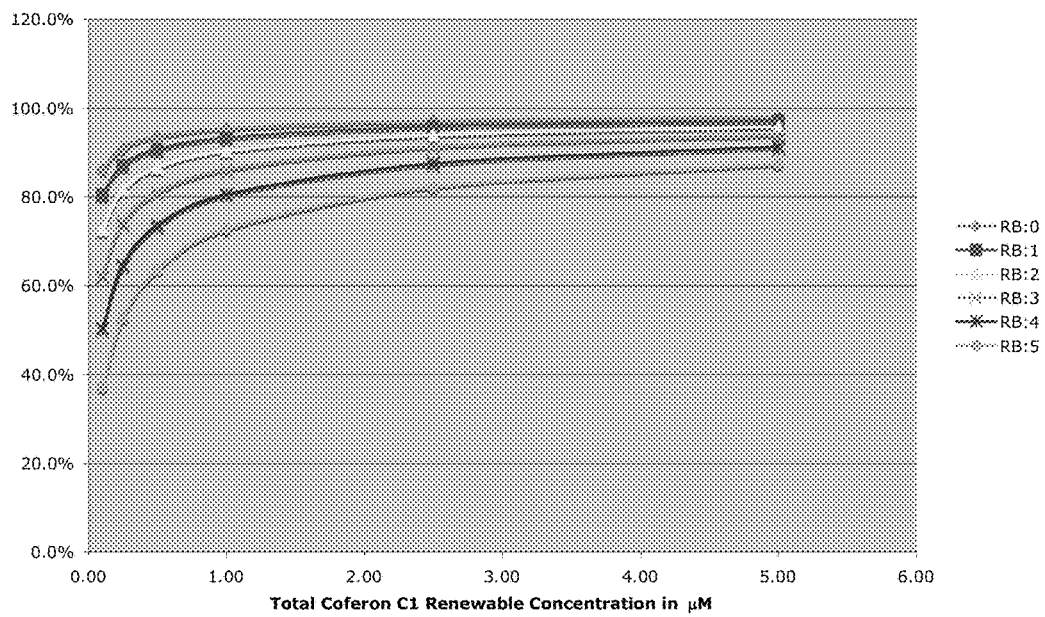

FIG. 141 is a graph showing the percent target T that is bound by coferon dimer C1C2 vs. "renewable" coferon C1 concentration. The total target [ST] is set at 10 µM, $K_{d1}$ is set at 1 µM, $K_{d2}$ is set at 10 µM, $K_{d5}$ is set at 100 µM, and steady-state or renewable coferon C1 concentration [C1]= steady-state or renewable coferon C2 concentration [C2], varying from 0.1 µM up to 5 µM concentration.

Figure 142:
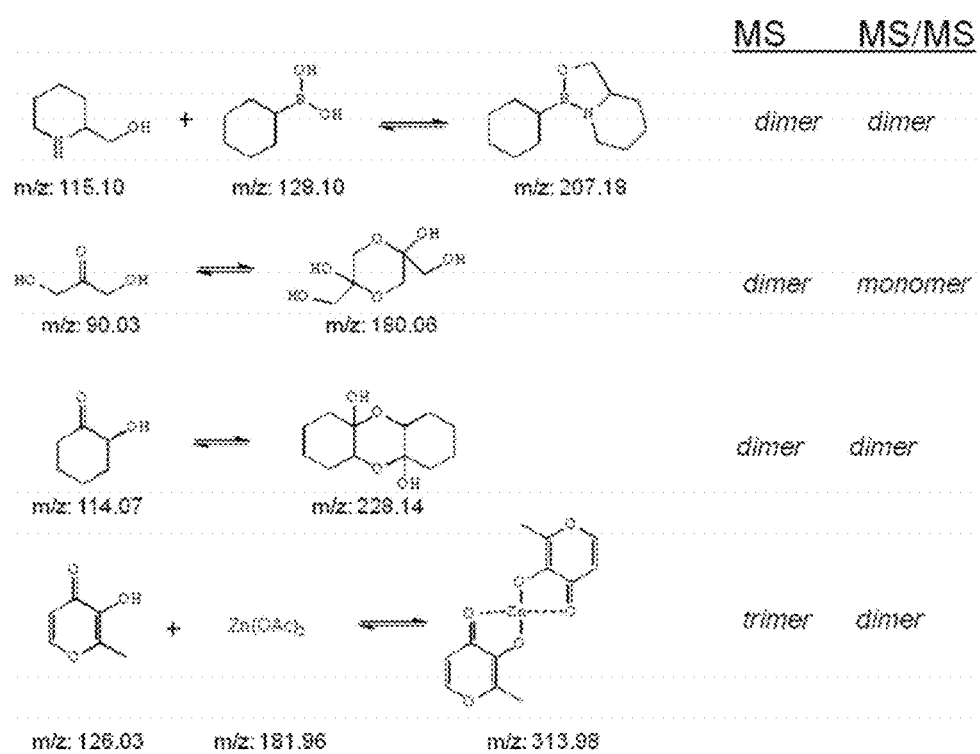

FIG. 142 shows the mass to charge ratios (m/z) for selected linker element precursors as well as data obtained from mass spectrometry (MS) and mass spectrometry/mass spectrometry (MS/MS) experiments on the ability of these linker element precursors to form dimers or stay as monomers in solution.

Figure 143:
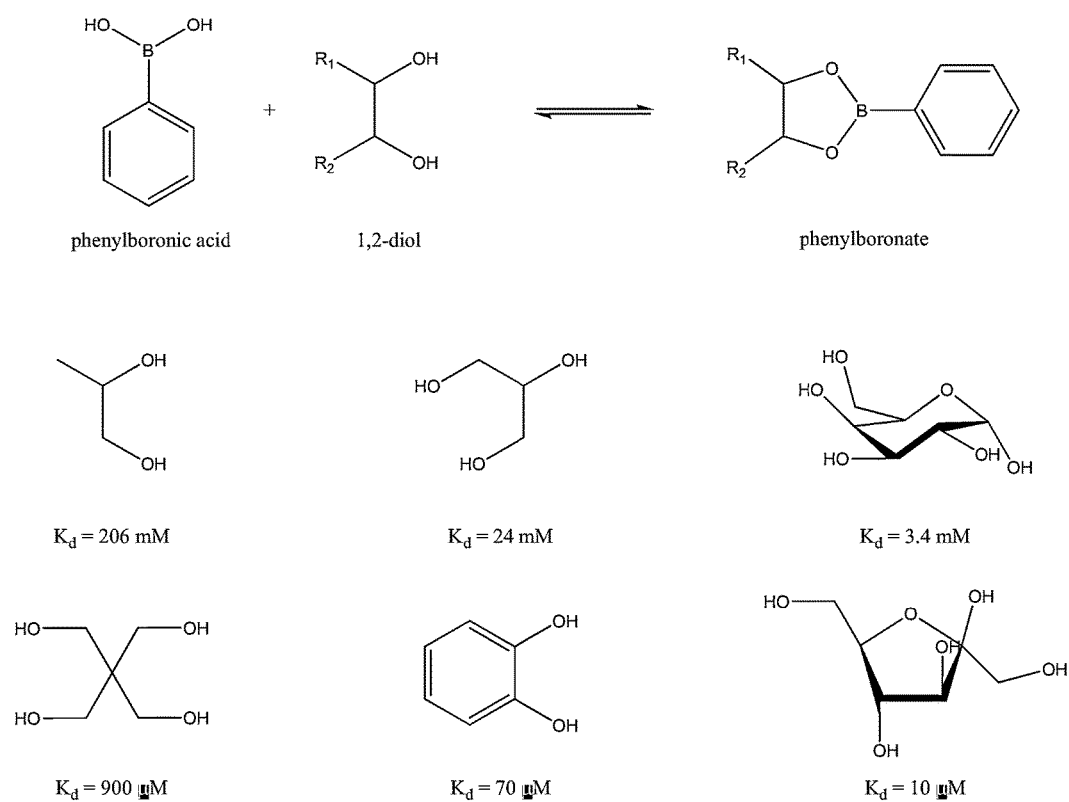

FIG. 143 shows the reversible equilibrium formation of a dimer (a phenyl boronate) from linker element precursors (phenylboronic acid and a cis-1,2-diol). kD values for this equlibrium for a set of cis-1,2-diols is shown and range from 10 µM to 206 mM.

DETAILED DESCRIPTION OF THE INVENTION

Basic Principles of Coferon Drugs

Coferons are orally active drugs that can enter cells and, once inside, combine with their partner to interfere with or modulate target protein activity. A coferon monomer is composed of a diversity element and a linker element.

In general, coferon drugs contain two ligands that bind to the target, and are held together through their respective linker element interactions. In order to assure that the coferon drugs bind to a given target, the design of coferon usually incorporates selecting from a known set of diversity elements and/or synthesizing a wide range of diversity elements for one or both of the coferon drug dimer.

Once a coferon dimer has been selected for, or screened by various assays, it is important to be able to identify the structure of the diversity element. This is especially true under conditions of dynamic combinatorial chemistry, where dozens to hundreds to thousands or even more different diversity elements are being interrogated simultaneously in the same well or when binding to a target on a solid surface (i.e. affinity column)

The basic coferon design contains the linker element, which is responsible for interacting with its partner linker element, and the diversity element, which is responsible for binding to the target. The linker element and the diversity element may be directly attached to each other, or linked together by a connector moiety. The linker element and/or connector portion may assist in positioning the diversity element in the ideal conformation or orientation for proper binding to the target. In addition, these elements in and of themselves may also interact with the target. The encryption element, if used, may be attached to the linker element or the connector portion of the molecule. Ideally, it should be linked to the linker element or connector portion in a manner allowing for easy release or cleavage to remove the DNA portion.

Coferon Monomers

Figure 1:
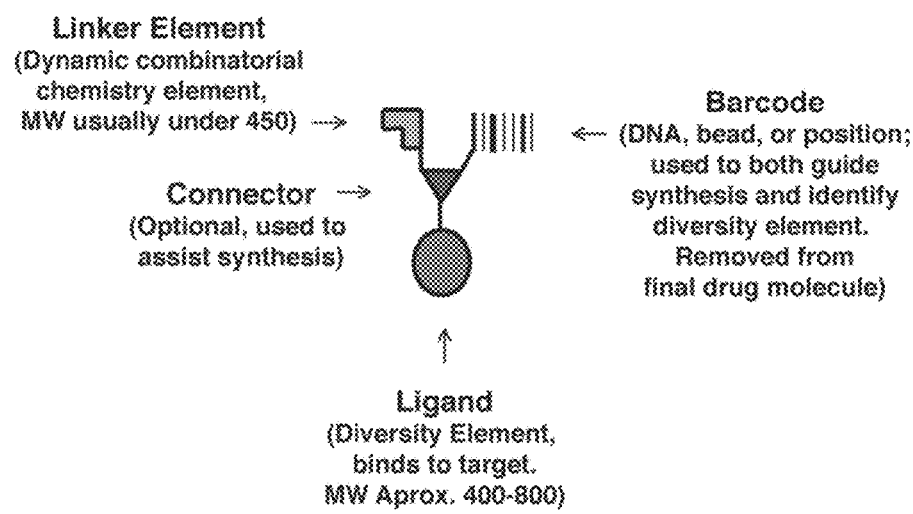
FIG. 1 is a schematic drawing of the components used in Coferon monomer.

As shown in FIG. 1, the coferon monomers may includes a linker element, a ligand or diversity element, a connector, and a DNA bar code. The linker element is a dynamic combinatorial chemistry element which may have a molecular weight under 500 daltons, preferably 45-450 daltons; it is responsible for interacting with its partner linker element, and the diversity element. The linker element can have a dissociation constant of 100 nM to 100 µM with or without a co-factor. The ligand or diversity element is provided to bind to a target molecule and has a molecular weight of about 400 to 800 with a dissociation constant of 100 nM to 100 µM. The linker element and the diversity element may be directly attached to each other or linked together by a connector moiety. An optional connector binds the linker element and the ligand or diversity element, assists in synthesis of the coferon monomer, and may assist in positioning the diversity element in the ideal conformation or orientation for proper binding to the target. An encryption element, usually a DNA bar code, can be attached to the linker element or connector for easy release or cleavage. The encryption element is included to guide synthesis and to identify coferon monomers; it is removed from final drug products. FIG. 2.1A is a schematic drawing of coferon monomers in accordance with the present invention attached to encoded beads via connectors. FIG. 2.1B is a schematic drawing of a coferon monomer in accordance with the present invention with a DNA barcode attached through a connector. FIG. 2.1C is a schematic drawing of a coferon dimer attached to an encoded bead via a connector to one monomer, with a DNA barcode attached to the other monomer. FIG. 2.1D is a schematic drawing of a coferon dimer, with DNA barcodes attached to each monomer via the connectors. FIG. 2.1E is a schematic drawing of a coferon dimer pursuant to the present invention. FIG. 2.1F is a schematic drawing of coferon monomers in accordance with the present invention attached to an encoded bead via the linker element. FIG. 2.1G is a schematic drawing of a coferon monomer in accordance with the present invention with a DNA barcode attached the linker element. FIG. 2.1H is a schematic drawing of a coferon dimer attached to an encoded bead via the linker element to one monomer, with a DNA barcode attached to the other monomer. FIG. 2.1I is a schematic drawing of a coferon dimer attached to an encoded bead via linker to one monomer. FIG. 2.1J is a schematic drawing of a coferon dimer, with DNA barcodes attached to each monomer via the linker elements. FIG. 2.1K is a schematic drawing of a coferon dimer pursuant to the present invention.

One aspect of the present invention is directed to a monomer useful in preparing therapeutic compounds. The monomer includes a diversity element, which potentially binds to a target molecule with a dissociation constant of less than 300 µM connected to a linker element, directly or indirectly through a connector, to said diversity element. The linker element has a molecular weight less than 500 daltons and is capable of forming a reversible covalent bond or non-covalent interaction with a binding partner of said linker element with a dissociation constant of less than 300 µM with or without a co-factor under physiological conditions.

The monomer can additionally include an encoding element, where the diversity element, the linker element, and the encoding element are coupled together. The encoding element can be an oligonucleotide or a labeled bead.

Linker Elements
Linker Elements Based on Forming Reversible Imine and Iminium Bonds The concept of the linker element is to coax two small molecules to bind to one another, taking advantage of hydrophobic, polar, ionic, hydrogen bonding, and/or reversible covalent interactions. The challenge is for that interaction to be sufficiently strong between the two linker elements, while simultaneously not so strong between a linker element and a cellular molecule as to effectively bind and remove the linker elements from solution.

The substituents on the linker elements can be varied to tune the equilibrium of the reversible association of the linker elements in aqueous solution.

For reversible covalent bond formation, linker elements may be derived from carbonyl groups or boronates.

These linker elements have the advantage of well-documented literature precedence for use in dynamic combinatorial chemistry selection.

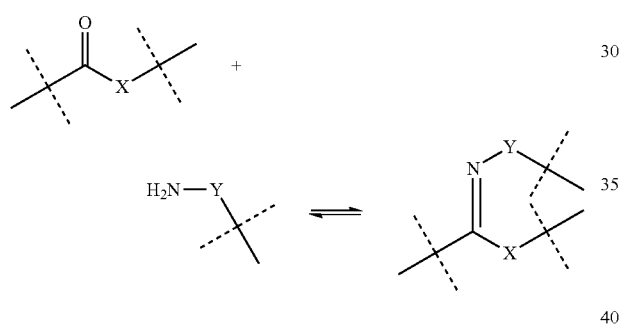

where X and Y may be varied to tune the equilibrium in aqueous solution and the lines crossed with a dashed line illustrate the one or more bonds formed joining the one or more diversity elements, directly or through a connector, to the molecule.

Examples of amines for reversible amine-carbonyl condensations

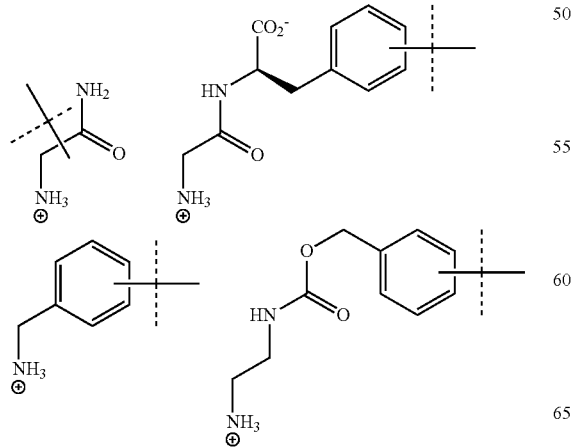

Examples of carbonyl containing molecules for reversible amine-carbonyl condensations

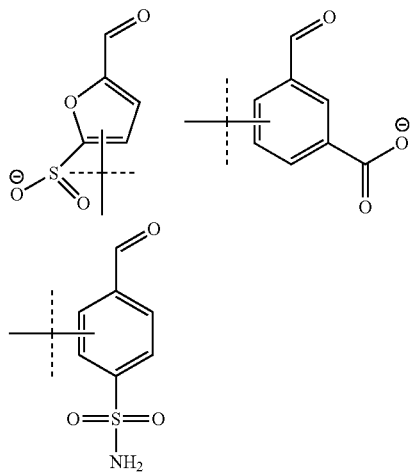

Example of amine-carbonyl condensation

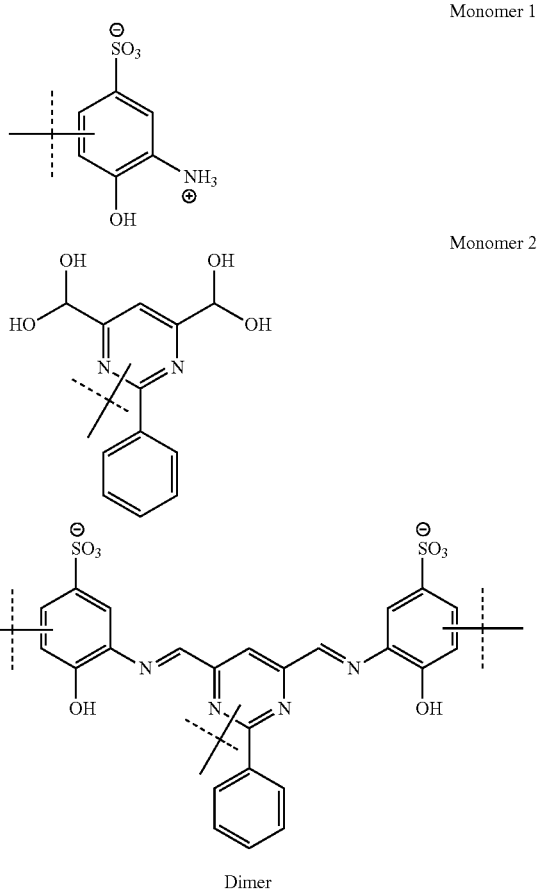

There is a high concentration of primary amines free in solution (lysine) and in proteins. Thus, when using a coferon containing a primary amine, it is important for the companion aldehyde or ketone containing coferon to find its partner on the surface of the target. As an added note of caution, the amine-containing linker element may react with sugars when in the aldehyde or ketone tautomeric form.

However, if the primary amine is beta to a thiol group (which may be in the protected disulfide form outside the cell), then it has the potential to form an irreversible thiazolidine linker in the final coferon dimer.

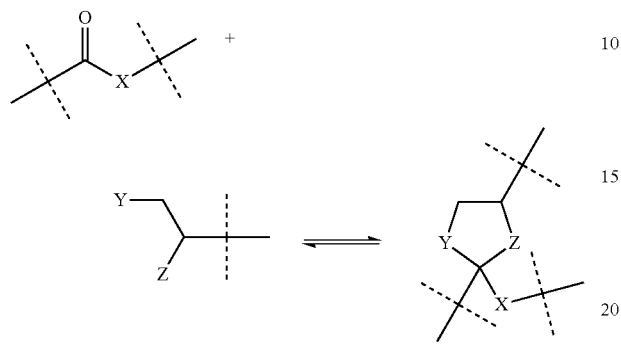

where Y, Z = N, O, S where X, Y and Z may be varied to tune the equilibrium in aqueous solution and the lines crossed with a dashed line illustrate the one or more bonds formed joining the one or more diversity elements, directly or through a connector, to the molecule.

Linker Elements Derived from a Carbonyl Group

Linker elements derived from carbonyl groups may participate in reversible hemiacetal and hemiketal formation with alcohols.

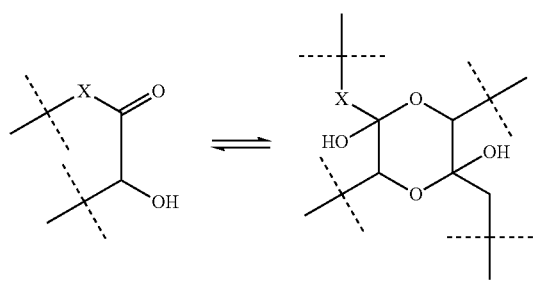

where X, may be varied to tune the equilibrium in aqueous solution and the lines crossed with a dashed line illustrate the one or more bonds formed joining the one or more diversity elements, directly or through a connector, to the molecule.

Linker elements derived from carbonyl groups may participate in reversible hydrazone formation with other amines.

Schematic Representation of Reversible Hydrazone Formation

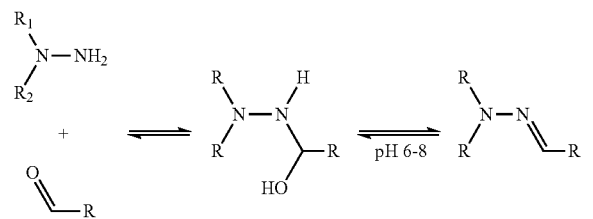

where $R_1$, $R_2$= —F, —Cl, —CF$_3$, —NO$_2$, —C=O, —COOH, or other electron withdrawing group.

Example of amines for reversible hydrazone formation.

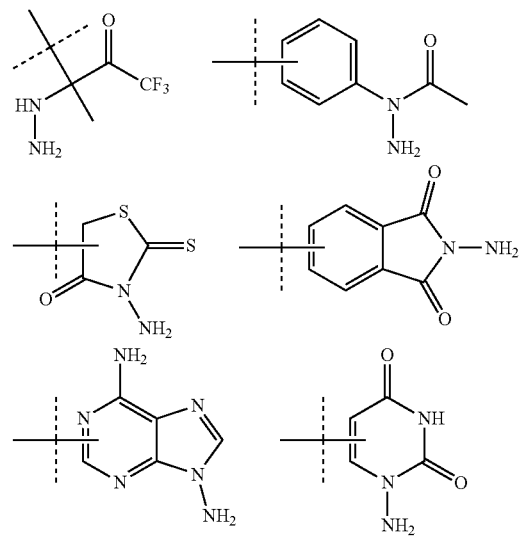

Example of carbonyl containing molecules for reversible hydrazone formation.

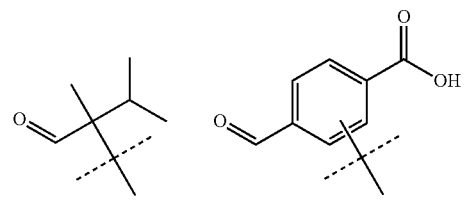

Linker Elements Based on Forming Reversible Boronate Esters.

These compounds may be ideal for screening purposes, as well as may work in vivo. One potential caveat is that many sugars have diols that may react with the boronic acid containing linker element. Boronates can also complex with amino alcohols and may also complex with amido acids.

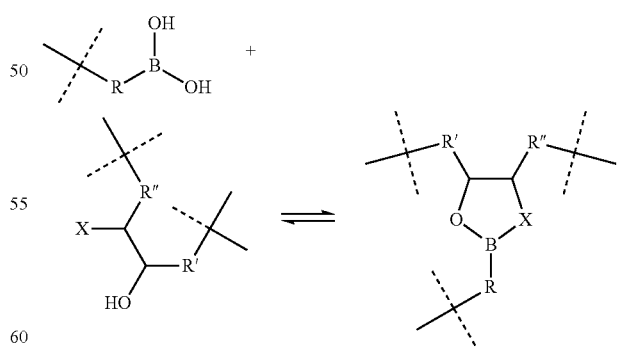

where X, R, R' and R" may be varied to tune the equilibrium in aqueous solution and the lines crossed with a dashed line illustrate the one or more bonds formed joining the one or more diversity elements, directly or through a connector, to the molecule.

Linker Elements Based on Binding to a Metal Co-Factor.

Linker elements that are capable of binding to a bioavailable metal, such as zinc or magnesium should work in vivo.

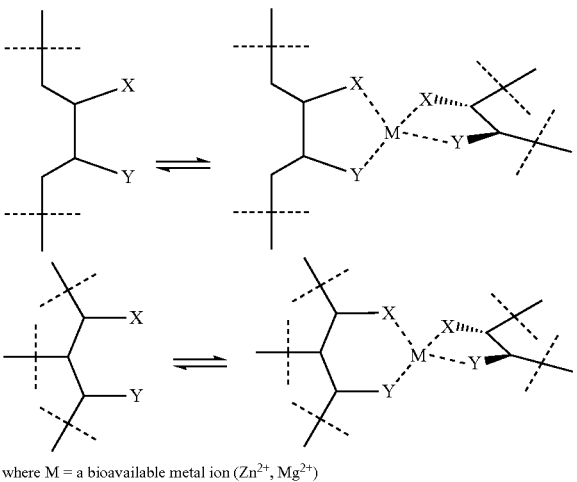

where M = a bioavailable metal ion ($Zn^{2+}$, $Mg^{2+}$)

where X and Y may be varied to tune the equilibrium in aqueous solution and the lines crossed with a dashed line illustrate the one or more bonds formed joining the one or more diversity elements, directly or through a connector, to the molecule.

Linker Elements Derived from Other Functional Groups that Undergo Other Reversible Reactions Linker elements may be derived from functional groups that undergo reversible reactions such as forming Diels-Alder adducts. These have been shown to work in dynamic combinatorial chemistry screens (Boul, P. J et al., *Organic Lett* 7:15-18 (2005), which is hereby incorporated by reference in its entirety).

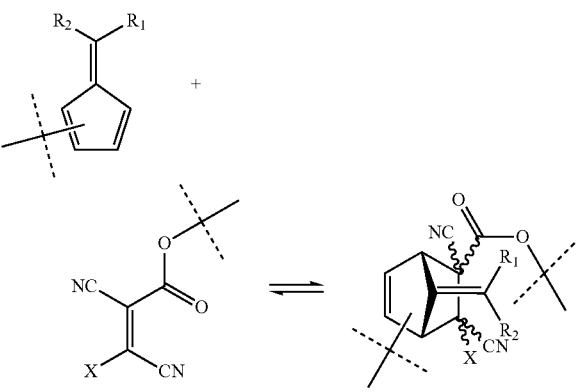

where X=CN or $CO_2R$ and the lines crossed with a dashed line illustrates the bonds formed joining the one or more diversity elements to the molecule.

The most sophisticated designs encourage heterodimer linker element formation, such that A-B pairs are preferred over A-A or B-B homodimer formation. Nevertheless, a successful linker element design that binds tightly to an identical linker element with a different ligand may also be used. If the ligands do not influence self-binding, then using two different ligands should generate the A-B heterodimer approximately half of the time.

One class of linker elements involve covalent interactions that occur and are reversible under physiological conditions. These are S—S disulfide bonds, alcohol to ketone to form hemi-ketals, and thiol to ketone to form hemi-thioketals.

An important variation in the linker element design is to have the linker element come together through two covalent bonds. The advantage of such an approach is that even though the individual reaction may be unfavored, once a single bond is made, the local concentration of the other two groups favors formation of the second covalent bond and helps drive the equilibrium towards linker element formation.

Some linker element designs may allow linker elements to bind to each other with minimal or no added binding help from the diversity elements. Such designs include linker elements that bind to each other with the aid of a metal cofactor. These designs expand the potential uses of coferons.

Some linker elements may be designed to associate irreversibly within the cell. For example, the two linker elements may have maltol or 2-picolinic acid groups to chelate $Zn^{2+}$ co-factors. In addition, one may have a boronic acid group, and the other an alcohol group. When the two linker elements are brought in close proximity by the presence of the zinc, the boronic ester forms easily. Either the boronic acid or the zinc chelation linkages by themselves are reversible, but once brought together the concentration of the other group is sufficiently high to keep the linker elements together.

A second and related concept is to prevent or minimize side reactions between the individual linker element and active groups on proteins, amino acids, or other molecules in the cell. Such side reactions may be reduced by designing linker element structures that may be sterically hindered when reacting with a large macromolecule, but more amenable to reacting when aligned with a partner linker element.

A third concept is to bring two linker elements together due to hydrophobic or other non-covalent affinities, and this increased proximity allows for a single or double covalent linkage to occur.

Further, the architecture of the linker element covalent interactions should favor intermolecular bond formation over intramolecular bond formation.

Another embodiment of the linker element is an aromatic compound, where, when the linker element and its diversity element are bound together, one or more aromatic rings of the binding partner are stacked to guide formation of one or more covalent bonds between the linker element and the binding partner.

Finally, when the linker elements are in use, they will each have an affinity to their target, and this too will help assemble the dimeric linker element structure. In other words, the intended target helps assemble its own inhibitor.

There are four categories of linker elements that form dimers. These include linker elements that bind reversibly with each other in the presence of target, linker elements that bind essentially irreversibly with each other once they are brought in proximity by the target, linker elements that bind reversibly with each other independent of target, and linker elements that bind essentially irreversibly with each other independent of target.

Derivatives Based on 1,3-Dihydroxyacetone

Derivatives based on 1,3-dihydroxyacetone (Linker Element 1) would most likely require bulky blocking groups to reduce the natural reactivity of the keto group. Nevertheless, this is the minimal linker element design.

One embodiment of the linker element is an aliphatic compound with a hydroxy group alpha, beta, or gamma to a carbonyl group, where the linker element and its binding partner, when bound together, form a 6 or 8 member di-hemiacetal or di-hemiketal rings, the linker element (i.e. Linker Element 1) is Generic Structure

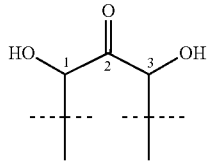

(I)

where
the lines crossed with a dashed line illustrate the one or more bonds formed joining the one or more diversity elements, directly or through a connector, to the molecule of Formula (I). If there is no diversity element at that position, the group may be chosen from the following: —H, —OH or —$CH_3$.

One example of this embodiment is 1,3-dihydroxyacetone (MW: 90) which naturally dimerizes under physiologic conditions.

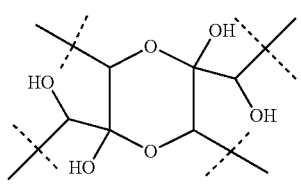

1.3-Dihydroxyacetone dimer

Another linker element design is based on 2-hydroxycyclohexanone (Linker Element 2). This linker element makes a rigid 3-ringed structure that may be ideal. Different adjacent substitutions may activate the hydroxyl group or the ketal to favor intermolecular interactions. The molecular weight of 2-hydroxycyclohexanone is 114.

Generic Structure

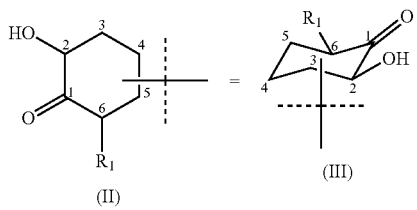

where
$R_1$=H, —OH, —$CH_3$, —F, —$CF_3$, or another electron withdrawing functional group,
the line crossed with a dashed line illustrates the bond formed joining the diversity element, directly or through a connector, to the molecule of Formula (II) and Formula (III).

Examples of this embodiment of the linker elements are as follows:

2A)

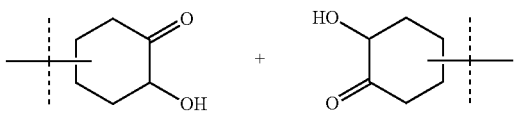

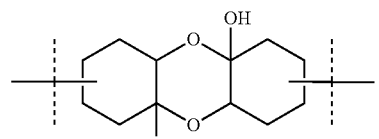

Molecular Weight: 256.34

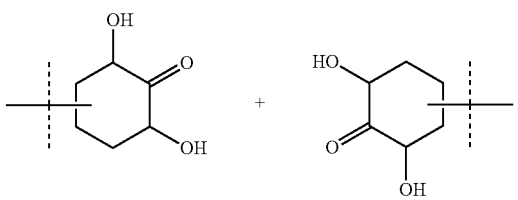

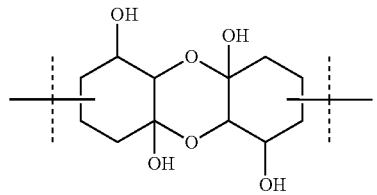

Molecular Weight: 228.28

Figure 6:
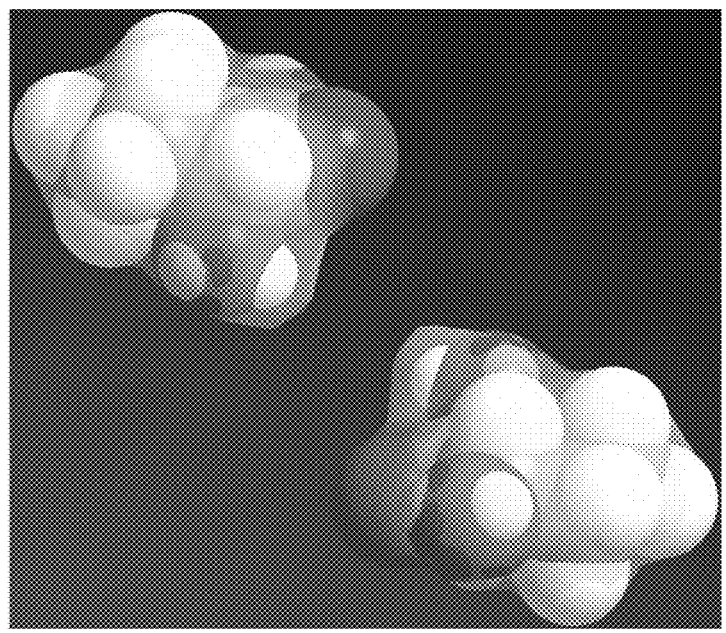
FIG. 6 shows a space filling 3-dimensional representation of linker elements derived from 2-hydroxycyclohexanone.
Figure 7:
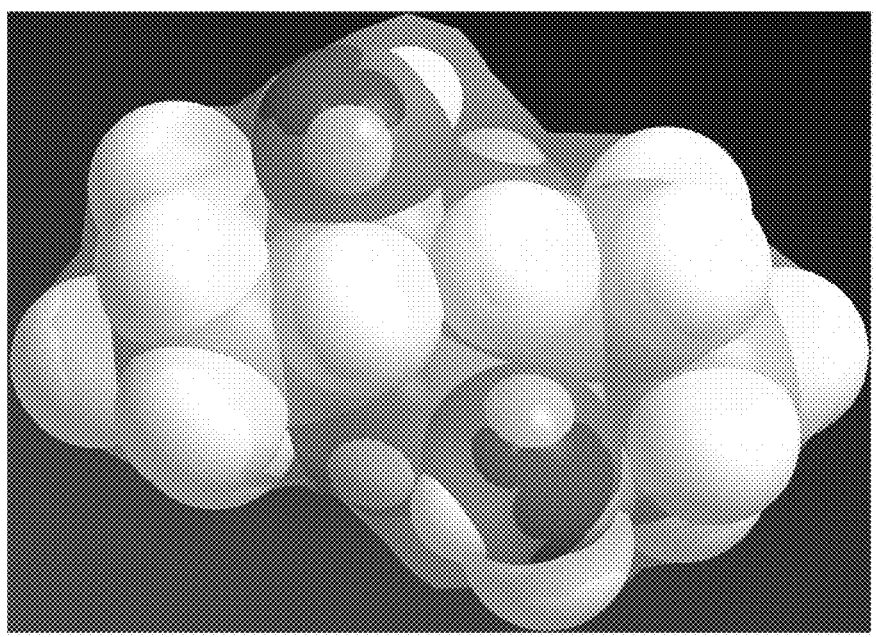
FIG. 7 shows a space filling 3-dimensional representation of the dimer formed by linker elements derived from 2-hydroxycyclohexanone.

2B)
See FIGS. 6-7 for three-dimensional depictions of these linker elements.

2C)

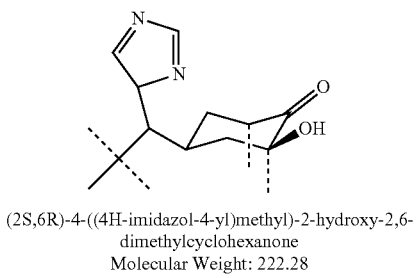

(2S,6R)-4-((4H-imidazol-4-yl)methyl)-2-hydroxy-2,6-dimethylcyclohexanone
Molecular Weight: 222.28

The imidazole group may function as an internal catalyst, through proton donation to the opposite linker element or by metal ion catalysis to facilitate reversible dimer formation.

2D)

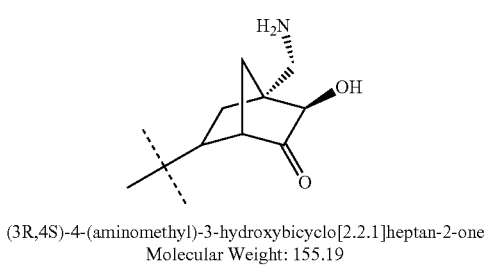

(3R,4S)-4-(aminomethyl)-3-hydroxybicyclo[2.2.1]heptan-2-one
Molecular Weight: 155.19

The bicyclo ring provides steric hindrance and directs attack from the bottom side of the ring. The amine will lead to imine formation and catalyze the condensation reaction. The protonated amino group may function as an internal catalyst to facilitate reversible dimer formation by acting as a potential proton donor to the opposite linker element.

2E)

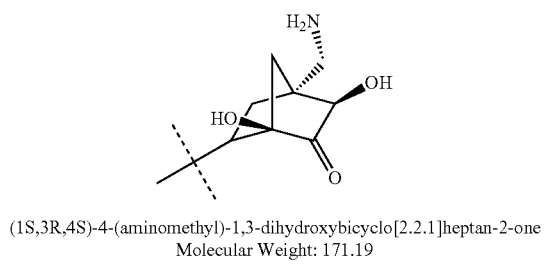

(1S,3R,4S)-4-(aminomethyl)-1,3-dihydroxybicyclo[2.2.1]heptan-2-one
Molecular Weight: 171.19

Derivatives Based on Cyclopentane Scaffold with a Strained 5-Membered Hemiacetal or Hemiketal Ring Another embodiment of the linker element is based on a cyclopentane scaffold (Linker Element 3), where one or more sides is also part of a strained 5-membered hemiacetal ring. $R_1$ (at ring position 1) and $R_3$ (at ring position 2) are aldehyde or keto groups. $R_2$ (at ring position 1) and $R_4$ (at ring position 2) are either hydroxyl or alkoxy groups. The diversity element may be attached to either position 3, 4, or 5 of the cyclopentane ring. The ring will be in equilibrium between the aldehyde and hemiacetal state. When two such linker elements in the aldehyde states are brought in close proximity, they may form 2 or even 4 intermolecular bonds. Additional hydroxyl residues may also be used to allow for formation of intermolecular hemiacetals, such as the more favored 6 membered rings. Linker element dimers with 4 intermolecular bonds may be exceedingly stable.

Generic Structure

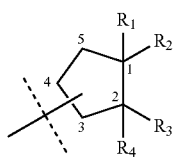

(IV)

where
$R_1=R_3=$—H,

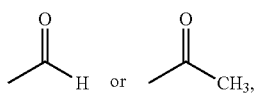

$R_2=R_4=$—H, —OH, or —CH$_2$OH the line crossed with a dashed line illustrates the bond formed joining the diversity element, directly or through a connector, to the molecule of Formula (IV).

Examples of this embodiment of linker elements are shown below as items 3A) to 3C).

3A) Intramolecular hemiacetal to intermolecular 6-membered diacetal ring (1S, 2R)-1-hydroxy-2-(hydroxymethyl)cyclopentanecarbaldehyde
Molecular Weight: 144.17

Figure 8:
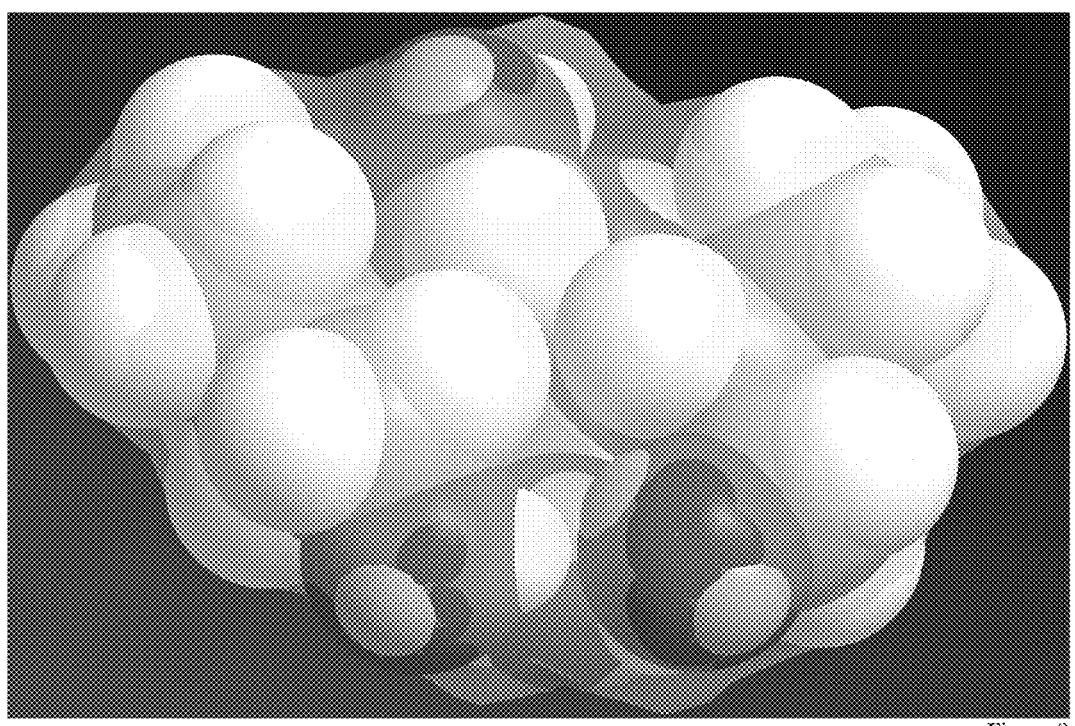
FIG. 8 shows a space filling 3-dimensional representation of the dimer formed by linker elements derived from 1-hydroxy-2-hydroxymethyl cyclopentanecarbaldehyde.
Figure 9:
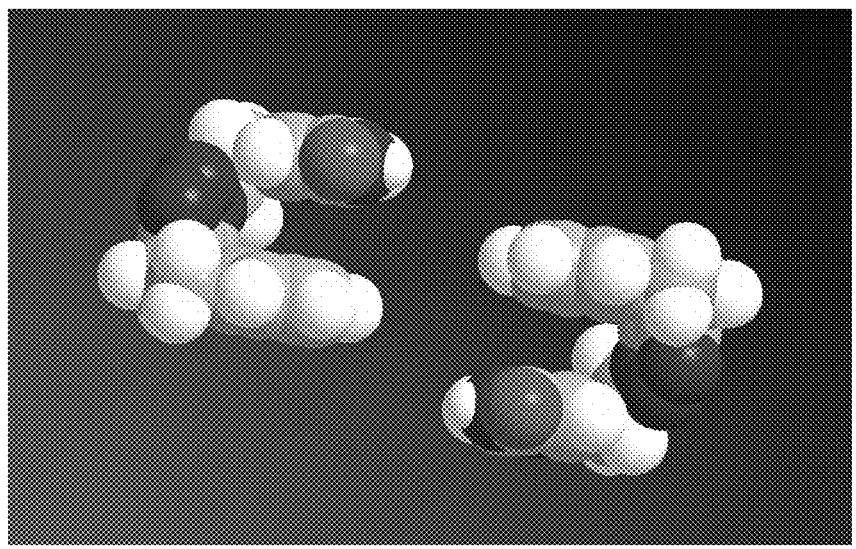
FIG. 9 shows a space filling 3-dimensional representation of triazole linked aromatic linker elements.
Figure 10:
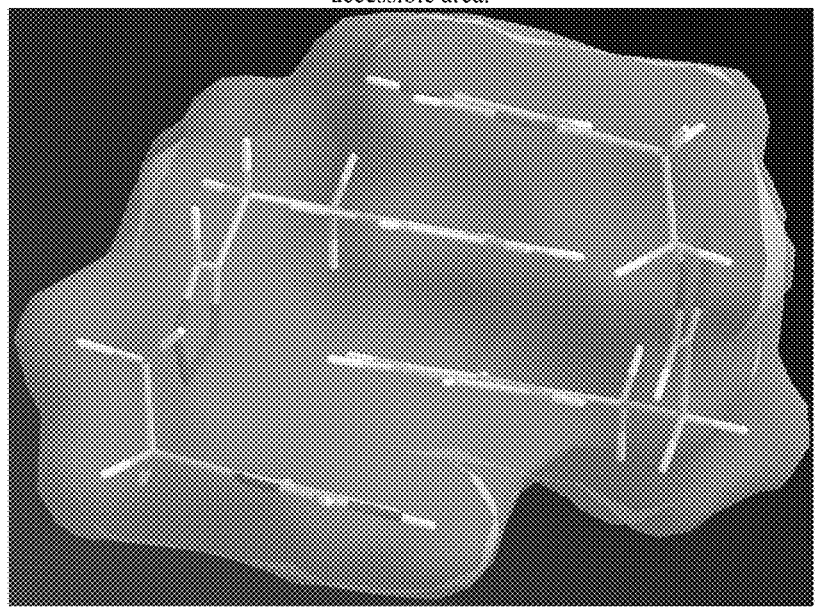
FIG. 10 shows a 3-dimensional representation of triazole linked elements dimerized through intercalation. The translucent surface represents a solvent accessible area.
Figure 11:
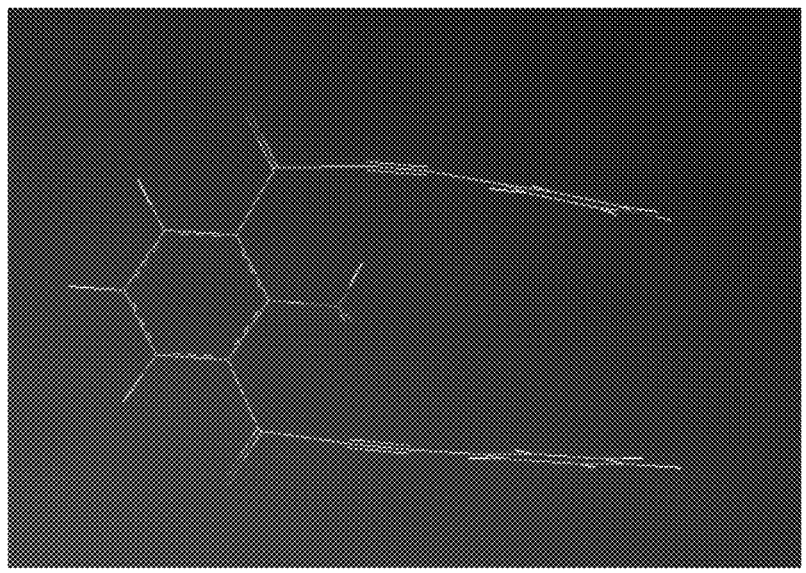
FIG. 11 shows a 3-dimensional representation of aromatic intercalator based linker element monomer.
Figure 12:
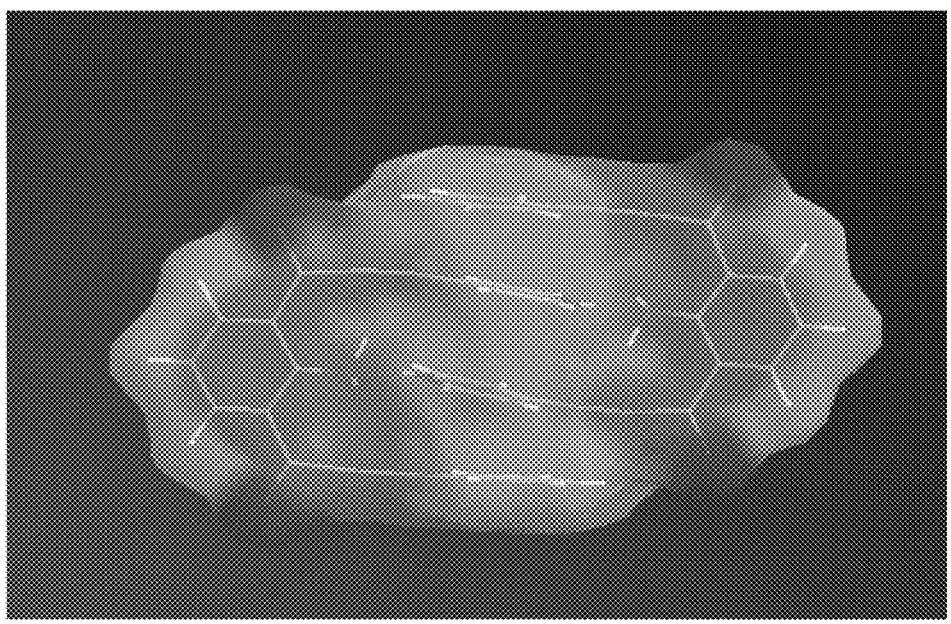
FIG. 12 shows a side view of a 3-dimensional representation of a linker element dimer with molecular surfaces.
Figure 13:
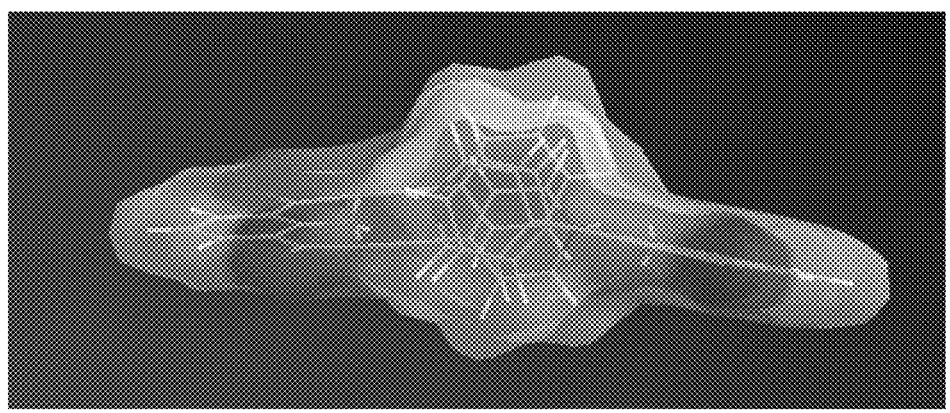
FIG. 13 is a top view of a 3-dimensional representation of a linker element dimer with molecular surfaces.

See FIG. 8 for a 3-dimensional depiction.

3B) Intramolecular hemiacetals to two intermolecular 6-membered diacetal rings

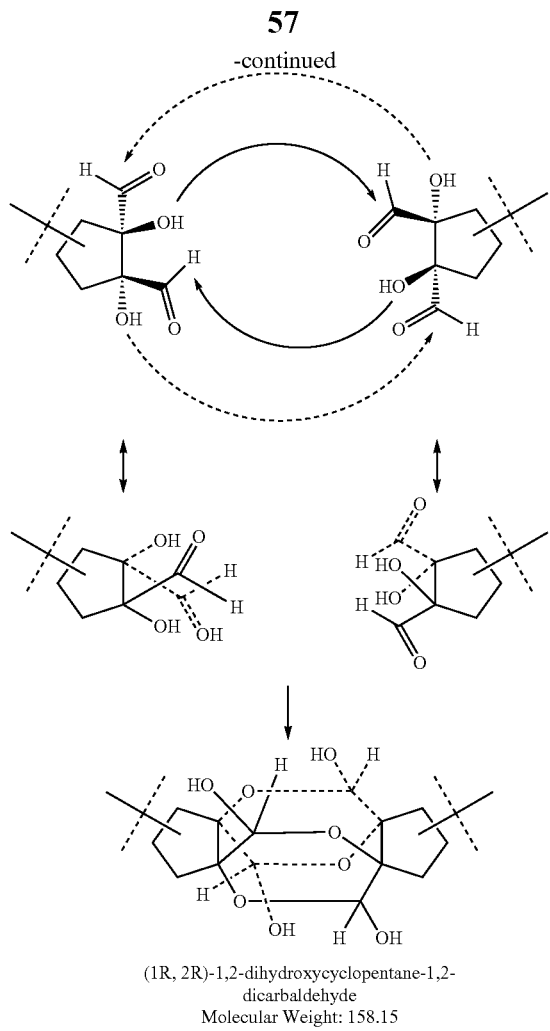

(1R, 2R)-1,2-dihydroxycyclopentane-1,2-dicarbaldehyde
Molecular Weight: 158.15

3C) Two strained 5-membered ring hemiacetals are in equilibrium with the free aldehyde form of the linker element.

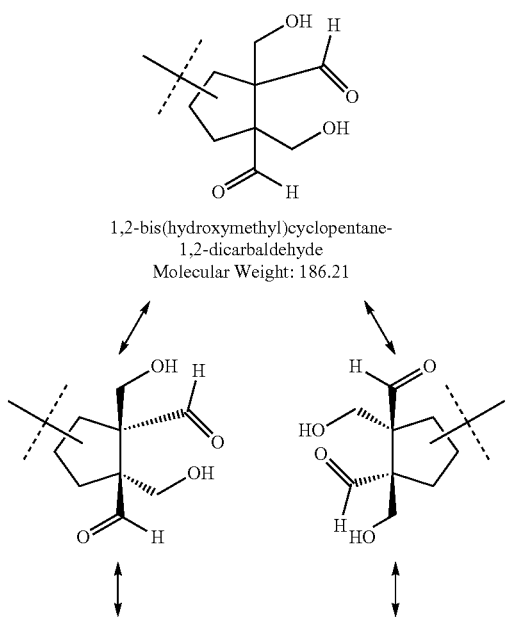

1,2-bis(hydroxymethyl)cyclopentane-1,2-dicarbaldehyde
Molecular Weight: 186.21

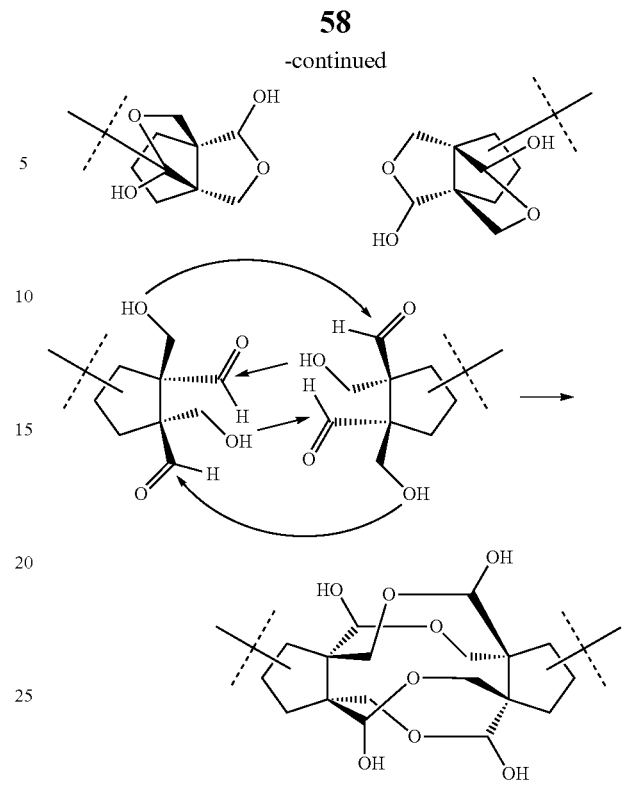

Derivatives Based on 5-Hydroxy-2-Oxo-1-Hexanal Structure

Another embodiment of the linker element is based on 5-hydroxy, 2-oxo-1-hexanal (Linker Element 4). This compound and its family of derivatives (see drawings below) also create rigid 3-ringed structures, analogous to the 2-hydroxycyclohexanone dimers. There are multiple opportunities to modulate the reactivity of various groups. Reactivity can be modulated by the addition of hydroxyl groups (3 and or 5 positions of the linear form), while methyl (or other bulky) substituents (3 position of the linear form) provide steric hindrance to protect the reactive centers from attack by extraneous electrophiles and nucleophiles. Substituents, such as carboxamide or imidazole, may be added to the 6 position (of the linear form) to enhance reactivity of the linker element. Diversity elements may be added to the 6 position (of the linear form).

Generic Structure

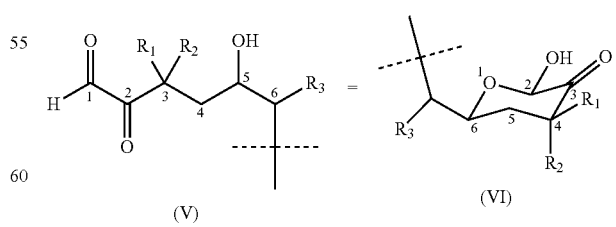

(V)  (VI)

where $R_1 = R_2 = $ —H, —OH, —CH$_3$, —F, or —CF$_3$ $R_3 = $ —H, —CH$_2$NH$_2$,

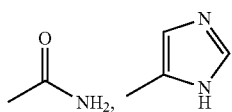

Examples of this embodiment of linker elements are shown below as items 4A) 4A) to 4L).

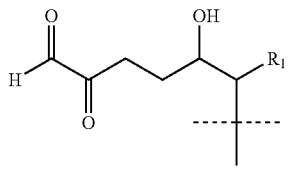

5-hydroxy-2-oxohexanal Derivative
Molecular Weight: 143.16

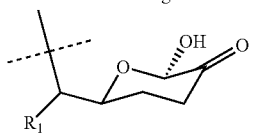

Circular Hemiacetal Form "A"
(2R)-2-hydroxy-3-oxo-
4-methylcyclohexanone

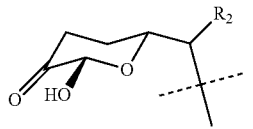

Circular, Hemiacetal Form "B"
(2S)-2-hydroxy-3-oxo-
4-methylcyclohexanone

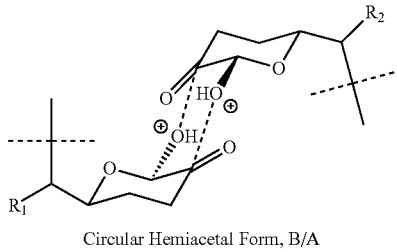

Circular Hemiacetal Form, B/A
Transition state

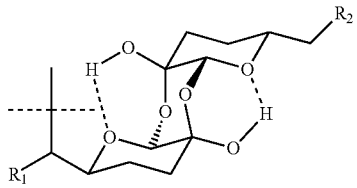

Circular Hemiacetal Form, B/A
Di-ketal dimer

4B)

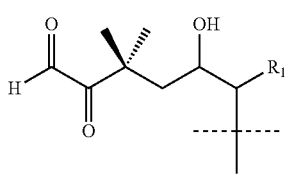

5-hydroxy-3,3-dimethyl-2-oxohexanal Derivative
Molecular Weight: 172.22

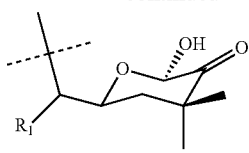

Circular Hemiacetal Form "A"
(2R)-2-hydroxy-3-oxo-4,6,6-trimethylcyclohexanone

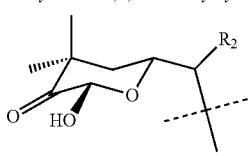

Circular Hemiacetal Form "B"
(2S)-2-hydroxy-3-oxo-4,6,6-trimethylcyclohexanone

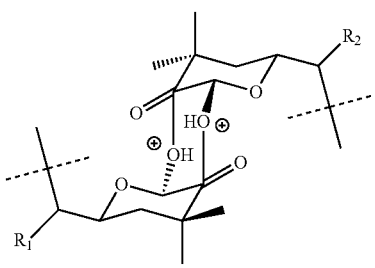

Circular Hemiacetal Form, B/A Transition state

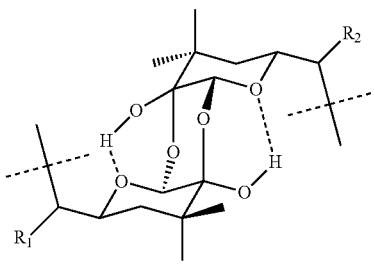

Circular Hemiacetal Form, B/A Di-ketal dimer

Addition of methyl groups at 3-position direct nucleophilic attack by the hydroxyl group from one direction only.

4C) Replacing one of the methyl groups at the 3-position with a hydroxyl group makes the carbonyl more reactive.

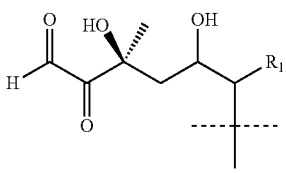

(3S)-3,5-dihydroxy-3-methyl-
2-oxohexanal Derivative
Molecular Weight: 173.19

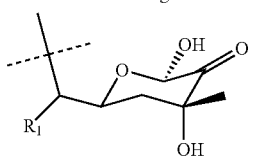

Circular Hemiacetal Form "A"
(2R,6R)-2,6-dihydroxy-3-oxo-4,
6-dimethylcyclohexanone

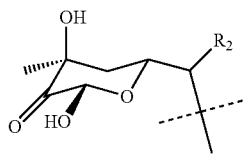

Circular, Hemiacetal Form "B"
(2S,6S)-2,6-dihydroxy-3-oxo-
4,6-dimethylcyclohexanone

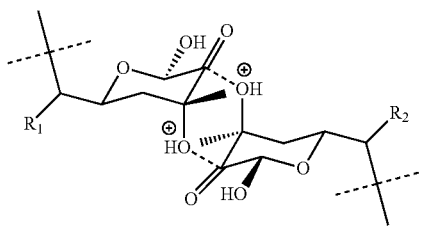

Circular Hemiacetal Form, A/B
Transition state

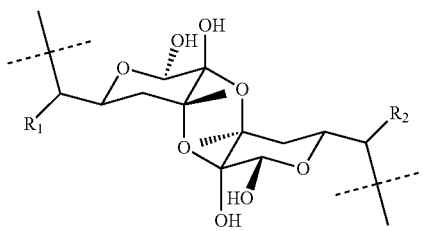

Circular Hemiacetal Form, A/B
Di-ketal dimer

4D) The 3,5-dihydroxy-2-oxohexanal derivative is predicted to be very active and can form dimers in two different orientations.

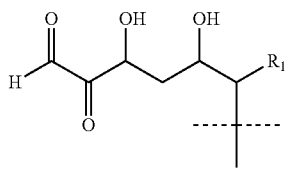

3,5-dihydroxy-
2-oxohexanal derivative
Molecular Weight: 159.16

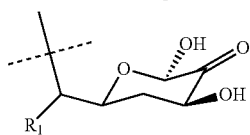

Circular Hemiacetal Form "A"
(2R,6S)-2,6-dihydroxy-3-oxo-4-
methylcyclohexanone

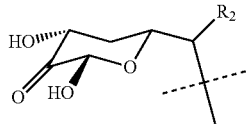

Circular, Hemiacetal Form "B"
(2S,6R)-2,6-dihydroxy-3-oxo-
4-methylcyclohexanone

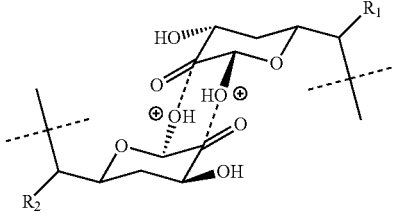

Circular Hemiacetal Form, B/A
Transition state

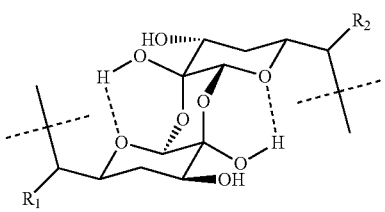

Circular Hemiacetal Form, B/A
Di-ketal dimer
Dimer 1

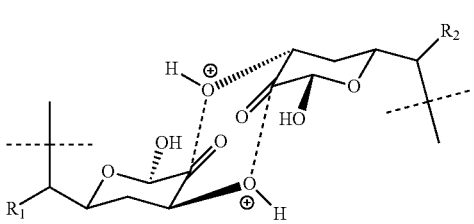

Circular Hemiacetal Form, B/A
Transition state 2

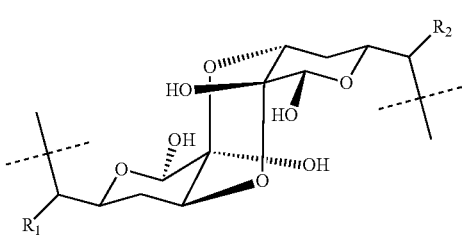

Circular Hemiacetal Form, B/A
Di-ketal Dimer 2
Dimer 2

4E) Addition of an acetamido group facilitates intermolecular dimer formation. The amide can act as a proton donor to the opposite linker element when both linker elements are in the correct orientation, functioning as an internal catalyst.

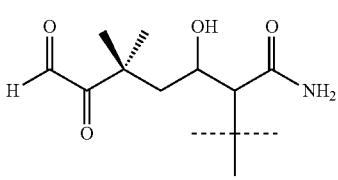

3-hydroxy-5,5-dimethyl-
6,7-dioxoheptanamide
Molecular Weight: 215.25

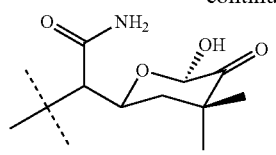

(2R)-2-hydroxy-3-oxo-4-
(2-acetamido)-6,6-
dimethylcyclohexanone
Circular Hemiacetal Form "A"

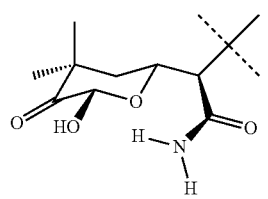

(2S)-2-hydroxy-3-oxo-4-
(2-acetamido)-6,6-
dimethylcyclohexanone
Circular, Hemiacetal Form "B"

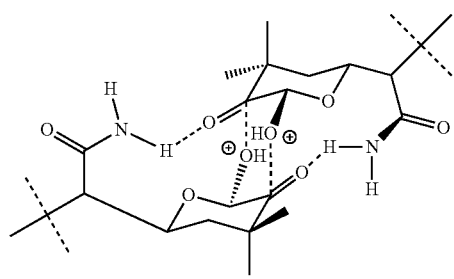

Circular Hemiacetal Form, B/A
Transition state

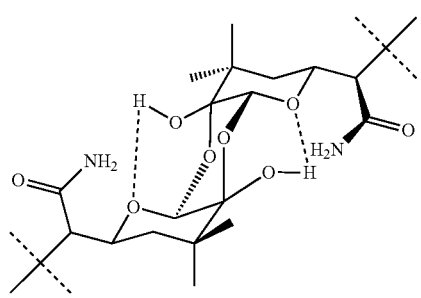

Circular Hemiacetal Form, B/A
Dimer

4F) Replacing one of the methyl groups at the 3 position with a hydroxyl makes the carbonyl more reactive.

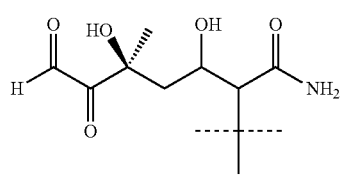

(5S)-3,5-dihydroxy-
5-methyl-6,7-dioxoheptanamide
Molecular Weight: 203.19

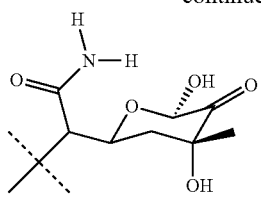

(2R,6R)-2,6-dihydroxy-3-oxo-6-
methyl-4-(2-acetamido)-cyclohexanone
Circular Hemiacetal Form "A"

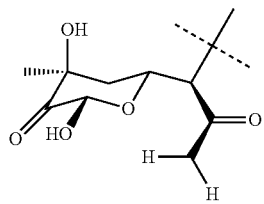

(2S,6S)-2,6-dihydroxy-3-oxo-
6-methyl-4-(2-acetamido)-
cyclohexanone
Circular, Hemiacetal Form "B"
Dimer 1

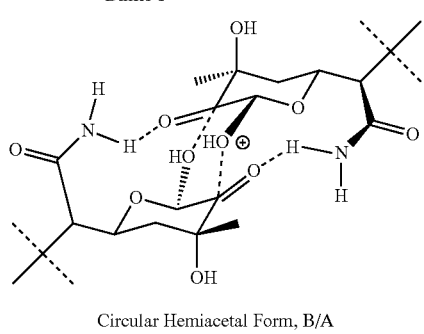

Circular Hemiacetal Form, B/A
Transition state

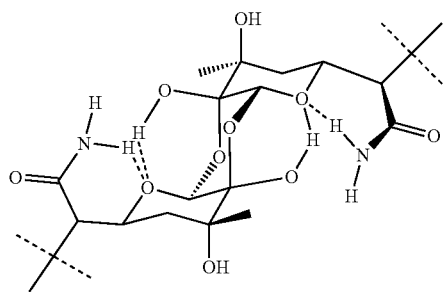

Circular Hemiacetal Form, B/A
Di-ketal dimer
Dimer 2

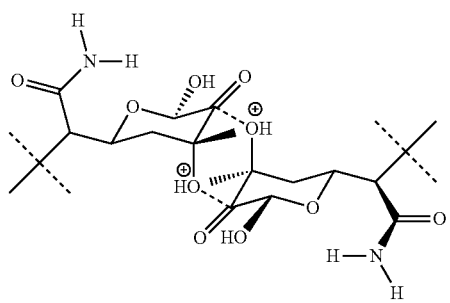

Circular Hemiacetal Form, A/B
Transition state

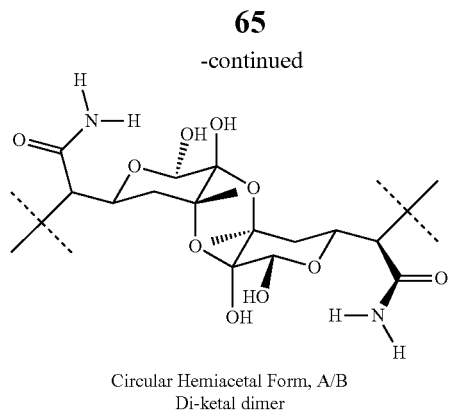

Circular Hemiacetal Form, A/B
Di-ketal dimer

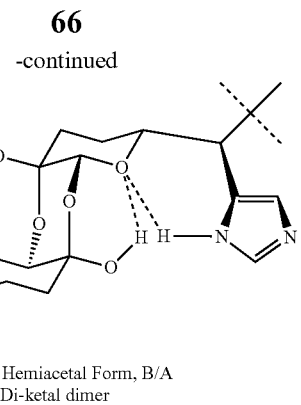

Circular Hemiacetal Form, B/A
Di-ketal dimer

4G) Addition of an imidazole substituent to function as an internal catalyst, facilitates reversible formation of the dimer by acting as a potential proton donor to the opposite linker element. The two linker elements need to be in the correct orientation for dimer formation. (Structures 4G through 4L)

4H) Dimethyl substitution at the 3-position provides steric hindrance to protect the carbonyl from extraneous nucleophiles Imidazole group at the 5-position may function as an internal catalyst to facilitate reversible dimer formation by acting as a potential proton donor to the opposite linker element.

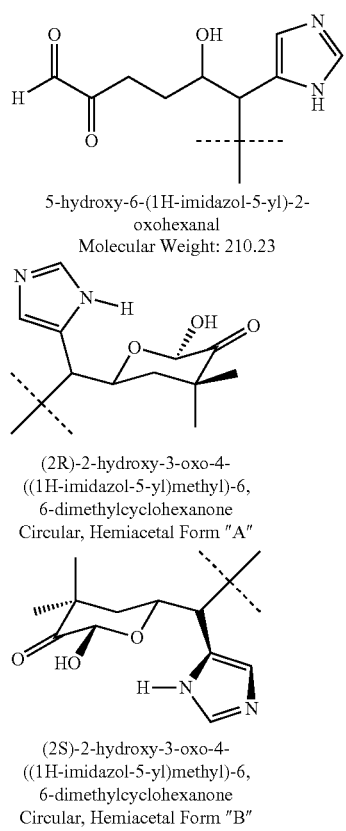

5-hydroxy-6-(1H-imidazol-5-yl)-2-oxohexanal
Molecular Weight: 210.23

(2R)-2-hydroxy-3-oxo-4-((1H-imidazol-5-yl)methyl)-6,6-dimethylcyclohexanone
Circular, Hemiacetal Form "A"

(2S)-2-hydroxy-3-oxo-4-((1H-imidazol-5-yl)methyl)-6,6-dimethylcyclohexanone
Circular, Hemiacetal Form "B"

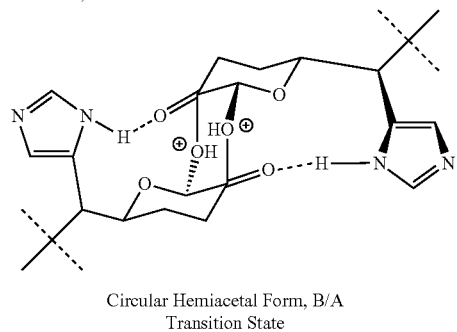

Circular Hemiacetal Form, B/A
Transition State

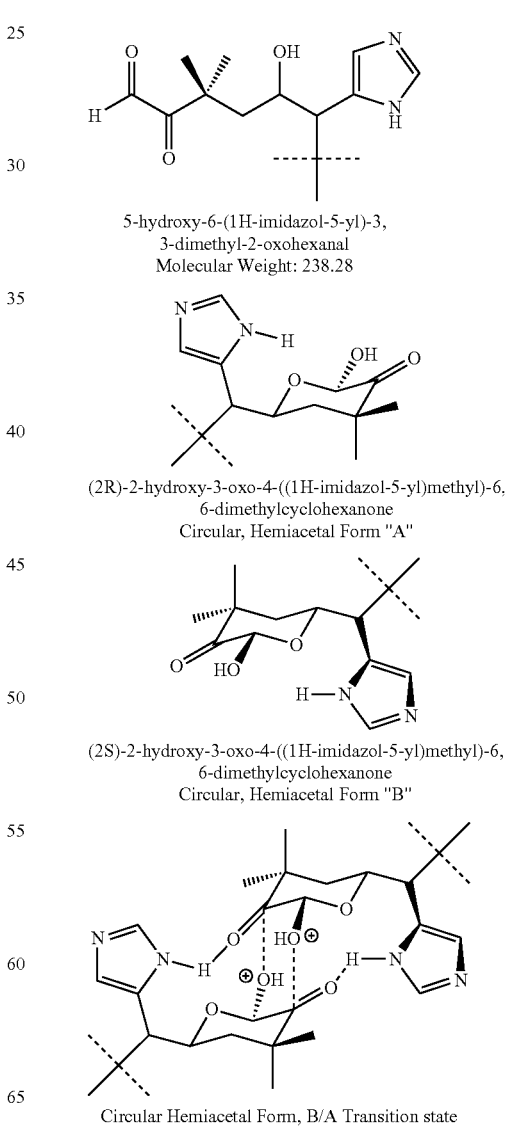

5-hydroxy-6-(1H-imidazol-5-yl)-3,3-dimethyl-2-oxohexanal
Molecular Weight: 238.28

(2R)-2-hydroxy-3-oxo-4-((1H-imidazol-5-yl)methyl)-6,6-dimethylcyclohexanone
Circular, Hemiacetal Form "A"

(2S)-2-hydroxy-3-oxo-4-((1H-imidazol-5-yl)methyl)-6,6-dimethylcyclohexanone
Circular, Hemiacetal Form "B"

Circular Hemiacetal Form, B/A Transition state

67

-continued

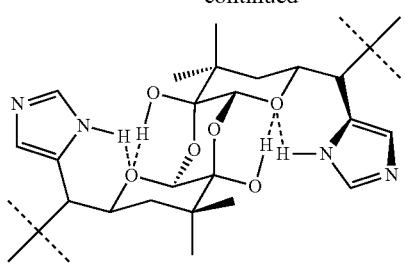

Circular Hemiacetal Form, B/A Di-ketal dimer

4I) Replacing one of the methyl groups at the 3 position with a hydroxyl makes the carbonyl more reactive.

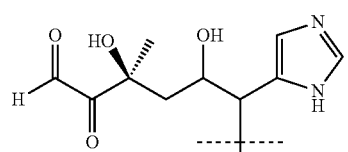

(3S)-3,5-dihydroxy-6-(1H-imidazol-5-yl)-3-methyl-2-oxohexanal
Molecular Weight: 240.26

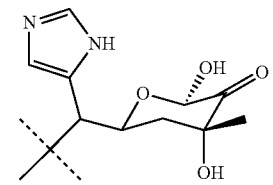

(2R,6R)-2,6-dihydroxy-4-((1H-imidazol-5-yl)methyl)-6-methylcyclohexanone
Circular, Hemiacetal Form "A"

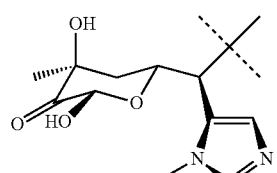

(2S,6S)-2,6-dihydroxy-4-((1H-imidazol-5-yl)methyl)-6-methylcyclohexanone
Circular, Hemiacetal Form "B"

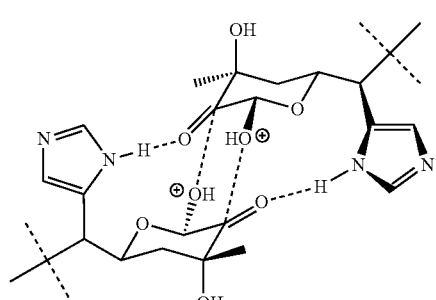

Circular Hemiacetal Form, B/A Transition state

68

-continued

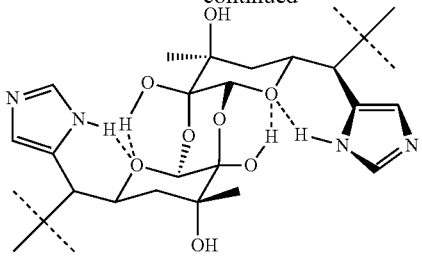

Circular Hemiacetal Form, B/A Di-ketal dimer

4J) The carbonyl is flanked by two hydroxyl groups to increase its reactivity

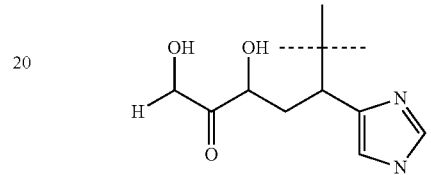

1,3-dihydroxy-5-(1H-imidazol-4-yl)pentan-2-one
Molecular Weight: 198.22

4K) Addition of a methyl group to the 3-position adds steric hindrance

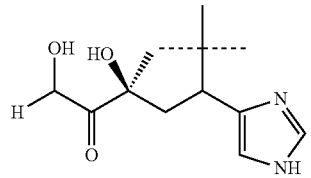

(S)-1,3-dihydroxy-5-(1H-imidazol-4-yl)-3-methylpentan-2-one
Molecular Weight: 212.25

4L) Dimethyl substitution at the 4 position provides steric hindrance.

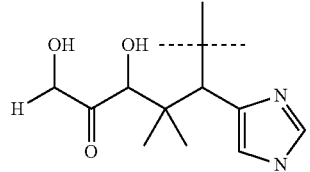

1,3-dihydroxy-5-(1H-imidazol-4-yl)-4,4-dimethylpentan-2-one
Molecular Weight: 226.27

Derivative Based on Using an Aromatic Heterocyclic or Non-Heterocyclic Ring

Derivatives (Linker Element 5) based on using an aromatic heterocyclic or non-heterocyclic ring with at least one bond to a diversity element directly or through a connector, said ring comprising of 5 or 6 membered rings either singly or fused together including but not limited to benzene, naphthalene, purine, pyrimidine, or other aromatic structures with varying degrees of solubility in aqueous vs. lipid bilayer to bring two linker elements together, where the linker elements contain additional alcohol, thiol, boronic acid, aldehyde, or ketone groups whose proximity (once the hydrophobic surfaces align) favors formation of one or more covalent bonds. This architecture allows for selection of linker elements that would have suboptimal alignment of the aromatic surfaces if forming self-dimers and, consequently, will be driven to form heterodimers. Further, for some of the structures, it will be advantageous for the two reactive groups to be attached to the aromatic ring pointing away from each other (but not necessarily in the para orientation) so they cannot form intramolecular bonds. In the examples below, n=1-3 and m=0-2. Six membered aromatic rings may have aliphatic thiol or alkoxy groups at positions 1 or 3 of the ring and aliphatic aldehyde or ketone substituents at position 3. Diversity elements may be added to positions 5 or 6 of the ring or may be appended to a C-atom belonging to $R_1$, $R_2$, or $R_3$. Additionally, the six-membered ring may contain N, O, or S atoms. Linker elements based on two aromatic rings, such as naphthalene, may have aliphatic thiol or alkoxy groups at positions 1, 3, or 8 of the ring and aliphatic aldehyde or ketone substituents at positions 1, 3, or 8 of the ring. Diversity elements may be added to positions 2, 5, or 7 of the ring or may be appended to a C-atom belonging to $R_1$, $R_2$, or $R_3$. Additionally the aromatic rings may contain N, O, or S atoms.

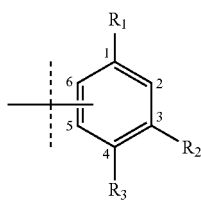

(VII)

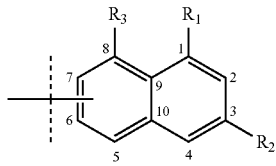

(VIII)

where $R_1$=—H, —$(CH_2)_n$OH, —$(CH_2)$SH, $B(OH)_2$ n=0-3, $R_2$ and $R_3$=—$(CH_2)_n$OH, —NH-Aliphatic

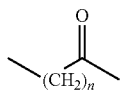

Examples of this embodiment of linker elements are shown below as items 5A) to 5J).

5A). The general format of Linker Element 5A involves a first linker element of the formula HS—$(CH_2)_n$-Aromatic-$(CH_2)_n$—C═O(OH) and a second linker element of the formula HS—$(CH_2)_n$-Aromatic-$(CH_2)_n$—$CH_3$. The following structures are specific examples of this embodiment.

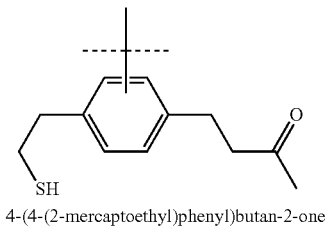

4-(4-(2-mercaptoethyl)phenyl)butan-2-one

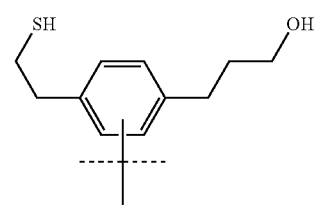

3-(4-(2-mercaptoethyl)phenyl)propan-1-ol

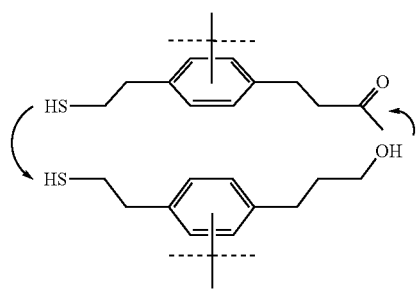

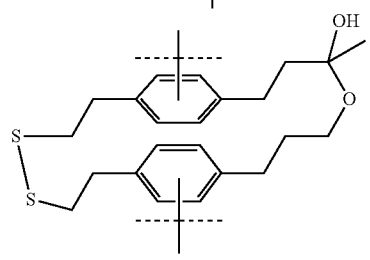

Front View

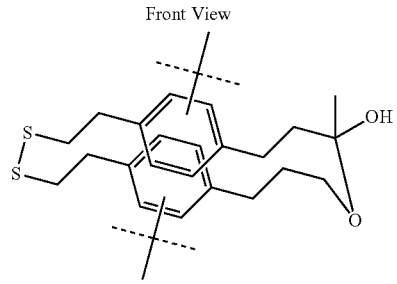

Top Angle View

5B) The general format of Linker Element 5B involves a first linker element of the formula

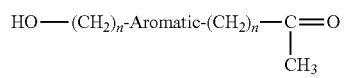

and a second linker element of the formula

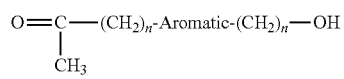

The following structures are specific for this embodiment.

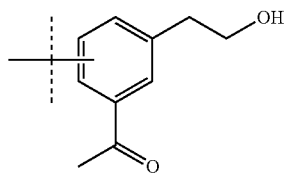
1(3-(2-hydroxyethyl)phenyl)ethanone

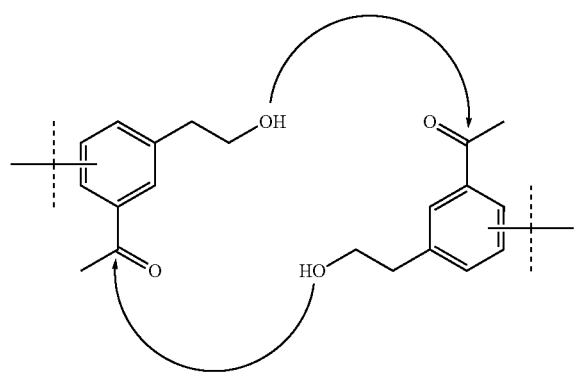

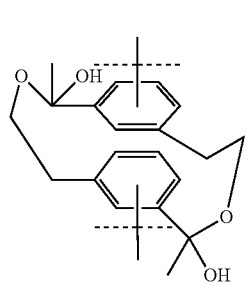
Side / Front View

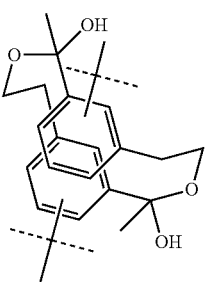
Top Angle View

5C) The general format of Linker Element 5C involves a first linker element of the formula HS—$(CH_2)_m$-Aromatic-$(CH_2)_m$—C=O$(CH_2)_n$—OH and a second linker element of the formula HS—$(CH_2)_n$-Aromatic-CH$_3$. The following structures are specific examples of this embodiment.

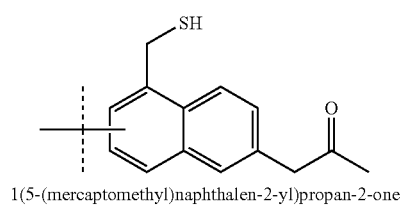
1(5-(mercaptomethyl)naphthalen-2-yl)propan-2-one

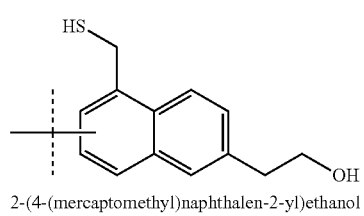
2-(4-(mercaptomethyl)naphthalen-2-yl)ethanol

-continued

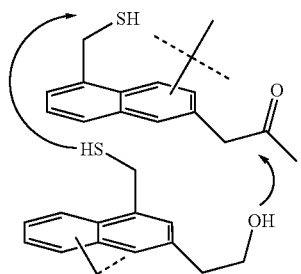

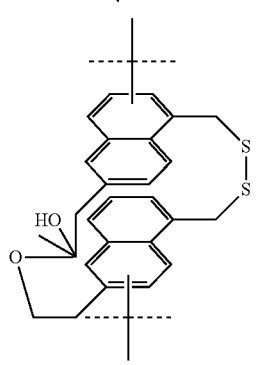
Side / Front View

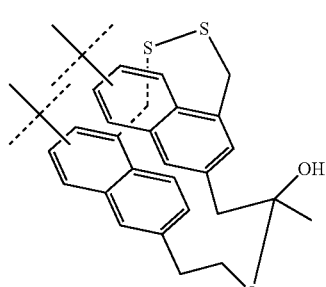
Top Angle View

5D) HS—$(CH_2)_m$-Aromatic-$(CH_2)_m$—C=O-Aromatic-$(CH_2)_n$—OH and a second linker element of the formula HS—$(CH_2)_n$—CH$_3$. The following structures are specific examples of this embodiment.

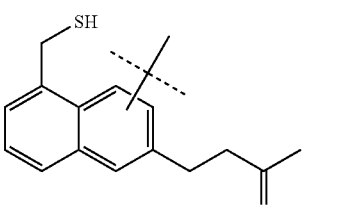
4-(5-(mercaptomethyl)naphthalen-2-yl)butan-2-one

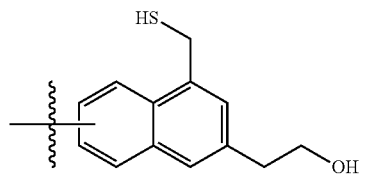
2-(4-(mercaptomethyl)naphthalen-2-yl)ethanol

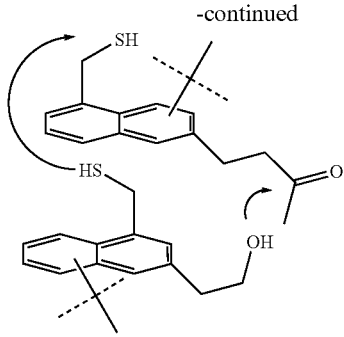

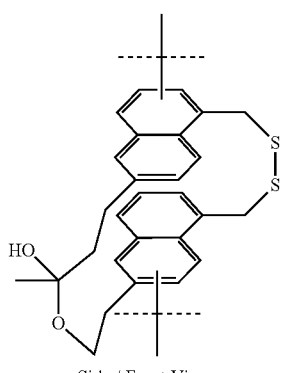

Side / Front View

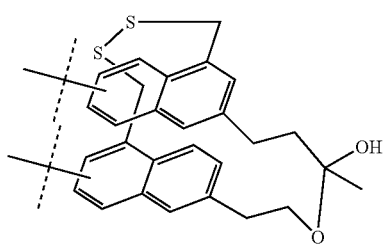

Top Angle View

5E) The general format of Linker Element 5E involves a first linker element of the formula HS—$(CH_2)_m$-Aromatic-$(CH_2)_m$—C=O-Aromatic-$(CH_2)_n$—OH and a second linker element of the formula HS—$(CH_2)_n$—CH$_3$. The following structures are specific examples of this embodiment.

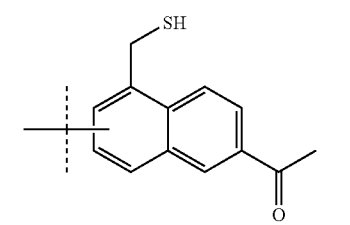

1(5-(mercaptomethyl)naphthalen-2-yl)ethanone

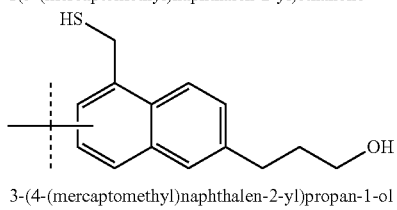

3-(4-(mercaptomethyl)naphthalen-2-yl)propan-1-ol

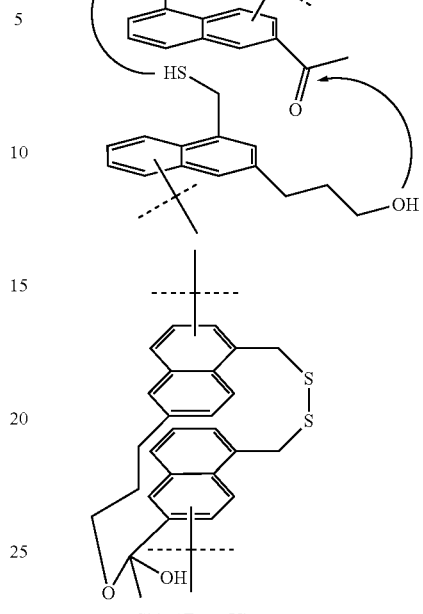

Side / Front View

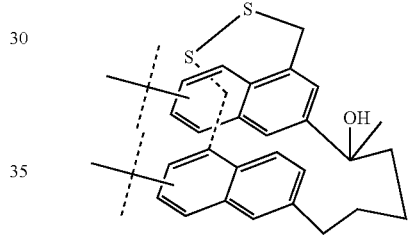

Top Angle View

5F) The general format of Linker Element 5F involves a first linker element of the formula HO—$(CH_2)_m$-Aromatic-$(CH_2)_m$—C=O-Aromatic-$(CH_2)_m$—OH and a second linker element of the formula O=C—$(CH_2)_m$—CH$_3$. The following structures are specific examples of this embodiment.

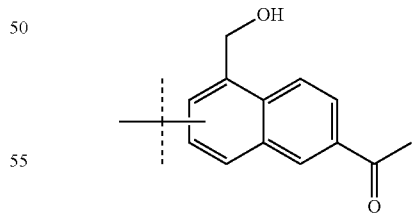

1(5-(hydroxymethyl)naphthalen-2-yl)ethanone

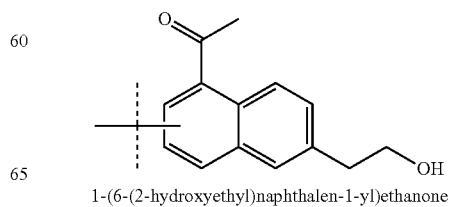

1-(6-(2-hydroxyethyl)naphthalen-1-yl)ethanone

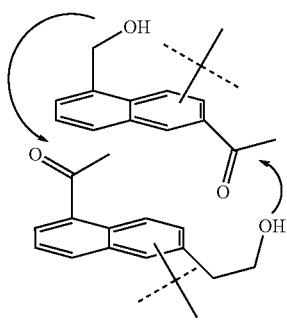

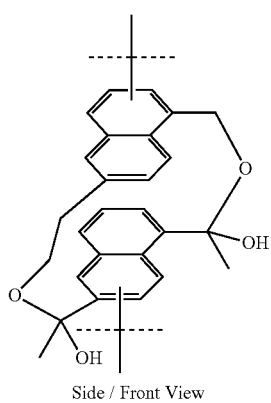

Side / Front View

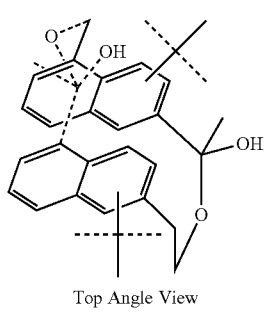

Top Angle View

5G) The general format of Linker Element 5G involves a first linker element of the formula HS—$(CH_2)_m$-Aromatic-$(CH_2)_m$—C=O-Aromatic-$(CH_2)_m$—SH and a second linker element of the formula O=C—$(CH_2)_m$—$CH_3$. The following structures are specific examples of this embodiment.

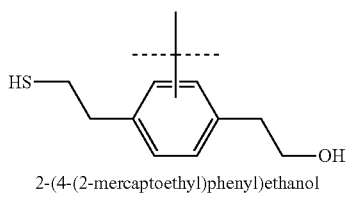

2-(4-(2-mercaptoethyl)phenyl)ethanol

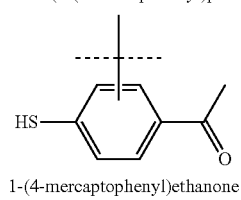

1-(4-mercaptophenyl)ethanone

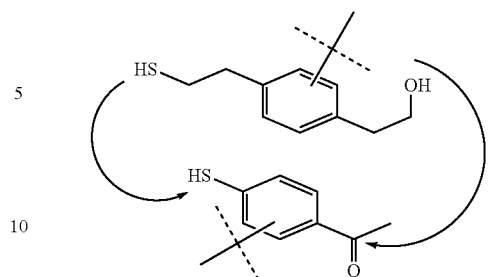

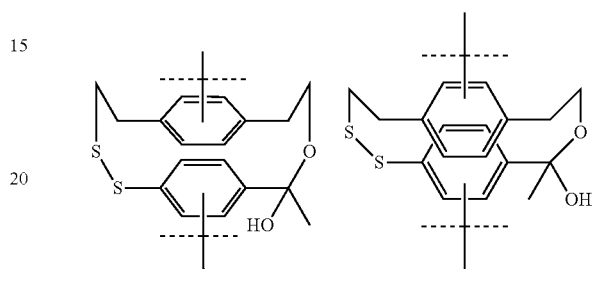

Side / Front View      Top Angle View

5H) The general format of Linker Element 5H involves a first linker element of the formula HO—$(CH_2)_n$-Aromatic-$B(OH)_2$ and a second linker element of the formula $(HO)_2$B-Aromatic-$(CH_2)$n-OH. The following structures are specific examples of this embodiment.

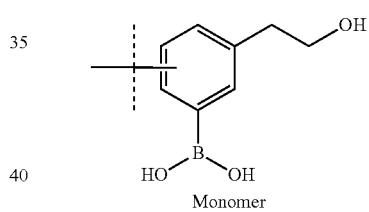

Monomer

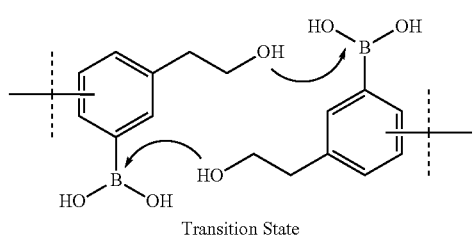

Transition State

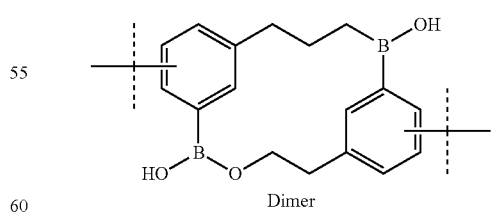

Dimer

5I) The general format of Linker Element 5I involves a first linker element of the formula HO—$(CH_2)_n$-Alicyclic-B(OH)$_2$ and a second linker element based on 2-hydroxycyclohexanone. The following structures are specific examples of this embodiment.

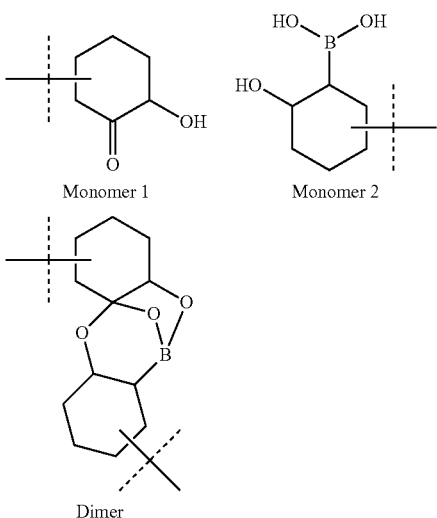

Monomer 1   Monomer 2

Dimer

5J) The general format of Linker Element 5J involves a first linker element of the formula CH3-(O=C)-Aromatic-B(OH)$_2$ and a second linker element based on Aromatic-NH-Aliphatic. The following structures are specific examples of this embodiment.

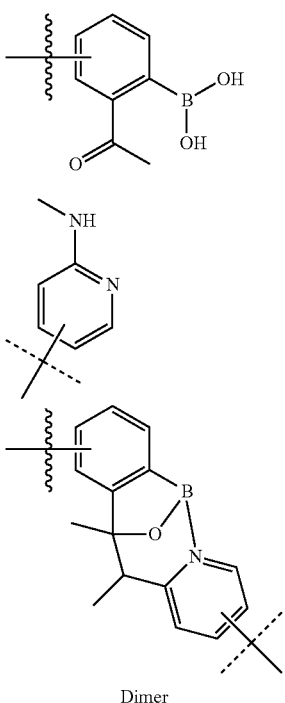

Monomer 1

Monomer 2

Dimer

The above derivatives (i.e., linker elements) can also be provided with additional potential to form non-covalent interactions between the covalent linker elements and/or aromatic rings, such as hydrophobic interactions, or hydrogen bonding, or polar, or charge interactions. These additional interactions (Linker Element 6) may help guide the rings together in the proper orientation, or may help guide formation of heterodimer linker elements.

The above derivatives (i.e. linker elements) can also be provided with an additional hydroxyl (alcohol) on the first and the second linker elements to form intramolecular—but sterically strained—hemiacetal. For example, an aromatic structure with one side as part of a 5-membered hemiacetal ring will be strained. These intramolecular structures (Linker Element 7) are in equilibrium between the aldehyde and hemiacetal state. Should the aldehyde from the linker element react with a lysine amino group or tyrosine hydroxyl group from a cellular protein, it may be more easily released from the protein by formation of the intramolecular hemiacetal. When the first linker element is brought in close proximity with the second linker element which contains a hydroxyl, there is a balance between forming an intermolecular hemiacetal vs. an intramolecular hemiacetal. Each linker element can form an intermolecular hemiacetal, and, thus, the presence of two intermolecular hemiacetals in the dimer is favored over formation of separate intramolecular hemiacetals for each monomer.

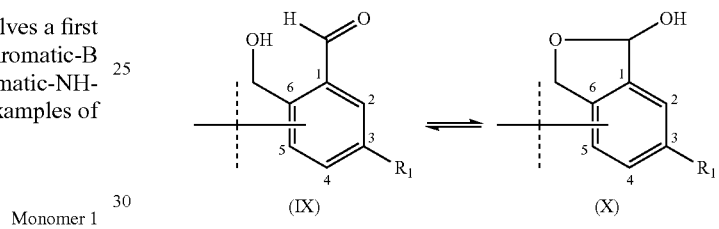

(IX)    (X)

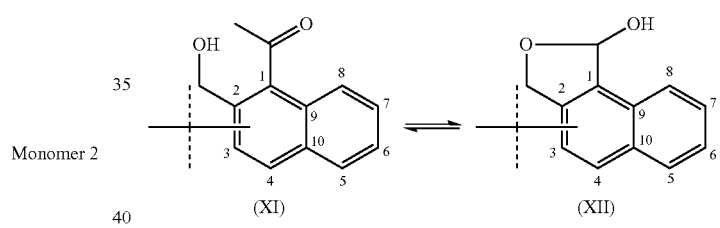

(XI)    (XII)

where
$R_1$=—(CH$_2$)$_n$OH, —(CH$_2$)$_n$SH or B(OH)$_2$

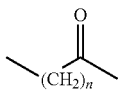

n=0-3

Examples of this embodiment of linker elements are shown below as items 7A) to 7D).

7A)

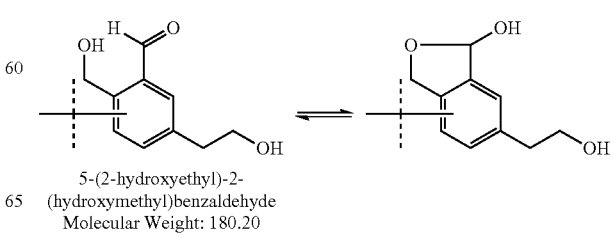

5-(2-hydroxyethyl)-2-(hydroxymethyl)benzaldehyde
Molecular Weight: 180.20

79
-continued
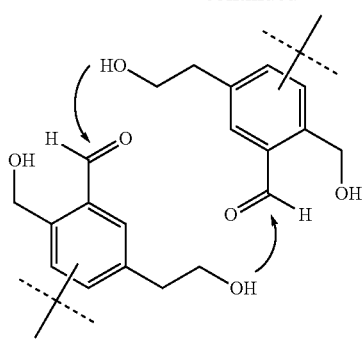
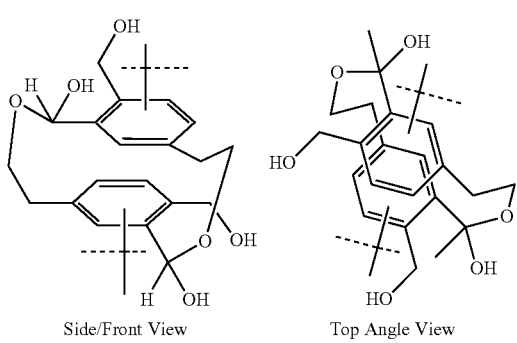
Side/Front View    Top Angle View
7B)
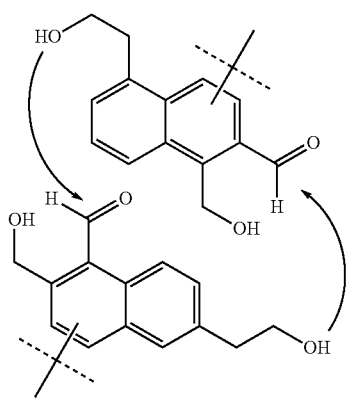
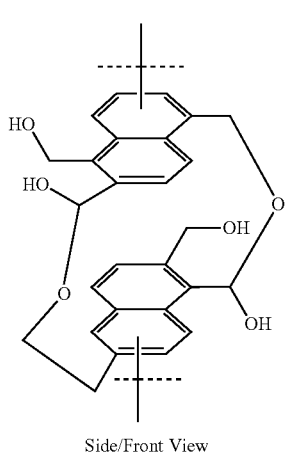
Side/Front View
80
-continued
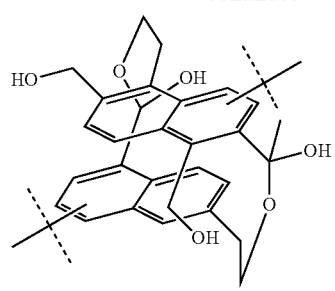
Top Angle View
7C)
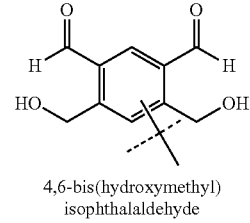
4,6-bis(hydroxymethyl)
isophthalaldehyde
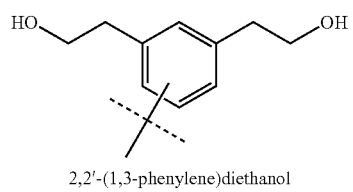
2,2'-(1,3-phenylene)diethanol
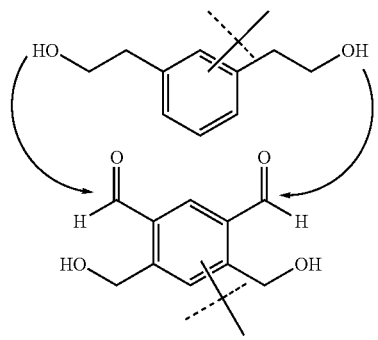
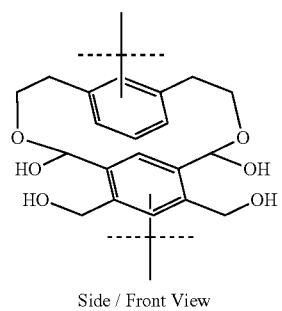
Side / Front View -continued

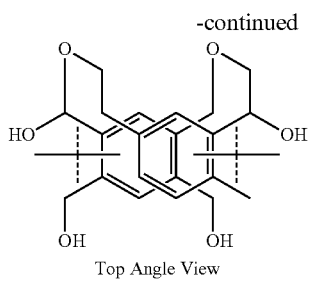
Top Angle View

7D)

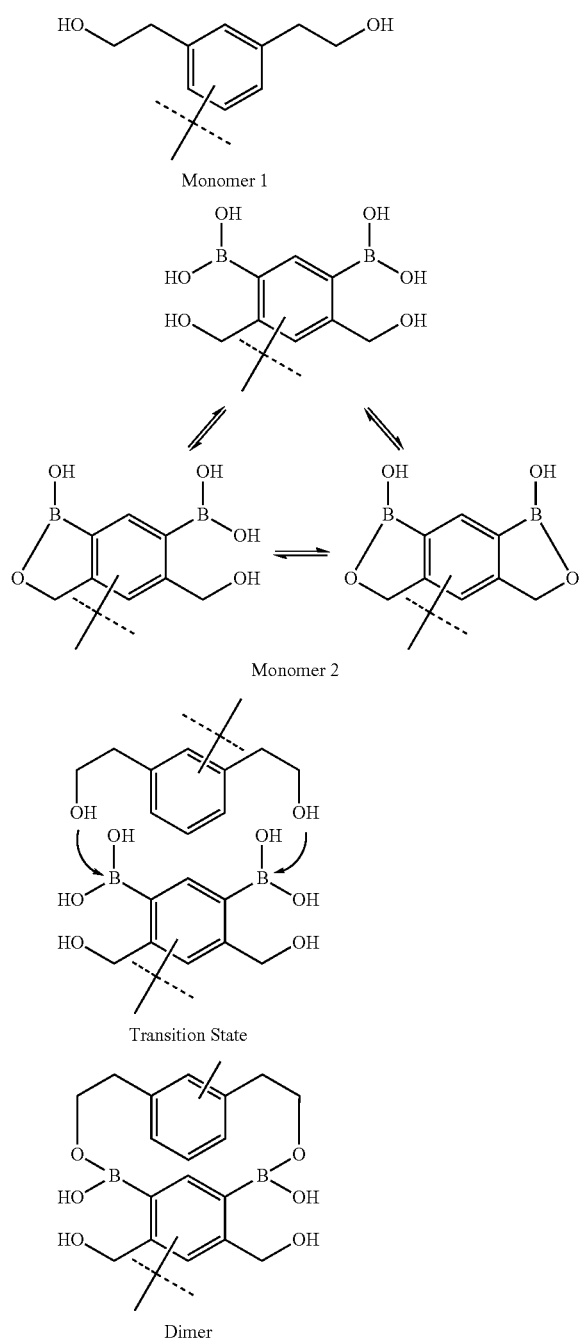
Monomer 1

Monomer 2

Transition State

Dimer

Derivatives Based on Using Base Pairs of 1,3-Diaminopyrimidine, Diaminopyridine or Aminopyrimidine with Cytosine or 5-Amino-2-Pyridone.

These derivatives may include a log p Tuner. A log tuner is any aliphatic or aromatic group containing substituents that when added to the linker element changes the overall log p of the molecule. The 1,3-diaminopyrimidine, diaminopyridine or aminopyrimidine, cytosine or 5-amino-2-pyridone base pair idea is based on enhancing nucleotide-like base-pairing with hydrophobic surfaces. While these linker elements (Linker Element 8) may not come together in the absence of target, once formed in the presence of target they may be rather stable. The nucleobases may be connected using peptide nucleotide analogue, peptide or other backbone allowing for base pairing and base stacking.

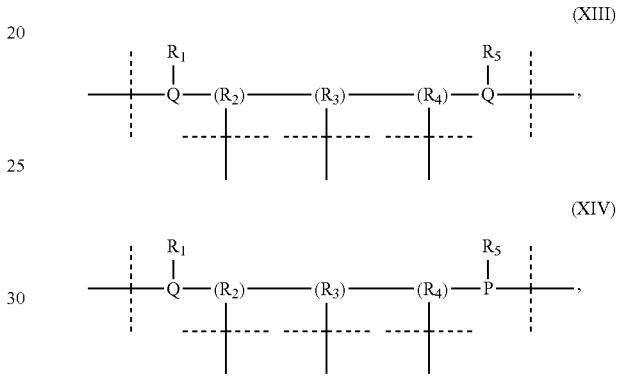

where Q is an aromatic heterocyclic or non-heterocyclic ring, said ring comprising of 5 or 6 membered rings either singly or fused together, including but not limited to benzene, naphthalene, purine, pyrimidine, triazine.

where P is an aromatic or aliphatic group used to modulate the polarity of the molecule, where $R_1$, $R_5$= —$NH_2$, —OH, ($CH_2$)—OH, —$B(OH)_2$, or

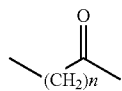

where $R_2$, $R_4$= —$(CH_2)_n$—, $O(CH_2)_n$—, —$(CH_2)_nO$—, —$NH(CH_2)_n$—, —$(CH_2)_nNH$—, H

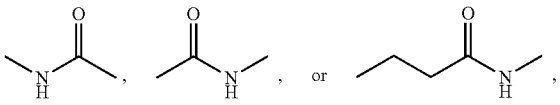

where $R_3$=

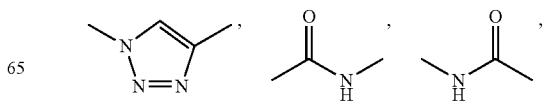

—(CH$_2$CH$_2$O)$_n$—

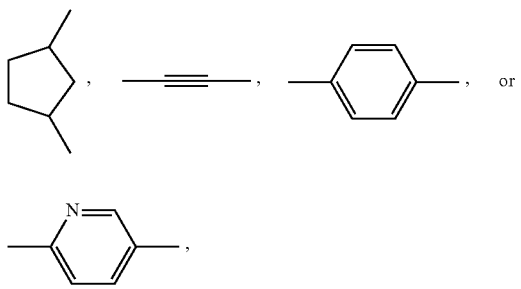

where n=0-3, where the lines crossed with a dashed line illustrate the bonds formed joining the one or more diversity elements of the molecule of Formula (XIII) or (XIV).

Examples of this embodiment of linker elements are shown below as items 8A) to 8H).

(i) A single base pair, each with an aliphatic log p Tuner that go above and below the bases.

8A)

Monomer 1

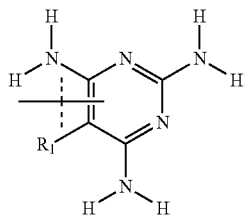

2,4,6-triaminopyrimidine

Monomer 2

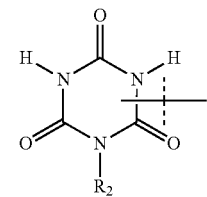

1,3,5-triazinane-2,4,6-trione

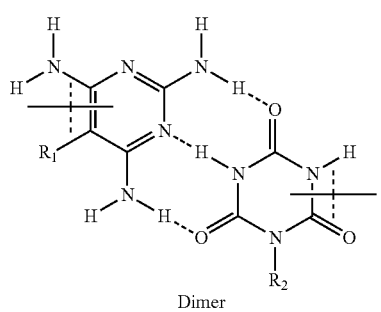

Dimer
where R$_1$ and R$_2$ = aliphatic carbon chain to modulate logP.

8B)

Monomer 1

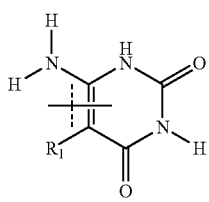

6-aminopyrimidine-2,4(1H,3H)-dione

Monomer 2

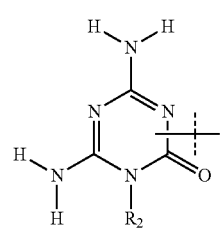

4,6-diamino-1,3,5-triazin-2(1H)-one

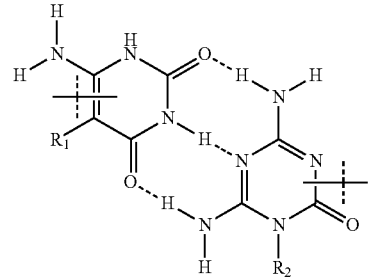

Dimer
where R$_1$ and R$_2$ = aliphatic carbon chain to modulate logP.

8C)

Monomer 1

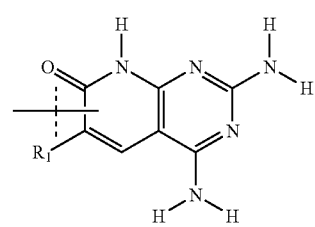

2,4-diaminopyridol[2,3-d]pyrimidin-7(8H)-one

Monomer 2

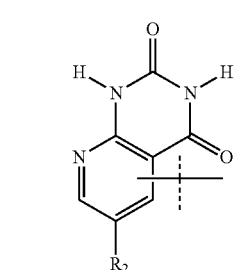

pyrido[2,3-d]pyrimidine-2,4(1H,3H)-dione

-continued

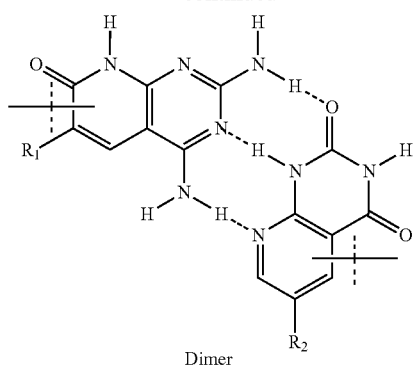

Dimer
where R₁ and R₂ = aliphatic carbon chain to modulate logP.

8D)

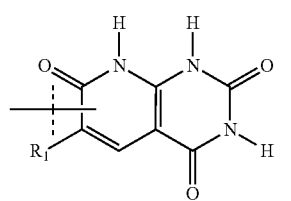

pyrido[2,3-d]pyrimidine-2,4,7(1H,3H,8H)-trione

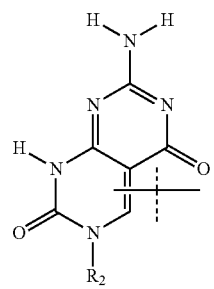

7-aminopyrimido[4,5-d]pyrimidine-2,5(1H,3H)-dione

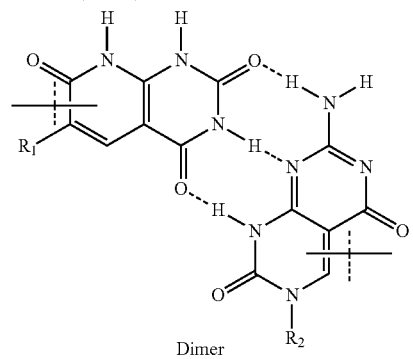

Dimer
where R₁ and R₂ = aliphatic carbon chain to modulate logP.

A single base pair, each with an aromatic log p Tuner, both go above the bases, allowing for covalent bonding between an aldehyde/ketone on one aromatic ring with an alcohol on the other ring.

8E)

Monomer 1

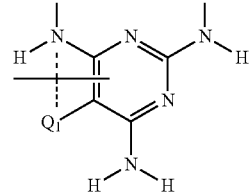

2,4,6-triaminopyrimidine

Monomer 2

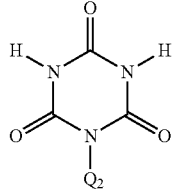

1,3,5-triazinane-2,4,6-trione

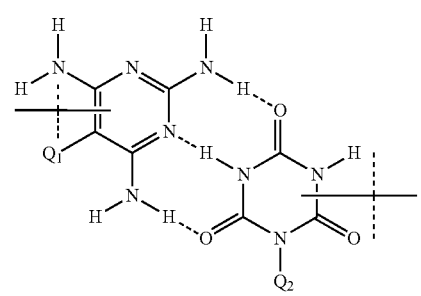

where Q₁ and Q₂ = aromatic groups to modulate logP.
Dimer

8F)

Monomer 1

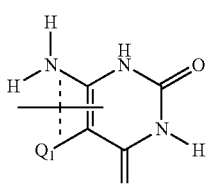

6-aminopyrimidine-2,4(1H,3H)-dione

Monomer 2

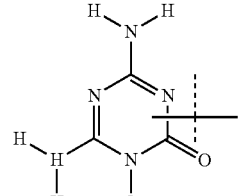

4,6-diamno-1,3,5-triazin-2(1H)-one

87
-continued

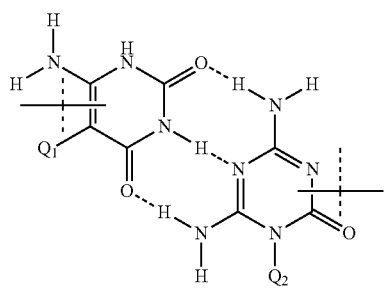

where $Q_1$ and $Q_2$ = aomatic groups to modulate logP.
Dimer

8G)

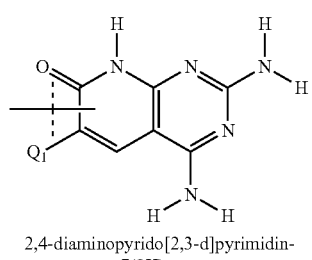

2,4-diaminopyrido[2,3-d]pyrimidin-7(8H)-one

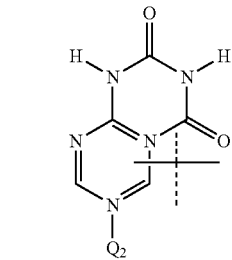

pyrido[2,3-d]pyrimidine-2,4(1H,3H)-dione

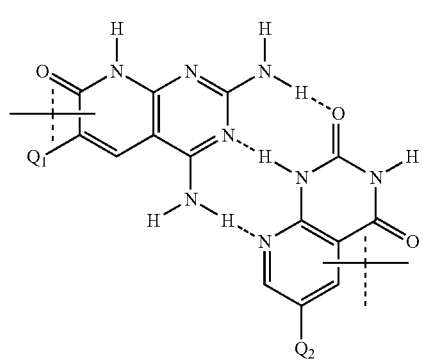

where $Q_1$ and $Q_2$ = aromatic groups to modulate logP.
Dimer

88

8H)

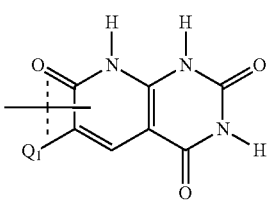

Monomer 1 pyrido[2,3-d]pyrimidine-2,4,7(1H,3H,8H)-trione

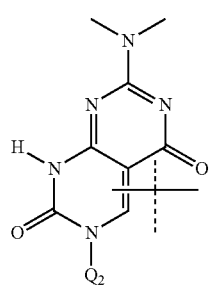

Monomer 2

7-aminopyrimido[4,5-d]pyrimidine-2,5(1H,3H)-dione

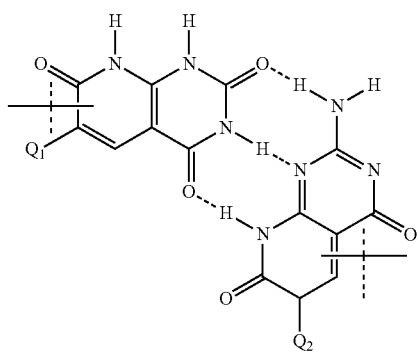

where $Q_1$ and $Q_2$ = aromatic groups to modulate logP.
Dimer

Derivatives Based on Forming Dimers of Nucleobases of, 1,3-Diaminopyrimidine, Diaminopyridine or Aminopyrimidine Base Pairs with Cytosine or 5-Amino-2-Pyridone.

These linker elements (Linker Element 9) are based on enhancing nucleotide base-pairing with hydrophobic surfaces. Each bottom nucleotide can form 3 hydrogen bonds with its pair. Each top nucleotide can form 2 hydrogen bonds with its pair, and is attached through a hemiacetal linker. The top nucleotides can become covalently linked across the hydrogen bond area in the "major groove". While these linker elements may not come together in the absence of target, once formed in the presence of target they may be stable.

Examples of this embodiment of linker elements are shown below as items 9A) to 9B)
9A) 4-aminopyrimidine:5-amino-2-pyridone base pair
Monomer 1
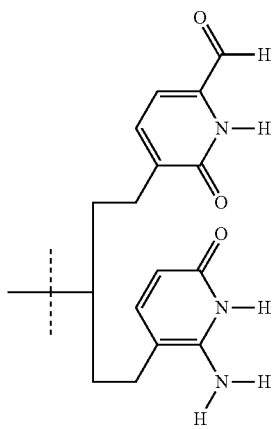
Monomer 2
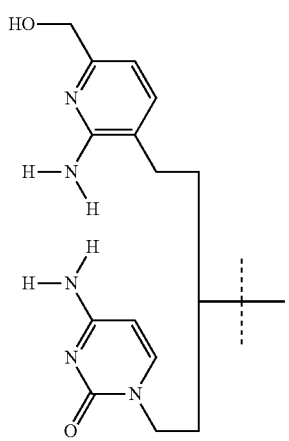
Transition State
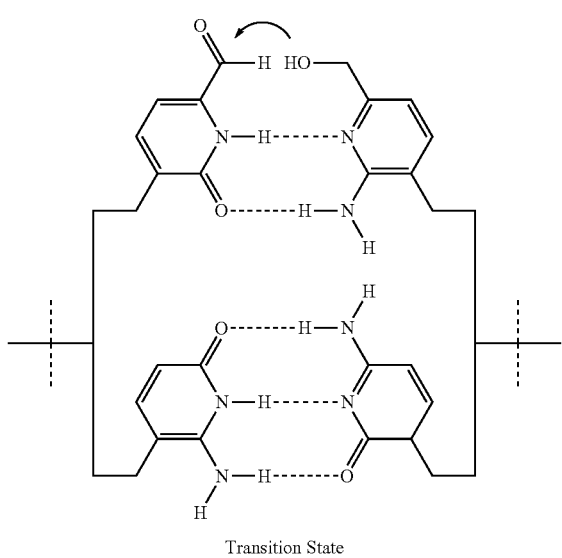
-continued
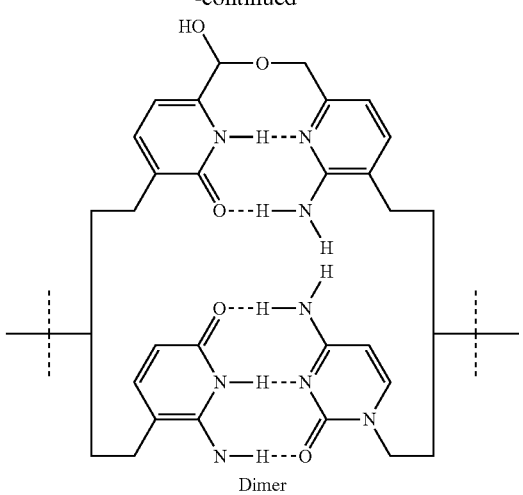
Dimer
9B): 5-amino-2-pyridone: 6-fluorouracil base pair.
Monomer 1
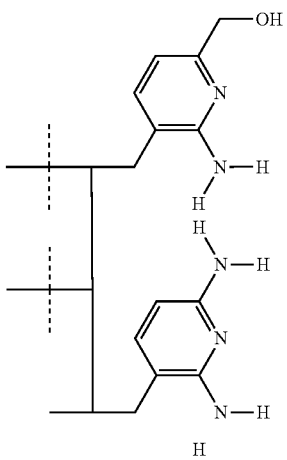
Monomer 2
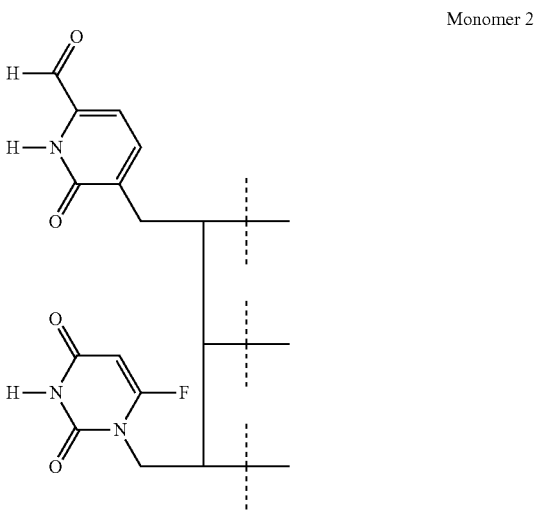

-continued

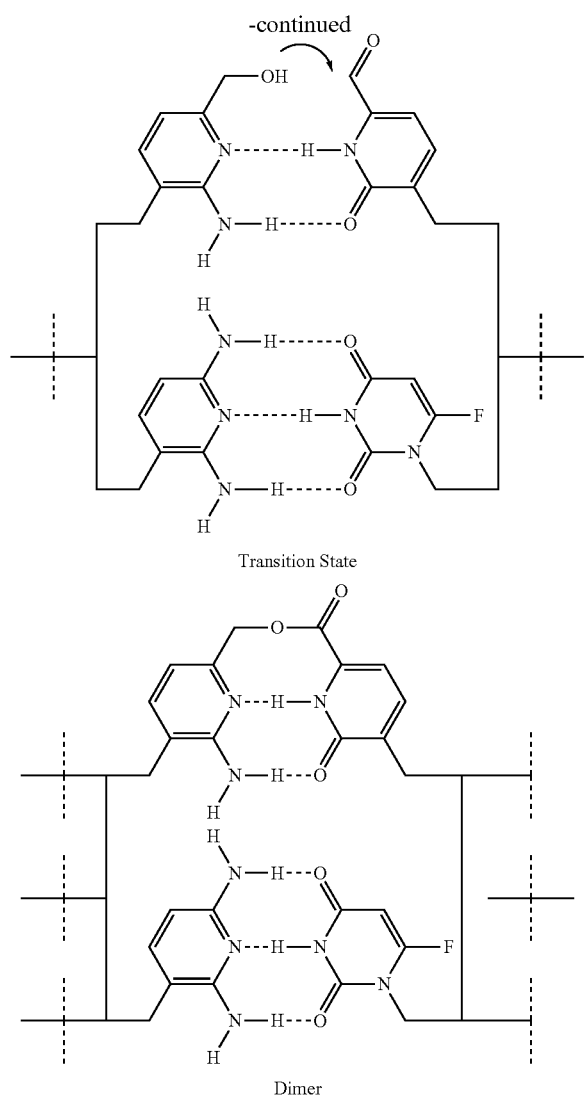

Transition State

Dimer

A linear peptide based backbone may be used for coferon monomers with base-pairing nucleobase linker elements. The diversity elements in these coferon monomers may be derived from alternating amino acid residues, while the nucleobases serve as the linker element elements that associate with the nucleobase linker element elements of another coferon monomer.

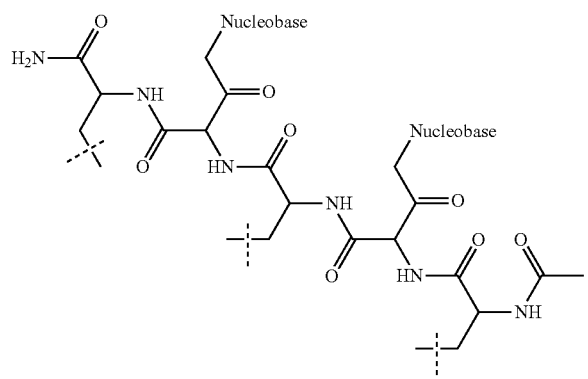

Linear Form of a Peptide Backbone for Coferon Monomer Elements

In another embodiment a circularized peptide nucleic acid (PNA) based backbone for coferon monomers may be used with base-pairing nucleobase linker elements. The diversity elements in these coferon monomers may be derived from adjacent amino acid residues, while the nucleobases serve as the linker element elements that associate with the nucleobase linker element elements of another coferon monomer. A final spacer linking the PNA to the peptide portion may be utilized to relieve ring strain.

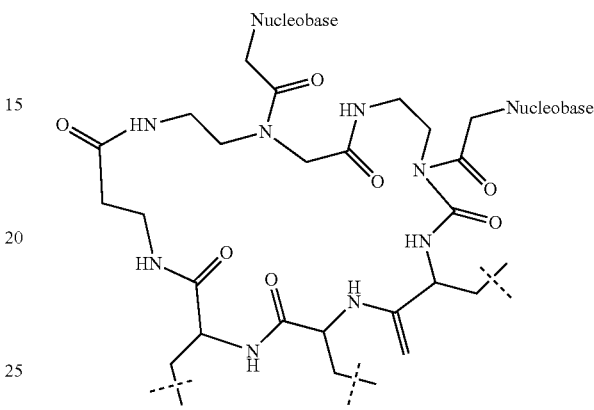

In another embodiment, a linear version of a backbone based on using the cyclopentane scaffold may be used for the coferon monomers. The choice of nucleobase and the substitutions determine whether base stacking or intercalation is preferred.

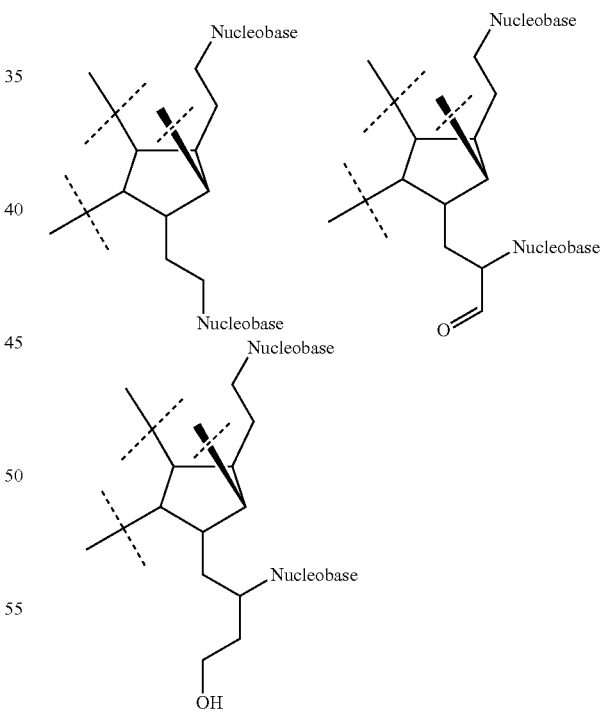

Derivatives Based on Forming Heterocycle Dimers Using Boric Acid Esters to Link the Nucleotides.

In this embodiment, covalent bonds are formed on both the upper and lower base pair. Four hydrogen bonds and two covalent bonds are formed to create a very stable dimer. For this linker element design, during the screening process under dynamic combinatorial conditions, only one covalent bond either on the top or bottom base pair would be allowed.

When the final coferons are synthesized in the therapeutic form covalent bonds would be allowed for both the top and bottom base pairs.
Examples of this embodiment of linker elements are shown below as items 10A) to 10C).
10A)
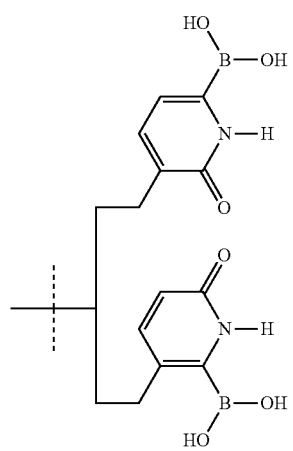
Monomer 1
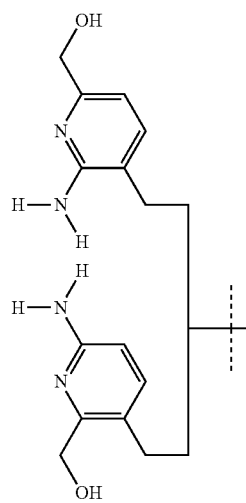
Monomer 2
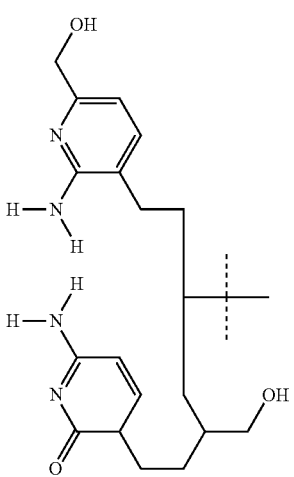
Transition State
-continued
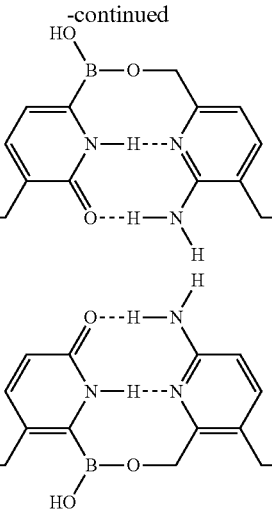
Dimer
10B)
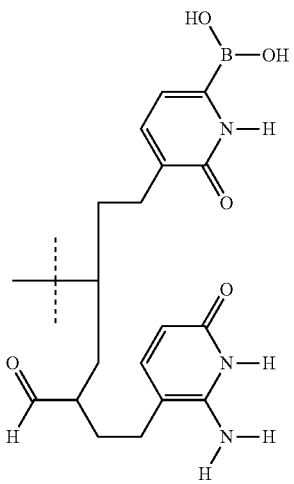
Monomer 1
Monomer 2

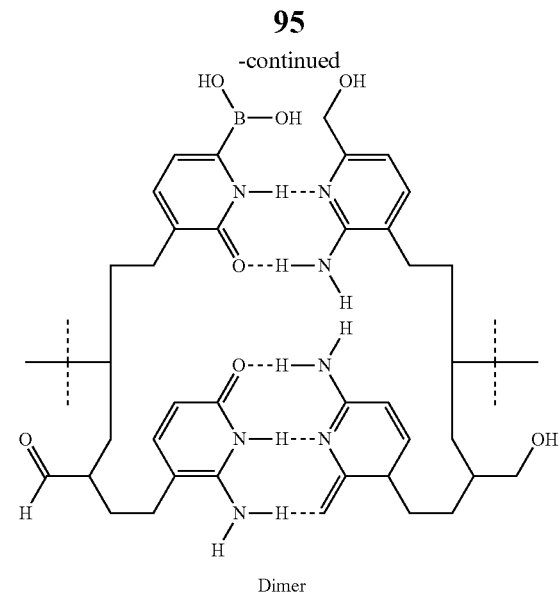

Dimer

10C)

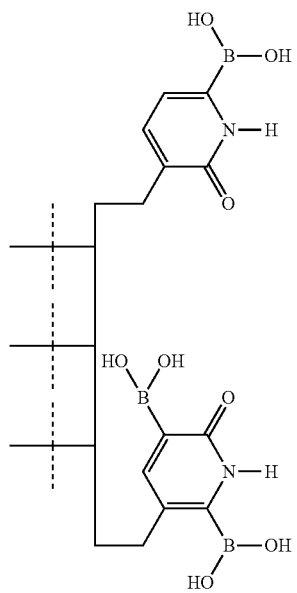

Monomer 1

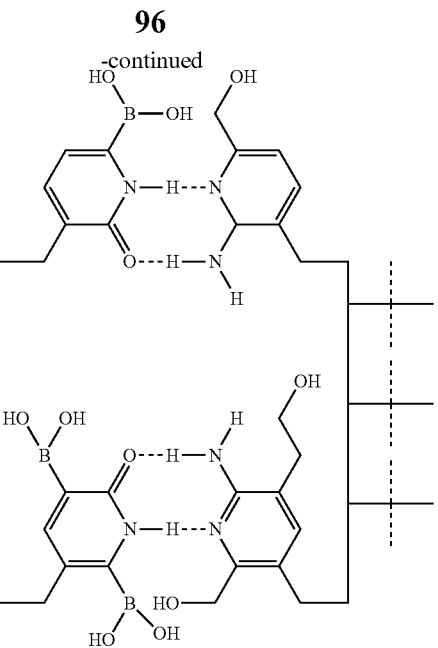

Dimer

Derivatives Based on Linker Elements that Bind Each Other with Aid of a Cofactor.

These linker elements (Linker Element 11) form mixed dimers through bidentate binding to zinc or other bioavailable metal ions. Once formed, these linker elements bind to each other very tightly, and can dimerize in the absence of target. Thus, these linker elements may be used to bring together two different drug molecules into cancer cells to increase their biological potency. For these linker elements, the diversity elements do not need to bind to the same target, although they will accelerate formation of the dimers if they do have affinity for the same target. These linker elements will be monomers in regions of the body with low levels of zinc, but may shift towards the dimer form in cells that have higher zinc content. Since cancer cells have increased expression of zinc transporter, this provides an additional opportunity for targeting these drugs to cancer cells.

Monomer 2

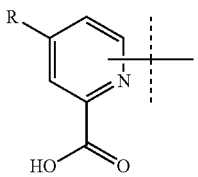
(Z1)

where R=H, B(OH)$_2$,

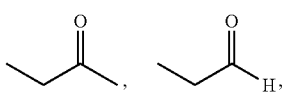

(CH$_2$)—OH and n=1-3 where R=—CH(OH)—(CH$_2$)$_m$OH and m=1-2 where the lines crossed with a dashed line illustrate the bonds formed joining the one or more diversity elements to, directly or through a connector, the molecule of Formula (Z1).

Examples of this embodiment of linker elements are shown below as items 11A) to 11C). The simplest form is based on derivatives of picolinic acid. This version is likely to be highly reversible, and will probably not dimerize in the absence of target at the concentrations of $Zn^{+2}$ and coferons found inside cells.

11A)

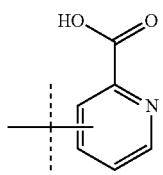

Picolinic acid
Monomer

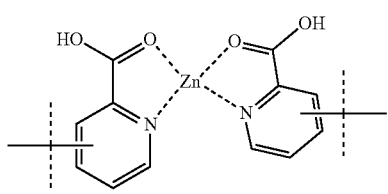

Picolinic acid dimer with Zinc
Dimer

11B)

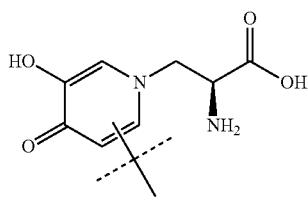

Mimosine
Monomer

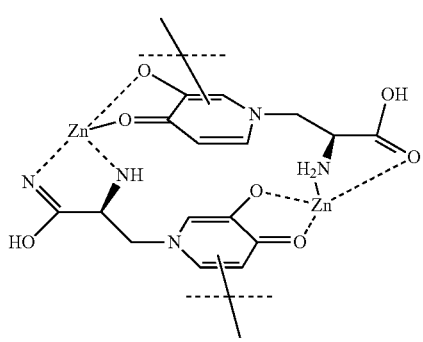

Mimosine dimer with Zinc
Dimer

The more sophisticated versions of these dimers have either two Zn cations, or one Zn cation and a second linking group, such as a boric acid ester

11C)

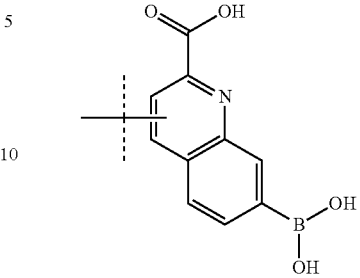

Monomer 1

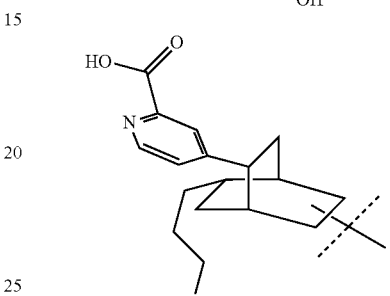

Monomer 2

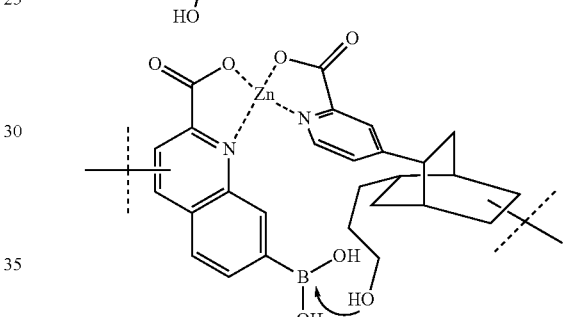

Transition State

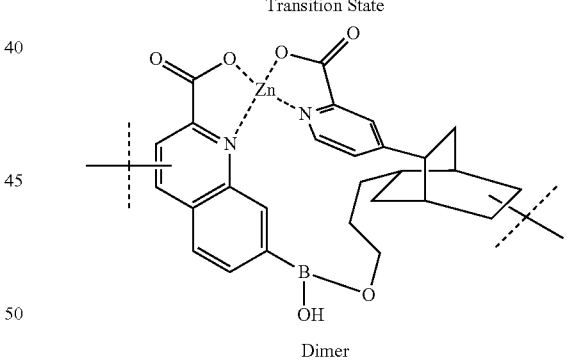

Dimer

11D)

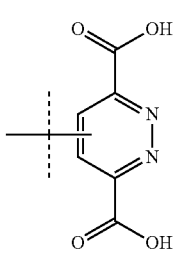

Monomer 1

-continued

Monomer 2

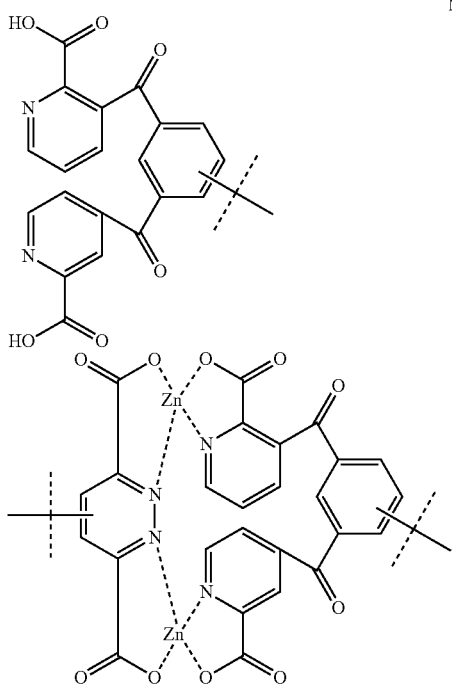

Dimer

Derivatives Based on Using Two Aromatic Rings Separated by a Rigid Line

Derivatives Based on Using Two Aromatic Rings, such as benzene, naphthalene, purine, pyrimidine, or other aromatic structures, with varying degrees of solubility in aqueous vs. lipid bilayer to bring two linker elements together, by favoring overall solubility in aqueous solution when aromatic surfaces interact (Linker Element 12). The preferred version of such a linker element has one aromatic ring that is poorly soluble in aqueous liquids (i.e. benzene, naphthalene), covalently linked through a partially rigid linker to a second aromatic ring that is more soluble in aqueous liquids (i.e., purine, pyrimidine). The partially rigid linker has a geometry that prevents optimal stacking of the two aromatic rings in an intramolecular fashion. However, the partially rigid linker allows for spacing of the two aromatic rings so they can intercalate with a partner linker element such that the four aromatic systems are stacked on top of one another. For example, if linker element A consisted of pyrimidine-linker-benzene, and linker element B consisted of benzene-linker-pyrimidine, then the stacking would be pyrimidine(A)-benzene(B)-benzene(A)-pyrimidine(B).

Derivatives Based on Using Aromatic Rings that Intercalate with these Binding Partners.

An additional embodiment of the linker element (Linker Element 9) is an aromatic compound which intercalates with one or more of its binding partner(s), such that intercalation guides formation of zero, one, or more covalent bonds between the linker element and the binding partner.

Generic Structure

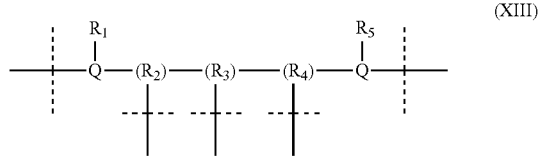

(XIII)

where Q is an aromatic heterocyclic or non-heterocyclic ring, said ring comprising of 5 or 6 membered rings either singly or fused together.

where the lines crossed with a dashed line illustrate the bonds formed joining the one or more diversity elements to, directly or through a connector, the molecule of Formula (XIII)

Examples of this embodiment of linker elements (i.e. Linker Element 13) are as follows:

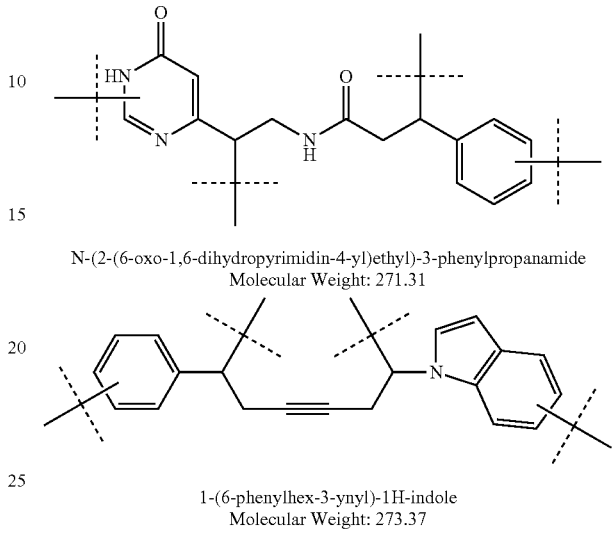

N-(2-(6-oxo-1,6-dihydropyrimidin-4-yl)ethyl)-3-phenylpropanamide
Molecular Weight: 271.31

1-(6-phenylhex-3-ynyl)-1H-indole
Molecular Weight: 273.37

3-D Representations

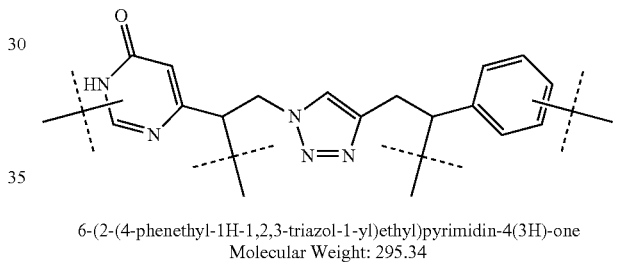

6-(2-(4-phenethyl-1H-1,2,3-triazol-1-yl)ethyl)pyrimidin-4(3H)-one
Molecular Weight: 295.34

Derivatives Based on Using an Aromatic Rings that Intercalate with their Binding Partners, with Additional Interactions.

Derivatives based on using two aromatic rings can be provided with additional potential for the two linker elements (i.e. Linker Element 14) to form non-covalent interactions between the partially rigid linker elements and/or aromatic rings, such as hydrophobic interactions, or hydrogen bonding, or polar, or charge interactions. Examples of this embodiment are set forth as items 14A) to 14B) below.

14A)

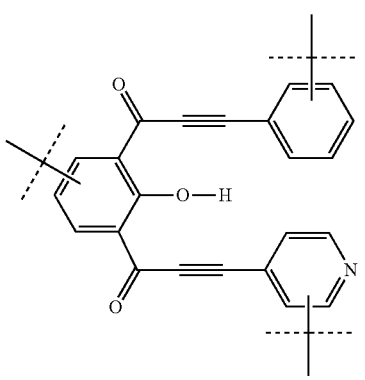

1-(2-hydroxy-3-(3-(pyridin-4-yl)propioloyl)phenyl)-
3-phenylprop-2-yn-1-one

-continued

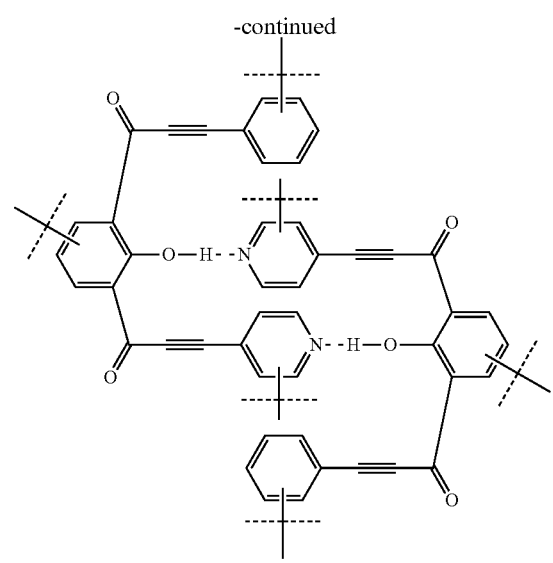

14B)

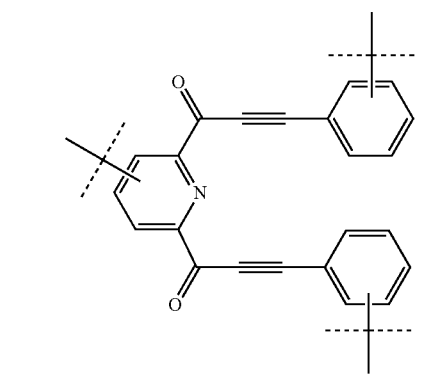

1,1'-(pyridine-2,6-diyl)bis(3-phenylprop-2-yn-1-one)

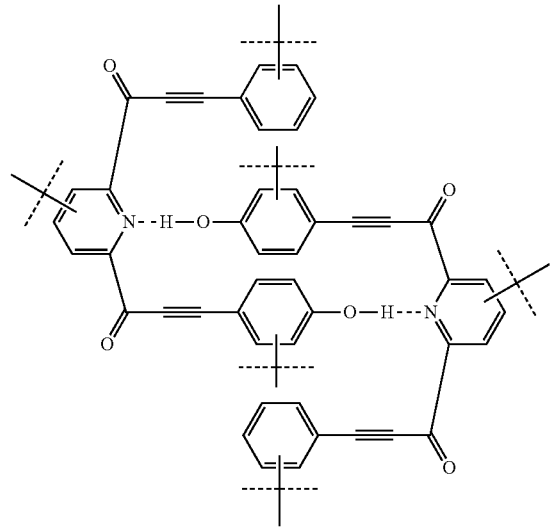

See also FIGS. 9-13.

In a further embodiment (i.e. Linker Element 15), the linker element has one or more active moieties in a protected state suitable for deprotection once inside the body, cell, or cellular compartment. The protected states include disulfide protection of a reactive thiol group, ester protection of a reactive alcohol group, hemiacetal protection of a reactive aldehyde group, hemiketal protection of a reactive ketone group or alcohol protection of a reactive boronate group.

Derivatives based on using two aromatic rings can be provided with additional potential for the two linker elements to form one or more reversible covalent bonds between the partially rigid linker elements and/or aromatic rings, such as S—S disulfide bonds, alcohol to aldehyde or ketone to form hemiacetals or hemiketals. Examples of this embodiment are set forth as Items 15A) to 15B) below.

15A)

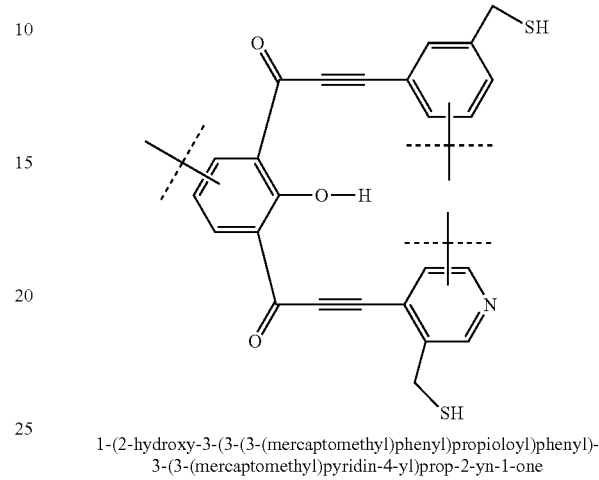

1-(2-hydroxy-3-(3-(3-(mercaptomethyl)phenyl)propioloyl)phenyl)-
3-(3-(mercaptomethyl)pyridin-4-yl)prop-2-yn-1-one

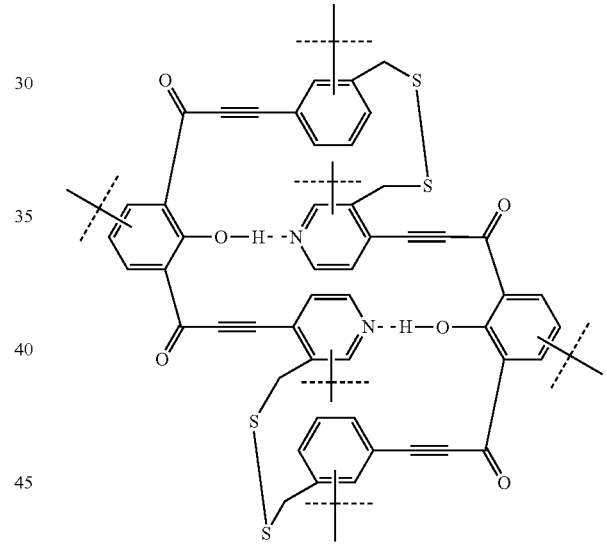

15B)

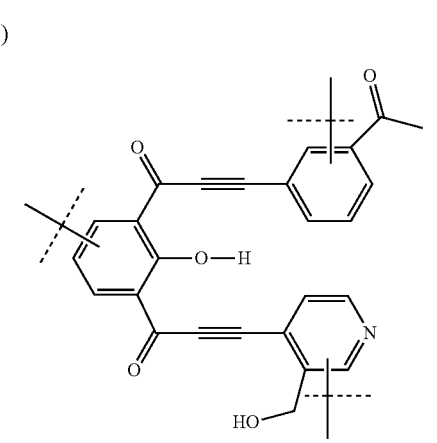

3-(3-acetylphenyl)-1-(2-hydroxy-3-(3-(3-hydroxymethyl)
pyridin-4-yl)-propioloyl)phenyl)prop-2-yn-1-one

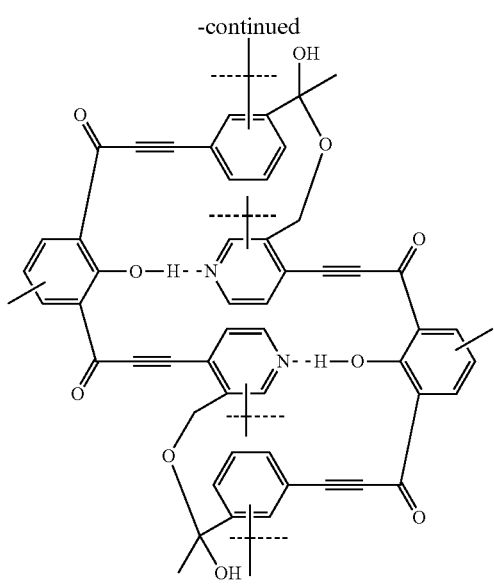

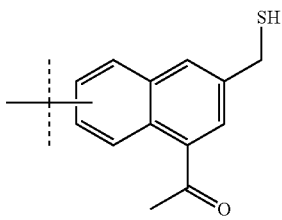

1-(3-(mercaptomethyl)naphthalen-1-yl)ethanone

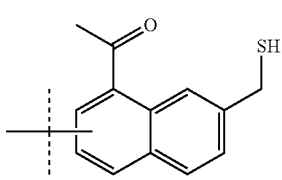

1-(7-(mercaptomethyl)naphthalen-1-yl)ethanone

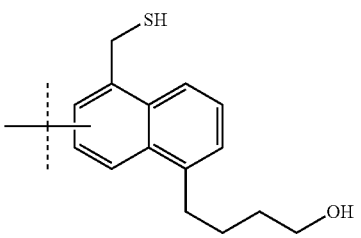

4-(5-(mercaptomethyl)naphthalen-1-yl)butan-1-ol

Derivatives Based on Combined Simple Linker Elements

Any of the preceding linker elements (i.e. Linker Elements 1-14) can be provided with potential to form complexes of more than two linker elements. This is Linker Element 16. For example, Linker Element 5, where aromatic rings stack on top of each other, may be designed to stack A-B-C. A may link to B and C below. B links to A above and C below, and C links to B and A above. Alternatively, Linker Element 5 would have two links from A to B, and two additional links from B to C. For Linker Element 7, the partially rigid linker of the central linker elements would allow stacking of two aromatic rings in between them, while the end linker elements would only permit stacking of one aromatic ring between them. For combining 3 such linker elements, the design would be linker element A consisting of pyrimidine-linker-benzene, linker element B consisting of benzene-linker (that is slightly longer)-benzene, and linker element C consisting of benzene-linker-pyrimidine, then the stacking of the aromatic rings would be pyrimidine(A)-benzene(B)-benzene(A)-benzene(C)-benzene(B)-pyrimidine(C).

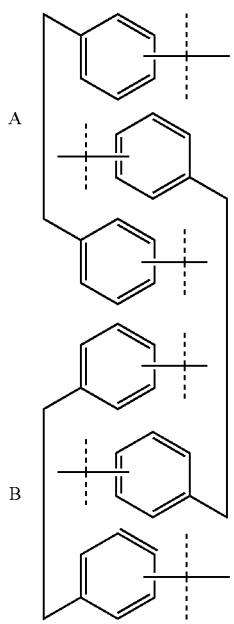

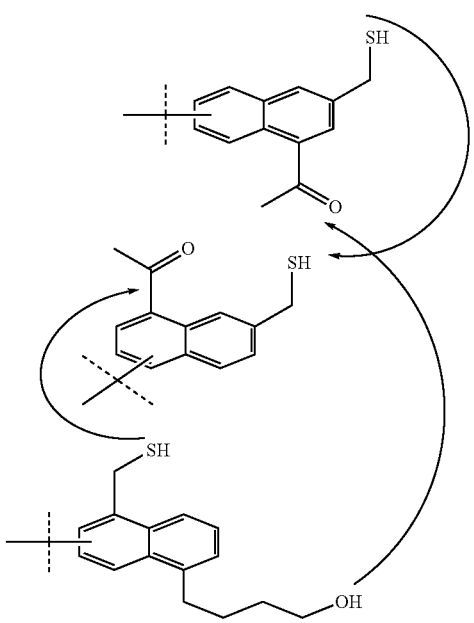

105
-continued
Monomers Reaction Mechanism
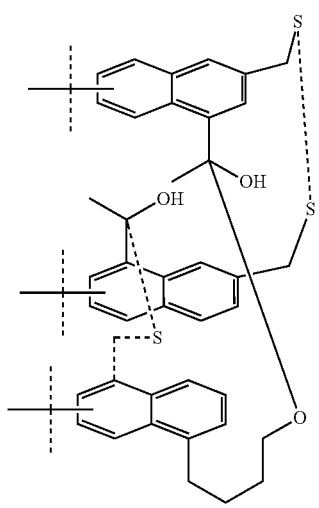
Side/Front View
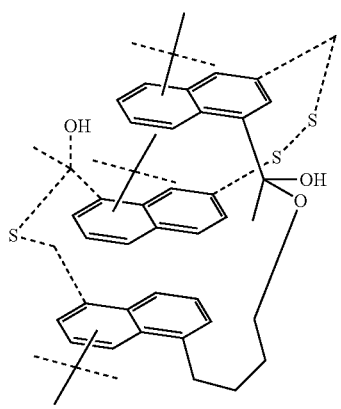
Top Angle View
16B)
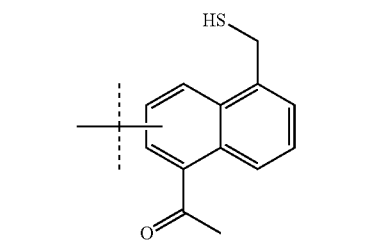
1-(5-mercaptomethyl)naphthalen-1-yl)ethanone
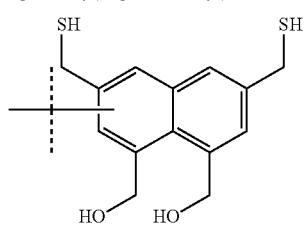
(3,6-bis(mercaptomethyl)naphthalene-1,8-diyl)dimethanol
106
-continued
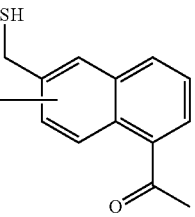
1-(6-bis(mercaptomethyl)naphthalen-1-yl)ethanone
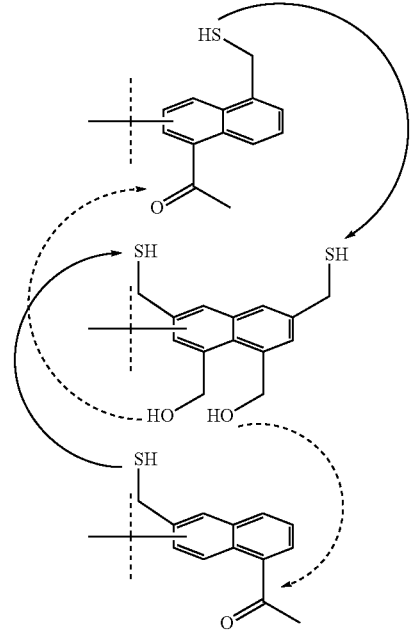
Monomers Reaction Mechanism
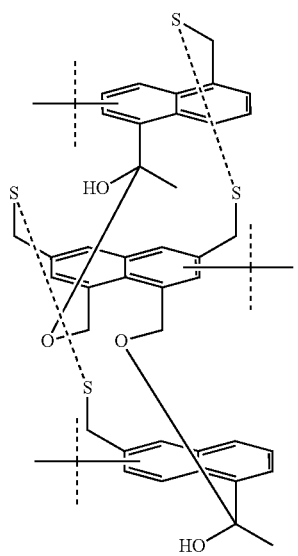
Side Front View -continued

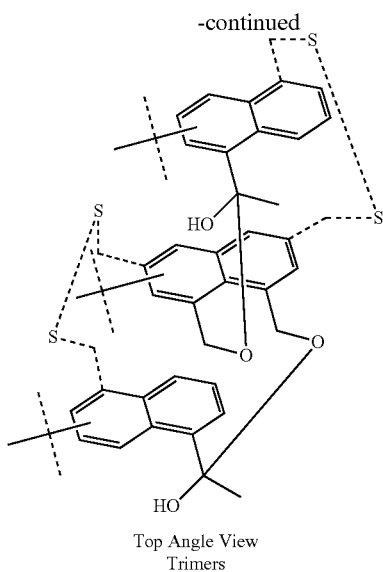

Top Angle View
Trimers

Linker elements that form multimers are divided in to four subcategories. These include linker elements that bind reversibly with each other in the presence of target, linker elements that bind essentially irreversibly with each other once they are brought in proximity by the target, linker elements that bind reversibly with each other independent of target and linker elements that bind essentially irreversibly with each other independent of target.

Linker elements that are part of multimeric structures may be designed in three basic formats as follows: (i) linker elements that dimerize, and then have the ability to form higher order structures; (ii) linker elements where one linker element has the ability to bind two or more linker elements, i.e. to make A-B-A trimers; and (iii) linker elements with the ability to make two or more covalent bonds to other linker elements, but in a geometry that inhibits two or more of those bonds going to the same linker element partner.

Derivatives Based on Hydrogen and/or Covalent Linking of Aromatic "Bases" that Form Hexameric Multimers The derivatives based on hexamers of uracil, diaminotriazine, triaminotriazine, 2,6-diaminopurine, 1,3-diaminopyrimidine, diaminopyridine, and 1,3-diaminopyrimidine bases.

i) Linker elements based on 6 "bases" forming a circular hexagonal planar structure through hydrogen bonding, each with an aliphatic log p Tuner that go above the bases (Linker Element 17).

Monomer 1

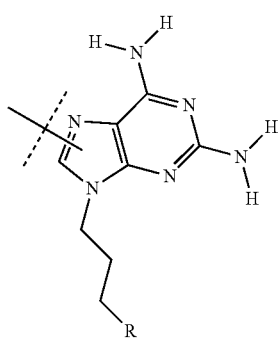

-continued

Monomer 2

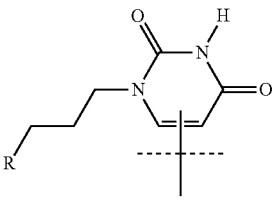

Where R=an aliphatic group that modulates log P and serves as a log P tuner.

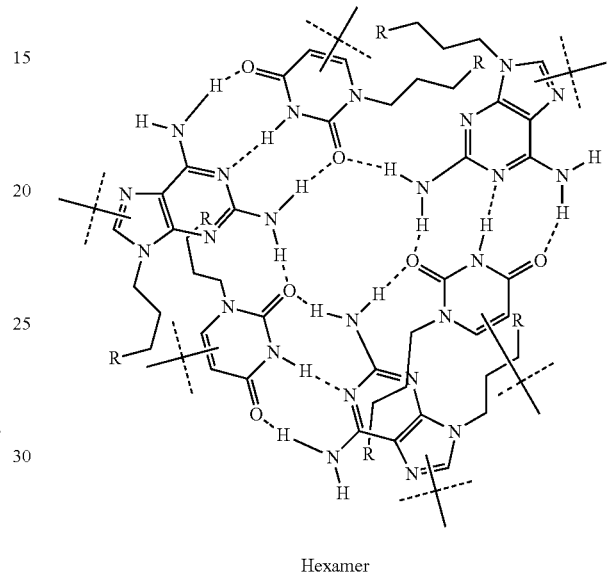

Hexamer (ii)) Linker elements based on 6 "bases" forming a circular hexagonal planar structure through hydrogen bonding, each with an aromatic log p Tuner that go above the bases, allowing for covalent bonding between an aldehyde/ketone on one side of the aromatic ring with an alcohol on the adjacent ring (Linker Element 18). The aldehyde/ketone and alcohol groups are in the meta orientation on the aromatic ring (120° orientation) to favor formation of hexameric structures. In another variation, there may be two aldehyde/ketone groups on the "bases" while the aromatic ring above the "bases" would have two alcohol groups Monomer 1

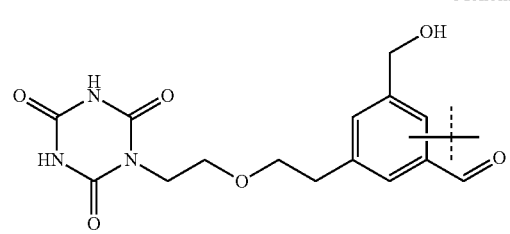

Monomer 2

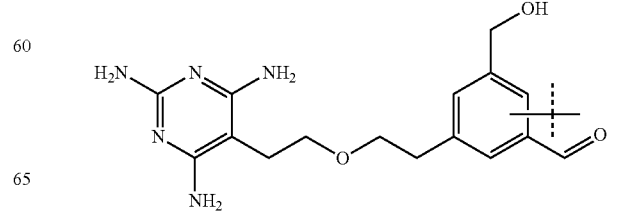

109
-continued

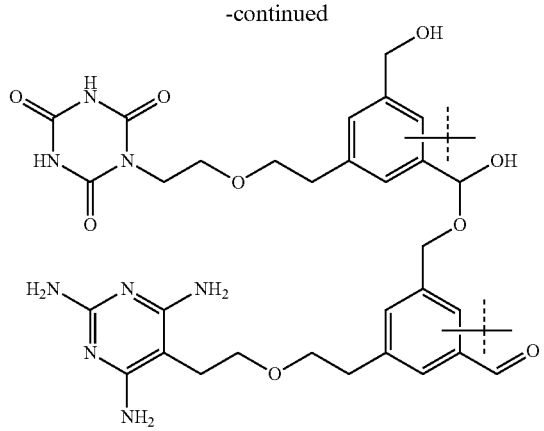

Dimer

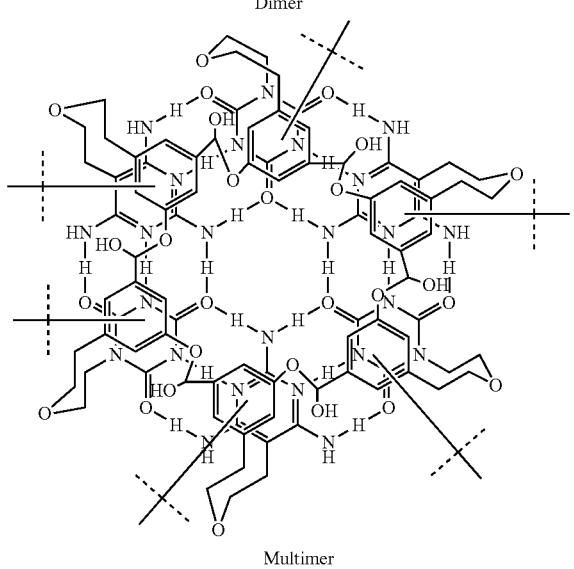

Multimer

The 6 "base" hexamer idea is based on enhancing nucleotide base-pairing with hydrophobic surfaces. Each heterocycle can form up to 6 hydrogen bonds with its neighbors. While these linker elements may not come together in the absence of target, once formed in the presence of target they may be rather stable.

In a variation of the above, the aromatic heterocycles are based on naphthalene framework (two fused 6-membered rings) instead of 6 member rings. The advantage of this design is it creates a larger aromatic hexameric surface. Once formed, such a hexameric structure may also help condense a head-to-head second hexameric structure onto the first aromatic face. The resulting super-structure would be composed of 12 coferons and could have an affinity to targets that rivals the affinity of antibodies.

In a variation of the above, one could form trimers instead of hexamers. For example, instead of double U, just use two coferons with U that have an aromatic ring containing a single aldehyde, and one coferon with a double mini-diamino A base and an aromatic ring with two alcohols in the meta positions. This structure may be nicknamed the "half-pipe". It can also form head-to-head structures so that 6 coferons are all pointing toward the same direction.

In other variations, not using hydrogen bonding among underlying nucleotides, but just focusing on the concept of having "N" coferon monomers come together in the proper

110 geometry, the aromatic ring idea can be extended to form pentameric coferon multimers by using 5 member heterocycles so that 108° geometries can be established.

Derivative Based on Base-Pairing Dimers that Form Multimers

These linker elements are derived from Linker Element 9. In this embodiment, a layer of 6 bases all pairing and forming 6 hydrogen bonds each in a circular hexagonal planar structure, each with a second layer of 6 bases all pairing and forming 4 hydrogen bonds each that goes above the bases, allowing for covalent bonding between an aldehyde/ketone on one side of the aromatic ring with an alcohol on the adjacent ring. The aldehyde/ketone and alcohol groups are in the ortho orientation on the aromatic ring (120° orientation) to favor formation of hexameric structures. This is Linker Element 19.

19A)

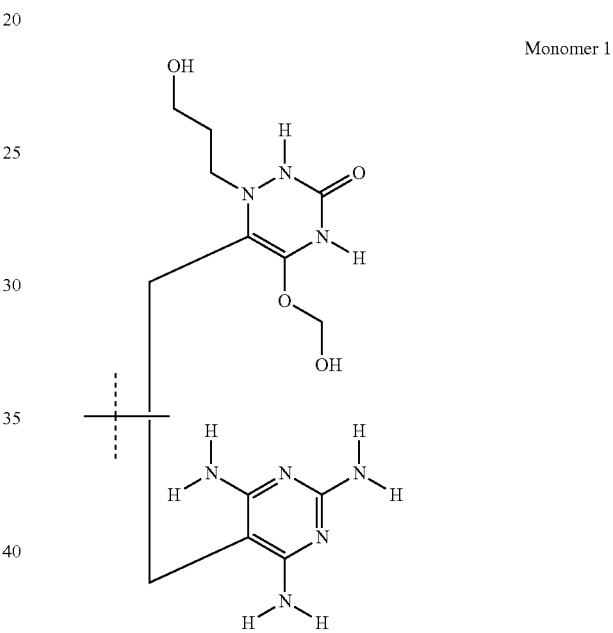

Monomer 1

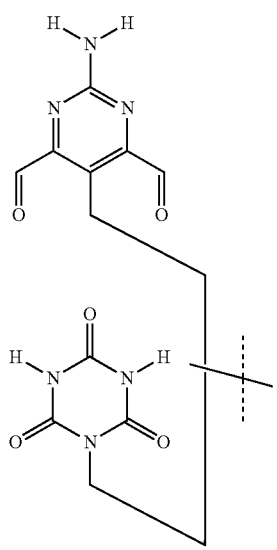

Monomer 2

-continued

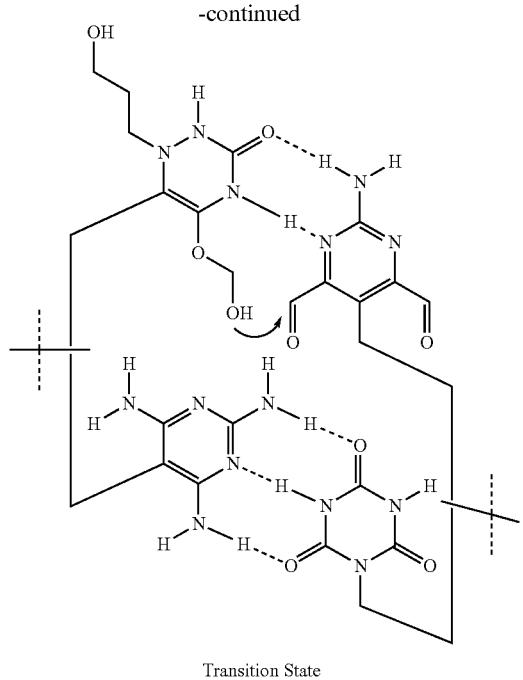

Transition State

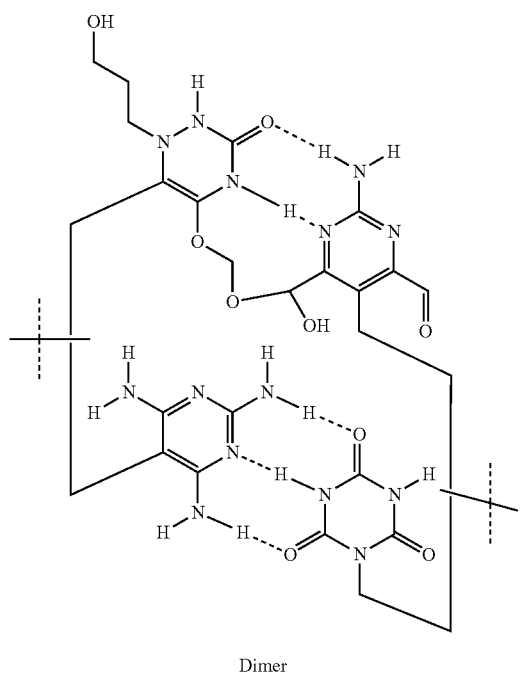

Dimer

In a first design boric acid esters form dimers that then form hexamers. In this design, both the top nucleotides and the bottom nucleotides are covalently linked through a boric acid ester in the ortho positions, but they do so alternating from top to bottom. Thus, the top nucleotides are linked from left to right, while the bottom nucleotides are linked right to left.

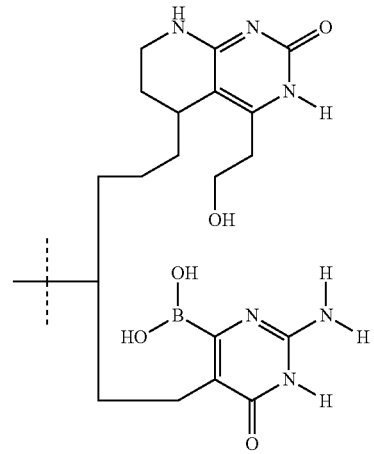

Monomer 1

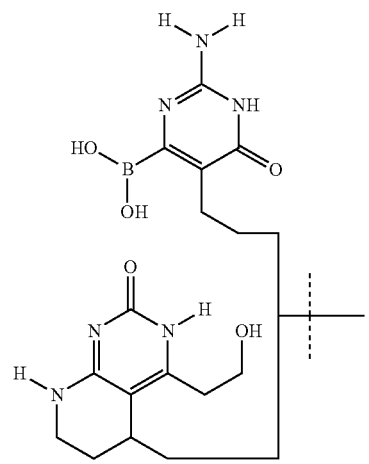

Monomer 2

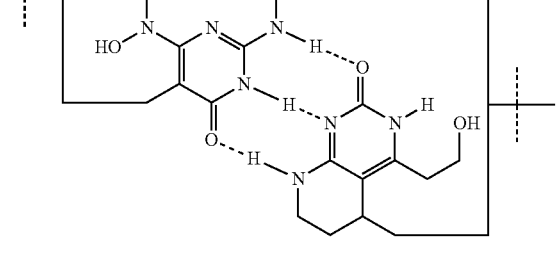

Transition State

113
-continued
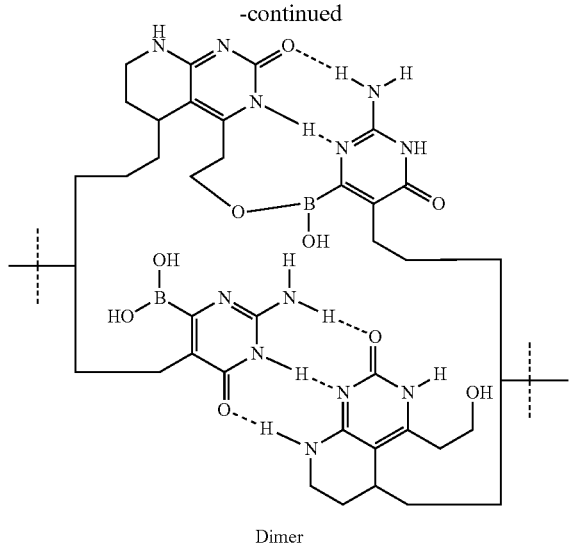
Dimer
114
-continued
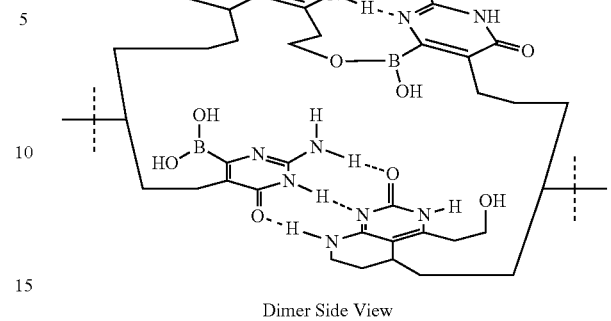
Dimer Side View
A top view of the top and bottom rosettes of the above design shows how all the nucleotides hydrogen bond at every position, and how the covalent linkages are offset from each other, so that all 6 coferons are covalently linked.
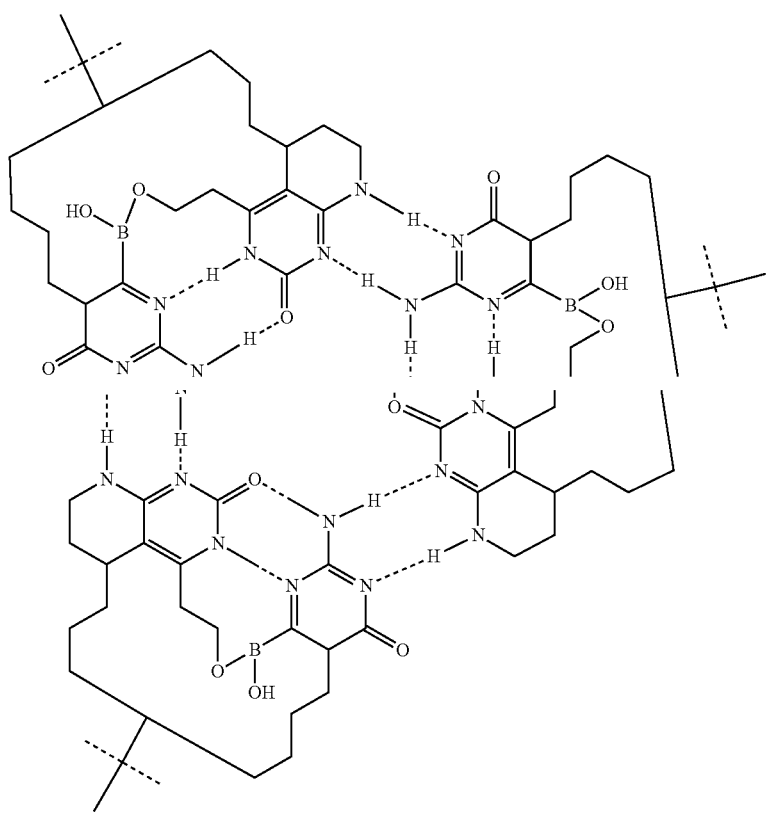
Top view of the upper layer.

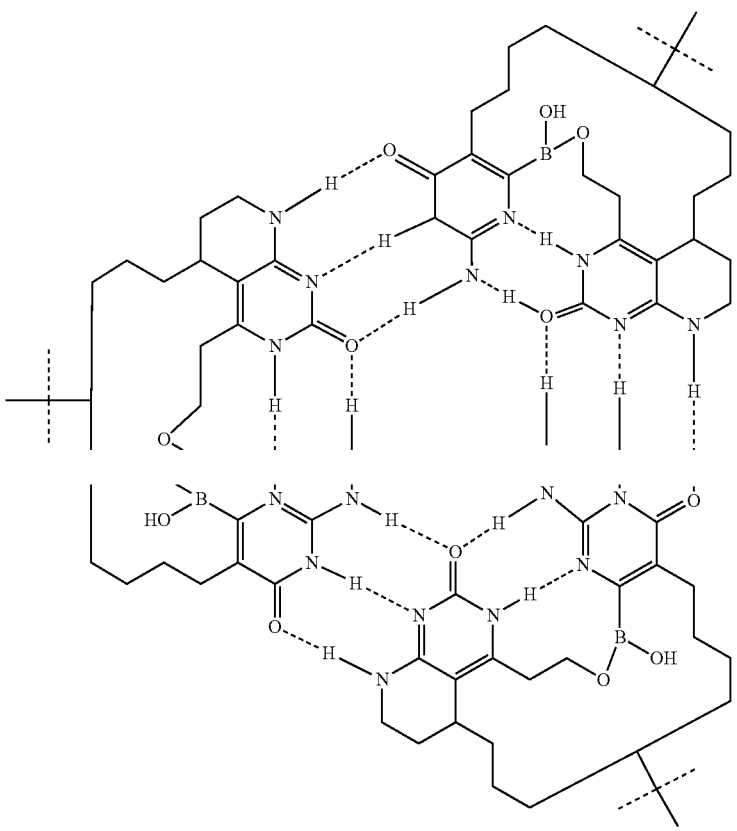
Top view of the bottom layer.
In a second design that uses boric acid esters to form dimers that form hexamers only the top nucleotides are covalently linked through a boric acid ester in the ortho positions. In this design, both nucleotides are symmetric along the 1-4 axis, and thus can rotate in either direction.
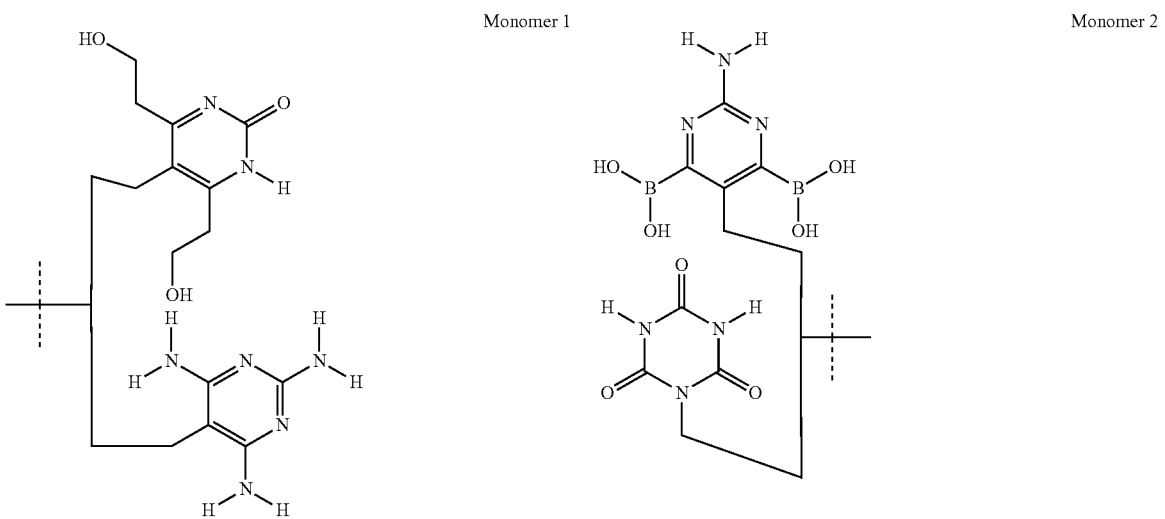

-continued
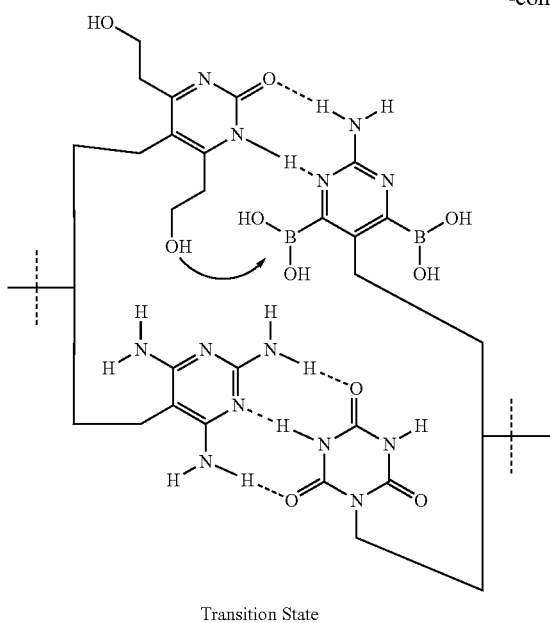
Transition State
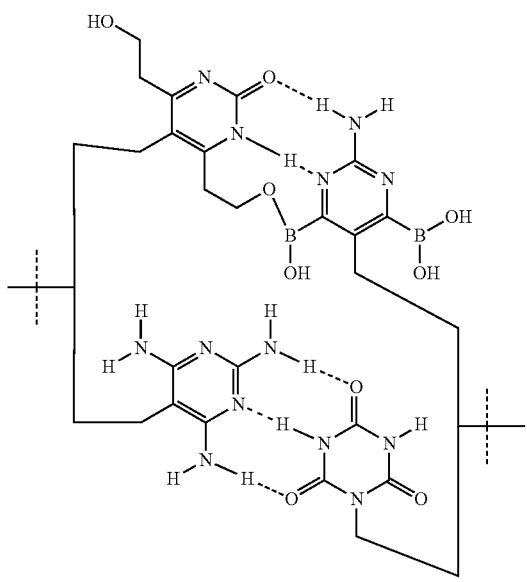
Dimer
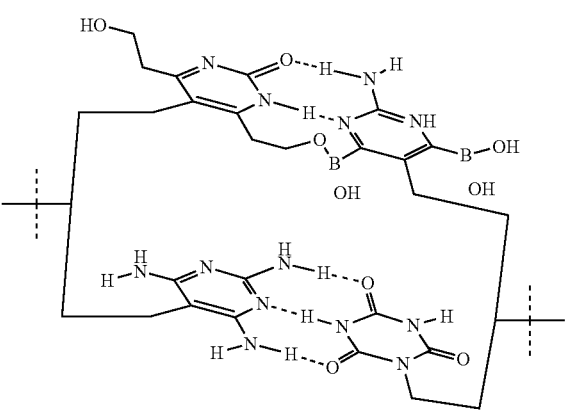
Dimer Side view -continued

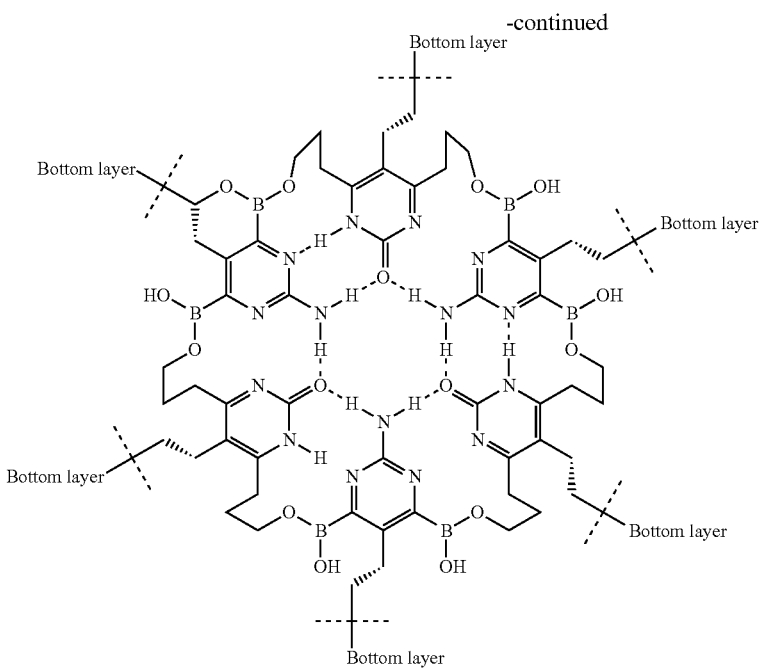

A top view of the rosette of the above design shows how all the nucleotides hydrogen bond at almost every position, skipping the middle hydrogen bond in every other pair. The advantage is that all 6 coferons are covalently linked on the top rosette.

Derivatives Based on Forming Tetramers of Nucleotides of 1,3-Diaminopyrimidine, Diaminopyridine, or Aminopyrimidine Base Pairs with Cytosine or 5-Amino-2-Pyridone.

These linker elements are also derived from Linker Element 9.

In one embodiment, the two backbones are linked through hemiacetals after stacking.

In another embodiment, a linear peptide backbone may be used for the nucleobase linker elements. In such a monomer, the diversity elements of the monomer are the side chains of alternating amino-acid residues In another embodiment, the backbone that bears the nucleobase linker elements may be a circular peptide nucleic acid backbone. In such a coferon monomer, the diversity groups are the side chains of adjacent amino acid residues. In yet another embodiment, a linear backbone based on a cyclopentane scaffold may be used.

The 1,3-diaminopyrimidine, diaminopyridine or aminopyrimidine base pairs with cytosine or 5-amino-2-pyridone tetramer idea is based on enhancing nucleotide base-pairing with hydrophobic surfaces. Each bottom nucleotide can form 3 hydrogen bonds with its pair. Each top nucleotide can form 2 hydrogen bonds with its pair and is attached through a hemiacetal linker. The top nucleotides can become covalently linked across the hydrogen bond area in the "major groove". This structure can now be flipped 180° and stacked with its pair so that there are 4 bases stacked onto each other on one discontinuous strand, and an additional 4 bases stacked onto each other in a second discontinuous strand. The two sets can be linked either through groups on the bases, or the backbone. The 4 diversity elements emanate from the backbones, and can be thought of as coming out of the minor groove of a 4 base double helix. This structure will be very stable once formed, and be able to create a binding surface of the same general size as a single antibody heavy or light chain. In the case of coferon dimers, the hemiacetals between backbones or between bases are not used.

Linker Elements Based on Forming Heterocycle Dimers Using Boric Acid Esters to Link the Nucleotides.

In this embodiment, covalent bonds are formed on the upper base pair through a boric acid ester in the "major groove". The top heterocycles have two hydrogen bonds. The lower base pair has either three hydrogen bonds, or two hydrogen bonds and a boric acid ester. This structure can now flip 180° and stack with it's pair so that there are 4 bases stacked onto each other on one discontinuous strand, and an additional 4 bases stacked onto each other in a second discontinuous strand. The two sets can be linked either through ethyl alcohol and aldehyde groups on the backbone or through boric acid and alcohol groups on the bases. This structure will have enhanced stability once formed, and be able to create a binding surface of the same general size as a single antibody heavy or light chain.

Monomer 1

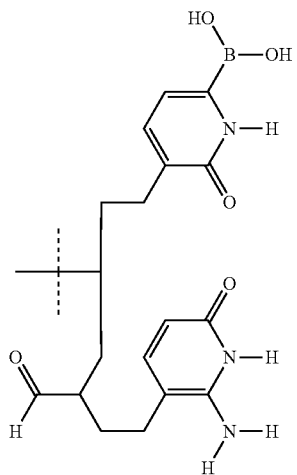

121
-continued
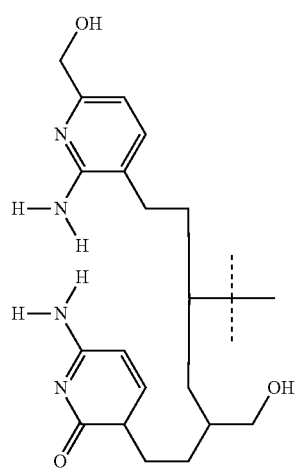
Monomer 2
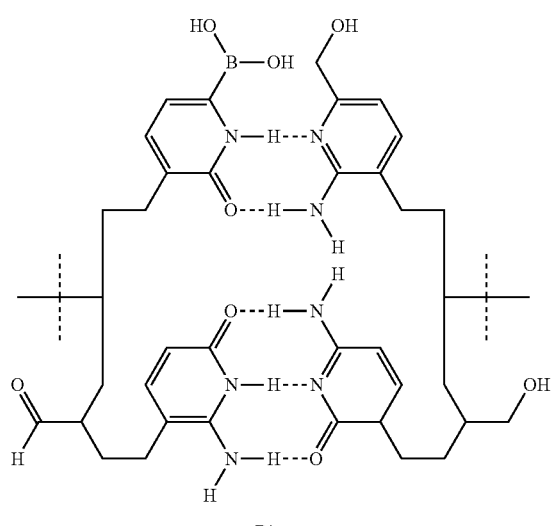
Dimer
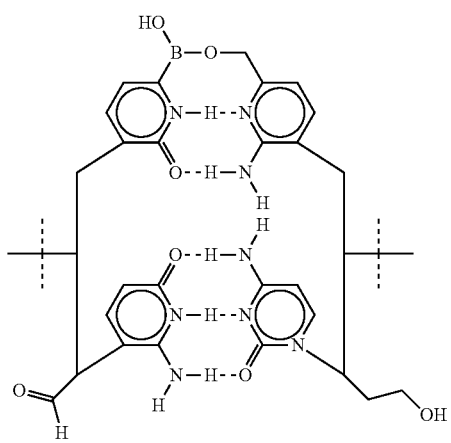
122
-continued
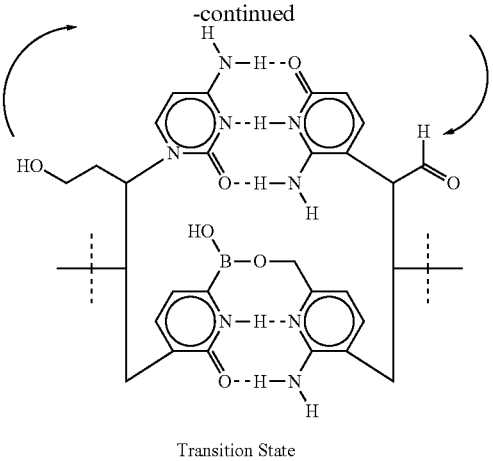
Transition State
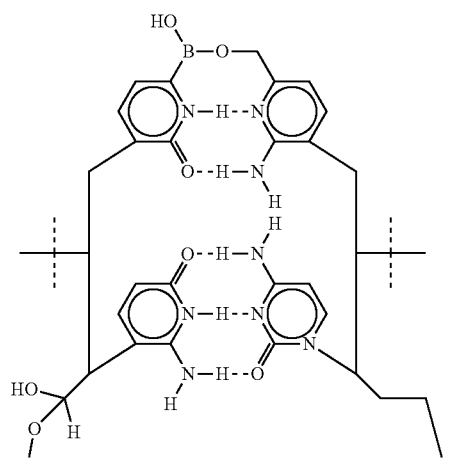
Tetramer 123 -continued
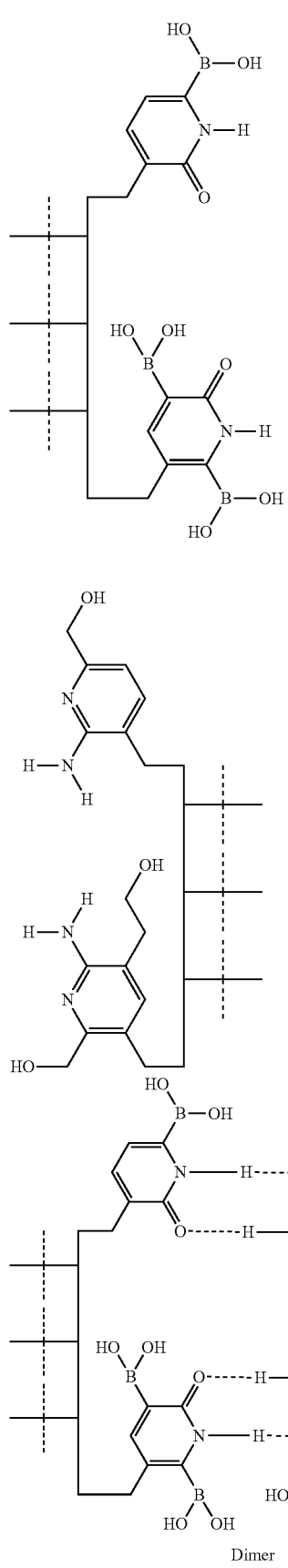
Dimer
124 -continued
Monomer 1
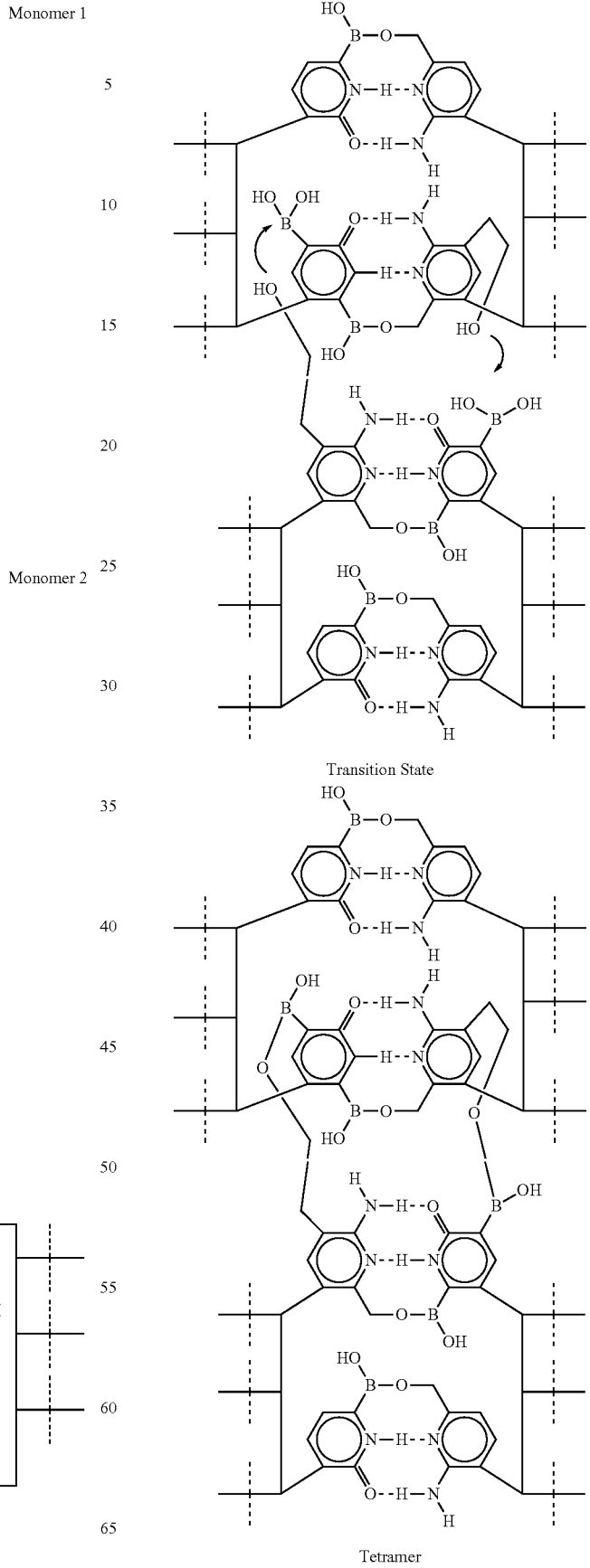
Monomer 2
Transition State
Tetramer Derivatives Based on [2.2.1]Bicyclo-Heptanone and [2.2.2]Bicyclo-Octanone Structure (Linker Element 21).

In one variation the ketone is in the 2 position, and the alcohol group is in the 6 position in the equatorial position (pointing slightly upward). In another variation an aldehyde or ketone group is attached at the 1 position, with an alcohol at the 4 position. Such bicyclo derivatives would not be able to form two covalent hemiacetals or hemiketals when forming a dimer.

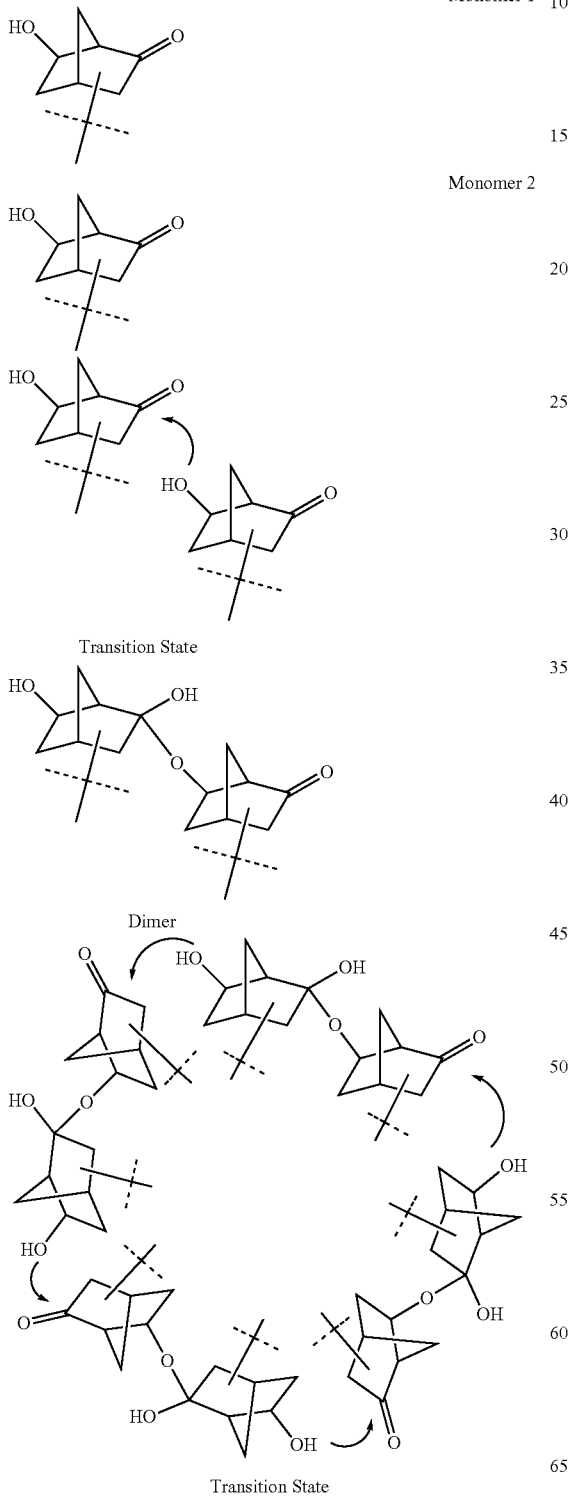

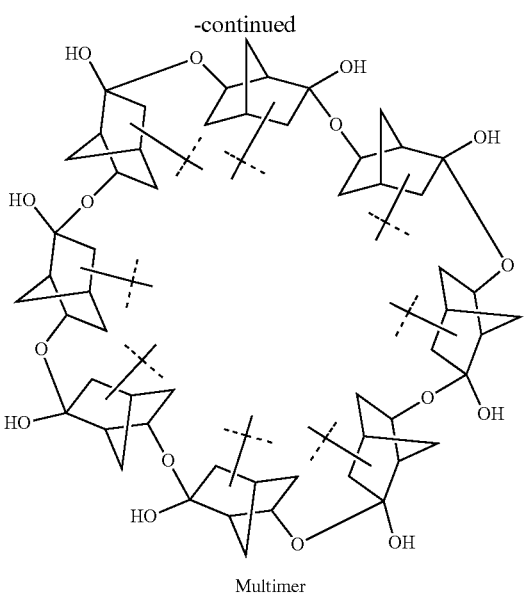

Derivatives Based on Alternate Stacking of Aromatic Rings

Derivatives based an alternate stacking of aromic rings containing alcohol and aldehyde groups, such that the groups cannot react simultaneously to form two covalent bonds between two linker elements (Linker Element 22).

In one variation of this theme, one linker element contains two aldehydes in the meta orientation (1,3), the second contains two alcohols, but there is a bulky substituent (such as tert-butyl, isopropyl, ethyl, methyl, Br, Cl, I) in-between the two (2 position on the ring).

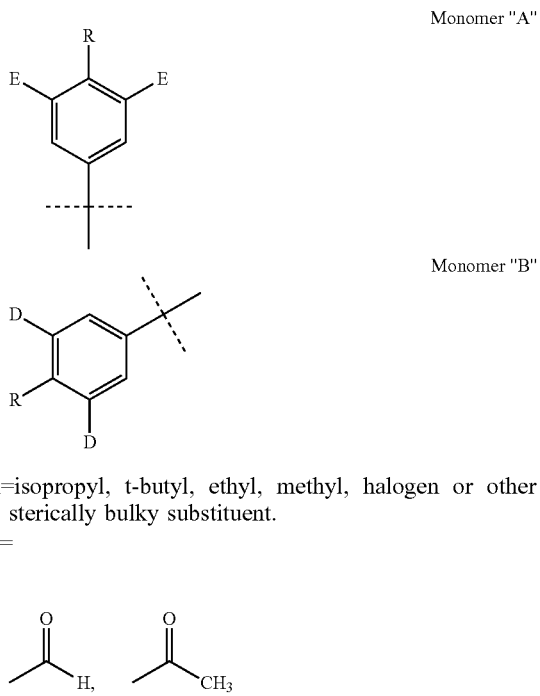

R=isopropyl, t-butyl, ethyl, methyl, halogen or other sterically bulky substituent.

E=

D=—$(CH_2)_n$OH, n=2-3 where the dashed line crossing the solid line represents the one or more diversity elements attached, directly or through a connector, to the linker elements.

Thus, when the two aromatic rings stack, they need to be offset by 120°. This type of design will also rotate the position of the diversity elements by 120°, however, this should not influence binding to the target if the linker elements are connected to the diversity elements via flexible ethylene glycol connectors.

In another variation of this theme, the two linking groups are designed such that when one pair covalently link, the other two pairs are too far apart to also react. For example, one linker element aromatic group could have two aldehye groups in the ortho orientation, while the other linker element would have the alcohol groups in the para orientation.

22B)

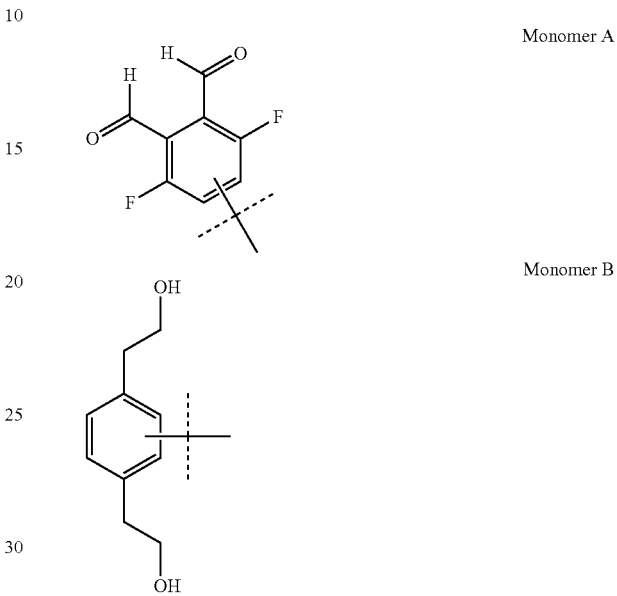

Monomer A

Monomer B

Alternatively, a naphthalene type structure could be used. When such linker elements stack, the aromatic group rotates back and forth, thus this set is known at the "flip/flop" design.

22C)

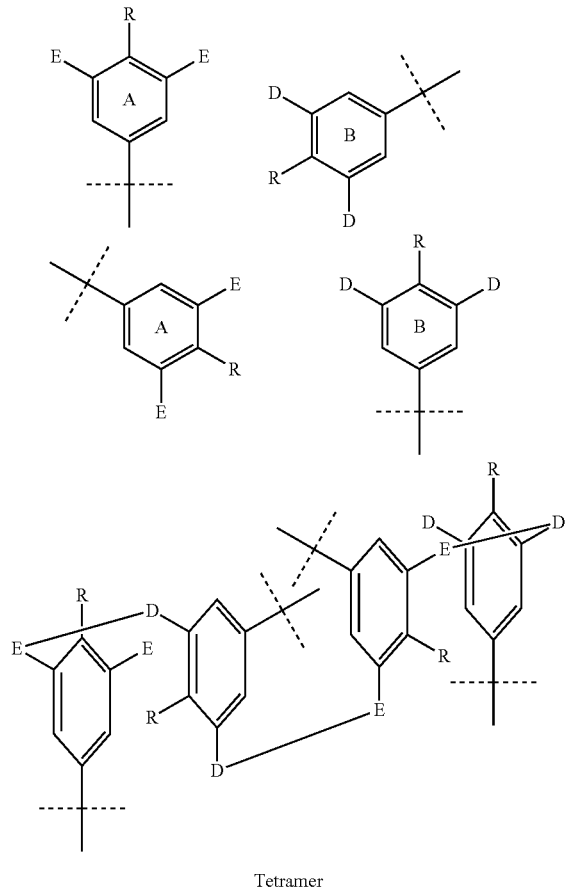

Tetramer

22A)

"Monomer A"

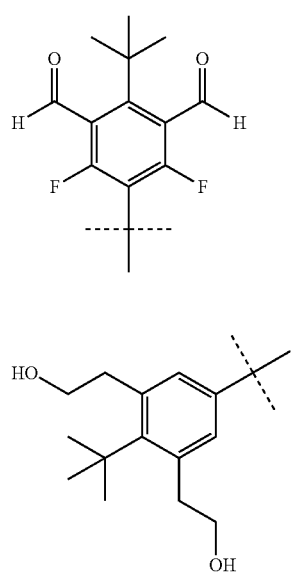

"Monomer B"

Monomer A

Monomer B

Derivative Based on Intercalating Aromatic Rings.

Linker elements that feature aromatic rings that are separated by a rigid spacer have been described earlier to form dimers and trimers. When the aromatic rings on two such linker elements intercalate, they reduce the total number of aromatic surfaces exposed to aqueous solution from 8 down to 2. Including aldehyde and/or ketone groups and alcohol groups on alternating linker elements such that they are offset with respect to each other, a linker element pair can stack onto of another linker element pair which then become covalently linked to each other. This architecture may be used to construct linear coferon multimers, as shown below.

Monomer A

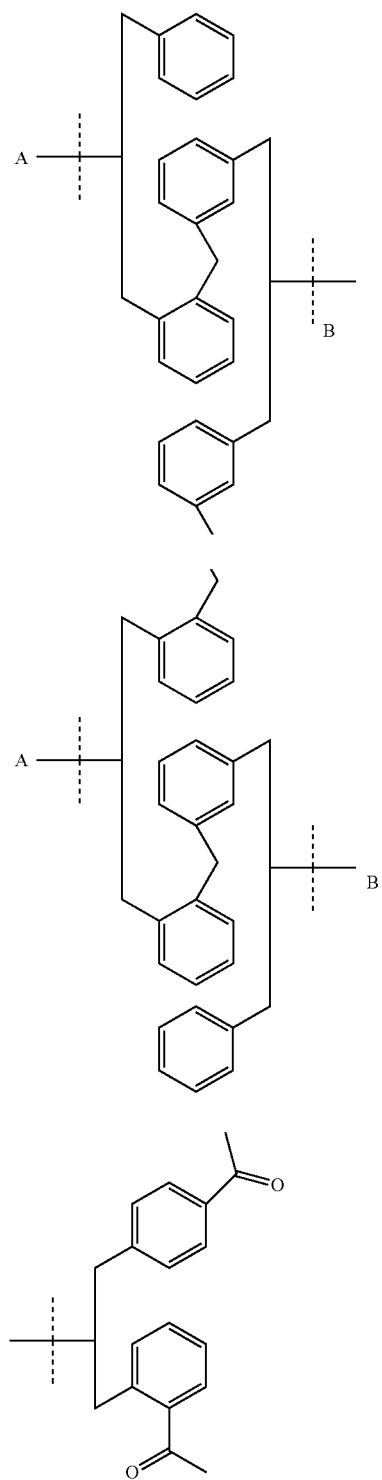

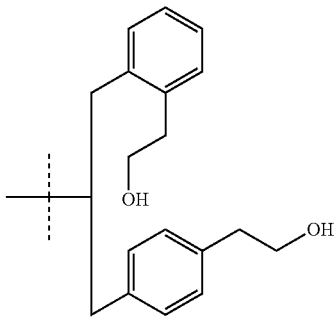

Monomer B

Derivatives that Combine Metal Binding Group with Covalent Bond Formation

Linker elements that combine zinc chelators with hemiacetal covalent bond formation allows assembly of tetramers. This is Linker Element 24. A variation using picolinic acid as the chelator is shown in the example below as 24A).

24A)

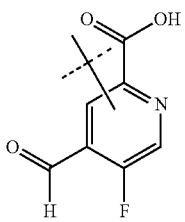

Monomer 1

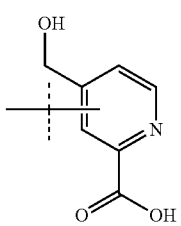

Monomer 2

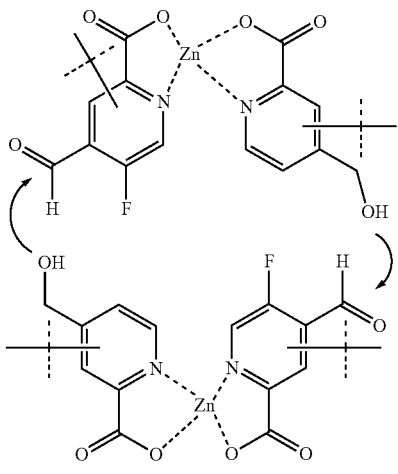

Transition State

131

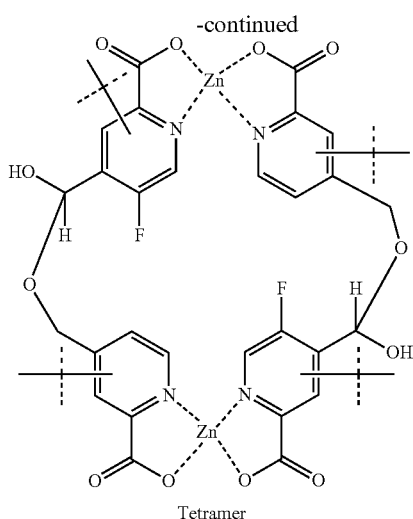
Tetramer

Another variation of Zn chelating coferons that form tetramers is based on binding of two zinc cations and formation of boric acid esters. This design takes advantage of aromatic ring stacking of the picolinic acid groups. The ethyl alcohol is perfectly positioned to form a covalent link to the boric acid on the aromatic of the neighboring picolinic acid linker element.

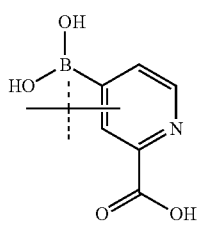
Monomer 1

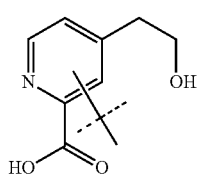
Monomer 2

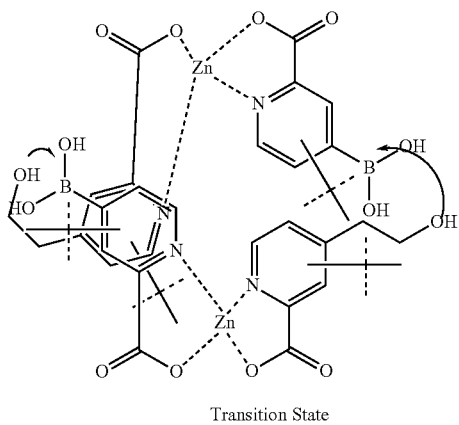
Transition State

132

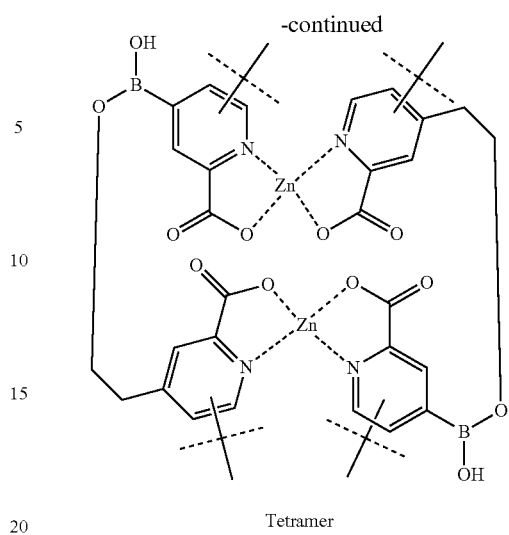
Tetramer

Derivatives Based on a Single Linker Element that Assembles to Form Trimers or Hexamers.

These derivatives are based on forming boronate esters between boronic acid and 1,2 and 1,3-diols (Linker Element 25). When derived from aliphatic molecules, these linker elements form dimers. When derived from an aromatic ring containing molecule, these linker elements can form trimers or hexamers. Boronates can also complex with amino alcohols and may also complex with amido alcohols.

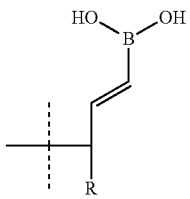
(B1)

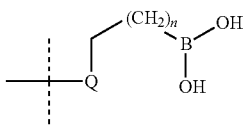
(B2)

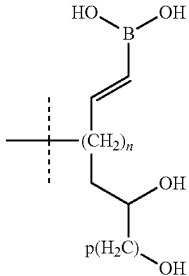
(B3)

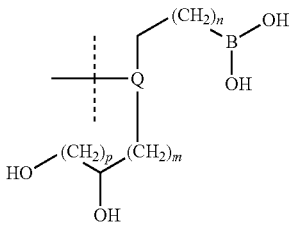
(B4)

where R is an aliphatic or alicyclic group including —H, —CH$_3$, —CF$_3$
where Q is an aromatic heterocyclic or nonheterocyclic ring
where n=0-3, m=1-3 and p=1-2 where the lines crossed with a dashed line illustrate the bonds formed joining the one or more diversity elements to, directly or through a connector, the molecules of Formula (B1), Formula (B2), Formula (B3) and Formula (B4). Examples of these embodiments are shown below as 25A) to 25 D)

In these designs an aromatic ring (that may contain N, S or O atoms at various positions within the ring) bears a boronic acid moiety as well as a 1,3-diol moiety in the meta position of the aromatic ring. These linker elements can form trimers as well as hexamers

25A)

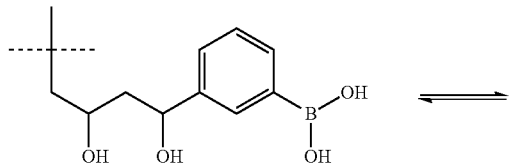

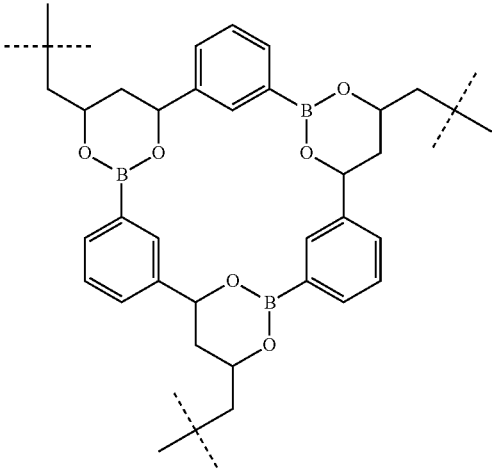

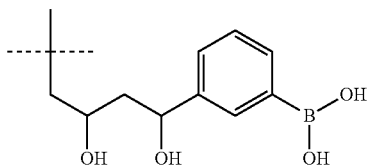

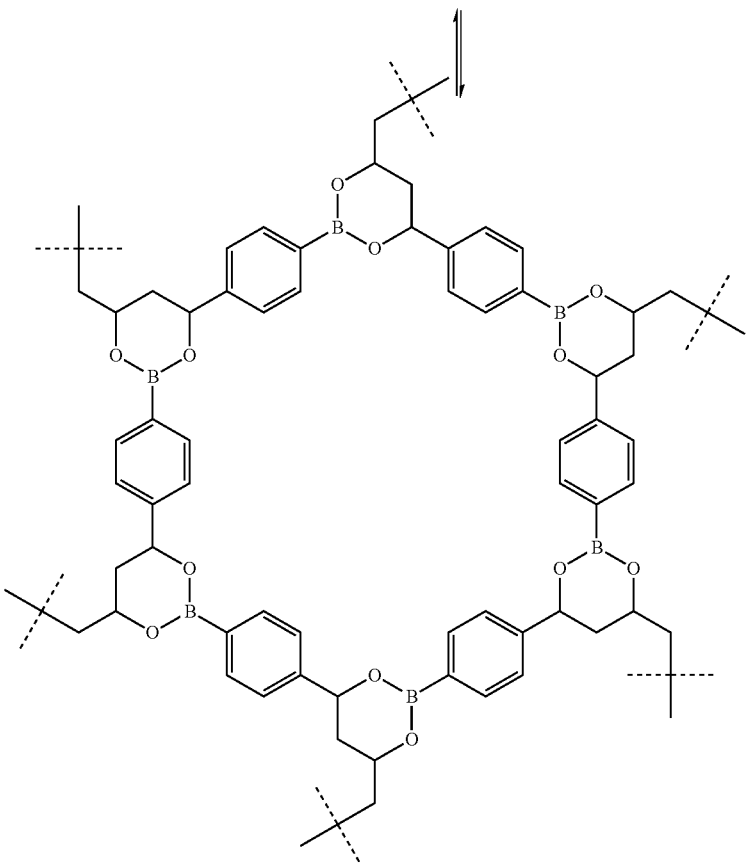

In another embodiment, the boronic acid moiety as well as the 1,3 diol moiety may be replaced by a hydroxymethyl ketone leading to hexameric assembly through the formation of hemiacetal covalent bond formation.

25B)

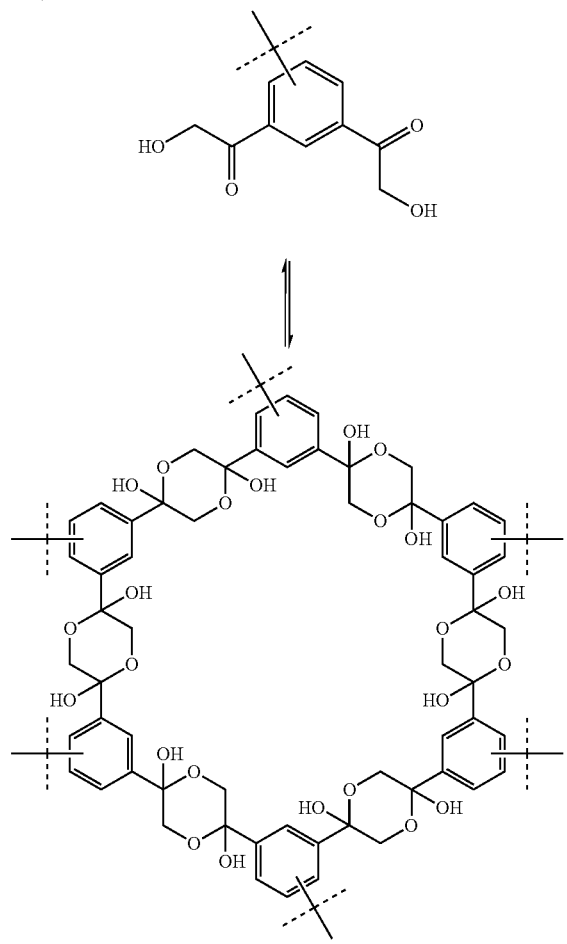

25C)

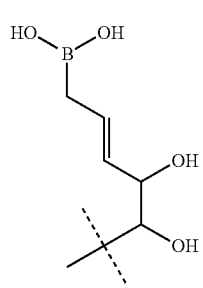

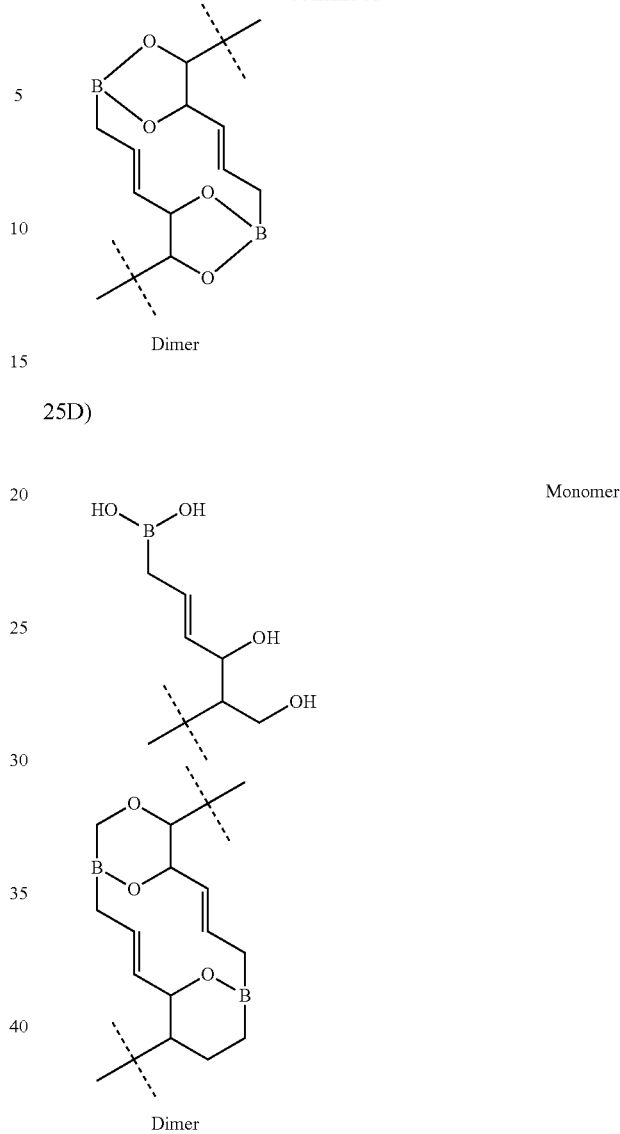

Dimer

25D)

Monomer

Dimer

Derivatives that Form Dimers which Interact with Different Monomers to Form Tetramers Derivatives based on linker elements that first form dimers through hemiacetal formation, thus positioning two sets of hydroxyl groups that are optimally positioned to react with a boronic acid moiety on an aromatic ring (that may contain N, S, or O atoms at any position within the ring). This is Linker Element 26.

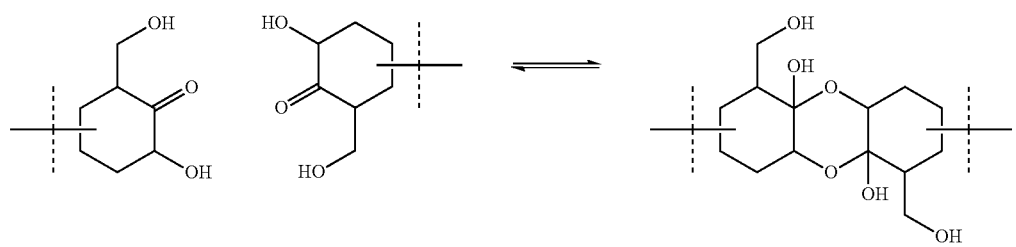

+

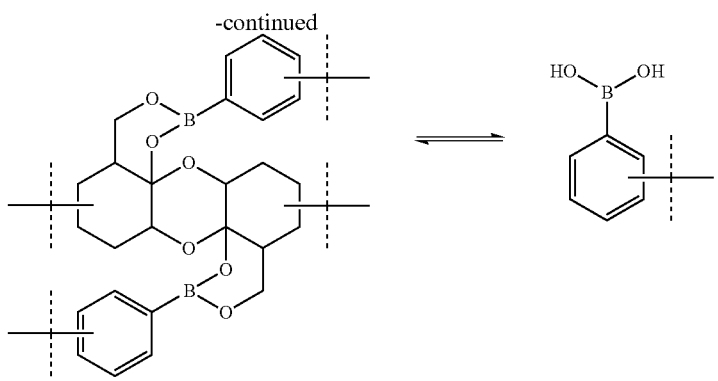

Derivatives Based on Assembly of Three Separate Linker Elements

Derivatives based on trimeric assembly of linker elements where covalent bond formation between a first linker element and a second linker element generates a new reactive group on the second linker element allowing it to form additional covalent bonds with a third linker element (Linker Element 27). The first linker element may be an aliphatic or aromatic amine or imidamide and reacts with a second linker element that may be a cyclohexanone bearing a hydroxymethyl substituent at the 2-position. The third linker element may be an aromatic ring (containing N, S, or O atoms at any position within the ring) and a boronic acid moiety. 27A)

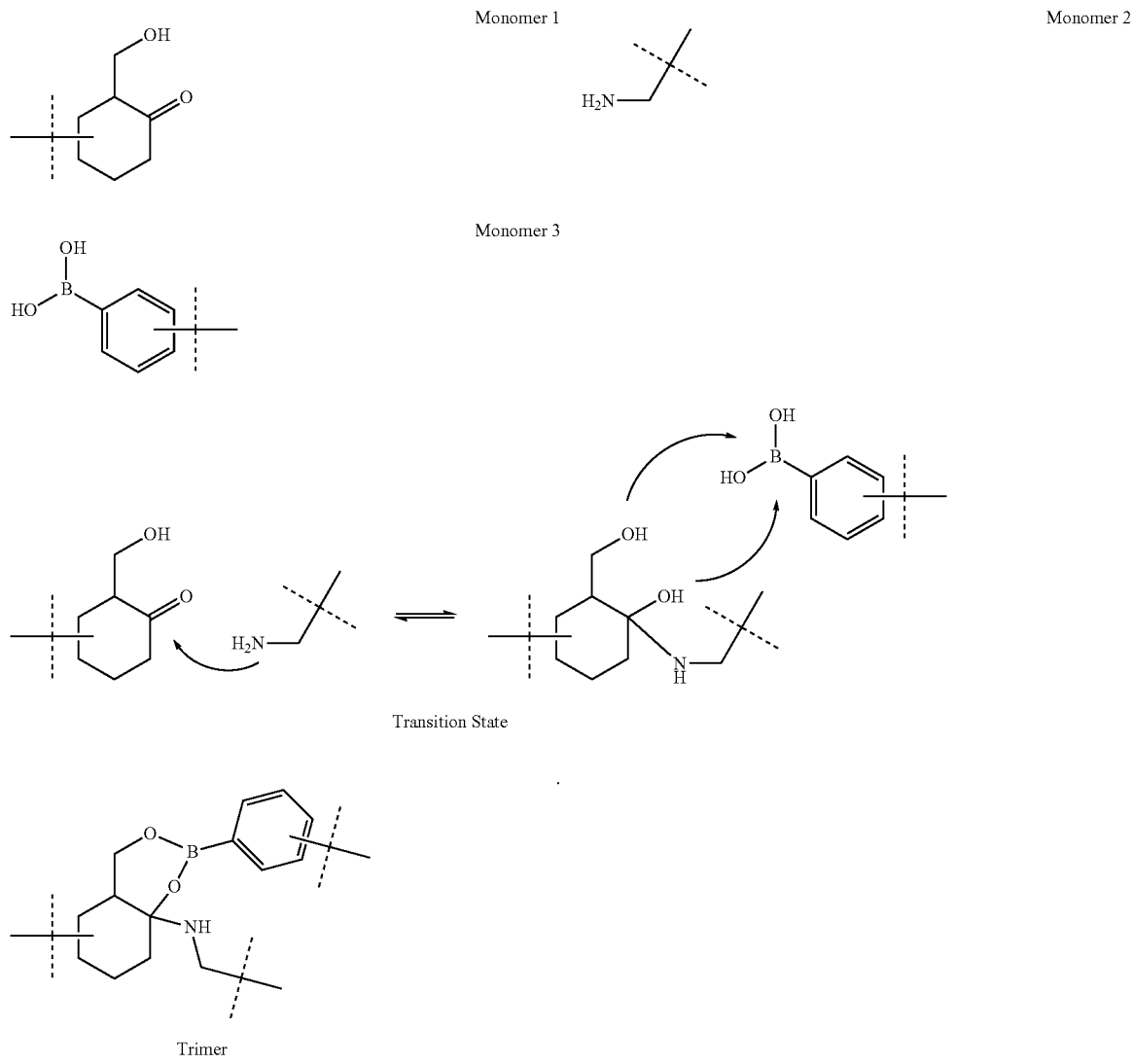

Example 2
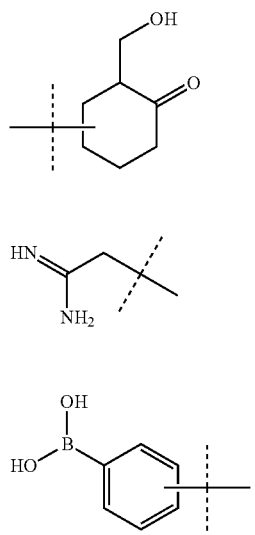
Monomer 1
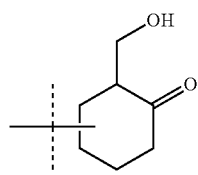
Monomer 2
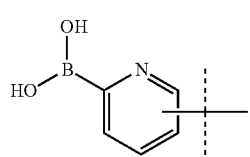
Monomer 3
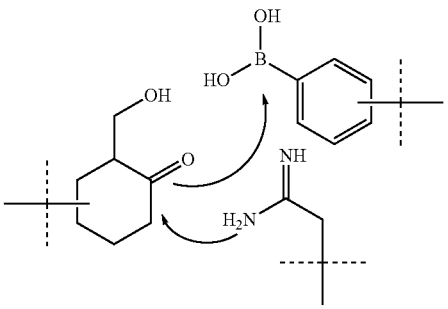
Transition State
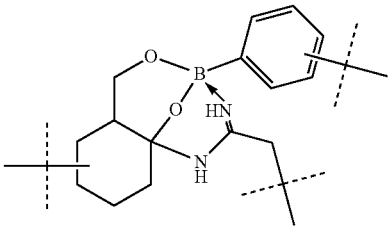
Trimer
27C)
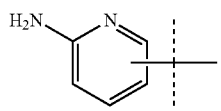
Monomer 1
Monomer 2
Monomer 3
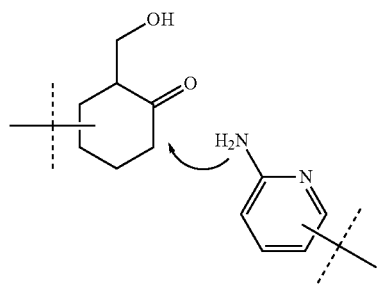
Transition State
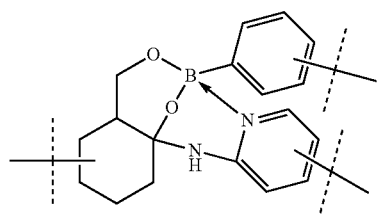
Trimer

Derivatives Based on Linker Elements that are Actively Transported into Target Cells Linker elements that contain folic acid will preferentially enter cancer cells using the folate transporter (Linker Elements 28). In one embodiment, diversity element is attached to the folic acid based linker element via an ethylene glycol linker.

28A)

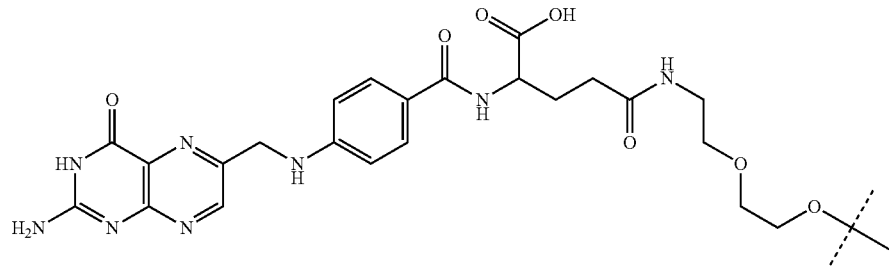

In another embodiment, the two folate moieties have the opportunity to become reversibly covalently linked to each other.

28B)

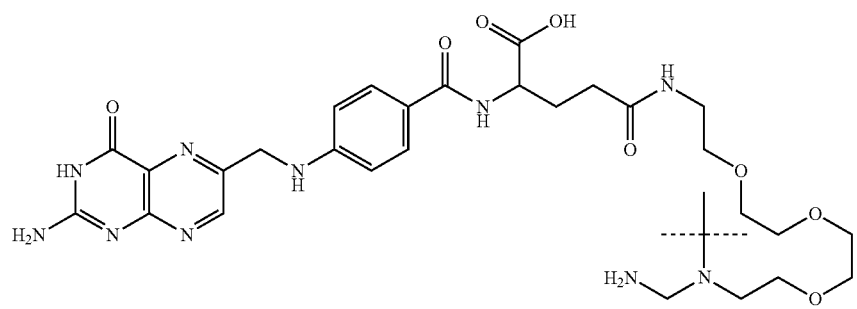

Monomer 1

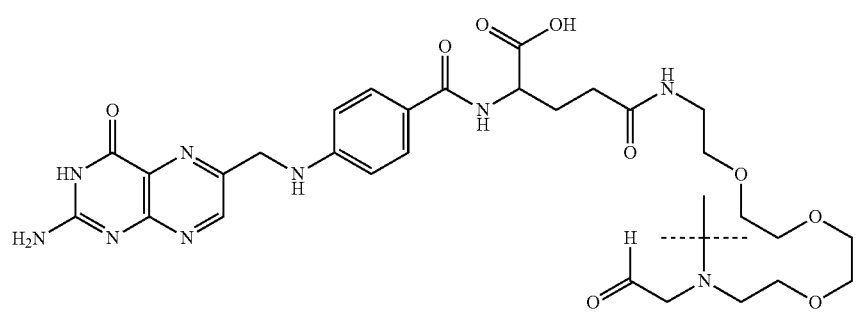

Monomer 2

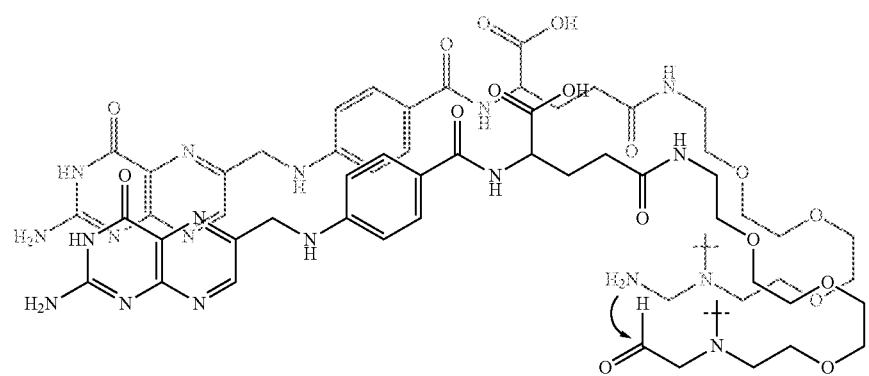

Transtition State

-continued

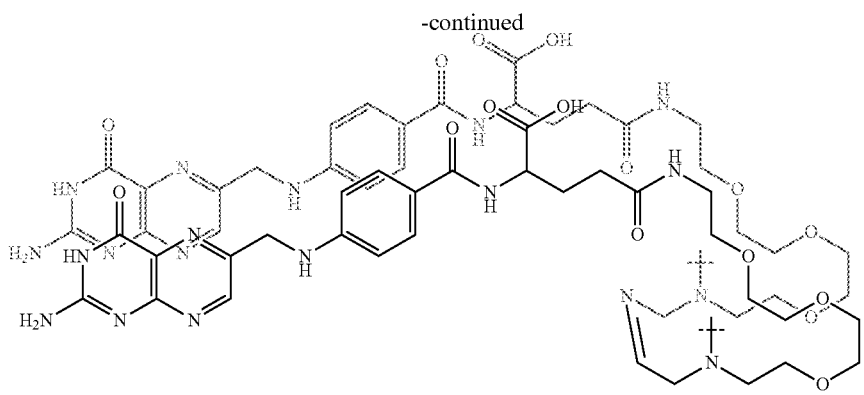

Reversibly-Linked Folic Acid Linker Element Dimer

In a third embodiment, the folic acid moiety is attached to a second linker element via a disulfide bond. Cleavage of the disulfide bond by glutathione within tumor cells now facilitates irreversible binding of two linker elements through formation of a thiazolidine ring. 28C)

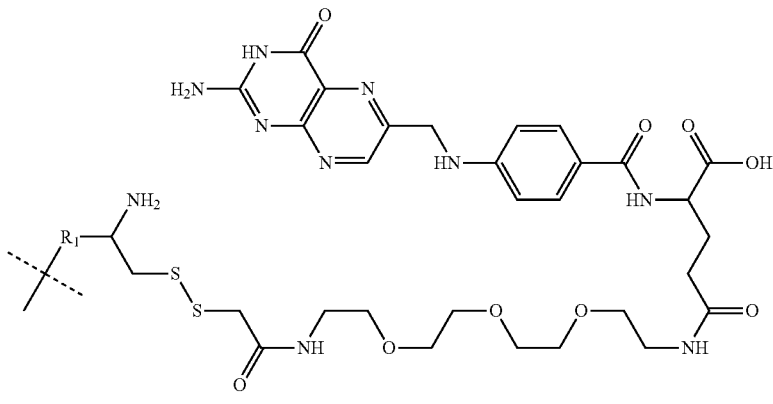

1) Folate receptor meidated intracellular uptake
2) Glutathione mediated dilsulfide cleavage

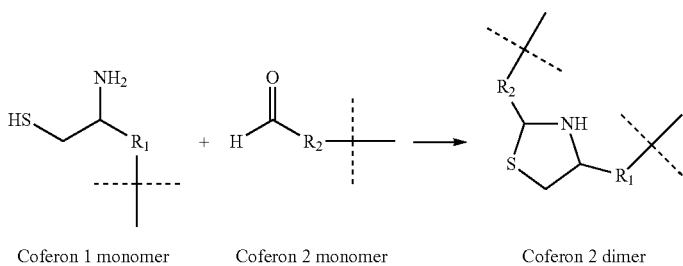

Coferon 1 monomer      Coferon 2 monomer      Coferon 2 dimer

In other variations, the linker element may be attached to other moieties to make linker element precursors that bind receptors or transporters that then facilitate transport or uptake of the linker element precursors in to the cell.

Derivatives Based on Intracellularly Activated Irreversible Crosslinking Linker Elements In these designs, the linker element contains a protected functional group that undergoes deprotection inside the cell. The resulting functional group allows for irreversible covalent bond formation between the linker elements (Linker Element 29). One embodiment of this design contains a protected disulfide. On entering cells the disulfide is reduced by glutathione releasing a free sulphydryl group that is beta to a primary amine. This moiety can then react irreversibly with a carbonyl on another coferon monomer to form a thiazolidine linkage.

29A)
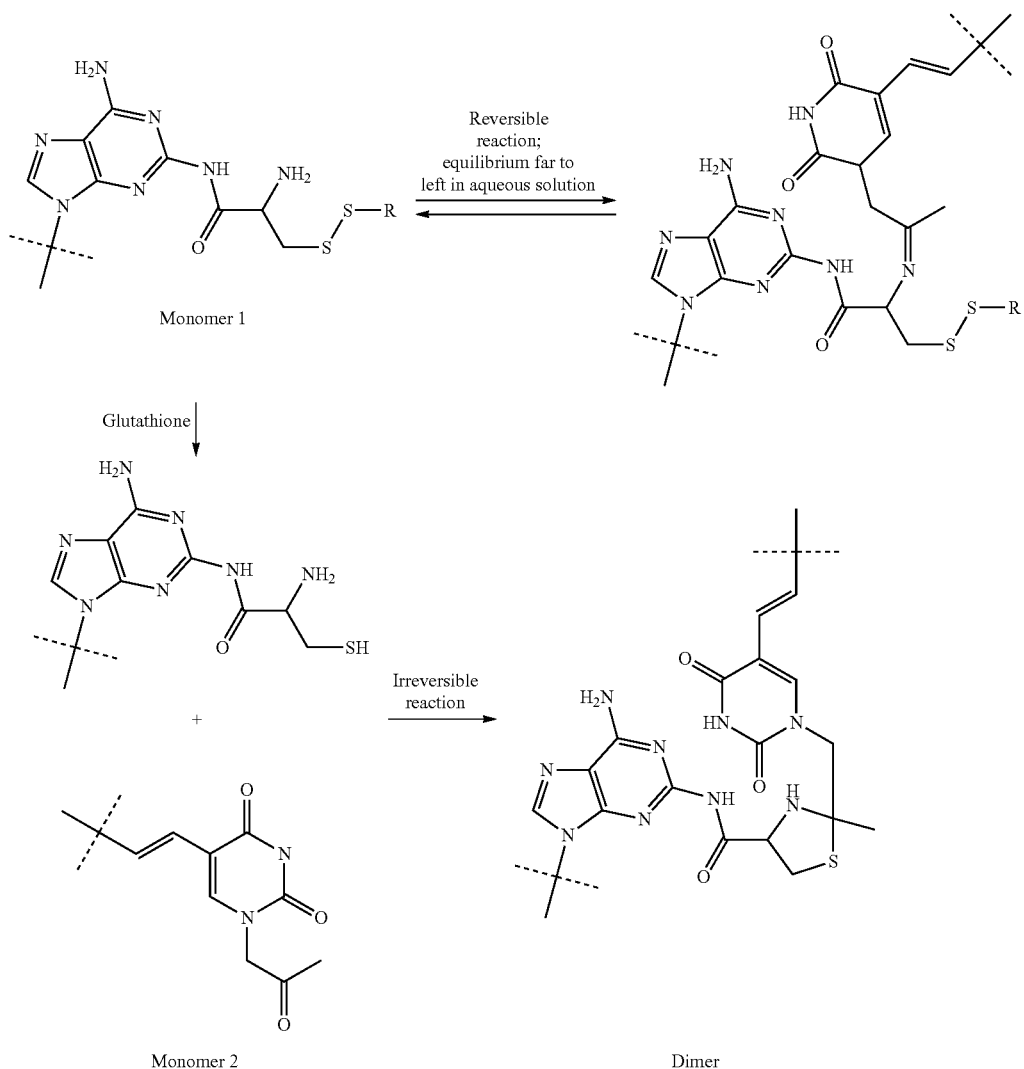
Such linker elements may be designed to carry both the protected disulfide as well as a carbonyl such that on generation of the free sulfhydryl group, the monomer can react with itself to form a homodimer. 29B)
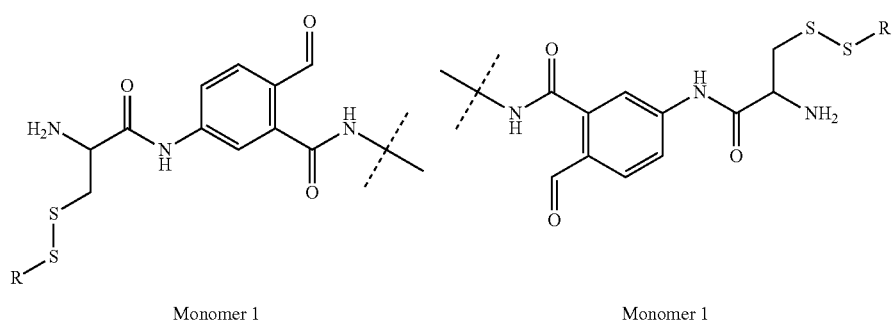
1) Glutathione mediated disulfide cleavage
2) Amide-aromatic ring stacking interactions (as in DNA polymerase)

-continued

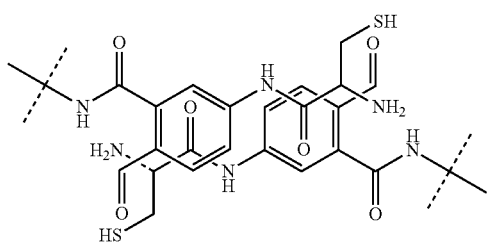 Dimerization 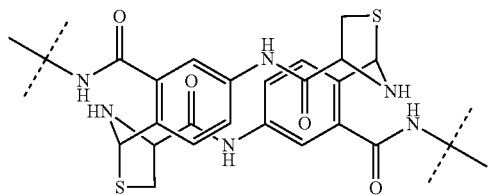

An alternative mode of dimerization for the above linker element is shown below

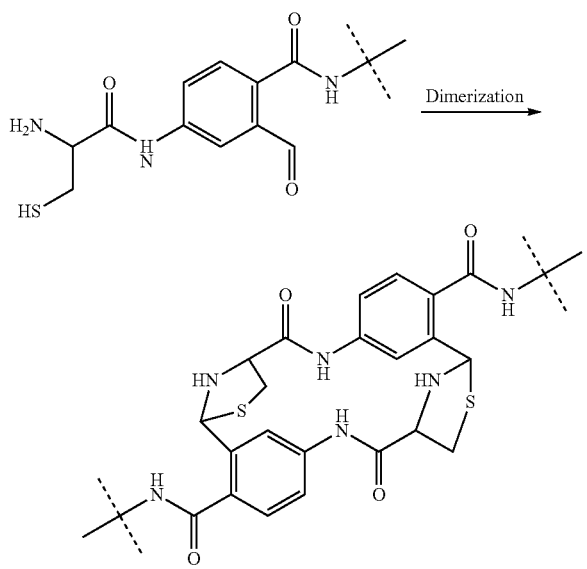

Diversity Elements

Most drugs work by blocking protein activity, clogging an enzymatic pocket, and thus inhibiting activity. In order for a drug to bind, there needs to be sufficient complementarity and surface area of contact such that van der Waals and ionic interactions provide the requisite binding energy. The field of combinatorial chemistry is based on the principle of creating ligands or diversity elements of different shapes and sizes, some of which can bind to the desired surface of the target, and thus serve as lead molecules for subsequent medicinal chemistry.

Coferons have the advantage of being able to bind the target through two ligands or diversity elements. These diversity elements combine to give the coferon a tighter binding than would be achieved through a single diversity element. In addition, coferons provide a linker element (and an optional connector), which may provide additional opportunities to maximize the surface area of interaction between the coferon and protein target.

Combinatorial chemistry approaches seek to maximize diversity elements, and such molecules are often synthesized using split and recombine or bead-based approaches. There are two general approaches used to generate a diversity library: (i) a single platform with multiple functional groups, each of which is reacted with a family of diversity reagents to create a library of surfaces and (ii) the diversity is generated using bifunctional reagents to create short linear or circular chains, such as peptides and peptide analogues.

In many of the examples below, the order of synthesis is a linker element is attached to a tri-functional connector, with one of the functionalities used to attach the connector-linker element to a bead or DNA barcode or tag sequence.

This is followed by attaching or combinatorial synthesis of the diversity library of ligands. The order of these steps and the geometry of the components may be altered. For example, the linker element may also double as the connector, being attached to the diversity element on one end and the bead on the other end. Also, the linker element may be added last, after synthesis of the diversity element. The examples below are by no means exhaustive of methods for synthesizing linker elements with diversity elements.

Diversity elements may be molecules previously known to bind to target proteins, molecules that have been discovered to bind to target proteins after performing high-throughput screening of previously synthesized commercial or non-commercial combinatorial compound libraries or molecules that are discovered to bind to target proteins by screening of newly synthesized combinatorial libraries. Since most pre-existing combinatorial libraries are limited in the structural space and diversity that they encompass, newly synthesized combinatorial libraries will include molecules that are based on a variety of scaffolds.

Monocyclic Scaffolds

These scaffolds may be used to generate the simplest types of combinatorial libraries.

Monocyclic Scaffolds

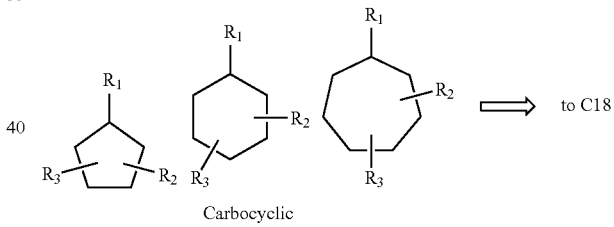 to C18

Carbocyclic

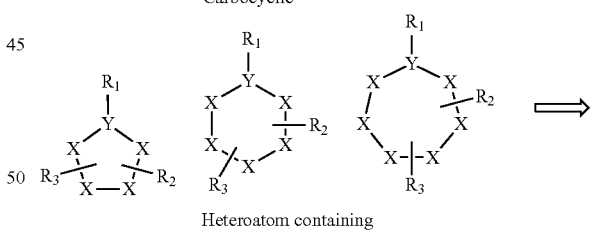 to (C,N,O)18

Heteroatom containing $X = C, C{=}O, S$ or $N$; $Y = C$ or $N$

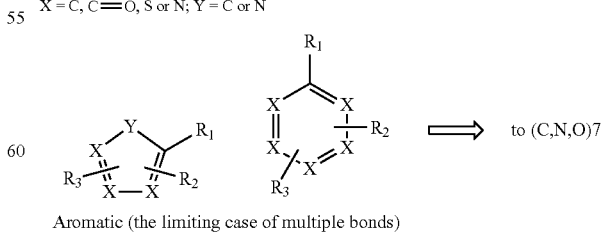 to (C,N,O)7

Aromatic (the limiting case of multiple bonds)

$X = C$ or $N$; $Y = NY, O, S$

In addition to those nitrogen and carbon atoms that are substituted by $R_2$ and $R_3$, other positions may contain additional substituents including H. Multiple bonds may also be incorporated between ring atoms.

Bicyclic Scaffolds

Each bicyclic scaffold may be substituted at different positions and contain heteroatoms and multiple bonds as illustrated for monocyclic scaffolds above.

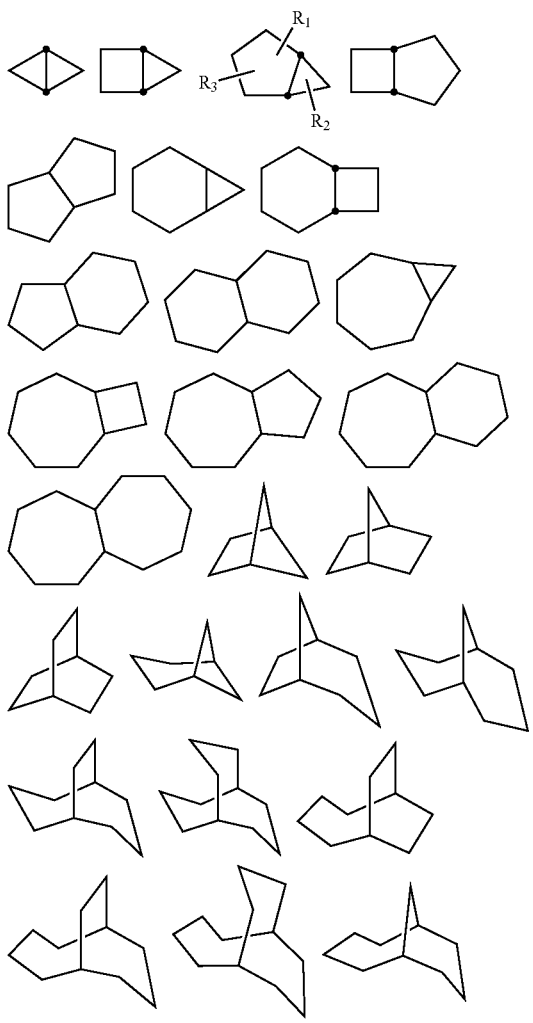

Tricyclic Scaffolds

Tricyclic scaffolds containing 3 rings fused to each other and may contain heteroatoms and multiple bonds as illustrated for monocyclic scaffolds above.

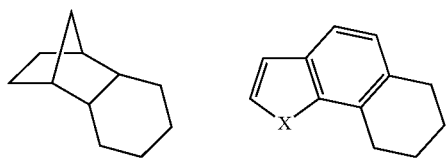

Tetracyclic Scaffolds

Tetracyclic scaffolds containing 4 rings fused to each other and may contain heteroatoms and multiple bonds as illustrated for monocyclic scaffolds above.

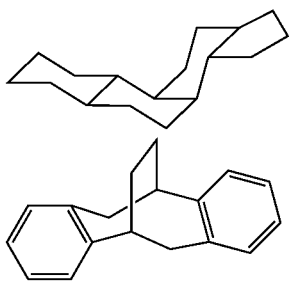

Spiro Scaffolds

Spiro scaffolds where two rings are fused to each other through a single common atom

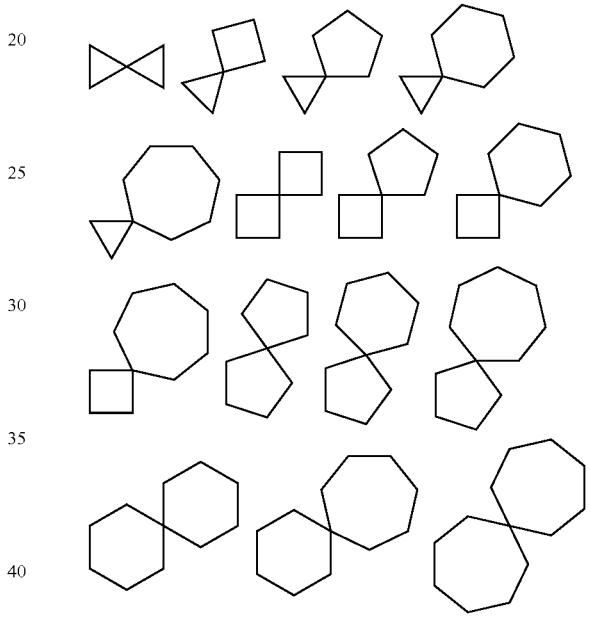

Multicore Scaffolds

Multicore scaffolds where each of the above scaffold core elements are linked by a covalent bond.

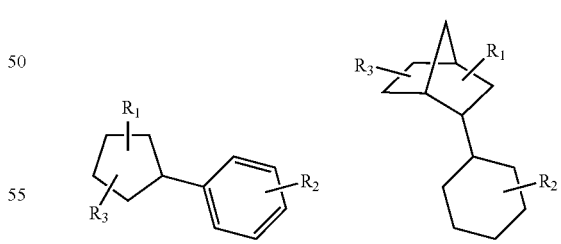

Connectors

In one embodiment, a linker element is attached to a tri-functional connector, with one of the functionalities used to attach the connector-linker elements to a bead. Beads are distributed to unique wells, and a set of diversity elements react with the third functional group on the connector (for example 500 different aldehyde containing moieties reacted with an amino group). In this embodiment, the well the synthesis took place in identities the diversity element.

In a second embodiment (FIG. 2.1A), a linker element is attached to a tri-functional connector, with one of the functionalities used to attach the connector-linker element to an encoded bead. For example, Veracode™ beads (Illumina, San Diego, Calif.) or silicon particles may be used, where each bead has a unique Veracode™ or barcode pattern. The beads or particles are distributed into a set of reaction chambers (for example 10 chambers), identified in each chamber, and then reacted with a bifunctional moiety (for example, a protected amino acid). The beads are mixed, split again into the reaction chambers, and the process is repeated (split-pool synthesis). In this embodiment, repeating the process a total of 4 times will result in 10,000 diversity elements in the library. In a variation of this approach, at the end of the synthesis, the last amino acid residue is reacted with the connector to create a circular diversity element. In this version, the diversity element is identified by the code on the bead or particle.

In a third embodiment, a linker element is attached to a tri-functional connector, with one of the functionalities used to attach the connector-linker element to a long DNA barcode sequence (FIG. 2.1B). The DNA barcode has two universal primer binding site sequences at the 3' and 5' end, and contains multiple internal zip-code sequences, which are sequences that have similar melting temperatures but are different in at least 25% of their bases so that they uniquely hybridize to their complementary sequences either in solution, on beads, or on array surfaces. The molecules comprised of connector-linker element-DNA barcode (=library members) are equilibrated with a set of columns (e.g., 10 columns), containing beads with complementary zip-code sequences. DNA hybridization captures library members containing the complementary zip-code sequence on their DNA barcode. At the end of this process, all the library members should be distributed in the 10 columns, depending on the zipcode sequence in the first position of the DNA barcode. The library members are eluted into separate new chambers, and reacted with a bifunctional moiety (e.g., a protected amino acid) that corresponds to the given zipcode. The library members are then re-pooled and then rerouted to the next series of columns, using the zipcode sequences in the second position of the DNA barcode for sequence-specific capture. In this embodiment, repeating the process a total of 4 times will result in 10,000 diversity elements in the library. As above, at the end of the synthesis, the last amino acid residue may be reacted with the connector to create a circular diversity element. In this embodiment, the identity of the diversity element is defined by the zip-code sequences in the DNA barcode.

In a fourth embodiment, a linker element is attached to a tri-functional connector, with one of the functionalities used to attach the connector-linker element to a DNA template sequence containing two universal primer binding site sequences at the 3' and 5' end, and multiple zipcode sequences. The DNA sequence serves as a template for adding bifunctional moieties to the remaining functional group on the connector. Each bifunctional moiety is attached to a complementary zip-code DNA molecule, which hybridizes on the DNA template containing the connector-linker element. This hybridization increases the local concentration of the reactant to such an extent that it can drive synthesis to very high yields. This method does not require split-pooling techniques. In this embodiment, the first set of bifunctional moieties are attached to complementary zip-code DNA molecules to the first set of zipcodes, the second set of bifunctional moieties are attached to complementary zip-code DNA molecules to the second set of zipcodes, etc. This approach has the disadvantage of requiring synthesis of functional moieties attached to every new set of complementary zip-code sequences. Another problem is each additional round moves the reactive group further away from the growing chain, a problem which can be ameliorated by using oligos designed to hybridize over a split sequence like an "omega" symbol. To circumvent the need to generate new reagents containing bifunctional moieties for each new set of zipcodes, another variation would use three oligonucleotide sets. The first set contains the connector-linker element-DNA template sequence library covalently linked to the growing diversity element. The second set contains a unique zipcode for each bifunctional moiety used. The third oligonucleotide set is complementary to the particular zipcode sequence on the bifunctional moiety from the second set as well as the particular zipcode in the DNA template sequence from the first set, and by hybridizing to both of these DNA elements, it brings the bifunctional moiety in close proximity with growing chain on the connector-linker element-DNA template thus increasing the local concentration and driving the reaction forward. This method has the advantage that it does not require split-pooling techniques. If 4 sets of 10 each bifunctional moieties are added, this will result in 10,000 diversity elements in the library. As above, at the end of the synthesis, the last amino acid residue may be reacted with the connector to create a circular diversity element. In this version, the identity of the diversity element is defined by the zipcode sequences in the DNA template.

In a fifth embodiment, a linker element is attached to a tri-functional connector, with one of the functionalities used to attach the connector-linker element to a DNA barcode sequence containing two universal primer binding site sequences at the 3' and 5' end, and a single zip-code sequence in the middle. The molecules are equilibrated with an array surface containing complementary zip-code sequences, positioned such that a multi-chambered cover could divide the array into chambers (e.g., 10 chambers). Each chamber is reacted with a different bifunctional moiety (e.g., a protected amino acid) that corresponds to the given zipcode. The library members are then re-pooled and then rerouted to the next array, where the complementary zipcode sequences are now rearranged. In this example, repeating the process a total of 4 times will result in 10,000 diversity elements in the library. In a variation of this approach, the array complementary zip-code sequences may be modified on their free end to become covalently attached to a given bifunctional moiety. The moieties are first added to the correct zipcodes using the chambers. Subsequently, the chambers are removed, and the library members containing DNA barcode sequences are added to the array. Once they hybridize to the correct addresses, they are properly oriented to react with the bifunctional group on the zipcode and add that moiety to the growing chain. In a full variation of this approach, the array addresses are printed to contain both the complementary zip-code sequences and a contiguous DNA sequence tag on the same strand. Under these conditions, both a DNA molecule complementary to the tag sequence and containing a bifunctional moiety, as well as the library member with the cognate zip-code sequence, can bind to the address to set up a DNA targeted synthesis step. This full variation would obviate the need for chambers to separate the individual reactions. As above, at the end of the synthesis, the last amino acid residue may be reacted with the connector to create a circular diversity element. In this version, the identity of the diversity element is defined by the single zipcode sequence in the DNA barcode.

In a sixth embodiment, a linker element is attached to a tri-functional connector, with one of the functionalities used to attach the connector-linker element to either a Veracode™ bead, bar code particle, or a DNA barcode sequence containing one or more zipcode sequences. The remaining functionality is connected to a "platform" containing additional functionalities. For example, the platform may be a cyclo-pentane derivatized on three carbons all in the syn orientation. In this version, one of the encoding processes described in embodiments 2-5 above is used to add mono-functional moieties to the appropriate functional groups on the platform. For example, if there are 20 moieties added in each step, the resultant library will contain 8,000 diversity elements. The advantage of this approach is to guide all the diversity components in a single orientation for maximum diversity in binding surfaces.

Encryption Portion

The most versatile encryption element is an attached bar code, typically a nucleic acid sequence, such as an oligo-nucleotide or DNA. The encryption element may be used to directly assist in synthesizing the diversity element (as in DNA Targeted Synthesis ("DTS")). Each encryption element is composed of multiple zipcode sequences. The encryption element has a chemical molecule attached to one end. Upon hybridization of a first zip-code complement bearing a reactant group with a diversity element, the reactant group is covalently linked to, and transferred to the chemical molecule on the nucleic acid. Each unique zipcode complement is charged with a reactant group containing a diversity element that corresponds to the zipcode sequence. The process is repeated with a second set of charged zipcode complements corresponding to the second zipcode in the encryption element sequence. At the end of several rounds of synthesis, adding diversity elements at each step, there is the optional step of circularizing the chain. Alternatively, the encryption element may be used to capturing certain products to defined columns. In this embodiment, each encryption element is also composed of multiple zipcode sequences. The sequences are passed over columns containing zip-code complements to the first set of zipcode sequences. The process is repeated until the nucleic acid sequences are bound to the proper column containing the correct zip-code complements. Subsequently, each nucleic acid column is eluted into a separate reaction chamber, whereupon the corresponding diversity element is chemically reacted to a chemical molecule attached to the encryption element. The process is repeated with a second set of columns containing zipcode complements corresponding to the second zipcode in the encryption element sequence. At the end of several rounds of synthesis, adding diversity elements at each step, there is the optional step of circularizing the chain. In another embodiment, the encryption element may be captured on beads, or addresses on solid supports for a subsequent round of synthesis, or used for zip-code identification of the final ligand. The finally selected ligands may be identified by PCR amplification, followed by sequencing the zip-code portions of the amplicons. Individually amplified molecules are captured onto beads or solid supports and amplified such that all the molecules on an individual bead or cluster on a solid support are identical. The sequence of each bead or cluster is then determined using sequencing by synthesis or pyrosequencing, or sequencing by ligation. The zipcode sequences on each bead or cluster may also be determined by hybridizing fluorescently labeled pooled zipcode complements, and scoring which set gave a signal, creating a binary code to finally identify unique zipcodes at defined positions. Alternatively, zip-codes may be identified by hybridizing onto an array.

An alternative approach, termed RADE (Random Access DNA Encryption) herein, is to randomly encrypt beads particles, or a solid support with a unique sequence, replicate multiple copies of that unique oligonucleotide sequence on the bead, and then leave a copy (footprint) of the complement of that unique sequence wherever that bead has gone. This marks where the bead was when a given diversity monomer was added to synthesize the complete ligand. Once the winning ligand(s) has/have been selected, PCR amplification followed by sequencing identifies the unique sequence(s) associated with the ligand(s). Unique PCR primers are designed to the unique regions of each sequence, and then may be used to interrogate wells to determine the tracks of each step in the synthesis.

Figure 3:
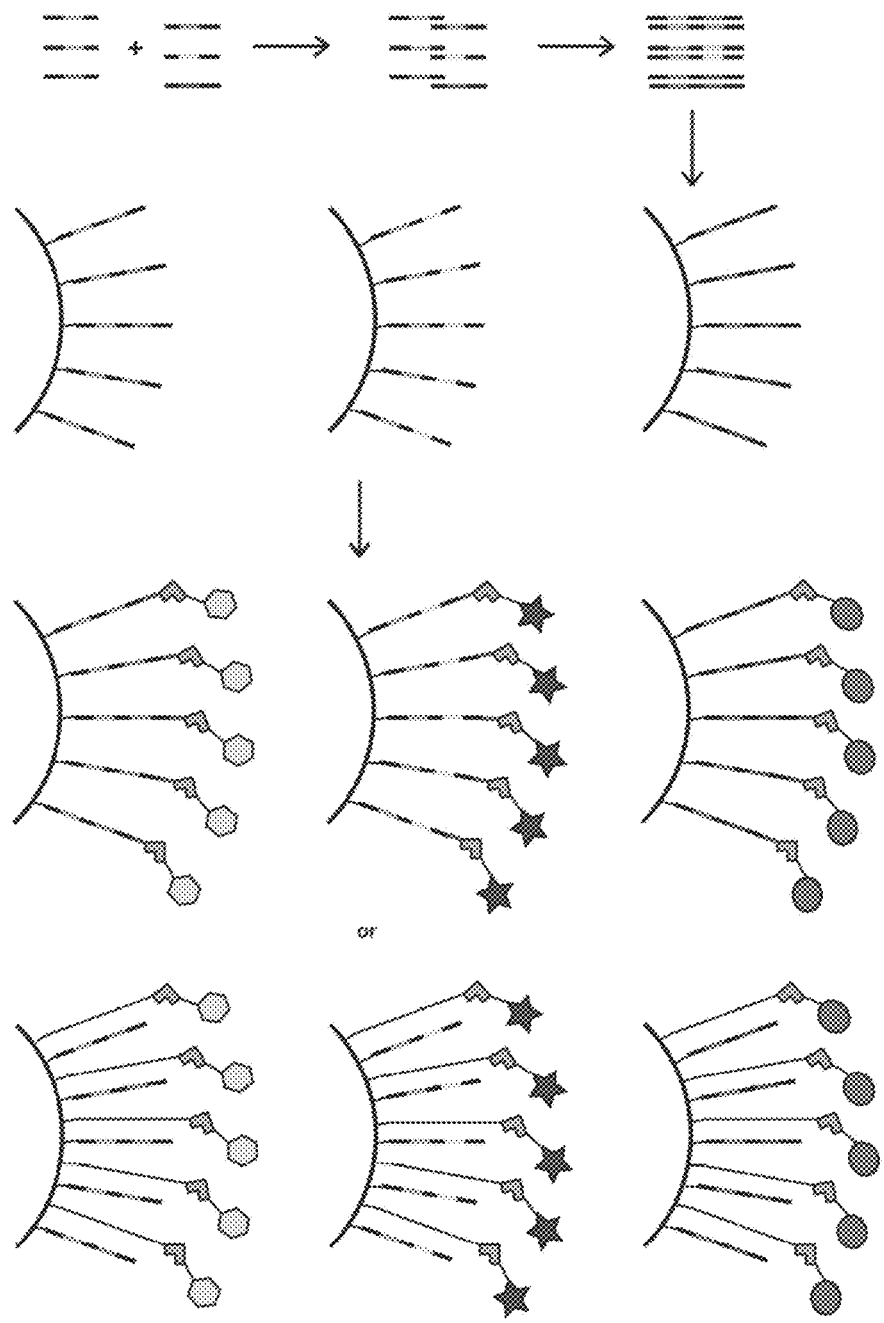
FIG. 3 shows a variation of encoding beads with unique identifier sequences for coferon ligand diversity synthesis. DNA with universal sequences is illustrated as a black line, while DNA with unique sequences is illustrated as a colored line. A bead is illustrated as an arc. Coferon 1 is illustrated as an orange "L" linker element tethered to a yellow hexagon ligand, coferon 2 as an orange "L" linker element tethered to a pink star ligand, and coferon 3 as an orange "L" linker element tethered to a green oval ligand. Two sets of oligonucleotide primers containing universal sequences at their ends and unique sequences in the middle are used to generate PCR products of the form: UniA (20)-Rand (20)-UniB (15)-Rand (20)-UniC (20), where UniA is universal sequence A, UniB is universal sequence B, UniC is universal sequence C, and Rand designates random (unique) sequences of about 20 bases in length. These are then amplified on unique beads using emulsion PCR, where one of the universal primers is on the beads. Coferons may be synthesized on activated groups directly on the surface of the bead, or in a variation, a primer containing a functional group is ligated to the end of the amplified product. Thus, the coferon will be synthesized at the end of the DNA strand. This presents two opportunities: (a) with the coferons at the end of the DNA, they are in easy reach of the protein target, and (b) this design provides the option of either cleaving the coferon off the end of the bead, or cleaving the DNA off the bead, and then it is still attached to the coferon.

There are several approaches for generating beads or particles with multiple copies of the same sequence on one bead, but with each bead carrying a unique sequence. To facilitate such attachment of oligonucleotides to the beads or solid support, the beads or solid support are functionalized on a fraction of its available surface. Subsequently, coferons are synthesized on either the bead, or on the end of the oligonucleotide barcode. In a preferred variation, the coferons are attached to the bead or oligonucleotide via a photolabile linker. A few of the approaches for generating such constructs are listed below:

A. Goal: Generate beads with hundreds to thousands of copies of the sequence (below) across the entire surface of the bead (See FIG. 3).

UniA (20)-Rand (20)-UniB (15)-Rand (20)-UniC (20)

Where:

UniA is universal or common sequence A, 20 mer.

Rand is a randomly generated or unique 20 mer sequence.

UniB is universal or common sequence B, 15 mer.

Rand is a randomly generated or unique 20 mer sequence.

UniC is universal or common sequence C, 20 mer.

Step 1A. Synthesize oligos of the following format.

Primer Seq. 1=Universal 20 mer A-Random 20 mer-Universal 15 mer B

Primer Seq. 2=Universal 15 mer B complement-Random 20 mer-Universal 20 mer C

Step 2A. Mix two primer sets together, and add universal primers (20 mers) whose 3' termini end in A and C, respectively, these will assemble during PCR amplification to generate 95 base sequences of the form:

UniA (20)-Rand (20)-UniB (15)-Rand (20)-UniC (20)

Step 3A. Prepare emulsion beads and PCR amplify so that each bead has several copies of the same 95 base sequence. In emulsion PCR, one primer (A) is attached to the bead, the 95 base sequence is captured at less than one per bead, and then a lower concentration of primer A and a higher concentration of primer C, Taq polymerase, dNTPs, Mg are added, emulsified around the beads and then generate copies of the same fragment on each bead as individual PCR chambers (Frank Diehl et al, *Proc. Nat'l Acad Sci USA*, 102:16368-16373 (2005), which is hereby incorporated by reference in its entirety).

Step 4A. Coferons may be synthesized on activated groups directly on the surface of the bead, or in a variation, a primer containing a functional group is ligated to the end of the amplified product. Thus, the coferon will be synthesized at the end of the DNA strand. This presents two opportunities: (a) with the coferons at the end of the DNA, they are in easy reach of the protein target, and (b) this design provides the option of either cleaving the coferon off the end of the bead, or cleaving the DNA off the bead, and then it is still attached to the coferon.

Figure 4:
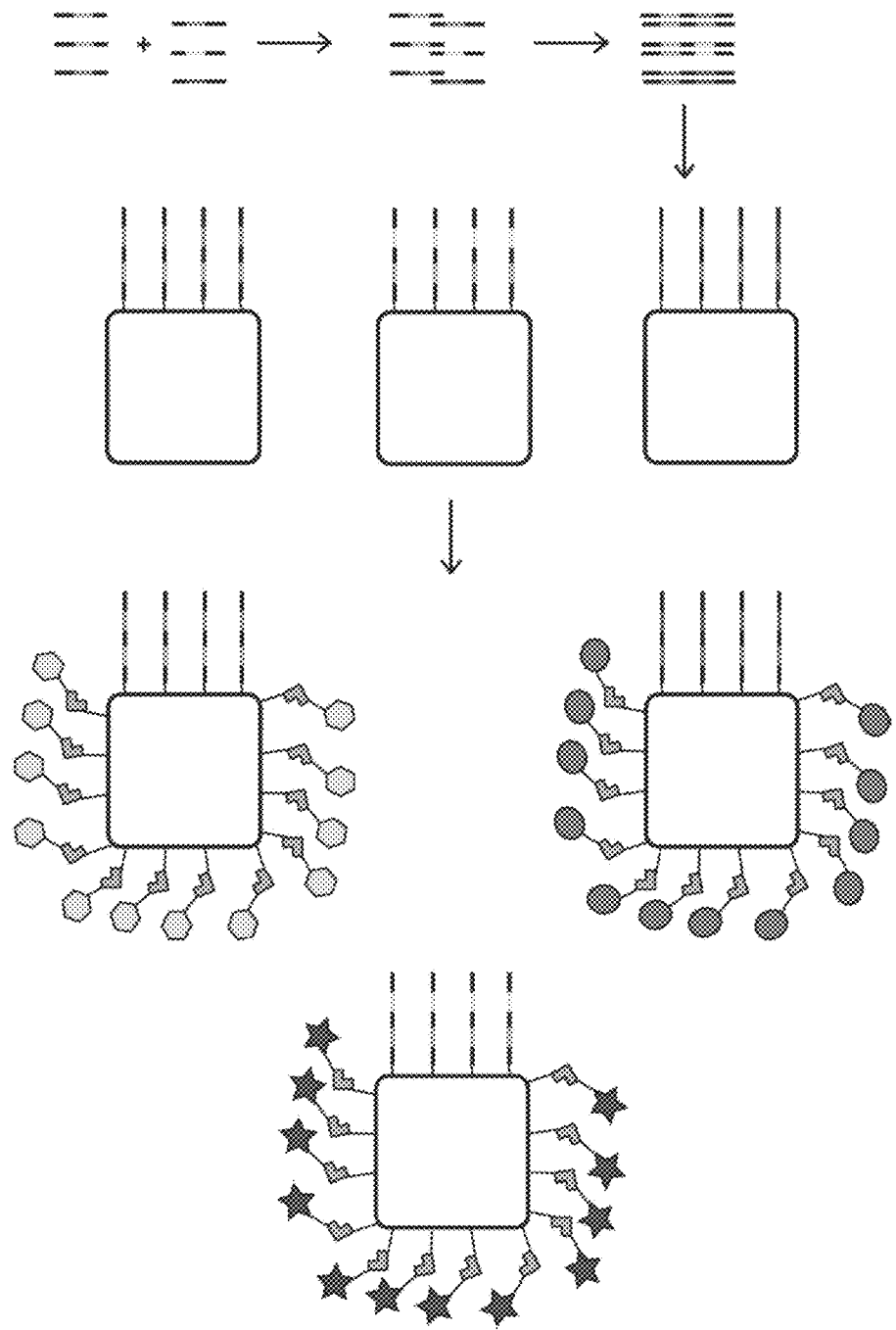
FIG. 4 shows a variation of encoding beads with unique identifier sequences for coferon ligand diversity synthesis. DNA with universal sequences is illustrated as a black line, while DNA with unique sequences is illustrated as a colored line. A bead is illustrated as a rounded square. Coferon 1 is illustrated as an orange "L" linker element tethered to a yellow hexagon ligand, coferon 2 as an orange "L" linker element tethered to a pink star ligand, and coferon 3 as an orange "L" linker element tethered to a green oval ligand. Two sets of oligonucleotide primers containing universal sequences at their ends and unique sequences in the middle are used to generate PCR products of the form: UniA (20)-Rand (20)-UniB (15)-Rand (20)-UniC (20), where UniA is universal sequence A, UniB is universal sequence B, UniC is universal sequence C, and Rand designates random (unique) sequences of about 20 bases in length. The beads are then activated on only one side. One may float the beads on the surface of a liquid, and spraying an activating chemical on only the exposed surface. Another approach is to print the activating group on the surface of a silicon or glass wafer, and etch away horizontal and vertical sections, leaving millions of particles that are just etched on one side. The random primers are then amplified on only one side of unique beads using emulsion PCR, where one of the universal primers is on the beads. Coferons may be synthesized on activated groups directly on the other surfaces of the bead. The advantage of limiting the PCR product to one face of the bead is to avoid having too many DNA molecules sticking out, that may later interfere with the coferon synthesis or binding of fluorescently labeled target (protein) to the bead.

B. Goal: Generate beads with hundreds to thousands of copies of the sequence (above) across one face of the bead or particle. (See Figure. 4).

Step 1B-2B. Same as above.

Step 3B. Activate only one side or surface for attaching the A primer. This may be done by having the beads float on the surface of some liquid, and spraying an activating chemical on only the exposed surface. Another approach is to print the activating group on the surface of a silicon or glass wafer, and etch away horizontal and vertical sections, leaving millions of particles that are just etched on one side.

Step 4B. Prepare emulsion PCR as above. The advantage of limiting the PCR product to one face of the bead is to avoid having too many DNA molecules sticking out, that may later interfere with the coferon synthesis or binding of fluorescently labeled target (protein) to the bead.

Figure 5:
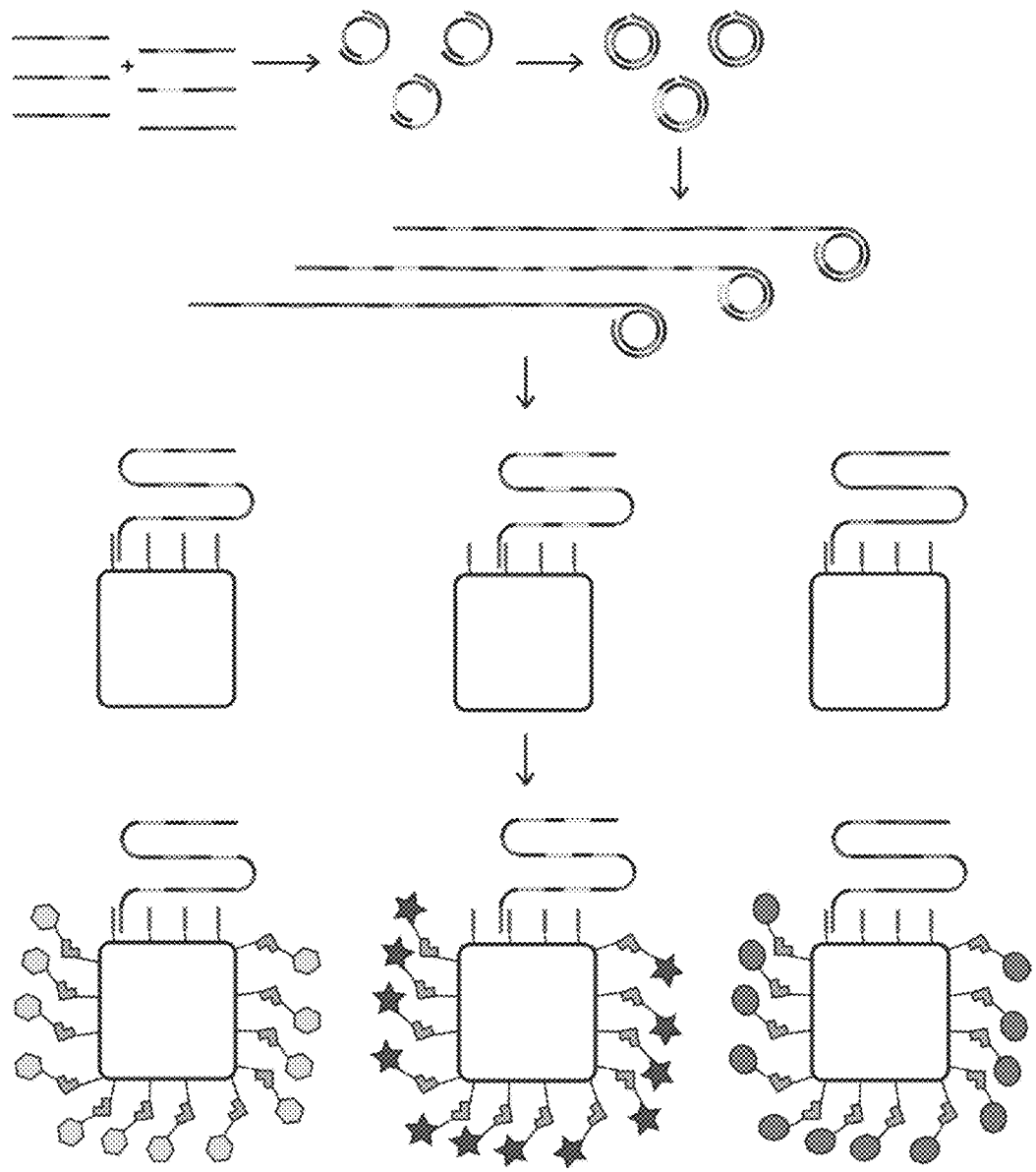
FIG. 5 shows a variation of encoding beads with unique identifier sequences for coferon ligand diversity synthesis. DNA with universal sequences is illustrated as a black line, the UniD sequence is indicated by a blue line, while DNA with unique sequences is illustrated as a colored line. A bead is illustrated as a rounded square. Coferon 1 is illustrated as an orange "L" linker element tethered to a yellow hexagon ligand, coferon 2 as an orange "L" linker element tethered to a pink star ligand, and coferon 3 as an orange "L" linker element tethered to a green oval ligand. Two sets of oligonucleotide primers containing universal sequences at their ends and unique sequences in the middle are used to generate rolling circle products of the form: UniA (20)-Rand (20)-UniB (15)-Rand (20)-UniC (20)-UniD (20), where UniA is universal sequence A, UniB is universal sequence B, UniC is universal sequence C, UniD is universal sequence D, and Rand designates random (unique) sequences of about 20 bases in length. The beads are then activated on only one side. One may float the beads on the surface of a liquid, and spraying an activating chemical on only the exposed surface. Another approach is to print the activating group on the surface of a silicon or glass wafer, and etch away horizontal and vertical sections, leaving millions of particles that are just etched on one side. The rolling circle amplicons are then captured on only one side of unique beads using the complementary sequence of the UniD primer on the beads. Coferons may be synthesized on activated groups directly on the other surfaces of the bead. The advantage of limiting the rolling circle product to one face of the bead is to avoid having too many DNA molecules sticking out, that may later interfere with the coferon synthesis or binding of fluorescently labeled target (protein) to the bead.

C. Goal: Generate beads with hundreds of tandem-repeat copies of the sequence (below) across one face of the bead or particle. (See FIG. 5).

UniA (20)-Rand (20)-UniB (15)-Rand (20)-UniC (20)-UniD (20)

Step 1C. Synthesize oligos of the following format.

Primer Seq. 3=5' blocked-T5-Universal 20 mer D-Universal 20 mer A-Random 20 mer-Universal 15 mer B Primer Seq. 4=5' p-Universal 15 mer B complement-Random 20 mer-Universal 20 mer C-Universal 20 mer D complement- Step 2C. Mix two primer sets together, they will hybridize at the two complementary regions to form a 115 base circle which is gapped on both strands. Add DNA polymerase lacking 5'-3' or strand displacement activity (such as Klenow), dNTPs, ATP, and T4 DNA ligase. The polymerase will extend both free 3' ends, but only ligate the Primer Seq.4 strand to form a circle. The other strand cannot ligate because the 5' end is blocked. By subsequently adding a strand displacement polymerase (such as Bst Polymerase or Phi-29 polymerase), hundreds of tandem-repeat copies of the sequence below may be generated using rolling circle amplification.

UniA (20)-Rand (20)-UniB (15)-Rand (20)-UniC (20)-UniD (20)

Step 3C. Using beads or particles with only one side or spot activated and containing the UniD complement sequence, capture the long single-stranded DNA, with one DNA multimer going per bead or particle. The original 5' end (synthesized Primer seq. 3) may have been modified allowing for covalent capture to the bead or particle. The strand will be captured at a number of positions along the length of the single strand. The UniD complement capture sequence may be composed of PNA, or 2' O-methyl containing sequences, such that this DNA stays hybridized even under conditions where copies of the UniA (20)-Rand (20)-UniB (15)-Rand (20)-UniC (20) sequence are generated, and then melted off the beads, the easiest being by using a helicase that does not recognize and unwind the PNA, or 2' O-methyl containing sequences.

Once beads or particles have been generated, they may be used to synthesize the coferons. For the purposes of this example, the coferon synthesis has three rounds of diversity, of 20 different groups, and there are 20 different scaffolds (160,000 fold diversity). After synthesis of the linker elements and connector portions, the beads are divided into 20 wells and the first round of diversity elements are added. Afterwards, a universal primer is added, hybridizing to all the DNA fragments, extended, and then melted off (by either heat or high pH, organic solvent such as formamide, or a helicase). After removal of the beads, the 20 wells contain a footprint of all the beads in those wells.

The beads from the 20 wells are then pooled and split into a new 20 wells. The process is repeated 3 more times, leaving 80 wells with footprints.

The beads are used in a selection (with the other coferon library added in solution) to bind the fluorescently labeled target. The winning beads are separated, and the DNA barcodes PCR amplified. The amplified fragments are sequenced using solid phase techniques (Next-Gen sequencing). Note also, that the same approach may be used with individual coferons that still contain the DNA tag attached to it.

The sequences are recorded, and forward and reverse primers are synthesized within the unique 20 mer sequences. There is some flexibility in the exact region used to synthesize the unique primer, for example it may use 14 to 15 bases of the random sequence and 5 bases of the UniA and UniC sequences, respectively. This flexibility allows the user to avoid using a primer that ends in a palindromic sequence which will most likely make a primer dimer.

Using the unique primer pairs synthesized for each winning sequence, the original 80 wells (a single run on a 96-well real-time PCR machine) are analyzed via PCR using the middle UniB sequence for detection with a Taqman probe. One well from each set of 20 wells should provide a positive result allowing the user to retrace the tracks of that bead during each synthesis round, i.e. it's synthesis history.

In practice, one may keep the final 20 wells split, such that each well contains 8,000 fold diversity, then when the winning ligand and its sequence are identified, only 60 PCR reactions are required. Likewise, if in the final 2 steps the separation of reactions is maintained=400 wells, then each well will contain a 400-fold diversity, and de-convolution requires just 40 PCR reactions.

Alternative means of identifying the diversity element include using synthetic steps which incorporate chemical moieties of different mass (for example, amino acid derivatives), and determining the molecular weight of the final product via mass spectroscopy. In addition, diversity elements may be defined by spatial separation, i.e. synthesizing different variants in different wells or chambers. Further, diversity elements may be encoded within the bead or glass surface used as the solid support for synthesis of ligand. For example, a bead may be encoded with a digital holographic image that may be illuminated by a laser beam and read by a CCD camera (Illumina Veracode™ system). Alternative barcoding schemes include gold/silver nanoparticles, bar coded silicon particles, or using different ratios of embedded quantum dot colors.

Linker Screening

Another embodiment of the present invention involves a method of screening for linker elements capable of binding to one another. This method includes providing a first and a second set of monomers. Each of the monomers in the first set comprise a linker element, having a molecular weight of less than 500 daltons and being capable of forming a reversible covalent bond or non-covalent interaction with a binding partner of said linker element, with or without a co-factor, under physiological conditions and a sulfhydryl group. The linker element and the sulfhydryl group for each monomer of the first set of monomers are coupled together. Each of the monomers in the second set comprise a linker element capable of forming a reversible covalent bond or reversible non-covalent bonds with a binding partner of the linker element under physiological conditions, an encoded bead, and a sulfhydryl group. The linker element, the encoded bead, and the sulfhydryl group for each monomer of the second set of monomers are coupled together. The first and second sets of monomers are contacted with one another under physiological conditions so that monomers from the first set of monomers and monomers from the second set of monomers bind together to form multimers linked together by disulfide bonds formed from their sulfhydryl groups and, potentially, covalent bonds or non-covalent interactions between their linker elements. The dimers where the linker elements from the monomers of the first and second sets of monomers are covalently bound or non-covalently linked together are then identified as being candidate multimers. The linker elements from the first and second monomers that are covalently bound or non-covalently joined together are then identified in the candidate multimers.

The step of contacting is carried out by cycling between conditions resulting in a high dissociation constant between said linker elements to allow for re-association of linker elements connected to different diversity elements and conditions resulting in a low dissociation constant between said linker elements to allow for preferential binding of monomers with the highest affinity diversity elements to the target.

The step of cycling of conditions is achieved by lowering and raising the pH or zinc concentration using a membrane permeable to cations and water.

The identifying dimers step is carried out by determining which dimers have first and second monomers that are more tightly bound together. This is determined by identifying the barcodes of the beads that contain labeled monomers from the first set. In the preferred embodiment, the label is a fluorescent group, and the most fluorescently labeled beads are identified, e.g. in a flow sorter, and separated for identifying the barcode. If the experiment is performed using the same set of linker elements both on the bead and in solution, then there will be at least two beads with different barcodes that are fluorescently labeled for each pair. Monomers are synthesized individually and tested for each combination. If the linker elements are different between the bead and in solution, the experiment is repeated a second time, however, in the second case the linker elements on the beads and in solution are now reversed.

In one embodiment of carrying out the identifying step, an encryption element comprising terminal universal primer binding sites can be provided. In using an encryption element, the therapeutic multimer precursor is contacted with universal primers to form an amplification mixture. The amplification mixture is subjected to a polymerase chain reaction to form amplification products. The amplification products are identified and the amplification products are correlated to the oligonucleotides of the monomers forming the therapeutic multimer precursor. The steps of providing a plurality of monomers, contacting the plurality of monomers, subjecting monomers to reaction conditions, and identifying the monomers are repeated to determine which of the therapeutic multimer precursors have a suitable binding affinity to the target molecule.

For the monomers with the identified linker elements, the steps of providing a first set of monomers, providing a second set of monomers, identifying dimers, and identifying, in the candidate dimers, the linker elements are repeated. This permits a determination of which of the linker elements from the first and second sets of monomers have a suitable binding affinity.

The first and second set of monomers may further include an encoding element, where the diversity element, the linker element, and the encoding element are coupled together. The encoding element can be an oligonucleotide or a labeled bead.

The effectiveness of the linker elements in binding together can be determined by a screening method, as described in FIGS. 14A-B.

In one embodiment (FIG. 14A), a library of low molecular weight linker elements are synthesized on beads which are individually identified through bar codes. A second library of linker elements, which contains a fluorescent label, is synthesized. Different combinations of linker elements can undergo "dynamic combinatorial chemistry"—i.e. they are associating and dissociating with each other. Some combinations will bind tighter than others, directing the evolution of combinations to the tightest pairs. For symmetrical libraries, a pair of beads will be detected for each monomer. The monomers can be resynthesized and tested individually to find matched pairs.

In the embodiment of FIG. 14B, a library of low molecular weight linker elements is synthesized on beads which may be individually identified with bar codes. A second library of linker elements, which are covalently linked to a DNA bar code, are step-wise synthesized. Different combinations of linker elements can undergo "dynamic combinatorial chemistry"—i.e. they are associating and dissociating with each other. Some combinations will bind tighter than others, directing the evolution of combinations to the tightest pairs. The DNA bar codes can be amplified using universal primers to identify individual linker elements.

In the embodiment of FIG. 15A, a library of low MW (approx. under 300) linker elements is synthesized on beads which may be individually identified through barcodes. A second library of linker elements is synthesized containing a fluorescent label. The bead library linkers contain tethered disulfide groups, while the solution library linkers contain tethered sulfhydryl groups. Under incubation conditions, solution linker elements can undergo disulfide exchange with bead linker elements. Some combinations will bind tighter than others, directing the evolution of combinations to the tightest pairs. For symmetrical libraries, a pair of beads will light up for each monomer. Monomers are resynthesized and tested individually to find the matched pairs.

A library of low MW (approx. under 300) linker elements is synthesized on beads which may be individually identified through barcodes, as shown in the embodiment of FIG. 15B. A second library of linker elements is synthesized, each monomer covalently linked to a DNA barcode (allowing for stepwise synthesis and identification of the binding ligand). Under incubation conditions, solution linker elements can undergo disulfide exchange with bead linker elements. Some combinations will bind tighter than others, directing the evolution of combinations to the tightest pairs.

Monomer Library Synthesis

Figure 16:
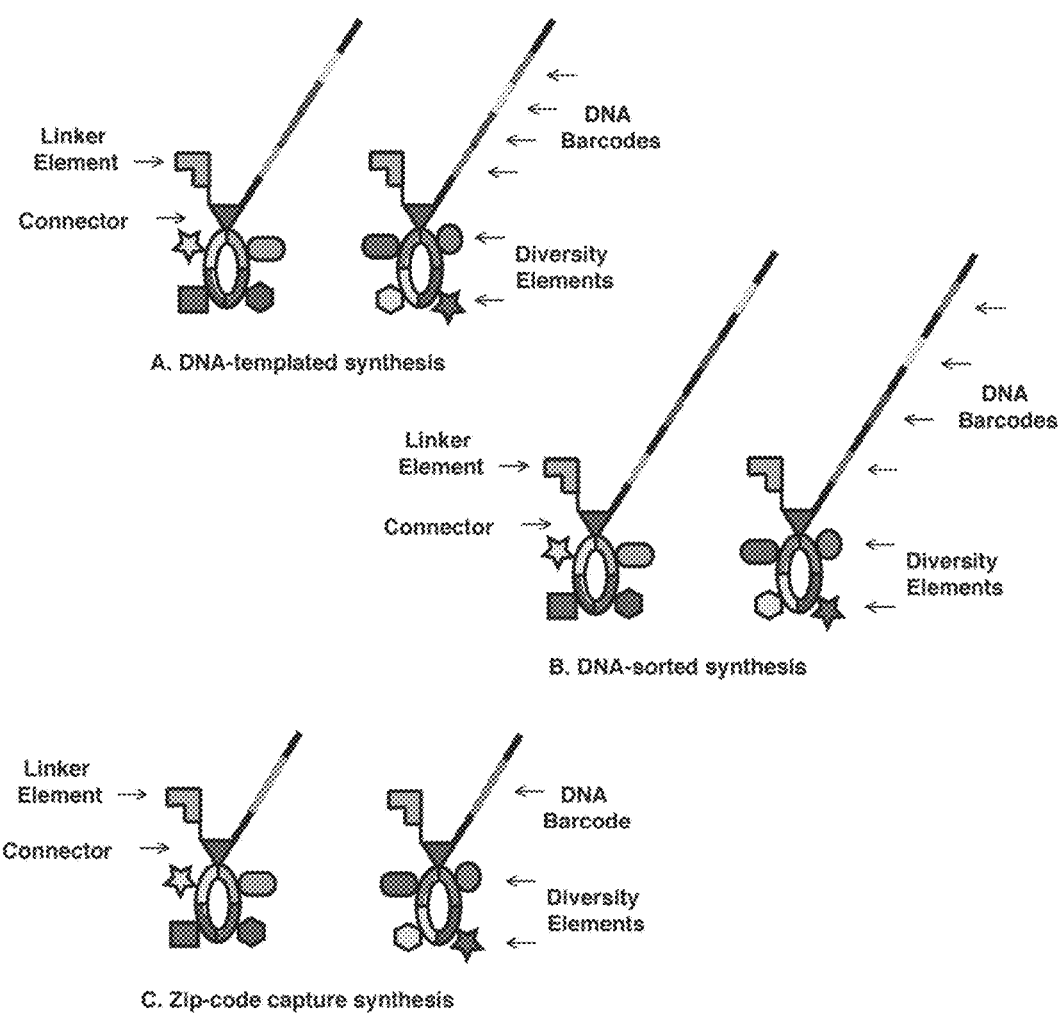
FIG. 16 shows schematic drawings of components used in diversity element library synthesis for DNA encoded libraries. A shows DNA template synthesis. B shows DNA sorted synthesis. C shows zipcode capture synthesis.

As shown in FIGS. 16A-C, monomer coferon synthesis is facilitated by using an encryption element. The most versatile encryption element is an attached nucleic acid sequence, such as DNA. The DNA encryption element may be used to directly assist in synthesizing the diversity element. See FIG. 16A. Each DNA encryption element is composed of multiple DNA barcode sequences, indicated as colored bars. The DNA encryption element has a chemical molecule attached to one end. Upon hybridization of a first barcode complement bearing a reactant group with a diversity element, the reactant group is covalently linked to, and transferred to the chemical molecule on the DNA encryption element. Each unique barcode complement is charged with a reactant group containing a diversity element that corresponds to the barcode sequence. The process is repeated with a second set of charged barcode complements corresponding to the second barcode in the DNA encryption element sequence. In the schematic diagram of FIG. 16A, the coferon monomer on the left shows barcodes in blue, purple, red, and yellow, with corresponding diversity elements of a blue oval, purple hexagon, red square, and yellow star. The coferon monomer on the right shows barcodes in green, red, yellow, and pink with corresponding diversity elements of a green circle, red star, yellow hexagon, and pink oval. At the end of several rounds of synthesis, adding diversity elements at each step, there is the optional step of circularizing the chain. Alternatively, the DNA encryption element may be used to capture certain products to defined columns (See FIG. 16B). In this embodiment, each DNA encryption element is also composed of multiple barcode sequences. The sequences are passed over columns containing barcode complements to the first set of barcode sequences. The process is repeated until the DNA sequences are bound to the proper column containing the correct barcode complements. Subsequently, each DNA column is eluted into a separate reaction chamber, whereupon the corresponding diversity element is chemically reacted to a chemical molecule attached to the DNA encryption element. The process is repeated with a second set of columns containing zipcode complements corresponding to the second zipcode in the DNA encryption element sequence. In the schematic diagram of FIG. 16B, the coferon monomer on the left shows barcodes in blue, purple, red, and yellow, with corresponding diversity elements of a blue oval, purple hexagon, red square, and yellow star. The coferon monomer on the right shows barcodes in green, red, yellow, and pink with corresponding diversity elements of a green circle, red star, yellow hexagon, and pink oval. At the end of several rounds of synthesis, adding diversity elements at each step, there is the optional step of circularizing the chain. In another embodiment, the DNA encryption element may be captured on beads, or addresses on solid supports for a subsequent round of synthesis, or used for zip-code identification of the final ligand (FIG. 16C). In the schematic diagram of FIG. 16C, the coferon monomer on the left shows a single barcode in green, with diversity elements of a blue oval, purple hexagon, red square, and yellow star. The coferon monomer on the right shows a single barcode in purple with diversity elements of a green circle, red star, yellow hexagon, and pink oval.

FIGS. 17A-C show monomer coferon synthesis using encoded beads. In FIG. 17A, a series of different known inhibitors or analogue ligands to the target protein are chemically attached to beads. For example, if there are 100 inhibitors, the beads are split into 100 reaction vessels. The inhibitors or analogue ligands added to a given individual bead is determined by reading the barcodes of each bead in each of the 100 sets, either before or after the reaction. In FIG. 17A, two inhibitors are indicated by orange and yellow hexagons. A given bead contains only a single set of inhibitors or analogue ligands. In FIG. 17B, a series of diversity elements are added to a common platform. In the schematic diagram of FIG. 17B, the common platform is indicated by a red triangle. In this process, the beads are split into (n) reaction vessels. A diversity element is chemically reacted to the common platform attached to the bead. The diversity element added to a given individual bead is determined by reading the barcodes of each bead in each of the (n) sets, either before or after the reaction. The products are pooled, and then split again into (n) reaction vessels and the process is repeated. Different reactant groups and protecting groups can guide addition of subsequent diversity elements either onto the platform or onto earlier added diversity elements. In the schematic diagram of FIG. 17B, the coferon monomers on the bead to the left has diversity elements of a green oval, blue circle, pink star, and yellow square. The coferon monomers on the bead to the right has diversity elements of a orange square, blue hexagon, pink oval, and yellow star. In FIG. 17C, a second example of using a common platform is shown, in this case a cyclopentane scaffold schematically shown as a red pentagon. In this process, the beads are split into (n) reaction vessels. A first bifunctional diversity element is chemically reacted to the linker element on the bead. The diversity element added to a given individual bead is determined by reading the barcodes of each bead in each of the (n) sets, either before or after the reaction. Next, the cyclopentane scaffold is added to the first diversity element. A second diversity element is chemically reacted to the cyclopentane scaffold attached to the bead. The diversity element added to a given individual bead is determined by reading the barcodes of each bead in each of the (n) sets, either before or after the reaction. The products are pooled, and then split again into (n) reaction vessels and the process is repeated. At the end of two or more rounds of synthesis, adding diversity elements at each step, there is the optional step of circularizing bifunctional diversity elements. In the schematic diagram of FIG. 17C, the coferon monomers on the bead to the left has diversity elements of a pink star attached to the linker element and the cyclopentane scaffold (red pentagon), which subsequently has attached the diversity elements of a green oval and yellow square. The coferon monomers on the bead to the right has diversity elements of a yellow star attached to the linker element and the cyclopentane scaffold (red pentagon), which subsequently has attached the diversity elements of blue hexagon and pink oval.

Target Screening

Yet a further embodiment of the present invention is directed to a method of screening for therapeutic compound precursors which bind to a target molecule associated with a condition. This method includes providing a plurality of monomers. Each monomer comprises a diversity element which potentially binds to a target molecule with a dissociation constant less than 300 µM and a linker element capable of forming a reversible covalent bond or non-covalent interaction with a binding partner of the linker element with or without a co-factor under physiological conditions. The linker has a molecular weight of less than 500 daltons. The diversity element and said linker element of each monomer are joined together directly or indirectly through a connector. The plurality of monomers are contacted with the target molecule under conditions effective to permit diversity elements able to bind to the target molecule to undergo such binding. The monomers are then subjected to reaction conditions effective for the linker elements of different monomers to undergo covalent bonding or non-covalent interactions to form therapeutic multimer precursors, either before, after, or during the contacting step. The monomers forming each therapeutic multimer precursor are then identified.

The step of identifying the monomers can be carried out by determining which therapeutic dimer precursors are more tightly bound to the target molecule. This is determined by identifying either DNA barcodes or bead barcodes. For DNA barcodes, the finally selected ligands may be identified by PCR amplification, followed by sequencing the barcode portions of the amplicons. Individually amplified molecules are captured onto beads or solid supports and amplified such that all the molecules on an individual bead or cluster on a solid support are identical. The sequence of each bead or cluster is then determined using sequencing by synthesis or pyrosequencing, or sequencing by ligation. The barcode sequences on each bead or cluster may also be determined by hybridizing fluorescently labeled pooled barcode complements, and scoring which set gave a signal, creating a binary code to finally identify unique barcodes at defined positions. Alternatively, barcodes may be identified by hybridizing onto an array.

When each monomer includes an encoding element coupled to the diversity element and the linker element for each monomer, the identifying step is carried out by detecting the encoding element in the therapeutic dimer precursor.

When the encoding element is an oligonucleotide, the oligonucleotide can comprise terminal universal primer binding sites. The identifying step can then include contacting the therapeutic dimer precursor with universal primers to form an amplification mixture. The amplification mixture is then subjected to a polymerase chain reaction to form amplification products. The amplification products are identified and correlated to the oligonucleotides of the monomers forming the therapeutic dimer precursor. The steps of providing a plurality of monomers, contacting the plurality of monomers, subjecting monomers whose diversity elements are bound to the target molecule, and identifying the monomers can be repeated to determine which of the therapeutic dimer precursors have a suitable binding affinity to the target molecule.

When the encoding element is a labeled bead, the steps of providing a plurality of monomers, contacting, subjecting, and identifying the monomers can be repeated to determine which of the therapeutic dimer precursors have a suitable binding affinity to the target molecule.

The therapeutic dimer resulting from the above method can be prepared by coupling the monomers resulting from the identifying step. Subjects with the condition are identified and the therapeutic dimer are administered to the selected subjects under conditions effective to treat the condition.

Therapeutic monomers resulting from the above method can be prepared by providing the monomers resulting from the identifying step. Subjects with the condition are selected and the therapeutic monomers are administered to the selected subjects under conditions effective to treat the condition.

Another aspect of the present invention relates to a therapeutic multimer precursor. The therapeutic multimer precursor includes a plurality of covalently or non-covalently linked monomers. Each monomer comprises a diversity element which potentially binds to a target molecule with a dissociation constant less than 300 µM, a linker element, and an encoding element. The linker element has a molecular weight less than 500 daltons and is capable of forming a reversible covalent bond or non-covalent interaction with a binding partner of said linker element with a dissociation constant less than 300 µM, with or without a co-factor, under physiological conditions. The diversity element and the linker, for each monomer are connected together, directly or indirectly through a connector, and the plurality of monomers are covalently bonded together or non-covalently linked together through their linker elements. The diversity elements for the plurality of monomers bind to proximate locations of the target molecule.

The libraries described above are in two formats: (i) on a bead or solid support with diversity element defined by position or Veracode™ encryption of particle, and (ii) off the bead with diversity element defined by an encoded DNA element. The advantage of working with coferon libraries attached to beads is that each bead contains multiple copies of the identical ligand. This property helps identify the strongest affinity ligand combinations by the intensity of fluorescently labeled entity captured (i.e. protein or other ligand). The advantage of working with coferon libraries encoded by DNA is that selected coferons may be amplified by using their DNA to template a second round of diversity element synthesis. This allows for evolutionary principles to be used in selecting the best coferons. Further, recent advances in massively parallel sequencing technology, such as the Roche 454 and Solexa/Illumina sequencers, allow for sequencing of hundreds of thousands to millions of DNA products in a single run. See FIGS. 18A-B. Likewise, use of individually encoded beads also allows for directed evolutionary principles to be used in selecting the best coferons. After the winning combinations are identified through the bead barcode, they can be resynthesized with slight variation in a new round of synthesis—followed by a second round of selection. Here, one needs to identify the chemical structure of both coferon monomers which form a dimer. In FIG. 18A, schematic diagrams were presented showing the selection process where one or both elements contained DNA encryption. In FIG. 18B, schematic diagrams are presented where the experiment is repeated so that the diversity elements from each half of the coferon may be identified.

FIG. 18A is a schematic overview of directed evolution selection of coferons, and their use inside the body. Each coferon monomer includes a binding ligand (diversity element) covalently linked to a DNA barcode as well as a low MW linker element (dynamic combinatorial chemistry element), which allow different combinations of ligands to reversibly associate with each other. As shown in step 1, when coferon monomers are brought in contact with the protein target on a solid support, some combinations will bind tighter than others and, consequently, are enriched. Unbound coferon monomers may be washed away. The most tightly bound pair(s) may be both identified and amplified through the DNA barcodes. Repeating this process of synthesis-selection-amplification mimics Darwinian evolution. In a variation of the above approach, as shown in step 2, one coferon monomer includes a binding ligand (diversity element) covalently linked to a DNA barcode as well as a low MW linker element (dynamic combinatorial chemistry element), while the other is linked to a coded bead. The linker elements allow different combinations of ligands to reversibly associate with each other. When the combination of solid-phase and solution coferon monomers are brought in contact with a labeled protein target, some combinations will bind tighter than others and, consequently, are enriched. The winning pair will cause that bead to be highly labeled, and this may be isolated by flow cytometry or other methods, and the code identified. The partner solution phase coferon monomer may be both identified and amplified through the DNA barcodes. Repeating this process of synthesis-selection-amplification mimics Darwinian evolution. The best coferon monomers are resynthesized without DNA barcodes for use as orally active drugs, as shown in step 3. Once ingested coferons are in a dynamic equilibrium between the monomer form (which can traverse the cell membrane) and the dimer form (which binds to and inhibits the protein target).

FIG. 18B is a schematic overview of directed evolution selection of coferons using only bead encryption. As shown in step 1, a first set of coferon monomers comprises a binding ligand (diversity element) covalently linked to a bead containing a unique barcode as well as a low MW linker element (dynamic combinatorial chemistry element), while a second set is free in solution. The linker elements allow different combinations of ligands to reversably associate with each other. When the combination of solid-phase and solution coferon monomers are brought in contact with a labeled protein target, some combinations will bind tighter than others and, consequently, are enriched. The winning pair will cause that bead to be highly labeled, and this may be isolated by flow cytometry or other methods, and the barcode identified. In a companion selection, as shown in step 2, the second set of coferon monomers is linked to unique encoded beads, while the first set is free in solution. The linker elements allow different combinations of ligands to reversibly associate with each other. When the combination of solid-phase and solution coferons are brought in contact with a labeled protein target, some combinations will bind tighter than others, and consequently are enriched. The winning pair will cause that bead to be highly labeled, and this may be isolated by flow cytometry or other methods, and the barcode identified. The diversity elements for both sides of the coferon may be decoded, and then resynthesized with additional variation. Repeating this process of synthesis-selection-amplification mimics Darwinian evolution. The best coferon monomers are resynthesized without the encoded beads for use as orally active drugs, as shown in step 3. Once ingested coferons are in a dynamic equilibrium between the monomer form (which can traverse the cell membrane), and the dimer form (which binds to and inhibits the protein target).

Figure 18C:
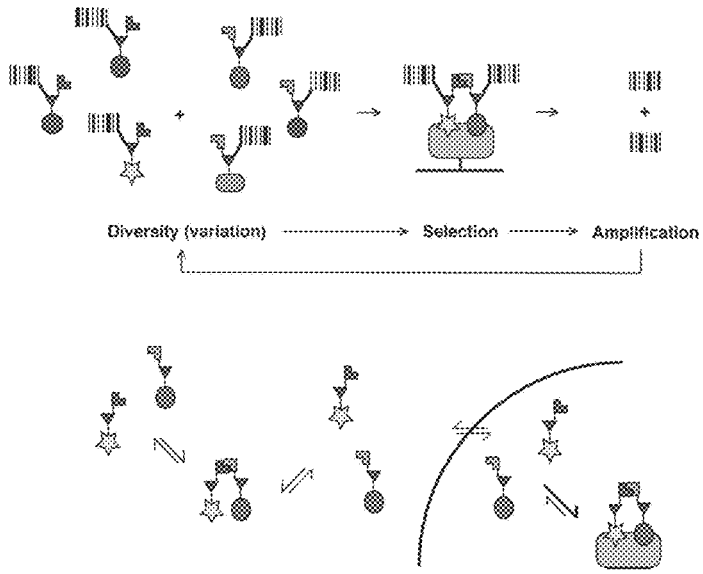
FIG. 18 A-C are schematic drawings of directed evolution of coferons.

FIG. 18C is a generic summation of screening for the tightest binding coferons using directed evolutionary principles. Individual coferons, or multiple copies of the identical coferon on individual beads or particles, or multiple copies of identical coferons within encoded droplets may be screened by a number of different assays that identify binding diversity elements. The nature of these diversity elements is determined by identifying the code that corresponds to the diversity element, which is then resynthesized, including minor variations. The process is repeated until the tightest binding elements are identified.

The best coferon monomers are resynthesized without DNA barcodes or encoded beads for use as orally active drugs. The coferons may be provided as (i) therapeutic dimers or multimers that dissociate/re-associate in the body, cell, or cellular compartment, (ii) therapeutic monomers in the same or different pills, or (iii) therapeutic monomer precursors where one or more active moieties is in a protected state, suitable for deprotection once inside the body, cell, or cellular compartment. Once ingested, coferons are in a dynamic equilibrium between the monomer form (which can traverse the cell membranes), and the dimer or multimer form (which binds to and inhibits the protein target).

Figure 19:
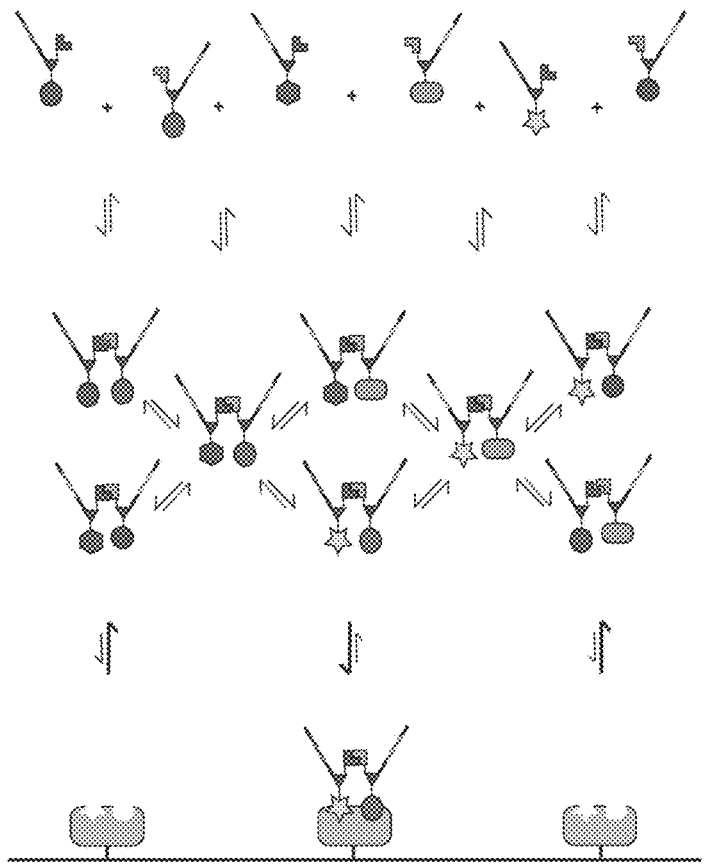
FIG. 19 is a schematic overview of selection of the tightest binding coferon protein interaction dimers taking advantage of the principles of dynamic combinatorial chemistry. As shown in step 1, each coferon monomer comprises a low MW binding ligand (diversity element) covalently linked to an encoding DNA strand (allowing for stepwise synthesis and identification of the binding ligand) as well as a low MW linker element (dynamic combinatorial chemistry element). Under physiological conditions, as shown in step 2, different combinations of ligands are forming and reassociating with each other. When the diversity elements are brought in contact with the protein target on a surface, as shown in step 3, some combinations will bind tighter than others. This directs the evolution of combinations to the preferred pairs. After removing unbound ligands, DNA encoding regions (colored lines, "zip-codes") may be amplified using universal primers (black lines) to identify individual ligands, which serve as lead molecules.

To recapitulate the opportunities presented by dynamic combinatorial chemistry, FIG. 19 illustrates an idealized case. Different combinations of linker elements may associate with each other. However, since the interaction between the linker elements is both weak and reversible, the molecules are in constant flux between the monomer and dimer forms. When a target is present, it will bind the winning pair of coferons tighter than other pairs. In doing so, it removes the winning pair from solution. Dimer coferons containing one of the winning pair diversity elements will now dissociate, and the resultant monomers reassociate with each other to bring the concentration of the winning pair back into equilibrium. However, now that new winning pair also gets bound by the target. The process repeats itself and drives concentration of the winning pair directly on the target. Dynamic combinatorial chemistry also works when the majority of coferons are monomers, and the diversity elements bind to the target individually as monomers, wherein the target literally acts as a catalyst to accelerate formation of its own inhibitor (FIGS. 40-47).

FIGS. 2.1C-2.1D show dimers resulting from screening coferon monomers with connectors, while FIGS. 2.1H-2.1I show dimers derived from a screen with coferon monomers which are not provided with connectors.

Each coferon monomer consists of a binding ligand (diversity element) covalently linked to a DNA barcode as well as a low MW linker element (dynamic combinatorial chemistry element), which allow different combinations of ligands to reversibly associate with each other. When coferons are brought in contact with the protein target on a solid support, some combinations will bind tighter than others and, consequently, are enriched. Unbound coferons may be washed away. The most tightly bound pair(s) may be both identified and amplified through the DNA barcodes. Repeating this process of synthesis-selection-amplification mimics Darwinian evolution.

Under physiological conditions, different combinations of ligands are forming and reassociating with each other. The term "physiological conditions" is hereby defined as aqueous conditions inside the body or the cell, comprising a temperature range of about 35-40° C., a pH range of about 6-8, a glucose concentration range of about 1-20 mM, and an ionic strength range of about 110 mM to about 260 mM.

When the diversity elements are brought in contact with the protein target on a surface, some combinations will bind tighter than others. This directs the evolution of combinations to the preferred pairs. After removing unbound ligands. DNA encoding regions (colored lines, "zip-codes") may be amplified using universal primers (black lines) to identify individual ligands, which serve as lead molecules.

In the examples below, the selected binding elements are referred to as the top set of coferons. This refers to the entire molecule, from the linker element to the connector to the diversity element ligand. In many cases, this also includes the encoding DNA template or barcode sequence. Appropriate controls are needed to assure that the monomeric linker element portion or the single-stranded DNA portion is not skewing the binding or selection process. One approach to nullify such effects is to add the partner linker element, with no diversity element attached. A second approach is to hybridize complementary universal PCR primer and synthesize the opposite strand of the DNA encoded element to make it double stranded.

As shown in FIG. 20, a first version of a screen uses diversity elements on beads. Fluorescently labeled target protein is added to the beads and, after a suitable period of incubation under conditions of gentle motion (known as panning), wells containing fluorescently labeled beads are identified. If the beads are in a single chamber, the Veracode™ is identified for the fluorescently labeled beads. This approach identifies the diversity elements that bind most tightly to the target (with affinities in the micromolar to nanomolar range). The top set of these coferons (for example, the top 100) are then re-synthesized onto individual beads. In a variation of this theme, each of these top ligands can be attached through a series of connectors that vary in size, flexibility, or for circular diversity elements, the size of the macrocycle. This new set of coferons are now combined with a library of coferons in solution. It can be the same set of diversity elements as above, but now instead of being on a bead they have been released in solution. Alternatively, they may have been synthesized with a DNA tag or identification sequence. Now, addition of the fluorescently labeled target protein to the coferon containing beads and the coferons in solution at the appropriate concentrations will allow for selection of the tightest binding combinations. The bound coferons are in equilibrium with the coferons in solution, both binding and coming apart. Meanwhile, the protein targets are binding and dissociating with coferons in solution and on the solid supports. The most stable complexes of bead coferon to solution coferon to target protein are removed from this equilibrium. The concentration of these components in solution has now decreased, so they dissociate from less stable complexes. This now drives the equilibrium towards forming even more of the most stable complexes, so that the tightest binding combinations are enriched. If the bead coferon contains a Veracode™ and the solution coferon a DNA tag, both ligands may be readily identified. Veracode™ beads which are fluorescently labeled may be sequestered into individual wells using FACS sorters or 454 sequencing instruments. DNA tags bound by individual beads may then be individually amplified and identified. If the solution coferon does not contain an identification tag, the ligand can still be identified by using the same set of diversity elements on the beads and in solution. Only the winning pairs will provide the strongest fluorescent signal, and, if it is just a few beads, the combinations may be tested individually. The coferon pairs selected by this protocol should have affinities to the target in the nanomolar range.

A second version of a screen, as shown in FIG. 21, is very similar to the first version, using diversity elements on both beads and in solution. Fluorescently labeled target protein is added to the beads and in solution coferons, and after a suitable period of panning, wells containing fluorescently labeled beads are identified. If the beads are in a single chamber, the Veracode™ is identified for the fluorescently labeled beads. In both cases, the in solution coferons are identified by PCR amplification and sequencing of the DNA tags. The PCR amplified tags may also be used to re-synthesize the diversity elements, such that evolutionary principles are used to select the winning pairs of coferons. Alternatively, each of the top ligands may be re-synthesized and can now be attached through a series of connectors that vary in size, flexibility, or for circular diversity elements, the size of the macrocycle. A further variation on this theme would be to regenerate not only the original diversity elements, but minor variations (for example vary just one amino acid residue at a time from a cognate sequence) as well, to be combined with the diverse set of connector elements. This refined set of coferons would be re-screened in the presence of the fluorescently labeled target protein at the appropriate concentrations to allow for selection of the tightest binding combinations. The same principles of dynamic combinatorial chemistry described above would apply. The winning pair of coferons are identified by their Veracode™ and DNA sequence tags. The coferon pairs selected by this protocol should have affinities to the target in the nanomolar range.

A third version of a screen, as shown in FIG. 22, is similar to the first version, using diversity elements on two sets of coferons in solution. Here a first set of DNA encoded coferon is either passed over or cycled through a column containing the target protein. After binding the library and an optional step of washing with buffer to remove non-specific binders, the diversity elements are identified by PCR amplification and sequencing of the DNA tags. This approach identifies the diversity elements that bind most tightly to the target (with affinities in the micromolar to nanomolar range). The PCR amplicons are used to resynthesize the top diversity elements. (In a variation, the above column selection procedure may be repeated to further enrich for the tightest binding diversity elements.) This first set of selected diversity elements is now combined in solution with a second complete set of diversity elements whose coferons bind to the first set of coferons. These coferon pairs are then panned on beads containing the protein target. The principles of dynamic combinatorial chemistry would select for and amplify those coferon pairs that bind most tightly to the targets on the beads. After a suitable period of time, the unbound coferons are removed, with the optional step of washing the beads to further remove non-specific binding coferons. The panning may be done in wells that have filter bottoms, or, alternatively, the beads containing the target proteins may be magnetic for magnetic capture to facilitate washing steps. The diversity elements for each set of coferons are identified by PCR amplification and sequencing of the DNA tags. Alternatively, each of the top ligands identified in the first screen may be re-synthesized and can now be attached through a series of connectors that vary in size, flexibility, or for circular diversity elements, the size of the macrocycle. A further variation on this theme would be to regenerate not only the original diversity elements, but minor variations (e.g., vary just one amino acid residue at a time from a cognate sequence) as well, to be combined with the diverse set of connector elements. This refined set of coferons would be re screened in the presence of the complete second coferon library in solution to find binders to the target protein on beads. The same principles of dynamic combinatorial chemistry described above would apply. The winning sets of coferon pairs are identified by their DNA sequence tags. A different set of universal primers may be used to amplify and distinguish the DNA tags from the first coferon diversity set compared to the second coferon diversity set. If multiple sets of coferons from different clades are selected, the individual combinations can be determined by resynthesizing individual coferons, and trying each set in independent binding assays. As above, the second set of coferons may also be optimized by introducing variations in the connectors and diversity elements. Thus, evolutionary selection pressures may be applied on both sets of the coferon diversity elements. The coferon pairs selected by this protocol should have affinities to the target in the nanomolar to picomolar range.

A fourth version of the screen, as shown in FIG. 23, is a variation of the first and third versions. In this case, the target is a protein with a known binding pocket, for example a tyrosine kinase. Here, molecules known to or inferred to fit within the binding pocket (and chemical variants whose structure would occupy a similar 3-dimensional space) are attached to a series of connectors that vary in size and flexibility. It is assumed (but should also be experimentally verified) that the majority of members of this library would bind to the target with micromolar or even nanomolar affinities. This is the equivalent of the first round of screening in the above first and third versions (FIGS. 20 and 22). Subsequently, this first library of binding pocket ligands is combined with the second library of coferons with various diversity elements. The pairs of binding elements are screened as described above. The coferon pairs selected by this protocol should inhibit enzymatic function if the binding pocket also has an active site, and have affinities to the target in the nanomolar to picomolar range.

A fifth version of the screen, as shown in FIG. 24, combines elements of the above versions. In the first version (FIG. 20), monomer diversity elements on beads are screened for binding to fluorescently labeled target, while in the third version (FIG. 22), monomer DNA tagged diversity elements are screened for binding to immobilized target on beads or a solid support. In both cases, the initial selection is for a monomer binding ligand to the target. Under these conditions, the connector and linker element would be anticipated to play a minor role in the binding affinity. These initial top ligands are then redeployed with a series of different connectors and now selected again in the presence of a second library of diversity elements to achieve even better binding. These screens are based on the principle that initial stronger binding monomer diversity elements would most likely be selected for in the strongest coferon dimer pair, and that a step-wise selection for the tightest binding elements would be successful. In the fifth version of the screen (FIG. 24), two sets of coferon libraries with encoded DNA barcodes are combined in solution to form dimer pairs. The DNA barcodes have the capacity for additional levels of diversity that were used in synthesis of the ligands. The coferon libraries are screened directly for binding to target immobilized on beads, and the tightest binding ligand pairs are enriched due to dynamic combinatorial chemistry. The winning ligand pairs are identified via PCR amplification of the encoded barcodes, and these amplicons are then used for an additional round of ligand synthesis. However, in this next round, additional diversity is added with a series of different connectors, which are encoded by using regions of the DNA barcode that were not used for generating the original ligand diversity. The products of this round of synthesis have been enriched for the tightest ligand pairs selected in the initial panning step, yet have additional diversity added for the second panning step. This type of chemical screening-selection mimics the type of evolutionary selection that occurs on eukaryotic organisms that reproduce by sexual means and thus are constantly reassorting chromosomal pairs. This two-step screening-enrichment allows for a greater degree of diversity elements at varying distances and orientation with respect to each other to be interrogated in the overall selection process. The coferon pairs selected by this protocol should have affinities to the target in the nanomolar to picomolar range.

The recent work of Whitesides (Krishnamurthy, et al., *J. Am. Chem. Soc.* 129:1312-1320 (2007), which is hereby incorporated by reference in its entirety) and Neri laboratories (Melkko, et al., *Nat. Biotechnol.* 22(5):568-574 (2004), which is hereby incorporated by reference in its entirety) suggest that diversity elements will bind to a target with almost as high binding affinity when attached through a flexible ethylene glycol linker as when attached by a rigid linker of the precisely correct geometry. This finding allows one to liberate the process of screening for the best diversity elements of a given target from the exact linker element (and/or connector) design used in the final coferon drug. Thus, diversity elements may be optimized for a given target using a set of linker elements which have a favorable equilibrium between the monomer and dimer state; i.e. one that favors the dynamic combinatorial chemistry selection process. Subsequently, these same or different linker elements may be optimized using either flexible or more rigid connectors between the diversity elements (ligands) and the linker elements to optimally bind the target.

For example, when performing in vitro screening of diversity elements binding to a target protein, it would be advantageous to use a first linker element containing an aldehyde or ketone, and a second linker element containing a primary or secondary amine. These two linker elements readily form the highly reversible Schiff base in the absence of target at the concentrations of diversity elements used for screening. There is a high concentration of primary amines free in solution (lysine) and in proteins. Thus, when using a coferon monomer containing a primary amine, it is important for the companion aldehyde or ketone containing coferon monomer to find its partner on the surface of the target molecule. As an added note of caution, the amine-containing linker element may react with sugars when in the aldehyde or ketone tautomeric form. However, these linker elements would not be preferred in the final coferon designs, since there is a high concentration of primary amines free in solution (lysine) and in proteins, and thus it may be difficult for the first aldehyde or ketone containing coferon to find its partner containing a primary amine in solution. Further, the primary amine in the second linker element may also react with aldehydes and ketones present in sugars that are in the linear isomeric form. However, if the primary amine is two carbons away from a thiol group (which may be in the protected disulfide form outside the cell), then it has the potential to form an essentially irreversible thiazolidine linker in the final coferon dimer. The thiazolidine linker is an excellent example of a linker element that may be activated upon entering a cancer cell and then form an essentially irreversible bond with its partner coferon.

In-silico screening can be performed with the aim of limiting the number of different diversity elements tested when performing in vitro screening. In-silico screening would be performed with either a known diversity library, or with an in-silico library, where the potential structures are all known or may be calculated. Such molecules can be virtually screened by matching the 3D models with the target protein structure. In-silico screening would allow the testing of huge virtual libraries of different diversity elements on different scaffolds, with the aim of eliminating the vast majority of potential diversity structures and focusing on a reasonable number of promising leads. Since the process of building such combinatorial libraries in vitro is straightforward, an in-silico pre-screen has the potential to accelerate the process of identifying lead candidate coferons. This will be especially useful for screening diversity elements in multimeric coferons.

Identification of a first diversity element may assist in identifying a second diversity element that binds the target adjacent to the first diversity element. Likewise, use of a known ligand as the first diversity element will assist in identifying a second diversity element that binds the target adjacent to the first diversity element. This approach may improve an existing drug by taking advantage of the larger surface area that a coferon pair can use to bind onto the target, thus imbuing the coferon with higher affinity or better specificity, or both.

The coferon concept takes advantage of having three weak interactions take place simultaneously as follows: (i) coferon 1 to coferon 2; (ii) coferon 1 to protein; and (iii) coferon 2 to protein, which results in a very strong interaction between the protein and the two coferon partners. The coferon interaction may be strengthened by covalent bonds between the coferons. The reactive groups on the coferons are chosen such that they are mostly unreactive with cellular molecules or off target proteins. If they do react with cellular components, such reactions should be reversible and non-toxic.

Just as the interactions between the coferons may be strengthened by covalent bonds, so too, the interactions between the coferons and the protein partners may also be strengthened by incorporating reactive groups within the diversity elements that bind the protein target. For example, a ketone or aldehyde in the correct orientation may form a Schiff base with a lysine on the protein target. Another example would be reaction of a coferon boronic acid group with a threonine or serine residue on the protein target or carbohydrate hydroxyl groups on glycoprotein targets. Coferons containing boronic esters could link with each other as well as with multiple sites on the carbohydrate portion of glycoproteins. Either one or both of these events would significantly shift the equilibrium towards coferon dimer binding to its target. Such designs are dependent on judiciously placed amino acid residues on the target protein. Although there is a risk of non-specific reaction between a reactive group on the coferon drug and an incorrect target, since the rest of the diversity element would not provide any additional binding energy, such an off-target effect would be quickly reversible.

The above principle extends even further when applied to coferon multimers, and especially to coferon multimers that bind multimeric protein targets. Multiple weak interactions add to the binding affinity of the overall coferon complex to the correct target.

When screening for the best coferons, either one of the coferons or the protein target is on a solid support (bead), with coferons binding to each other and/or the protein target. The bound coferons are in equilibrium with the coferons in solution, both binding and coming apart through their linker element moieties. Meanwhile, the protein targets are binding and dissociating with coferons in solution and on the solid supports. The most stable complexes of bead coferon to solution coferon to target protein are removed from this equilibrium. The concentration of these components in solution has now decreased, so they dissociate from less stable complexes. This now drives the equilibrium towards forming even more of the most stable complexes, so that the tightest binding combinations are enriched.

For this screening process to work most effectively, the coferon monomers need to efficiently cycle between the monomeric and dimeric (or multimeric) state. This will allow for the greatest number of combinations to be tested, and also for enriching the best binding combinations onto the solid support.

However, as mentioned above, some linker elements may associate slowly until brought in close proximity by the target, but once they associate and form one or more covalent (i.e. hemiacteal) or ionic bond (i.e. through two coferons chelating the same zinc ion), they do not dissociate easily. Thus these types of reactions are essentially irreversible. While such a property of a coferon may be desirable for linker elements in the final drug molecule, they would inhibit the screening process.

In order to use such linker elements during the dynamic combinatorial chemistry screening process, it is preferable for the dissociation process to occur as rapidly as the association process. One approach is to change the assay conditions, for example, low pH will favor dissociation of hemi-acetals. Another approach is to use linker elements with the same geometry, but now unable to form all the potential covalent bonds.

A new approach is to cycle between conditions that favor formation of dimers and multimers, and conditions that favor dissociation to monomers. Herein, this approach is termed cyclic combinatorial chemistry, or C3 screening.

Consider a coferon pair that associates quickly at pH 9, and dissociates quickly at pH 5. The coferon association is initiated by combining a bead-library and a solution library of coferons with the protein target, for example in a phosphate buffer at pH 9. As library members come together, some pairs will favor binding to the protein target. Other non-productive pairs will also come together. The pH may now be titrated down to pH of 5 by addition of acid. Under these conditions, coferons that are not bound to the target will dissociate, but coferons bound to the target are held in place, and do not dissociate. Subsequently the pH is shifted back to pH 9. Now fresh combinations of coferon pairs form, and again, the pairs that favor binding of the protein will accumulate more protein on the beads or particle. This process may be repeated until sufficient (fluorescently) labeled protein accumulates on the beads containing the best coferon pairs. One caveat with this approach is that the ion concentration in the solution keeps increasing (for example, if HCl and NaOH are used to decrease and increase the pH, respectively, then NaCl will accumulate with each cycle). On the positive side, higher salt concentrations will select for more specific binding. Further, this process is easy and amenable to automation.

As another example, consider coferons that pair through a $Zn^{2+}$ cofactor. Addition of 1 mM $ZnCl_2$ will allow the coferons to dimerize, with the more favorable pairs binding to the target. Addition of a suitable zinc chelating agent (such as 1 mM EDTA) will be able to displace coferons from the zinc so the coferons dissociate into monomers. The chelating agent should not be strong enough to dissociate the zinc when the two coferons are held in place by binding a target. Alternating addition of 1 mM $ZnCl_2$ and 1 mM EDTA will cycle the "free" $Zn^{2+}$ cofactor in solution between approximately 1 mM and 0 mM, cycling the coferons between the dimer (or multimer) and the monomer states. As noted previously with pH cycling, this will eventually accumulate Zn-EDTA (in the process, forming NaCl if the original EDTA was in the disodium salt). This process is also amenable to automation.

To avoid accumulating salt, alternative approaches may be used to modulate pH or divalent metal concentration. For example, the chelating moiety may be attached to a solid support and brought in contact with the coferon screening solution by circulating the screening solution past the solid support. Coferon on beads or particles may be separated from chelator beads or particles by using different size beads or particles, or using paramagnetic beads or particles. To modulate pH, organic molecules that act as buffers may be attached to a solid support. Among these are "Good's buffers", which can stabilize pH values over very precise ranges. The coferon screening solution may be circulated between two chambers, each containing the solid support with the organic molecule that will buffer the screening solution to the right pH. In both of these examples, the solid support may eventually become saturated (with divalent cation, or exceed it's buffering capacity), and thus may need to be replaced after a certain number of cycles. As before, this process is also amenable to automation.

In the above examples, the binding of coferons to each other is controlled by the concentration of a positively charged ion or cation: $H^+$ or $Zn^{2+}$. Certain membranes are permeable to small molecules and ions. The Nafion-117 membrane is permeable to $H^+$, and cations such as $Li^+$, $Mg^{2+}$, $Zn^{2+}$, $Na^+$, and $K^+$; but impermeable to coferons, anions, buffers, large cations, nucleic acids, peptides and proteins. This membrane may be used in a device that allows for cyclic combinatorial chemistry.

In one embodiment (See FIGS. 25 and 26), the membrane separates an upper compartment A from a lower compartment B. Compartment A contains beads, coferons, buffer (such as PIPS, TEEN, or PIPPS), and target protein. The buffer is chosen to provide the desired pH range based on pKa values (PIPPS buffer has a pKa1 3.85; pKa2 7.99; PIPES buffer has a pKa1 2.7; pKa2 6.81; and TEEN buffer has a pKa1 6.69; pKa2 10.10). At the higher pH, the coferons are more stable in the multimer form, while at the lower pH, the coferons dissociate to form monomers—unless they are bound to the protein target, where they remain as multimers.

Compartment B is used to wash in and out different buffers in reservoirs C-E. Reservoir C contains an aqueous wash solution. Reservoir D contains $H^+$ or a low pH buffer. Reservoir E contains NaOH (or equivalent base), or a high pH buffer. During cycling, ionic strength and amount of buffer remain unchanged in Compartment A. Cation and water exchange across the Nafion-117 membrane between compartments A and B is mediated by piston pumps, stirring liquid in either compartments, applying pressure, or combinations thereof. Cations cycle between H+ and Na+ (or equivalent cation).

If the coferons bind through a $Zn^{2+}$ cofactor, then reservoir D contains the $Zn^{2+}$ and reservoir E contains a chelator, such as EDTA. During cycling, ionic strength and amount of buffer remain unchanged in Compartment A. The $Zn^{2+}$ and $Na^+$ cations (and water) exchange across the Nafion-117 membrane between compartments A and B is mediated by piston pumps, stirring liquid in either compartments, applying pressure, or combinations thereof. Cations cycle between $Zn^{2+}$ and $Na^+$.

The above design is amenable to a multiple well format and automation. A 24 well microtiter plate may be constructed from 2 parts: The top part has cylindrical openings in 24 well format. The bottom part has shallow wells and grooves from a single entry port on the front splitting into 24 lines going into each well, and 24 lines (grooves) out of each well coming together at a single exit port in the back. Such a design can be manufactured very quickly in a simple stamping process. The top and bottom part are welded together with the Nafion-117 membrane in between them. The entry and exit ports both have valves and are attached to piston pumps.

Since the 24 top wells are open, they can be filled with coferons, beads, fluorescent target protein, etc. using a multi-channel pipette or a robotic platform.

The bottom of the wells can be filled with the appropriate reagents by opening the entry and exit valves, and moving the two piston pumps in the same direction. The simplest way to accelerate the exchange is to have the entire device on a rotating platform (microtiter plate shaker). Alternatively, magnetic agitation (stirring) may be used. If it is necessary to speed up the process, the exit pump can be closed, and the volume of all 24 top wells will increase when the entry pump keeps pumping. To decrease the volume of the 24 top wells, the entry valve is closed, and the exit valve is opened and the pump withdraws fluid. This design also makes it easy to transfer a number of reactions into a second microtiter plate for bulk washing away unbound coferons etc.

A fluorescent chelator or dye may be used to monitor the zinc concentration or pH. Examples of fluorescent zinc chelator and some fluorescent pH dyes are: TFLZn, 4-(6-Methoxy-8-quinaldinyl-aminosulfonyl)benzoic acid potassium salt; HPTS, 8-hydroxypyrene-1,3,6-trisulfonic acid trisodium salt; umbelliferone-3-carboxylic acid, 7-hydroxycoumarin-3-carboxylic acid; and 5(6)-carboxynaphthofluorescein.

After the selection is complete, the dye or fluorescent group may be washed away so that it does not interfere with scoring of the beads for those that bound labeled target protein.

The dyes can also be linked to a solid support to make it easy to read and separate from coferon beads (although a separation step may not be needed).

It may be useful to verify the rate and efficiency of exchange using a model system. One such model system would use iminobiotin as the ligand, and fluorescently labeled streptavidin as the target protein. A functional coferon would be synthesized containing the linker element connected to the iminobiotin via a flexible linker, i.e. ethylene glycol chain. When synthesizing this functional coferon on a solid support, spacing would be sufficiently distant to minimize two coferons in close enough proximity to bind to the same streptavidin target. A non-functional coferon would be synthesized containing the linker element connected to another unrelated small molecule or just an amine group via an ethylene glycol chain. The functional coferon containing bead would be mixed in with a 1,000-fold excess of beads containing non-functional coferon. Likewise, the functional coferon in solution would be mixed in with a 1,000-fold excess of non-functional coferon in solution. In the example here, the solution coferon can only make dimers or multimers with the bead-bound coferon.

In the presence of fluorescently labeled streptavidin, two functional coferons, one on the bead, the other in solution bind to the target and provide a small amount of fluorescent label to the single bead. With repeated cycling (100 to 1,000 cycles), the amount of fluorescent signal on the functional coferon bead should steadily increase. Comparing different cycling conditions will help determine the optimal cycling times and pH or cation concentrations.

Considerations for Screening Coferons Binding to Targets

In FIGS. 2.1 through 2.16, coferons are described from monomers to hexamers; design components and variations, suitable for synthesis, screening, and therapeutic use.

In consideration of the screening process, the following encryption formats—illustrated below using the simplest case of forming dimers between "A" and "B" coferons—may be considered:

Multiple A Coferons with Multiple B Coferons.

1. Multiple A coferons and multiple B coferons both contain DNA encryption. DNA encryption of coferons, using either DNA targeted synthesis or DNA directed synthesis has been described in the literature. The coferons are blended with an immobilized target, and after the appropriate incubation period are washed off. Addition of the appropriate primers allows for PCR amplification of the DNA bar-codes, and sequence analysis allows for identification of the ligands in both the "A" and "B" coferons.

2. Multiple A coferons and multiple B coferons, A coferons are on beads, B coferons in solution. In this variation, the A coferons are on encoded beads, and the B coferons have a DNA encryption or no encryption. Fluorescently labeled target is added, and beads that become fluorescently labeled in the presence of B coferons are isolated. Ligand on the bead may be identified through (i) optical bar-coding of the bead, (ii) mass-tag bar-coding of the bead, (iii) DNA bar-coding of the bead. B coferon may be identified using the DNA bar-code (as described above) or by mass spectroscopy. Alternatively, the selection is repeated with the B coferons are on encoded beads, and the A coferons in solution to find the matched pairs.

Single A Coferon with Multiple B Coferons.

1. Single A coferon with multiple B coferons, B coferons on beads. These are conditions where the A coferons are either known ligands, or have been pre-screened against the target so there are a limited number of A coferons to test, compared with a vast excess of B coferons. Fluorescently labeled target is added, and beads that become fluorescently labeled in the presence of B coferons are isolated. Ligand on the bead may be identified through (i) optical bar-coding of the bead, (ii) mass-tag bar-coding of the bead, (iii) DNA bar-coding of the bead.

2. Single A coferon with multiple B coferons, both coferons in solution. These are conditions where the A coferons are either known ligands, or have been pre-screened against the target so there are a limited number of A coferons to test, compared with a vast excess of B coferons. For the purposes of this example, the coferons are used in a whole-cell assay, where inhibition of the target is lethal, and thus amenable to HTS. Consider 96 A coferons to be tested in combination with 9,600 B coferons (One 96 well plate vs. 100×96 well plates). Ordinarily, that would require 921,600 assays (=2,400×384 well plates). However, by pooling coferons by rows and columns, the total number of screens for the A coferon plate vs 1 B coferon plate would be 8 A rows×12 B columns+12 A colums×8 B rows=192 wells. If one coferon combination worked, then one of the first 96 well assays will give a positive result, and one in the second 96 well assays will also give a positive result, allowing identification of the correct row and column in both the A and B plate to identify the precise coferon pair that works. If this process is now repeated for each of the 100 B plates, this would require 19,200 assays (=50×384 well plates). Since dynamic combinatorial chemistry selects the tightest binding inhibitors, the pooling strategy allows for almost a 50-fold reduction in the number of HTS assays required.

Single A Coferon with Single B Coferon.

1. Single A coferon with single B coferon, with coferon biological activity determined using whole-cell assays. Examples of biological readout are provided below. In these schemes, both coferons are in solution. The identity of the coferon is given by the location of the well where the ligand was synthesized, for example by split synthesis protocols, without re-pooling. Such assays may be compatible with the pooling strategies described above. Alternatively, where assays are not compatible with pooling, ultra high-throughput assays may be developed using nano-droplet (Raindance) technology. Such technology can generate 3,000 droplets per second. Consider the example above of 96 A coferons to be tested in combination with 9,600 B coferons, where the whole-cell assay generates a fluorescent signal. The A coferons are in 1×96 well plate, each well containing a 100,000 beads with a unique barcode and the A coferon attached to the bead. The B coferons are in 25×384 well plates, each well containing a 1,000 beads with a unique barcode and the B coferon attached to the bead. In practice, either the A or B coferon plate may pool the coferons by using split synthesis protocols, with re-pooling, provided the barcodes are attached to the beads. All the A coferons are pooled together and emulsified in oil such that each bead is in its own nanodrop. Likewise, all the B coferons are pooled together and emulsified in oil such that each bead is in its own nanodrop. The A coferon droplets and B coferon droplets are fused, each fused droplet containing one bead each for a total of 9,600,000 droplets. This process (not including setup) takes 3,200 seconds, or just under an hour. These droplets are then exposed to light (or heat, or reagent that may be subsequently neutralized if needed to be biologically compatible) to release the coferons from the beads. Subsequently, the droplets are fused with new droplets containing the cells with the biological target whose inhibition/activation will result in a change in fluorescent signal. This second droplet fusion will also take just under an hour, and this may be followed by a period of incubation to allow the coferons to enter the cells and bind the intended target, resulting in the biological readout. The droplets are placed in a flow sorter, such that the fluorescently altered droplets are separated. Dilution into 384 or 1536 well plates, such that a given well has one or less nanodroplets containing the original bead pair, followed by addition of aqueous solution and centrifugation separates the aqueous layer from the hydrophobic oil and allows for PCR amplification and sequence analysis to identify the winning coferon ligands. If the bar-codes are mass tags attached to the beads, they may be identified by mass spectroscopy.

2. Single A coferon with single B coferon, with coferon binding determined using in vitro readout. Examples of in vitro readout are provided below. In these schemes, both coferons are in solution. The identity of the coferon is given by the location of the well where the ligand was synthesized, for example by split synthesis protocols, without re-pooling.

Coferon Binding Determined Using In Vitro Readout.

Two screens, termed "AlphaScreen" and "AlphaLISA" have been developed (sold by Perkin-Elmer) to measure cell signaling, including protein:protein, protein:peptide, protein:small molecule or peptide:peptide interactions. The assays are based on detecting the close proximity of donor beads containing a first molecule or protein that binds to a second molecule or protein on the acceptor beads. Singlet oxygen molecules, generated by high energy irradiation of donor beads, travel over a constrained distance (approx. 200 nm) to acceptor beads. This results in excitation of a cascading series of chemical reactions, ultimately generating a chemiluminescent signal. (Eglen, et. al., *Curr. Chem Genomics* 1:1-19 (2008), which is hereby incorporated by reference in its entirety).

The donor bead contains phthalocyanine. Excitation of the donor bead by a laser beam at a wavelength of 680 nM allows ambient oxygen to be converted to singlet oxygen. This is a highly amplified reaction since approx. 60,000 singlet oxygen molecules can be generated and travel at least 200 nm in aqueous solution before decay. Consequently, if the donor and acceptor beads are brought within that proximity as a consequence of protein:protein, protein:peptide, or protein:small molecule interactions, energy transfer occurs. Singlet oxygen molecules react with chemicals in the acceptor beads to produce a luminescent response. If the acceptor bead contains Europium, as in the AlphaLISA assay, an intense luminescence is emitted at a wavelength of 615 nm. (Eglen, et. al., *Curr. Chem Genomics* 1:1-19 (2008), which is hereby incorporated by reference in its entirety).

For the purposes of the discussion below, this system will be referred to as linking various proteins, fragments or molecules on donor and acceptor beads. Such linking may be chemical in nature, or may be due to tight binding of a tethered ligand, such as if the donor bead is coated with strepavidin and the donor molecule or protein has a biotin attached to it. There are many systems for binding recombinant proteins to beads, including His-Tag, Myc-Tag, GST fusions, Maltose binding protein (MBP) fusions.

A. Identifying Initial Sets of Coferon A Ligands that (Weakly) Bind to the Target Protein Target protein is linked or bound to the donor bead. A generic coferon B, containing a linker element that binds the linker element of coferon A is attached to the acceptor bead. A generic ligand may contain the scaffold and then the simplest diversity element in all the diversity positions, for example, alanine if the diversity positions are filled with amino acid moieties. An HTS assay is setup containing acceptor and donor beads in each well, with from 1 to 100 or even 1,000 or more coferon A variants added to each well. The number of variants will depend on the background level and hit level, determined experimentally. Likewise, the number of "generic" variants that can be tested within the same well may range from 1 to 100 or more. Since dynamic combinatorial chemistry takes place, the acceptor bead will bind those variants that bind the donor bead the tightest, as more than one protein will interact with more than one coferon pair to form more than one bridge to the acceptor bead. By using different sets of pools (i.e. rows vs. columns) a large number of potential binders may be rapidly tested.

B. Identifying Optimized Coferon B Ligands that Ppair with the Initial Sets of Coferon A Ligands to Tightly Bind to the Target Protein Target protein is linked or bound to the donor bead. The initials sets of coferon A ligands, (containing a linker element that binds the linker element of the test coferon B ligands) are attached to the acceptor beads. An HTS assay is set up containing acceptor and donor beads in each well, with from 1 to 100 or even 1,000 or more coferon B variants added to each well. The number of variants will depend on the background level and hit level, determined experimentally. The strongest binding coferon B ligands will give the brightest signals. As above, when testing more than one coferon B ligand per well, use of different sets of pools (i.e. rows vs. columns) allow a large number of potential binders to be rapidly tested.

C. Identifying Coferon Dimers that Enhance Binding of Two Proteins with Weak or No Binding Affinity to Each Other Target protein 1 is linked or bound to the donor bead. Target protein 2 is linked or bound to the acceptor bead. To identify a new weak binding partner to a given target protein, a yeast two-hybrid or other fish-bait protein complementation assay is set up, with both weak and strong hits identified. An HTS assay is set up containing acceptor and donor beads in each well, with from 1 to 10 or even 100 or more coferon A & B dimer variants added to each well. The number of variants will depend on the background level and hit level, determined experimentally. The coferon dimers that best enhance binding of the two proteins to each other will give the brightest signals. If necessary, candidate coferon A and B monomers that bind either or both protein targets may be identified as in procedure A.

D. Identifying Coferon Dimers that Further Enhance Binding of Two Proteins with Medium to Strong Binding Affinity to Each Other Target protein 1 or a mutant variant with weaker binding is linked or bound to the donor bead. Target protein 2 or a mutant variant with weaker binding is linked or bound to the acceptor bead. If the original proteins are used, they are linked to the beads at low concentration. Often some structural or sequence information is available to guide alanine scanning or targeted mutagenesis to generate variants with the potential to bind weakly. To identify mutations that convert a strong binding partner into a weak binding partner to a given target protein, a yeast two-hybrid or other fish-bait protein complementation assay is set up to test mutant variants, with both weak and strong hits identified. An HTS assay is set up containing acceptor and donor beads in each well, with from 1 to 10 or even 100 or more coferon A & B dimer variants added to each well. The number of variants will depend on the background level and hit level, determined experimentally. The coferon dimers that best enhance binding of the two proteins to each other will give the brightest signals. The winning coferon dimer sets are then retested to determine which set enhances binding of the wild-type proteins to each other.

E. Identifying Coferon Dimers that Inhibit Binding of Two Proteins to Each Other Target protein 1 is linked or bound to the donor bead. Target protein 2 is linked or bound to the acceptor bead. An HTS assay is set up containing acceptor and donor beads in each well, with from 1 to 10 or more coferon A & B dimer variants added to each well. The number of variants will depend on the background level and hit level, determined experimentally. The coferon dimers that best inhibit binding of the two proteins to each other will give the weakest signals. If necessary, candidate coferon A and B monomers that bind either protein targets in the absence of the other protein may be identified as in procedure A.

F. Identifying Coferon Dimers that Inhibit Binding of Two Proteins to Each Other Target protein 1 is linked or bound to the donor bead. Target protein 2 is either added in solution, or linked or bound to neutral beads. A weak or medium binding partner of target protein 1, or an antibody that binds to target protein 1 is linked or bound to the acceptor bead. An HTS assay is set up containing acceptor and donor beads, as well as sufficient target protein 2 in each well, such that target protein 2 interferes with binding of the proteins on the acceptor and donor beads resulting in low or background level signal. Addition of from 1 to 10 or more coferon A & B dimer variants that bind to target protein 2 in such a way as to disrupt binding to target protein 1, allowing for binding of the protein on the acceptor bead to the donor bead, and thus generating positive signal. The number of variants will depend on the background level and hit level, determined experimentally. The coferon dimers that best inhibit binding of the two proteins to each other will give the strongest signals. If necessary, candidate coferon A and B monomers that bind target protein 2 in the absence of the other protein may be identified as in procedure A.

G. Identifying Coferon Dimers that Inhibit Binding of Two Proteins to Each Other The inverse of the above procedure may be performed using target protein 2 linked or bound to the donor bead, and target protein 1 either added in solution, or linked or bound to neutral beads. In this procedure, a weak or medium binding partner of target protein 2, or an antibody that binds to target protein 2 is linked or bound to the acceptor bead. Again, if necessary, candidate coferon A and B monomers that bind target protein 1 in the absence of the other protein may be identified as in procedure A.

H. Identifying Coferon Dimers that Inhibit Binding of Two Proteins to Each Other, Using a Helper Protein Target protein 1 is linked or bound to the donor bead. Target protein 2 is linked or bound to the acceptor bead. A helper protein may have weak or no affinity to target protein 1. An HTS assay is set up containing helper protein, acceptor and donor beads in each well, with from 1 to 10 or more coferon A & B dimer variants added to each well. The number of variants will depend on the background level and hit level, determined experimentally. The coferon dimer that enhances binding of the helper protein to target protein 1, and thus best inhibits binding of the two target proteins to each other will give the weakest signals. If necessary, candidate coferon A and B monomers that enhance binding of the helper protein to target protein 1 in the absence of the other protein may be identified as in procedure C.

I. Identifying Coferon Dimers that Inhibit Binding of Two Proteins to Each Other, Using a Helper Protein Target protein 1 is linked or bound to the donor bead. Target protein 2 is either added in solution, or linked or bound to neutral beads. A weak or medium binding partner of target protein 1, or an antibody that binds to Target protein 1 is linked or bound to the acceptor bead. A helper protein may have weak or no affinity to Target protein 2. An HTS assay is set up containing acceptor and donor beads, as well as sufficient target protein 2 and helper protein in each well, such that target protein 2 interferes with binding of the proteins on the acceptor and donor beads resulting in low or background level signal. Addition of from 1 to 10 or more coferon A & B dimer variants that enhance binding of the helper protein to target protein 2 in such a way as to disrupt binding to target protein 1, allowing for binding of the protein on the acceptor bead to the donor bead, and thus generating positive signal. The number of variants will depend on the background level and hit level, determined experimentally. The coferon dimer that enhances binding of the helper protein to target protein 2, and thus best inhibit binding of the two target proteins to each other will give the strongest signals. If necessary, candidate coferon A and B monomers that enhance binding of the helper protein to target protein 2 in the absence of the other protein may be identified as in procedure C.

J. Identifying Coferon Dimers that Inhibit Binding of Two Proteins to Each Other, Using a Helper Protein The inverse of the above procedure may be performed using target protein 2 linked or bound to the donor bead, and target protein 1 either added in solution, or linked or bound to neutral beads. In this procedure, a weak or medium binding partner of target protein 2, or an antibody that binds to target protein 2 is linked or bound to the acceptor bead. A helper protein may have weak or no affinity to target protein 1. Again, if necessary, candidate coferon A and B monomers that enhance binding of the helper protein to target protein 1 in the absence of the other protein may be identified as in procedure C.

Coferon Biological Activity Determined Using Whole-Cell Assays.

The last few years has seen an explosion of biological assays designed to study protein signaling and protein-protein interactions in whole cells. Many of these are based on protein complementation assays (PCA's) that reconstitute activity of two peptide chains to form a functional reporter protein, which generates either a fluorescent or chemiluminescent signal. Proteins have evolved to code for all the information needed to fold into stable 3-dimensional structures. In some cases, the complementary N-terminal and C-terminal peptide chains can fold independently, and find each other to form a functional (reporter) protein. However, kinetically this process competes with non-specific aggregation, so in many cases expression of complementary N-terminal and C-terminal peptide chains in a cell does not lead to reconstruction of activity. PCA works by fusing interacting proteins to the fragments, which increase the effective concentration of the two fragments, thus favoring the correct folding over any non-productive process. Addition of coferon drugs that would interfere with the two proteins from interacting with each other would lower the effective concentration of the two fragments with each other, and thus cause a disruption or loss of signal from the complementing reporter protein fragments.

One of the oldest forms of protein complementation in based on the alpha-peptide complementation of the enzyme beta-galactosidase. DiscoveRx has developed this enzyme fragment complementation (EFC) technology into a cell-based luminscent platform. Beta-galactosidase is active as a tetramer, but when missing the N-terminal 60 amino acid peptide forms only dimers, which are inactive. By reintroducing the alpha-peptide into the protein, it forms the tetramer and revives activity. Two forms of the alpha-peptide are commercially available, ProLabel™ (DiscoveRx Corp., Fremont, Calif.) with higher affinity to the C-terminal enzyme acceptor protein, and ProLink™ (DiscoverRx Corp., Fremont, Calif.), with lower affinity, and thus optimized to detect protein-protein interactions. By engineering G-Protein Coupled Receptors (GPCRs) to contain the ProLink peptide on one of their termini, and using an engineered beta-arrestin to contain the C-terminal enzyme acceptor protein, DiscoveRx has developed an assay for drug-activation of GPCR with EFC readout in the form of a chemiluminsescent signal. Similarly, the ProLabel tag has been used to measure protein expression, degradation, secretion and translocation for a variety of drug discovery target classes.

An alternative approach is marketed by Invitrogen (Carlsbad, Calif.) and termed "GeneBLAzer Technology". GeneBLAzer Technology uses a mammalian-optimized beta-lactamase gene combined with a FRET-enabled substrate. Cells are loaded with an engineered fluorescent substrate containing two fluoroprobes, coumarin and fluorescein. In the absence of beta-lactamase gene expression, the substrate molecule remains intact. In this state, excitation of the coumarin results in fluorescence resonance energy transfer to the fluorescein moiety and emission of green light. However, in the presence of beta-lactamase gene expression, the substrate is cleaved, separating the fluorophores, and disrupting energy transfer. Excitation of the coumarin in the presence of enzyme beta-lactamase activity results in a blue fluorescence signal. The resulting blue:green ratio provides a normalized reporter response.

Invitrogen (Carlsbad, Calif.) has exploited GeneBLAzer to build "Tango" assays that report drug binding to GPCRs. The Tango assay platform is based upon ligand binding to GPCRs that triggers desensitization, a process mediated by the recruitment of intracellular arrestin proteins to the activated receptor. As a result, the ligand-induced activation of GPCRs may be assayed by monitoring the interaction of arrestin with the test GPCR. A major advantage of this approach is that it does not depend on knowledge of the G-protein signaling specificity of the target receptor.

The target GPCR is fused at its intracellular C-terminus to an exogenous transcription factor. Interposed between the receptor and the transcription factor is a specific cleavage sequence for a non-native protease. This chimeric receptor protein is expressed in a cell line containing the beta-lactamase reporter gene responsive to the transcription factor. The cell line also expresses an arrestin-protease fusion protein that recognizes and cleaves the site between the receptor and transcription factor. The assay is performed by adding a ligand to the growing cells for a defined period and measuring the activity of the reporter gene. Activation of the reporter gene provides a quantifiable measurement of the degree of interaction between the target receptor and the protease-tagged arrestin partner. Additionally, the Invitrogen Tango assay is unaffected by other signaling pathways in the cell, thus providing a highly selective readout of target receptor activation.

Protein complementation assays have been developed using (a) dihydrofolate reductase, (b) Green fluorescent protein and variants, (c) beta-lactamase, (d) luciferases, (e) aminogycosidephosphotransferase, and (f) CRE-recombinase to screen for drugs that modulate protein-protein interactions, protein subcellular location, protein complex localization, and the association/dissociation of protein complexes Michnick, et. al., *Drug Discov.* 6:569-82 (2007), which is hereby incorporated by reference in its entirety.

For the whole-cell assays described below, in some cases a preliminary in vitro screen using purified proteins as described in the next section, or a preliminary whole-cell assay at higher drug concentrations may be used to identify initial coferon ligands. In some of the descriptions below, a beta-galactosidase system developed by DiscoveRx Corp. (Fremont, Calif.) is used, where the alpha-peptide with independent affinity to the C-terminal enzyme acceptor protein (EA) is referred to as ProLabel, and the alpha-peptide with weak to no affinity to EA is referred to as ProLink. Chemiluminescent or fluorescent signal generated by the reconstructed beta-galactosidase is determined as described (Eglen review). Whole cell assays may not be as amenable to using pooling techniques to screen for coferon pairs, thus the nanodrop technology developed by Raindance Technologies (Lexington, Mass.) may be more appropriate, (Leaman et. al, *Nat. Methods* 3(7): 541-43 (2006), which is hereby incorporated by reference in its entirety). The advantage of using whole cell assays is their immediate screen for coferons that enter cells when targeting intracellular components. The potential disadvantage to whole-cell screens include identifying coferons that elicit the desired phenotype, but not through the intended target. Carefully designed controls can reduce such false positives, and occasionally, these "off-target" results will lead to drugs that influence the process through alternative pathways.

K. Identifying Initial Sets of Coferon A Ligands that (Weakly) Bind to the Target Protein The gene for the target protein is linked to the coding sequence for the ProLink alpha-complementing peptide. Upon activation, target protein recruits a second protein (i.e., GPCR recruits arrestin). The gene for the second protein is linked to the gene for the EA acceptor protein. Linking of two proteins to each other may be accomplished by fusing the C terminus of one protein to the N-terminus of the second protein, with or without a flexible linker peptide, or alternatively using an intein to splice the two proteins together, such that both proteins retain biological function. Both of the above constructs are introduced into the target cell. An HTS assay containing the target cells in each well or nanodrop is set up, with from 1 to 10 or more coferon A variant ligands and 1 or more coferon B generic ligands added to each well or nanodrop. A generic ligand may contain the scaffold and then the simplest diversity element in all the diversity positions, for example, alanine if the diversity positions are filled with amino acid moieties. The number of variants will depend on the background level and hit level, determined experimentally. Likewise, the number of "generic" variants that can be tested within the same well or nanodrop may range from 1 to 10 or more. The coferon dimer that best activates the target protein to recruit the second protein will best reconstruct the beta-galactosidase ProLink and EA domains and give the strongest signals. By using different sets of pools (i.e. rows vs. columns) a large number of potential binders may be rapidly tested.

L. Identifying Optimized Coferon B Ligands that Pair with the Initial Sets of Coferon A Ligands to Tightly Bind to the Target Protein The gene for the target protein is linked to the coding sequence for the ProLink alpha-complementing peptide. Upon activation, target protein recruits a second protein (e.g., GPCR recruits arrestin). The gene for the second protein is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. Both of the above constructs are introduced into the target cell. An HTS assay containing the target cells in each well or nanodrop is set up, with from 1 or more coferon A initially selected ligands and 1 to 10 or more coferon B ligands added to each well or nanodrop. The number of variants will depend on the background level and hit level, determined experimentally. The coferon dimer that best activates the target protein to recruit the second protein will best reconstruct the beta-galactosidase ProLink and EA domains and give the strongest signals. As above, when testing more than one coferon B ligand per well, use of different sets of pools (i.e. rows vs. columns) allow a large number of potential binders to be rapidly tested.

In the procedures K and L above, the ProLink alpha-complementing peptide was linked to a membrane bound receptor protein, which upon activation recruits arrestin protein linked to the EA acceptor protein. Under these conditions, agonist coferons may be identified by increased beta-galactosidase signal. Alternatively, the system may be turned on by addition of a known agonist, and then antagonist coferons may be identified by decreased beta-galactosidase signal. The above concept may be expanded to include linking the target protein to the ProLabel alpha-complementing peptide. Upon activation, the target protein moves from the cellular membrane to the nucleus, where it can complement an EA acceptor protein that is localized to the nucleus. In the generalized version of this assay, binding of coferon to the target protein results in either an increase or decrease of reporter signal, cell growth or viability.

M. Identifying Coferon Dimers that Enhance Binding of Two Proteins with Weak or No Binding Affinity to Each Other The gene for target protein 1 is linked to the coding sequence for the ProLink alpha-complementing peptide. The gene for target protein 2 is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. To identify a new weak binding partner to a given target protein, a yeast two-hybrid or other fish-bait protein complementation assay is set up, with both weak and strong hits identified. Both of the above constructs are introduced into the target cell. A HTS assay containing the target cells in each well or nanodrop is set up, with from 1 to 10 or more coferon A and B dimer variants added to each well or nanodrop. The number of variants will depend on the background level and hit level, determined experimentally. The coferon dimer that best enhance binding of the two proteins to each other will best reconstruct the beta-galactosidase ProLink and EA domains and give the strongest signals. If necessary, candidate coferon A and B monomers that bind either or both protein targets may be identified by a preliminary in vitro screen (as in procedure A) or whole cell screen (as in procedure K).

N. Identifying Coferon Dimers that Further Enhance Binding of Two Proteins with Medium to Strong Binding Affinity to Each Other The gene for target protein 1 or a mutant variant with weaker binding is linked to the coding sequence for the ProLink alpha-complementing peptide. The gene for target protein 2 or a mutant variant with weaker binding is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. If one or both of the original proteins are used, they may be expressed at a lower level. Often, some structural or sequence information is available to guide alanine scanning or targeted mutagenesis to generate variants with the potential to bind weakly. To identify mutations that convert a strong binding partner into a weak binding partner to a given target protein, a yeast two-hybrid or other fish-bait protein complementation assay is set up to test mutant variants, with both weak and strong hits identified. Both of the above constructs are introduced into the target cell. A HTS assay containing the target cells in each well or nanodrop is set up, with from 1 to 10 or more coferon A and B dimer variants added to each well or nanodrop. The number of variants will depend on the background level and hit level, determined experimentally. The coferon dimer that best enhance binding of the two proteins to each other will best reconstruct the beta-galactosidase ProLink and EA domains and give the strongest signals. The winning coferon dimer sets are then retested to determine which set enhances binding of the wild-type proteins to each other.

O. Identifying Coferon Dimers that Inhibit Binding of Two Proteins to Each Other The gene for target protein 1 is linked to the coding sequence for the ProLink alpha-complementing peptide. The gene for target protein 2 is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. Both of the above constructs are introduced into the target cell. A HTS assay containing the target cells in each well or nanodrop is set up, with from 1 to 10 or more coferon A and B dimer variants added to each well or nanodrop. The number of variants will depend on the background level and hit level, determined experimentally. The coferon dimer that best inhibit binding of the two proteins to each other will interfere with reconstructing the beta-galactosidase ProLink and EA domains and give the weakest signals. If necessary, candidate coferon A and B monomers that bind either protein targets in the absence of the other protein may be identified by a preliminary in vitro screen (as in procedure A) or whole cell screen (as in procedure K).

P. Identifying Coferon Dimers that Inhibit Binding of Two Proteins to Each Other The gene for target protein 1 is linked to the coding sequence for the ProLabel alpha-complementing peptide. The ProLabel peptide sequence may be modified to include a nuclear localization signal. The gene for target protein 2 is either currently or is modified to prefer localization in the cytoplasm or at the cellular membrane. The gene for the EA acceptor protein is modified to include a nuclear localization signal. These constructs are introduced into the target cell, and if needed, expression is adjusted such that under normal conditions binding of target protein 1 (containing the ProLabel peptide) to target protein 2 localizes the two proteins in the cytoplasm or at the cell membrane, thus preventing the ProLabel portion from entering the nucleus and complementing the EA acceptor protein, resulting in low or no background level signal. Addition of from 1 to 10 or more coferon A and B dimer variants (in wells or nanodrops) that bind to target protein 2 in such a way as to disrupt binding to target protein 1, allowing for transport of the ProLabel peptide (linked to target protein 1) to enter the nucleus and combine with the EA acceptor protein, and thus generating positive signal. The number of variants will depend on the background level and hit level, determined experimentally. The coferon dimers that best inhibit binding of the two proteins to each other will give the strongest signals. If necessary, candidate coferon A and B monomers that bind target protein 2 in the absence of the other protein may be identified by a preliminary in vitro screen (as in procedure A) or whole cell screen (as in procedure K).

In this example, the ProLabel alpha-complementing peptide was localized to the cytoplasm or cellular membrane by the two target proteins binding each other, while the EA acceptor protein was localized to the nucleus. The above concept may be expanded to include localization of these proteins to the reverse or other compartments. In addition, in some cases binding of the two target proteins to each other will create a bulky complex that would inhibit binding of the ProLabel alpha-complementing peptide to the EA acceptor protein, even if they are in the same compartment. The generalized version of this assay is one where binding of the two target proteins to each other squelches, inhibits, or occludes binding of the ProLabel alpha-complementing peptide to the EA acceptor protein.

Q. Identifying Coferon Dimers that Inhibit Binding of Two Proteins to Each Other The inverse of the above procedure may be performed using Target protein 2 linked to the coding sequence for the ProLabel alpha-complementing peptide, and Target protein 1 localized to the cytoplasm or at the cellular membrane. The gene for the EA acceptor protein is modified to include a nuclear localization signal. Addition of from 1 to 10 or more coferon A and B dimer variants that bind to target protein 1 in such a way as to disrupt binding to target protein 2, allowing for transport of the ProLabel peptide (linked to target protein 2) to enter the nucleus and combine with the EA acceptor protein, and thus generating positive signal. Again, if necessary, candidate coferon A and B monomers that bind target protein 1 in the absence of the other protein may be identified by a preliminary in vitro screen (as in procedure A) or whole cell screen (as in procedure K).

R. Identifying Coferon Dimers that Inhibit Binding of Two Proteins to Each Other, Using a Helper Protein The gene for target protein 1 is linked to the coding sequence for the ProLink alpha-complementing peptide. The gene for target protein 2 is linked to the gene for the EA acceptor protein. Linking of two proteins to each other may be accomplished by fusing the C terminus of one protein to the N-terminus of the second protein, with or without a flexible linker peptide or, alternatively, using an intein to splice the two proteins together, such that both proteins retain biological function. Both of the above constructs are introduced into the target cell, which also produces a helper protein that may have weak or no affinity to target protein 1. A HTS assay containing the target cells in each well or nanodrop is set up, with from 1 to 10 or more coferon A and B dimer variants added to each well or nanodrop. The number of variants will depend on the background level and hit level, determined experimentally. The coferon dimer that enhances binding of the helper protein to target protein 1, and thus best inhibits binding of the two target proteins to each other will give the weakest signals. If necessary, candidate coferon A and B monomers that enhance binding of the helper protein to target protein 1 in the absence of the other protein may be identified by a preliminary in vitro screen (as in procedure C) or whole cell screen (as in procedure M).

S. Identifying Coferon Dimers that Inhibit Binding of Two Proteins to Each Other, Using a Helper Protein The gene for target protein 1 is linked to the coding sequence for the ProLabel alpha-complementing peptide. The ProLabel peptide sequence may be modified to include a nuclear localization signal. The gene for target protein 2 is either currently or is modified to prefer localization in the cytoplasm or at the cellular membrane. The gene for the EA acceptor protein is modified to include a nuclear localization signal. These constructs are introduced into the target cell, which also produces a helper protein that may have weak or no affinity to target protein 2. If needed, expression is adjusted such that under normal conditions binding of target protein 1 (containing the ProLabel peptide) to target protein 2 localizes the two proteins in the cytoplasm or at the cell membrane, thus preventing the ProLabel portion from entering the nucleus and complementing the EA acceptor protein, resulting in low or no background level signal. Addition of from 1 to 10 or more coferon A and B dimer variants (in wells or nanodrops) that enhance binding of the helper protein to target protein 2 in such a way as to disrupt binding to target protein 1, allowing for transport of the ProLabel peptide (linked to target protein 1) to enter the nucleus and combine with the EA acceptor protein, and thus generating positive signal. The number of variants will depend on the background level and hit level, determined experimentally. The coferon dimers that enhances binding of the helper protein to target protein 2, and thus best inhibit binding of the two target proteins to each other will give the strongest signals. If necessary, candidate coferon A and B monomers that enhance binding of the helper protein to target protein 2 in the absence of the other protein may be identified by a preliminary in vitro screen (as in procedure C) or whole cell screen (as in procedure M).

T. Identifying Coferon Dimers that Inhibit Binding of Two Proteins to Each Other, Using a Helper Protein The inverse of the above procedure may be performed using target protein 2 linked to the coding sequence for the ProLabel alpha-complementing peptide, and target protein 1 localized to the cytoplasm or at the cellular membrane. The gene for the EA acceptor protein is modified to include a nuclear localization signal. Both of the above constructs are introduced into the target cell, which also produces a helper protein that may have weak or no affinity to target protein 1. Addition of from 1 to 10 or more coferon A and B dimer variants (in wells or nanodrops) that enhance binding of the helper protein to target protein 1 in such a way as to disrupt binding to target protein 2, allowing for transport of the ProLabel peptide (linked to target protein 2) to enter the nucleus and combine with the EA acceptor protein, will generate a positive signal. Again, if necessary, candidate Coferon A and B monomers that enhance binding of the helper protein to target protein 1 in the absence of the other protein may be identified by a preliminary in vitro screen (as in procedure C) or whole cell screen (as in procedure M).

Screening of Multimer Coferons

Figure 27:
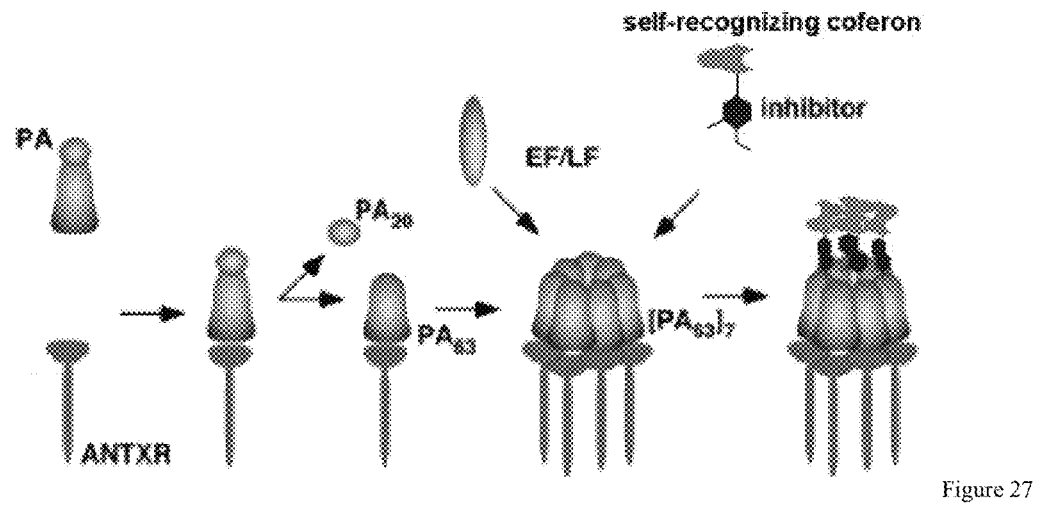

There are many proteins that function only when they assemble into multimeric structures. The coferon design allows for expanding on the multivalency concept. One example is for inhibition of the heptameric protective antigen which is responsible for anthrax toxicity. See FIG. 27.

When considering coferon multimers, it should be recognized that this creates both unique opportunities in drug design, as well as unique challenges in screening for the best multimers. Multimeric coferons may be used to bind to monomeric protein targets, targets comprised of multiple protein monomers or dimer subunits, or targets comprised of multiple different subunits. For example, consider a transporter composed of 3 identical membrane subunits. A coferon drug could be designed wherein the linker element allows for self-assembly of 3 molecules, each with the same diversity element "A".

Figure 28:
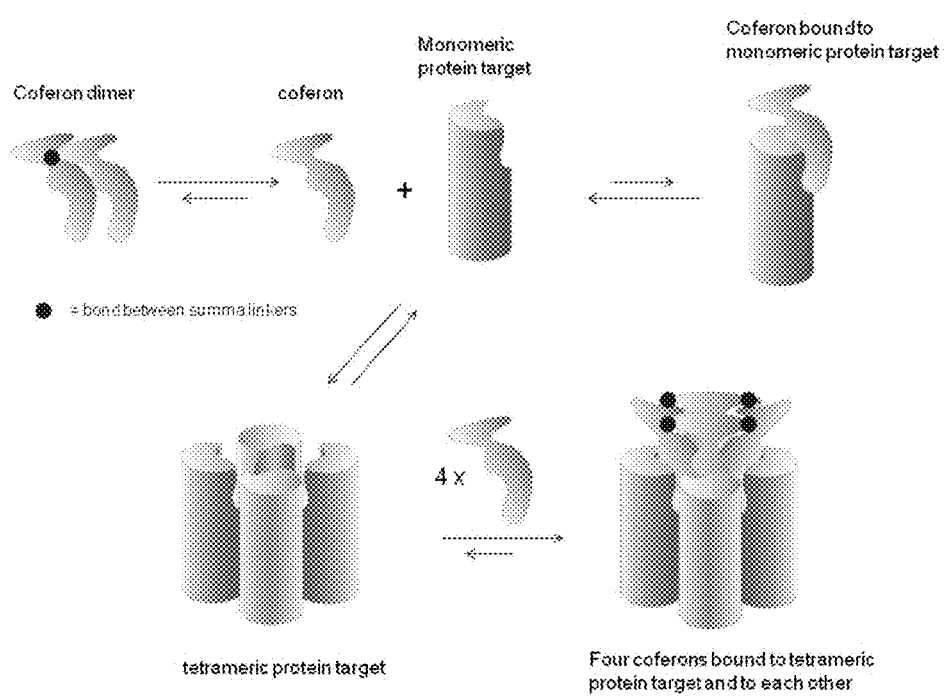
FIG. 28 is a schematic representation of a tetrameric protein being bound by a coferon that can assemble in to tetramers. The coferon dimer is in reversible equilibrium with the monome which accelerates formation of the dimer. Since the dimer binds tightly to the protein target, it does not dissociate easily, and the majority of the protein targets are bound.

In the absence of assembled protein target the coferons bind reversibly and weakly to each other. In addition, each individual coferon may have weak binding to the transporter, but when combining four such interactions together, the tetrameric coferon structure may bind essentially irreversibly. See FIG. 28.

Alternatively, the coferon drug could be composed of two subunits ("A" and "B"), that assemble to form A-B heterodimers, and then continue to assemble to form a 6-membered circular structure of alternating A-B coferons. Each individual coferon may have weak binding to the transporter, but when combining 6 such interactions together, the hexameric coferon structure may bind with the same avidity as full-sized antibodies.

Assembly of linker elements into multimeric structures is discussed in greater detail below (above), but there are some general concepts. It may be very difficult to identify the best binding coferon multimers if more than 3 of the ligands arise from diversity elements. Thus, one theme is to screen for the best coferons under conditions where the same diversity element is connected two or more times to the dynamic combinatorial chemistry element. Here the linker element will be connected to two or more of the same drug molecule and may be in the same geometry to cover two or more linker elements that would be present in the final monomeric form of the coferon drug molecule.

The connection between the linker element and the diversity element may also vary. For example, when the same ligand binds to the same active site in a dimer or tetrameric multimer of the same protein target subunit, the connector would most likely be a flexible (such as an ethylene glycol) chain, to allow for each ligand to bind to an active site, even though the active sites are on different faces of the multimeric protein. Alternatively, if the coferon is binding in a large groove, then the linker element geometry may be critical, both in generating the overall shape of the multimeric scaffold, and in positioning the diversity elements in the proper orientation.

Coferons, by virtue of their ability to bind to an extended surface area of one or more macromolecules provide the opportunity to develop enhanced versions of existing drugs, as well as entirely new classes of inhibitors (See Table 1).

TABLE 1

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| G-PROTEIN COUPLED RECEPTORS | $\beta_2$ adrenergic receptors | epinephrine, norepinephrine | albuterol, salbutamol, terbutaline, salmeterol | propranolol, butoxamine | HitHunter, PathHunter (DiscoverX), cAMP assay, Intracellular calcium flux, TANGO, GeneBlazer, ELISA, binding assays |
| G-PROTEIN COUPLED RECEPTORS | Acetylcholine | Muscarinic receptors | Acetylcholine, Pilocarpine | Scopolamine, atropine, ipratropium, caproctamine | HitHunter, PathHunter (DiscoverX), cAMP assay, Intracellular calcium flux, TANGO, GeneBlazer, ELISA, binding assays |
| G-PROTEIN COUPLED RECEPTORS | H1 histamine receptor | histamine | Histamine | diphenhydramine, doxylamine, pyrilamine, brompheniramine, chlorpheniramine, Loratadine, Fexofenadine, Cetrizine, Desoratadine | HitHunter, PathHunter (DiscoverX), cAMP assay, Intracellular calcium flux, TANGO, GeneBlazer, ELISA, binding assays |
| NUCLEAR RECEPTORS | Estrogen receptor[1-3] | Estriol, estrone, estradiol | 17-beta-estradiol, Chlorotrianisene, Dienestrol, Fosfestrol, Diethylstilbestrol, Zeranol | Tamoxifen, ICI 164,384, Keoxifene, Mepitiostane | Hit-hunter (Discoverx), reporter assays, TANGO, GeneBlazer, ELISA, ligand binding assays, |
| VOLTAGE GATED ION CHANNELS | voltage-gated sodium channels[4-6] | | veratridine, aconitine | tetrodotoxin, saxitoxin, | Intracellular ion flux assays |
| VOLTAGE GATED ION CHANNELS | voltage-gated calcium channels[7-9] | | BAY K 8644, CGP 28392 | ω-conotoxin, ω-agatoxins, dihydropyridine, nifedipine | Intracellular ion flux assays |
| LIGAND GATED ION CHANNELS | kainate receptor[10] | glutamate | kainic acid, domoic acid, LY339434, ATPA, iodowillardiine, (2S,4R)-4-methylglutamic acid | CNQX, LY293558, LY294486 | HitHunter, PathHunter (DiscoverX), cAMP assay, Intracellular ion flux, TANGO, GeneBlazer, ELISA, ligand binding assays, |
| RECEPTOR TYROSINE KINASES | epidermal growth factor receptor (EGFR)[11, 12] | epidermal growth factor | EGF, TGFa, amphiregulin, betacellulin, epiregulin, neuregulins | PD153035, anti-EGFR antibody C225, aeroplysinin-1, AG18, AG82, AG99, AG112, AG213, AG490, AG494, AG527, AG555, AG556 | reporter assays, kinase assays, CO-IP, BRET, FRET, TANGO, GeneBlazer, HitHunter, PathHunter (DiscoverX), ELISA |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| GROWTH FACTORS | Vascular endothelial growth factor[13-16] | VEGFR | | Ranibizumab, bevacizumab, sunitinib, sorafenib, axitinib, pazopanib, Naphthamides | Hit-hunter (Discoverx), reporter assays, TANGO, GeneBlazer, ELISA, ligand binding assays, |
| PROTEASES | Caspase[17] | granzyme B; caspase | Granzyme B, caspase | Z-VAD(OMe)-FMK, Z-VAD-CHO | caspase assays, apoptosis assays, mitochondrial Dy, CO-IP, BRET, FRET, TANGO, GeneBlazer, HitHunter, PathHunter (DiscoverX), ELISA |
| PHOSPHATASES | PP1[18,19] | phosphoserine/threonine residues | | calyculin A, nodularin, tautomycin | protein tyrosine phosphatase assay, CO-IP, BRET, FRET, TANGO, GeneBlazer, HitHunter, PathHunter (DiscoverX), ELISA |
| PROTEIN KINASES | ERK[20-22] | MEK | | AG126, apigenin, Ste-MPKKKPTPIQLNP-NH2 (SEQ ID NO. 5), H-GYGRKKRRQRRR-G-MPKKKPTPIQLNP-NH2 (SEQ ID NO. 6), PD98059, U0126, | kinase assay, CO-IP, BRET, FRET, reporter assays, TANGO, GeneBlazer, HitHunter, PathHunter (DiscoverX) |
| MISC ENZYMES | Adenylate cyclase[23,24] | G proteins, calcium | bordetella pertussis, cholera toxin, forskolin | NKY80, 2',3'-Dideoxyadenosine, 2',5'-Dideoxyadenosine, SQ22536, MDL-12330A | BRET, FRET, calcium flux assays, cAMP assays, TANGO, GeneBlazer, HitHunter, PathHunter (DiscoverX) |
| MISC ENZYMES | Acetylcholin esterase[25-27] | | | Caproctamine, Metrifonate, Physostigmine, Galantamine, Dyflos, Neostigmine | Acetylcholinesterase Assay, Amplex Red, Ellman method, HPLC |
| BIOACTIVE LIPIDS | Ceramide[28-30] | sphingomyelin | TNFα, Fas ligand, 1,25 dihydroxy vitamin D, γ-interferon | fumonisin B | TLC lipid charring, diacylglycerol kinase labeling in vitro |
| CYTOKINES | IL2[31-37] | IL2R | BAY 50-4798, P1-30, SP4206 | daclizumab, basiliximab, SP4206 | TANGO, GeneBlazer, HitHunter, PathHunter (DiscoverX), IL2 dependent mouse CTLL cell line, ELISA |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| MISC PROTEINS | BCLXL[38-40] | BAD | | BH3I-1, A-371191, ABT-737 | TANGO, GeneBlazer, HitHunter, PathHunter (DiscoverX), CO-IP, BRET, FRET, ELISA |
| MISC PROTEINS | p53[41-44] | MDM2, JNK1-3, ERK1-2, p38 MAPK, ATR, ATM, Chk1, Chk2, DNA-PK, CAK | PRIMA-1, MIRA-1, RITA, | Pifithrin-α | caspase assays, apoptosis assays, mitochondrial Dy, CO-IP, BRET, FRET, TANGO, GeneBlazer, HitHunter, PathHunter (DiscoverX), ELISA |
| MISC PROTEINS | Tubulin[27,45,46] | tubulin | | ALB109564, ABT-751, D24851, D64131, benomyl, estramustine, LY290181 | kinase assay, CO-IP, BRET, FRET, reporter assays, TANGO, GeneBlazer, β-arrestin(DiscoverX |
| MISC PROTEINS | β-amyloid[47-51] | | | L 1,10-phenanthroline derivatives, KLVFF (SEQ ID NO. 7), LVFFA (SEQ ID NO. 8), Memoquin, SLF-CR | Stagnant Amyloid Fibril Formation Assay, amyloid fibrillization assay |
| MISC PROTEINS | thymidylate synthase[52-56] | | | raltitrexed, pemetrexed, nolatrexed, ZD9331, GS7904L, fluorouracil | caspase assays, apoptosis assays, mitochondrial Dy, CO-IP, BRET, FRET, TANGO, GeneBlazer, HitHunter, PathHunter (DiscoverX), ELISA |
| UBIQUITIN LIGASES | MDM2[57-59] | p53 | | trans-4-Iodo, 4'-boranyl-chalcone, Nutlins, MI-219, MI-63, RITA, HLI98 | TANGO, GeneBlazer, HitHunter, PathHunter (DiscoverX), CO-IP, BRET, FRET, ELISA, reporter assay |
| VIRAL REGULATORS | HPV E2[60,61] | HPV E1 | | indandiones, podophyllotoxin | E2 displacement assay, TANGO, GeneBlazer, HitHunter, PathHunter (DiscoverX), CO-IP, BRET, FRET, ELISA, reporter assay |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| BACTERIAL CELL DIVISION PROTEINS | ZipA[62] | FtsZ | | substituted 3-(2-indolyl) piperidines, 2-phenyl indoles | TANGO, GeneBlazer, HitHunter, PathHunter (DiscoverX), CO-IP, BRET, FRET, ELISA, reporter assay, polarization competition assay, |
| CYTOKINES | TNF[63] | TNFR | | infliximab, adalimumab, etanercept | TANGO, GeneBlazer, HitHunter, PathHunter (DiscoverX), CO-IP, BRET, FRET, ELISA, |
| SCAFFOLD PROTEINS | JIP1[64, 65] | JNK | | BI-78D3, TIJIP | TANGO, GeneBlazer, HitHunter, PathHunter (DiscoverX), CO-IP, BRET, FRET, ELISA, kinase assay |
| DNA REPAIR | PARP[66-69] | | | INO-1001, AG014699, BS-201, AZD2281, BS-401 | TANGO, GeneBlazer, HitHunter, PathHunter (DiscoverX), CO-IP, BRET, FRET, ELISA, |
| RIBOSOMES | Antibiotics[70] | ribosomes | | tetracyclins, macrolides, lincosamides, streptogramins | cell death assay, |
| HISTONE DEACETYLASES | HDAC1[71-73] | | | suberoylanilide hydroxamic acid, trichostatin A, LBH589 | TANGO, GeneBlazer, HitHunter, PathHunter (DiscoverX), CO-IP, BRET, FRET, ELISA, |
| APOPTOSIS REGULATORS | XIAP[74, 75] | SMAC/DIABLO, caspase 3, caspase 7, caspase 9 | | SM102-SM130 | CO-IP, BRET, FRET, reporter assays, TANGO, GeneBlazer, HitHunter, PathHunter (DiscoverX), cell death assays |
| CHAPERONE PROTEINS | Hsp90[76, 77] | Cdc37, survivin | | Celastrol, shepherdin | CO-IP, BRET, FRET, reporter assays, TANGO, GeneBlazer, HitHunter, PathHunter (DiscoverX), |
| SERINE/THREONINE PROTEIN KINASES | mTOR[78, 79] | Raptor, mLST8/GβL | | Rapamycin, caffeine, farnesylthiosalicylic acid, curcumin, temsirolimus, everolimus | kinase assay, CO-IP, BRET, FRET, reporter assays, TANGO, GeneBlazer, HitHunter, PathHunter (DiscoverX) |

TABLE 1-continued

Examples of Protein Families and Their Pharmacological Targets

| TARGET FAMILY | TARGET EXAMPLE | ENDOGENOUS LIGAND (MODULATORS) | EXAMPLES OF CURRENT AGONISTS (ACTIVATORS) | EXAMPLES OF CURRENT ANTAGONISTS (INHIBITORS) | EXAMPLES OF DETECTION ASSAYS |
|---|---|---|---|---|---|
| SERINE/THREONINE-PROTEIN KINASES | B-raf & B-raf V600E[80] | K-ras | | PLX4720 | kinase assay, CO-IP, BRET, FRET, reporter assays, TANGO, GeneBlazer, HitHunter, PathHunter (DiscoverX), |
| CYCLIN DEPENDENT KINASES | CDK2 [81,82] | Cyclin A, cyclin E | | Variolin, Meriolin | kinase assay, CO-IP, BRET, FRET, reporter assays, TANGO, GeneBlazer, HitHunter, PathHunter (DiscoverX), |
| GROWTH FACTOR RECEPTORS | IGF-1R [83] | IGFII | | PQIP | CO-IP, BRET, FRET, reporter assays, TANGO, GeneBlazer, HitHunter, PathHunter (DiscoverX), |
| PROTEASOME | 20S [84,85] | 19S | | Bortezomib, salinosporamide A, | CO-IP, BRET, FRET, cell viability |

All of the following citations are hereby incorporated by reference in their entirety.
1. Jordan, V. C., et al., *J Clin Oncol*, 25: 5815-24 (2007).
2. Jordan, V. C., et al., *Steroids*, 72: 7-25 (2007).
3. Dahlman-Wright, K., et al., *Pharmacological Rev*, 58: 773-81 (2006).
4. Johannessen Landmark, C., *CNS Drugs*, 22: 27-47 (2008).
5. Roselli, F., et al., *Recent Patents on CNS Drug Discovery*, 1: 83-91 (2006).
6. Heinemann, S H., et al., *Cell Mol Life Sci*, 64: 1329-40 (2007).
7. Hidalgo, P., et al., *Cell Calcium*, 42: 389-96 (2007).
8. Gribkoff, V. K., *Semin Cell Dev Biol*, 17: 555-64 (2006).
9. Le Guennec, J. Y., et al., *Recent Patents on Anti-Cancer Drug Discovery*, 2: 189-202 (2007).
10. Lees, G. J., *Drugs*, 59: 33-78 (2000).
11. Voelzke, W. R., et al., *Curr Treat Options Oncol*, 9: 23-31, (2008).
12. Ng, K., et al., *Critical Rev Oncol Hematol*, 65: 8-20 (2008).
13. Harmange, J. C., et al., *J Med Chem*, 51: 1649-67 (2008).
14. Borzilleri, R. M., et al., *J Med Chem*, 48: 3991-4008 (2005).
15. Ignoffo, R. J., *Am J Health-Syst Ph*, 61: S21-6 (2004).
16. Bates, D. O., et al., *Microcirculation*, 6: 83-96 (1999).
17. Denault, J. B., et al., *Meth Mol Biol*, 414: 191-220 (2008).
18. Ishida, A., et al., *Pharmacol Therap*, 100: 291-305 (2003).
19. Vogt, A., et al., *Pharmacol Therap*, 107: 212-21 (2005).
20. Ohori, M., *Drug News Perspect*, 21: 245-50 (2008).
21. Kelemen, B. R., et al., *J Biol Chem*, 277: 8741-8 (2002).
22. Favata, M. F., et al., *J Biol Chem*, 273: 18623-32 (1998).
23. Onda, T., et al., *J Biol Chem*, 276: 47785-93 (2001).
24. Iwatsubo, K., et al., *Endocr Metab Immune Disord Drug Targets*, 6: 239-47 (2006).
25. Rosini, M., et al., *J Med Chem*, 51: 4381-4 (2008).
26. Tumiatti, V., et al., *J Med Chem*, 46: 954-66 (2003).
27. Singh, P., et al., *IUBMB Life*, 60: 368-75 (2008).
28. Marasas, W. F., et al., *J Nutrition*, 134: 711-6 (2004).
29. Soriano, J. M., et al., *Prog Lipid Res*, 44: 345-56 (2005).
30. Menaldino, D. S., et al., *Pharmacol Res*, 47: 373-81 (2003).
31. Mottershead, M., et al., *Expert Opin Biol Th*, 7: 1583-96 (2007).
32. Kapic, E., et al., *Medicinski Arhiv*, 58: 373-6 (2004).
33. Thanos, C. D., et al., *Proc Natl Acad Sci USA*, 103: 15422-7 (2006).
34. Hartmann, G., *Curr Opin Mol Ther*, 6: 221-7 (2004).
35. Eckenberg, R., et al., *Cell Mol Biol*, 47: 703-7 (2001).
36. Arkin, M. R., et al., *Proc Natl Acad Sci USA*, 100: 1603-8 (2003).
37. Braisted, A. C., et al., *J Am Chem Soc*, 125: 3714-5 (2003).
38. Hetschko, H., et al., *J Neuro-Oncol*, 86: 265-72 (2008).
39. Schwartz, P. S., et al., *Mol Cancer Ther*, 6: 2073-80 (2007).
40. Wang, L., et al., *Bioorg Med Chem Lett*, 18: 236-40 (2008).
41. Bykov, V. J., et al., *Nature Med*, 8: 282-8 (2002).
42. Bykov, V. J., et al., *J Biol Chem*, 280: 30384-91 (2005).
43. Issaeva, N., et al., *Nature Med*, 10: 1321-8 (2004).
44. Komarov, P. G., et al., *Science*, 285: 1733-7 (1999).
45. Kuppens, I. E., *Curr Clin Pharmacol*, 1: 57-70 (2006).
46. Galmarini, C. M., *Curr Opin Investig D*, 6: 623-30 (2005).
47. Barnham, K. J., et al., *Proc Natl Acad Sci USA*, 105: 6813-8 (2008).

48. Kelly, J. W., *New Engl J Med*, 352: 722-3 (2005).
49. Blazer, L. L., et al., *Neuropsychopharmacology*, (2008)
50. Takahashi, T., et al., *Accounts Chemical Res*, 41: 1309-18 (2008).
51. Green, N. S., et al., *J Am Chem Soc*, 125: 13404-14 (2003).
52. Van Cutsem, E., *Expert Opin Inv Drug*, 7: 823-34 (1998).
53. Taylor, E. C., *Adv Exp Med Biol*, 338: 387-408 (1993).
54. Dash, A. K., et al., *J Pharm Sci*, 85: 1123-7 (1996).
55. Jackman, A. L., et al., *Adv Exp Med Biol*, 370: 185-8 (1994).
56. Chu, E., et al., *Cancer Chemo Pharmacol*, 52: S80-9 (2003).
57. Kumar, S. K., et al., *J Med Chem*, 46: 2813-5 (2003).
58. Vassilev, L. T., *Cell Cycle*, 3: 419-21 (2004).
59. Shangary, S., et al., *Proc Natl Acad Sci USA*, 105: 3933-8 (2008).
60. Liu, Y., et al., *Biochemistry*, 42: 8862-9 (2003).
61. Schaack, J., et al., *J Virol*, 64: 78-85 (1990).
62. Jennings, L. D., et al., *Bioorgan Med Chem*, 12: 5115-31 (2004).
63. Hochberg, M. C., et al., *Ann Rheum Dis*, 62: 13-6 (2003).
64. Stebbins, J. L., et al., *Proc Natl Acad Sci USA*, 105: 16809-13 (2008).
65. Arthur, P. G., et al., *J Neurochem*, 102: 65-76 (2007).
66. Woodhouse, B. C., et al., *DNA Repair*, 7: 1077-86 (2008).
67. Ashworth, A., *J Clin Oncol*, 26: 3785-90 (2008).
68. Martin, S. A., et al., *Curr Opin Gen Dev*, 18: 80-6 (2008).
69. Haince, J. F., et al., *Trends Mol Med*, 11: 456-63 (2005).
70. Tenson, T., et al., *Mol Microbiol*, 59: 1664-77 (2006).
71. Carew, J. S., et al., *Cancer Lett*, 269: 7-17 (2008).
72. Shankar, S., et al., *Adv Exp Med Biol*, 615: 261-98 (2008).
73. Jones, P., et al., *Curr Pharm Design*, 14: 545-61 (2008).
74. Sun, H., et al., *Accounts Chemical Res*, 41: 1264-77 (2008).
75. Nikolovska-Coleska, Z., et al., *Anal Biochem*, 374: 87-98 (2008).
76. Plescia, J., et al., *Cancer Cell*, 7: 457-68 (2005).
77. Zhang, T., et al., *Mol Cancer Ther*, 7: 162-70 (2008).
78. Cruzado, J. M., *Transplantation Rev*, 22: 73-81 (2008).
79. LoPiccolo, J., et al., *Drug Res Update*, 11: 32-50 (2008).
80. Tsai, J., et al., *Proc Natl Acad Sci USA*, 105: 3041-6 (2008).
81. Echalier, A., et al., *J Med Chem*, 51: 737-51 (2008).
82. Bettayeb, K., et al., *Cancer Res*, 67: 8325-34 (2007).
83. Ji, Q. S., et al., *Mol Cancer Ther*, 6: 2158-67 (2007).
84. Guedat, P., et al., *BMC Biochemistry*, 8: S14 (2007).
85. Williamson, M. J., et al., *Mol Cancer Ther*, 5: 3052-6 (2006).

At their most basic level, coferons may interfere or enhance protein activity where the substrate ranges in size from a medium to macromolecule. For example, coferons may be designed to inhibit sequence-specific proteases, such as the caspases, which play a role in the apoptotic pathway (See FIGS. 2.17A and B).

Coferons may be used to inhibit or facilitate protein-protein interactions, including activating or inactivating a signaling pathway (FIGS. 2.17C, 2.19H and I). Coferons may activate signaling through more than one mechanism. For example, the coferon may do more than link two proteins together more tightly. It also further affects the conformation of the target protein so that it is more active compared to when the two proteins are bound in the absence of coferon (FIG. 2.19H). Alternatively, coferons may shift the equilibrium to tighter binding so that the numbers of complexes in the bound state is greater. In some cases, the coferon may act as a mimetic of a protein-protein interaction, either activating or inactivating signaling from that target (FIGS. 2.18D-G).

To illustrate these concepts, consider the Wnt signaling pathway, which is often disregulated in colon cancer. Wnt proteins bind to and activate the Frizzled receptor, which in turn act via Dishevelled to suppress the activity of GSK-3 3. Under normal conditions, GSK-3β is part of a complex with axin and APC, which binds β-catenin. However, when Dishevelled suppresses the activity of GSK-3β, this prevents GSK-3β from phosphorylating β-catenin, which therefore escapes degradation and accumulates in the cytoplasm and in the nucleus. Once in the nucleus, β-catenin associates with Tcf/Lef transcription factor to drive the expression of a variety of genes, such as Myc, which enable cell proliferation.

In this Wnt signaling pathway, coferons could be designed to: (i) Inhibit Wnt binding to Frizzled; (ii) Inhibit frizzled activation of disheveled; (iii) Inhibit Dishevelled inactivation of GSK-3β; (iv) Enhance binding of β-catenin to Axin; and (v) Inhibit binding of β-catenin to Tcf/Lef.

In colon tumors, the APC gene is often truncated or reduced in copy number or expression, thus it no longer binds β-catenin, liberating β-catenin to migrate into the nucleus. However, coferons designed to enhance binding of β-catenin to Axin, allow active GSK-3beta to phosphorylate β-catenin and send it down a path of degradation, thus avoiding proliferation and inhibiting tumor growth.

Some proteins, such as the tumor suppressor p53, are mutated in cancer cells, causing them to unfold more easily and thus not function properly. Binding of a coferon across the surface of such a protein may act as a molecular staple, keeping the domains or regions in the proper conformation (FIG. 2.20). Likewise, some proteins undergo conformational changes, which may activate or deactivate enzymatic activity or additional signaling. Coferons may be designed to bind one or the other conformer more tightly, and thus act as an activator or inhibitor of protein function (FIG. 2.18).

There are examples in nature where a small molecule (FK506, rapamycin) uses a helper protein (FKBP) to create a composite surface that binds the target protein (calcineurin, FRAP) more tightly. This helper protein may be used to either recruit additional protein(s) or inhibit binding of other proteins to the target protein. Coferons may be designed to mimic the role of FK506 to either enhance binding of a new protein to the complex (FIG. 2.22O, FIGS. 2.24R-T), or inhibit binding of a new protein to the complex (FIG. 2.23Q). In these examples (FIG. 2.22O, FIGS. 2.24R-S), the linker elements were designed to mimic the portion of FK506 that binds tightly to FKBP ("orange" protein), but many other configurations may also be used.

Many proteins use protein interaction domains as modular units within their structure to achieve their desired functions. (See Table 2)

TABLE 2

Examples of Protein Domains

| DOMAIN | PARTNER | EXAMPLE OF PROTEIN CONTAINING DOMAIN | EXAMPLES OF KNOWN INHIBITORS | EXAMPLES OF DETECTION ASSAYS | APPROXIMATE $K_D$ OF BINDING PARTNERS |
|---|---|---|---|---|---|
| SH2 | Phospho-tyrosine residues | Grb2 | Fmoc-Glu-Tyr-Aib-Asn-NH2; Ac-SpYVNVQ-NH2, macrocycles, STATTIC[1-4] | Surface plasmon resonance (SPR) technology, | 0.2 - 11 μM[5-10] |
| FHA | Phospho-threonine and phospho-tyrosine residues | KIF13B | | | 1 - 100 μM[11, 12] |
| 14-3-3 | Phospho-serine residues | 14-3-3 | R18[13] | | 7 nM - 20 μM[14-16] |
| WW | ligands containing PpxY, Proline-rich sequences | Pin1 | Zn(II) Dipicolylamine-based artificial receptors[17] | | 6 nM - 190 nM[18-20] |
| WD40 | | Apaf-1 | | | 1 μM[21] |
| MH2 | phospho-serine residues | SMAD2 | | | 240 nM[22] |
| BROMO | acetylated lysine residues | CBP | | | 1 μM - 4 mM[23-25] |
| UBA | mono-, di-, tri-, and tetra-ubiquitin | HHR23A | | | 6 μM - 2.35 mm[26-28] |
| PTB | Phospho-tyrosine residues, Asn-Pro-X-Tyr motifs (SEQ ID NO. 4) | IRS-1 | LSNPTX-NH2 (SEQ ID NO. 9), LYASSNOAX-NH2 (SEQ ID NO. 10), LYASSNPAX-NH21_2[29] (SEQ ID NO. 11) | PTB domain binding assays | 160 nM - 10 μM[30-33] |
| SH3 | Proline-rich peptides with consensus Pro-X-X-Pro (SEQ ID NO. 3), | Grb2 | Peptidimer-c, VPPPVPPRRR (SEQ ID NO. 12), (VPPPVPPRRR)2K)[10, 34] (SEQ ID NO. 12) | | 1-500 μM[10, 35-37] |
| EVH1 | FPxΦP motifs, PPxxF motifs | ActA | | | 10-50 μM[38-40] |
| GYF | proline-rich sequences, | CDBP2 | | | 10-160 μM[41] |
| VHS | | TOM1 | | | 11 - 50 μM[42-44] |
| PDZ | PDZ, Val-COOH | MNT1 | NSC668036, FJ9[45,46] | | 1 - 500 μM[47-50] |
| PUF | RNA | PUM1 | | | 10 - 100 nM[51-53] |
| TUBBY | DNA, phosphotidylinositol | TULP1 | | | |
| SAM | | CNK | | | 71 nM - 1 μM[54-56] |
| DD | DD | FADD | | | |
| CARD | CARD | Apaf-1 | | | 1.4 μM[57] |
| PyD | PyD | Pyrin | | | 4 μM[58] |
| PB1 | PB1 | Bem1 | | | 4 - 500 nM[59-61] |
| BRCT | BRCT | BRCA1 | | | 113 nM - 6 μM[62-66] |

TABLE 2-continued

Examples of Protein Domains

| DOMAIN | PARTNER | EXAMPLE OF PROTEIN CONTAINING DOMAIN | EXAMPLES OF KNOWN INHIBITORS | EXAMPLES OF DETECTION ASSAYS | APPROXIMATE $K_D$ OF BINDING PARTNERS |
|---|---|---|---|---|---|
| PH | phosphatidylinositol-4,5-bisphosphate, PI-3,4-P2 or PI-3,4,5-P3 | AKT1 | NSC 348900, perifosine, SH5, SH23, SH24, SH25, ml14, ml15, ml16 [67-69] | | 1.76 nM - 350 µM [30, 70-75] |
| FYVE | Phosphatidylinositol 3-phosphate, zinc | SARA | | | 50 nM - 140 µM |
| C1 | phorbol esters, diacylglycerol | PKC isoforms | | | 0.58 - 800 nM [76-79] |
| FERM | PI(3)P, PI(4)P, PI(5)P, IP3, | PTLP 1 | | | 200 nM - 30 µM [80-82] |
| C2 | Calcium, acidic phospholipids | Nedd4 | | | 250 nM - 94 µM [83-85] |
| PX | PI(3,4)P2, PI(3)P, PI(3,5)P2, PI(4)P, PI(5)P, PI(3,4,5)P3, PI(4,5)P2 | CISK | | | 1.8 nM - 50 µM [36, 86, 87] |
| ENTH | PtdIns(4,5)P2, PtdIns(1,4,5)P3, PI(3,4)P2; PI(3,5)P2 | Epsin1 | | | 98 nM - 1 µM [88-90] |

All of the following citations are hereby incorporated by reference in their entirety.

1. Choi, W. J., et al., *Bioorg Med Chem Lett*, 16: 5265-9 (2006).
2. Lung, F. D., et al., *Biopolymers*, 80: 628-35 (2005).
3. Ogura, K., et al., *J Biomol NMR*, 42: 197-207 (2008).
4. Schust, J., et al., *Chem Biol*, 13: 1235-42 (2006).
5. Domchek, S. M., et al., *Biochemistry*, 31: 9865-70 (1992).
6. Piccione, E., et al., *Biochemistry*, 32: 3197-202 (1993).
7. Case, R. D., et al., *J Biol Chem*, 269: 10467-74 (1994).
8. Ladbury, J. E., et al., *Proc Natl Acad Sci USA*, 92: 3199-203 (1995).
9. Porter, C. J., et al., *Eur Biophys J*, 34: 454-60 (2005).
10. Garbay, C., et al., *Biochem Pharmacol*, 60: 1165-9 (2000).
11. Byeon, I.-J. L., et al., *J Mol Biol*, 314: 577 (2001).
12. Byeon, I. J., et al., *Nat Struct Mol Biol*, 12: 987-93 (2005).
13. Petosa, C., et al., *J Biol Chem*, 273: 16305-10 (1998).
14. Masters, S. C., et al., *Biochemistry*, 38: 5216-21 (1999).
15. Rajagopalan, S., et al., *Nucleic Acids Res*, 36: 5983-91 (2008).
16. Wang, B., et al., *Biochemistry*, 38: 12499-504 (1999).
17. Ojida, A., et al., *J Am Chem Soc*, 128: 2052-8 (2006).
18. Koepf, E. K., et al., *Biochemistry*, 38: 14338-51 (1999).
19. Kanelis, V., et al., *Nat Struct Biol*, 8: 407-12 (2001).
20. Dalby, P. A., et al., *Protein Sci*, 9: 2366-76 (2000).
21. Nash, P., et al., *Nature*, 414: 514 (2001).
22. Chong, P. A., et al., *J Biol Chem*, 279: 40707-14 (2004).
23. Sun, H., et al., *Biochem Biophys Res Comm*, 358: 435 (2007).
24. Dhalluin, C., et al., *Nature*, 399: 491 (1999).
25. Mujtaba, S., et al., *Mol Cell*, 13: 251 (2004).
26. Murphy, J. M., et al., *Proc Natl Acad Sci USA*, 104: 14336-41 (2007).
27. Trempe, J. F., et al., *Embo J*, 24: 3178-89 (2005).
28. Matta-Camacho, E., et al., *J Mol Biol*, 386: 569 (2009).
29. Giorgetti-Peraldi, S., et al., *Mol Cell Biol*, 17: 1180-8 (1997).
30. Zwahlen, C., et al., *Embo J*, 19: 1505-15 (2000).
31. Li, S. C., et al., *Proc Natl Acad Sci USA*, 94: 7204-9 (1997).
32. Takeuchi, H., et al., *Biochem J*, 334: 211-8 (1998).
33. Dhalluin, C., et al., *Mol Cell*, 6: 921 (2000).
34. Ye, Y. B., et al., *Biochem Pharmacol*, 75: 2080-91 (2008).
35. Demers, J.-P., et al., *J Am Chem Soc*, 131: 4355-67 (2009).
36. Hiroaki, H., et al., *Nat Struct Biol*, 8: 526-30 (2001).
37. Donaldson, L. W., et al., *Proc Natl Acad Sci USA*, 99: 14053-8 (2002).
38. Zimmermann, J., et al., *J Biol Chem*, 278: 36810-8 (2003).
39. Ball, L. J., et al., *Embo J*, 19: 4903-14 (2000).
40. Machner, M. P., et al., *J Biol Chem*, 276: 40096-103 (2001).
41. Kofler, M., et al., *J Biol Chem*, 280: 33397-402 (2005).
42. Zhu, G., et al., *FEBS Lett*, 537: 171 (2003).
43. He, X., et al., *Biochemistry*, 42: 12174-80 (2003).
44. Yoon-Hun, H., et al., *FEBS Lett*, 583: 287 (2009).
45. Fujii, N., et al., *Cancer Res*, 67: 573-9 (2007).
46. Shan, J., et al., *Biochemistry*, 44: 15495-503 (2005).
47. Li, X., et al., *Protein Sci*, 15: 2149-58 (2006).
48. Hoffmoller, U., et al., *Angewandte Chemie International Ed*, 38: 2000-4 (1999).
49. Harris, B. Z., et al., *Biochemistry*, 40: 5921-30 (2001).
50. Niethammer, M., et al., *Neuron*, 20: 693 (1998).
51. Hook, B., et al., *Rna*, 11: 227-33 (2005).
52. Miller, M. T., et al., *Nat Struct Mol Biol*, 15: 397 (2008).
53. Stumpf, C. R., et al., *RNA*, 14: 1550-7 (2008).
54. Kim, C. A., et al., *Nat Struct Biol*, 9: 453-7 (2002).
55. Kim, C. A., et al., *J Biol Chem*, 280: 27769-75 (2005).

56. Bhunia, A., et al., *Proteins*, 74: 328-43 (2009).
57. Chen, Y. R., et al., *Protein Sci*, 13: 2196-206 (2004).
58. Srimathi, T., et al., *J Biol Chem*, 283: 15390-8 (2008).
59. Wilson, M. I., et al., *Mol Cell*, 12: 39 (2003).
60. Massenet, C., et al., *J Biol Chem*, 280: 13752-61 (2005).
61. Muller, S., et al., *FEBS Lett*, 580: 341-4 (2006).
62. Manke, I. A., et al., *Science*, 302: 636-9 (2003).
63. Williams, R. S., et al., *Nat Struct Mol Biol*, 11: 519-25 (2004).
64. Yu, X., et al., *Science*, 302: 639-42 (2003).
65. Ekblad, C. M., et al., *Protein Sci*, 13: 617-25 (2004).
66. Shiozaki, E. N., et al., *Mol Cell*, 14: 405 (2004).
67. Mahadevan, D., et al., *Mol Cancer Ther*, 7: 2621-32 (2008).
68. Kondapaka, S. B., et al., *Mol Cancer Ther*, 2: 1093-103 (2003).
69. Caron, R. W., et al., *Mol Cancer Ther*, 4: 257-70 (2005).
70. Chen, R. H., et al., *Embo J*, 16: 1351-9 (1997).
71. Zheng, J., et al., *J Mol Biol*, 255: 14 (1996).
72. Bourguignon, L. Y., et al., *J Biol Chem*, 279: 26991-7007 (2004).
73. Zhu, G., et al., *Embo J*, 26: 3484-93 (2007).
74. Levine, T. P., et al., *Curr Biol*, 8: 729 (1998).
75. Landgraf, K. E., et al., *Biochemistry*, 47: 12260-9 (2008).
76. Harjes, E., et al., *Structure*, 14: 881-8 (2006).
77. Lorenzo, P. S., et al., *Mol Pharmacol*, 57: 840-6 (2000).
78. Eing, A., et al., *Chembiochem*, 3: 190-7 (2002).
79. Aroca, P., et al., *FEBS Lett*, 483: 27-32 (2000).
80. Takai, Y., et al., *Acta Crystallogr F*, 63: 49-51 (2007).
81. Terawaki, S., et al., *Acta Crystallogr F*, 64: 911-3 (2008).
82. Yang, Y., et al., *Proc Natl Acad Sci USA*, 106: 4189-94 (2009).
83. Reddy Nanga, R. P., et al., *Protein Expr Purif*, 52: 329-33 (2007).
84. Sanchez-Bautista, S., et al., *J Mol Biol*, 362: 901 (2006).
85. Benes, C. H., et al., *Cell*, 121: 271-80 (2005).
86. Karathanassis, D., et al., *Embo J*, 21: 5057-68 (2002).
87. Stahelin, R. V., et al., *J Biol Chem*, 279: 54918-26 (2004).
88. Horn, R. A., et al., *J Mol Biol*, 373: 412-23 (2007).
89. RA, T., et al., *Science*, 291: 1047-51 (2001).
90. Hussain, N. K., et al., *J Biol Chem*, 278: 28823-30 (2003).

For example, SH2 domains are miniature receptors for protein regions containing a phosphorylated tyrosine. SH2 domains are found in proteins that act as, or play a role in: adaptors, scaffolds, kinases, phosphatases, ras signalling, transcription, ubiquitination, cytoskeletal regulation, signal regulation, and phospholipid second messenger signaling. As another example, SH3 domains bind peptide loops with the motif RXXK (SEQ ID NO. 13) or PXXP (SEQ ID NO. 3). Many proteins have both SH2 and SH3 domains, which act as "receptors" to bind one or more protein partners. Coferons may be designed to inhibit binding of a phosphotyrosine protein to its cognate SH2 domain. Alternatively, coferons may be designed so one ligand binds one motif (i.e. SH2), and a second ligand binds a second motif (i.e. SH3), either on the same or different proteins.

Many large proteins or macromolecular complexes (such as ribosomes—see below, tubulin filaments) have multiple binding sites with known drug inhibitors. Coferons may be used to bring together two previous drugs on the same target to: (i) bind the target with higher affinity; (ii) exhibit a stronger inhibition than either drug alone; (iii) exhibit greater activation than either drug alone; or (iv) create a binding entity covering a larger surface area of the target, making it harder for the organism/cell/virus to develop resistance to the drug via point mutations.

Coferons may be used to create bifunctional drugs that bind to the same target, for example, protein receptor tyrosine kinases. One ligand would bind to the ATP binding site, while the other mimics the auto-inhibiting peptide. These two ligands would be attached to separate coferons, which when brought into the proper proximity by linker element binding, would lock down into both binding pockets and bind the receptor kinase with excellent specificity. This approach would overcome limitations of earlier inhibitor designs that bind only to one pocket and, consequently, lack either proper specificity, or sufficient binding affinity to be effective drugs in vivo.

Combining multiple known drugs using coferons may generate new classes of agonists or antagonists for: protein kinases, calcium channel proteins, muscarinic receptors (antagonists), beta-2 adrenergic receptor (agonist), sodium channel drugs, and H1 histamine receptor (antagonists). See Table 1. Receptor proteins provide multiple opportunities for coferon design to inhibit, activate, dampen, or amplify signals (FIG. 2.28 and FIG. 2.29).

Many proteins act as dimers. Homodimer coferons could act as agonists to help keep two receptors close enough for auto-phosphorylation and activation (FIG. 2.25 B2). Homodimers could also act as antagonists, by preventing two receptors from undergoing auto-phosphorylation (FIG. 2.26 C2). Coferon heterodimers may also act to dampen (FIG. 2.26 D2) or amplify (FIG. 2.27 E2) ligand directed signaling.

Use of coferon homodimers may also help inhibit dimer enzymes by blocking both ligand-binding sites simultaneously (FIG. 2.30 A3). Such homodimer, homotetramer, heterotetramer, hexamer, and other multimer coferons may have PEG linkers or other spacers to the linker elements, allowing for binding two sites that are several nanometers apart (FIGS. 2.30 B3 and C3, FIGS. 2.31 D3-F3). They may use linker elements that bind to each other with minimal or no added help from the ligand binding events.

Many proteins have allosteric sites to either activate or inhibit enzymatic activity. Such sites are generally too distant from the active site to allow for a traditional small molecule drug to bind to both sites simultaneously. However, heterodimer coferons composed of ligands that bind into both the allosteric and either adjacent or active site regions would be potent activators or inhibitors.

Microtubulins play a key role during mitosis and differentiation, and thus are targeted in treating tumors. Microtubulins are composed of two subunits, alpha and beta tubulin that are in a dynamic instability either assembling or disassembling during the cell cycle. During mitosis, the rates of both assembly and disassembly are increased so that the chromosomes can capture the microtubules forming the mitotic spindle. During differentiation, microtubule-associated proteins help stabilize the filaments, thus allowing cellular cytoplasm to organize. Vinca alkaloid anticancer agents such as vincristine and vinblastine are cytotoxic by disrupting microtubules, while taxanes such as palitaxel and docetaxel stabilize microtubules, and thus may nudge tumor cells toward differentiation. Coferon pairs composed of one or two tubulin ligands may have enhanced antitumor activity (see FIG. 2.32).

Many neurodegenerative diseases arise due to misfolding of proteins that aggregate to form plaques. For example, Alzheimer's disease arises due to plaques composed of amyloid beta-peptide. Since coferons assemble at the target site, there is an opportunity to design coferons small enough to traverse the blood-brain barrier, yet large enough to combine on the surface of amyloid beta-peptide monomers and inhibit formation of oligomers and ultimately amyloid fibrils (FIG. 2.33).

Some linker element designs may allow linker elements to bind to each other with minimal or no added binding help from the diversity elements. Such designs include linker elements that bind to each other with the aid of a metal cofactor (see below). These designs expand the potential uses of coferons.

As another example of irreversible association within a cell, one coferon may have a disulfide group beta to a primary amine, while the other may have a ketone group. In the blood stream or in non-cancerous cells, the two coferons may associate through forming a Schiff base between the amine and the ketone group. However, upon entering cancer cells, the disulfide is reduced to a thiol, which may then act in concert with the primary amine to create a thiazolidine linker. Such dimer coferons may be used to bring two target proteins into close proximity.

Coferons using linker elements that bind to each other with minimal or no added help from the target binding event may be used to generate bifunctional drugs to different targets. Such drugs would concentrate two cancer-fighting ligands into the same cancer cell. This approach is also being used with HIV drugs.

Such coferons may also be used to create trap-door drugs. One coferon would be designed to bind to a target that is found in abundance in the target cancer cell, but not so frequently in normal cells. This coferon would be administered first to the patient. Subsequently, a second coferon with known drug moiety would be administered. The second coferon enters most cells, but then is preferentially trapped in target cancer cells. This approach may need to use coferons with almost irreversible linkages between linker elements.

The trap-door concept may be used in reverse to clog drug export pumps, many of which are responsible for resistance to chemotherapy. Coferons are designed to enter cells as monomers. One of the diversity elements is a substrate for export. However, when the first coferon covalently attaches to second coferon, this creates a plug to clog the export pump. Such a coferon "plug" would be combined with a traditional cancer drug. This concept is similar to augmentin (amoxicillin clavulanate), where the clavulanic acid inhibits beta-lactamase.

The above examples emphasize the ability of coferons to inhibit, modulate, or activate protein-protein interactions. Coferons may also inhibit, modulate, or activate other major worlds of macromolecule interactions. For example, coferons may be used to tune protein-protein-nucleic acid interactions when transcription factors bind to dsDNA, or proteins that bind to RNA (e.g. ribosome). These could be every bit as significant wherein one targets the protein and the nucleic acid interaction by coferons. Many proteins undergo modifications (i.e. phosphorylation, acetylation, methylation, sumolation, prenylation, and ubiquitination), where these modifications allow for signaling, transport, or degradation through additional protein interactions. All of these processes may be inhibited or activated by judiciously designed coferons. Larger modifications, such as synthesis of glycoproteins provide the potential for coferons blocking interactions when proteins bind to the carbohydrate moieties.

Many proteins have signals to move them to various compartments or macromolecular structures.

Coferons may be used to bring together two proteins to either accelerate or inhibit movement of the two proteins to the: (i) membrane, (ii) cytoplasm, (iii) mitochondria, (iv) lysosome, (v) proteosome, (vi) golgi, (vii) endoplasmic reticulum, (viii) extracellular space, (ix) nucleus, (x) cellular filaments or scaffolding, or (xi) other intracellular or extracellular compartment, cellular structure, or space.

Coferons provide a unique opportunity for targeted entry into cancer cells. In the most direct form, folic acid is used as both the linker element and a means to transport the drug moiety into cancer cells. The folate transporter is found over-expressed in many cancers and especially in metastatic cancer cells. Thus, the folate transporter helps concentrate the drug molecule within cancer cells. Folic acid and derivatives are very "sticky" and tend to associate with each other. This association may be enhanced by addition of appropriate reactive groups (preferably, those forming reversible covalent bonds) to the two folic acid linker elements.

An alternative use of folic acid is as a transporter of a coferon precursor into the cells. Here, the folic acid group is linked to the coferon via a disulfide bond. Glutathione levels are 1,000-fold higher in tumor cells than in the blood. Inactive form of thiol-containing coferon is internalized, then opened by glutathione, brought into proximity with it's coferon pair (also activated by glutathione). The released thiol groups are then available to participate in crosslinking reactions when two coferons come together ultimately leading to cell death. This approach has the advantage that the coferon drug molecules are in an inactive precursor form in the blood stream as well as normal cells, but are activated upon entering cancer cells.

Potential transporters of coferon or coferon-cofactors include: glucose transporter, taurine transporter, cationic amino acids transporter, organic anion transporter, proline transporter, monoamine transporter, Anion exchange transporter, folate transporter, monocarboxylic acid transporter, Zn transporter, amino acid transporter, Na dependent vitamin transporter, fatty acid transporter, nucleoside transporter, and proton-coupled divalent metal ion transporter.

Subunits of the above transporters are overexpressed in both primary and metastatic colon tumors. Use of transporters or receptors may provide a second life for existing drugs. An existing drug is attached to a linker element that binds its pair independent of target to create the first coferon. The second coferon has affinity to transporter specific to the target organ or target tumor, specific to a receptor protein on the cell surface or even to a cytoplasmic protein, any one of which may help pull the drug on the first coferon into the desired cells. Some uptake systems bring the solute into an endosome where it is released from the transporter (for example by a change in pH). In some of these cases, the drug molecule may still need to cross a membrane. One advantage of coferons is that the linker element portion may be modified, for example made more lipophilic, such that the entire coferon is more easily transported into the target cell.

For the folate transporter, the folic acid may be used as a linker element. For the zinc or other divalent metal ion transporter, the zinc could be a co-factor to assist two linker element in binding with each other. Zinc is uniquely suited to be a cofactor as it is generally a non-toxic metal ion that may be ingested in large quantities, up to 40 mg per day for adults for up to a week. Thus, a cancer patient would be able to preload the cancer cells with zinc, which would then help trap coferon drugs that bind each other through linker elements that chelate a zinc ion as a cofactor. Further, bidentate organic molecules that bind zinc depend on a very precise geometric and electronic configuration of the ligand structure, thus such coferon drugs would be less likely to bind other divalent cations nonspecifically.

Cancer cells provide multiple opportunities to take advantage of the unique properties of coferons. For example, coferon pairs may be synthesized to contain spatially separated ketone and a disulfide group two carbons from a primary or secondary amine. When screening for suitable diversity elements in vitro, the disulfide group remains oxidized. Coferon pairs can form via a reversible imine (primary amine) or imminium ion (secondary amine) formation. Dynamic combinatorial chemistry is used to select the best diversity elements. When the winning pair of coferons is introduced into the patient, the coferons remain as monomers (occasionally associating to form dimers) until they enter the cell. The disulfide bond is reduced by internal glutathione, and then the liberated thiol group on the coferon can now react with the imine or imminium ion to form an irreversible thiazolidine link between the two coferon pairs. Judicious choice of the linker element design can drive the reaction forward only inside cancer cells containing the desired target.

Additional approaches to unmasking reactive groups of coferons upon entering target cells include but are not limited to use of esterases to cleave esters and liberate a reactive alcohol group, and peptidases to liberate a reactive amino group.

Coferons as Multivalent Drugs Against Bacteria.

There are a number of antibiotics that inhibit or interfere with proper ribosome function Aminoglycosides (gentamicin, tobramycin, amikacin, kanamycin, neomycin, paromomycin) induce formation of aberrant, nonfunctional complexes, as well as causing misreading of the mRNA. In a second mechanism, some aminoglycodies also prevent the transfer of peptidyl tRNA from the A-site to the P-site, thus preventing elongation of the polypeptide chain. Aminoglycosides bind irreversibly to specific ribosomal proteins. Streptomycin binds S12 in 30S subunit, while others bind to the L6 protein of the 50S subunit.

Tetracyclines (tetracycline, minocycline, doxycycline, demeclocycline) binds reversibly to 30S ribosome.

Inhibits binding of aminoacyl tRNA into the A site of the bacterial ribosome. Chloramphenicol inhibits peptide bond formation by binding to a peptidyltransferase enzyme on the 50S ribosome.

Macrolides (erythromycin, azithromycin, clarithromycin, dirithromycin) are large lactone ring compounds that bind reversibly to the 50S ribosomes and impair the peptidyltransferase reaction (i.e. prevent forming a peptide bond between the amino acids), or translocation (i.e. preventing transfer of the peptidyl tRNA from the A-site to the P-site), or both.

Oxazolidinones (Linezolid) bind to the 50S subunit and interfere with formation of the mRNA, f-met-tRNA and 50S subunit complex. Lincosamides (clindamycin) also inhibits protein synthesis by binding to the 50S ribosome.

Coferon dimers containing one each of the above drugs from two different binding regions as the ligands may show greater biological activity than the monomers. This may be especially true if the drugs bind synergistically, and are kept in the approximate proper orientation by the linker element tether. Such drugs may also stay within cells longer, allowing for more intermittent dosing of the drug. Finally, it may be more difficult for the bacteria to mutate both monomeric drug binding sites simultaneously.

Coferons as Drugs Against Rapidly Evolving Viruses.

RNA viruses are a constant public health threat as their rapidly evolving genomes have outwitted repeated attempts to generate neutralizing antibodies or vaccines. The last 20 years has seen enormous strides in the synthesis of inhibitors to various viral proteins, such as proteases and reverse transcriptase. Nevertheless, in time viruses escape these drugs through mutational selection to resistance. Coferons provide two unique opportunities to inhibit RNA viruses. Resistant variants for many existing drugs are now known, and thus coferons may be screened against both sensitive and resistant variants, allowing for selection of the winning families or clades of coferon monomers. Use of a limited number of each family member (for example 10 each for coferon "A" and coferon "B") allows for addition of a "therapeutic cocktail" where the protein target selects the tightest binding pair (which will be 10% of the total molecules) and thus selects for its own strongest inhibitor. A second opportunity arises from viral protein interactions with a human host protein, and this interaction may be disrupted by identifying coferons that bind to the host protein, or bind and recruit a second protein to the host protein, and thus either directly or indirectly inhibit binding of the viral protein to the host protein. Below are some examples based on HIV.

HIV Protease

From structural work and alanine scanning mutagenesis studies, the contact points for HIV protease and its substrates are determined. Then, families of "A" and "B" coferons are designed, such that the combination of A+B provide enough structural space to allow binding to mutational variations in the target HIV protease, thus achieving desired inhibition of said protease. Since coferons A+B bind reversibly, dynamic combinatorial chemistry will assure that each protease variant binds the tightest inhibitor combination.

HIV Entry

HIV entry into cells depends on binding to the CCR5 receptor. While attempts to make vaccines to the HIV envelope protein have been unsuccessful, coferons could be designed to bind to the CCR5 receptor, either as a dimer, tetramer, or recruiting another protein to CCR5, thus blocking the HIV from binding to the same receptor.

HIV Reverse Transcriptase

Traditional reverse transcriptase inhibitors are based on nucleotide analogues. However, resistant variant reverse transcription easily arises. Coferons could be more effective in inhibiting this enzyme by designing a family of nucleotide analogs "A" which bind both "wild-type" and different drug resistant variations of HIV reverse transcriptase, and a family of second drugs "B" that bind the HIV RT elsewhere. Combining coferons A+B provides enough structural space to allow binding to mutational variations in the target HIV reverse transcriptase, while still inhibiting its activity.

HIV Vif Protein

Human cellular protein A3G sabotages HIV by dramatically mutating its genes. HIV Vif protein interferes with this process. One approach is to use coferons to generate a mimetic decoy of A3G, such that the HIV Vif protein binds the coferons instead of the A3G protein. A second approach is to use coferons to bind to A3G, or bind and recruit another cellular protein to A3G, thus blocking Vif binding to A3G. Since A3G is a human protein, and not undergoing the same mutational drift as the HIV Vif protein, it is easier to design coferons that either mimic, or bind to A3G.

HIV Integrase

HIV integrase, with the help of the human cellular protein LEDGF, integrates the ds DNA copy of the virus into the human genome. Coferons may be selected to interfere with HIV integrase activity, as well as integrase binding to LEDGF. As above, since LEDGF is a human protein, and not undergoing the same mutational drift as the HIV integrase protein, it is easier to design coferons that either mimic, or bind to LEDGF.

Coferons Containing Nucleic Acid and Oligonucleotide Analogues Ligands.

Antisense and siRNA studies have provided an excellent tool for knocking down specific transcripts in individual cells. To date, with a few exceptions, this promise has not been born out in whole mammalian organisms.

Coferons provide an opportunity to overcome problems related to transport of RNA or RNA analogues into cells. Coferons can combine two oligonucleotide ligands through their linker elements. Thus, current approaches that are being used to transport RNA or oligonucleotide analogues into cells may become more efficient if the transport oligonucleotide is half the size, i.e. reducing from a size of 19 to 22 bases, to two oligonucleotides ranging from approximately 9 to 12 bases and containing linker elements, allowing for their assembly on the target to full length RNA with the appropriate biological activity (see FIG. 2.34). For siRNA, double-stranded RNA of sizes 21 to 27 bases have been used, again allowing for assembly of smaller oligonucleotides after transport. Efforts to transport nucleic acid and analogue macromolecules into the cell include using lipophilic carriers, and attaching them to other molecules (such as folic acid) that are actively transported into target cells (such as cancer cells, which often over-produce the folic acid transporter.

Coferons may also help transport RNA, or oligonucleotide analogues into cell using two new formulations herein termed "Lipocoferons" and "Aminoglycoferons" (see FIG. 2.35).

"Lipocoferons" consist of 2 or 3 amino groups spaced to bind to the negatively charged nucleic acid backbone. Lipocoferons have a hydrophobic face to help transport nucleic acid fragment into the target cell. In one variation, Lipocoferons have free thiol groups allowing the lipocoferons to form multimers when binding to the nucleic acid fragment, but then once inside the cell, internal glutathione reduces those thiol linkages releasing the lipocoferons from the RNA or oligonucleotide analogues.

"Aminoglycoferons" are based on known aminoglycosides that bind RNA. In one variation, they are designed to allow for linking together using thiol linkages. They can bind to RNA and help transport nucleic acid fragment into the target cell. Once inside the cell, internal glutathione reduces those thiol linkages releasing the aminoglycoferons from the RNA or oligonucleotide analogues.

Once the nucleic acid fragments or nucleotide analogue fragments are inside the cell, they will bind to RNA sequences. The coferon design provides an opportunity to dramatically improve the efficacy of antisense type drugs by using shorter RNA or oligonucleotide analogues, preferably ranging from 9 to 12 bases, whose sequences are complementary to the upstream half and downstream half of the target RNA sequence. In the preferred embodiment, each Coferon contains a linker element, such that when the two portions bind to their target with perfect complementarity at the junction, the linker elements are positioned to join via either covalent or non-covalent binding. Such joining increases the binding energy and avidity to the correct target, allowing for the appropriate biological activity.

Oligonucleotides with lengths of 9 to 12 bases bind to complementary sequences with melting temperatures ranging from on average 27° C. (for 9-mers) to 37° C. (for 12-mers), although Tm's for specific oligonucleotides of this size may vary from a low of about 18° C. to a high of about 48° C. Under physiological conditions and at human temperatures of 37° C., individual oligonucleotides will be in equilibrium between binding to the desired RNA target, other RNA, and not binding to the target. Coferons with nucleic acid or nucleotide ligands of a given length may be modified in the backbone (i.e. 2'-O-methyl, PNA, LNA), base (i.e. 5-propynyl C) and/or with additional groups (i.e. hydrophobic groups, minor-groove binding moieties) to increase the overall binding to an RNA target at a given temperature. Such an increase will shift the equilibrium to greater binding at both the desired target site as well as at off-target sites. However, once two coferon-nucleic acid/analogue bind adjacent to each other on the correct target, they become linked, thus stabilizing and greatly increasing the affinity of the coferon dimer to only the correct target. The Tm's for coferon dimers ranging in length from 18 to 24 bases will be on average from 54° C. to 72° C., although Tm's for specific oligonucleotides of this size may vary from a low of about 36° C. to a high of about 92° C. Thus, the coferon dimers bind to the correct sequence with 100 to 1,000-fold higher avidity then either monomer alone, and furthermore, once assembled on the correct target will not dissociate at any appreciable rate.

Coferon-nucleic acid/analogue drugs thus have a tremendous advantage over traditional antisense oligonucleotides in the fact that the coferon monomer moieties are substantially smaller, and therefore are easily dissociated from binding to off target sites—in contrast to the full-length antisense oligonucleotides, which have been shown to have substantial off-target effects in certain cases.

Coferon-nucleic acid/analogue drugs may also be designed to interact with the RNA degradation machinery (See FIG. 2.36). For example, RNA coferons may be designed with antisense coferons of 12 and 15 bases in length, and the sense oligonucleotides being of 15 and 10 nucleotide length respectively. Once transported into cells, hybridization of these oligonucleotides would allow for assembly of an antisense oligonucleotide of 27 nucleotides held together by the linker elements, and a "split" sense strand of 25 nucleotides. This structure would be a substrate for Dicer and suitable for uptake by the RISC complex resulting in an enzyme complex that would catalytically degrade mRNA complementary to the antisense RNA composed of two coferon-nucleic acid/analogue drugs. Other configurations of coferons could interfere with other biological activity, including interfering with translation (siRNA), degrading or inhibiting transcripts (miRNA), or enhancing transcription (aRNA).

The approach for Coferon-nucleic acid/analogue drugs may be expanded to include (i) linking more than two coferon-nucleic acid/analogues together, (ii) using two coferons, one composed of an aminoglycocide known to bind bacterial or fungal ribosome, with a second coferon-nucleic acid/analogues designed to bind an adjacent region of ribosomal RNA in the target, and (iii) using two coferons, one composed of a coferon-nucleic acid/analogue that binds a ribozyme or RNA target, with the second coferon composed of a small molecule ligand that binds at an adjacent position in the ribozyme or RNA target.

Screening Multimer Coferons.

For multimer coferon screening, one starts with diversity libraries and known ligands or group of ligands in the following formats: (i) on a bead or solid support with monomer diversity element defined by position or bar-code encryption of particle, (ii) same as previous, except now two or more identical diversity elements are on the same coferon and defined by position or bar-code encryption of particle, (iii) in solution (off the bead) with monomer diversity element defined by an encoded DNA element, (iv) same as previous, except now two or more identical diversity elements are on the same coferon and defined by an encoded DNA element, (v) one or more known ligands on a bead or solid support, with ligand defined by position or bar-code encryption of particle, and (iv) one or more known ligands in solution, with ligand defined by position or encoded DNA element.

The advantage of working with coferon libraries attached to beads is that each bead contains multiple copies of the identical ligand. This property helps identify the strongest affinity ligand combinations by the intensity of fluorescently labeled entity captured (i.e. protein or other ligand). When synthesizing coferons on a solid support, the spacing of individual coferons should be sufficient to avoid binding the target by multiple copies of the same coferon. This potential artifact has led to "identification" of target binding peptides through phage or other display technologies, only to find the original effect disappears when using individual in-solution peptides. This artifact may be avoided or mostly limited by the following approaches:

(i). Use of limited loading of a reactive group on the bead or solid surface—such that on average only 1 out of every 100 adducts is close enough to the next so that both can bind to the same target.

(ii). Use of Streptavidin coated (magnetic) beads, followed by loading the reactive group on biotin. In a slightly more sophisticated version of this, the bead is coated with biotin on very short spacers, such that only one group can bind a streptavidin. A reactive group containing three biotin "hooks" is added. Once one catches the streptavidin, the other two will bind the remaining sites. Thus, on average 1 reactive group is bound per streptavidin tetramer.

The advantage of working with coferon libraries encoded by DNA is that selected coferons may be amplified by using their DNA to template a second round of diversity element synthesis. This allows for evolutionary principles to be used in selecting the best coferons. Finally, we also consider that diversity elements may be synthesized on beads and then released without any encoded DNA element. When used under conditions where sufficient coferon binds to both protein target and beads, the structure of the diversity element may be identified or narrowed down using mass spectroscopy. This approach has the advantage of obviating the need to attach an encoded DNA element to the coferon, which may influence the binding event. If the number of coferons tested can be limited by in silico pre-screening of potential diversity elements binding to a known 3-dimensional structure of the target, then use of mass spectroscopy to identify the winning coferon from in vitro screening becomes a highly efficient process.

Screening multimer coferons binding to the target is based on liberating the process of screening for the best diversity elements from the process of identifying the best linker element design to be used in the final coferon drug. During the screening process, two or more identical diversity elements may be tethered together. The tethering may recapitulate the precise geometry of the linker elements and diversity elements by simply tethering two linker elements together, or the tethering may approximate the geometry of the diversity elements and replace the linker elements altogether. Once the optimal diversity elements have been identified, the final coferons are re-synthesized as monomer subunits containing the correct linker element and the selected diversity element.

Figure 29:
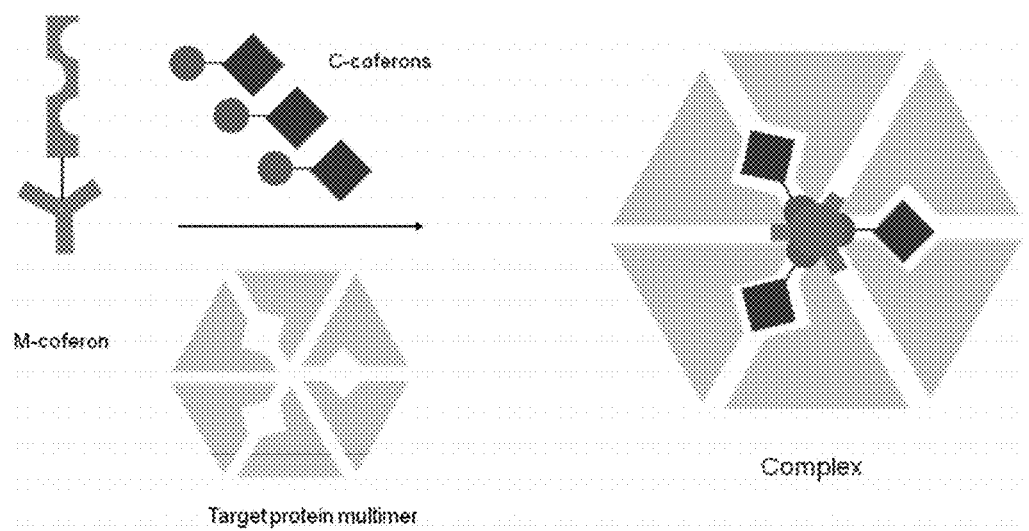

Derivatives based on mother-child linker elements (M-Coferons) M-coferons are coferons that possess a single "mother" linker element capable of linking to multiple "child" linker elements from C-coferons. The M,C coferon system is designed to target protein multimers, especially those that contain a channel or cavity. Examples would include transporters (p-glycoprotein, polyamine transporter), proteasomes, viral protein coats, biomolecular machines. This is illustrated in FIG. 29.

An example of the M,C coferon system which utilizes a disaccharide (lactose in the following example) as the M-coferon and a boronate as the C-coferon. Disaccharides are of particular interest since there are specific transporters for them, e.g. galactose receptors are found on the surface of cancer cells.

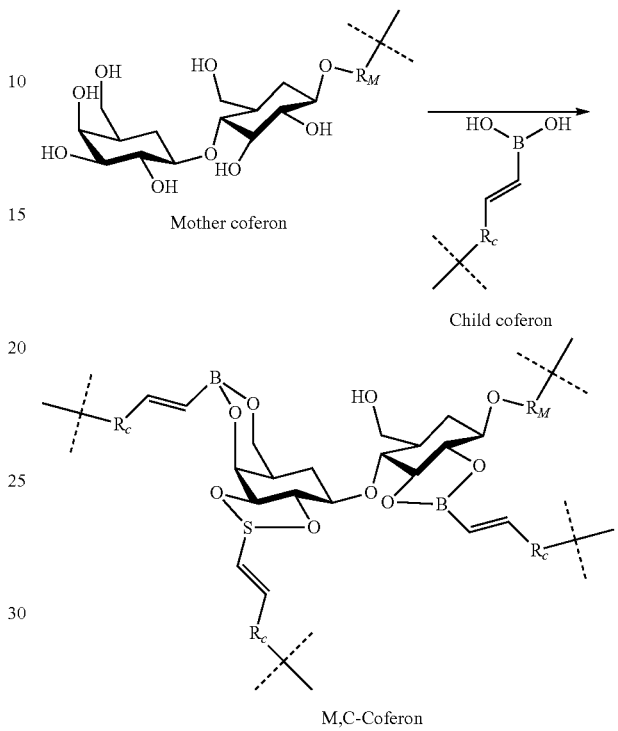

Mother coferon

Child coferon

M,C-Coferon

Non-saccharide polyols may also serve as M-coferons as shown in the example below.

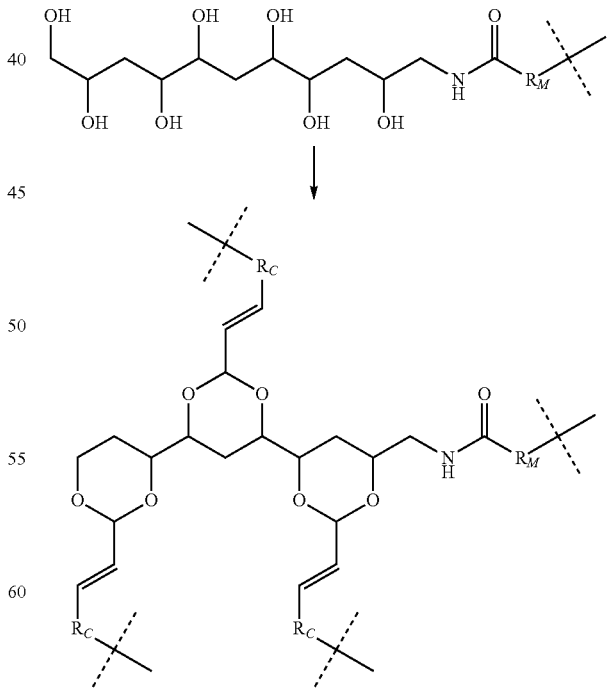

Screening for A-B-C Target Binding Coferons

Two types of geometries for these trimeric coferons are envisioned. The first has both the A and C linker elements binding with the B linker element. The simplest version of such linker elements would contain aromatic rings that stack on each other. The second geometry has A binding to B, B to C, and C to A. This may be achieved using linker elements that incorporate a cyclopropane scaffold to achieve 60° C. angles between the three linking groups. Each cyclopropane would be disubstituted with groups suitable for making reversible linkages. For example, both A and B may contain an aldehyde and sulfhydryl in the trans stereochemistry, and form a disulfide bond. The aldehyde groups would both be on the same side of the cyclopropane's and would thus be able to link up with a linker element containing cis diols. Less constrained cyclopentane structures would also be compatible with this selection linking groups for generating tri-meric coferons.

A variation of this theme is the A-B-A or A-A-B target binding coferon. Here one of the diversity elements is repeated twice, but adds additional binding energy.

A first version of a screen (similar to that in FIG. 9) uses diversity elements on both beads and in solution. Fluorescently labeled target protein is added to the beads (containing "A" coferon) and in-solution "B" coferons, and after a suitable period of panning, wells containing fluorescently labeled beads are identified. If the beads are in a single chamber, the barcode is identified for the fluorescently labeled beads. In both cases, the in-solution "B" coferons are identified by PCR amplification and sequencing of the DNA tags, or by mass spectroscopy if there is no bar-code. This process will identify many "A"-"B" coferon pairs that bind to the target. These winning pairs are then used to fish out the "C" coferon. This may be accomplished by synthesizing either a dimer, or individual monomers of "A" and "B" coferons in solution, adding to "C" coferons on beads, and fluorescently labeled target protein, panning under more stringent conditions and identifying wells containing fluorescently labeled beads. The "A" and "B" coferons bound to each fluorescent bead are identified either by PCR amplification and sequencing of the DNA tags, or by mass spectroscopy if there is no barcode.

In a variation of this theme, the "A" coferon on the bead is synthesized with two identical diversity elements. This allows both of them to provide an increased binding affinity. A simple way of accomplishing this is to increase the loading of the "A" coferon on the solid support, such that many can readily dimerize. Those beads containing "A" coferons that are close enough to form dimers, and that provide a selective advantage in binding the (fluorescently) labeled target protein will show the highest label (i.e. fluorescence). Using this approach the overall geometry of a tri-meric coferon would be maintained, with the second "A" coferon acting as a placeholder. The second A coferon could be replaced by a "C" coferon in an additional screen, although if the initial binding energy is strong enough, the final drug could be composed of two identical "A" subunits, and one "B" subunit. This idea may also be extended to identify tetrameric target binding coferons, composed of two identical "A" subunits and two identical "B" subunits.

The PCR amplified tags may also be used to re-synthesize the diversity elements, such that evolutionary principles are used to select the winning sets of coferons. Alternatively, each of the top ligands may be re-synthesized and can now be attached through a series of connectors that vary in size, flexibility, or for circular diversity elements, the size of the macrocycle. A further variation on this theme would be to regenerate not only the original diversity elements, but minor variations (for example vary just one amino acid residue at a time from a cognate sequence) as well, to be combined with the diverse set of connector elements. This refined set of coferons would be rescreened in the presence of the fluorescently labeled target protein at the appropriate concentrations to allow for selection of the tightest binding combinations. The same principles of dynamic combinatorial chemistry described above would apply. The winning triplet of coferons would be identified by their bar-code, DNA sequence tags, or by mass spectroscopy. The coferon trimers selected by this protocol should have affinities to the target in the nanomolar to picomolar range.

A second version of the screen (similar to that in FIG. 11) depends on some prior knowledge of potential ligands, or molecular modeling to identify a set of potential binding elements. For example, the target may be a protein with a known binding pocket, such as a tyrosine kinase. Here, molecules known to or inferred to fit within the binding pocket (and chemical variants whose structure would occupy a similar 3-dimensional space) are attached to a series of connectors that vary in size and flexibility. It is assumed (but should also be experimentally verified) that the majority of members of this library would bind to the target with micromolar or even nanomolar affinities. Subsequently, this first library of binding pocket ligands is combined with a second library of coferons with various diversity elements on beads, and a third library of diversity elements in solution. The trimers of binding elements are screened as described above. The coferon trimers selected by this protocol should inhibit enzymatic function if the binding pocket also has an active site, and have affinities to the target in the nanomolar to picomolar range.

Screening for A-B-A-B Target Binding Coferons

Three types of geometries for these tetrameric coferons are envisioned. The first alternates the A and B linker elements. The simplest version of such linker elements would contain aromatic rings that stack on each other. The second geometry has an A-A dimer binding to a B-B dimer. This may be achieved using linker elements that form head-to-head homodimers, but also have groups that allow for linking of the two dimers on their sides to achieve bonding between the four linker element groups. The dimers may not stack directly over one another, but may be offset. The third geometry has an A-B dimer binding to a B-A dimer. This may be achieved using linker elements that form head-to-head heterodimers, but also have groups that allow for linking of the two dimers on their sides to achieve 90° C. angles between the four linker element groups. For example, linker elements based on nucleotide analogue base hydrogen bonding or base intercalation could form A-B heterodimers, and two A-B heterodimers could stack on each other by taking advantage of aromatic stacking interactions, held in place by additional covalent bonding.

There are many variations for screening A-B-A-B tetramer coferons, which follow the initial variations for screening coferon dimers (FIGS. 8-12), except instead of synthesizing monomer diversity elements, one synthesizes duplicate diversity elements and tethers the linker elements to each other. Also, one may synthesize the "A" set of coferons on beads or particles at a density that allows two such coferons to participate in forming an A-B-A-B tetramer, and then add the "B" coferons in solution.

Screening for Circular Sets of Target Binding Coferons

Two types of screens and two types of geometries for circular sets of coferons, ranging from tri-, tetra-, penta-, hexa-hepta- to octa-coferons, are envisioned. In the first design, all the coferons are identical, i.e. circular A-A-A-A-A pentamer coferon. In the second design, the coferons alternate, i.e. circular A-B-A-B-A-B hexamer coferon.

In designing screens for multiple coferons, it is important that the coferons assemble in the proper order and correct number. One approach to achieving this is to create a circular scaffold onto which the coferons or just the diversity elements are attached. Once the best set is identified, the coferons are resynthesized without the scaffold.

For example, a circular peptide of the form -Lys-Asp-Gly-Asp-Gly-Asp-Gly-Asp-Gly-Asp-Gly-Asp-(SEQ ID NO: 1) would allow for attachment to a bar-coded bead through the lysine gamma amino group. Ethylene glycol spacers of suitable length could then be attached to all 6 aspartic acids. This would be followed by synthesis of identical diversity elements at all 6 positions. Such a "crown" design would give the diversity elements the flexibility needed to bind to the target. Other crown type scaffolds include calixarenes and cyclodextrins.

An alternative variation of the above would attach linker elements that have been optimized to assemble into hexagonal structures. The diversity elements could then be built directly from the linker elements, or to add even more flexibility, use an additional ethylene glycol spacer between the linker elements and the diversity elements. This design is ideally suited for identifying hexameric coferons composed of 6 identical diversity elements.

To generate mixed diversity element coferons, i.e. a circular A-B-A-B-A-B hexamer coferon, one approach would be to start with a circular peptide of the form -Lys-Asp-Gly-Cys-Gly-Asp-Gly-Cys-Gly-Asp-Gly-Cys- (SEQ ID NO: 2). Again, the peptide is attached to a bar-coded bead through the lysine gamma amino group. Either the Cys or Asp groups may be protected to avoid further chemistry, ethylene glycol spacers attached to the remaining three groups, then linker elements, and then identical diversity elements are built on those 3 chains. Once the first three diversity elements are built, the protecting groups on the other three amino acids are removed, and the process repeated by adding ethylene glycol spacers and linker elements to the remaining three groups. Since the beads already code for the "A" diversity elements, the "B" elements are now synthesized as identical "cores" on every bead, for example using alanine for every position. Alternatively, if there are an excess number of beads containing the identical "A" diversity elements, limited diversity could be tested for the "B" coferon position, by dividing the beads into 3N wells, and synthesizing the "B" coferon with N different R groups in the first diversity position, or N different R groups in the second diversity position, or N different R groups in the third diversity position. A given well will have a large number (i.e. 1,000,000) beads containing a large diversity of structures in the "A" coferon position, but a given bead will have the identical "A" diversity in all three coferons that were synthesized off the circular peptide. All the beads in this single well will have the identical "B" coferon in all three positions. Fluorescently labeled target protein is added to the beads (containing diverse "A" coferon and identical "B" coferons), and after a suitable period of panning, wells containing fluorescently labeled beads are identified. If the beads are in a single chamber, the bar-code is identified for the fluorescently labeled beads.

Once the best candidate "A" coferons have been identified (with or without the added limited diversity of the "B" coferons) the process is repeated, however this time the beads contain molecules that are diversified in the "B" positions, while the "A" positions are limited to the best "A" coferon(s). (Again, if there are an excess number of beads containing the identical "B" diversity elements, limited diversity could be included for the "A" coferon). Fluorescently labeled target protein is added to the beads (containing diverse "B" coferon and identical "A" coferons), and after a suitable period of panning, wells containing fluorescently labeled beads are identified. If the beads are in a single chamber, the bar-code is identified for the fluorescently labeled beads. This process first optimized the "A" coferon, and then the "B" coferon, and may be reiterated if needed, to find the best candidate diversity elements. The coferon hexamers (comprised of 3 A-B dimers) selected by this protocol should have affinities to the target in the nanomolar to picomolar range.

Another approach relies on synthesis of the "A" and "B" set coferons on separate macromolecules, allowing for screening diversity in both coferons simultaneously. For example, the "A" coferons could be attached through ethylene glycol spacers to the 4 meso positions of a porphyrin ring. Likewise, the "B" coferons could be attached through ethylene glycol spacers to the 4 meso positions of a second porphyrin ring. The two structures could interact through aromatic stacking of the two porphyrin rings. If the rings are coaxial, the diversity elements could be in an alternating geometry, allowing for all 8 coferon diversity elements to fall to one side and bind the target with high affinity. One coferon set could be on a bead, with the other set in solution, allowing for screening of both sets simultaneously.

In all the above cases, once the winning diversity element "multiplex" has been identified, the coferons are re-synthesized with monomer diversity elements with the suitable linkers to allow for multimer coferon binding to suitable targets.

Selection Based on Screening

Coferons may be thought of as miniature antibodies that may disassemble outside a cell and reassemble inside a cell to influence macromolecule interactions. There are two issues at play, how well the coferon can distinguish between the correct target and other closely related targets (i.e. specificity), and how it modulates the biological activity in question.

The evolutionarily driven selections described above are all based on binding to the target, but they do not address binding to a specific surface or face of the target, nor do they address the specificity issue. For example, aptamers can be selected for to bind known proteins with very high binding affinities; however, these often turn out to be driven by the negatively charged DNA backbone interacting with positively charged residues on the protein target—and such aptamers often have substantial non-specific binding to incorrect targets.

With current recombinant techniques, it is straightforward to generate purified wild-type and specific mutant variants of virtually any protein, covalently attach protein targets to solid surfaces such as beads, as well as fluorescently label such proteins. In addition, there are several reagents for attaching fluorescent and quenching groups onto small molecules, binding ligands etc. Combinations of such groups may be used to detect close binding of two macromolecules by observing a FRET signal, or conversely, detect two macromolecules no longer binding by separating the fluorescent group from a nearby quenching group. Finally, for many protein targets that require an energy source, such as ATP, to signal or function properly, there are many analogues which may "freeze" the protein in either an "active" or "inactive" conformation.

Selecting coferons to bind to a particular face or substrate-binding pocket of a protein. Under these conditions a non-binding target protein is synthesized or engineered, wherein the protein contains one or more mutations or chemical modifications or inhibitor binding to the face in question, such that the non-binding target protein no longer has the ability to bind its partner protein, or substrate.

When one coferon is attached to a bead, and the binding of protein is detected using a fluorescently labeled protein: Add unlabeled engineered non-binding target protein at a molar excess to the labeled target protein, for example at a 100:1 excess. Beads containing coferon pairs that bind uniquely to the target protein but not the engineered non-binding target protein will bind fluorescently labeled protein and can then be distinguished.

When the protein is attached to beads, and the coferon selected by tighter binding to the protein on beads: target proteins can be attached to magnetic beads, or coded beads that may be separated from the other beads. Engineered non-binding target protein may be attached to other beads, which are present at a greater level, for example at a 100:1 excess. Excess beads containing engineered non-binding target protein will swamp out coferons binding at the wrong surface. However, coferons binding the correct surface of target proteins may be selected by (i) magnetic separation or (ii) FACS sorting of these beads, respectively.

Selecting coferons to bind to a particular conformation of the protein, for example when it is binding ATP. Under these conditions, a non-reversible ATP analogue is used to bind to the protein to "freeze" it in the active conformation. Under these conditions a non-analogue binding target protein is synthesized or engineered, where the protein contains one or more mutations or chemical modifications, such that the non-analogue binding target protein no longer has the ability to "freeze" it in the active conformation.

When one coferon is attached to a bead, and the binding of protein in the active conformation is detected using a fluorescently labeled protein bound to the non-reversible analogue substrate, unlabeled engineered non-analogue binding target protein is added at a molar excess to the labeled target protein, for example at a 100:1 excess. Beads containing coferon pairs that bind uniquely to the target protein but not the engineered non-analogue binding target protein will bind to fluorescently labeled protein and can then be distinguished.

When the protein in the active conformation is attached to beads, and the coferon selected by tighter binding to the protein on beads, target proteins in the active conformation are attached (by using the non-reversible analogue substrate) to magnetic beads, or coded beads that may be separated from the other beads. Engineered non-analogue binding target protein are attached to other beads, which are present at a greater level, for example at a 100:1 excess. Excess beads containing engineered non-analogue binding target protein will inhibit coferons binding the wrong conformation. However, coferons binding the correct conformation of target proteins may be selected by (i) magnetic separation or (ii) FACS sorting of these beads, respectively.

Coferons can be selected to bind to a particular face of a protein to interfere with that protein binding a second protein.

When one coferon is attached to a bead, and the binding of target protein is detected using a fluorescently labeled protein, a target protein with a fluorescent signal, and an excess of secondary protein with quenching group(s) that binds to the target protein are used to quench the fluorescent signal. Beads containing coferon pairs that bind uniquely to the target protein in a way that interferes with binding of the second protein will bind fluorescently labeled protein and can then be distinguished.

Coferons can be selected to bind to enhance a protein-protein binding interaction.

When one coferon is attached to a bead, and the binding of target protein is detected using a fluorescently labeled protein, use a target protein with a fluorescent signal, and a secondary protein with another fluorescent group that will generate a FRET signal when binding to the target protein. Beads containing coferon pairs that bind uniquely to the target protein and second target protein so as to enhance their interaction will generate a FRET signal and can then be distinguished.

Coferons can be selected to inhibit or enhance enzymatic action or protein function.

When one coferon is attached to a bead, and the binding of target protein is detected using a fluorescently labeled protein, those beads which are fluorescently labeled are selected, indicating binding of proteins into microtiter wells, and assay for individual protein activity.

Therapeutics

An additional embodiment of the present invention relates to a therapeutic multimer which includes a plurality of covalently or non-covalently linked monomers. Each monomer comprises a diversity element which binds to a target molecule with a dissociation constant of less than 300 µM and a linker element having a molecular weight less than 500 daltons, and capable of forming a reversible covalent bond or non-covalent tight interaction with a binding partner of the linker element with a dissociation constant less than 30 µM, with or without a co-factor under physiological conditions. The diversity element and the linker element are joined together for each monomer. The plurality of monomers are covalently bonded together or non-covalently linked together through their linker elements, and the diversity elements for the plurality of monomers bind to proximate locations of the target molecule.

A method of treating a subject for a condition associated with target molecule can be carried out by providing the therapeutic dimer, selecting a subject with the condition, and administering the treatment dimer to the selected subject under conditions effective to treat the condition.

Another embodiment of the present invention relates to a plurality of therapeutic monomers capable of combining to form a therapeutic multimer. Each monomer includes a diversity element which binds to a target molecule and a linker element having a molecular weight less than 500 daltons and capable of forming a covalent bond or non-covalent tight interaction with a binding partner of the linker element with a dissociation constant less than 300 µM, with or without a co-factor, under physiological conditions. The diversity element, which has a dissociation constant less than 300 µM, and the linker element are connected together directly or indirectly through a connector for each monomer. A plurality of monomers are capable of covalently bonding together or being non-covalently linked together through their linker elements, and the diversity elements for the plurality of monomers bind to proximate locations of the target molecule.

A method of treating a subject for a condition associated with target molecule is carried out by providing a plurality of the therapeutic monomers, selecting a subject with the condition, administering the plurality of treatment monomers to the selected subject under conditions effective to treat the condition.

Therapeutic dimers are those dimers from which DNA and beads have been removed. These are shown in FIGS. 2.1E, where there is a connector, and FIG. 2J where there is no connector.

Therapeutically effective doses of compounds of the present invention may be administered orally, topically, parenterally, by inhalation spray, or rectally in dosage unit formulations containing conventional non-toxic pharmaceutically acceptable carriers, adjuvants, and vehicles. The term parenteral, as used herein, includes subcutaneous injections, intravenous, intramuscular, intrasternal injection, or infusion techniques.

The pharmaceutical compositions containing the active ingredient may be in the form suitable for oral use, for example, as tablets, troches, lozenges, aqueous or oily suspensions, dispersible powders or granules, emulsions, hard or soft capsules, or syrups or elixirs. The pharmaceutical compositions of the present invention contain the active ingredient formulated with one or more pharmaceutical excipients. As used herein, the term "pharmaceutical excipient" means a non-toxic, inert solid, semi-solid or liquid filler, diluent, encapsulating material, or formulation auxillary of any type. Some examples of pharmaceutical excipients are sugars such as lactose, glucose, and sucrose; starches such as corn starch or potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; non-toxic, compatible lubricants such as sodium lauryl sulfate and magnesium stearate; as well as coloring agents, releasing agents, sweetening, and flavoring and perfuming agents. Preservatives and antioxidants, such as ethyl or n-propyl p-hydroxybenzoate, can also be included in the pharmaceutical compositions.

Dosage forms for topical or transdermal administration of compounds disclosed in the present invention include ointments, pastes, creams, lotions, gels, plasters, cataplasms, powders, solutions, sprays, inhalants, or patches. The active component is admixed under sterile conditions with a pharmaceutically acceptable carrier and any needed preservatives or buffers, as may be required. The ointments, pastes, creams and gels may contain, in addition to an active compound of the present invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

For nasal administration, compounds disclosed in the present invention can be administered, as suitable, in liquid or powdered form from a nasal applicator. Forms suitable for ophthalmic use will include lotions, tinctures, gels, ointment and ophthalmic inserts, as known in the art. For rectal administration (topical therapy of the colon), compounds of the present invention may be administered in suppository or enema form, in solution in particular, for example in vegetable oil or in an oily system for use as a retention enema.

Compounds disclosed in the present invention may be delivered to the lungs by the inhaled route either in nebulizer form or as a dry powder. The advantage of the inhaled route, over the systemic route, in the treatment of asthma and other diseases of airflow obstruction and/or chronic sinusitis, is that patients are exposed to very small quantities of the drug and the compound is delivered directly to the site of action.

Dosages of compounds of the present invention employed will vary depending on the site of treatment, the particular condition to be treated, the severity of the condition, the subject to be treated (who may vary in body weight, age, general health, sex, and other factors) as well as the effect desired.

The amount of active ingredient that may be combined with the pharmaceutical carrier materials to produce a single dosage form will vary depending upon the host treated and the particular mode of administration.

The target molecule can be selected from the group consisting of: (1) G-protein coupled receptors; (2) nuclear receptors; (3) voltage gated ion channels; (4) ligand gated ion channels; (5) receptor tyrosine kinases; (6) growth factors; (7) proteases; (8) sequence specific proteases; (9) phosphatases; (10) protein kinases; (11) bioactive lipids; (12) cytokines; (13) chemokines; (14) ubiquitin ligases; (15) viral regulators; (16) cell division proteins; (17) scaffold proteins; (18) DNA repair proteins; (19) bacterial ribosomes; (20) histone deacetylases; (21) apoptosis regulators; (22) chaperone proteins; (23) serine/threonine protein kinases; (24) cyclin dependent kinases; (25) growth factor receptors; (26) proteasome; (27) signaling protein complexes; (28) protein/nucleic acid transporters; and (29) viral capsids.

The therapeutic multimer, or plurality of therapeutic monomers contains one or more known ligands as diversity elements and achieves greater efficacy against both wild-type and mutant variants of the target molecule than would be achieved with a single ligand.

The therapeutic multimer or plurality of therapeutic monomers bind to or mimics one or more of the domains selected from the group consisting of SH2, FHA, 14-3-3, WW, WD40, MH2, BROMO, UBA, PTB, SH3, EVH1, GYF, VHS, PDZ, PUF, TUBBY, SAM, DD, CARD, PyD, PB1, BRCT, PH, FYVE, C1, FERM, C2, PX, and ENTH.

The therapeutic multimer or plurality of monomers either interferes with, inhibits binding of, or inhibits activation of the following: (1) target cleavage of a substrate, by binding to the target with a dissociation constant that is less than or equal to the dissociation constant of the substrate from the target; (2) binding of a binding protein to a target, by binding to the target with a dissociation constant that is less than or equal to the dissociation constant of the binding protein; (3) inactivation of a target that by a binding partner, by binding to the target and mimicking the binding partner; (4) inactivation of a target or mutant target by a binding partner, by binding to an inactivating binding partner-target complex or inactivating binding partner-mutant target complex; (5) binding of a first binding partner to a target, by binding to the target and recruiting a second binding partner to bind to the target and the multimer and forming a multimer-target-second binding protein complex, whose dissociation constant is less than or equal to the dissociation constant of the first binding protein; (6) binding to a receptor target, by binding to the receptor target and interfering with receptor dimerization; (7) binding to a binding partner by reducing its recruitment to a receptor target, by binding the receptor target at a ligand binding site to act as an antagonist, or binding the receptor target at the binding partner binding site to act as an antagonist; (8) polymerization of a target into filaments, by binding on a monomer or dimer target; and (13) aggregation of a target, by binding a monomer or dimer target.

The therapeutic multimer or plurality of therapeutic monomers either enhances activation of, enhances binding of, or activates the following: (1) activation of a target by a binding partner, by binding to the target and mimicking the binding partner; (2) activation of a target or mutant target by a binding partner, by binding to an activating binding partner-target complex or activating binding partner-mutant target complex; (3) a first weak binding partner to a target, by binding to the target and recruiting a second binding partner to bind to the target, multimer, and first binding partner and forming a multimer-target-second binding protein complex, or forming a multimer-target-first binding protein-second binding protein complex; (4) a receptor target by binding to the receptor target at the ligand binding site, and facilitating receptor dimerization; (5) a receptor target by binding to an allosteric site on the receptor target and facilitating receptor dimerization in the presence of activating ligand; and (6) a binding partner that is recruited to a receptor target by a ligand binding to the receptor target, by binding to the receptor target at the ligand binding site to act as an agonist, which recruits and activates the binding partner, or binding to the receptor target and the ligand or the receptor target and the binding partner, to accelerate recruitment and activation of the binding partner.

The therapeutic multimer or plurality of therapeutic monomers either enhances or alters protein metabolism by: (1) stabilizing target or mutant target folding; (2) enhancing or interfering with a covalent signaling event; (3) mimicking a covalent signaling event; (4) inhibiting multi-subunit assembly; (5) inhibiting multi-subunit disassembly; or (6) inhibiting degradation by binding the target or target binding partner.

The therapeutic multimer or plurality of therapeutic monomers interferes with, activates, enhances, or mimics covalent modification of the target by phosphorylation, dephosphorylation, acetylation, methylation, sumolation, ubiquitination, farnesylation, and addition of sugar and carbohydrate moieties, by binding to the target or the target-modifying enzyme complex to inhibit, activate, enhance, or modulate protein signaling, transport, or degradation through additional protein interactions.

The therapeutic multimer or plurality of therapeutic monomers interferes with or inhibits either: (1) an essential viral target from a set of targets that includes reverse transcriptase, protease, or viral integration proteins, by providing a plurality of monomers that can bind at a first site, and a plurality of monomers that can bind at an adjacent second site, said plurality of monomers creating a cocktail of therapeutic multimers providing broad inhibition of viral target and mutant variant viral targets; (2) viral entry into cells by binding to and inhibiting the cellular receptor responsible for assisting viral entry; (3) a cellular protein that assists with viral function; or (4) a viral protein such that it no longer inhibits a host defense protein.

The therapeutic multimer has a dissociation constant from the target molecule that is from within a ten-fold range of about 47 pM or lower to within a ten-fold range of 48 nM such that binding of the therapeutic multimer to the target molecule is sufficient to displace another protein, protein domain, macromolecule, or substrate with an equal or higher dissociation constant from binding to the target protein, or is of sufficiently tight binding to activate, enhance, or inhibit the biological activity of the target molecule or its binding partners such that about 70% to 100% of the target molecule within the target cells is bound by the therapeutic multimer to achieve the desired therapeutic effect. This method includes providing a first monomer, wherein the dissociation constant of the diversity element from the target molecule is from within a three-fold range of 100 nM to within a three-fold range of 10 μM. A second monomer, wherein the dissociation constant of the diversity element from the target molecule is from within a three-fold range of 1 μM to within a three-fold range of 10 μM is also provided. The dissociation constant between the linker element of the first monomer and its binding partner of the second monomer is from within a three-fold range of 10 μM to within a three-fold range of 100 μM. The connector joining the linker element to the diversity element for each monomer is in the range of about 2 or less rotatable bonds to about 5 rotatable bonds. The therapeutic multimer is present so that the steady-state concentrations of the monomers in the blood are in the range of from about 0.1 μM to about 5.0 μM or higher.

PROPHETIC EXAMPLES

The following prophetic examples sets forth the procedure for preparation of coferons. The steps include: 1) synthesis of bead-bound and solution libraries of linker element monomers; 2) screening and selection of the pair of linker element monomers that provide the tightest binding linker element dimer; 3) synthesis of a library of diversity elements attached to each of the selected linker element monomers to generate a library of coferon monomers; and 4) screening and selection of the coferon dimers that have the highest affinity for a target protein.

Prophetic Example 1

Synthesis of a Library of Linker Element Monomers

Figure 30:
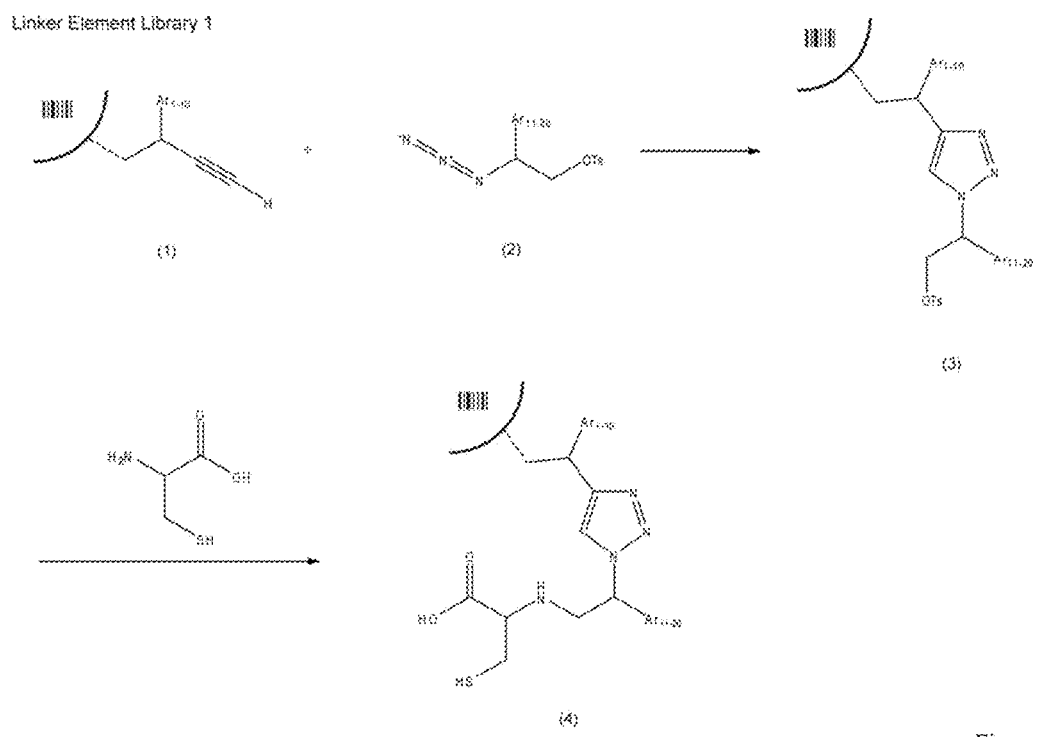

In this portion of the prophetic example, as described in FIG. 30, the synthesis of linker elements of the type Linker Element 9, is shown by the generic Formula XIII, an aromatic compound that intercalates with one or more of its binding partners, is described. For the processes below, beads are used where each bead has a unique identifier. This identifier may be a Veracode™ barcode, a sequence of DNA, a set of molecules that may be distinguished spectrally, or a set of molecules that may be distinguished by their mass. In general, the number of beads exceeds the number of different final product structures, such that more than one barcode can encode for the same final product on independent beads, but no two beads have the same barcode and different product molecules (other than stereoisomers). Ten different sets of Veracode™ beads (each bead bearing a different barcode) are individually reacted with 10 different alkynes to form a covalent bond between the alkynes and the beads. This produces a set of alkynes of the formula (1) covalently attached to beads where $Ar_1$ through $Ar_{10}$ represent 10 different aromatic groups. The alkyne added to a given individual bead is determined by reading the barcodes of each bead in each of the 10 sets, either before or after the alkyne reaction. The alkynes may be attached to Veracode™ beads functionalized with —$NH_2$, —COOH, or other reactive groups, such that the covalent bond formed between the aromatic alkynes and the beads may be cleaved with the use of appropriate reagents. The beads are then pooled, split into 10 new different sets, and each set reacted with one of 10 different azides of the formula (2) where $Ar_{11}$ through $Ar_{20}$ represent 10 different aromatic groups. The azide added to a given individual bead is determined by reading the barcodes of each bead in each of the 10 sets, either before or after the azide reaction. The reaction results in the synthesis of a library of 100 distinct disubstituted 1,2,3-triazoles of the formula (3) covalently attached to the Veracode™ beads. The nature of the particular aromatic rings attached to the triazole on a given bead may be deduced from the barcode encoding each bead. The beads bearing the disubstituted 1,2,3-triazoles are then reacted with cysteine to form a library of bead bound disubstituted 1,2,3-triazole linker elements of the formula (4), which bears a cysteine residue. The cysteine residue may be added in its disulfide form to prevent the cysteine thiol from competing with the amination. In this case, subsequent treatment with thioethanol will generate the free cysteine thiol.

Figure 31:
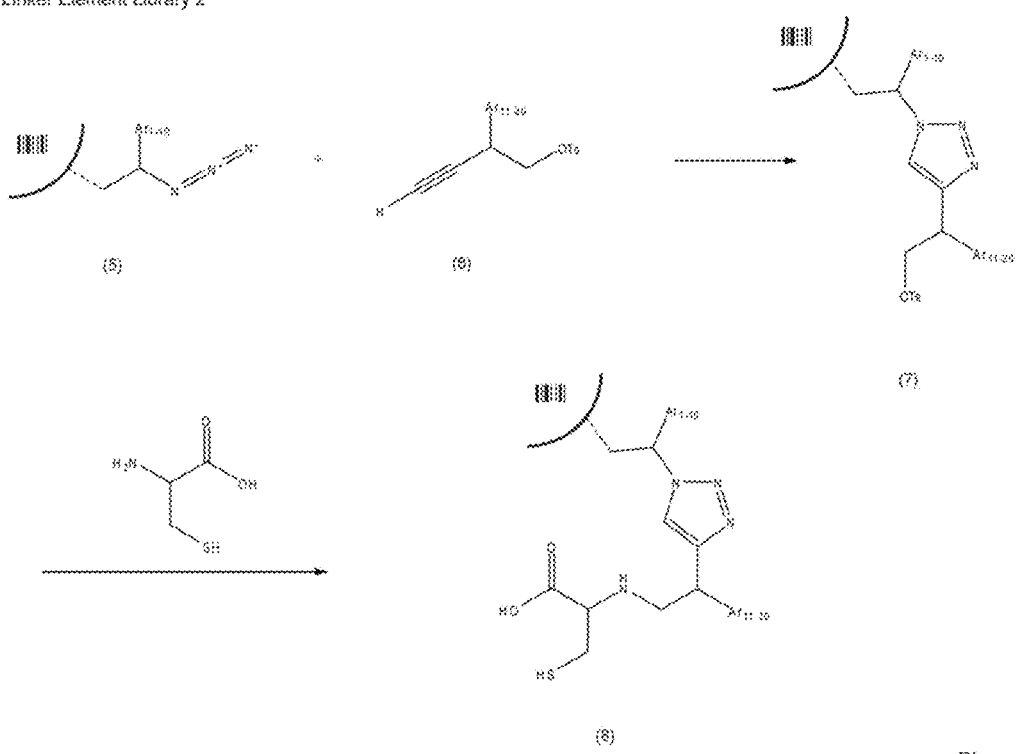

The process is then repeated as shown in FIG. 31, where 10 new sets of different Veracode™ beads (each bead bearing a different barcode) are individually reacted with 10 different azides. This produces a set of azides of the formula (5) covalently attached to beads where $Ar_1$ through $Ar_{10}$ represent 10 different aromatic groups. The azide added to a given individual bead is determined by reading the barcodes of each bead in each of the 10 sets, either before or after the azide reaction. The beads are then pooled, split into 10 new different sets, and each set reacted with one of 10 different alkynes of the formula (6) where $Ar_{11}$ through $Ar_{20}$ represent 10 different aromatic groups. The alkyne added to a given individual bead is determined by reading the barcodes of each bead in each of the 10 sets, either before or after the alkyne reaction. The reaction results in the synthesis of a library of 100 distinct disubstituted 1,2,3-triazoles of the formula (7) covalently attached to the Veracode™ beads. The beads bearing the disubstituted 1,2,3-triazoles are then reacted with cysteine to form a library of bead bound disubstituted 1,2,3-triazole linker elements of the formula (8), which bears a cysteine residue. The cysteine residue may be added in its disulfide form to prevent the cysteine thiol from competing with the amination. In this case, subsequent treatment with thioethanol will generate the free cysteine thiol. This is the Linker Element Library 2.

Figure 32:
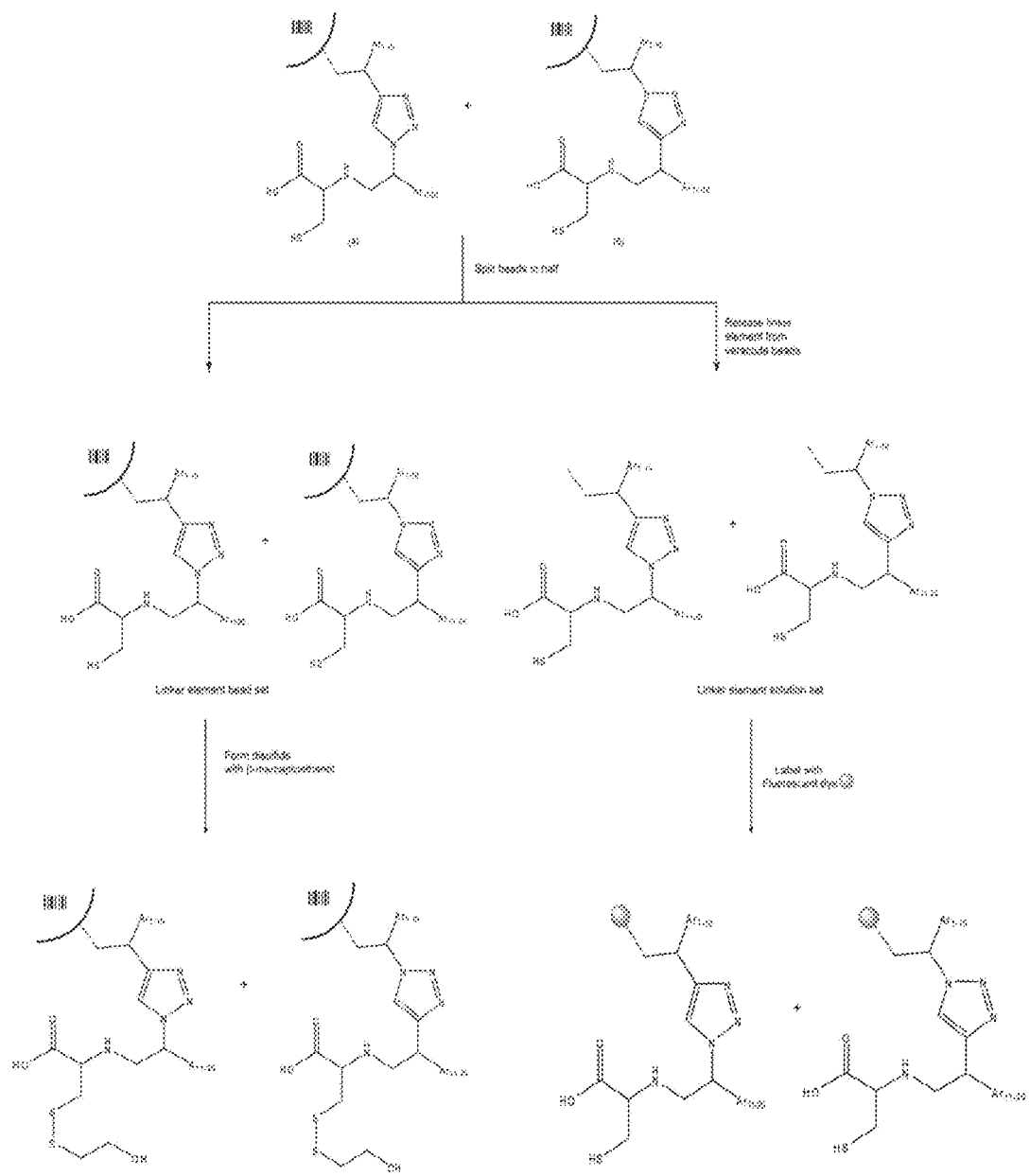

The beads comprising the two Linker Element Libraries (Library 1 and 2) are first combined and then split into equal halves. One half of the beads are retained as the bead set of linker element monomers. This set is reacted with beta-mercaptoethanol, or a similar agent to create a mixed disulfide link. The other half of the beads is treated with the appropriate reagents to cleave the linker elements from the beads and release them into the solution. The released linker element molecules are then reacted with a fluorescent dye such that they are covalently linked to the fluorescent dye. These fluorescently labeled linker element monomers are the solution set of linker element monomers. See FIG. 32.

Prophetic Example 2

Figure 33:
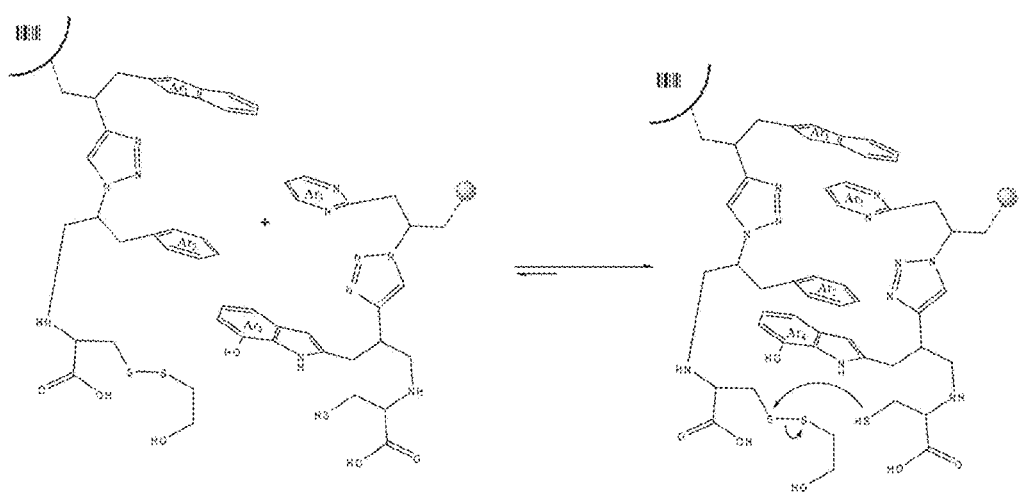

Screening of Linker Element Monomers to Find Pairs of Linker Elements that Bind Each Other to with the Greatest Affinity The bead set of linker element monomers is allowed to interact with the solution set of linker element monomers in an aqueous buffer that mimics physiological conditions (pH 7.4, 37° C.). The linker elements in solution intercalate with the linker elements on beads in a reversible manner. For the tightest binding pair of linker element monomers, this equilibrium is shifted towards the formation of linker element dimers (FIG. 33). In this portion of the prophetic example, the greatest affinity is seen between the monomer containing the aromatic groups $Ar_1$ and $Ar_e$ and the monomer containing the aromatic groups $Ar_3$ and $Ar_4$. The linker element monomer 1,2,3-triazole flanked by the aromatic groups $Ar_1$ and $Ar_2$, is bound to a Veracode™ bead and can be identified based on the barcode on the Veracode™ bead. The linker element monomer 1,2,3-triazole flanked by the aromatic groups $Ar_3$ and $Ar_4$, is in solution and also bears a fluorescent label. When the solution is screened, beads that provide a fluorescent signal are selected. The Veracode™ barcode identifies the linker element monomer attached to the bead (with $Ar_1$ and $Ar_2$). The solution also contains the exact same linker element monomers where the monomer containing the aromatic groups $Ar_1$ and $Ar_e$ is in solution and bears a fluorescent label and the monomer containing the aromatic groups $Ar_3$ and $Ar_4$ is attached to a Veracode™ bead with a different barcode. The dimers formed between these linker element monomers are also selected and the Veracode™ barcode identifies the linker element monomer attached to the bead (with $Ar_3$ and $Ar_4$).

In the next step, diversity element libraries are synthesized on each of these linker element monomers.

Prophetic Example 3

Figure 34:
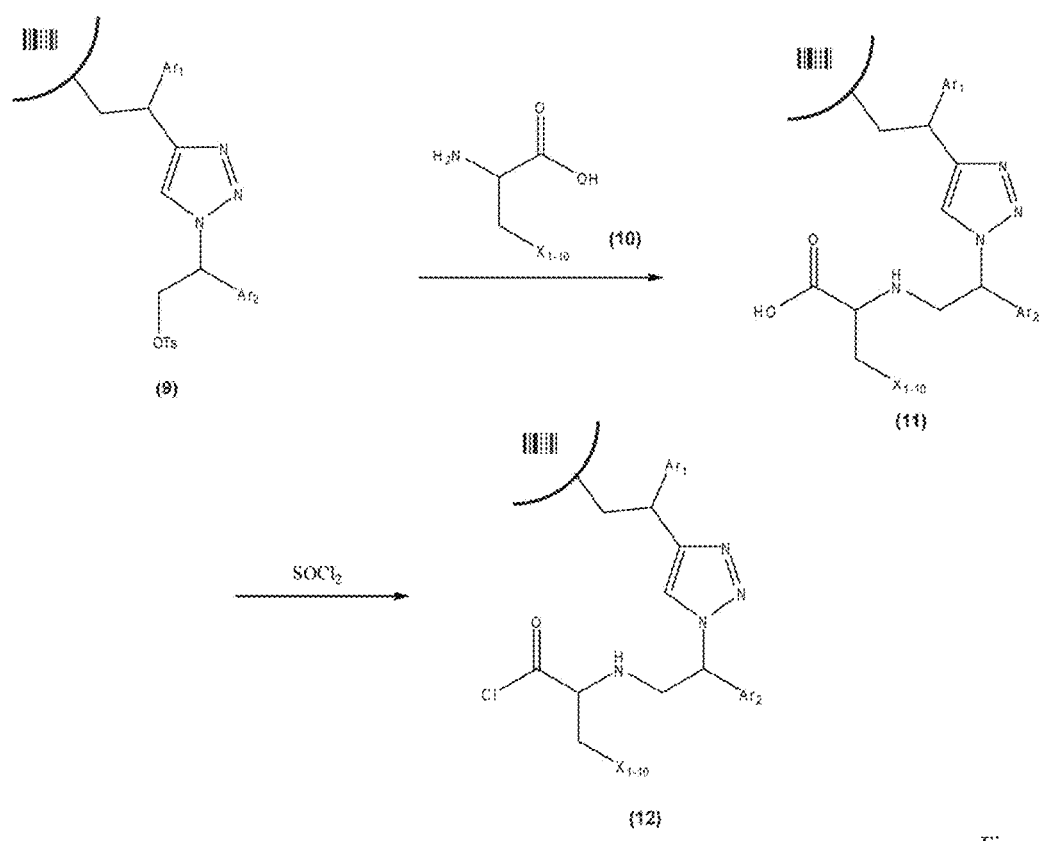

Synthesis of a Library of Diversity Elements Attached to Each of the Selected Linker Element Monomers to Generate a Library of Coferon Monomers A diversity element library based on a tri-substituted cyclopentane scaffold is synthesized and attached to the first linker element. The linker element is re-synthesized on a set of Veracode™ beads, each bead containing a unique barcode (formula (9)) and reacted with 10 different amino acids (formula (10)) to form a library of linker element-amino acids of the formula (11). The Veracode™ barcode identifies the particular amino acid attached to the linker element. The side chains of the amino acids represent an area of diversity in the final coferon monomer. The bead bound library is then reacted with thionyl chloride to convert the carboxylic acid groups of the amino acids to acid chlorides thus forming a bead bound library of linker element-amino acid chlorides (formula 12)). See FIG. 34.

Figure 35:
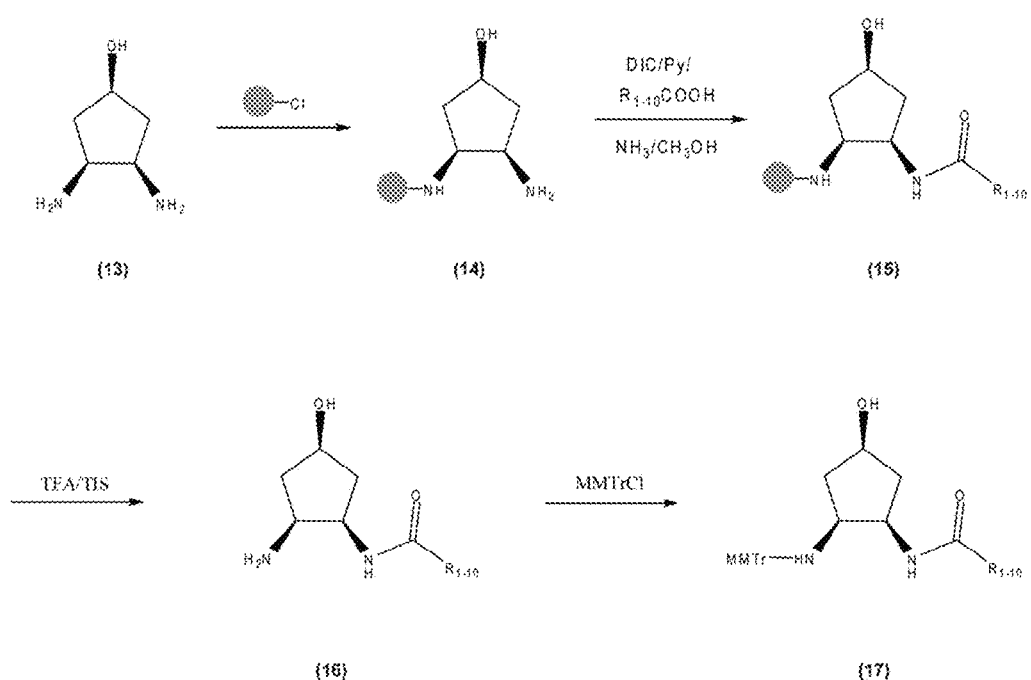

As shown in FIG. 35, (1R,3R,4S)-3,4-diaminocyclopentanol (13) is reacted with a resin to covalently link one of the amino groups to the resin. The resin bound structure (14) is then treated with N,N'-Diisopropylcarbodiimide (DIC) and reacted in 10 different reaction vessels with one each of 10 different carboxylic acids $R_{1-10}COOH$ where $R_{1-10}$ represent 10 different aliphatic, alicyclic, or aromatic groups to form amide linkages between the free amine of the cylopentanol and the acid (15). These carboxylic acid amides represent another area of diversity in the final coferon monomer. Transiently formed esters between the carboxylic acids and the hydroxyl group of the cyclopentanol are hydrolyzed with a mixture of ammonia and methanol. Each individual set of amides (15) is treated with trifluoroacetic acid (TFA) and triisopropylsilane (TIS) to cleave each set from the resin to generate 10 different sets of cyclopentanol amides with a free amino group (16) and then reacted with monomethoxytrityl chloride (MMTrCl) to protect the amino group (17). The identity of each R group is known since the sets are kept separate.

Figure 36:
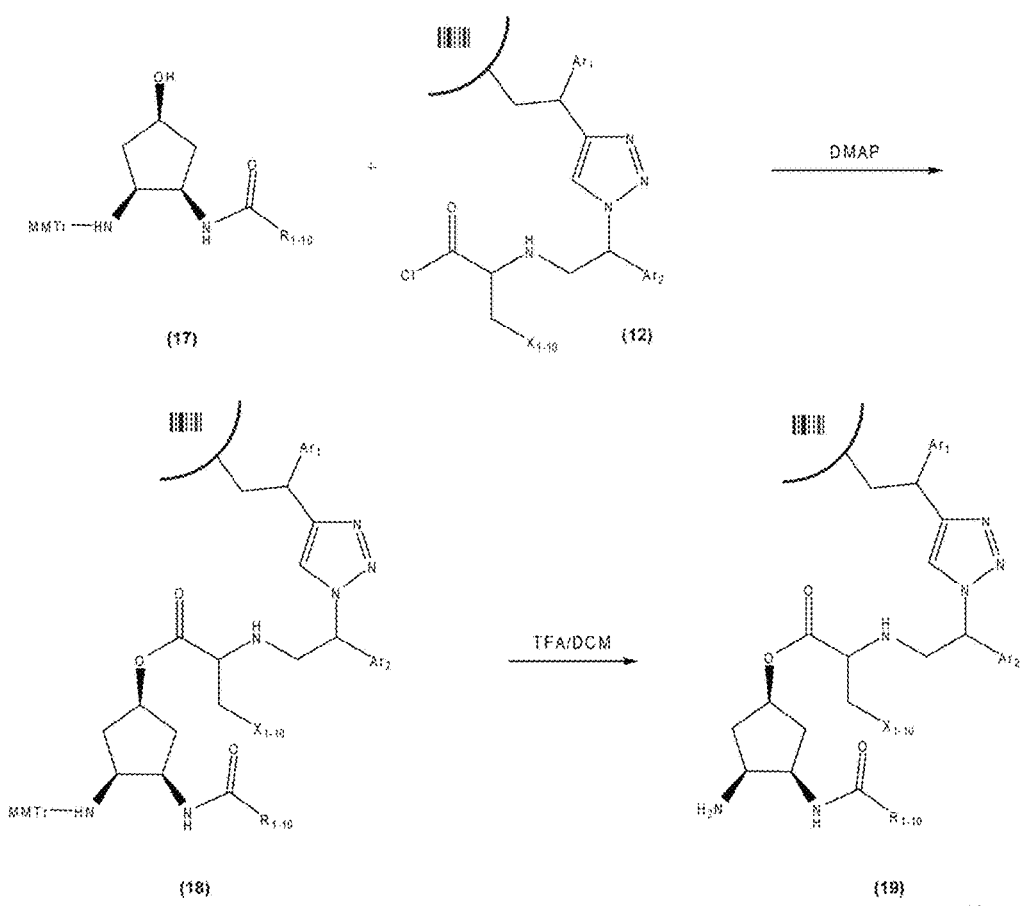

As shown in FIG. 36, the 10 sets of cyclopentanol amides (17) are then reacted with the bead bound library of linker element-amino acid chlorides (12) in 4-dimethylaminopyridine (DMAP) to form a library of linker elements where the amino acids form an ester linkage with the hydroxyl group of the cyclopentanol amides (18). The carboxylic acid added to a given individual bead is determined by reading the barcodes of each bead in each of the 10 sets, either before or after the amide reaction. The molecules are then treated with trifluoroacetic acid (TFA) in dichloromethane (DCM) to remove the monomethoxytrityl protecting group to generate the free amine (19).

Figure 37:
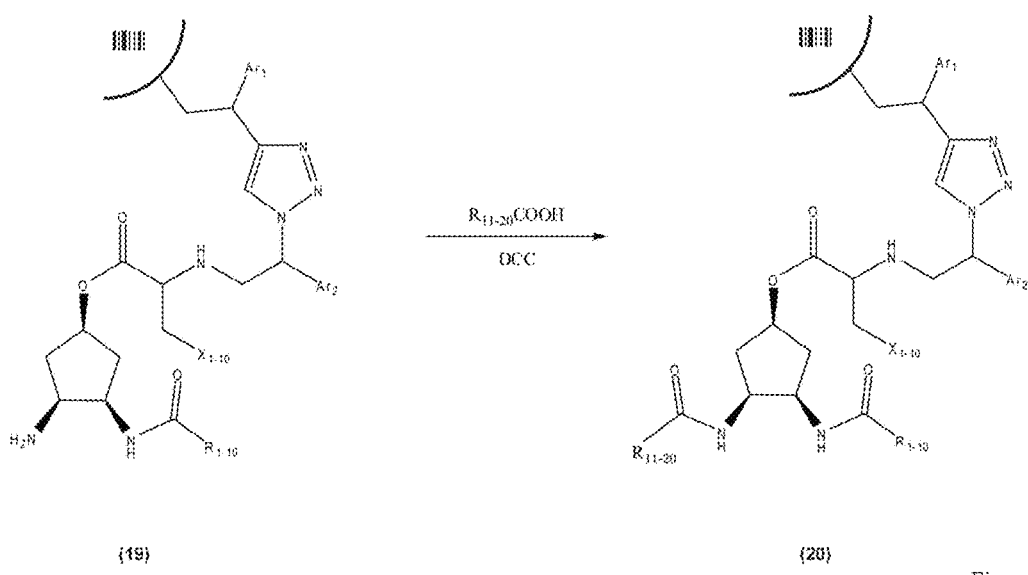
Figure 38:
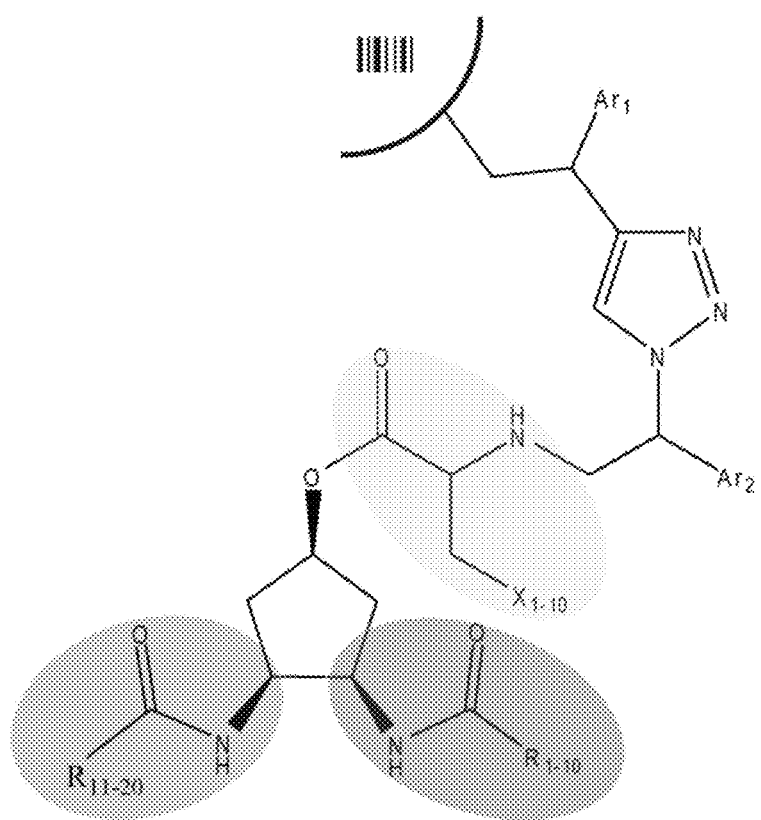

The beads are pooled to generate a library, which now contains beads attached to linker element monomers that bear a cyclopentane scaffold with 10 different esters at position 1, 10 different amides at position 3 and a free amino group at position 4 (19). The library is then split into 10 sets, and each set is treated with one of 10 different carboxylic acids $R_{11\text{-}20}COOH$ where $R_{11\text{-}20}$ represent 10 different aliphatic, alicyclic, or aromatic groups and dicyclohexyl carbodiimide (DCC) to form amides between the carboxylic acids and the amino group at position 4 of the cyclopentane scaffold to form the library of coferon monomers (20), as shown in FIG. 37. The carboxylic acid added to a given individual bead is determined by reading the barcodes of each bead in each of the 10 sets, either before or after the amide reaction. These carboxylic acid amides represent a third area of diversity in the final coferon monomer. FIG. 38 shows the three distinct areas of structural diversity in the coferon monomer overlaid with green, yellow and magenta ovals.

The entire process is repeated with the second linker element monomer (to create the diversity element library attached to the linker element with $Ar_a$ and $Ar_4$. The library is released from the beads and used in conjunction with the bead bound library above (where the linker element monomer contains $Ar_1$ and $Ar_2$) to screen for coferon dimers with the greatest affinity for a target protein.

Prophetic Example 4

Figure 39:
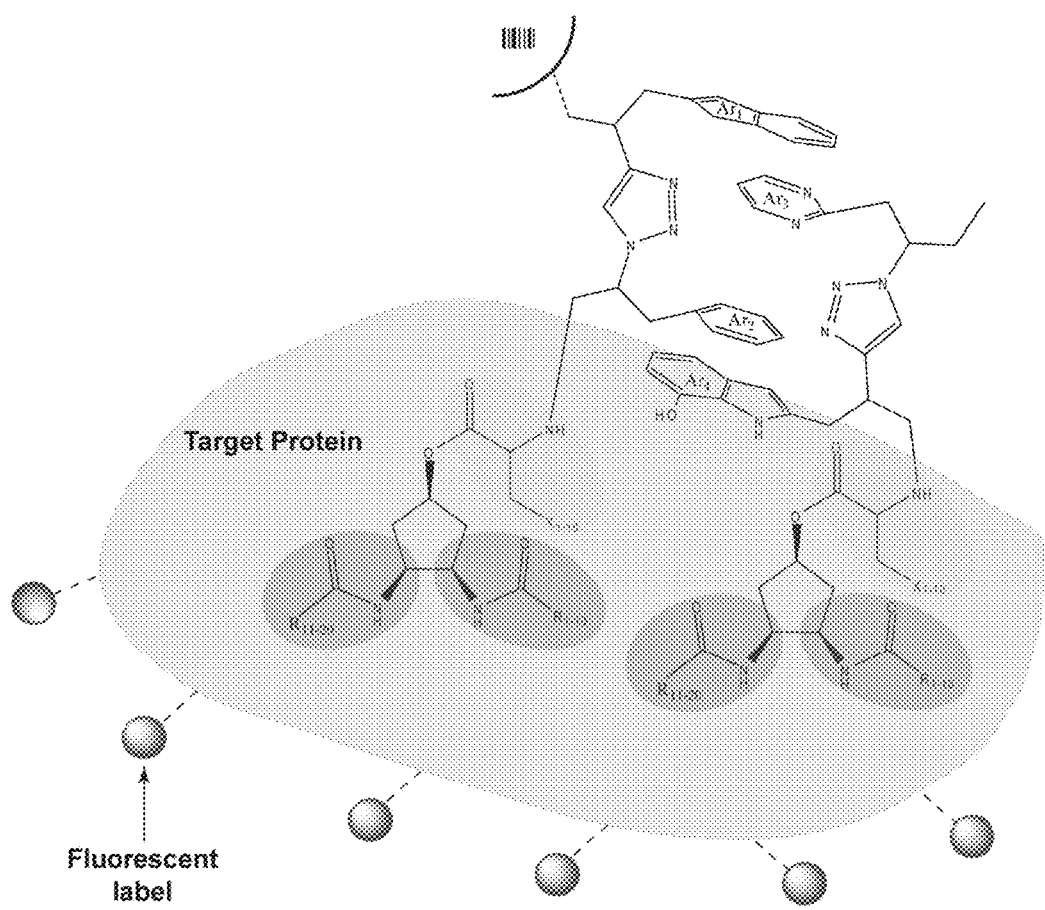

Screening of Coferon Monomers to Find Pairs of Coferons that Bind to a Target Protein with the Greatest Affinity The target protein is labeled with a fluorophore and incubated with the two coferon libraries, one coferon library bound to Veracode™ beads and the other coferon library in solution. The coferon monomers bind to the target reversibly. Coferon monomers that bind to the target with greater affinity are progressively removed from the solution as the equilibrium shifts from free monomer in solution to monomer bound to the protein for these higher affinity monomers. Coferon monomers with the greatest affinity interact with each other when bound to the protein and form coferon dimers. Some coferon dimers comprise monomers where both monomers are attached to Veracode™ beads. Other coferon dimers comprise monomers where both monomers are from the coferon library in solution. A third set of coferon dimers comprise of monomers where one monomer is attached to a Veracode™ bead and the other monomer is in solution (See FIG. 39). Judicious choice of coferon linker elements may favor the formation of heterodimer coferons such that the majority of coferon dimers contain one monomer on a Veracode™ bead and the other monomer from soluiton, both binding the target protein to the bead. After a suitable period of incubation, the beads are sorted to select for beads that provide the strongest fluorescent signal. The Veracode™ barcode on the bead identifies one of the coferon monomers that binds to the target protein. To determine the identity of the second coferon monomer from the solution library, one repeats the experiment so that the libraries on the bead and in solution are reversed.

The coferon monomer pairs that make up the winning coferon dimers can then be individually synthesized for use as therapeutic monomers.

These prophetic examples use 3 synthetic steps where each step introduces a 10-fold increase in diversity. The diversity is actually higher due to stereoisomers and chirality in the various structures. At a minimum, 1,000 diversity elements are generated for each coferon monomer set. Thus, when used as a dimer, the diversity is $10^6$.

The above prophetic examples need not be limited to just 10 additions per synthetic step. For example there are some 2,000 commercially available low molecular weight amino acids, and an equivalent order of magnitude of commercially available low molecular weight carboxylic acids.

In molecular biology, those skilled in the art of robotic instruments know it is straightforward to perform reactions in a 96 well or 384 well format. For the purposes of the discussions below, these numbers can be rounded up to 100 reactions and 400 reactions, to simplify the calculations of diversity generated by the process. By way of comparison, the peptide recognition arms of individual antibodies have a diversity of the order of $10^9$ to $10^{12}$.

When considering making a coferon monomer library comprised of three steps with 100 diversity elements in each of the three steps, the diversity of the final library is $10^6$. If this library is then combined with another library in solution with an equal diversity, the dimer diversity is now at $10^{12}$, the same level as the best antibody diversity loop. However, it may turn out that the time to reach equilibrium through dynamic combinatorial chemistry is too long, or the concentration of each reactant is too low. Consequently, background or non-specific effects may impede identification of the winning coferon pair.

In order to overcome this possible limitation at high levels of coferon diversity, an alternative approach can be used for screening the coferon dimers.

Since synthesis is straightforward in 96 well format (again, here it will just be called 100 wells), the last step can keep these 100 wells separated as individual reaction chambers, both for those reactions that are retained on beads, as well as those that are cleaved from the solid support. In such a case, one could screen 100 plates of 100 wells (in reality 96 plates of 96 wells), such that the individual diversity being queried in each well is only $10^4 \times 10^4 = 10^8$, even though the overall diversity being queried is $10^6 \times 10^6 = 10^{12}$.

Likewise, for synthesis in 384 well format (again, here it will just be called 400 wells), the last step can keep these 400 wells separated as individual reaction chambers, both for those reactions that are retained on beads, as well as those that are cleaved from the solid support. In such a case, one could screen 400 plates of 400 wells (in reality 384 plates of 384 wells), such that the individual diversity being queried in each well is only $1.6 \times 10^5 \times 1.6 \times 10^5 = 2.6 \times 10^{10}$, even though the overall diversity being queried is $6.4 \times 10^7 \times 6.4 \times 10^7 = 4.1 \times 10^{15}$. This level of diversity, allowing for easy screening and identification of the best lead molecules is difficult to achieve by standard combinatorial chemistry means.

Prophetic Example 5

Simulation of Binding Equilibria for Coferon Dimer to Target Protein: Determination of Concentrations of Coferon Dimers Binding to a Target Protein for Varying Concentrations of Each Coferon Monomer and Target Protein and for Varying Values of Dissociation Constants for Each Coferon Monomer to the Target Protein and Between the Coferon Monomers Most drugs function by binding to a biological target in competition with a natural substrate. In the case of infectious diseases, this competitive binding can turn off an essential function and kill or deactivate the infectious agent. In diseases such as cancer the competitive binding can either selectively kill malfunctioning cells or re-adjust endogenous biochemical processes so that cells can again function normally.

Two types of simulations of coferon dimers binding to target proteins have been performed. In the first type of simulation, an excess of coferons over target (FIGS. 48-81) was used. In some of these simulations, the amount of coferons used would be larger than a reasonable concentration in the blood stream. However, rarely is a target present at high concentration throughout the entire body. Often the cells that are being targeted by the drug have a higher concentration of target protein than cells not targeted by drug. This is especially true when the targeted cells are tumor cells.

A large tumor of half a pound (8 oz) represents only 1/300th to 1/400th of the average male body weight, and thus the vast majority of cells will have far less target. Therefore, starting with even a low concentration of the coferons in the body will be sufficient to bind to and inhibit the protein target, even if the concentration of that protein target in the specific cells is 10 to 40-fold higher than in the body.

Figure 47:
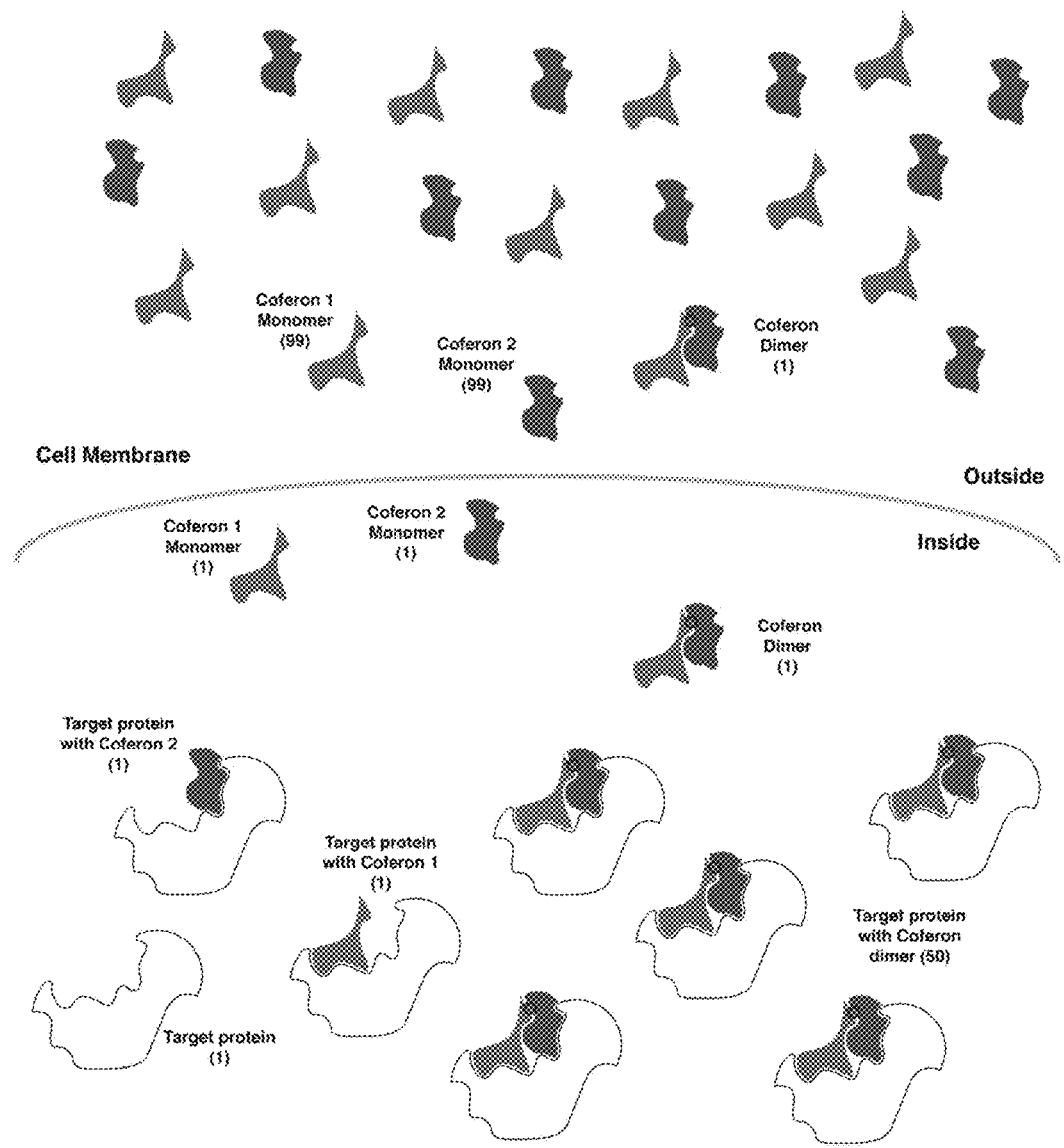
FIG. 47 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, the covalent bond between the two coferons as a red dot, and the target protein as a white shape. In this example, the linker elements of the two coferons do not easily come together, so that only a very small percentage of the coferons are in the dimer state. Although only monomers traverse the cell membrane, once inside, they bind to the target protein, which accelerates formation of its own inhibitor. Linker element association is via an irreversible covalent bond, such that once the dimer forms on the target protein, its dissociation from the target is very rare.

When coferon monomers enter the target cell, they bind to the target protein. When they form dimers on the protein target, the concentrations of monomers inside the cell decrease. To more accurately simulate conditions in vivo, the steady-state or "renewable" concentrations of the coferons were set at a given level, reflecting the ability to provide a steady dose of drug over time (FIGS. 47-106). This may be illustrated by the following example: consider a situation where the concentration of coferon monomers is at 1 μM outside the cell, but the target is at 10 μM inside the cell. When each monomer has a low $K_d$ value (for example, 1 μM) of dissociation from the target, and the two monomers have a low $K_d$ value (for example 10 μM) of dissociation from each other, then approximately 95% of the monomers inside the cell will form a dimer on the target—even though at this point, 90% of the target is still free. However, when the target binds monomer and coferon dimers inside the cell, the effective concentration of free monomer within the cell would decrease to about 0.05 μM. Thus, if the patient continues to take pills to keep the concentration of monomer in the blood stream at 1 μM, after taking 10 pills (simplifying assuming good bioavailability and no excretion) the patient should achieve on the order of from 95% of the target bound, even when the target is present at a concentration of 10 μM. Again, as mentioned above, in most cases only a very small fraction of the body will have the target protein at high concentration, so in practice, it will take fewer pills.

The large contact surfaces, (~1,500-3,000 Å$^2$) of a protein-protein interactions are several fold larger than protein-small molecule interactions (~300-1,000 Å$^2$). Typically, the dissociation constant of protein-protein interactions are in the nanomolar to micromolar range, often similar to the molecules that also bind these proteins. For example, $K_d$ values for various protein-protein interactions are as follows: p53-Mdm2, 600 nM; RAS-RAF, 80 nM; β-catenin-pAPC, 10 nM; Grb7-SH2, 11 μM; NF2-MPP1, 3.7 nM; CDC25B-Cdk2-pTyP/CycA, 10 nM (Table 3).

TABLE 3

Examples of Dissociation Constants for Known Protein Interactions

| PROTEIN | SUBSTRATE | DISSOCIATION CONSTANT ($K_d$) |
|---|---|---|
| CDC25B | Cdk2-pTpY/CycA | 10 nM[1] |
| Bcl-xL | cytochrome c | 120 nM[2] |
| Bcl-xL | BAK peptide | 200 nM[3] |
| DnaK | GrpE | 30 nM[4] |
| GABP β | GABP β | 600 nM[5] |
| Grb7 | SH2 | 11 μM[6] |
| NF2 | MPP1 | 3.7 nM[7] |
| HPV E2 | E1 | 60 nM[8] |
| IL-2Rα | IL2 | 60 nM[9,10] |
| p53 | MDM2 | 600 nM[11] |
| p53 | DNA | 14 μM[12] |
| p53 | HmtSSB | 12.7 μM[13] |
| pAKT | 14-3-3 | 22 nM[14] |
| AKT | 14-3-3 | 27 nM[14] |
| c-Jun/c-Jun (AP1) | DNA | 190 nM[15,16] |
| ERK | MEK1 | 610 nM[17] |
| CDK2 | ATP | 227 nM[18] |
| CDK2 | ADP | 2.7 μM[18] |
| CDK2 | Cyclin A | 48 nM[18] |
| RAS | RAF | 80 nM[19] |
| CaMKII | Calmodulin | 30 nM[20] |
| β CATENIN | ICAT | 3.1 nM[21] |
| β CATENIN | APC | 310 μM[21] |
| β CATENIN | pAPC | 10 nM[21] |
| EGFR | EGF | 2 nM[22] |
| ZipA | FtsZ-derived peptide | 21.6 μM[23] |
| ASK1 | ASK1 | 220 nM[24] |
| MKK4 | JNK3 | 35 μM[25] |
| MEK2 | ERK2 | 9 μM[26] |
| MEK1 | ERK1 | 29 μM[26] |
| SMAC/DIABLO | SMAC/DIABLO | 35 zM[27] |
| SMAC/DIABLO | XIAP | 800 nM[28] |
| Apaf-1 | Peptoid 1a | 57 nM[29] |

All of the following citations are hereby incorporated by reference in their entirety.
1. Sohn, J., et al., Biochemistry, 46: 807-18 (2007).
2. Yadaiah, M., et al., Biochim Biophys Acta, 1774: 370-9 (2007).
3. Sattler, M., et al., Science, 275:983-6 (1997).
4. Gelinas, A. D., et al., J Mol Biol, 339:447-58 (2004).
5. Desrosiers, D. C., et al., J Mol Biol, 354:375-84 (2005).
6. Porter, C. J., et al., Eur Biophys J, 34:454-60 (2005).
7. Seo, P.-S., et al., Exp Biol Med, 234:255-62 (2009).
8. Abbate, E. A., et al., Genes Dev, 18:1981-96 (2004).
9. Arkin, M. R., et al., Proc Natl Acad Sci USA, 100: 1603-8 (2003).
10. Braisted, A. C., et al., J Am Chem Soc, 125 3714-5 (2003).
11. Kussie, P. H., et al., Science, 274:948-53 (1996).
12. Joerger, A. C., et al., J Biol Chem, 280:16030-7 (2005).
13. Wong, T. S., et al., Nucleic Acids Res, 37: 568-81 (2009).
14. Sadik, G., et al., J Neurochem, 108: 33-43 (2009).
15. Kobayashi, T., et al., Anal Biochem, 332:58 (2004).
16. John, M., et al., Nucleic Acids Res, 24:4487-94 (1996).
17. Horiuchi, K. Y., et al., Biochemistry, 37: 8879-85 (1998).
18. Heitz, F., et al., Biochemistry, 36: 4995-5003 (1997).
19. Kiel, C., et al., J Mol Biol, 340:1039-58 (2004).
20. Brokx, R. D., et al., J Biol Chem, 276:14083-91 (2001).
21. Choi, H. J., et al., J Biol Chem, 281:1027-38 (2006).
22. Swindle, C. S., et al., J Cell Biol, 154:459-68 (2001).
23. Mosyak, L., et al., Embo J, 19:3179-91 (2000).
24. Bunkoczi, G., et al., Structure, 15: 1215 (2007).
25. Bardwell, L., et al., Methods, 40:213 (2006).
26. Bardwell, A. J., et al., J Biol Chem, 276: 10374-86 (2001).
27. Goncalves, R. B., et al., Biochemistry, 47:3832-41 (2008).
28. Kipp, R. A., et al., Biochemistry, 41: 7344-9 (2002).
29. Malet, G., et al., Cell Death Differ, 13: 1523-32 (2006).

In contrast, independent protein domains interacting with peptides or proteins can demonstrate $K_d$ values up to millimolar ranges, demonstrating the importance of the complete protein structure for binding affinities in addition to the other environmental factors that determine pharmacokinetic properties. For example $K_d$ values for the following domain-domain interactions are: SH2-phosphotyrosine residue in Grb2, 0.2-11 µM; FHA-phospho-threonine and phospho-tyrosine residues in KIF13B, 1-100 µM; MH2-phospho-serine residues in SMAD2, 240 nM; PTB-phospho-tyrosine residues, Asn-Pro-X-Tyr motifs in IRS-1, 160 nM-10 µM; SH3-proline-rich peptides with consensus Pro-X-X-Pro (SEQ ID NO. 3), where X is an amino acid. In Grb2, 1-500 µM; FYVE-phosphatidylinositol 3-phosphate, zinc in SARA, 50 nM-140 µM (Table 2).

In order for a coferon dimer or multimer to be an effective inhibitor of a given protein-protein interaction, the highest dissociation constant of the coferon dimer from the protein target (usually $K_{d3}$ or $K_{d4}$, but also $K_{d6}$ when using irreversible linker elements) needs to be lower than or about equal to the dissociation constant of the native protein binding partner from the protein target.

The simulations are idealized. All of the simulations assume non-competitive binding. That is, the site bound by the coferon dimer is either not bound by any natural ligand or the natural ligand binds far less tightly and/or is at much lower concentration. It is not necessary to correct for binding of the coferon dimer to other biomolecules in the system. The concentrations assumed for coferon monomers C1 and C2 are after loss due to binding to serum albumin, etc. In the simulations, the dissociation constants for the three different dissociation pathways are provided (see below). The highest value will be the pathway of dissociation. If this value is lower than the value between the protein target and another protein binding partner, the coferon dimers will displace the protein binding partner. Even if the dissociation value for the coferon dimer is higher than for the natural protein binding partner, the coferons may still have an inhibitory effect if used at a higher concentration.

An effective drug is one that binds to a target with high affinity, but does not have significant affinity for other proteins and biological molecules in the body. Such a drug is said to be selective for its target. Binding is characterized by a change in free energy designated by the symbol ΔG. The greater the change in free energy on binding, the higher the affinity. A negative value for ΔG indicates a spontaneous process. When ΔG is positive binding is not favorable.

One can estimate the dissociation constants, $K_d$, for monomer or dimer-target complexes using standard equilibria expressions:

$$K_d = \frac{[L][R]}{[LR]} \text{ and the equilibrium expression } [LR] \rightleftarrows [L] + [R] \quad \text{[Equation 1]}$$

where [L] is the concentration of drug or ligand, [R] is the concentration of receptor (typically a protein), and [LR] is the concentration of the complex. $K_d$ is typically in units of moles/liter (M) and is equivalent to the concentration of drug at which the concentration of protein and protein-drug complex are equal ($K_1$=[L] when [R]=[LR]).

$K_d$ is related to the free energy by the equations:

$$\Delta G = -RT \ln K_d \quad \text{[Equation 2]}$$

or $$K_d = e^{-\Delta G/RT} \quad \text{[Equation 3]}$$

At 37° C. ln $K_d$=-ΔG/(8.3145 J/K) (310 K) when ΔG is given in J/mol.

Figure 40:
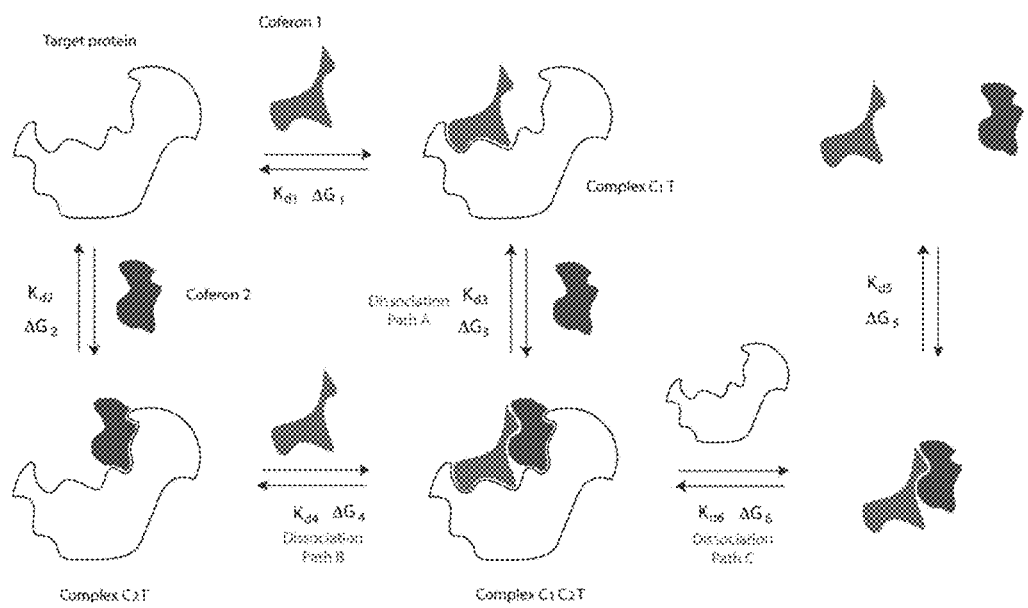

FIG. 40, is a schematic representation of a system of two coferon monomers (C1 and C2) that bind to orthogonal sites on a protein target (T) and to each other. Coferon 1 is illustrated as a green shape, coferon 2 as a blue shape, and the target protein as a white shape. The equilibrium of coferon 1 (C1) binding to the target is given by the dissociation constant $K_{d1}$. The equilibrium of coferon 2 (C2) binding to the target is given by the dissociation constant $K_{d2}$. In turn, coferon C2 may bind the complex of C1T (with dissociation constant of $K_{d3}$), while coferon C1 may bind the complex of C2T (with dissociation constant of $K_{d4}$). The C1-C2 coferon dimer itself is in equilibrium with the target, with dissociation constant of $K_{d6}$. Finally, the dimer will dissociate to form the two monomers, with dissociation constant of $K_{d5}$.

The enhanced binding achieved by coferon dimers can be understood by consideration of an ideal case it which each monomer does not compromise the binding of the other monomer and the entropy loss of the tertiary complex is no greater than the sum of the entropy losses for each two component binding step. If a ligand such as coferon monomer 1 binds to a protein target with a gain in free energy equal to ΔG1, then the final assembly step by addition of coferon monomer 2 would occur with a free energy change ΔG4. In the ideal case ΔG4=ΔG1+ΔG5, and $K_d$=e−(ΔG1+ΔG5)/RT. The assembled complex (PE FIG. 40) can dissociate by any of three pathways (A-C) with the dissociation free energies given by:

Path A ΔG3=ΔG2+ΔG5 ln $K_{d3}$=−(ΔG2+ΔG5)/(8.3145 J/K) (310 K)

Path B ΔG4=ΔG1+ΔG5 ln $K_{d4}$=−(ΔG1+ΔG5)/(8.3145 J/K) (310 K)

Path C ΔG6=ΔG1+ΔG2 ln $K_{d5}$=−(ΔG1+ΔG2)/(8.3145 J/K) (310 K)

The preferred pathway for dissociation will be the one with the lowest value of ΔG dissociation.

The free energy of binding between the two coferon monomers, ΔG5 can be tuned by varying the structure of the linker elements within each family in multiple ways, including incorporation of electron withdrawing and/or releasing groups, addition or subtraction of groups that influence steric interactions, and the addition or subtraction of groups that influence rotational freedom of bonds. The ability to adjust the $K_d$ of linker elements allows one to vary the concentration of coferon monomer commensurate with necessary therapeutic dose.

Figure 41:
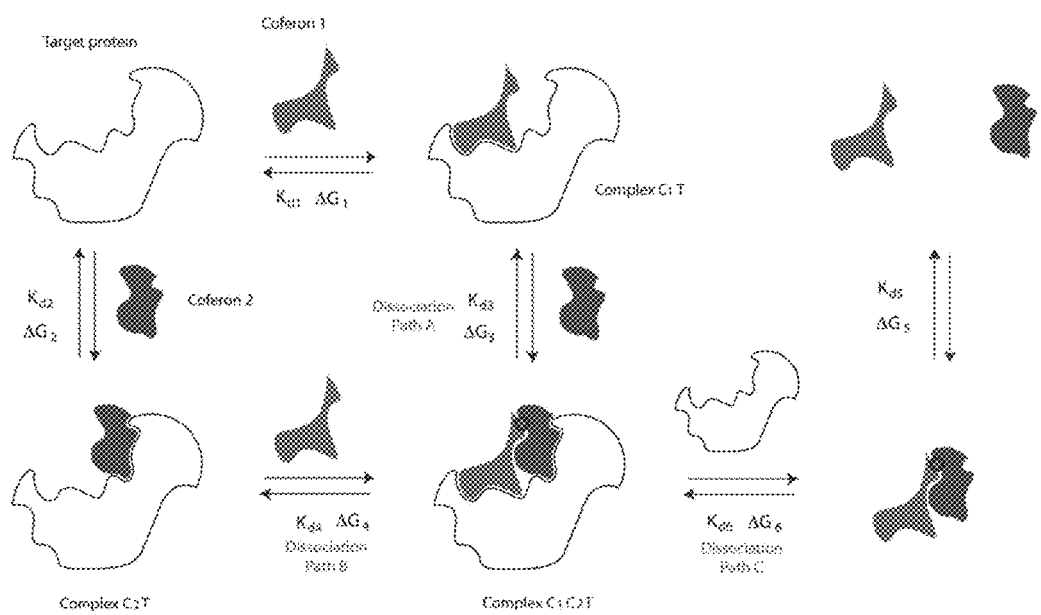

In many of the molecular designs, the linker elements bind to each other via a covalent association, depicted as a red dot in FIG. 41. The covalent association between the linker elements may be either reversible, or essentially irreversible. One example of essentially irreversible linker elements is the formation of thiazolines by reaction of β-aminothiols (e.g. cysteine) with aldehydes or ketones. Formation of a covalent bond between the monomers is facilitated by the target protein, because it creates a high local concentration of the two individual monomers at the target surface. Moreover the thiol component would be protected as a disulfide and not undergo conversion to the free thiol until the disulfide prodrug enters the cell and is cleaved by glutathione. Note that when both monomers bind to the target, the two linker elements are brought in close proximity with each other, effectively increasing their relative concentration to 1M or higher. If formation of the covalent bond(s) is irreversible, the $K_{d5}$ dissociation value will be zero. Under these conditions, dissociation of the coferon dimer from the target protein will be exclusively through $K_{d6}$, and may be 100-fold or even 1,000-fold lower.

In some cases, covalent linkage between two monomers may decrease the binding contributions of each monomer. In these cases, ΔG3 may be less than the sum ΔG1+ΔG5 and/or ΔG4 less than the sum ΔG2+ΔG5. If the difference in binding energy is modest (not more than a few kJ/mole), then monomer association is still advantageous. This scenario is possible and likely when known monovalent ligands or drugs are redeveloped as monomer pairs. Alternatively, when monomer pairs are developed by dynamic combinatorial strategies, the selection process is likely to uncover candidates for which ΔG3>ΔG1+ΔG5 and ΔG4>ΔG2+ΔG5. That is, each component of the covalently linked monomer pairs will actually bind more strongly to the target protein than individual unlinked monomers.

To calculate the dissociation constants $K_{d3}$, $K_{d4}$, and $K_{d6}$, we start with an input set of defined $K_{d1}$, $K_{d2}$, and $K_{d5}$. The total (or steady-state) concentrations of monomers C1 and C2, as well as the total concentration of protein target within the cell, are also provided. The MatLab program (The Mathworks, Natick, Mass.) is used to solve the following equations in two parts:

Part 1

Input set 1: $K_{d1}$, $K_{d2}$, $K_{d5}$

Equation set 1: Calculation of ΔG1, ΔG2, ΔG5 in units of kJ/mole $\Delta G1 = -RT \ln K_{d1} = -(8.3145 \text{ J/K})(10^{-3} \text{ kJ/K})(310 \text{ K}) \ln K_{d1}$ $\Delta G2 = -RT \ln K_{d2} = -(8.3145 \text{ J/K})(10^{-3} \text{ kJ/K})(310 \text{ K}) \ln K_{d2}$ $\Delta G5 = -RT \ln K_{d5} = -(8.3145 \text{ J/K})(10^{-3} \text{ kJ/K})(310 \text{ K}) \ln K_{d5}$ Input set 2: ΔG1, ΔG2, ΔG5

Equation set 2: Calculation of ΔG3, ΔG4, ΔG6 in units of kJ/mole $\Delta G3 = \Delta G2 + \Delta G5$ $\Delta G4 = \Delta G1 + \Delta G5$ $\Delta G6 = \Delta G1 + \Delta G2$ To account for loss of entropy due to restriction of free rotation, the above equations are corrected to account for 0 to 5 rotatable bonds between the monomer ligand and the linker element.

$\Delta G3 = \Delta G2 + \Delta G5 + n\Delta Gr$ $\Delta G4 = \Delta G1 + \Delta G5 + n\Delta Gr$ $\Delta G6 = \Delta G1 + \Delta G2 + n\Delta Gr$ Where n=total number of single bond rotations gained upon dissociation of complex C1C2T, and ΔGr=change in free energy per single bond rotation. A reasonable estimate for the value of ΔGr for rotation about a C–C single bond is –2 kJ/mol.

Input set 3: ΔG3, ΔG4, ΔG6

Equation set 3: Calculation of $K_{d1}$, $K_{d2}$, $K_{d3}$ $\ln K_{d3} = (-\Delta G3)/(8.3145 \text{ J/K})(310 \text{ K})$ $\ln K_{d4} = (-\Delta G4)/(8.3145 \text{ J/K})(310 \text{ K})$ $\ln K_{d6} = (-\Delta G6)/(8.3145 \text{ J/K})(310 \text{ K})$ or $K_{d3} = e^{-(\Delta G3)/(8.3145 \text{ J/K})(310 \text{ K})}$ $K_{d4} = e^{-(\Delta G4)/(8.3145 \text{ J/K})(310 \text{ K})}$ $K_{d6} = e^{-(\Delta G6)/(8.3145 \text{ J/K})(310 \text{ K})}$ Part 2

Input set 4: $K_{d1}$, $K_{d2}$, $K_{d3}$, $K_{d4}$, $K_{d5}$, $K_{d6}$ and starting concentration $[SC_1]$ and $[SC_2]$ of each monomer and the initial concentration of the target protein [ST].

Note that the starting concentrations of each monomer and the target are not the same as the final concentrations after equilibrium is obtained, but are related by the following equations:

$[T] + [C_1T] + [C_2T] + [C_1C_2T] = [ST]$     Equation 1

$[C_1] + [C_1T] + [C_1C_2T] + [C_1C_2] = [SC_1]$     Equation 2

$[C_2] + [C_2T] + [C_1C_2T] + [C_1C_2] = [SC_2]$     Equation 3

$K_{d1} = \dfrac{[C_1][T]}{[C_1T]}$     Equation 4

$K_{d2} = \dfrac{[C_2][T]}{[C_2T]}$     Equation 5

$K_{d3} = \dfrac{[C_1T][C_2]}{[C_1C_2T]}$     Equation 6

$K_{d4} = \dfrac{[C_2T][C_1]}{[C_1C_2T]}$     Equation 7

$K_{d5} = \dfrac{[C_1][C_2]}{[C_1C_2]}$     Equation 8

$K_{d6} = \dfrac{[C_1C_2][T]}{[C_1C_2T]}$     Equation 9

These equations are linear equations and can be solved using the following code in Matlab:

```
function [ ] = solvenonlineqn5(outfile)
%Define threshold:
thresh = eps;%Change this to the desired threshold; for example 1e-10;
%This would look for solutions with +ve real parts and
%imaginary/real<threshold
%Current threshold is set to 2.220446049250313e-016 (2^{-52})
load data; % This file contains the data from the XLS
gp = fopen(outfile,'w');
fprintf(gp,'T,C1,C2,C1T,C2T,C1C2,C1C2T\n');
for ctr= 1:size(data(:,1));
    flag = 0;
    syms C1T C1T C2 C2T C1C2 C1C2T;
```

```
%% The equations
    f(1) = C1*T/C1T - K_d1(ctr);
    f(2) = C2*T/C2T - K_d2(ctr);
    f(3) = C1T*C2/C1C2T - K_d3(ctr);
    f(4) = C2T*C1/C1C2T - K_d4(ctr);
    f(5) = C1*C2/C1C2 - K_d5(ctr);
    f(6) = C1C2*T/C1C2T - K_d6(ctr);
    f(7) = C1+C1T+C1C2T+C1C2 - SC1(ctr);
    f(8) = C2+C2T+C1C2T+C1C2 - SC2(ctr);
    f(9) = T+C1T+C2T+C1C2T - ST(ctr);
    list = [1 2 4 5 7 8 9];
%% Solution part
    S1 = solve(f(list(1)),f(list(2)),f(list(3)),f(list(4)),f(list(5)),f(list(6)),f(list(7)));
    outdata =
[subs(S1.T),subs(S1.C1),subs(S1.C2),subs(S1.C1T),subs(S1.C2T),subs(S1.C1C2),subs(S1.C
1C2T)];
    for ctr2 = 1:size(outdata,1)
        if (length(find(real(outdata(ctr2,:))>0))==length(outdata(ctr2,:)))
            if (isempty(find(imag(outdata(ctr2,:)))))
                disp(['Found real positive solution for set: ' num2str(ctr)]);
                parsedoutdata = outdata(ctr2,:);
                flag = 1;
            else
                index = find(imag(outdata(ctr2,:)));
if(isempty(find(abs(imag(outdata(ctr2,index)))./abs(real(outdata(ctr2,index)))>thresh)))
                    disp(['Found solution with +ve real part and negligible imaginary part for set: '
num2str(ctr)]);
                    parsedoutdata = real(outdata(ctr2,:));
                    flag = 1;
                end
            end
        end
    end
    if flag==0
        parsedoutdata = parsedoutdata*0;
    end
%% Generating output
    fprintf(gp,'%s\n',num2str(parsedoutdata));
end
fclose(gp);
```

Note:
Input set in excel file provides: $K_{d1}$, $K_{d2}$, $K_{d3}$, $K_{d4}$, $K_{d5}$, $K_{d6}$ and starting concentration [$SC_1$] and [$SC_2$] of each monomer and the initial concentration of the target protein [ST].

Figure 42:
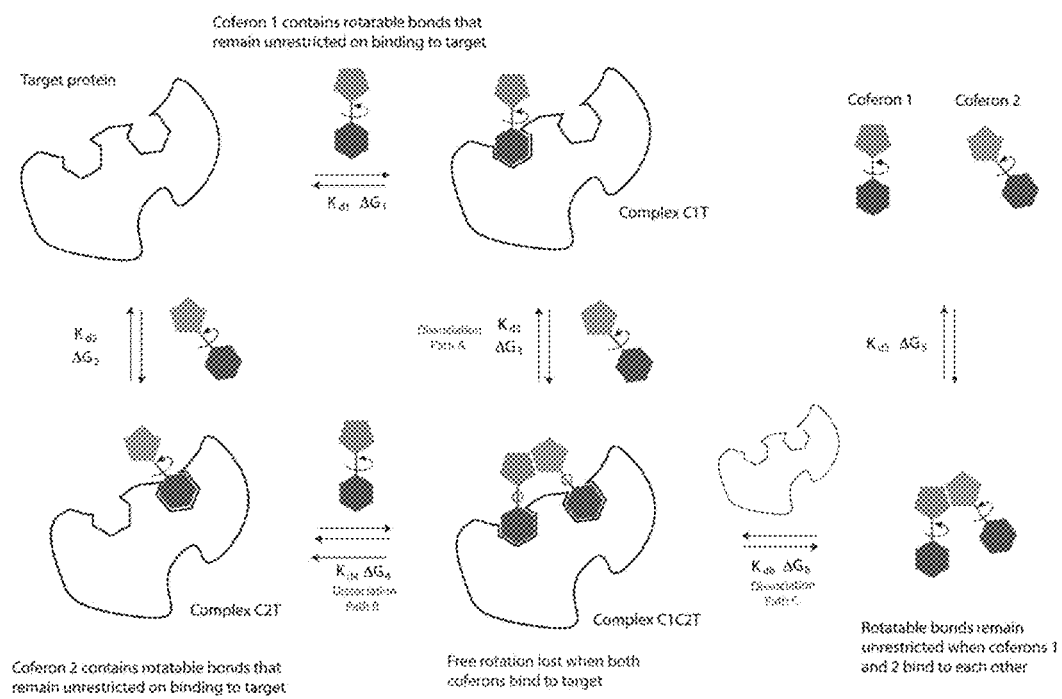
Figure 43:
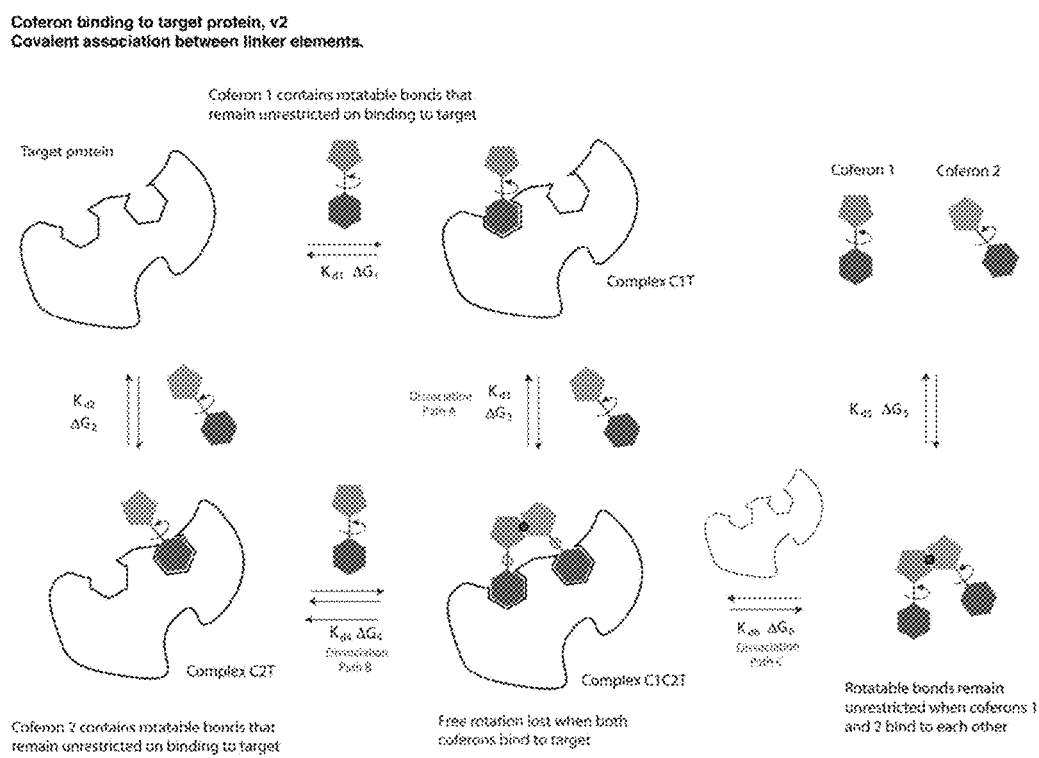
Figure 44:
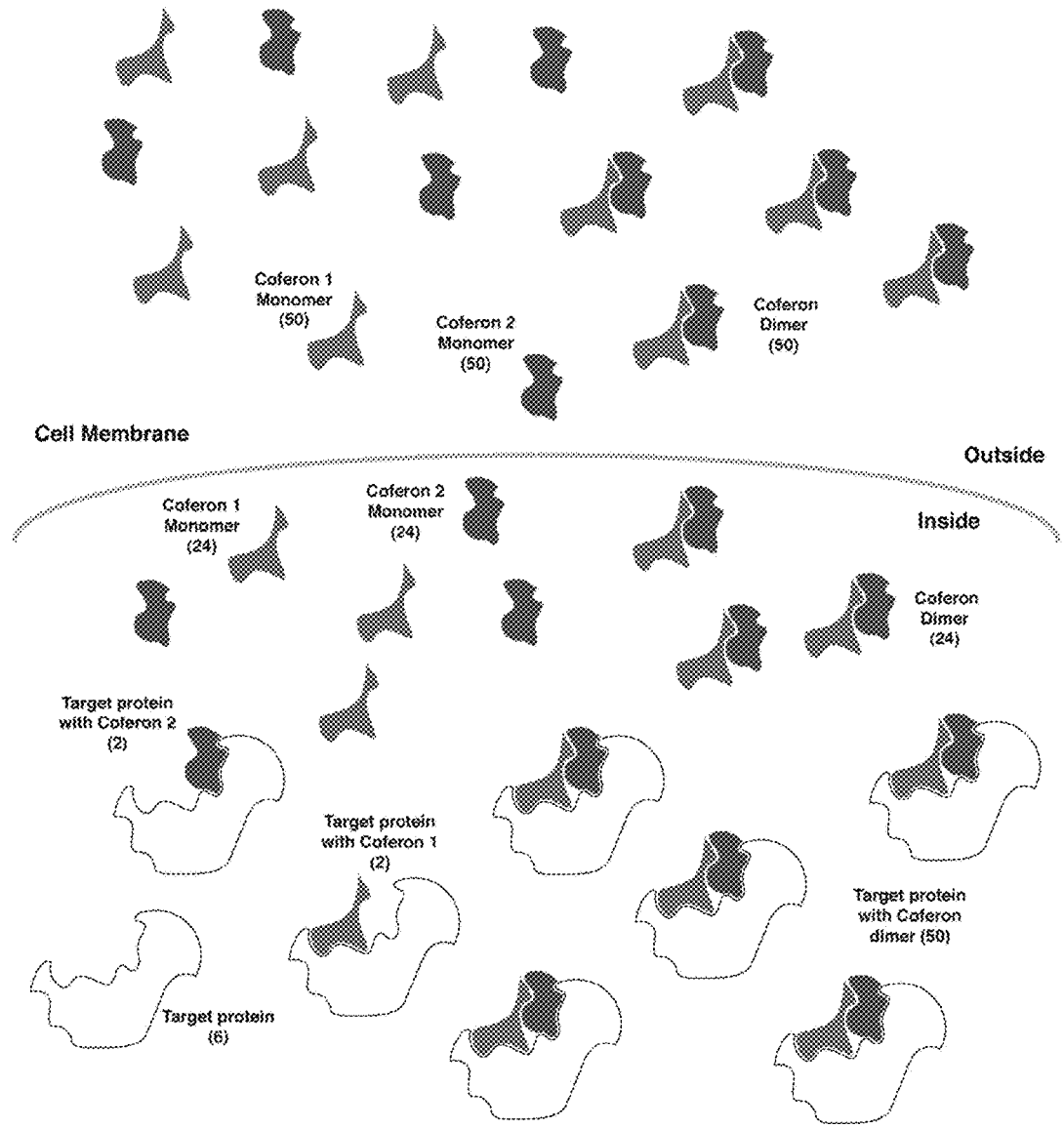
Figure 45:
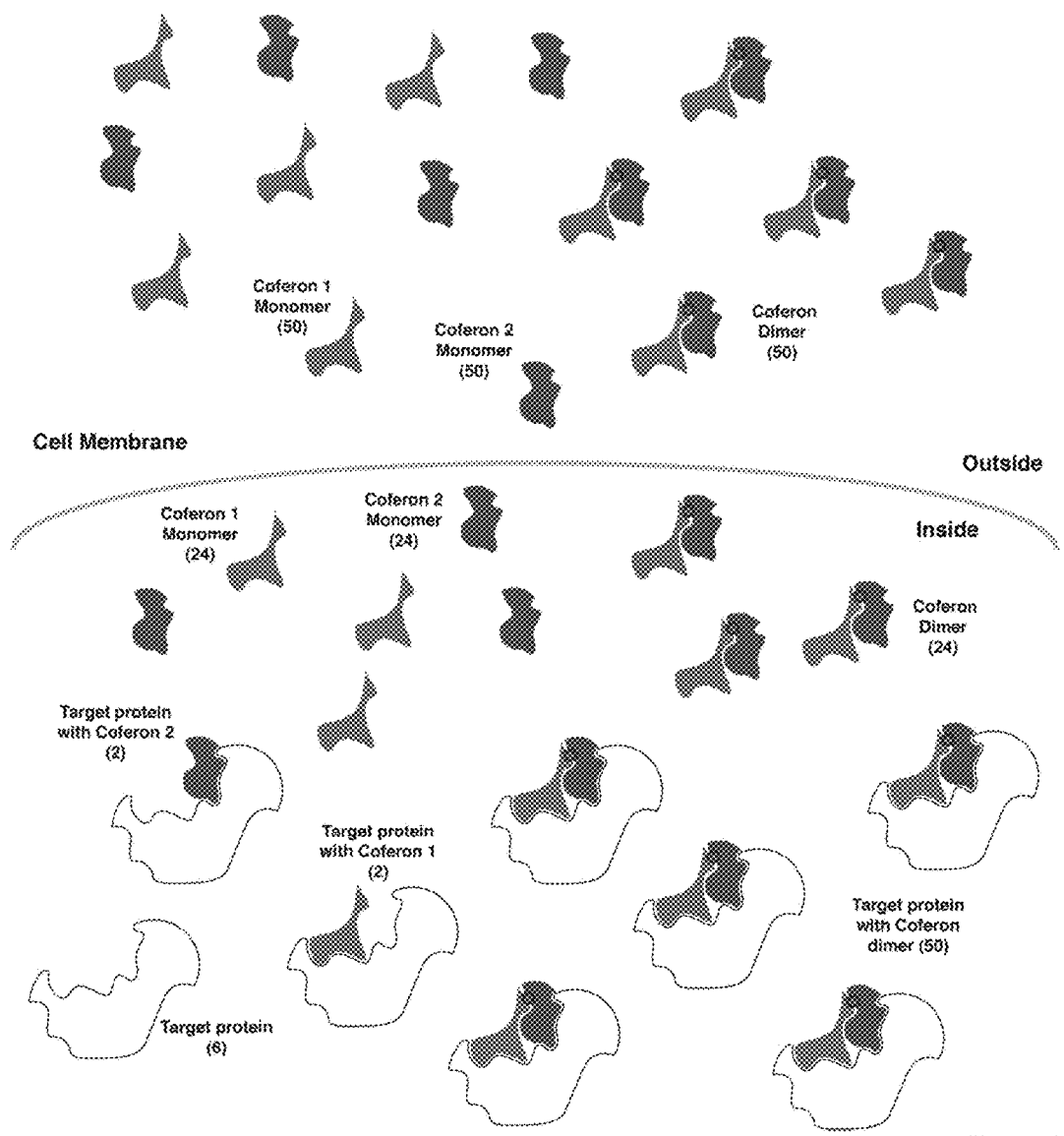
Figure 46:
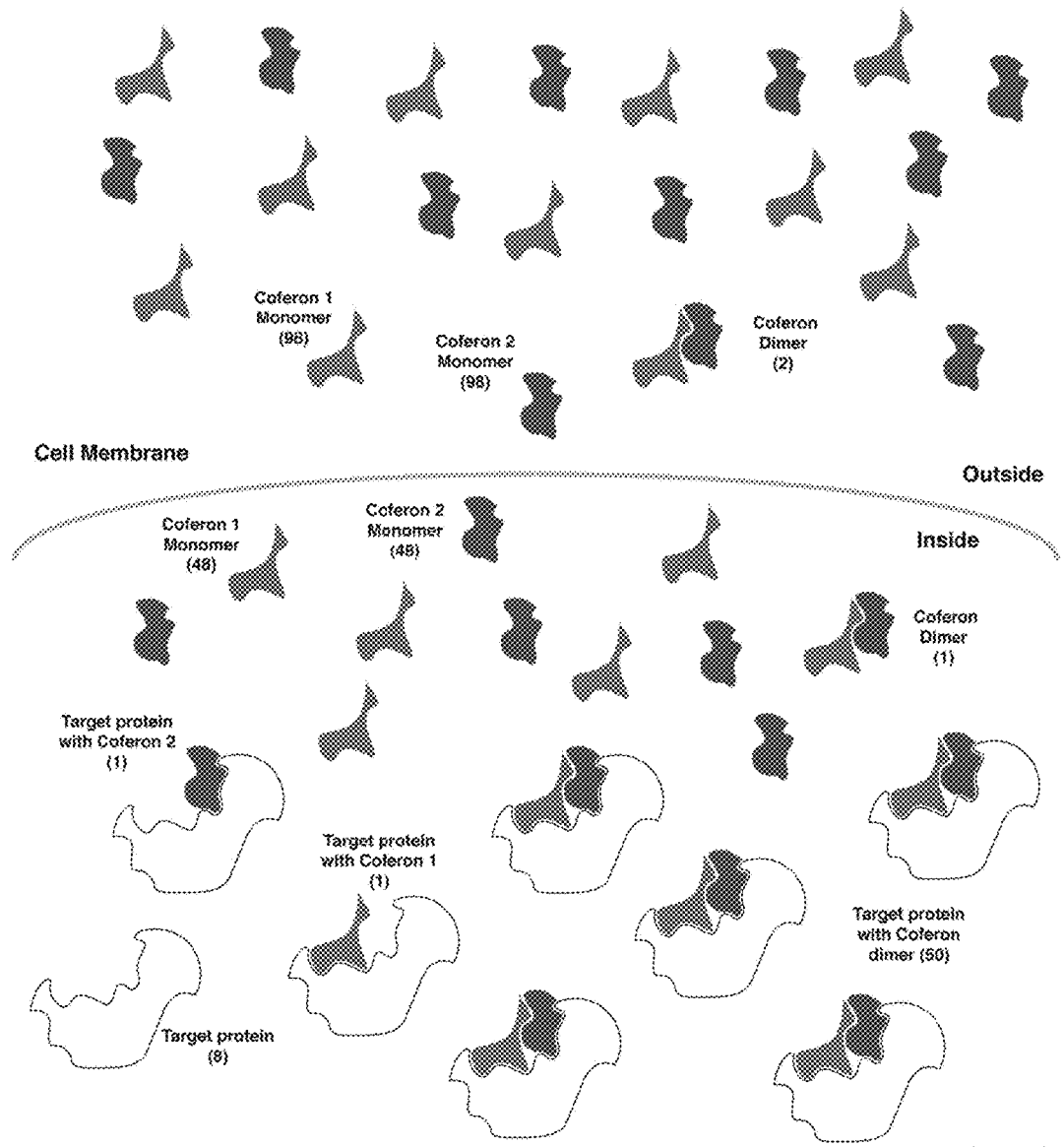

In these simulations, the entropy cost of binding both monomers to each other when they are also bound to the target has been considered. When a coferon monomer binds to the target, the rotatable bonds between the ligand and the linker element remain unrestricted. When two coferon monomers bind to each other, the rotatable bonds also remain unrestricted. Only when the coferon dimer forms on the target is there a loss of free rotation, and this has an entropy cost. FIG. 42, is a schematic representation of a system of two monomers (C1, and C2) that bind to orthogonal sites on a protein target (T) and to each other. Monomer 1 is illustrated as a green pentagon linker element tethered to a blue hexagon ligand, monomer 2 as an orange pentagon linker element tethered to a blue hexagon ligand, and the target protein as a white shape. The tether represents one or more rotatable bonds between the linker element and the ligand that binds to the target protein.

For these simulations, from 0 to 5 rotatable bonds between the linker elements and ligands of each coferon monomer—for a total of up to 10 rotatable bonds has been considered. While zero rotatable bonds represents a rigid architecture, and thus would be predicted to achieve the strongest binding, it also puts a considerable constraint on finding the correct combination of linker element and ligand binding portion to achieve the precisely desired geometry for maximum binding to both target and the other linker element in the coferon dimer. In contrast, a flexible connector between the linker elements and the ligands allows for systematic optimization of each binding event, albeit at an entropic cost that reflects the greater degree of freedom. A recent paper from the Whiteside group suggests that use of an oligo-ethylene oxide spacers mitigates the cost of using flexible connectors (V. M. Krishnamurthy, et. al, *J. Am. Chem. Soc.* 129:1312-1320 (2007), which is hereby incorporated by reference in its entirety). In the figures presented, $K_d$ values placed next to (r2) and (r5) represent 2 and 5 rotatable bonds between the linker elements and ligands of each coferon monomer—for a total of 4 and 10 rotatable bonds respectively. It is predicted that use of an oligo-ethylene oxide or similar spacer would provide $K_d$ values approximately within the same range of values provided.

The calculations are based on several idealized assumptions, which may need to be refined based on additional experimental evidence. It may be difficult to tune the binding energies of the ligands or linker elements to each other. Thus, when the $K_{d1}$, $K_{d2}$, and $K_{d5}$ values are set for these simulations, it is also considered that these constants may vary three-fold. For example, monomer C1 with dissociation constant $K_{d1}$ will be referred to the target of within a three-fold range of 1 µM. Since the dissociation of the coferon dimer from the target reflects the contribution of at least two of these constants, the range expands approximately nine to ten-fold. For example, the dissociation constant of the coferon dimer from the target will be referred to within a ten-fold range of about 47 pM or lower to within a ten-fold range of about 480 pM. As another example, if the linker elements bind to each other via irreversible covalent bonds, the dissociation constant of the coferon dimer from the target will be within a ten-fold range of about 4.7 pM or lower to within a ten-fold range of about 48 pM.

For the steady-state calculations, influx of additional monomer under conditions where the concentration of the monomer was equal to the concentration of the target was not corrected. Consequently, those numbers are artificially suppressed and result in a "dip" in the graphs. Further, steady-state simulations where target is in excess of monomer were not corrected for the decrease in free target as additional monomer monomer enter the cell and bind to target and form dimers. Therefore, such numbers may be slightly higher than would be reflected in an experimental system. Nevertheless, the numbers provide a rough guide of conditions within a range that may vary about three-fold.

Figure 58:
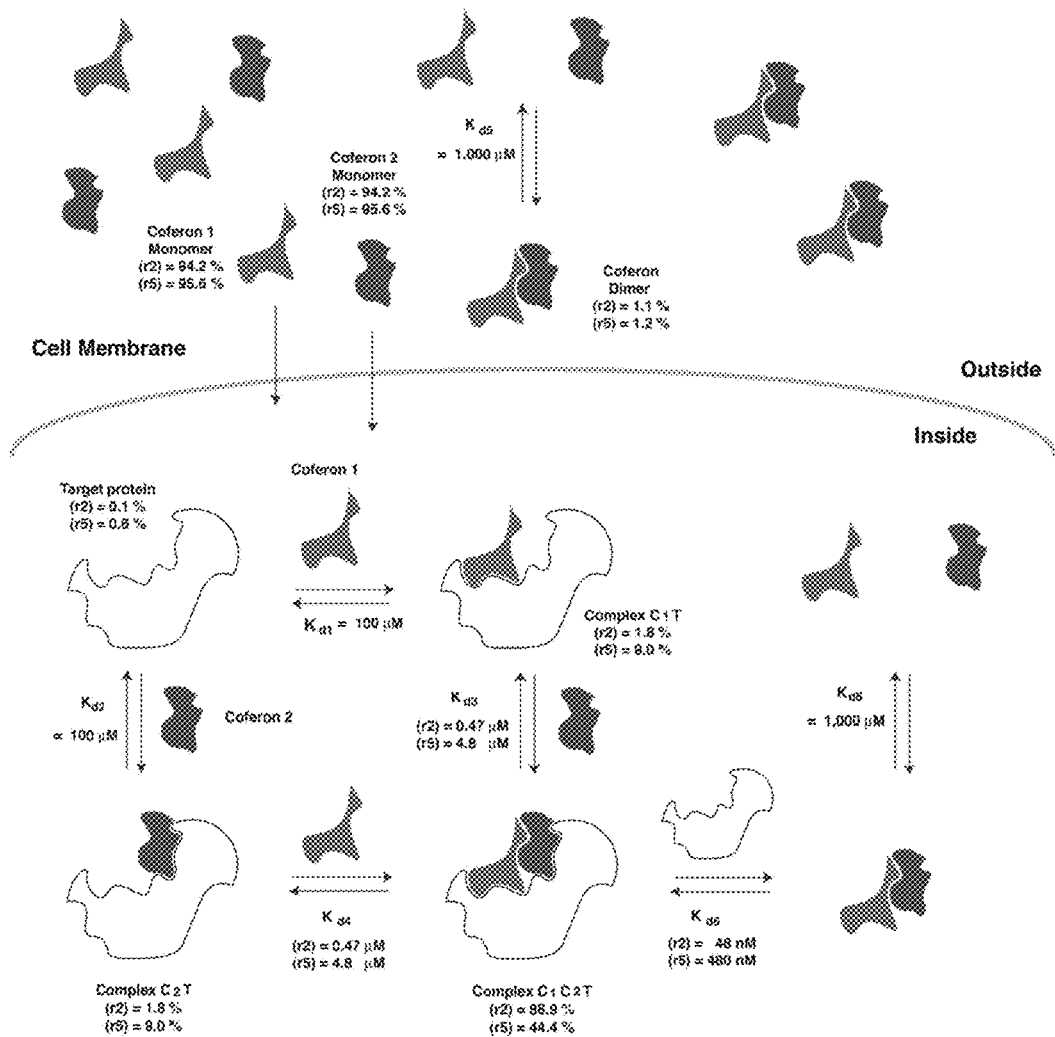
FIG. 58 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 25 µM, the total protein concentration inside the cell is 1 µM, about 1,000,000 targets per cell. The dissociation constants $K_{d1}$ and $K_{d2}$ between coferon C1 and target T, as well as between coferon C2 and target T are given at 100 µM. The dissociation constant between the two coferons, $K_{d5}$ is given at 1,000 µM.
Figure 59:
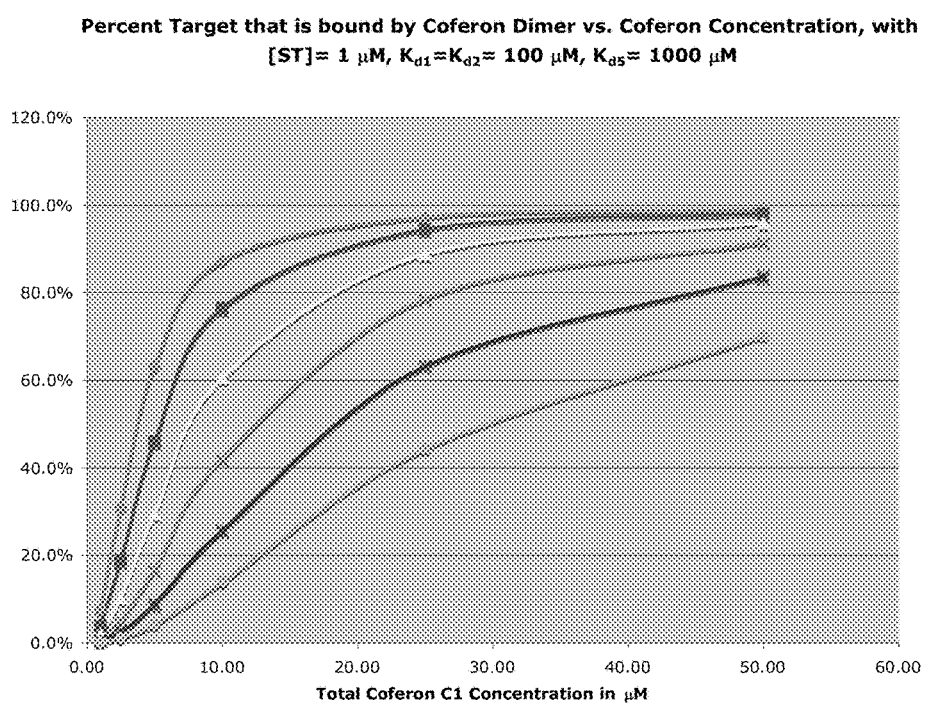
FIG. 59 is a graph showing the percent target T that is bound by coferon dimer C1C2 vs. coferon C1 concentration. The total target [ST] is set at 1 µM, $K_{d1}=K_{d2}$ is set at 100 µM, $K_{d5}$ is set at 1,000 µM, and total coferon C1 concentration [C1]=total coferon C2 concentration [C2], varying from 1 µM up to 50 µM concentration.
Figure 60:
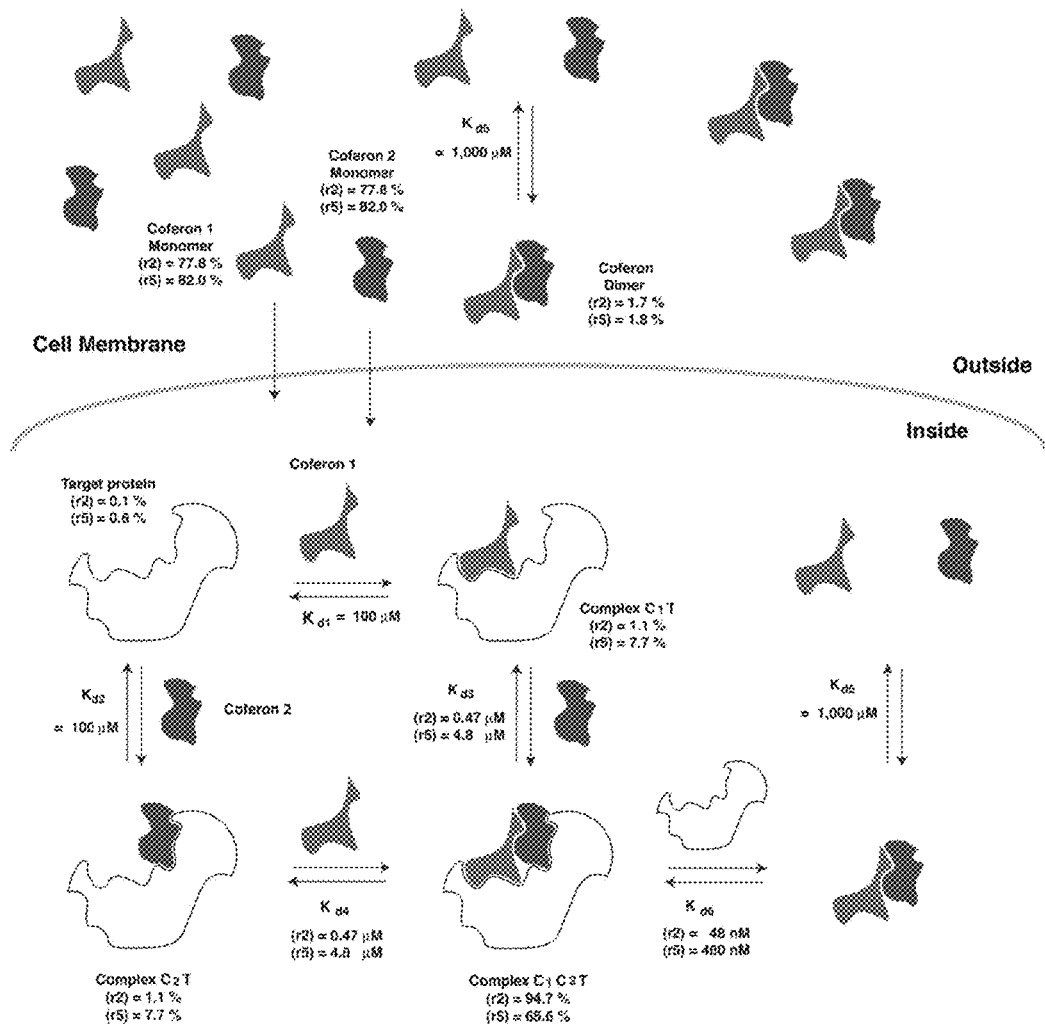
FIG. 60 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 50 µM, the total protein concentration inside the cell is 10 µM, about 10,000,000 targets per cell. The dissociation constants $K_{d1}$ and $K_{d2}$ between coferon C1 and target T, as well as between coferon C2 and target T are given at 100 µM. The dissociation constant between the two coferons, $K_{d5}$ is given at 1,000 µM.
Figure 61:
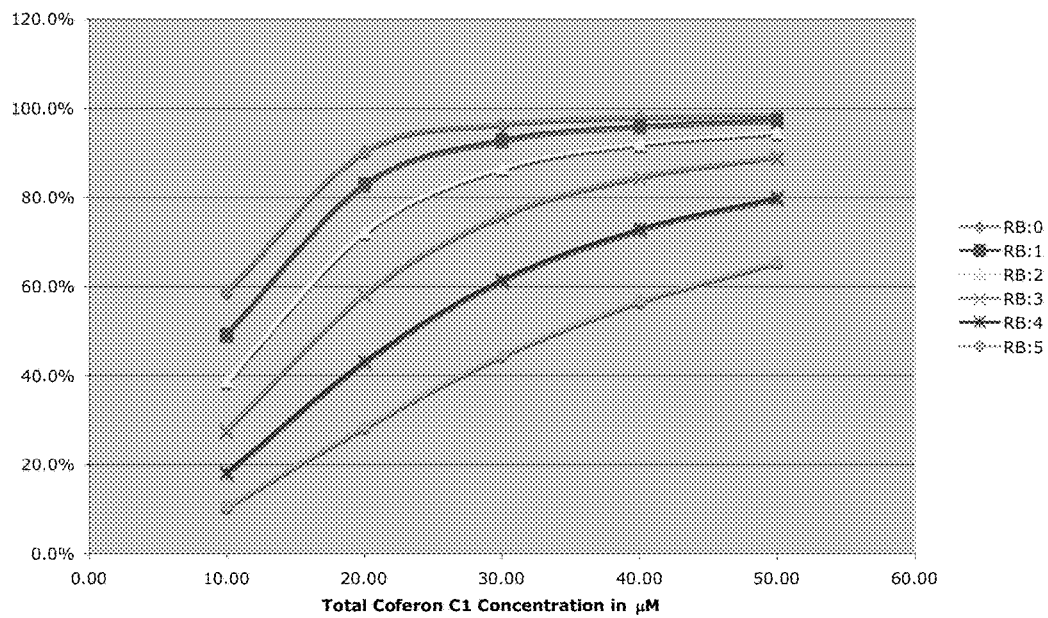
FIG. 61 is a graph showing the percent target T that is bound by coferon dimer C1C2 vs. coferon C1 concentration. The total target [ST] is set at 10 µM, $K_{d1}$=$K_{d2}$ is set at 100 µM, $K_{d5}$ is set at 1,000 µM, and total coferon C1 concentration [C1]=total coferon C2 concentration [C2], varying from 10 µM up to 50 µM concentration.
Figure 62:
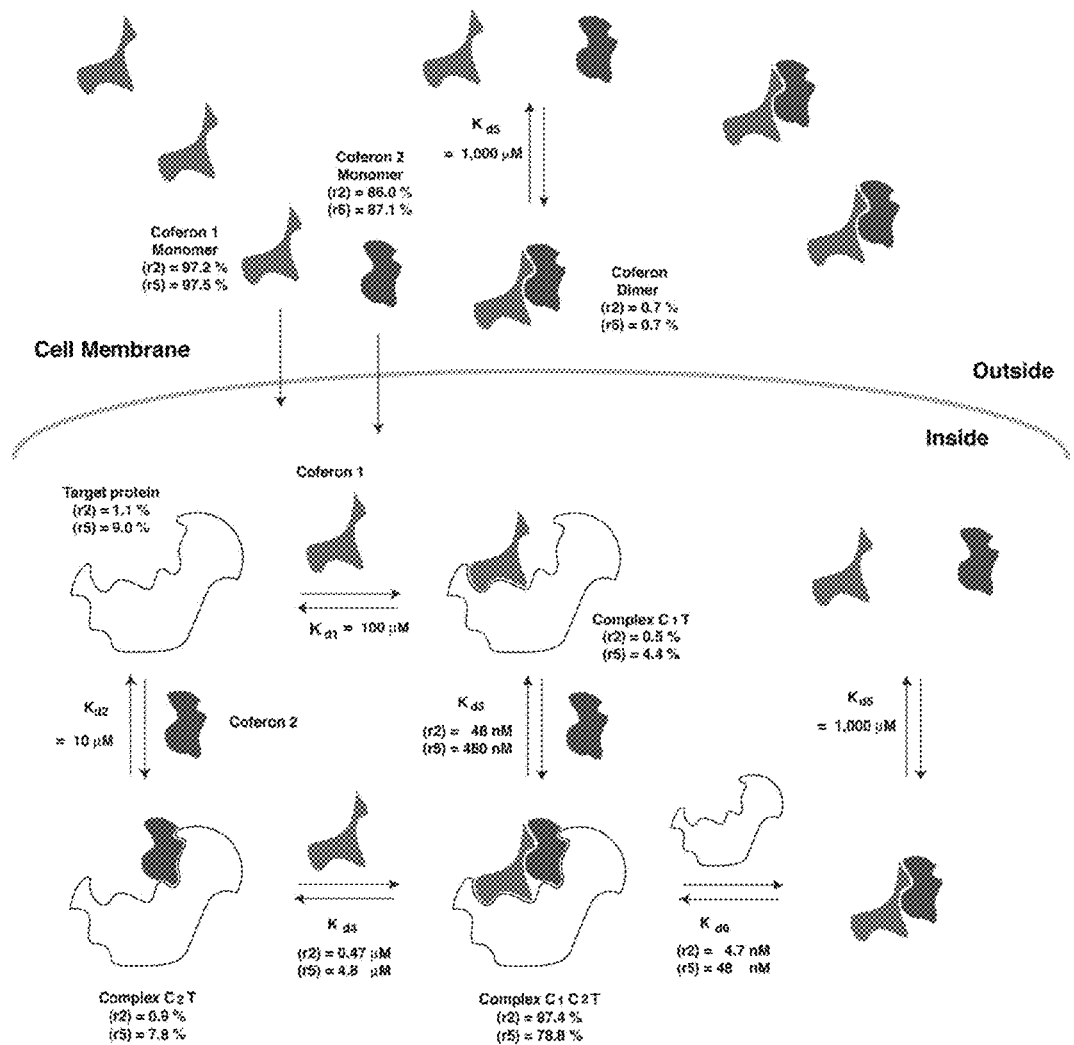
FIG. 62 is a schematic representation of two coferons (C1, and C2) that can enter cells as monomers, and bind to orthogonal sites on an internal protein target (T) to inhibit its activity. The two coferons have a 10-fold difference in binding affinity. Coferon 1 (C1) is illustrated as a green shape, coferon 2 (C2) as a blue shape, and the target protein as a white shape. The total concentrations of C1 is at 50 µM, C2 is at 10 µM, the total protein concentration inside the cell is 1 µM, about 1,000,000 targets per cell. The dissociation constants $K_{d1}$ between coferon C1 and target T is given at 100 µM; that between coferon C2 and target T is given at 10 µM. The dissociation constant between the two coferons, $K_{d5}$ is given at 1,000 µM.
Figure 63:
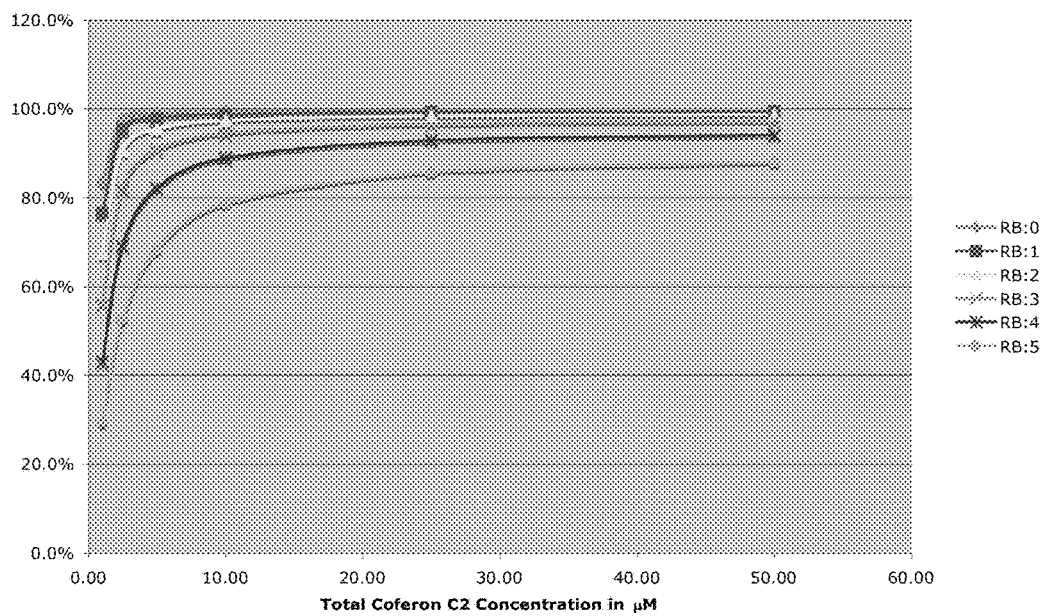
FIG. 63 is a graph showing the percent target T that is bound by coferon dimer C1C2 vs. coferon C2 concentration. The total target [ST] is set at 1 µM, $K_{d1}$ is set at 100 µM, $K_{d2}$ is set at 10 µM, $K_{d5}$ is set at 1,000 µM, and total coferon C1 concentration [C1]=50 µM, and total coferon C2 concentration [C2], varying from 1 µM up to 50 µM concentration.
Figure 64:
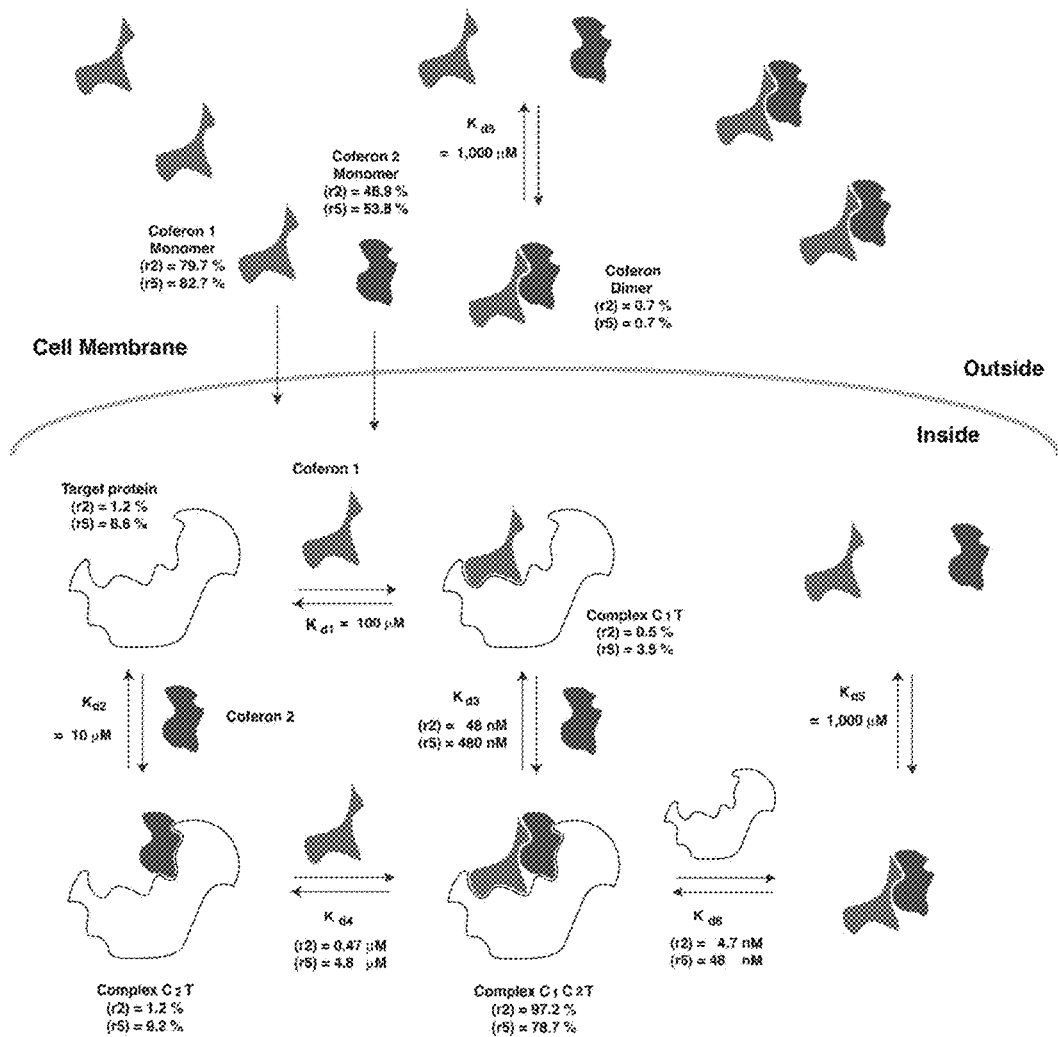
FIG. 64 is a schematic representation of two coferons (C1, and C2) that can enter cells as monomers, and bind to orthogonal sites on an internal protein target (T) to inhibit its activity. The two coferons have a 10-fold difference in binding affinity. Coferon 1 (C1) is illustrated as a green shape, coferon 2 (C2) as a blue shape, and the target protein as a white shape. The total concentrations of C1 is at 50 µM, C2 is at 20 µM, the total protein concentration inside the cell is 10 µM, about 10,000,000 targets per cell. The dissociation constants $K_{d1}$ between coferon C1 and target T is given at 100 µM; that between coferon C2 and target T is given at 10 µM. The dissociation constant between the two coferons, $K_{d5}$ is given at 1,000 µM.
Figure 65:
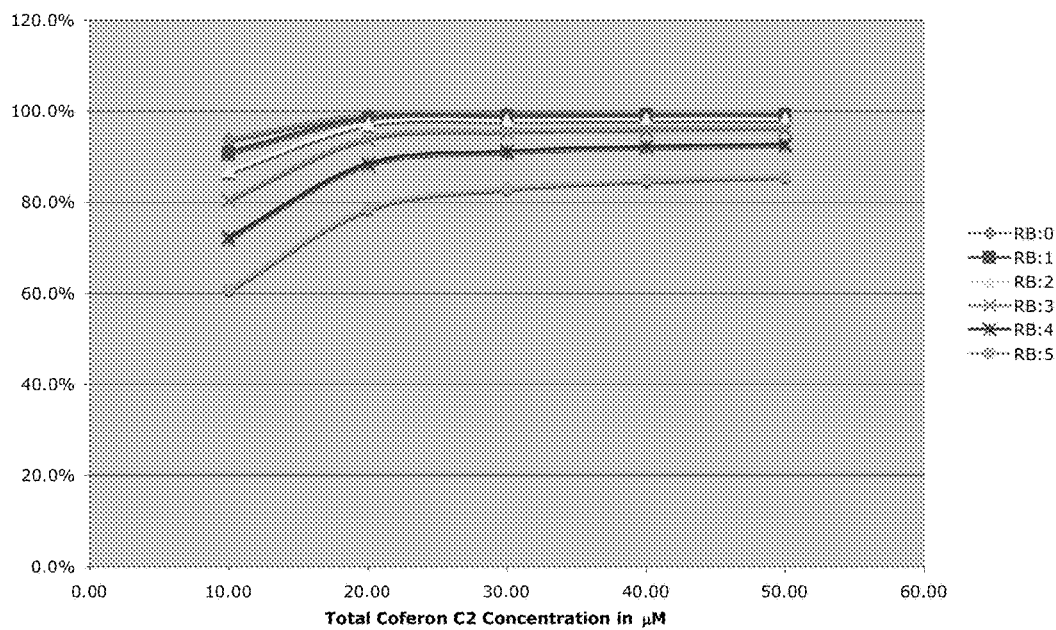
FIG. 65 is a graph showing the percent target T that is bound by coferon dimer C1C2 vs. coferon C2 concentration. The total target [ST] is set at 10 µM, $K_{d1}$ is set at 100 µM, $K_{d2}$ is set at 10 µM, $K_{d5}$ is set at 1,000 µM, and total coferon C1 concentration [C1]=50 µM, and total coferon C2 concentration [C2], varying from 1 µM up to 50 µM concentration.
Figure 66:
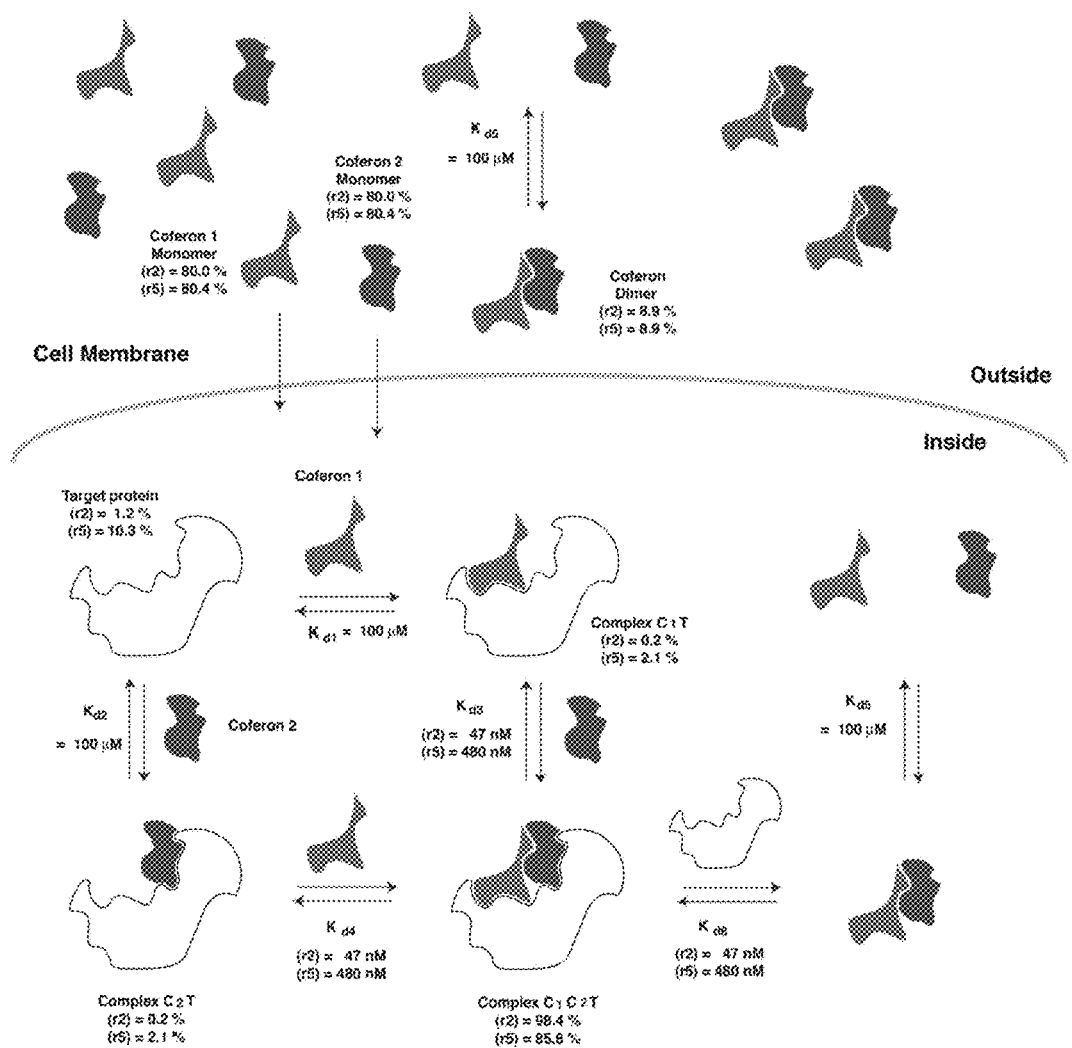
FIG. 66 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 25 µM, the total protein concentration inside the cell is 1 µM, about 1,000,000 targets per cell. The dissociation constants $K_{d1}$ and $K_{d2}$ between coferon C1 and target T, as well as between coferon C2 and target T are given at 100 µM. The dissociation constant between the two coferons, $K_{d5}$ is given at 100 µM.
Figure 67:
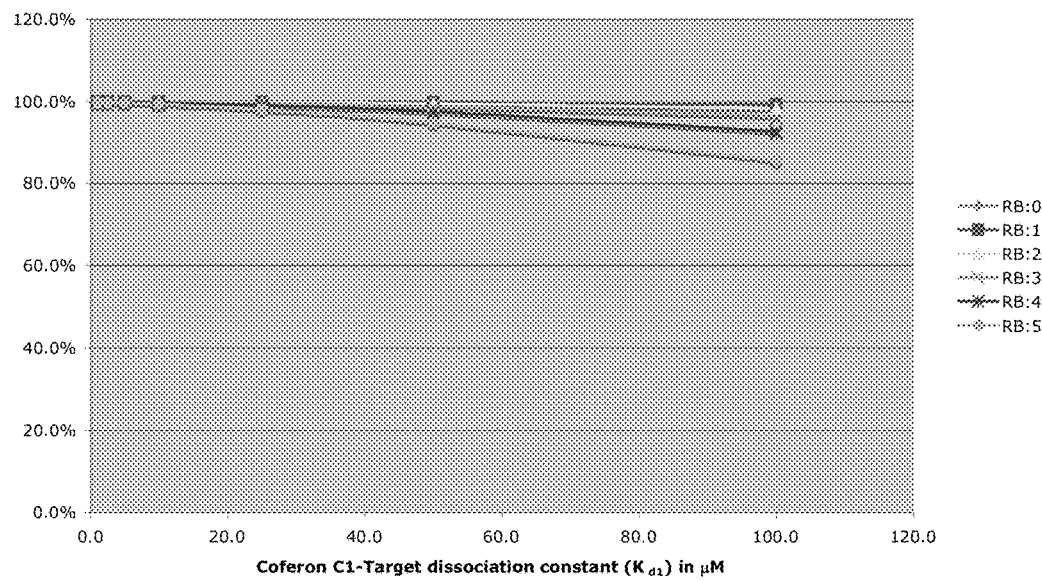
FIG. 67 is a graph showing the percent target T that is bound by coferon dimer C1C2 vs. coferon C1-Target dissociation constant ($K_{d1}$). The total target [ST] is set at 1 µM, $K_{d5}$ is set at 100 µM, and total coferon C1 concentration [C1]=total coferon C2 concentration [C2], set at 25 µm, and $K_{d1}$=$K_{d2}$ varying from 1 µM up to 100 µM.
Figure 68:
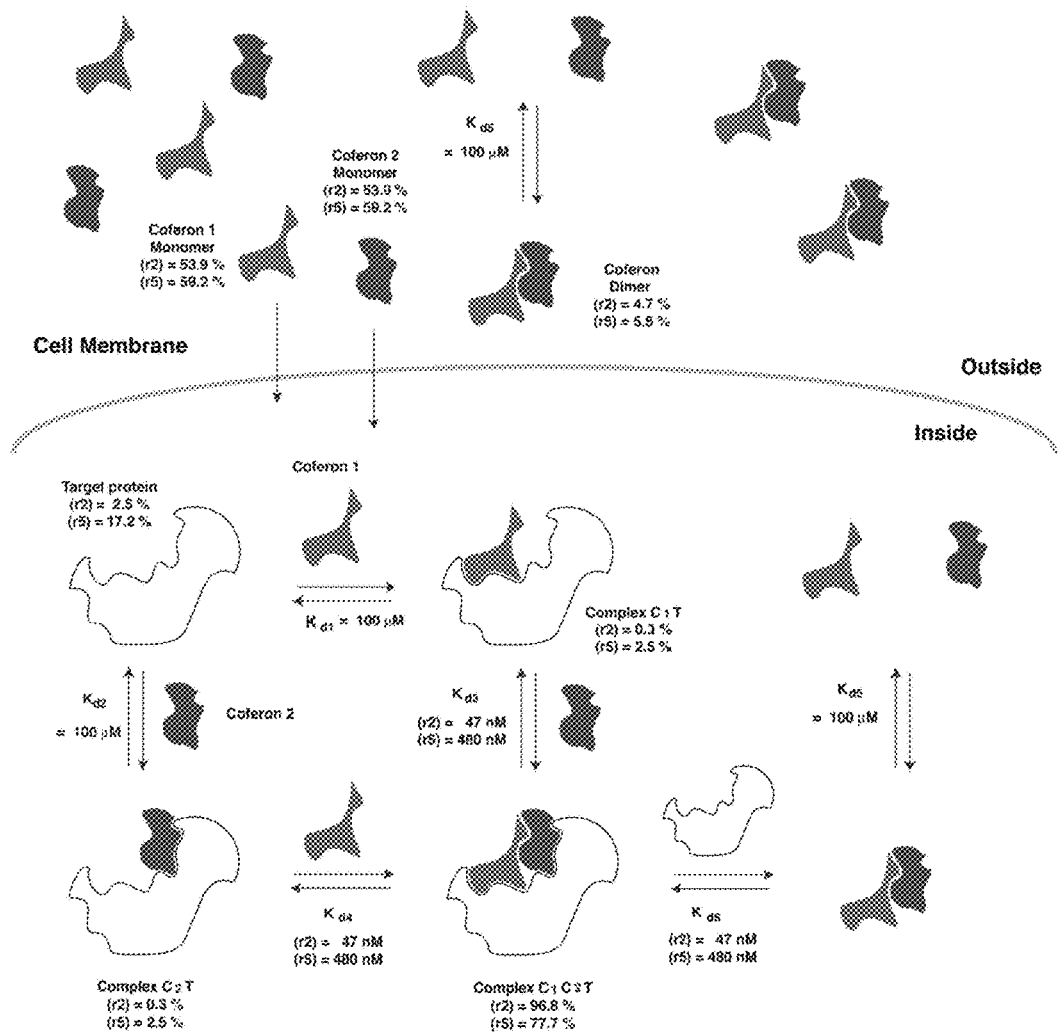
FIG. 68 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 25 µM, the total protein concentration inside the cell is 10 µM, about 10,000,000 targets per cell. The dissociation constants $K_{d1}$ and $K_{d2}$ between coferon C1 and target T, as well as between coferon C2 and target T are given at 100 µM. The dissociation constant between the two coferons, $K_{d5}$ is given at 100 µM.
Figure 69:
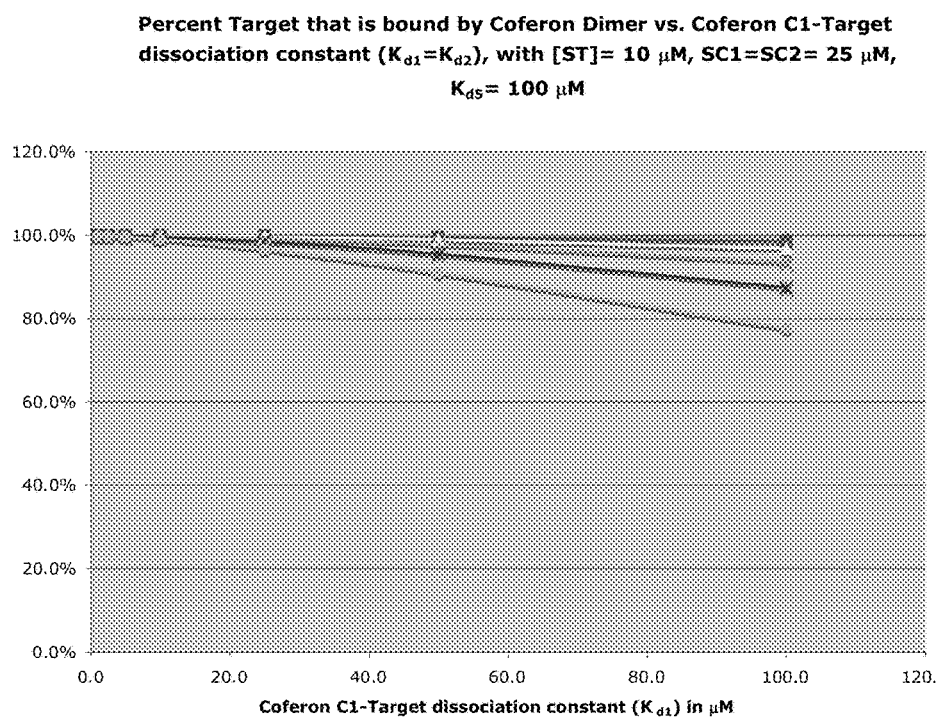
FIG. 69 is a graph showing the percent target T that is bound by coferon dimer C1C2 vs. coferon C1-Target dissociation constant ($K_{d1}$). The total target [ST] is set at 10 µM, $K_{d5}$ is set at 100 µM, and total coferon C1 concentration [C1]=total coferon C2 concentration [C2], set at 25 µM, and $K_{d1}$=$K_{d2}$ varying from 1 µM up to 100 µM.
Figure 70:
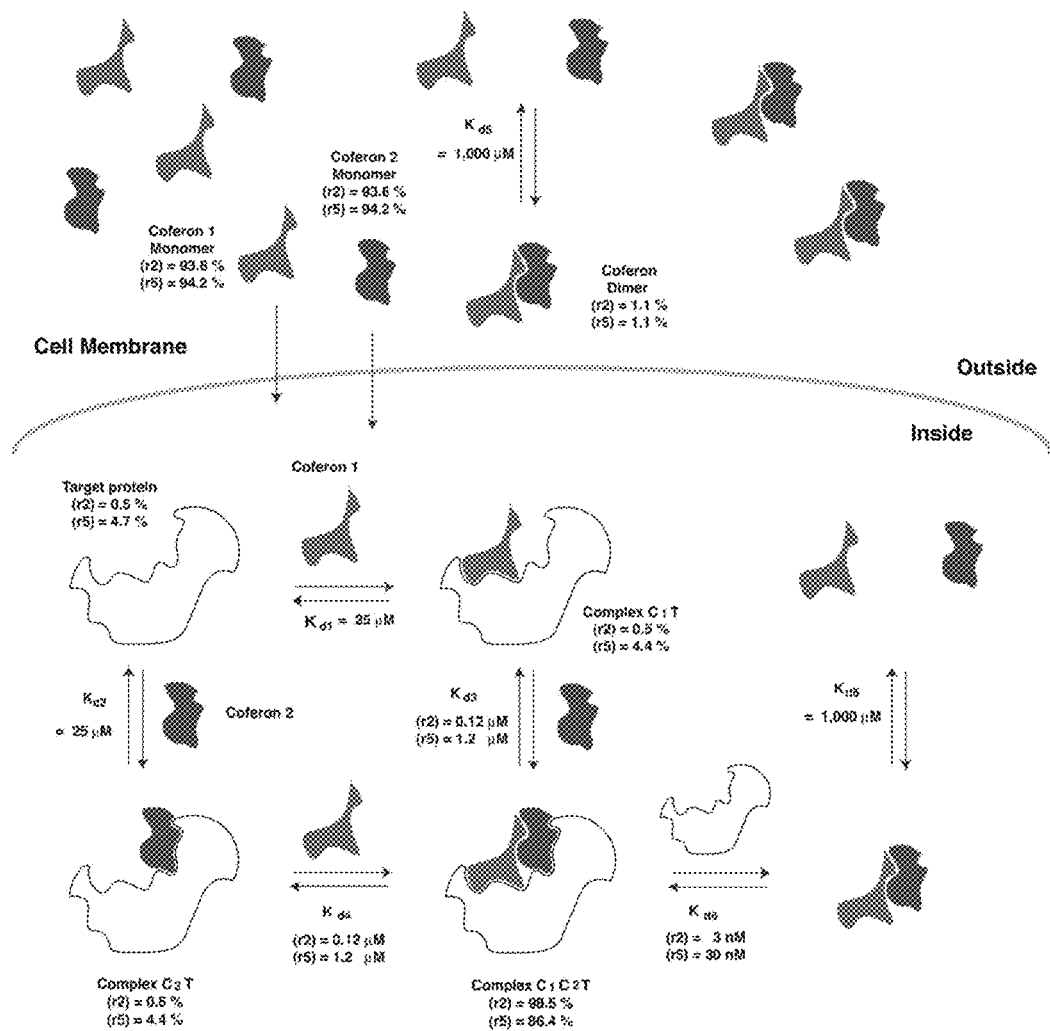
FIG. 70 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 25 µM, the total protein concentration inside the cell is 1 µM, about 1,000,000 targets per cell. The dissociation constants $K_{d1}$ and $K_{d2}$ between coferon C1 and target T, as well as between coferon C2 and target T are given at 25 µM. The dissociation constant between the two coferons, $K_{d5}$ is given at 1,000 µM.
Figure 71:
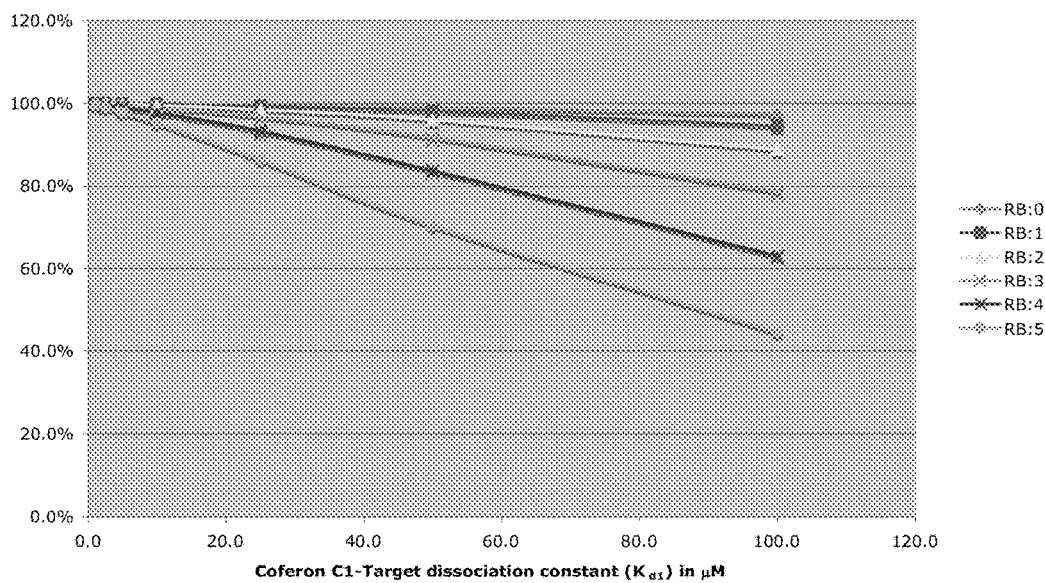
FIG. 71 is a graph showing the percent target T that is bound by coferon dimer C1C2 vs. coferon C1-Target dissociation constant ($K_{d1}$). The total target [ST] is set at 1 µM, $K_{d5}$ is set at 1,000 µM, and total coferon C1 concentration [C1]=total coferon C2 concentration [C2], set at 25 µm, and $K_{d1}$=$K_{d2}$ varying from 1 µM up to 100 µM.
Figure 72:
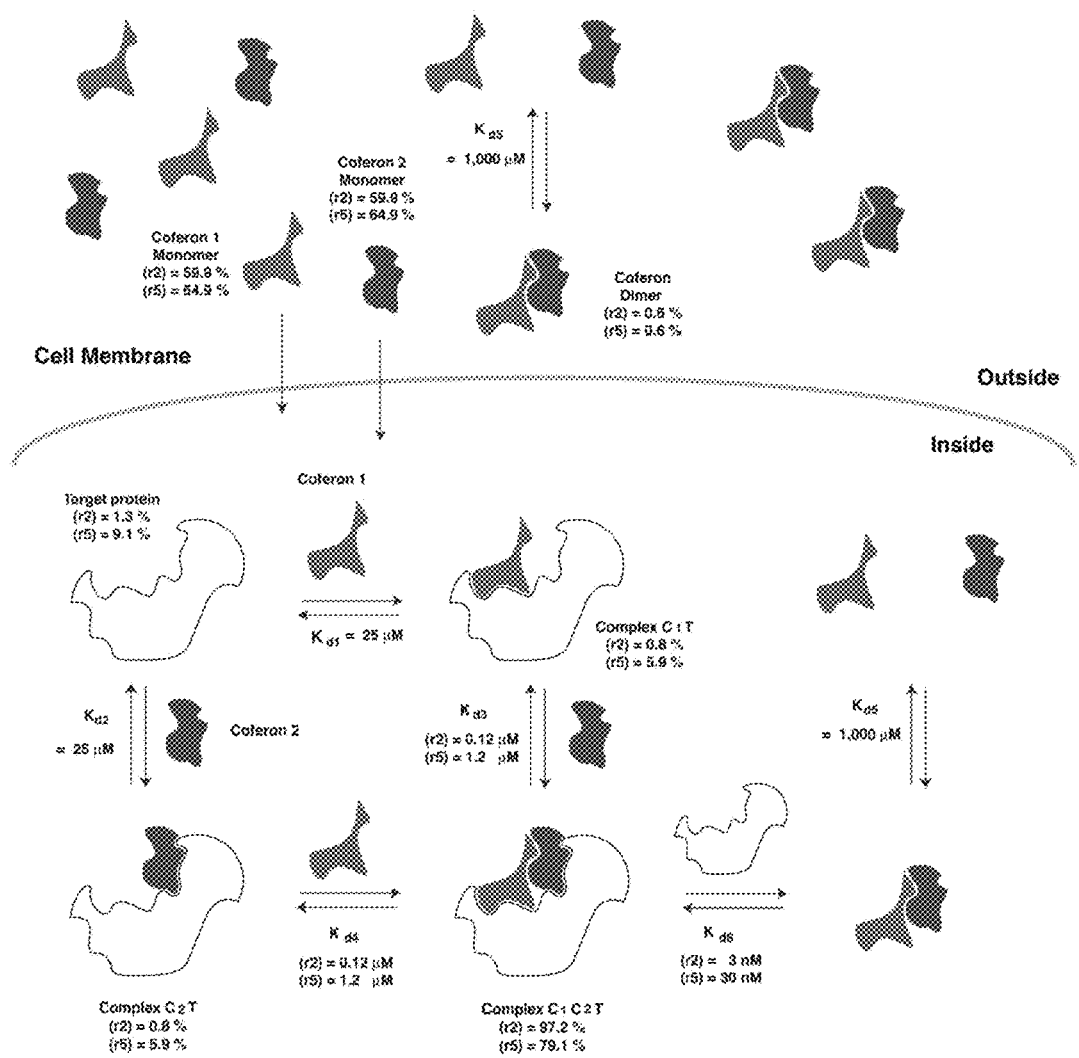
FIG. 72 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 25 µM, the total protein concentration inside the cell is 10 µM, about 10,000,000 targets per cell. The dissociation constants $K_{d1}$ and $K_{d2}$ between coferon C1 and target T, as well as between coferon C2 and target T are given at 25 µM. The dissociation constant between the two coferons, $K_{d5}$ is given at 1,000 µM.
Figure 73:
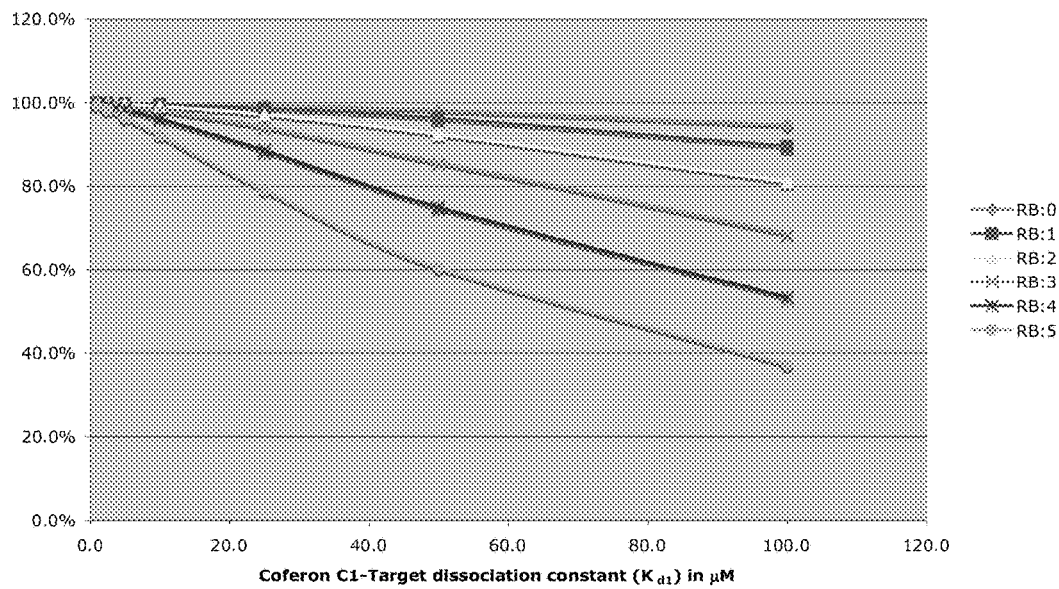
FIG. 73 is a graph showing the percent target T that is bound by coferon dimer C1C2 vs. coferon C1-Target dissociation constant ($K_{d1}$). The total target [ST] is set at 10 µM, $K_{d5}$ is set at 1,000 µM, and total coferon C1 concentration [C1]=total coferon C2 concentration [C2], set at 25 µM, and $K_{d1}$=$K_{d2}$ varying from 1 µM up to 100 µM.
Figure 74:
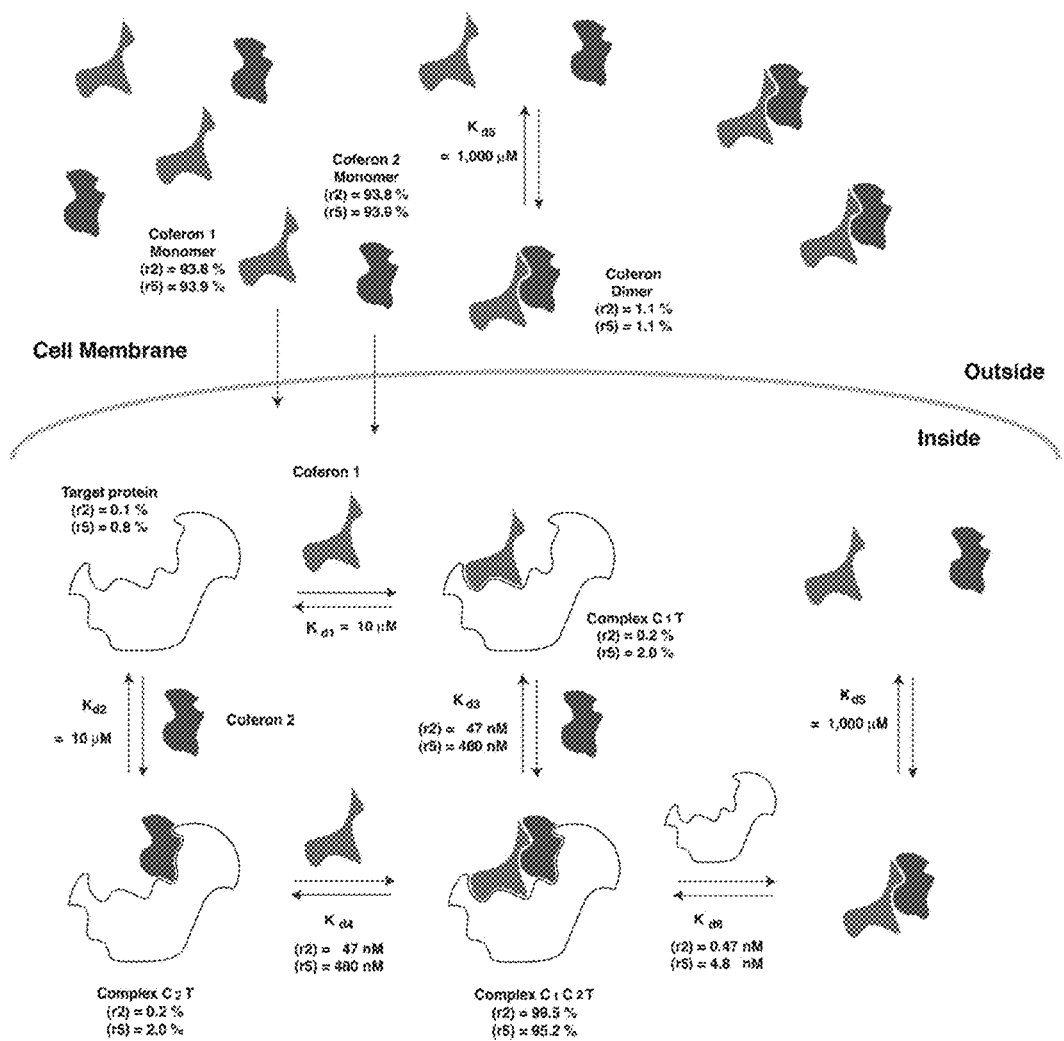
FIG. 74 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 25 µM, the total protein concentration inside the cell is 1 µM, about 1,000,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 1,000 µM.
Figure 75:
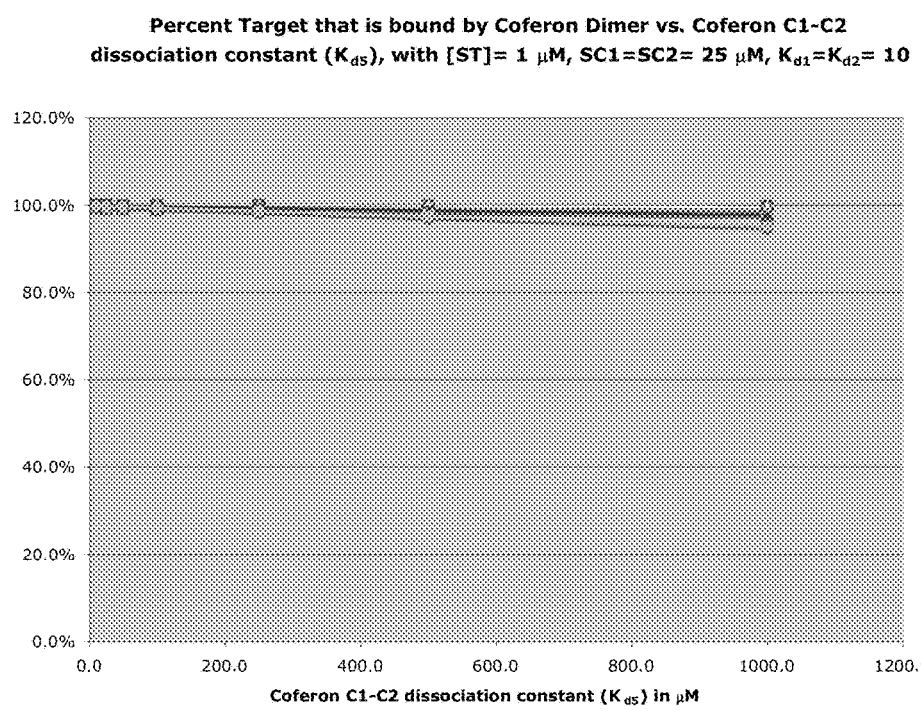
FIG. 75 is a graph showing the percent target T that is bound by coferon dimer C1C2 vs. coferon C1-C2 dissociation constant ($K_{d5}$). The total target [ST] is set at 1 µM, $K_{d1}=K_{d2}$ is set at 10 µM, and total coferon C1 concentration [C1]=total coferon C2 concentration [C2], set at 25 µm, and $K_{d5}$ varying from 10 µM up to 1,000 µM.
Figure 76:
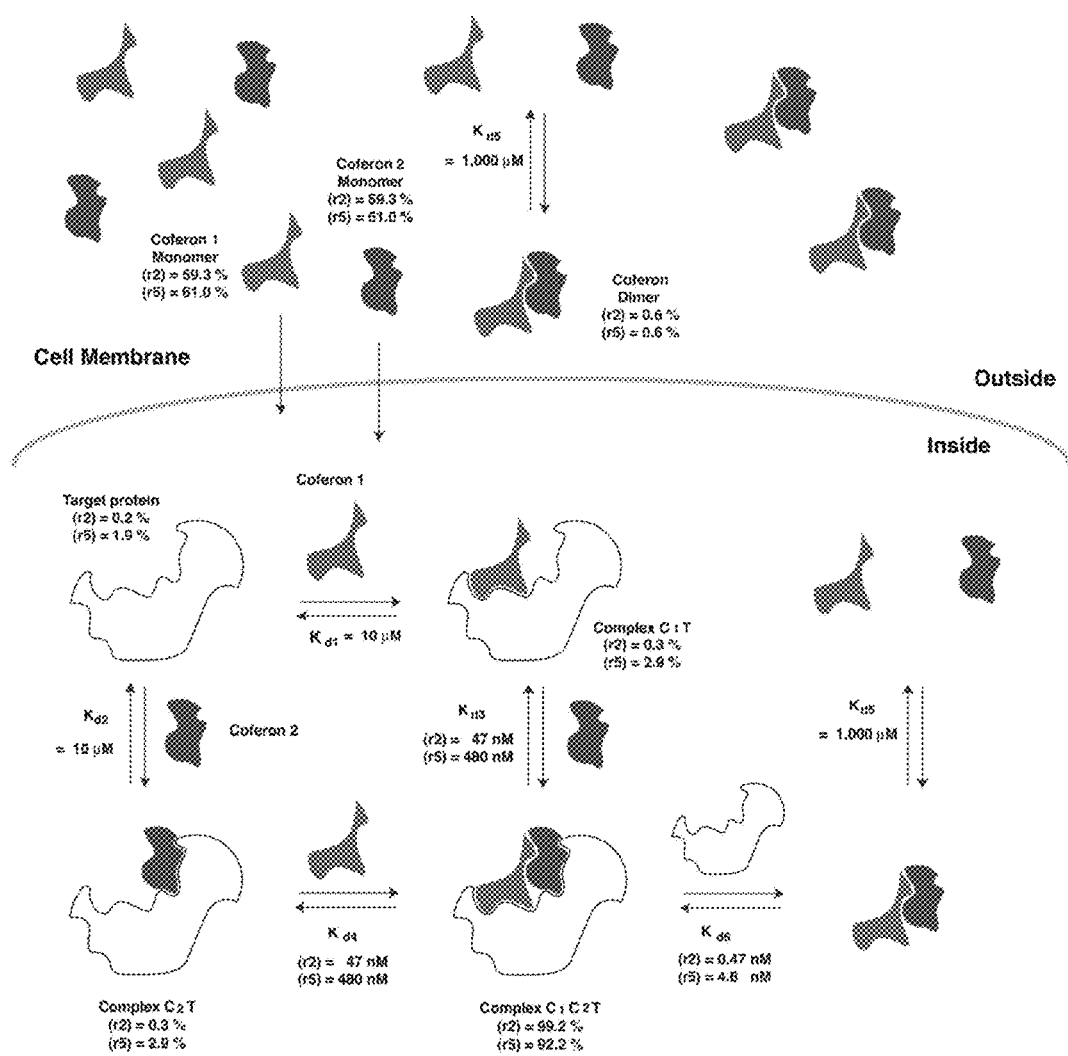
FIG. 76 is a schematic representation of two coferons (C1, and C2) that can enter cells as monomers, and bind to orthogonal sites on an internal protein target (T) to inhibit its activity. Coferon 1 is illustrated as a green shape, coferon 2 as a blue shape, and the target protein as a white shape. The total concentrations of C1 and C2 are 25 µM, the total protein concentration inside the cell is 10 µM, about 10,000,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 1,000 µM.
Figure 77:
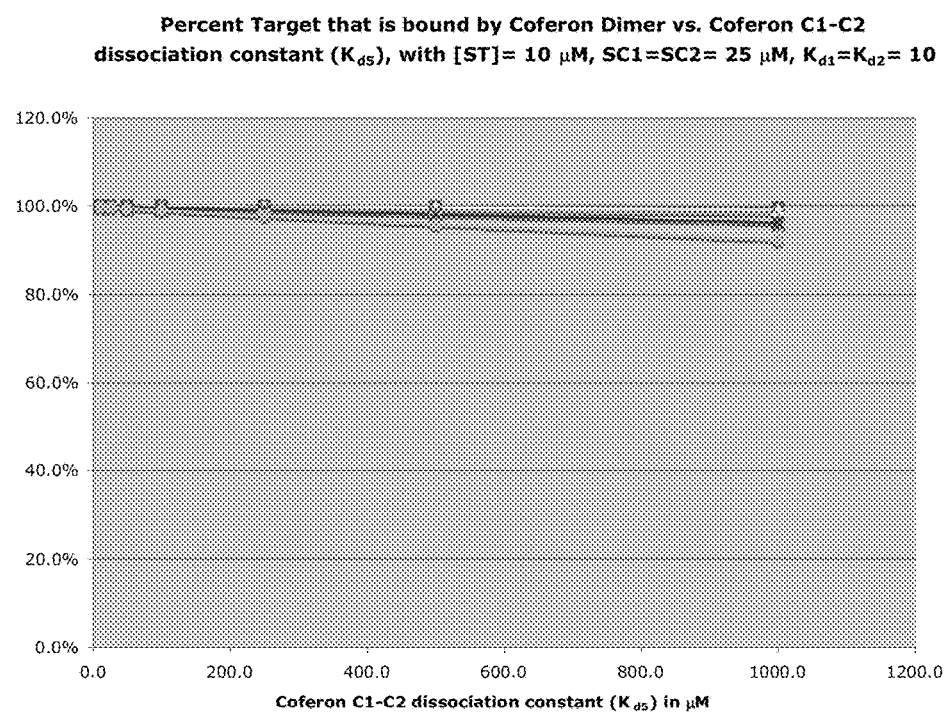
FIG. 77 is a graph showing the percent target T that is bound by coferon dimer C1C2 vs. coferon C1-C2 dissociation constant ($K_{d5}$). The total target [ST] is set at 10 µM, $K_{d1}=K_{d2}$ is set at 10 µM, and total coferon C1 concentration [C1]=total coferon C2 concentration [C2], set at 25 µm, and $K_{d5}$ varying from 10 µM up to 1,000 µM.
Figure 78:
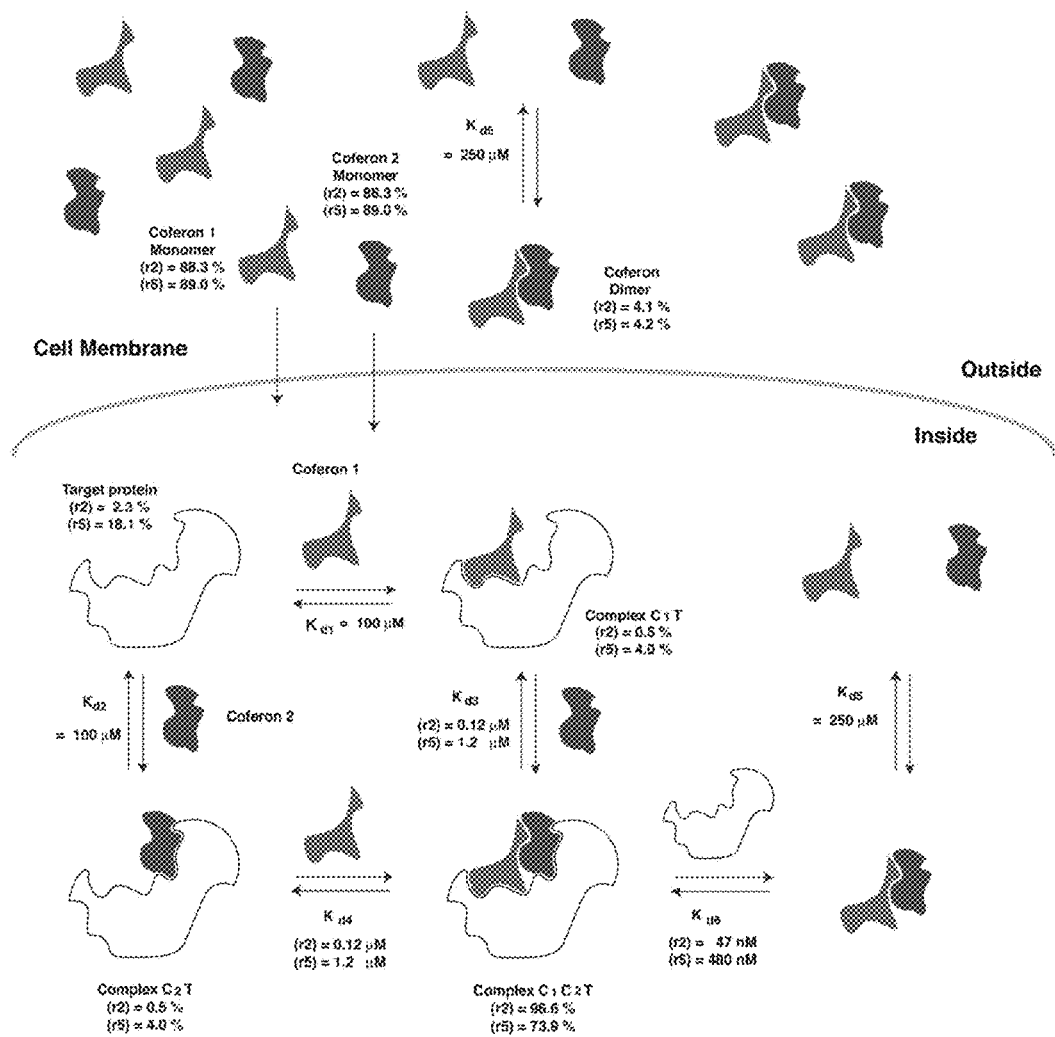
FIG. 78 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 25 µM, the total protein concentration inside the cell is 1 µM, about 1,000,000 targets per cell. The dissociation constants $K_{d1}$ and $K_{d2}$ between coferon C1 and target T, as well as between coferon C2 and target T are given at 100 µM. The dissociation constant between the two coferons, $K_{d5}$ is given at 250 µM.
Figure 79:
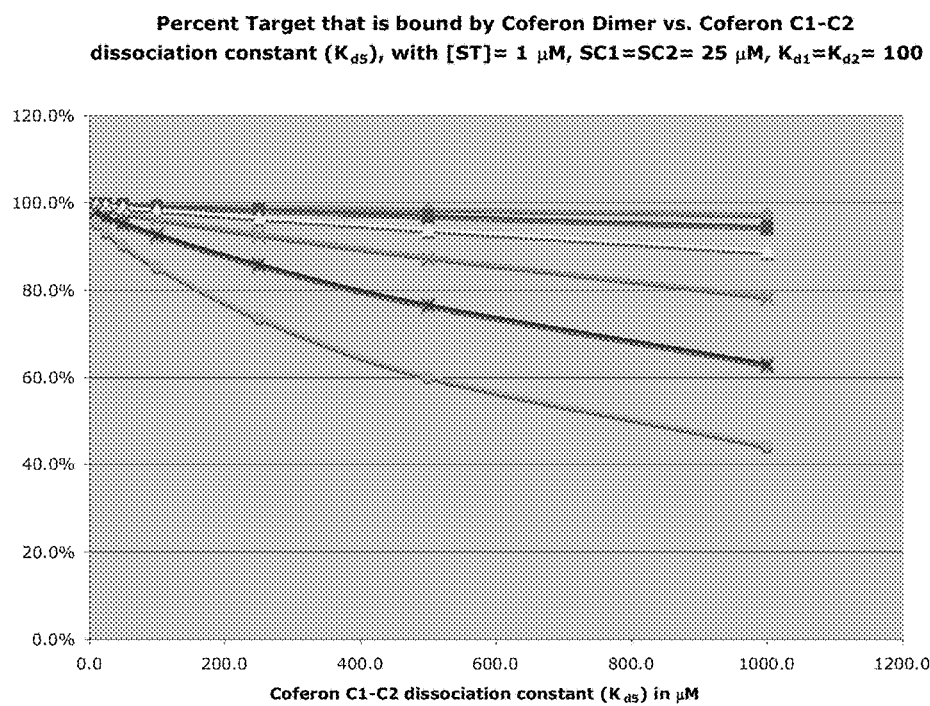
FIG. 79 is a graph showing the percent target T that is bound by coferon dimer C1C2 vs. coferon C1-C2 dissociation constant ($K_{d5}$). The total target [ST] is set at 1 µM, $K_{d1}=K_{d2}$ is set at 10 µM, and total coferon C1 concentration [C1]=total coferon C2 concentration [C2], set at 25 µm, and $K_{d5}$ varying from 10 µM up to 1,000 µM.
Figure 80:
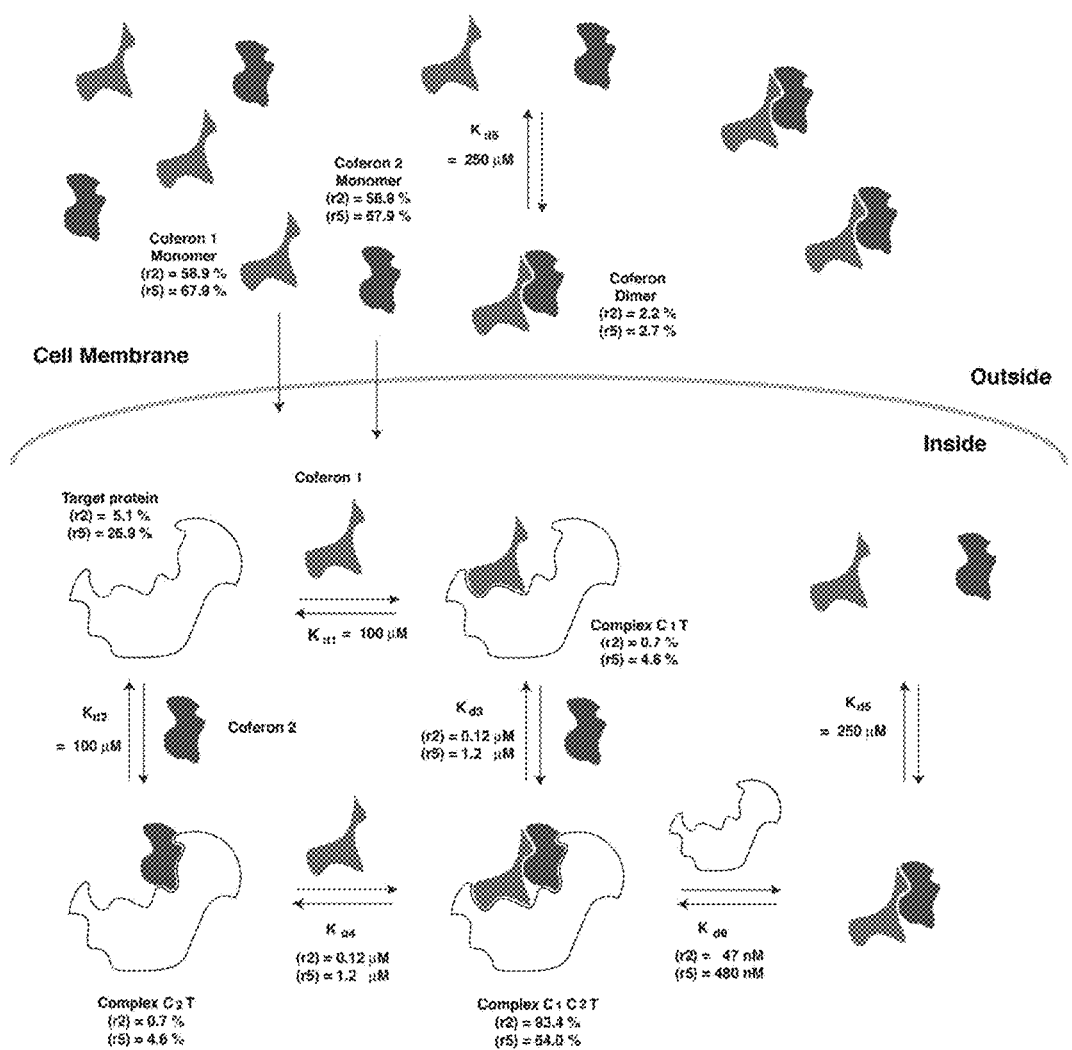
FIG. 80 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 25 µM, the total protein concentration inside the cell is 10 µM, about 10,000,000 targets per cell. The dissociation constants $K_{d1}$ and $K_{d2}$ between coferon C1 and target T, as well as between coferon C2 and target T are given at 100 µM. The dissociation constant between the two coferons, $K_{d5}$ is given at 250 µM.
Figure 81:
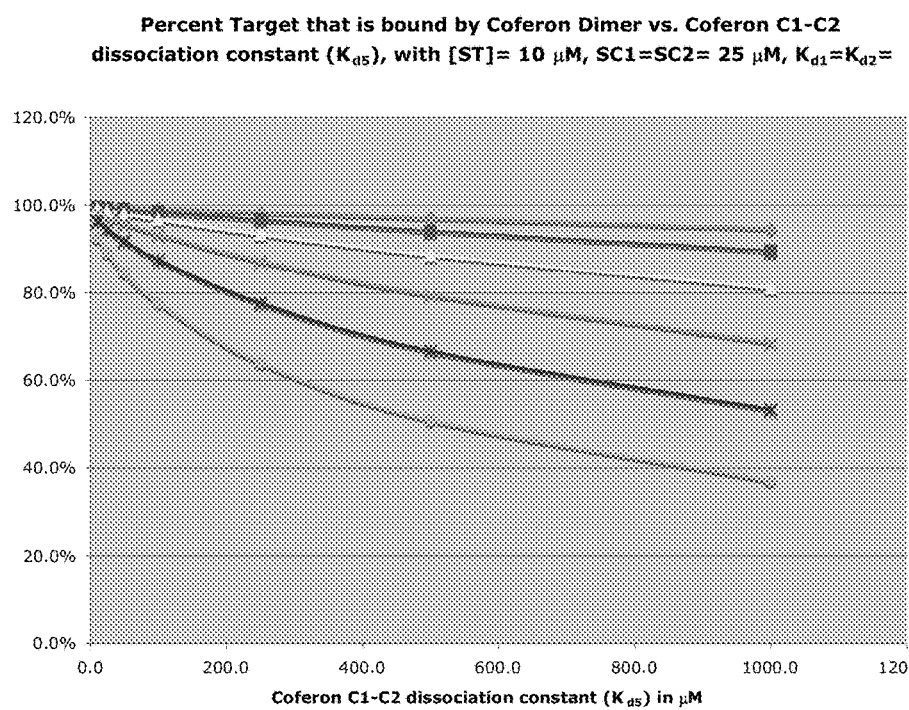
FIG. 81 is a graph showing the percent target T that is bound by coferon dimer C1C2 vs. coferon C1-C2 dissociation constant ($K_{d5}$). The total target [ST] is set at 10 µM, $K_{d1}=K_{d2}$ is set at 10 µM, and total coferon C1 concentration [C1]=total coferon C2 concentration [C2], set at 25 µm, and $K_{d5}$ varying from 10 µM up to 1,000 µM.
Figure 82:
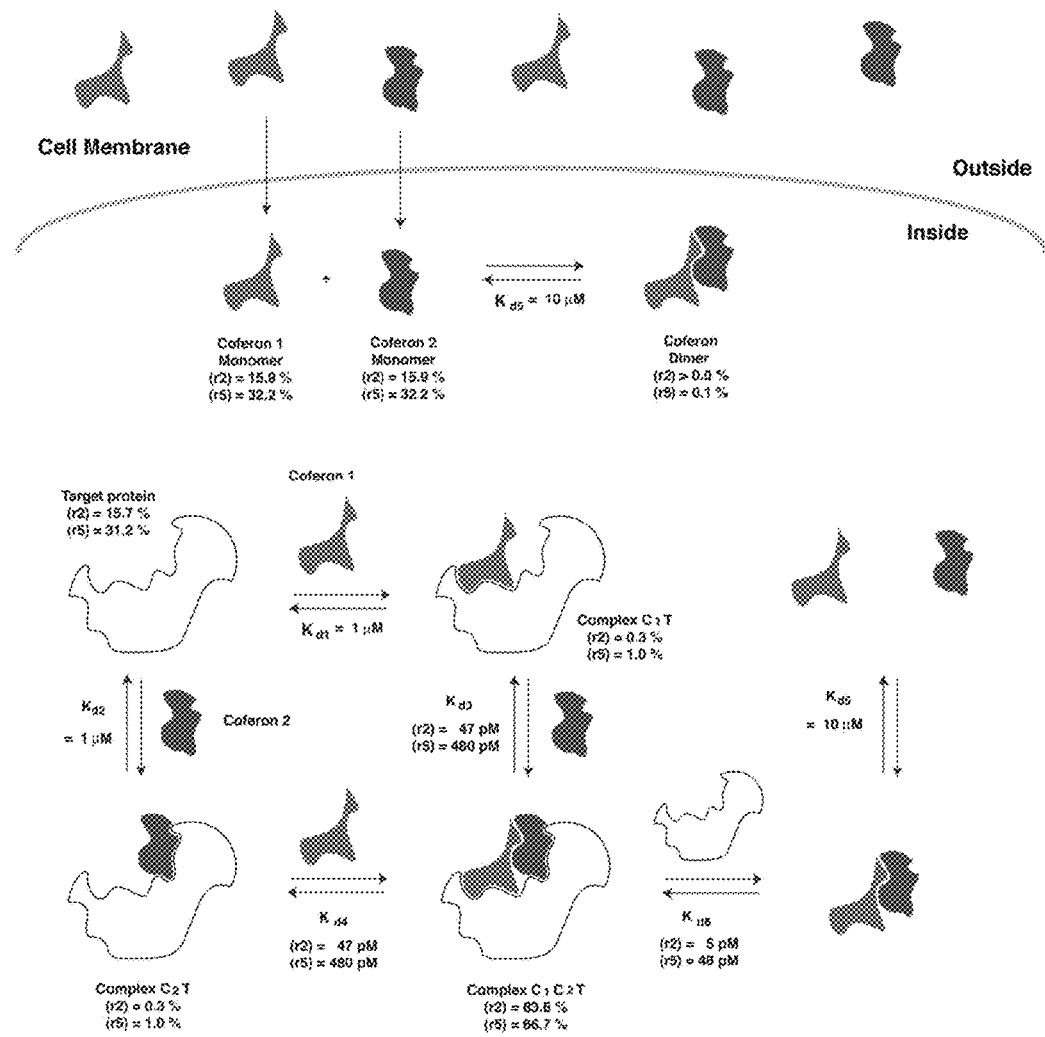
FIG. 82 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.1 µM, reflecting the ability to provide a steady dose of drug over time. The total protein concentration inside the cell is 0.1 µM, about 100,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 10 µM.
Figure 83:
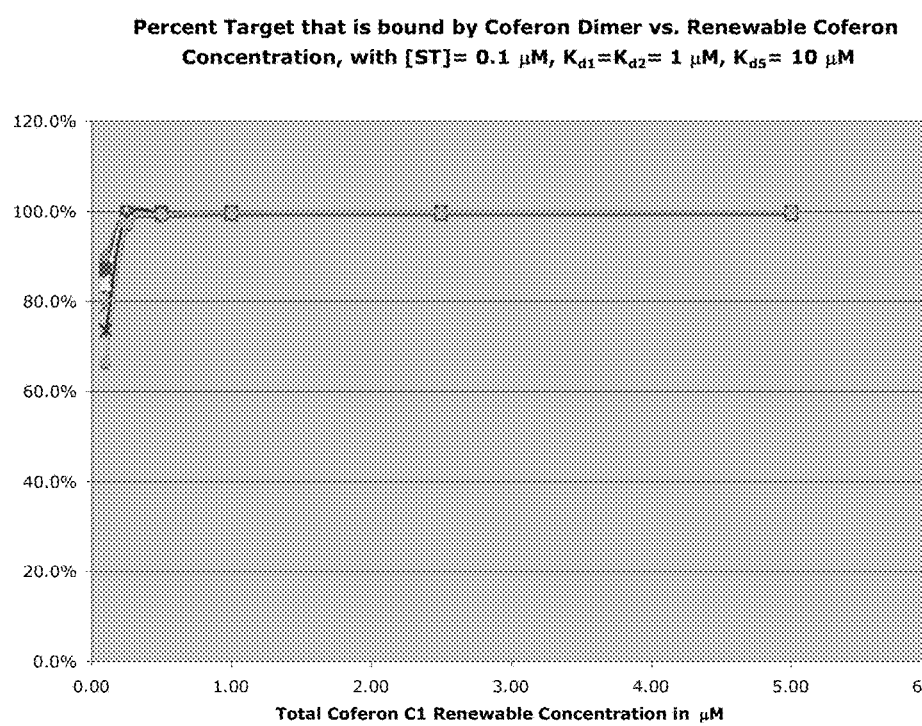
FIG. 83 is a graph showing the percent target T that is bound by coferon dimer C1C2 vs. "renewable" coferon C1 concentration. The total target [ST] is set at 0.1 µM, $K_{d1}=K_{d2}$ is set at 1 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 84:
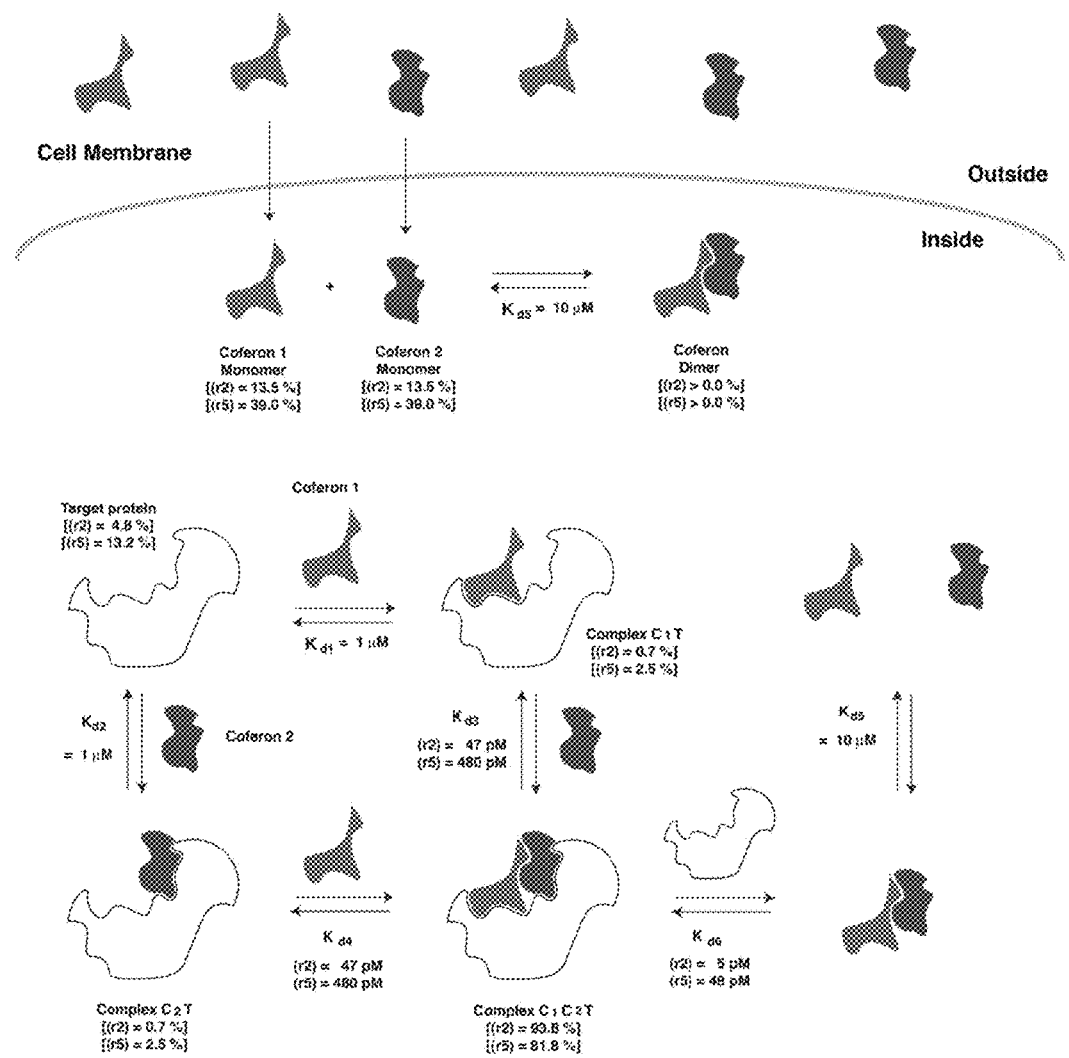
FIG. 84 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.1 µM, reflecting the ability to provide a steady dose of drug over time. The total protein concentration inside the cell is 0.25 µM, about 250,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 10 µM.
Figure 85:
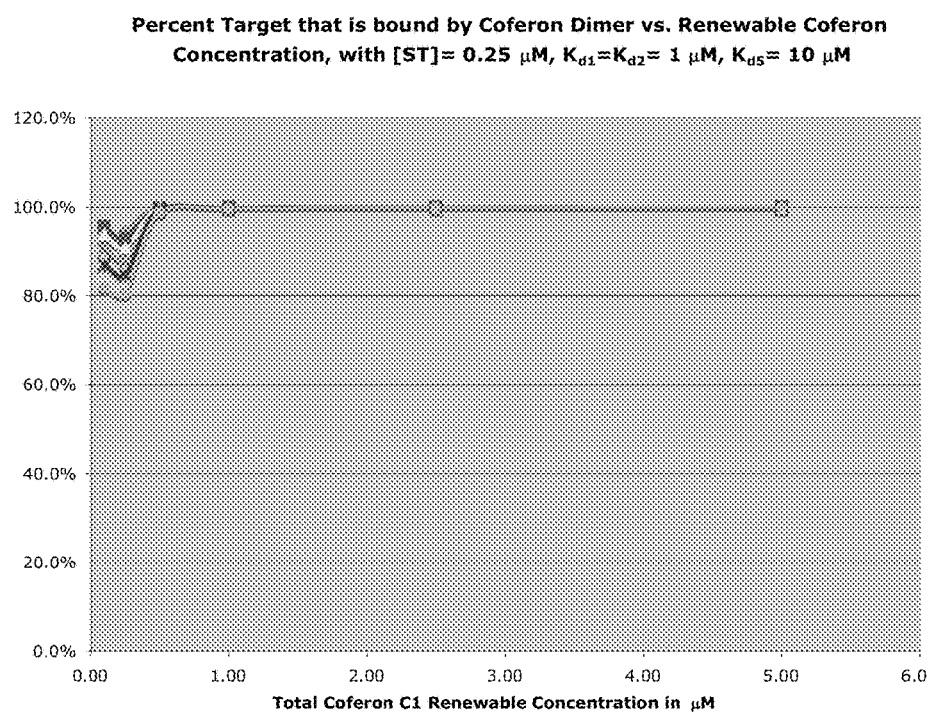
FIG. 85 is a graph showing the percent target T that is bound by coferon dimer C1C2 vs. "renewable" coferon C1 concentration. The total target [ST] is set at 0.25 µm, $K_{d1}=K_{d2}$ is set at 1 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 86:
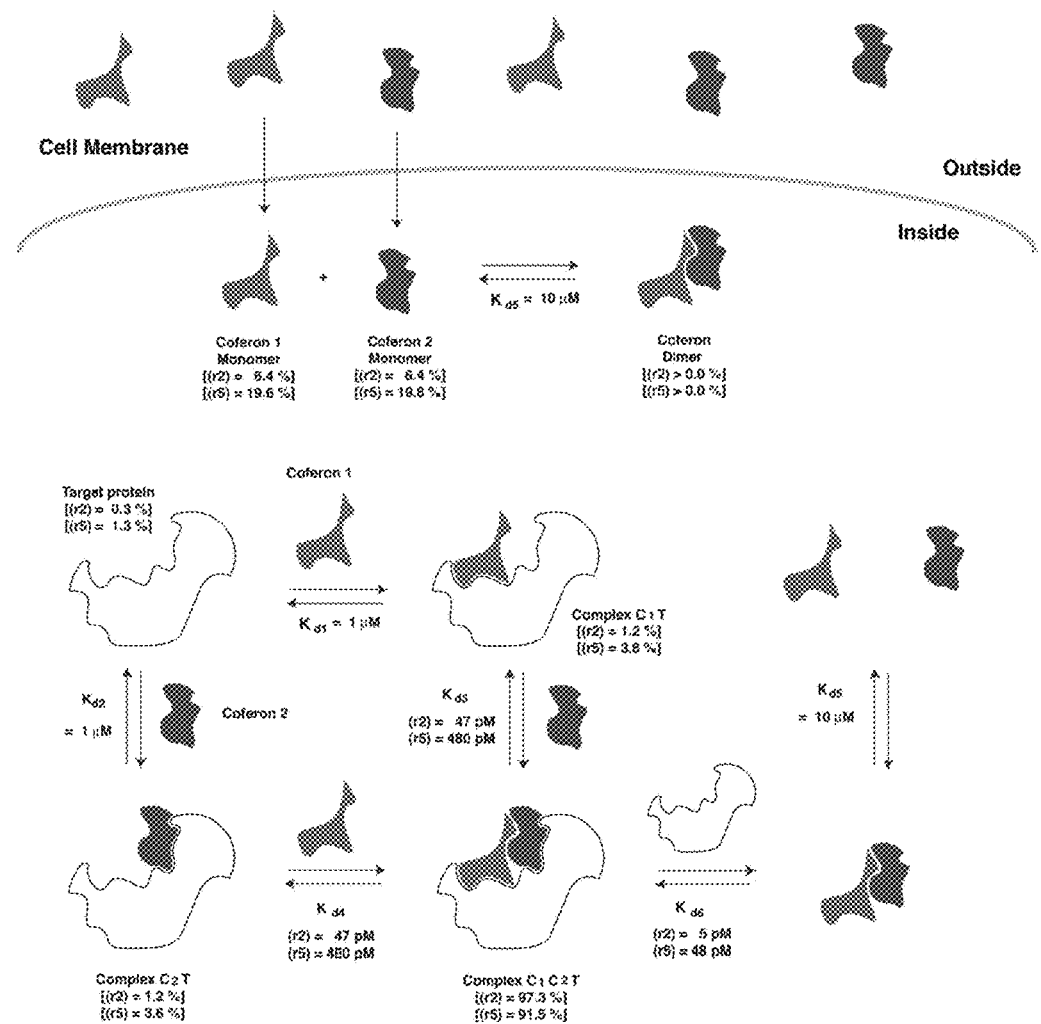
FIG. 86 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 1 µM, about 1,000,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 10 µM.
Figure 87:
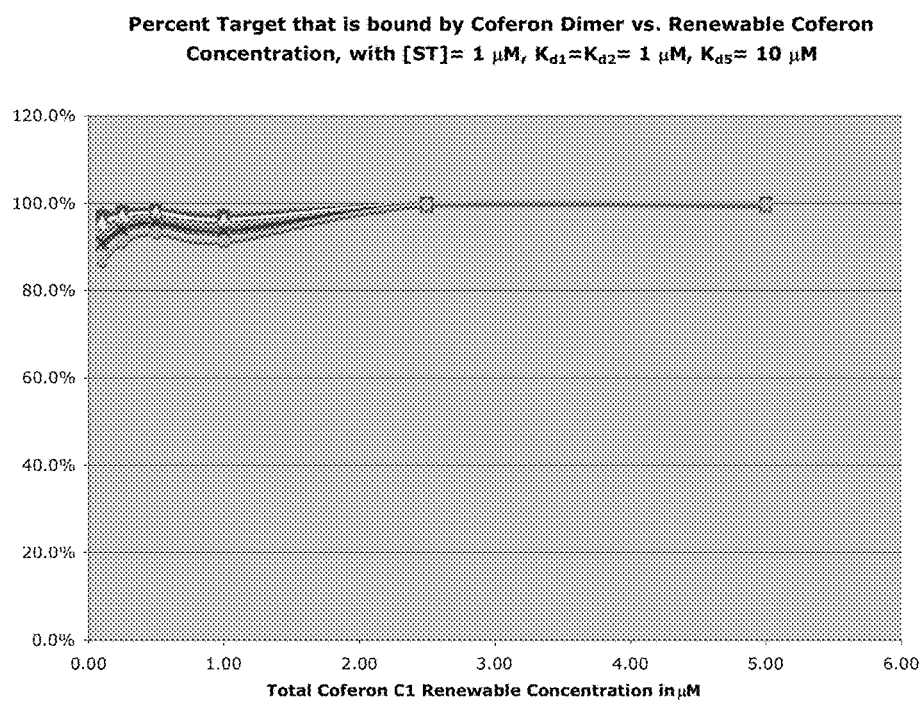
FIG. 87 is a graph showing the percent target T that is bound by coferon dimer C1C2 vs. "renewable" coferon C1 concentration. The total target [ST] is set at 1 µM, $K_{d1}=K_{d2}$ is set at 1 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 88:
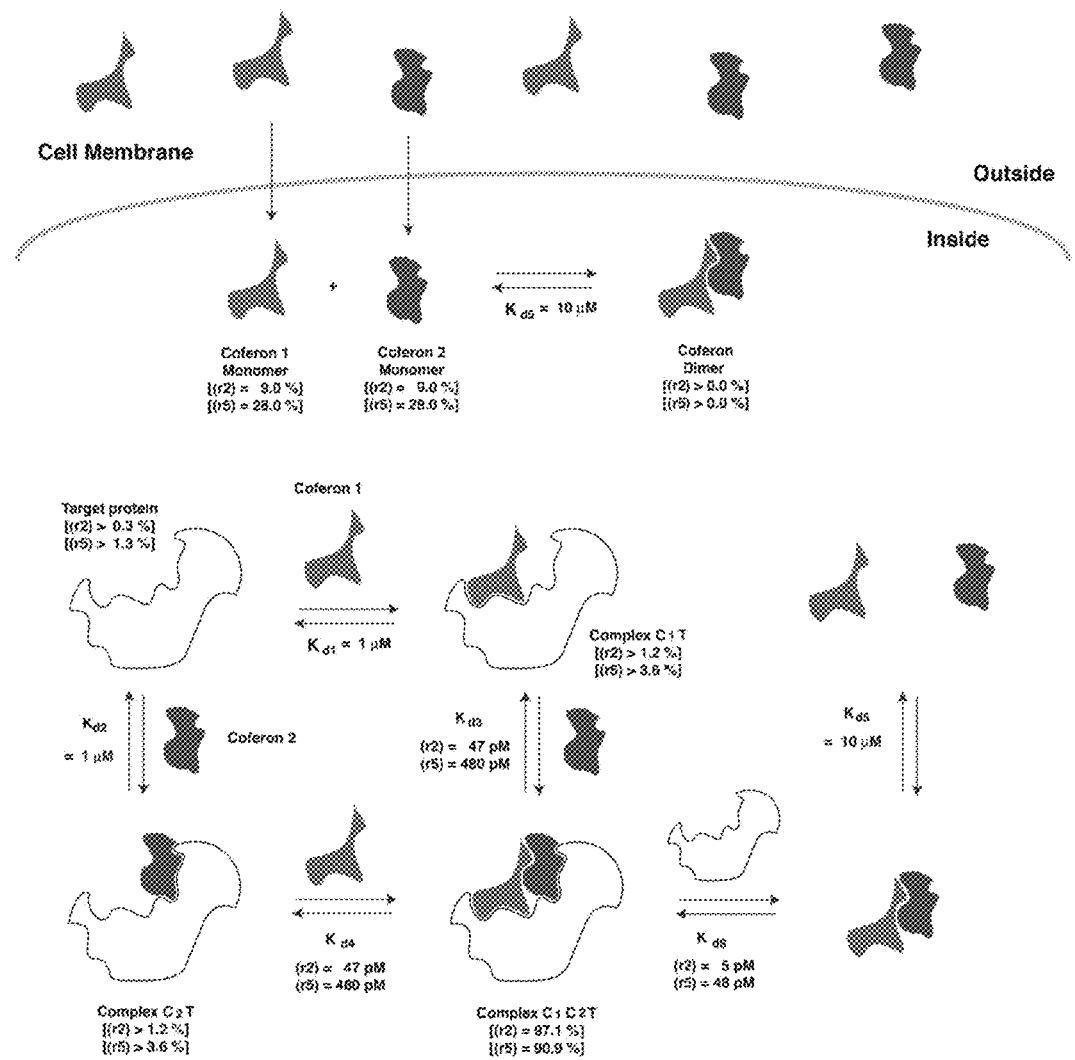
FIG. 88 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 2.5 µM, about 2,500,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 10 µM.
Figure 89:
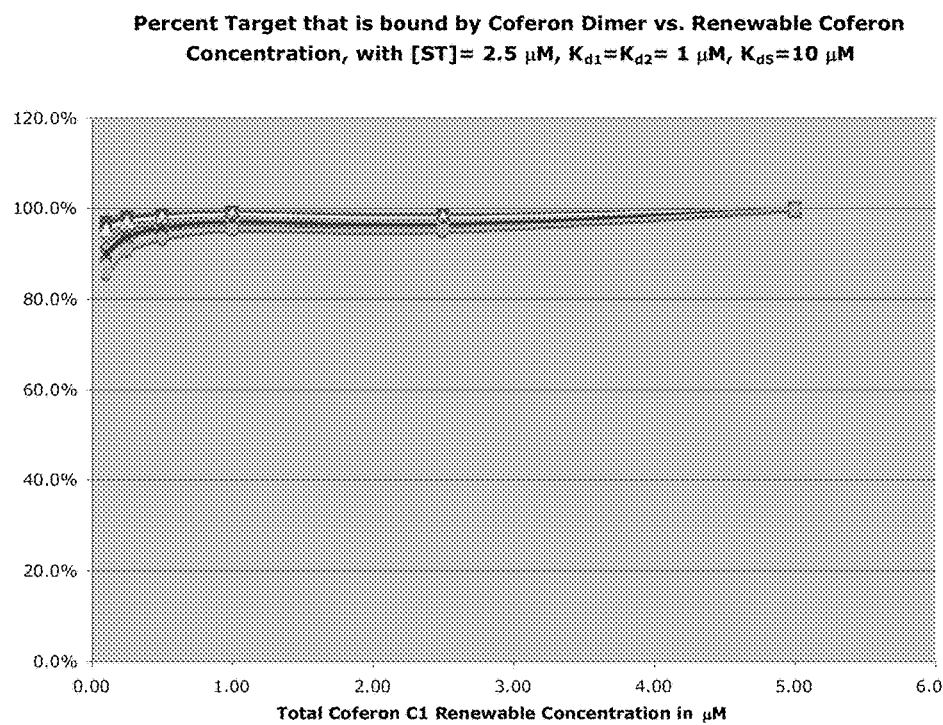
FIG. 89 is a graph showing the percent target T that is bound by coferon dimer C1C2 vs. "renewable" coferon C1 concentration. The total target [ST] is set at 2.5 µm, $K_{d1}=K_{d2}$ is set at 1 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 90:
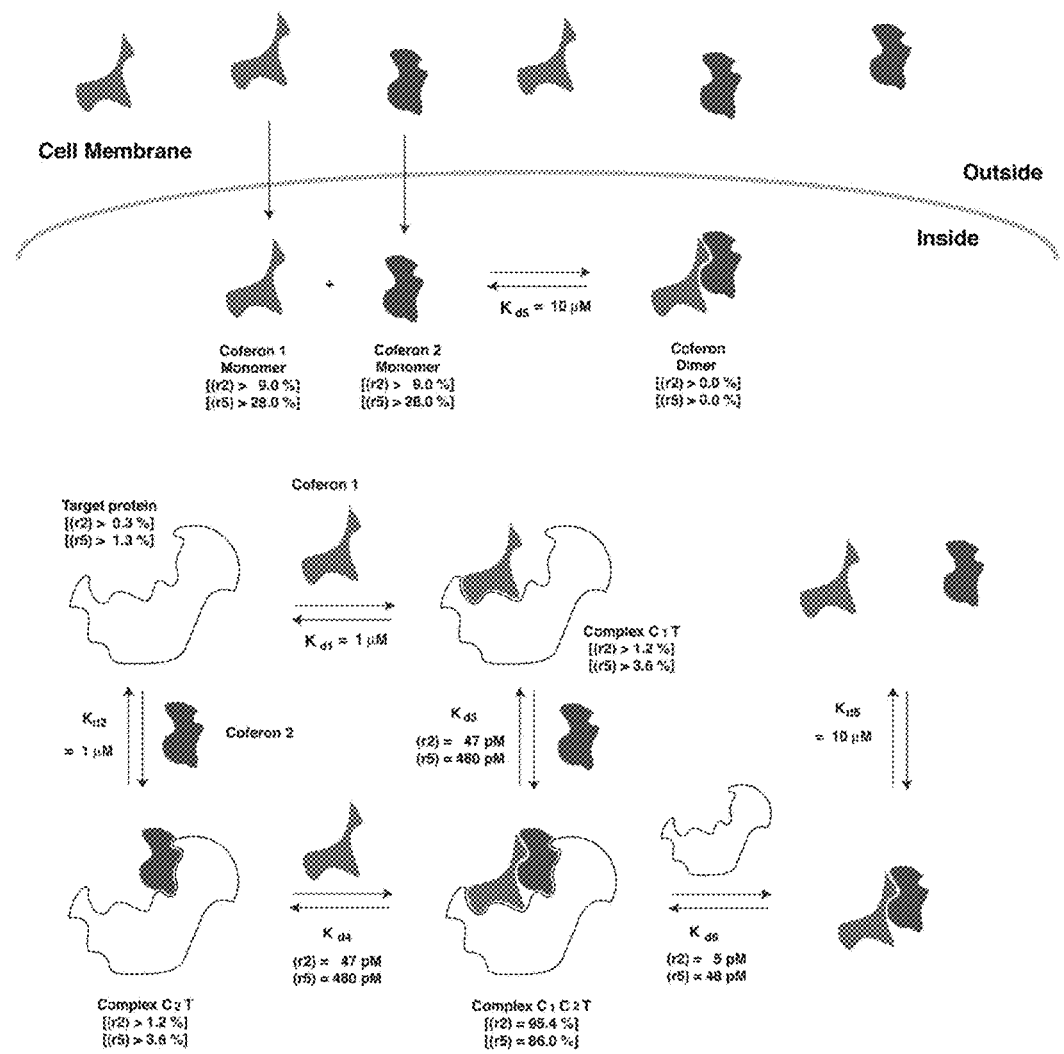
FIG. 90 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 10 µM, about 10,000,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 10 µM.
Figure 91:
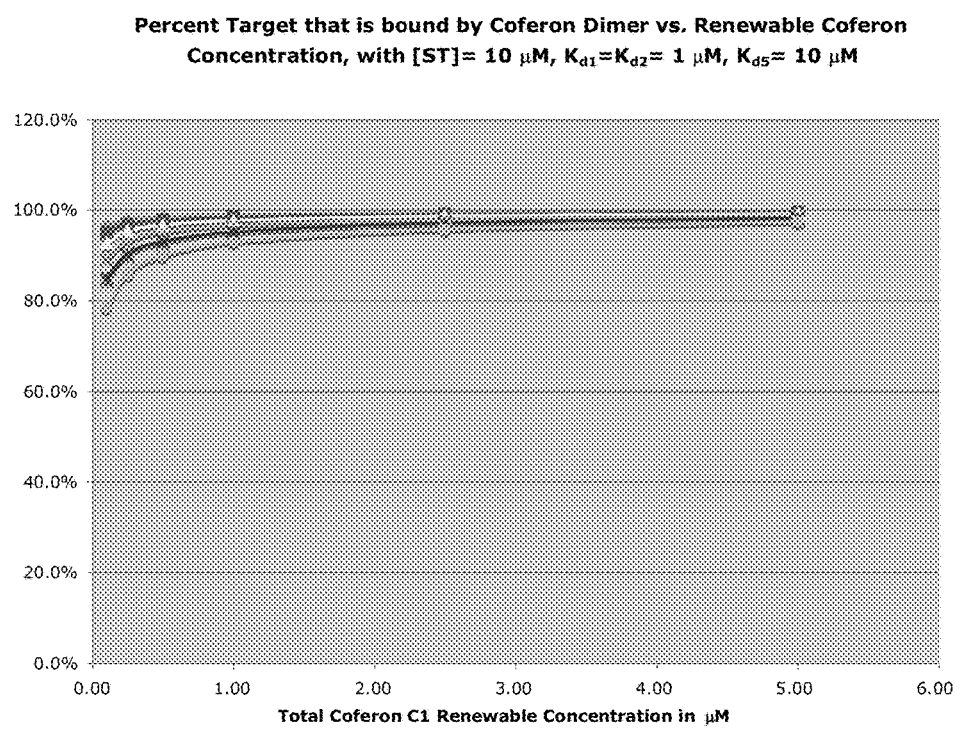
FIG. 91 is a graph showing the percent target T that is bound by coferon dimer C1C2 vs. "renewable" coferon C1 concentration. The total target [ST] is set at 10 µM, $K_{d1}=K_{d2}$ is set at 1 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 92:
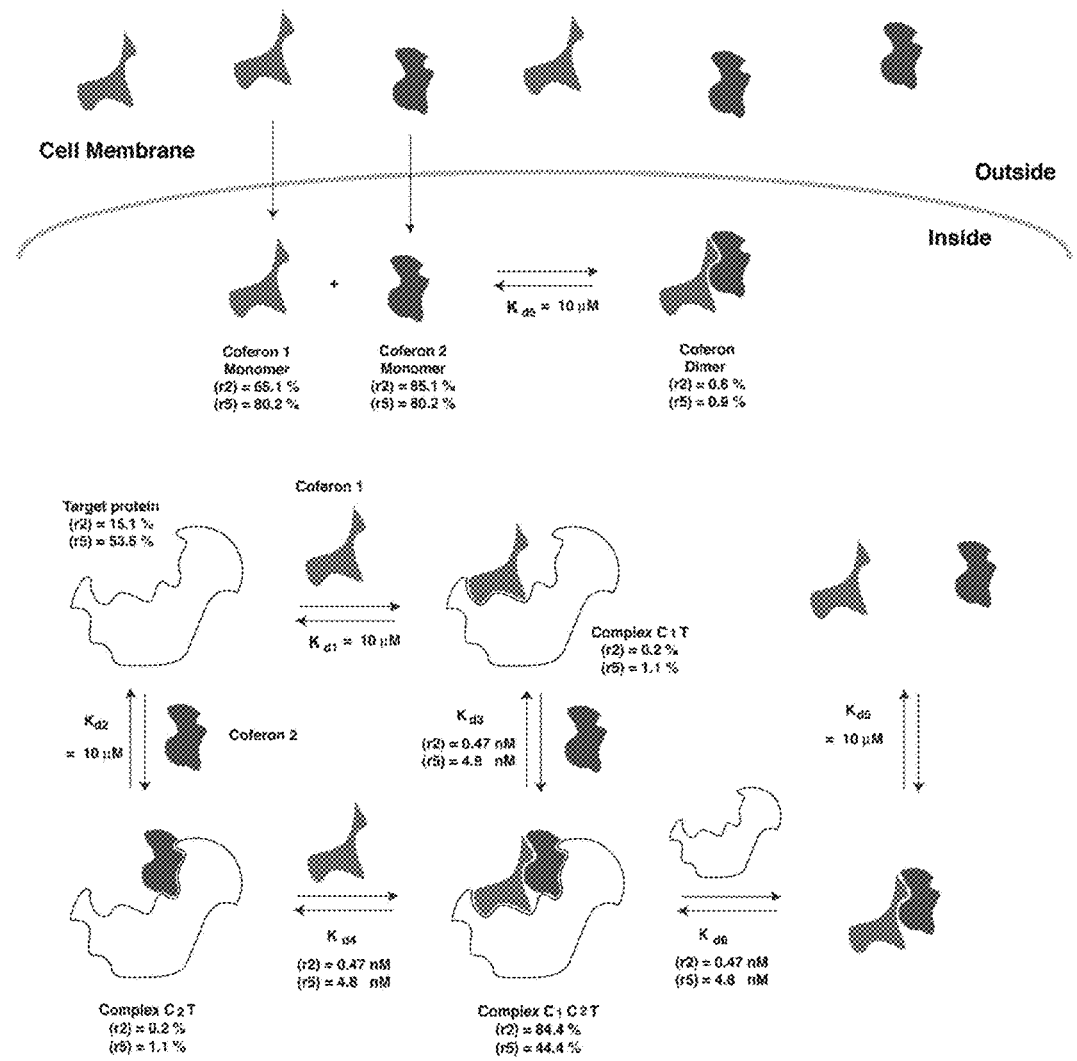
FIG. 92 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 0.1 µM, about 100,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 10 µM.
Figure 93:
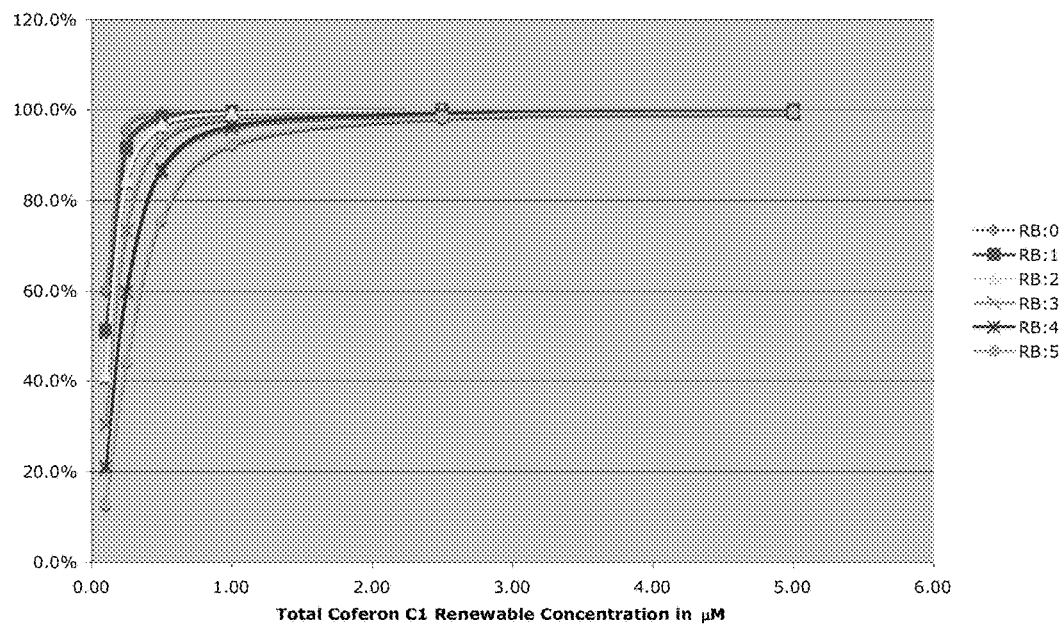
FIG. 93 is a graph showing the percent target T that is bound by coferon dimer C1C2 vs. "renewable" coferon C1 concentration. The total target [ST] is set at 0.1 µm, $K_{d1}=K_{d2}$ is set at 10 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 94:
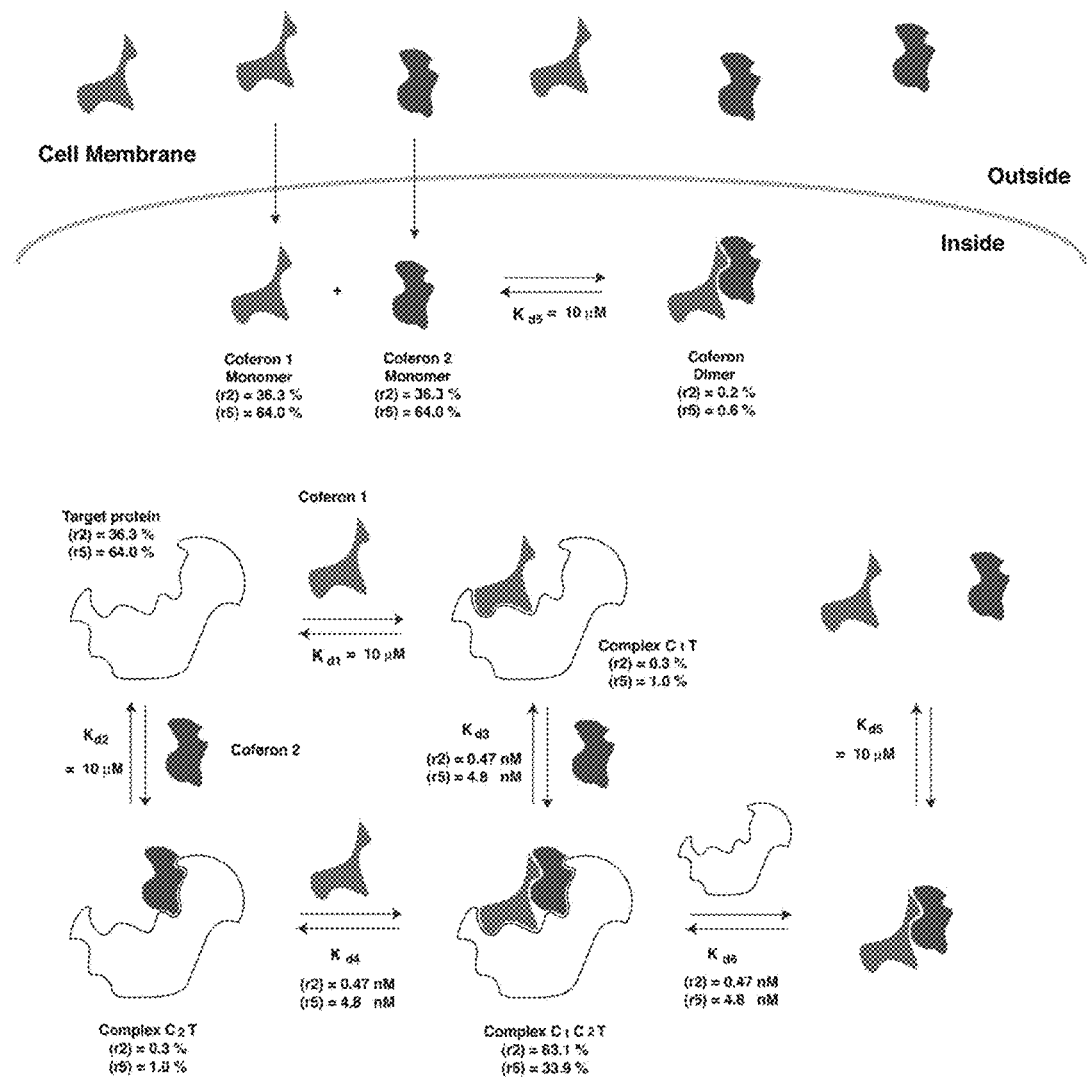
FIG. 94 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 0.25 µM, about 250,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 10 µM.
Figure 95:
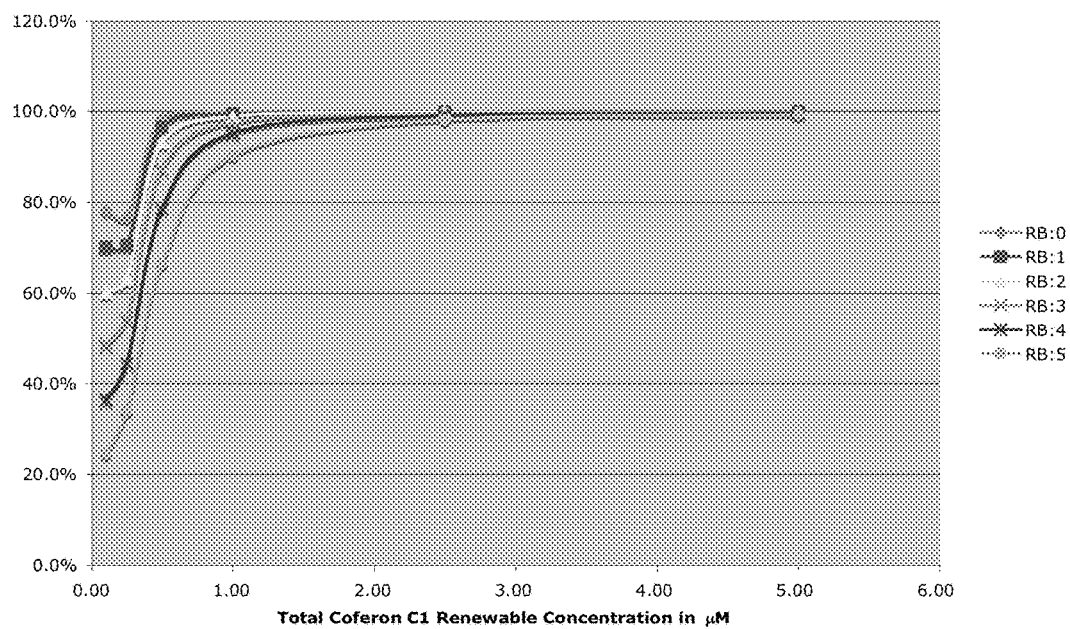
FIG. 95 is a graph showing the percent target T that is bound by coferon dimer C1C2 vs. "renewable" coferon C1 concentration. The total target [ST] is set at 0.25 µM, $K_{d1}=K_{d2}$ is set at 10 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 96:
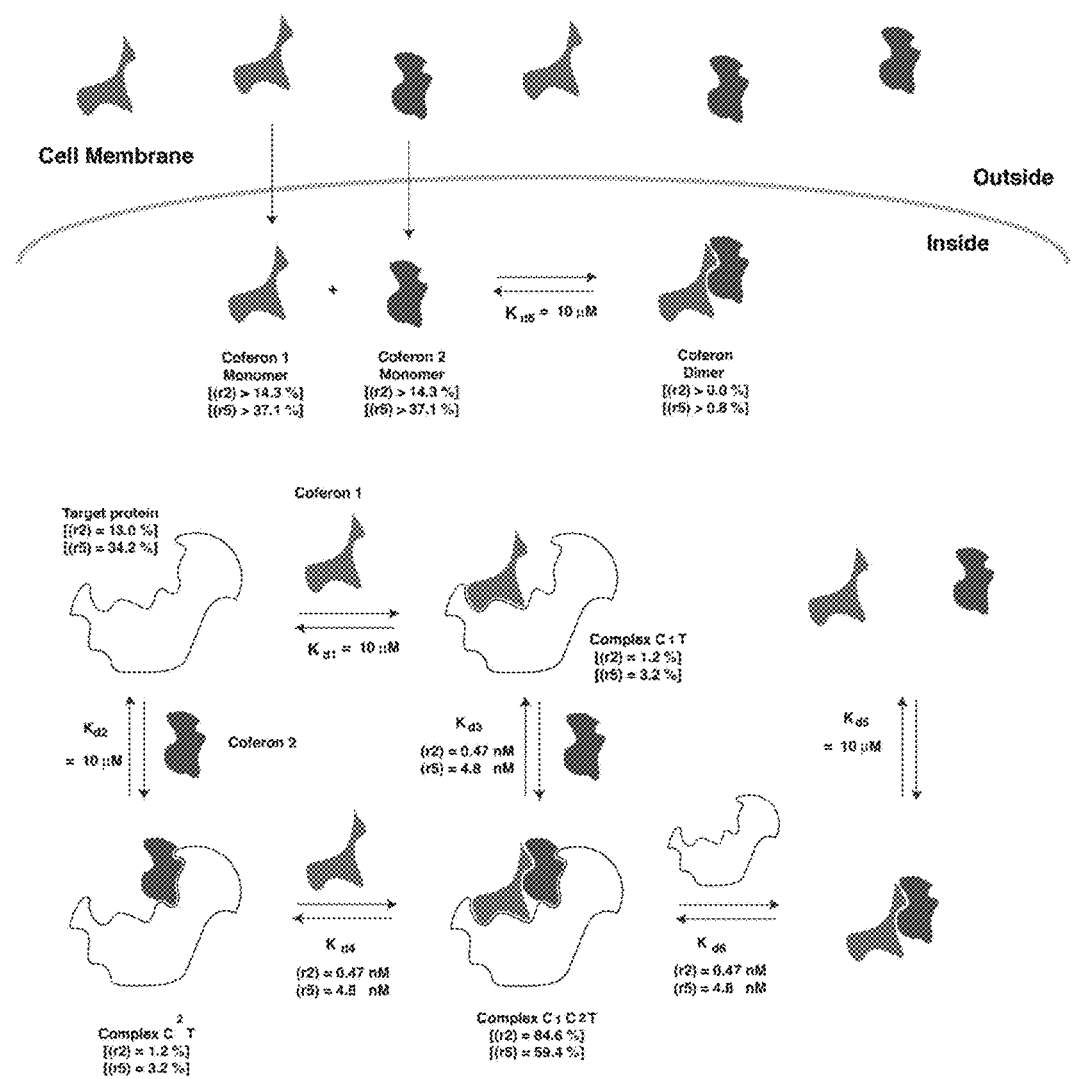
FIG. 96 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 1 µM, about 1,000,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 10 µM.
Figure 97:
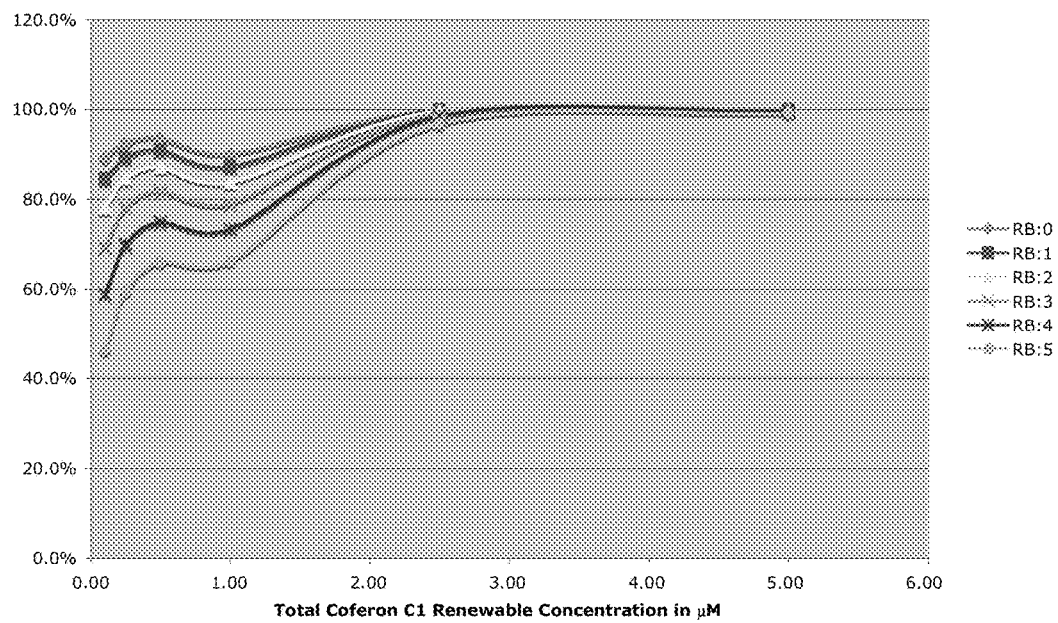
FIG. 97 is a graph showing the percent target T that is bound by coferon dimer C1C2 vs. "renewable" coferon C1 concentration. The total target [ST] is set at 1 µM, $K_{11}=K_{d2}$ is set at 10 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 98:
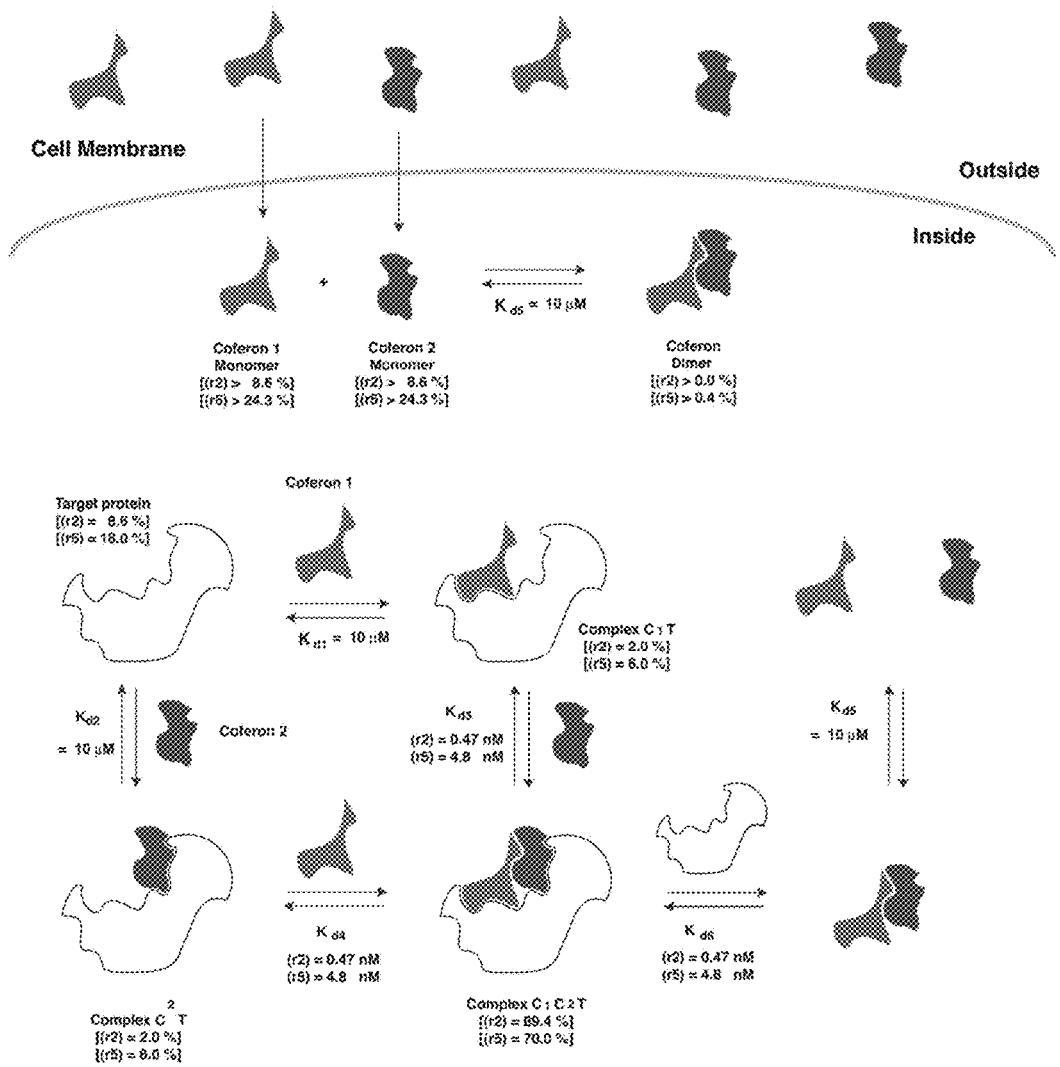
FIG. 98 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 2.5 µM, about 2,500,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 10 µM.
Figure 99:
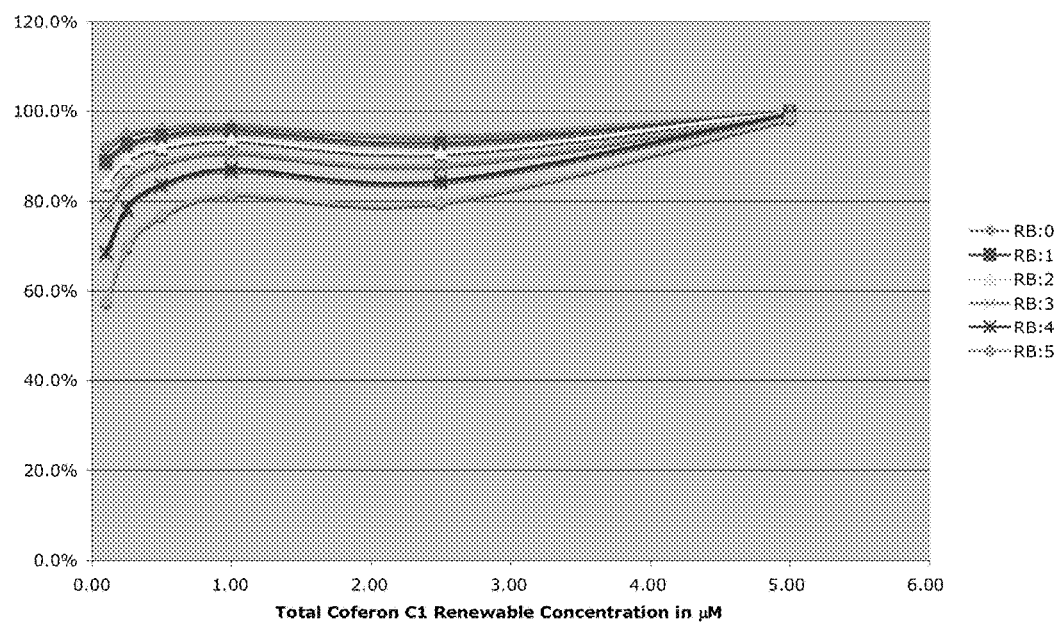
FIG. 99 is a graph showing the percent target T that is bound by coferon dimer C1C2 vs. "renewable" coferon C1 concentration. The total target [ST] is set at 2.5 µM, $K_{d1}=K_{d2}$ is set at 10 µM, $K_{d5}$ is set at 10 µM, and steady-state or renewable coferon C1 concentration [C1]=steady-state or renewable coferon C2 concentration [C2], varying from 0.1 µM up to 5 µM concentration.
Figure 100:
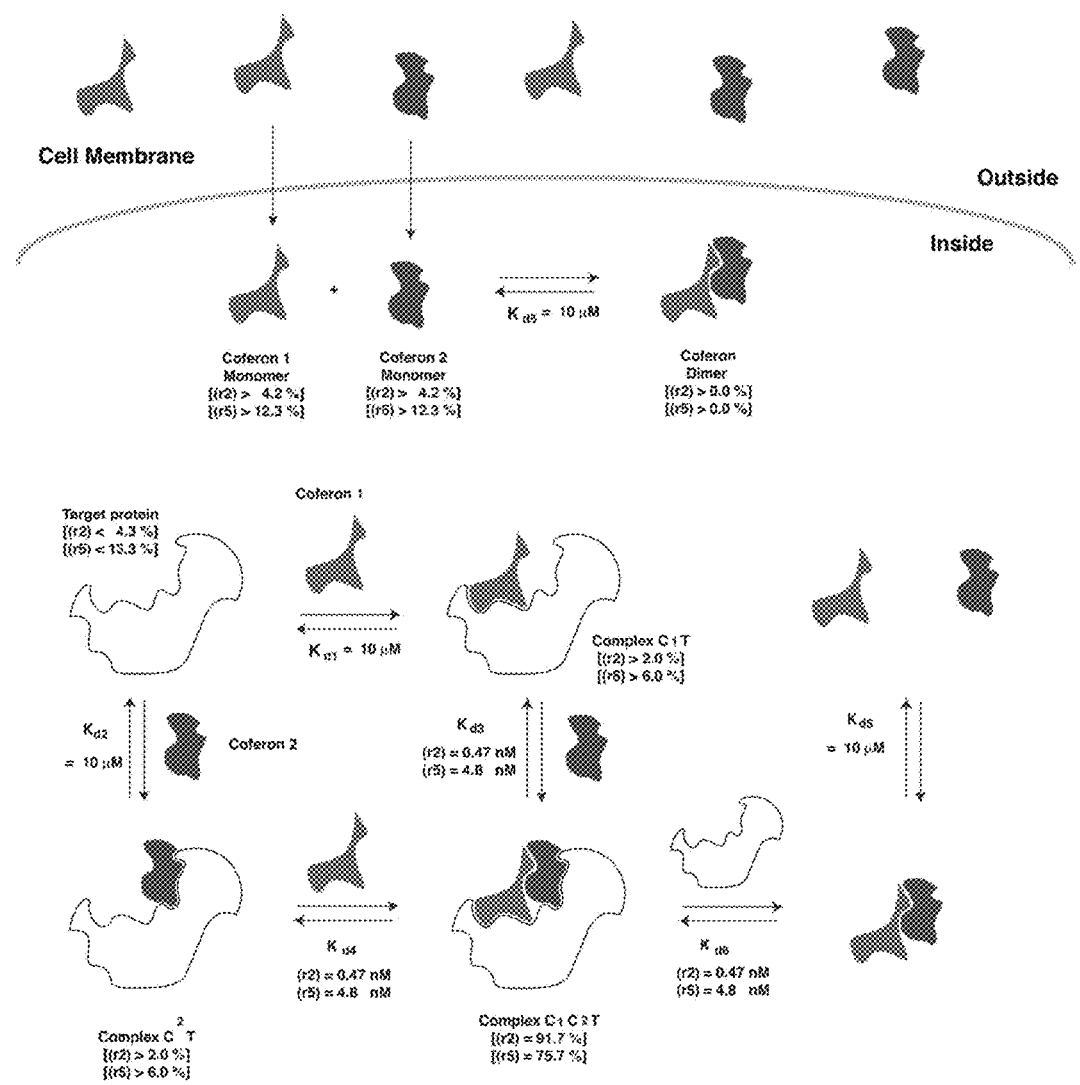
FIG. 100 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.25 µM, reflecting the ability to provide a steady dose of drug over time. The total protein concentration inside the cell is 10 µM, about 10,000,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 10 µM.
Figure 101:
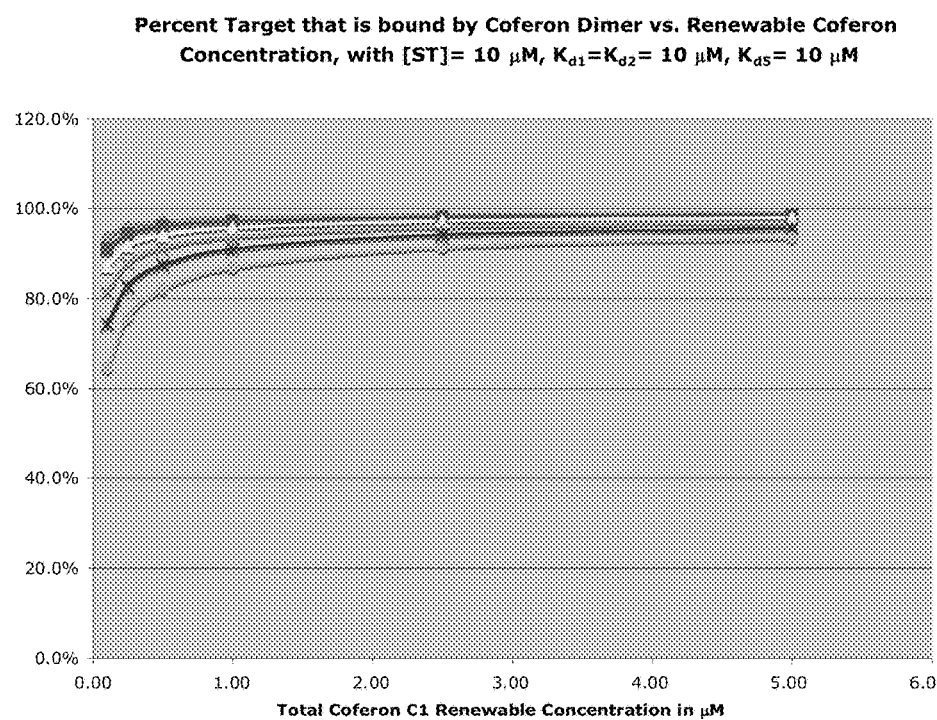
FIG. 101 is a graph showing the percent target T that is bound by coferon dimer C1C2 vs. "renewable" coferon C1 concentration. The total target [ST] is set at 10 μM, $K_{d1}=K_{d2}$ is set at 10 μM, $K_{d5}$ is set at 10 μM, and steady-state or renewable coferon C1 concentration [C1]=steady-state or renewable coferon C2 concentration [C2], varying from 0.1 μM up to 5 μM concentration.
Figure 102:
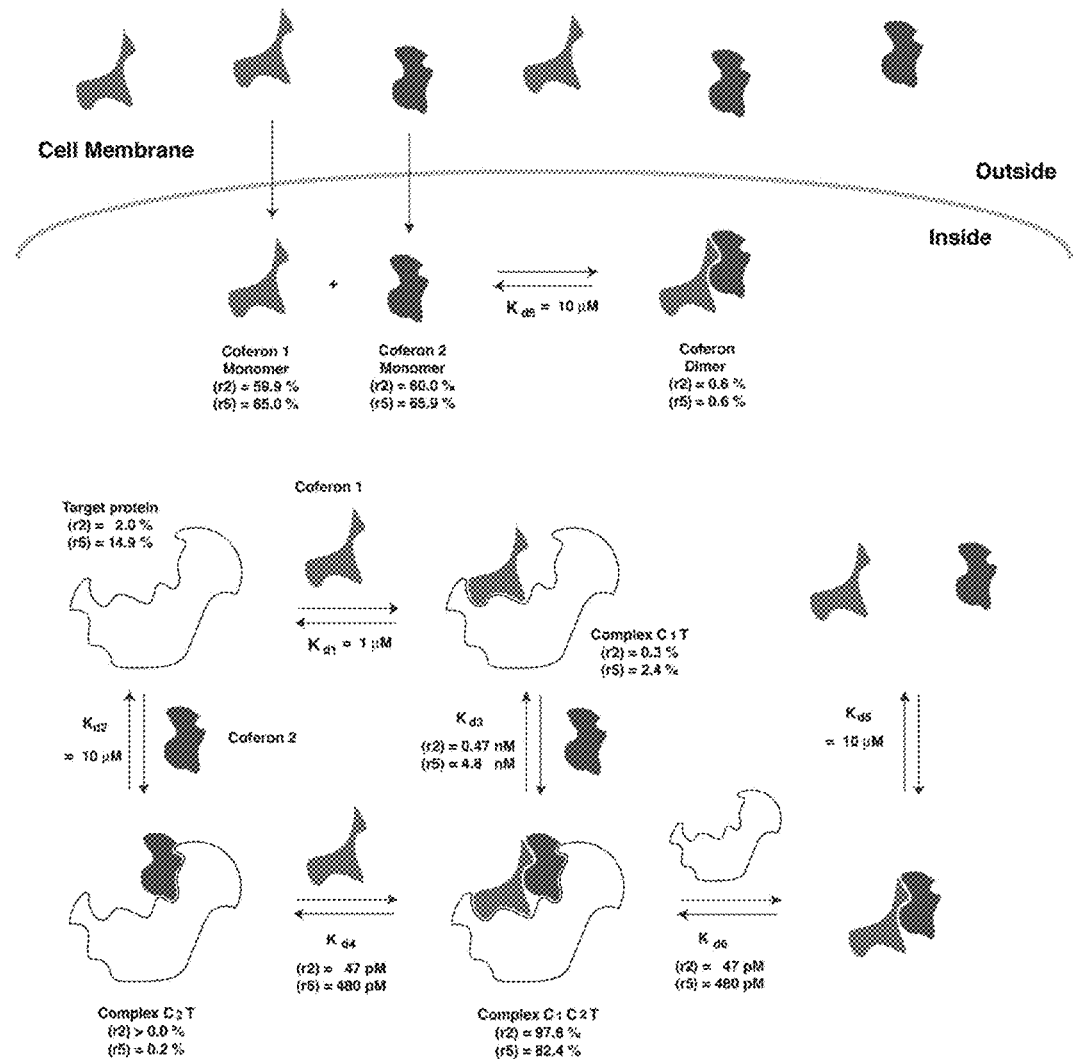
FIG. 102 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. To more accurately simulate conditions in vivo, the steady-state or "renewable" concentrations of C1 and C2 are 0.1 μM, reflecting the ability to provide a steady dose of drug over time. The total protein concentration inside the cell is 0.1 μM, about 100,000 targets per cell. The dissociation constant $K_{d1}$ between coferon C1 and target T, is given at 1 μM, and the dissociation constant $K_{d2}$ between coferon C2 and target T, is given at 10 μM. The dissociation constant between the two coferons, $K_{d5}$ is given at 10 μM.

A few general rules arise from analysis of the data. In almost all the cases, the dissociation of one monomer from the C1-C2-target complex ($K_{d3}$, $K_{d4}$) is easier than dissociation of the dimer ($K_{d6}$)—so that will be the preferred pathway. If one monomer binds poorly, even if the concentration of that monomer is 10-fold higher, that monomer will always dissociate first, and thus binding of the dimer may not be sufficiently strong enough to displace the native protein-protein interaction. This may be observed in several examples where $K_{d1}$ or $K_{d2}$ is 100 μM or higher, or $K_{d5}$ is 1,000 μM—under the concentrations shown, more than 80% of the target is bound, but the dissociation constant is too high: FIGS. 58 and 59, $K_{d3}$=0.47 μM to 4.8 μM, FIGS. 60 and 61, $K_{d3}$=0.47 μM to 4.8 μM, FIGS. 62 and 63, $K_{d4}$=0.47 μM to 4.8 μM, FIGS. 64 and 65, $K_{d4}$=0.47 μM to 4.8 μM, FIGS. 66 and 67, $K_{d4}$=47 nM to 480 nM, FIGS. 68 and 69, $K_{d4}$=47 nM to 480 nM, FIGS. 70 and 71, $K_{d4}$=0.12 μM to 1.2 μM, FIGS. 72 and 73, $K_{d4}$=0.12 μM to 1.2 μM, FIGS. 74 and 75, $K_{d4}$=47 nM to 480 nM, FIGS. 76 and 77, $K_{d4}$=47 nM to 480 nM, FIGS. 78 and 79, $K_{d4}$=0.12 μM to 1.2 μM, and FIGS. 80 and 81, $K_{d4}$=0.12 μM to 1.2 μM. The strength of the linker element binding to each other is critical to achieve the desired enhancement of binding two adjacent ligands to the protein target. However, if the linker elements become associated using essentially irreversible covalent linkage, then dissociation of the dimer ($K_{d6}$) is the only path and, consequently, is from 10-fold to 1,000-fold stronger than the $K_{d4}$ value when using reversible binding between the linker elements.

Figure 48:
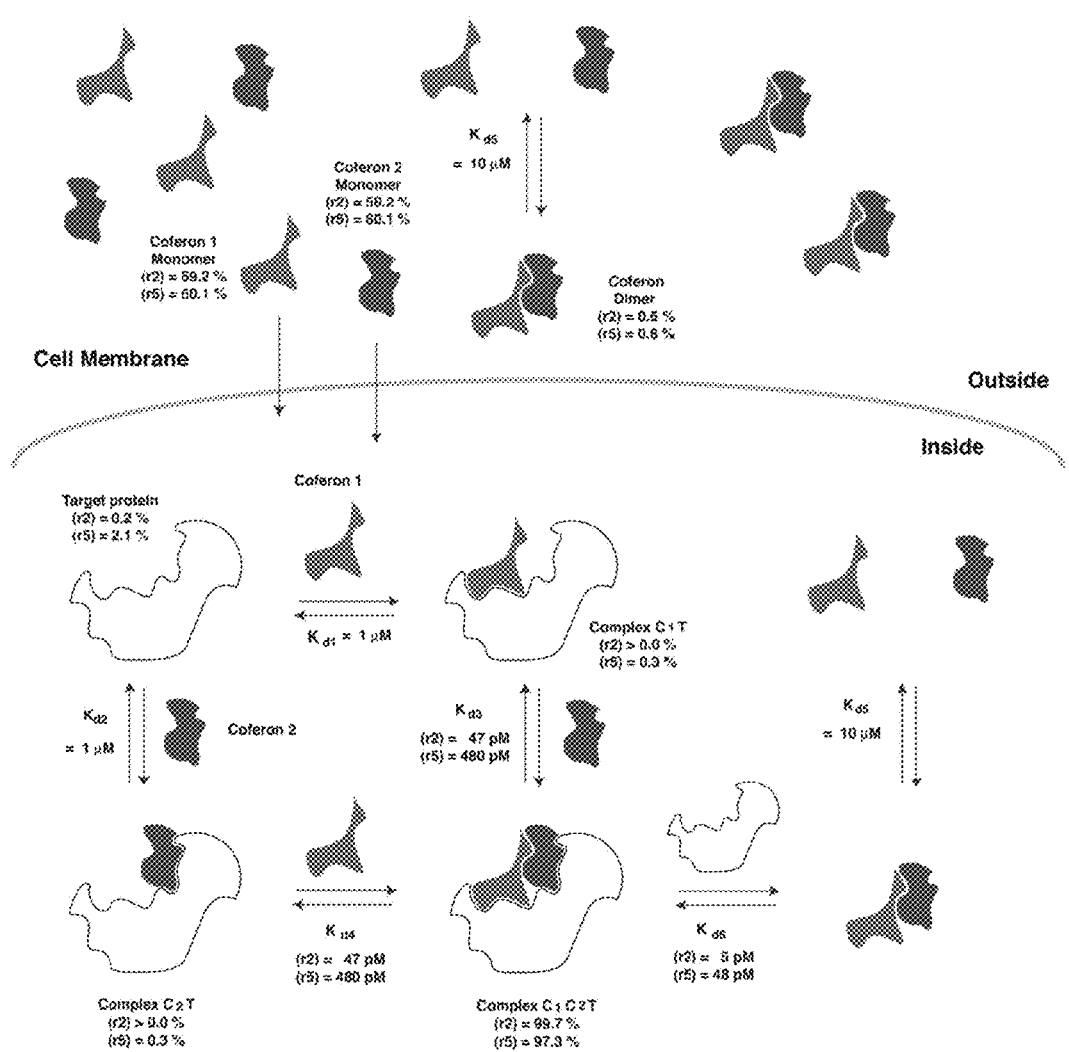
FIG. 48 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 0.25 µM, the total protein concentration inside the cell is 0.1 µM, about 100,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 10 48 µM.
Figure 49:
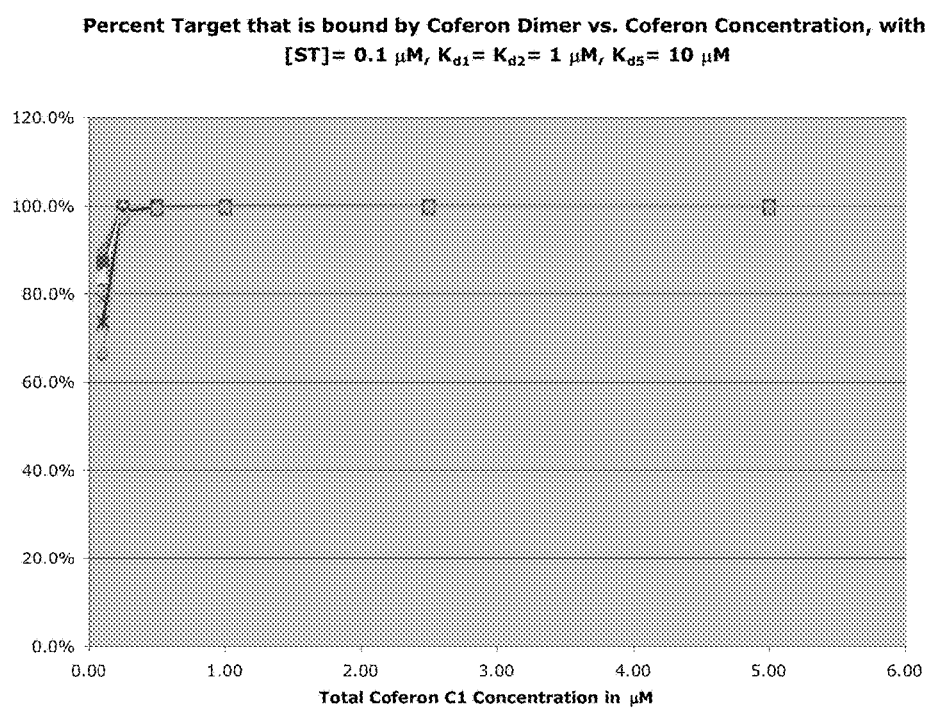
FIG. 49 is a graph showing the percent target T that is bound by coferon dimer C1C2 vs. coferon C1 concentration. The total target [ST] is set at 0.1 µM, $K_{d1}=K_{d2}$ is set at 1 µM, $K_{d5}$ is set at 10 µM, and total coferon C1 concentration [C1]=total coferon C2 concentration [C2], varying from 0.1 µM up to 5 µM concentration.
Figure 50:
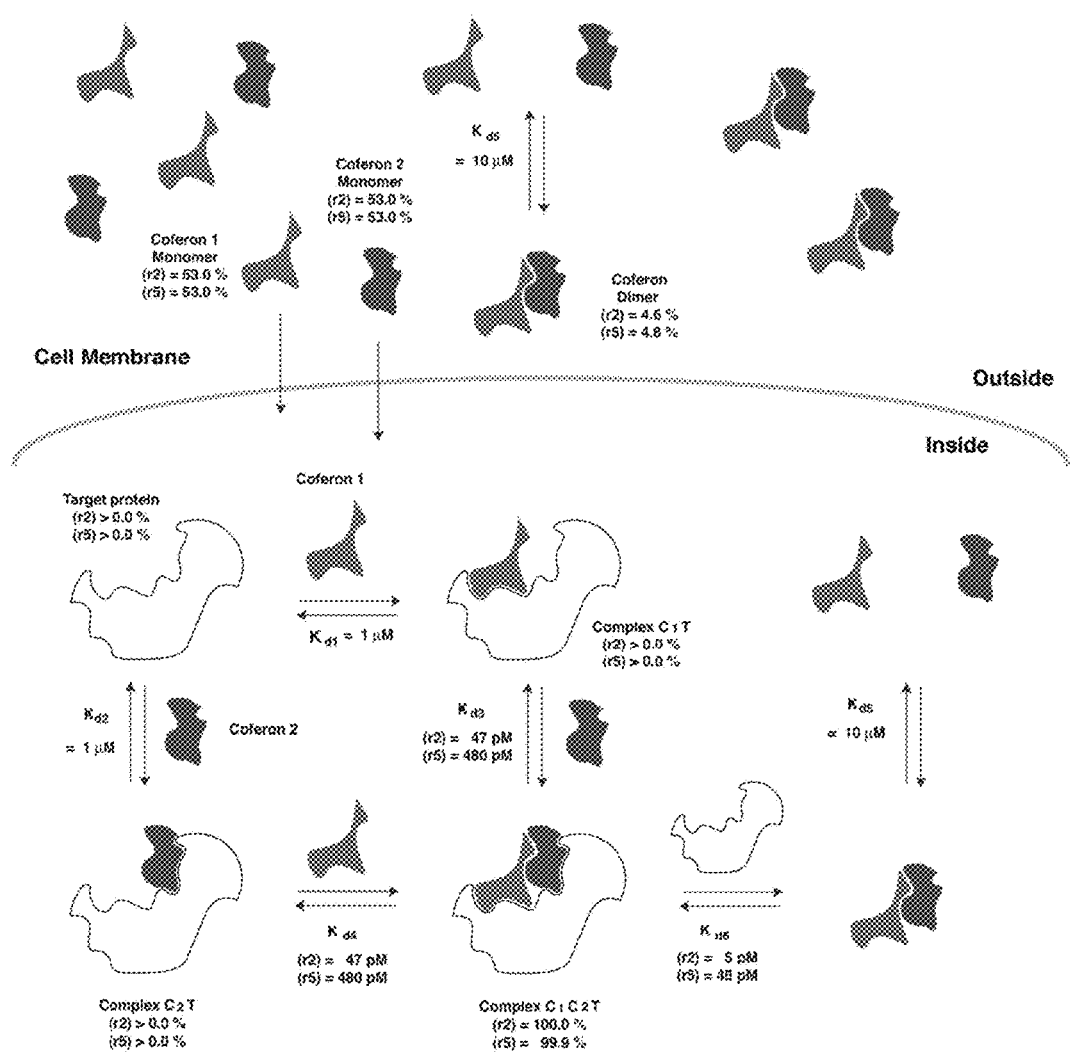
FIG. 50 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 2.5 µM, the total protein concentration inside the cell is 1 µM, about 1,000,000 targets per cell. The dissociation constants $K_{d1}$ and $K_{d2}$ between coferon C1 and target T, as well as between coferon C2 and target T are given at 1 µM. The dissociation constant between the two coferons, $K_{d5}$ is given at 10 µM.
Figure 51:
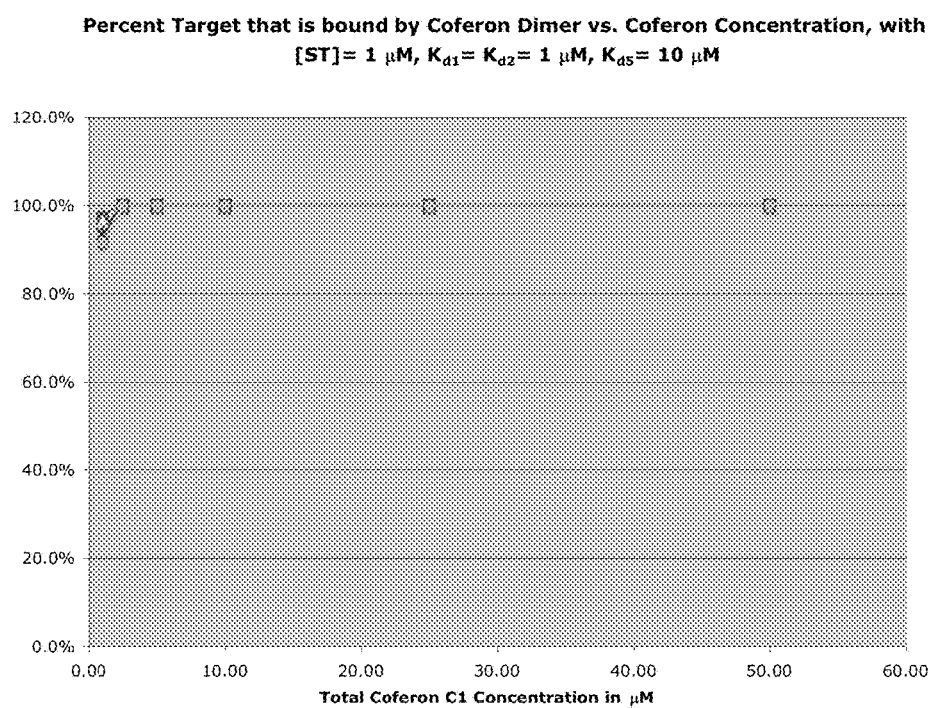
FIG. 51 is a graph showing the percent target T that is bound by coferon dimer C1C2 vs. coferon C1 concentration. The total target [ST] is set at 1 µM, $K_{d1}=K_{d2}$ is set at 1 µM, $K_{d5}$ is set at 10 µM, and total coferon C1 concentration [C1]=total coferon C2 concentration [C2], varying from 1 µM up to 50 µM concentration.
Figure 52:
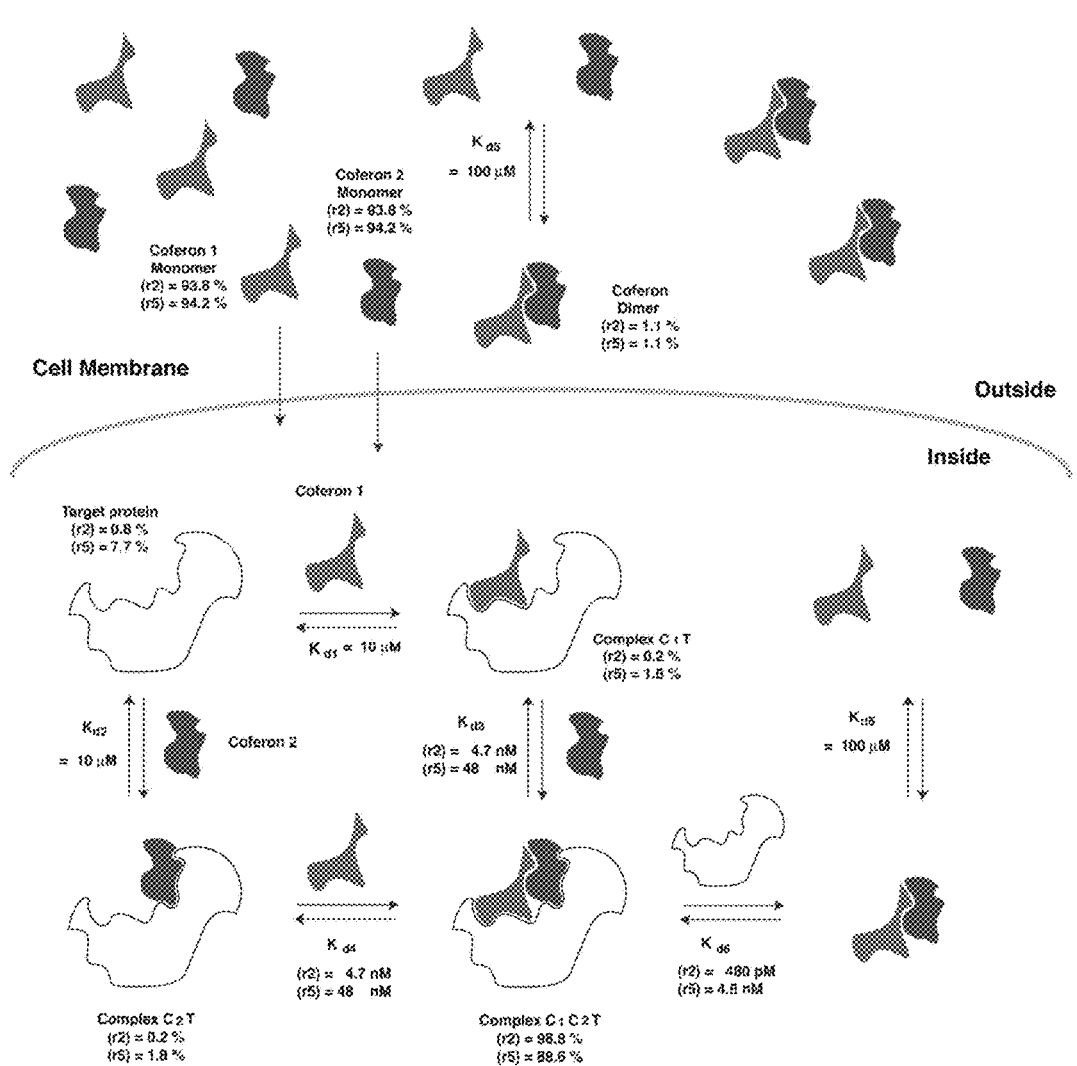
FIG. 52 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 2.5 µM, the total protein concentration inside the cell is 0.1 µM, about 100,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 100 µM.
Figure 53:
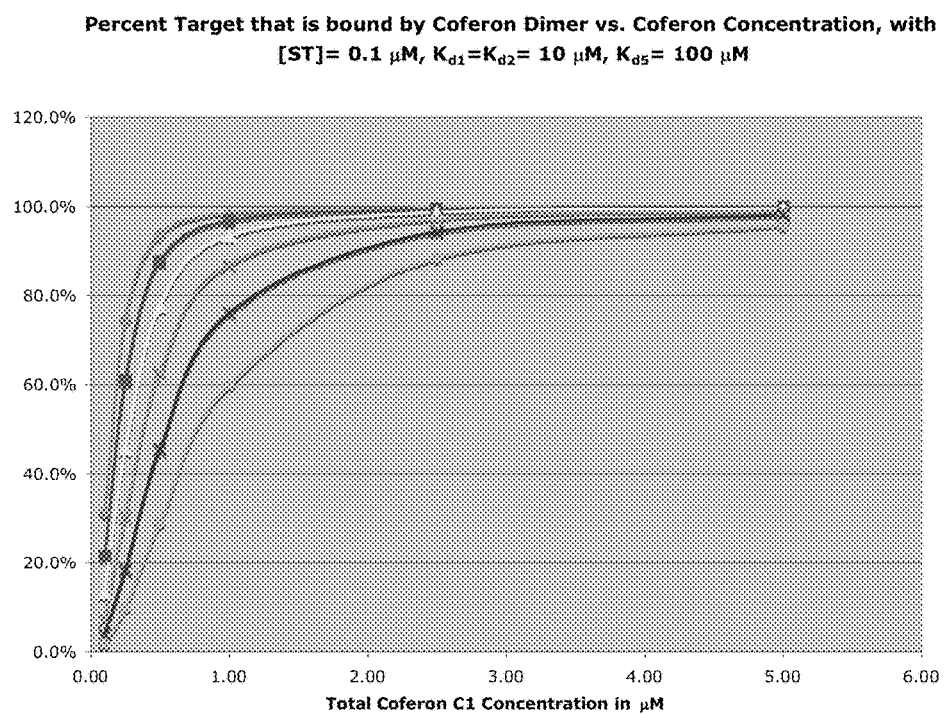
FIG. 53 is a graph showing the percent target T that is bound by coferon dimer C1C2 vs. coferon C1 concentration. The total target [ST] is set at 0.1 µM, $K_{d1}=K_{d2}$ is set at 10 µM, $K_{d5}$ is set at 100 µM, and total coferon C1 concentration [C1]=total coferon C2 concentration [C2], varying from 0.1 µM up to 5 µM concentration.
Figure 54:
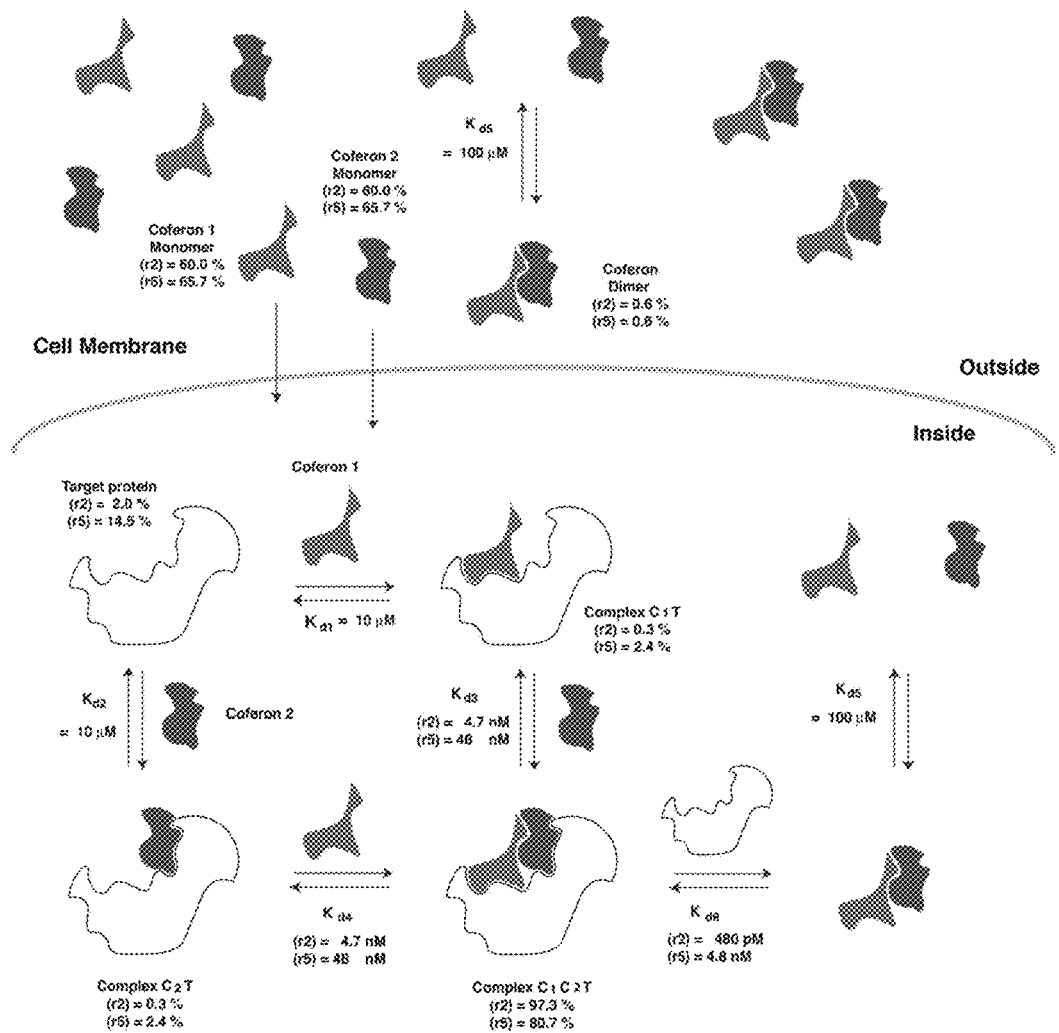
FIG. 54 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 2.5 µM, the total protein concentration inside the cell is 1 µM, about 1,000,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 100 µM.
Figure 55:
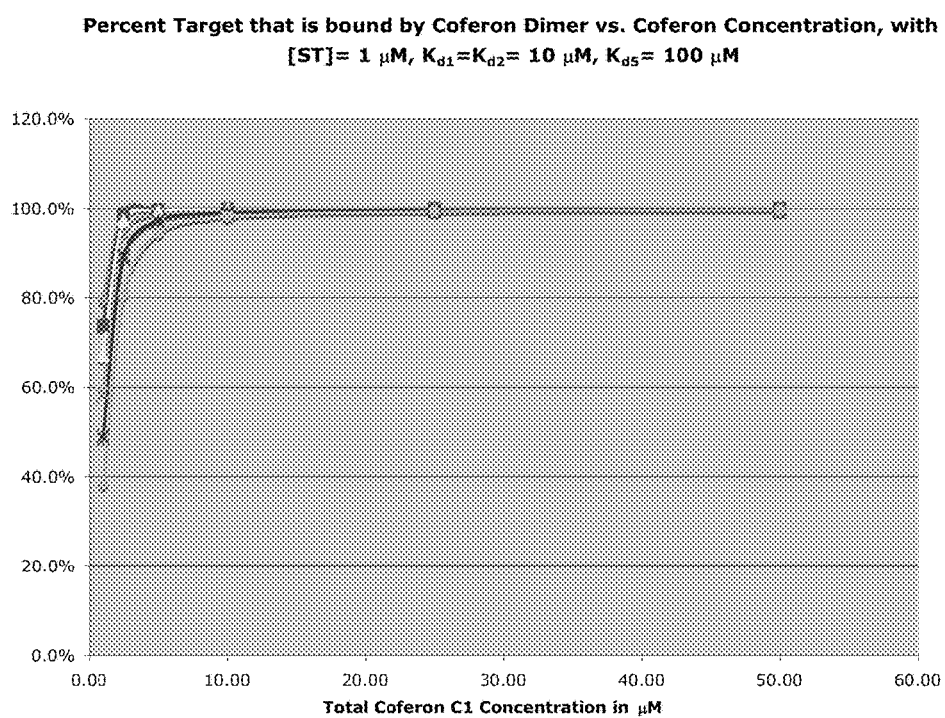
FIG. 55 is a graph showing the percent target T that is bound by coferon dimer C1C2 vs. coferon C1 concentration. The total target [ST] is set at 1 µM, $K_{d1}=K_{d2}$ is set at 10 µM, $K_{d5}$ is set at 100 µM, and total coferon C1 concentration [C1]=total coferon C2 concentration [C2], varying from 1 µM up to 10 µM concentration.
Figure 56:
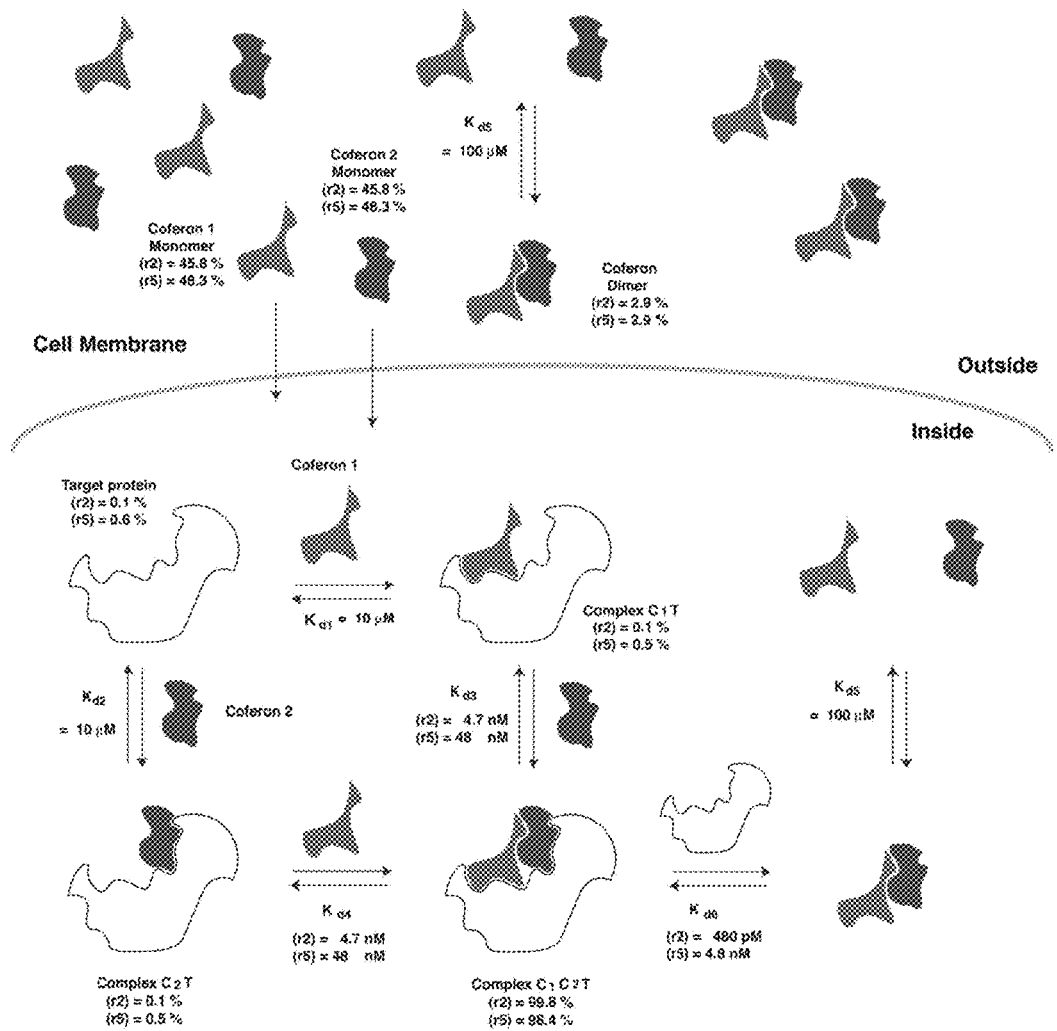
FIG. 56 is a schematic representation of two coferons (C1, and C2) that can enter cells as monomers, and bind to orthogonal sites on an internal protein target (T) to inhibit its activity. Coferon 1 (C1) is illustrated as a green shape, coferon 2 (C2) as a blue shape, and the target protein as a white shape. The total concentrations of C1 and C2 are 20 µM, the total protein concentration inside the cell is 10 µM, about 10,000,000 targets per cell. The dissociation constants $K_{d1}$ and $K_{d2}$ between coferon C1 and target T, as well as between coferon C2 and target T are given at 10 µM. The dissociation constant between the two coferons, $K_{d5}$ is given at 100 µM.
Figure 57:
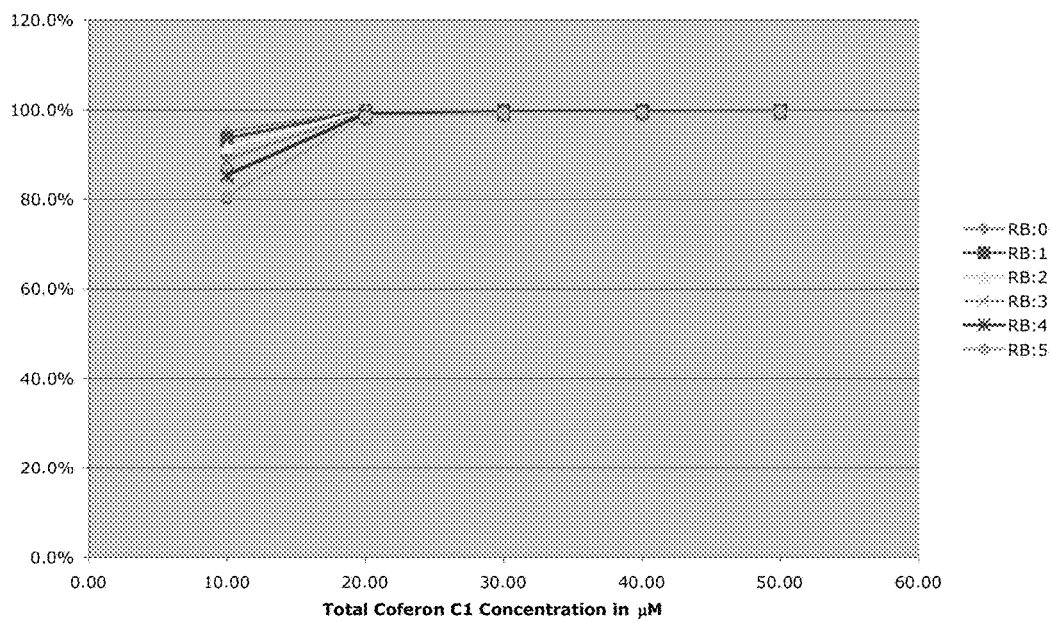
FIG. 57 is a graph showing the percent target T that is bound by coferon dimer C1C2 vs. coferon C1 concentration. The total target [ST] is set at 10 µM, $K_{d1}=K_{d2}$ is set at 10 µM, $K_{d5}$ is set at 100 µM, and total coferon C1 concentration [C1]=total coferon C2 concentration [C2], varying from 10 µM up to 50 µM concentration.

Consider the simulation where the total concentrations of C1 and C2 are 0.25 μM, the total protein concentration inside the cell is 0.1 μM, about 100,000 targets per cell (FIGS. 48 and 49). The dissociation constants $K_{d1}$ and $K_{d2}$ between monomer C1 and target T, as well as between monomer C2 and target T are given at 1 μM. The linker element dissociation constant, $K_{d5}$ is given at 10 μM. The values next to (r2) and (r5) represent 2 and 5 rotatable bonds between the linker elements and ligands of each monomer—for a total of 4 and 10 rotatable bonds respectively. In this example, the dissociation constant between the linker elements of the two monomers has been tuned so that at the monomer concentration of 0.1 μM each, approximately 1% of the free monomers are in the dimer state. Although only monomers traverse the cell membrane, once inside, they bind to the target protein, which accelerates formation of the dimer. Dissociation of either monomer from the dimer bound to target ($K_{d3}$, $K_{d4}$) is 47 pM and 480 pM for 2 and 5 rotatable bonds, respectively. Under these starting conditions, the coferon dimer dissociation from the target ($K_{d6}$) is 4.7 pM and 48 pM for 2 and 5 rotatable bonds, respectively. If the linker elements form an irreversible covalent bond when bringing the two monomers together, then dissociation will be through $K_{d6}$, i.e. binding will be even 10-fold tighter than if the linker elements form reversible bonds. Since the dimer binds tightly to the protein target, even with reversible linker elements, it does not dissociate easily, and the majority of the protein targets (99.7% and 97.3% for r2 and r5, respectively) are bound to achieve the desired therapeutic effect. When increasing the total protein concentration inside the cell to 1 μM, about 1,000,000 targets per cell (FIGS. 50 and 51), and 10 μM, about 10,000,000 targets per cell (FIGS. 50-51), the target is saturated with dimer.

The results of these simulations for various values (in μM) of $K_{d1}$, $K_{d2}$, $K_{d5}$, total monomer 1 concentration [SC1], total monomer 2 concentration [SC2], total target protein concentration [ST], the number of rotatable bonds between the linker element and the diversity element for each monomer (Rot Bond), and the highest $K_d$ value are enumerated in Table 4. In each instance, the highest $K_d$ value (either $K_{d3}$ or $K_{d4}$) is reported in the $K_d$ highest column.

TABLE 4

Equilibrium dissociation constants derived from simulations of coferon monomer interactions with target protein.

| Figure# | $K_{d1}$ | $K_{d2}$ | $K_{d5}$ | [SC1] | [SC2] | [ST] | Rot Bond | $K_d$ highest |
|---|---|---|---|---|---|---|---|---|
| 48 | 1 | 1 | 10 | 0.1 to 5.0 | 0.1 to 5.0 | 0.1 | 2 | 47 pM |
| 49 | 1 | 1 | 10 | 0.1 to 5.0 | 0.1 to 5.0 | 0.1 | 5 | 480 pM |
| 50 | 1 | 1 | 10 | 1 to 50 | 1 to 50 | 1 | 2 | 47 pM |
| 51 | 1 | 1 | 10 | 1 to 50 | 1 to 50 | 1 | 5 | 480 pM |
| 52 | 10 | 10 | 100 | 0.1 to 5 | 0.1 to 5 | 0.1 | 2 | 4.7 nM |
| 53 | 10 | 10 | 100 | 0.1 to 5 | 0.1 to 5 | 0.1 | 5 | 48 nM |
| 54 | 10 | 10 | 100 | 1 to 50 | 1 to 50 | 1 | 2 | 4.7 nM |
| 55 | 10 | 10 | 100 | 1 to 50 | 1 to 50 | 1 | 5 | 48 nM |
| 56 | 10 | 10 | 100 | 10 to 50 | 10 to 50 | 10 | 2 | 4.7 nM |
| 57 | 10 | 10 | 100 | 10 to 50 | 10 to 50 | 10 | 5 | 48 nM |
| 58 | 100 | 100 | 1000 | 1 to 50 | 1 to 50 | 1 | 2 | 4.7 μM |
| 59 | 100 | 100 | 1000 | 1 to 50 | 1 to 50 | 1 | 5 | 48 μM |
| 60 | 100 | 100 | 1000 | 10 to 50 | 10 to 50 | 10 | 2 | 4.7 μM |
| 61 | 100 | 100 | 1000 | 10 to 50 | 10 to 50 | 10 | 5 | 48 μM |
| NS | 10 | 1 | 100 | 5 | 0.1 to 5.0 | 0.1 | 2 | 4.7 nM |
| NS | 10 | 1 | 100 | 5 | 0.1 to 5.0 | 0.1 | 5 | 48 nM |
| NS | 10 | 1 | 100 | 50 | 1 to 50 | 1 | 2 | 4.7 nM |
| NS | 10 | 1 | 100 | 50 | 1 to 50 | 1 | 5 | 48 nM |
| NS | 10 | 1 | 100 | 50 | 10 to 50 | 10 | 2 | 4.7 nM |
| NS | 10 | 1 | 100 | 50 | 10 to 50 | 10 | 5 | 48 nM |

TABLE 4-continued

Equilibrium dissociation constants derived from simulations of coferon monomer interactions with target protein.

| Figure# | $K_{d1}$ | $K_{d2}$ | $K_{d5}$ | [SC1] | [SC2] | [ST] | Rot Bond | $K_d$ highest |
|---|---|---|---|---|---|---|---|---|
| 62 | 100 | 10 | 1000 | 50 | 1 to 50 | 1 | 2 | 0.47 µM |
| 63 | 100 | 10 | 1000 | 50 | 2 to 50 | 1 | 5 | 4.8 µM |
| 64 | 100 | 10 | 1000 | 50 | 10 to 50 | 10 | 2 | 0.47 µM |
| 65 | 100 | 10 | 1000 | 50 | 11 to 50 | 10 | 5 | 4.8 µM |
| 66 | 25 | 25 | 100 | 25 | 25 | 1 | 2 | 47 nM |
| 67 | 25 | 25 | 100 | 25 | 25 | 1 | 5 | 480 nM |
| 68 | 25 | 25 | 100 | 25 | 25 | 10 | 2 | 47 nM |
| 69 | 25 | 25 | 100 | 25 | 25 | 10 | 5 | 480 nM |
| 70 | 25 | 25 | 1000 | 25 | 25 | 1 | 2 | 0.12 µM |
| 71 | 25 | 25 | 1000 | 25 | 25 | 1 | 5 | 1.2 µM |
| 72 | 25 | 25 | 1000 | 25 | 25 | 10 | 2 | 0.12 µM |
| 73 | 25 | 25 | 1000 | 25 | 25 | 10 | 5 | 1.2 µM |
| 74 | 10 | 10 | 1000 | 25 | 25 | 1 | 2 | 47 nM |
| 75 | 10 | 10 | 1000 | 25 | 25 | 1 | 5 | 480 nM |
| 76 | 10 | 10 | 1000 | 25 | 25 | 10 | 2 | 47 nM |
| 77 | 10 | 10 | 1000 | 25 | 25 | 10 | 5 | 480 nM |
| 78 | 100 | 100 | 250 | 25 | 25 | 1 | 2 | 0.12 µM |
| 79 | 100 | 100 | 250 | 25 | 25 | 1 | 5 | 1.2 µM |
| 80 | 100 | 100 | 250 | 25 | 25 | 10 | 2 | 0.12 µM |
| 81 | 100 | 100 | 250 | 25 | 25 | 10 | 5 | 1.2 µM |

($K_{d1}$, $K_{d2}$, $K_{d5}$ are in µM. [SC1], [SC2], and [ST] represent the total concentration of monomer 1, monomer 2, and target, respectively, and are in µM. Rot bonds indicates the number of rotatable bonds between the linker element and the diversity element for each monomer. NS = Figure not shown)

Prophetic Example 6

Simulation of Binding Equilibria for Coferon Dimer to Target Protein: Determination of Concentrations of Coferon Dimer Binding to a Target Protein for Various Values of Dissociation Constants for Both Monomers and for Reversible Association of Monomers The simulations described in Prophetic Example 6 are performed as described above in Example 5. These simulations, where the steady-state or renewable concentrations of C1 and C2 are 0.25 µM, and the total protein concentration inside the cell is varied, can be extended to include 0.25 µM=250,000 targets, 1 µM=1,000,000 targets, 2.5 µM=2,500,000 targets, and 10 µM=10,000,000 targets per cell (FIGS. 82, 84, 86, 88, and 90, respectively). In all these cases, we see the dissociation of either monomer from the dimer bound to target ($K_{d3}$, $K_{d4}$) is 47 pM and 480 pM for 2 and 5 rotatable bonds, respectively. Under these starting conditions, the coferon dimer dissociation from the target ($K_{d6}$) is 4.7 pM and 48 pM for 2 and 5 rotatable bonds, respectively. Since the coferon dimer binds tightly to the protein target, even with reversible linker elements it does not dissociate easily, and the majority of the protein targets (ranging from 70% to 100% across C1 and C2 concentrations ranging from 0.25 µM to 5 µM) are bound to achieve the desired therapeutic effect.

Note that under these dissociation values for each monomer to the target ($K_{d1}$, $K_{d2}$=1 µM) or to each other (K, =10 µM)—considered weak by most standards, the free dimer in solution is often less than 1%. Even if monomer concentrations were brought to 25 µM in solution, the percentage dimer would at most be 35% of the total, leaving sufficient monomer to enter the cells. However, once the first monomer binds to the target, the second monomer can then also bind to the target as it now has the added advantage of two potential interactions (i) to the target, and (ii) to the neighboring monomers. Thus, the dissociation constant of the complex from the target jumps down to an impressive 0.5 to 0.05 nM. In other words, the improvement in binding affinity of a dimer over a monomer is from 2,000 to 20,000-fold. If the monomers become irreversibly linked, the improved binding of a dimer over a monomer is from 20,000 to 200,000-fold.

Consider increasing both monomer dissociation constants $K_{d1}$ and $K_{d2}$, such that $K_{d1}$=$K_{d2}$=10 µM, and the linker element dissociation constant $K_{d5}$=10 µM, where the steady-state or renewable concentrations of C1 and C2 are 0.25 µM, the total protein concentration inside the cell is varied from 0.1 µM=100,000 targets to 10 µM=10,000,000 targets per cell as above (FIGS. 92, 94, 96, 98, and 100, respectively). In all these cases, the dissociation of either monomer from the dimer bound to target ($K_{d3}$, $K_{d4}$) is 0.47 nM and 4.8 nM for 2 and 5 rotatable bonds, respectively. Under these starting conditions, the coferon dimer dissociation from the target ($K_{d6}$) is also 0.47 nM and 4.8 nM for 2 and 5 rotatable bonds, respectively. Since the dimer binds tightly to the protein target, even with reversible linker elements it does not dissociate easily, and the majority of the protein targets (ranging from 70% to 100% across C1 and C2 concentrations ranging from 0.5 µM to 5 µM) are bound to achieve the desired therapeutic effect.

Further, at the lowest C1 and C2 concentrations of 0.1 µM and 0.25 µM, the percentage of bound target increases as the target concentration increases, for example from 12.9% (under conditions of 5 rotatable bonds), with concentration of C1=0.1 µM, concentration of target at 0.1 µM=100,000 targets, to 64.6% with concentration of target at 10 µM=10,000,000 targets. In another example, bound target increases from 44.4% (under conditions of 5 rotatable bonds), with concentration of C1=0.25 µM, concentration of target at 0.1 µM=100,000 targets, to 75.7% with concentration of target at 10 µM=10,000,000 targets. Thus, under some conditions, these coferons may be used to bind a significantly higher percentage of protein target present at high concentration in the targeted cells—and thus have a greater influence on those cells—than when binding to lower percentage of protein target present at low concentration in the non-targeted cells—and thus have lower side-effects.

Consider altering the simulations so the monomer dissociation constants are different, with monomer C1 dissociation constant $K_{d1}=1$ µM, monomer C2 dissociation constant $K_{d2}=10$ µM, and the linker element dissociation constant $K_{d5}=10$ µM, where the steady-state or renewable concentrations of C1 and C2 are 0.25 µM, the total protein concentration inside the cell is varied from 0.25 µM=250,000 targets to 10 µM=10,000,000 targets per cell (FIGS. 102, 104, 106, 108, and 110, respectively). In all these cases, the dissociation of monomer C2 from the dimer bound to target ($K_{d3}$) is 0.47 nM and 4.8 nM for 2 and 5 rotatable bonds, respectively. Under these starting conditions, the coferon dimer dissociation from the target ($K_{d6}$) is 47 pM and 480 pM for 2 and 5 rotatable bonds, respectively. Since the dimer binds tightly to the protein target, even with reversible linker elements it does not dissociate easily, and the majority of the protein targets (ranging from 70% to 100% across C1 and C2 concentrations ranging from 0.25 µM to 5 µM) are bound to achieve the desired therapeutic effect.

Further, at the lowest C1 and C2 concentrations of 0.1 µM and 0.25 µM, the percentage of bound target increases as the target concentration increases. The increase in percentage binding when target concentration is higher is consistent in the context of an open system: there is a constant influx of monomers from outside the cell to always maintain the low concentration (i.e. 0.1 µM or 0.25 µM) inside the cell. For example the percentage of bound target increases from 39.7% (under conditions of 5 rotatable bonds), with concentration of C1=0.1 µM, concentration of target at 0.1 µM=100,000 targets to 72.3% with concentration of target at 10 µM=10,000,000 targets. Thus, under some conditions, coferons may be used to bind a significantly higher percentage of protein target present at high concentration in the targeted cells—and thus have a greater influence on those cells—than when binding to lower percentage of protein target present at low concentration in the non-targeted cells—and thus have lower side-effects.

The above simulations have been repeated for linker element dissociation constant $K_{d5}=100$ µM, (For C1=1 µM, C2=1 uM, FIGS. 112, 114, 116, 118 and 120, respectively; for C1=10 µM, C2=10 µM, FIGS. 122, 124, 126, 128, and 130, respectively; for C1=1 µM, C2=10 µM, FIGS. 132, 134, 136, 138, and 140, respectively).

The results of these simulations for various values (in µM) of $K_{d1}$, $K_{d2}$, $K_{d5}$, total monomer 1 concentration [SC1], total monomer 2 concentration [SC2], total target protein concentration [ST], the number of rotatable bonds per monomer (Rot Bond), and the highest $K_d$ value are enumerated in Table 5. In each instance, the highest $K_d$ value (either $K_{d3}$ or $K_{d4}$) is reported in the $K_d$ highest column. Since the highest $K_d$ value is driven by the weakest binding monomer, the 2nd monomer may have $K_d$ values ranging from 100 nM up to the $K_d$ value of the 1st monomer.

TABLE 5

Equilibrium dissociation constants derived from simulations of steady state interactions of monomers and dimers with target protein where the interaction between linker elements is reversible and $K_{d1}$ and $K_{d2}$ vary between 1 and 10 µM, and $K_{d5}$ varies between 10 and 100 µM.

| Fig. # | $K_{d1}$ | $K_{d2}$ | $K_{d5}$ | [SC1] | [SC2] | [ST] | Rot Bond | $K_d$ highest |
|---|---|---|---|---|---|---|---|---|
| 82 | 1 | 1 | 10 | 0.1 to 5.0 | 0.1 to 5.0 | 0.1 | 2 | 47 pM |
| 83 | 1 | 1 | 10 | 0.1 to 5.0 | 0.1 to 5.0 | 0.1 | 5 | 480 pM |
| 84 | 1 | 1 | 10 | 0.1 to 5.0 | 0.1 to 5.0 | 0.25 | 2 | 47 pM |
| 85 | 1 | 1 | 10 | 0.1 to 5.0 | 0.1 to 5.0 | 0.25 | 5 | 480 pM |
| 86 | 1 | 1 | 10 | 0.1 to 5.0 | 0.1 to 5.0 | 1 | 2 | 47 pM |
| 87 | 1 | 1 | 10 | 0.1 to 5.0 | 0.1 to 5.0 | 1 | 5 | 480 pM |
| 88 | 1 | 1 | 10 | 0.1 to 5.0 | 0.1 to 5.0 | 2.5 | 2 | 47 pM |
| 89 | 1 | 1 | 10 | 0.1 to 5.0 | 0.1 to 5.0 | 2.5 | 5 | 480 pM |
| 90 | 1 | 1 | 10 | 0.1 to 5.0 | 0.1 to 5.0 | 10 | 2 | 47 pM |
| 91 | 1 | 1 | 10 | 0.1 to 5.0 | 0.1 to 5.0 | 10 | 5 | 480 pM |
| 92 | 10 | 10 | 10 | 0.1 to 5.0 | 0.1 to 5.0 | 0.1 | 2 | 0.47 nM |
| 93 | 10 | 10 | 10 | 0.1 to 5.0 | 0.1 to 5.0 | 0.1 | 5 | 4.8 nM |
| 94 | 10 | 10 | 10 | 0.1 to 5.0 | 0.1 to 5.0 | 0.25 | 2 | 0.47 nM |
| 95 | 10 | 10 | 10 | 0.1 to 5.0 | 0.1 to 5.0 | 0.25 | 5 | 4.8 nM |
| 96 | 10 | 10 | 10 | 0.1 to 5.0 | 0.1 to 5.0 | 1 | 2 | 0.47 nM |
| 97 | 10 | 10 | 10 | 0.1 to 5.0 | 0.1 to 5.0 | 1 | 5 | 4.8 nM |
| 98 | 10 | 10 | 10 | 0.1 to 5.0 | 0.1 to 5.0 | 2.5 | 2 | 0.47 nM |
| 99 | 10 | 10 | 10 | 0.1 to 5.0 | 0.1 to 5.0 | 2.5 | 5 | 4.8 nM |
| 100 | 10 | 10 | 10 | 0.1 to 5.0 | 0.1 to 5.0 | 10 | 2 | 0.47 nM |
| 101 | 10 | 10 | 10 | 0.1 to 5.0 | 0.1 to 5.0 | 10 | 5 | 4.8 nM |
| 102 | 1 | 10 | 10 | 0.1 to 5.0 | 0.1 to 5.0 | 0.1 | 2 | 0.47 nM |
| 103 | 1 | 10 | 10 | 0.1 to 5.0 | 0.1 to 5.0 | 0.1 | 5 | 4.8 nM |
| 104 | 1 | 10 | 10 | 0.1 to 5.0 | 0.1 to 5.0 | 0.25 | 2 | 0.47 nM |
| 105 | 1 | 10 | 10 | 0.1 to 5.0 | 0.1 to 5.0 | 0.25 | 5 | 4.8 nM |
| 106 | 1 | 10 | 10 | 0.1 to 5.0 | 0.1 to 5.0 | 1 | 2 | 0.47 nM |
| 107 | 1 | 10 | 10 | 0.1 to 5.0 | 0.1 to 5.0 | 1 | 5 | 4.8 nM |
| 108 | 1 | 10 | 10 | 0.1 to 5.0 | 0.1 to 5.0 | 2.5 | 2 | 0.47 nM |
| 109 | 1 | 10 | 10 | 0.1 to 5.0 | 0.1 to 5.0 | 2.5 | 5 | 4.8 nM |
| 110 | 1 | 10 | 10 | 0.1 to 5.0 | 0.1 to 5.0 | 10 | 2 | 0.47 nM |
| 111 | 1 | 10 | 10 | 0.1 to 5.0 | 0.1 to 5.0 | 10 | 5 | 4.8 nM |
| 112 | 1 | 1 | 100 | 0.1 to 5.0 | 0.1 to 5.0 | 0.1 | 2 | 0.47 nM |
| 113 | 1 | 1 | 100 | 0.1 to 5.0 | 0.1 to 5.0 | 0.1 | 5 | 4.8 nM |
| 114 | 1 | 1 | 100 | 0.1 to 5.0 | 0.1 to 5.0 | 0.25 | 2 | 0.47 nM |
| 115 | 1 | 1 | 100 | 0.1 to 5.0 | 0.1 to 5.0 | 0.25 | 5 | 4.8 nM |
| 116 | 1 | 1 | 100 | 0.1 to 5.0 | 0.1 to 5.0 | 1 | 2 | 0.47 nM |
| 117 | 1 | 1 | 100 | 0.1 to 5.0 | 0.1 to 5.0 | 1 | 5 | 4.8 nM |
| 118 | 1 | 1 | 100 | 0.1 to 5.0 | 0.1 to 5.0 | 2.5 | 2 | 0.47 nM |
| 119 | 1 | 1 | 100 | 0.1 to 5.0 | 0.1 to 5.0 | 2.5 | 5 | 4.8 nM |

TABLE 5-continued

Equilibrium dissociation constants derived from simulations of steady
state interactions of monomers and dimers with target protein where the interaction
between linker elements is reversible and $K_{d1}$ and $K_{d2}$ vary between 1 and 10
µM, and $K_{d5}$ varies between 10 and 100 µM.

| Fig. # | $K_{d1}$ | $K_{d2}$ | $K_{d5}$ | [SC1] | [SC2] | [ST] | Rot Bond | $K_d$ highest |
|---|---|---|---|---|---|---|---|---|
| 120 | 1 | 1 | 100 | 0.1 to 5.0 | 0.1 to 5.0 | 10 | 2 | 0.47 nM |
| 121 | 1 | 1 | 100 | 0.1 to 5.0 | 0.1 to 5.0 | 10 | 5 | 4.8 nM |
| 122 | 10 | 10 | 100 | 0.1 to 5.0 | 0.1 to 5.0 | 0.1 | 2 | 4.7 nM |
| 123 | 10 | 10 | 100 | 0.1 to 5.0 | 0.1 to 5.0 | 0.1 | 5 | 48 nM |
| 124 | 10 | 10 | 100 | 0.1 to 5.0 | 0.1 to 5.0 | 0.25 | 2 | 4.7 nM |
| 125 | 10 | 10 | 100 | 0.1 to 5.0 | 0.1 to 5.0 | 0.25 | 5 | 48 nM |
| 126 | 10 | 10 | 100 | 0.1 to 5.0 | 0.1 to 5.0 | 1 | 2 | 4.7 nM |
| 127 | 10 | 10 | 100 | 0.1 to 5.0 | 0.1 to 5.0 | 1 | 5 | 48 nM |
| 128 | 10 | 10 | 100 | 0.1 to 5.0 | 0.1 to 5.0 | 2.5 | 2 | 4.7 nM |
| 129 | 10 | 10 | 100 | 0.1 to 5.0 | 0.1 to 5.0 | 2.5 | 5 | 48 nM |
| 130 | 10 | 10 | 100 | 0.1 to 5.0 | 0.1 to 5.0 | 10 | 2 | 4.7 nM |
| 131 | 10 | 10 | 100 | 0.1 to 5.0 | 0.1 to 5.0 | 10 | 5 | 48 nM |
| 132 | 1 | 10 | 100 | 0.1 to 5.0 | 0.1 to 5.0 | 0.1 | 2 | 4.7 nM |
| 133 | 1 | 10 | 100 | 0.1 to 5.0 | 0.1 to 5.0 | 0.1 | 5 | 48 nM |
| 134 | 1 | 10 | 100 | 0.1 to 5.0 | 0.1 to 5.0 | 0.25 | 2 | 4.7 nM |
| 135 | 1 | 10 | 100 | 0.1 to 5.0 | 0.1 to 5.0 | 0.25 | 5 | 48 nM |
| 136 | 1 | 10 | 100 | 0.1 to 5.0 | 0.1 to 5.0 | 1 | 2 | 4.7 nM |
| 137 | 1 | 10 | 100 | 0.1 to 5.0 | 0.1 to 5.0 | 1 | 5 | 48 nM |
| 138 | 1 | 10 | 100 | 0.1 to 5.0 | 0.1 to 5.0 | 2.5 | 2 | 4.7 nM |
| 139 | 1 | 10 | 100 | 0.1 to 5.0 | 0.1 to 5.0 | 2.5 | 5 | 48 nM |
| 140 | 1 | 10 | 100 | 0.1 to 5.0 | 0.1 to 5.0 | 10 | 2 | 4.7 nM |
| 141 | 1 | 10 | 100 | 0.1 to 5.0 | 0.1 to 5.0 | 10 | 5 | 48 nM |

($K_{d1}$, $K_{d2}$, $K_{d5}$ are in µM. [SC1], [SC2], and [ST] represent the total concentration of monomer 1, monomer 2, and target, respectively, and are in µM. Rot bonds indicates the number of rotatable bonds between the linker element and the diversity element for each monomer.)

Thus, a first coferon monomer C1 with dissociation constant $K_{d1}$ of the diversity element from the target molecule of within a three-fold range of from 100 nM to within a three-fold range of 1 µM, providing a second coferon monomer C2 with dissociation constant $K_{d2}$ of the diversity element from the target molecule of within a three-fold range of 1 µM to within a three-fold range of 10 µM, with a dissociation constant $K_{d5}$ between the linker element of the first monomer and the linker element of the second monomer of within a three-fold range of 10 µM to within a three-fold range of 100 µM, with each monomer containing from 0 to 5 rotatable bonds or equivalent degrees of rotational freedom between the linker element portion and target binding portions, with steady-state concentrations of the coferon monomers C1 and C2 in the blood ranging from about 0.1 µM to about 5.0 µM or higher, and with the concentration of the target protein in the target cells ranging from about 0.1 µM to 10 µM or higher. As a result, such dimers will achieve binding to the target, such that about 70% to 100% of the target protein in the cells are bound by the dimer, which has a dissociation constant from the target molecule that is from within a ten-fold range of about 47 pM or lower to within a ten-fold range of 48 nM, such that binding of these coferon dimers to the target protein is sufficient to displace another protein, protein domain, macromolecule, or substrate with an equal or higher dissociation constant from binding to the target protein, or is of sufficiently tight binding to activate, enhance, or inhibit the biological activity of the target protein or its binding partners. The monomers C1 and C2 achieve the desired therapeutic effect.

Prophetic Example 7

Simulation of Binding Equilibria for Coferon Dimers to Target Protein: Determination of Concentrations of Coferon Dimers Binding to a Target Protein for Various Values of Dissociation Constants for Both Monomers and for Very Tight or Irreversible Association of Monomers The above simulations was repeated for linker element dissociation constant $K_{d5}$=0.1 µM, as described in Examples 5 and 6.

The results of these simulations for various values (in µM) of $K_{d1}$, $K_{d2}$, $K_{d5}$, total monomer 1 concentration [SC1], total monomer 2 concentration [SC2], total target protein concentration [ST], the number of rotatable bonds per monomer (Rot Bond), and the highest $K_d$ value are enumerated in Table 6. In each instance, the highest $K_d$ value ($K_{d6}$) is reported in the $K_d$ highest column Since the highest $K_d$ value is driven by the binding of the two monomers to the target, dissociation of the monomers from each other, i.e. $K_{d5}$ values may range from 1 nM (or 0 nM for a completely irreversible covalent bond) up to the $K_d$ value of the tightest binding monomer.

TABLE 6

Equilibrium dissociation constants derived from simulations of steady
state interactions of coferon monomers and dimers with target protein
where the interaction between linker elements is very tight or
irreversible, and $K_{d1}$ and $K_{d2}$ vary between 1 and 100 µM.

| $K_{d1}$ | $K_{d2}$ | $K_{d5}$ | [SC1] | [SC2] | [ST] | Rot Bond | $K_d$ highest |
|---|---|---|---|---|---|---|---|
| 1 | 1 | 0.1 | 0.1 to 5.0 | 0.1 to 5.0 | 0.1 | 2 | 4.7 pM |
| 1 | 1 | 0.1 | 0.1 to 5.0 | 0.1 to 5.0 | 0.1 | 5 | 48 pM |
| 1 | 1 | 0.1 | 0.1 to 5.0 | 0.1 to 5.0 | 0.25 | 2 | 4.7 pM |
| 1 | 1 | 0.1 | 0.1 to 5.0 | 0.1 to 5.0 | 0.25 | 5 | 48 pM |

TABLE 6-continued

Equilibrium dissociation constants derived from simulations of steady state interactions of coferon monomers and dimers with target protein where the interaction between linker elements is very tight or irreversible, and $K_{d1}$ and $K_{d2}$ vary between 1 and 100 μM.

| $K_{d1}$ | $K_{d2}$ | $K_{d5}$ | [SC1] | [SC2] | [ST] | Rot Bond | $K_d$ highest |
|---|---|---|---|---|---|---|---|
| 1 | 1 | 0.1 | 0.1 to 5.0 | 0.1 to 5.0 | 1 | 2 | 4.7 pM |
| 1 | 1 | 0.1 | 0.1 to 5.0 | 0.1 to 5.0 | 1 | 5 | 48 pM |
| 1 | 1 | 0.1 | 0.1 to 5.0 | 0.1 to 5.0 | 2.5 | 2 | 4.7 pM |
| 1 | 1 | 0.1 | 0.1 to 5.0 | 0.1 to 5.0 | 2.5 | 5 | 48 pM |
| 1 | 1 | 0.1 | 0.1 to 5.0 | 0.1 to 5.0 | 10 | 2 | 4.7 pM |
| 1 | 1 | 0.1 | 0.1 to 5.0 | 0.1 to 5.0 | 10 | 5 | 48 pM |
| 1 | 10 | 0.1 | 0.1 to 5.0 | 0.1 to 5.0 | 0.1 | 2 | 47 pM |
| 1 | 10 | 0.1 | 0.1 to 5.0 | 0.1 to 5.0 | 0.1 | 5 | 480 pM |
| 1 | 10 | 0.1 | 0.1 to 5.0 | 0.1 to 5.0 | 0.25 | 2 | 47 pM |
| 1 | 10 | 0.1 | 0.1 to 5.0 | 0.1 to 5.0 | 0.25 | 5 | 480 pM |
| 1 | 10 | 0.1 | 0.1 to 5.0 | 0.1 to 5.0 | 1 | 2 | 47 pM |
| 1 | 10 | 0.1 | 0.1 to 5.0 | 0.1 to 5.0 | 1 | 5 | 480 pM |
| 1 | 10 | 0.1 | 0.1 to 5.0 | 0.1 to 5.0 | 2.5 | 2 | 47 pM |
| 1 | 10 | 0.1 | 0.1 to 5.0 | 0.1 to 5.0 | 2.5 | 5 | 480 pM |
| 1 | 10 | 0.1 | 0.1 to 5.0 | 0.1 to 5.0 | 10 | 2 | 47 pM |
| 1 | 10 | 0.1 | 0.1 to 5.0 | 0.1 to 5.0 | 10 | 5 | 480 pM |
| 10 | 10 | 0.1 | 0.1 to 5.0 | 0.1 to 5.0 | 0.1 | 2 | 0.47 nM |
| 10 | 10 | 0.1 | 0.1 to 5.0 | 0.1 to 5.0 | 0.1 | 5 | 4.8 nM |
| 10 | 10 | 0.1 | 0.1 to 5.0 | 0.1 to 5.0 | 0.25 | 2 | 0.47 nM |
| 10 | 10 | 0.1 | 0.1 to 5.0 | 0.1 to 5.0 | 0.25 | 5 | 4.8 nM |
| 10 | 10 | 0.1 | 0.1 to 5.0 | 0.1 to 5.0 | 1 | 2 | 0.47 nM |
| 10 | 10 | 0.1 | 0.1 to 5.0 | 0.1 to 5.0 | 1 | 5 | 4.8 nM |
| 10 | 10 | 0.1 | 0.1 to 5.0 | 0.1 to 5.0 | 2.5 | 2 | 0.47 nM |
| 10 | 10 | 0.1 | 0.1 to 5.0 | 0.1 to 5.0 | 2.5 | 5 | 4.8 nM |
| 10 | 10 | 0.1 | 0.1 to 5.0 | 0.1 to 5.0 | 10 | 2 | 0.47 nM |
| 10 | 10 | 0.1 | 0.1 to 5.0 | 0.1 to 5.0 | 10 | 5 | 4.8 nM |
| 10 | 100 | 0.1 | 0.1 to 5.0 | 0.1 to 5.0 | 0.1 | 2 | 4.7 nM |
| 10 | 100 | 0.1 | 0.1 to 5.0 | 0.1 to 5.0 | 0.1 | 5 | 48 nM |
| 10 | 100 | 0.1 | 0.1 to 5.0 | 0.1 to 5.0 | 0.25 | 2 | 4.7 nM |
| 10 | 100 | 0.1 | 0.1 to 5.0 | 0.1 to 5.0 | 0.25 | 5 | 48 nM |
| 10 | 100 | 0.1 | 0.1 to 5.0 | 0.1 to 5.0 | 1 | 2 | 4.7 nM |
| 10 | 100 | 0.1 | 0.1 to 5.0 | 0.1 to 5.0 | 1 | 5 | 48 nM |
| 10 | 100 | 0.1 | 0.1 to 5.0 | 0.1 to 5.0 | 2.5 | 2 | 4.7 nM |
| 10 | 100 | 0.1 | 0.1 to 5.0 | 0.1 to 5.0 | 2.5 | 5 | 48 nM |
| 10 | 100 | 0.1 | 0.1 to 5.0 | 0.1 to 5.0 | 10 | 2 | 4.7 nM |
| 10 | 100 | 0.1 | 0.1 to 5.0 | 0.1 to 5.0 | 10 | 5 | 48 nM |

($K_{d1}$, $K_{d2}$, $K_{d5}$ are in μM. [SC1], [SC2], and [ST] represent the total concentration of monomer 1, monomer 2, and target, respectively, and are in μM. Rot bonds indicates the number of rotatable bonds between the linker element and the diversity element for each monomer.)

Thus, when providing a first coferon monomer C1 with dissociation constant $K_{d1}$ of the diversity element from the target molecule of within a three-fold range of from 1 μM to within a three-fold range of 10 μM, providing a second coferon monomer C2 with dissociation constant $K_{d2}$ of the diversity element from the target molecules of within a three-fold range of 1 μM to within a three-fold range of 100 μM, with a dissociation constant $K_{d5}$ between the linker element of the first monomer and the linker element of the second monomer of within a three-fold range of 1 nM (or 0 nM for a completely irreversible covalent bond) to within a three-fold range of 10 μM, with each monomer containing from 0 to 5 rotatable bonds or equivalent degrees of rotational freedom between the linker element portion and target binding portions, with steady-state concentrations of the monomers C1 and C2 in the blood ranging from about 0.1 μM to about 5.0 μM or higher, with the concentration of the target protein in the target cells ranging from about 0.1 μM to 10 μM or higher, such dimers will achieve binding to the target. As a result, about 70% to 100% of the target protein in the cells are bound by the dimer, which has a dissociation constant from the target molecule that is from within a ten-fold range of about 4.7 pM or lower to within a ten-fold range of 48 nM, binding of these coferon dimers to the target protein is sufficient to displace another protein, protein domain, macromolecule, or substrate with an equal or higher dissociation constant from binding to the target protein, or is of sufficiently tight binding to activate, enhance, or inhibit the biological activity of the target protein or its binding partners. The coferon monomers C1 and C2 achieve the desired therapeutic effect.

Prophetic Example 8

Characterization of Dimerization for Selected Linker Element Precursors by Mass Spectrometry The ability of precursors to linker elements to form dimers in aqueous solutions was determined by mass spectrometry (MS) and mass spectrometry/mass spectrometry (MS/MS). Linker elements that form dimers (or multimers) only as a result of the ionization during mass spectrometry can be distinguished from those that truly form dimers in aqueous solution by determination of the fragmentation during mass spectrometry/mass spectrometry.

Thus, piperidin-2-ylmethanol and cyclohexylboronic acid form a dimer (1-cyclohexylhexahydro-1H-[1,3,2]oxazaborolo[3,4-a]pyridine) in aqueous solution. 1,3-dihydroxyacetone forms a dimer (2,5-bis(hydroxymethyl)-1,4-dioxane-2,5-diol) during ionization but in aqueous solution exists mostly as the monomer. On the other hand, 2-hydroxycyxlohexanone forms a dimer (dodecahydrodibenzo[b,e][1,4]dioxine-4a,9a-diol) in aqueous solution as determined by MS/MS. 3-hydroxy-2-methyl-4H-pyran-4-one and zinc acetate form a dimer containing 2 molecules of 3-hydroxy-2-methyl-4H-pyran-4-one coordinating one Zn cation in aqueous solution as determined by MS/MS.

Prophetic Example 9

Representative Dissociation Constants for Reversible Boronate Formation Between Phenylboronic Acid and Selected 1,2-Diols FIG. 141 shows the equilibrium $K_d$ values for a series of 1,2-diols when reacted with phenyl boronic acid. The $K_d$ values range between 206 mM for the simplest 1,2-diol, such as 2-hydroxy propanol to 10 μM for a furanose sugar.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A therapeutic dimer having:

a boronate ester moiety formed from a phenylboronic acid linker element and a cis-1,2 diol binding partner;

a diversity element joined to the phenylboronic acid linker element through a connector; and a diversity element joined to the cis-1,2 diol binding partner through another connector, wherein the diversity element joined to the cis-1,2 diol binding partner and the diversity element joined to the phenylboronic acid linker each bind to proximate locations on a target molecule, and wherein said diversity element is a molecule having a structure based on one or more of monocyclic scaffolds, bicyclic scaffolds, tetracyclic scaffolds, spiro scaffolds, or combinations thereof linked by a covalent bond forming multicore scaffolds; and wherein said target molecule is (1) G-protein coupled receptors, (2) nuclear receptors, (3) voltage gated ion channels, (4) ligand gated ion channels, (5) receptor tyrosine kinases, (6) growth factors, (7) proteases, (8) sequence specific proteases, (9) phosphatases, (10) protein kinases, (11) bioactive lipids, (12) cytokines, (13) chemokines, (14) ubiquitin ligases, (15) viral regulators, (16) cell division proteins, (17) scaffold proteins, (18) DNA repair proteins, (19) bacterial ribosomes, (20) histone deacetylases, (21) apoptosis regulators, (22) chaperone proteins, (23) serine/threonine protein kinases, (24) cyclin dependent kinases, (25) growth factor receptors, (26) proteasome, (27) signaling protein complexes, (28) protein/nucleic acid transporters, or (29) viral capsids.

2. The therapeutic dimer of claim 1, wherein the cis-1,2 diol binding partner is a catechol.

3. A therapeutic multimer comprising:

a monomer having a diversity element and a linker element with an aromatic non-heterocyclic ring containing a boronic acid group, wherein the linker element is joined to the diversity element through a connector;

another monomer having a binding partner linker element having a 1,2 or 1,3 diol, and joined to another diversity element through another connector, wherein the linker element and the binding partner linker element form a reversibly covalently bonded 5 or 6 membered boronate diester ring; and wherein each diversity element independently for each occurrence binds to a target molecule with a dissociation constant less than 300 µM, and wherein said diversity element is a molecule having a structure based on one or more of monocyclic scaffolds, bicyclic scaffolds, tetracyclic scaffolds, spiro scaffolds, or combinations thereof linked by a covalent bond forming multicore scaffolds; and wherein said target molecule is (1) G-protein coupled receptors, (2) nuclear receptors, (3) voltage gated ion channels, (4) ligand gated ion channels, (5) receptor tyrosine kinases, (6) growth factors, (7) proteases, (8) sequence specific proteases, (9) phosphatases, (10) protein kinases, (11) bioactive lipids, (12) cytokines, (13) chemokines, (14) ubiquitin ligases, (15) viral regulators, (16) cell division proteins, (17) scaffold proteins, (18) DNA repair proteins, (19) bacterial ribosomes, (20) histone deacetylases, (21) apoptosis regulators, (22) chaperone proteins, (23) serine/threonine protein kinases, (24) cyclin dependent kinases, (25) growth factor receptors, (26) proteasome, (27) signaling protein complexes, (28) protein/nucleic acid transporters, or (29) viral capsids; and the diversity elements of the therapeutic multimer bind to proximate locations of the target molecule, wherein the therapeutic multimer binds to the target molecule with a dissociation constant of less than 10 µM.

4. The therapeutic multimer of claim 3, wherein one or more of said diversity elements is capable of forming a reversible covalent bond with the target molecule.

5. The therapeutic multimer of claim 3, wherein the linker element and the binding partner linker element each has a molecular weight less than 500 daltons.

* * * * *

UNITED STATES PATENT AND TRADEMARK OFFICE
CERTIFICATE OF CORRECTION

PATENT NO. : 9,943,603 B2  
APPLICATION NO. : 14/445887  
DATED : April 17, 2018  
INVENTOR(S) : Barany et al.

Page 1 of 1

It is certified that error appears in the above-identified patent and that said Letters Patent is hereby corrected as shown below:

Column 1 at Lines 11-15, delete "This invention was made with government support under Public Health Service grant AI062579-03 from the National Institute of Allergy and Infectious Diseases and Grant No. CA65930-08 from the National Cancer Institute. The government has certain rights in this invention." and insert --This invention was made with government support under AI062579 & CA065930 awarded by the National Institutes of Health. The government has certain rights in the invention.--

Signed and Sealed this  
Fifteenth Day of May, 2018

Andrei Iancu  
*Director of the United States Patent and Trademark Office*

SEQUENCE LISTING

<160> NUMBER OF SEQ ID NOS: 13

<210> SEQ ID NO 1
<211> LENGTH: 12
<212> TYPE: PRT
<213> ORGANISM: Artificial

```
<220> FEATURE:
<223> OTHER INFORMATION: circular peptide

<400> SEQUENCE: 1

Lys Asp Gly Asp Gly Asp Gly Asp Gly Asp Gly Asp
1               5                   10

<210> SEQ ID NO 2
<211> LENGTH: 12
<212> TYPE: PRT
<213> ORGANISM: Artificial
<220> FEATURE:
<223> OTHER INFORMATION: circular peptide

<400> SEQUENCE: 2

Lys Asp Gly Cys Gly Asp Gly Cys Gly Asp Gly Cys
1               5                   10

<210> SEQ ID NO 3
<211> LENGTH: 4
<212> TYPE: PRT
<213> ORGANISM: Artificial
<220> FEATURE:
<223> OTHER INFORMATION: proline-rich peptide motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 3

Pro Xaa Xaa Pro
1

<210> SEQ ID NO 4
<211> LENGTH: 4
<212> TYPE: PRT
<213> ORGANISM: Artificial
<220> FEATURE:
<223> OTHER INFORMATION: phospho-tyrosine peptide motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Asn Pro Xaa Tyr
1

<210> SEQ ID NO 5
<211> LENGTH: 13
<212> TYPE: PRT
<213> ORGANISM: Artificial
<220> FEATURE:
<223> OTHER INFORMATION: ERK peptide inhibitor

<400> SEQUENCE: 5

Met Pro Lys Lys Lys Pro Thr Pro Ile Gln Leu Asn Pro
1               5                   10

<210> SEQ ID NO 6
<211> LENGTH: 27
<212> TYPE: PRT
<213> ORGANISM: Artificial
<220> FEATURE:
<223> OTHER INFORMATION: ERK peptide inhibitor
```

```
<400> SEQUENCE: 6

His Gly Tyr Gly Arg Lys Lys Arg Arg Gln Arg Arg Arg Gly Met Pro
1               5                   10                  15

Lys Lys Lys Pro Thr Pro Ile Gln Leu Asn Pro
            20                  25

<210> SEQ ID NO 7
<211> LENGTH: 5
<212> TYPE: PRT
<213> ORGANISM: Artificial
<220> FEATURE:
<223> OTHER INFORMATION: beta-amyloid peptide inhibitor

<400> SEQUENCE: 7

Lys Leu Val Phe Phe
1               5

<210> SEQ ID NO 8
<211> LENGTH: 5
<212> TYPE: PRT
<213> ORGANISM: Artificial
<220> FEATURE:
<223> OTHER INFORMATION: beta-amyloid peptide inhibitor

<400> SEQUENCE: 8

Leu Val Phe Phe Ala
1               5

<210> SEQ ID NO 9
<211> LENGTH: 6
<212> TYPE: PRT
<213> ORGANISM: Artificial
<220> FEATURE:
<223> OTHER INFORMATION: IRS-1 peptide inhibitor
<220> FEATURE:
<221> NAME/KEY: misc_feature
<222> LOCATION: (6)..(6)
<223> OTHER INFORMATION: Xaa can be any naturally occurring amino acid

<400> SEQUENCE: 9

Leu Ser Asn Pro Thr Xaa
1               5

<210> SEQ ID NO 10
<211> LENGTH: 8
<212> TYPE: PRT
<213> ORGANISM: Artificial
<220> FEATURE:
<223> OTHER INFORMATION: IRS-1 peptide inhibitor
<220> FEATURE:
<221> NAME/KEY: misc_feature
<222> LOCATION: (8)..(8)
<223> OTHER INFORMATION: Xaa can be any naturally occurring amino acid

<400> SEQUENCE: 10

Leu Tyr Ala Ser Ser Asn Ala Xaa
1               5

<210> SEQ ID NO 11
<211> LENGTH: 9
<212> TYPE: PRT
<213> ORGANISM: Artificial
<220> FEATURE:
<223> OTHER INFORMATION: IRS-1 peptide inhibitor
<220> FEATURE:
<221> NAME/KEY: misc_feature
<222> LOCATION: (9)..(9)
<223> OTHER INFORMATION: Xaa can be any naturally occurring amino acid
```

```
<400> SEQUENCE: 11

Leu Tyr Ala Ser Ser Asn Pro Ala Xaa
1               5

<210> SEQ ID NO 12
<211> LENGTH: 10
<212> TYPE: PRT
<213> ORGANISM: Artificial
<220> FEATURE:
<223> OTHER INFORMATION: GRb2 peptide inhibitor

<400> SEQUENCE: 12

Val Pro Pro Pro Val Pro Pro Arg Arg Arg
1               5                   10

<210> SEQ ID NO 13
<211> LENGTH: 4
<212> TYPE: PRT
<213> ORGANISM: Artificial
<220> FEATURE:
<223> OTHER INFORMATION: SH3 binding domain peptide motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 13

Arg Xaa Xaa Lys
1
```